(12) United States Patent
Pfeiffer et al.

(10) Patent No.: US 11,131,664 B2
(45) Date of Patent: *Sep. 28, 2021

(54) METHODS AND SYSTEMS FOR MACROMOLECULE LABELING

(71) Applicant: 10X Genomics, Inc., Pleasanton, CA (US)

(72) Inventors: Katherine Pfeiffer, Pleasanton, CA (US); Sarah Taylor, Fremont, CA (US); Michael Stubbington, Cambridge (GB)

(73) Assignee: 10X GENOMICS, INC., Pleasanton, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/375,129

(22) Filed: Apr. 4, 2019

(65) Prior Publication Data

US 2019/0361010 A1 Nov. 28, 2019

Related U.S. Application Data

(63) Continuation of application No. PCT/US2019/017723, filed on Feb. 12, 2019.
(Continued)

(51) Int. Cl.
*C40B 50/06* (2006.01)
*G01N 33/532* (2006.01)
(Continued)

(52) U.S. Cl.
CPC ..... *G01N 33/532* (2013.01); *C07K 14/70539* (2013.01); *C12N 15/1037* (2013.01);
(Continued)

(58) Field of Classification Search
None
See application file for complete search history.

(56) References Cited

U.S. PATENT DOCUMENTS

| 4,124,638 A | 11/1978 | Hansen |
| 5,185,099 A | 2/1993 | Delpuech et al. |

(Continued)

FOREIGN PATENT DOCUMENTS

| EP | 1019496 B1 | 9/2004 |
| EP | 1841879 A2 | 10/2007 |

(Continued)

OTHER PUBLICATIONS

Abate, A.R. et al. "Beating Poisson encapsulation statistics using close-packed ordering" Lab on a Chip (Sep. 21, 2009) 9(18):2628-2631.
(Continued)

*Primary Examiner* — Christian C Boesen
(74) *Attorney, Agent, or Firm* — Wilson Sonsini Goodrich & Rosati

(57) ABSTRACT

The present disclosure provides compositions, methods, systems, and devices for polynucleotide processing and analyte characterization from one or more cells. Such polynucleotide processing may be useful for a variety of applications, including generation of labeled macromolecules, including major mistocompatability complex (MHC) molecules, dextramers, etc. Labeled macromolecules may be generated using an in vitro transcription reaction. Labeled macromolecules may be generated in one or more partitions.

29 Claims, 185 Drawing Sheets

Specification includes a Sequence Listing.

Related U.S. Application Data

(60) Provisional application No. 62/629,602, filed on Feb. 12, 2018.

(51) Int. Cl.

| | | |
|---|---|---|
| *C07K 14/74* | (2006.01) | |
| *C12N 15/85* | (2006.01) | |
| *G01N 33/543* | (2006.01) | |
| *G01N 33/548* | (2006.01) | |
| *C12N 15/10* | (2006.01) | |
| *C12Q 1/6804* | (2018.01) | |
| *C12Q 1/6806* | (2018.01) | |
| *G01N 33/50* | (2006.01) | |
| *G01N 33/53* | (2006.01) | |
| *G01N 33/58* | (2006.01) | |
| *C12Q 1/6818* | (2018.01) | |
| *C12Q 1/6827* | (2018.01) | |
| *C12Q 1/6881* | (2018.01) | |
| *C12N 15/11* | (2006.01) | |
| *G01N 33/569* | (2006.01) | |
| *C40B 70/00* | (2006.01) | |
| *C40B 30/04* | (2006.01) | |

(52) U.S. Cl.
CPC ..... *C12N 15/1055* (2013.01); *C12N 15/1065* (2013.01); *C12N 15/1075* (2013.01); *C12N 15/11* (2013.01); *C12N 15/85* (2013.01); *C12Q 1/6804* (2013.01); *C12Q 1/6806* (2013.01); *C12Q 1/6818* (2013.01); *C12Q 1/6827* (2013.01); *C12Q 1/6881* (2013.01); *G01N 33/505* (2013.01); *G01N 33/5032* (2013.01); *G01N 33/5304* (2013.01); *G01N 33/5306* (2013.01); *G01N 33/5308* (2013.01); *G01N 33/548* (2013.01); *G01N 33/54306* (2013.01); *G01N 33/54366* (2013.01); *G01N 33/56977* (2013.01); *G01N 33/58* (2013.01); *C12N 2310/20* (2017.05); *C12N 2320/10* (2013.01); *C12Q 2537/164* (2013.01); *C12Q 2563/179* (2013.01); *C12Q 2563/185* (2013.01); *C12Q 2565/1015* (2013.01); *C40B 30/04* (2013.01); *C40B 50/06* (2013.01); *C40B 70/00* (2013.01)

(56) References Cited

U.S. PATENT DOCUMENTS

| | | |
|---|---|---|
| 5,270,183 A | 12/1993 | Corbett et al. |
| 5,478,893 A | 12/1995 | Ghosh et al. |
| 5,736,330 A | 4/1998 | Fulton |
| 5,756,334 A | 5/1998 | Perler et al. |
| 5,846,719 A | 12/1998 | Brenner et al. |
| 5,900,481 A | 5/1999 | Lough et al. |
| 5,942,609 A | 8/1999 | Hunkapiller et al. |
| 5,994,056 A | 11/1999 | Higuchi |
| 6,033,880 A | 3/2000 | Haff et al. |
| 6,057,149 A | 5/2000 | Burns et al. |
| 6,123,798 A | 9/2000 | Gandhi et al. |
| 6,171,850 B1 | 1/2001 | Nagle et al. |
| 6,172,218 B1 | 1/2001 | Brenner |
| 6,176,962 B1 | 1/2001 | Soane et al. |
| 6,306,590 B1 | 10/2001 | Mehta et al. |
| 6,327,410 B1 | 12/2001 | Walt et al. |
| 6,379,929 B1 | 4/2002 | Burns et al. |
| 6,406,848 B1 | 6/2002 | Bridgham et al. |
| 6,409,832 B2 | 6/2002 | Weigl et al. |
| 6,410,246 B1 | 6/2002 | Zhu et al. |
| 6,492,118 B1 | 12/2002 | Abrams et al. |
| 6,524,456 B1 | 2/2003 | Ramsey et al. |
| 6,586,176 B1 | 7/2003 | Trnovsky et al. |
| 6,632,655 B1 | 10/2003 | Mehta et al. |
| 6,915,679 B2 | 7/2005 | Chien et al. |
| 7,041,481 B2 | 5/2006 | Anderson et al. |
| 7,115,400 B1 | 10/2006 | Adessi et al. |
| 7,129,091 B2 | 10/2006 | Ismagilov et al. |
| 7,268,167 B2 | 9/2007 | Higuchi et al. |
| 7,282,370 B2 | 10/2007 | Bridgham et al. |
| 7,294,503 B2 | 11/2007 | Quake et al. |
| 7,323,305 B2 | 1/2008 | Leamon et al. |
| 7,544,473 B2 | 6/2009 | Brenner |
| 7,595,060 B2 | 9/2009 | Duke et al. |
| 7,622,076 B2 | 11/2009 | Davies et al. |
| 7,622,280 B2 | 11/2009 | Holliger et al. |
| 7,645,596 B2 | 1/2010 | Williams et al. |
| 7,708,949 B2 | 5/2010 | Stone et al. |
| 7,772,287 B2 | 8/2010 | Higuchi et al. |
| 7,776,927 B2 | 8/2010 | Chu et al. |
| 7,842,457 B2 | 11/2010 | Berka et al. |
| 7,910,354 B2 | 3/2011 | Drmanac et al. |
| 7,927,797 B2 | 4/2011 | Nobile et al. |
| 7,960,104 B2 | 6/2011 | Drmanac et al. |
| 7,968,287 B2 | 6/2011 | Griffiths et al. |
| 8,053,192 B2 | 11/2011 | Bignell et al. |
| 8,133,719 B2 | 3/2012 | Drmanac et al. |
| 8,168,385 B2 | 5/2012 | Brenner |
| 8,268,564 B2 | 9/2012 | Roth et al. |
| 8,273,573 B2 | 9/2012 | Ismagilov et al. |
| 8,298,767 B2 | 10/2012 | Brenner et al. |
| 8,304,193 B2 | 11/2012 | Ismagilov et al. |
| 8,318,433 B2 | 11/2012 | Brenner |
| 8,329,407 B2 | 12/2012 | Ismagilov et al. |
| 8,394,590 B2 | 3/2013 | Kwong et al. |
| 8,592,150 B2 | 11/2013 | Drmanac et al. |
| 8,658,430 B2 | 2/2014 | Miller et al. |
| 8,691,510 B2 | 4/2014 | Faham et al. |
| 8,822,148 B2 | 9/2014 | Ismagliov et al. |
| 8,835,358 B2 | 9/2014 | Fodor et al. |
| 8,871,444 B2 | 10/2014 | Griffiths et al. |
| 8,889,083 B2 | 11/2014 | Ismagilov et al. |
| 8,975,302 B2 | 3/2015 | Light et al. |
| 9,012,390 B2 | 4/2015 | Holtze et al. |
| 9,029,083 B2 | 5/2015 | Griffiths et al. |
| 9,029,085 B2 | 5/2015 | Agresti et al. |
| 9,034,601 B2 | 5/2015 | Hufton et al. |
| 9,085,798 B2 | 7/2015 | Chee |
| 9,089,844 B2 | 7/2015 | Hiddessen et al. |
| 9,126,160 B2 | 9/2015 | Ness et al. |
| 9,156,010 B2 | 10/2015 | Colston et al. |
| 9,194,861 B2 | 11/2015 | Hindson et al. |
| 9,216,392 B2 | 12/2015 | Hindson et al. |
| 9,217,176 B2 | 12/2015 | Faham et al. |
| 9,238,206 B2 | 1/2016 | Rotem et al. |
| 9,266,104 B2 | 2/2016 | Link |
| 9,290,808 B2 | 3/2016 | Fodor et al. |
| 9,328,382 B2 | 5/2016 | Drmanac et al. |
| 9,347,059 B2 | 5/2016 | Saxonov |
| 9,365,901 B2 | 6/2016 | Pepin et al. |
| 9,388,465 B2 | 7/2016 | Hindson et al. |
| 9,417,190 B2 | 8/2016 | Hindson et al. |
| 9,486,757 B2 | 11/2016 | Romanowsky et al. |
| 9,498,761 B2 | 11/2016 | Holtze et al. |
| 9,499,865 B2 | 11/2016 | Faham et al. |
| 9,500,664 B2 | 11/2016 | Ness et al. |
| 9,506,119 B2 | 11/2016 | Faham et al. |
| 9,512,487 B2 | 12/2016 | Faham et al. |
| 9,567,631 B2 | 2/2017 | Hindson et al. |
| 9,623,384 B2 | 4/2017 | Hindson et al. |
| 9,637,799 B2 | 5/2017 | Fan et al. |
| 9,644,204 B2 | 5/2017 | Hindson et al. |
| 9,689,024 B2 | 6/2017 | Hindson et al. |
| 9,694,361 B2 | 7/2017 | Bharadwaj et al. |
| 9,701,998 B2 | 7/2017 | Hindson et al. |
| 9,708,657 B2 | 7/2017 | Asbury et al. |
| 9,764,322 B2 | 9/2017 | Hiddessen et al. |
| 9,824,068 B2 | 11/2017 | Wong |
| 9,946,577 B1 | 4/2018 | Stafford et al. |
| 9,951,386 B2 | 4/2018 | Hindson et al. |
| 9,957,558 B2 | 5/2018 | Leamon et al. |
| 9,975,122 B2 | 5/2018 | Masquelier et al. |
| 10,011,872 B1 | 7/2018 | Belgrader et al. |
| 10,017,759 B2 | 7/2018 | Kaper et al. |

(56) References Cited

U.S. PATENT DOCUMENTS

| | | |
|---|---|---|
| 10,059,989 B2 | 8/2018 | Giresi et al. |
| 10,066,265 B2 | 9/2018 | Klinger et al. |
| 10,077,478 B2 | 9/2018 | Faham et al. |
| 10,168,328 B2 | 1/2019 | Berka |
| 10,221,436 B2 | 3/2019 | Hardenbol et al. |
| 10,221,442 B2 | 3/2019 | Hindson et al. |
| 10,253,364 B2 | 4/2019 | Hindson et al. |
| 10,273,541 B2 | 4/2019 | Hindson et al. |
| 10,323,279 B2 | 6/2019 | Hindson et al. |
| 10,347,365 B2 | 7/2019 | Wong et al. |
| 10,357,771 B2 | 7/2019 | Bharadwaj et al. |
| 10,392,663 B2 | 8/2019 | Emerson et al. |
| 10,395,758 B2 | 8/2019 | Schnall-Levin |
| 10,400,280 B2 | 9/2019 | Hindson et al. |
| 10,428,325 B1 | 10/2019 | Klinger |
| 10,428,326 B2 | 10/2019 | Belhocine et al. |
| 10,533,221 B2 | 1/2020 | Hindson et al. |
| 10,544,413 B2 | 1/2020 | Bharadwaj et al. |
| 10,549,279 B2 | 2/2020 | Bharadwaj et al. |
| 10,590,244 B2 | 3/2020 | Delaney et al. |
| 10,745,742 B2 | 8/2020 | Bent et al. |
| 10,829,815 B2 | 11/2020 | Bharadwaj et al. |
| 2002/0005354 A1 | 1/2002 | Spence et al. |
| 2002/0051971 A1 | 5/2002 | Stuelpnagel et al. |
| 2002/0058332 A1 | 5/2002 | Quake et al. |
| 2002/0092767 A1 | 7/2002 | Bjornson et al. |
| 2002/0119455 A1 | 8/2002 | Chan |
| 2002/0127736 A1 | 9/2002 | Chou et al. |
| 2003/0036206 A1 | 2/2003 | Chien et al. |
| 2003/0075446 A1 | 4/2003 | Culbertson et al. |
| 2003/0124509 A1 | 7/2003 | Kenis et al. |
| 2003/0215862 A1 | 11/2003 | Parce et al. |
| 2004/0068019 A1 | 4/2004 | Higuchi et al. |
| 2005/0130188 A1 | 6/2005 | Walt et al. |
| 2005/0250147 A1 | 11/2005 | Macevicz |
| 2005/0266582 A1 | 12/2005 | Modlin et al. |
| 2005/0287572 A1 | 12/2005 | Mathies et al. |
| 2006/0177832 A1 | 8/2006 | Brenner |
| 2006/0275782 A1 | 12/2006 | Gunderson et al. |
| 2007/0020640 A1 | 1/2007 | McCloskey et al. |
| 2007/0042419 A1 | 2/2007 | Barany et al. |
| 2007/0172873 A1 | 7/2007 | Brenner et al. |
| 2007/0190543 A1 | 8/2007 | Livak |
| 2007/0196397 A1 | 8/2007 | Torii et al. |
| 2007/0264320 A1 | 11/2007 | Lee et al. |
| 2008/0056948 A1 | 3/2008 | Dale et al. |
| 2008/0166720 A1 | 7/2008 | Hsieh et al. |
| 2008/0242560 A1 | 10/2008 | Gunderson et al. |
| 2009/0011943 A1 | 1/2009 | Drmanac et al. |
| 2009/0047713 A1 | 2/2009 | Handique |
| 2009/0099041 A1 | 4/2009 | Church et al. |
| 2009/0131543 A1 | 5/2009 | Weitz et al. |
| 2009/0148961 A1 | 6/2009 | Luchini et al. |
| 2009/0155563 A1 | 6/2009 | Petsev et al. |
| 2009/0202984 A1 | 8/2009 | Cantor |
| 2009/0235990 A1 | 9/2009 | Beer |
| 2009/0269248 A1 | 10/2009 | Falb et al. |
| 2009/0286687 A1 | 11/2009 | Dressman et al. |
| 2010/0035254 A1 | 2/2010 | Williams |
| 2010/0069263 A1 | 3/2010 | Shendure et al. |
| 2010/0086914 A1 | 4/2010 | Bentley et al. |
| 2010/0105866 A1 | 4/2010 | Fraden et al. |
| 2010/0184928 A1 | 7/2010 | Kumacheva |
| 2010/0216153 A1 | 8/2010 | Lapidus et al. |
| 2010/0248991 A1 | 9/2010 | Roesler et al. |
| 2010/0304982 A1 | 12/2010 | Hinz et al. |
| 2011/0217736 A1 | 9/2011 | Hindson |
| 2011/0305761 A1 | 12/2011 | Shum et al. |
| 2012/0071331 A1 | 3/2012 | Casbon et al. |
| 2012/0172259 A1 | 7/2012 | Rigatti et al. |
| 2012/0190032 A1 | 7/2012 | Ness et al. |
| 2012/0196288 A1 | 8/2012 | Beer |
| 2012/0219947 A1 | 8/2012 | Yurkovetsky et al. |
| 2013/0028812 A1 | 1/2013 | Prieto et al. |
| 2013/0109575 A1 | 5/2013 | Kleinschmidt et al. |
| 2013/0261196 A1 | 10/2013 | Diamond et al. |
| 2014/0065234 A1 | 3/2014 | Shum et al. |
| 2014/0221239 A1 | 8/2014 | Carman et al. |
| 2014/0272996 A1 | 9/2014 | Bemis |
| 2014/0274740 A1 | 9/2014 | Srinivasan et al. |
| 2014/0302503 A1 | 10/2014 | Lowe et al. |
| 2014/0315725 A1 | 10/2014 | Faham et al. |
| 2014/0338753 A1 | 11/2014 | Sperling et al. |
| 2015/0066385 A1 | 3/2015 | Schnall-Levin et al. |
| 2015/0220532 A1 | 8/2015 | Wong |
| 2015/0267191 A1 | 9/2015 | Steelman et al. |
| 2015/0329617 A1 | 11/2015 | Winther et al. |
| 2015/0361418 A1 | 12/2015 | Reed |
| 2015/0376605 A1 | 12/2015 | Jarosz et al. |
| 2015/0376608 A1 | 12/2015 | Kaper et al. |
| 2015/0376609 A1 | 12/2015 | Hindson et al. |
| 2015/0376700 A1 | 12/2015 | Schnall-Levin et al. |
| 2015/0379196 A1 | 12/2015 | Schnall-Levin et al. |
| 2016/0008778 A1 | 1/2016 | Weitz et al. |
| 2016/0024493 A1 | 1/2016 | Robins |
| 2016/0024558 A1 | 1/2016 | Hardenbol et al. |
| 2016/0024572 A1 | 1/2016 | Shishkin et al. |
| 2016/0025726 A1 | 1/2016 | Altin et al. |
| 2016/0053253 A1 | 2/2016 | Salathia et al. |
| 2016/0059204 A1 | 3/2016 | Hindson et al. |
| 2016/0060621 A1 | 3/2016 | Agresti et al. |
| 2016/0122753 A1 | 5/2016 | Mikkelsen et al. |
| 2016/0122817 A1 | 5/2016 | Jarosz et al. |
| 2016/0203196 A1 | 7/2016 | Schnall-Levin et al. |
| 2016/0232291 A1 | 8/2016 | Kyriazopoulou-Panagiotopoulou et al. |
| 2016/0244809 A1 | 8/2016 | Belgrader et al. |
| 2016/0257993 A1 | 9/2016 | Fu et al. |
| 2016/0281160 A1 | 9/2016 | Jarosz et al. |
| 2016/0289769 A1 | 10/2016 | Schwartz et al. |
| 2016/0304956 A1 | 10/2016 | Robins |
| 2016/0314242 A1 | 10/2016 | Schnall-Levin et al. |
| 2016/0348093 A1 | 12/2016 | Price et al. |
| 2017/0016041 A1 | 1/2017 | Greenfield et al. |
| 2017/0128937 A1 | 5/2017 | Hung et al. |
| 2017/0144161 A1 | 5/2017 | Hindson et al. |
| 2017/0145476 A1 | 5/2017 | Ryvkin et al. |
| 2017/0159109 A1 | 6/2017 | Zheng et al. |
| 2017/0192013 A1 | 7/2017 | Agresti |
| 2017/0235876 A1 | 8/2017 | Jaffe et al. |
| 2017/0260584 A1 | 9/2017 | Zheng et al. |
| 2017/0268056 A1 | 9/2017 | Vigneault et al. |
| 2018/0016634 A1 | 1/2018 | Hindson et al. |
| 2018/0030515 A1 | 2/2018 | Regev et al. |
| 2018/0071695 A1 | 3/2018 | Weitz et al. |
| 2018/0080075 A1 | 3/2018 | Brenner et al. |
| 2018/0080078 A1 | 3/2018 | Robins et al. |
| 2018/0105808 A1 | 4/2018 | Mikkelsen et al. |
| 2018/0112212 A1 | 4/2018 | Nicol et al. |
| 2018/0180601 A1 | 6/2018 | Pedersen et al. |
| 2018/0216162 A1 | 8/2018 | Belhocine et al. |
| 2018/0312822 A1 | 11/2018 | Lee et al. |
| 2018/0312873 A1 | 11/2018 | Zheng |
| 2018/0334670 A1 | 11/2018 | Bharadwaj et al. |
| 2018/0340169 A1 | 11/2018 | Belhocine et al. |
| 2018/0371545 A1 | 12/2018 | Wong et al. |
| 2019/0060890 A1 | 2/2019 | Bharadwaj et al. |
| 2019/0060904 A1 | 2/2019 | Bharadwaj et al. |
| 2019/0060905 A1 | 2/2019 | Bharadwaj et al. |
| 2019/0064173 A1 | 2/2019 | Bharadwaj et al. |
| 2019/0071656 A1 | 3/2019 | Chang et al. |
| 2019/0085391 A1 | 3/2019 | Hindson et al. |
| 2019/0100632 A1 | 4/2019 | Delaney et al. |
| 2019/0127731 A1 | 5/2019 | McDermott |
| 2019/0134633 A1 | 5/2019 | Bharadwaj et al. |
| 2019/0136316 A1 | 5/2019 | Hindson et al. |
| 2019/0145982 A1 | 5/2019 | Chee et al. |
| 2019/0153532 A1 | 5/2019 | Bharadwaj et al. |
| 2019/0176152 A1 | 6/2019 | Bharadwaj et al. |
| 2019/0177800 A1 | 6/2019 | Boutet et al. |
| 2019/0249226 A1 | 8/2019 | Bent et al. |
| 2019/0323088 A1 | 10/2019 | Boutet et al. |
| 2019/0345636 A1 | 11/2019 | McDermott et al. |
| 2019/0352717 A1 | 11/2019 | Schnall-Levin |

(56) References Cited

U.S. PATENT DOCUMENTS

| | | |
|---|---|---|
| 2019/0367997 A1 | 12/2019 | Bent et al. |
| 2019/0376118 A1 | 12/2019 | Belhocine et al. |
| 2020/0002763 A1 | 1/2020 | Belgrader et al. |
| 2020/0005902 A1 | 1/2020 | Mellen et al. |
| 2020/0032335 A1 | 1/2020 | Martinez |
| 2020/0033237 A1 | 1/2020 | Hindson et al. |
| 2020/0033366 A1 | 1/2020 | Alvarado Martinez |
| 2020/0105373 A1 | 4/2020 | Zheng |
| 2020/0291454 A1 | 9/2020 | Belhocine et al. |
| 2020/0407775 A1 | 12/2020 | Bharadwaj et al. |

FOREIGN PATENT DOCUMENTS

| | | |
|---|---|---|
| EP | 1923471 A1 | 5/2008 |
| EP | 1967592 B1 | 4/2010 |
| EP | 2540389 A1 | 1/2013 |
| EP | 2635679 B1 | 4/2017 |
| GB | 2097692 A | 11/1982 |
| GB | 2097692 B | 5/1985 |
| WO | WO-84/02000 | 5/1984 |
| WO | WO-8402000 A1 | 5/1984 |
| WO | WO-9301498 A1 | 1/1993 |
| WO | WO-95/30782 | 11/1995 |
| WO | WO-9530782 A1 | 11/1995 |
| WO | WO-9942597 A1 | 8/1999 |
| WO | WO-99/52708 | 10/1999 |
| WO | WO-9952708 A1 | 10/1999 |
| WO | WO-0008212 A1 | 2/2000 |
| WO | WO-2000008212 A1 | 2/2000 |
| WO | WO-0102850 A1 | 1/2001 |
| WO | WO-2001002850 A1 | 1/2001 |
| WO | WO-0114589 A2 | 3/2001 |
| WO | WO-0189787 A2 | 11/2001 |
| WO | WO-0190418 A1 | 11/2001 |
| WO | WO-02072631 A2 | 9/2002 |
| WO | WO-2004002627 A2 | 1/2004 |
| WO | WO-2004065617 A2 | 8/2004 |
| WO | WO-2004069849 A2 | 8/2004 |
| WO | WO-2004091763 A2 | 10/2004 |
| WO | WO-2005003394 A2 | 1/2005 |
| WO | WO-2005021151 A1 | 3/2005 |
| WO | WO-2005049787 A9 | 6/2005 |
| WO | WO-2005082098 A2 | 9/2005 |
| WO | WO-2006040551 A2 | 4/2006 |
| WO | WO-2006078841 A1 | 7/2006 |
| WO | WO-2006096571 A2 | 9/2006 |
| WO | WO-2007081385 A2 | 7/2007 |
| WO | WO-2007081387 A1 | 7/2007 |
| WO | WO-2007089541 A2 | 8/2007 |
| WO | WO-2007133710 A2 | 11/2007 |
| WO | WO-2007140015 A2 | 12/2007 |
| WO | WO-2007147079 A2 | 12/2007 |
| WO | WO-2008021123 A1 | 2/2008 |
| WO | WO-2008109176 A2 | 9/2008 |
| WO | WO-2008121342 A2 | 10/2008 |
| WO | WO-2008134153 A1 | 11/2008 |
| WO | WO-2008150432 A1 | 12/2008 |
| WO | WO-2009011808 A1 | 1/2009 |
| WO | WO-2009015296 A1 | 1/2009 |
| WO | WO-2009085215 A1 | 7/2009 |
| WO | WO-2009152928 A2 | 12/2009 |
| WO | WO-2010009735 A2 | 1/2010 |
| WO | WO-2010033200 A2 | 3/2010 |
| WO | WO-2010104604 A1 | 9/2010 |
| WO | WO-2010117620 A2 | 10/2010 |
| WO | WO-2010148039 A2 | 12/2010 |
| WO | WO-2011028539 A1 | 3/2011 |
| WO | WO-2011047870 A1 | 4/2011 |
| WO | WO-2011056546 A1 | 5/2011 |
| WO | WO-2011066476 A1 | 6/2011 |
| WO | WO-2012048340 A2 | 4/2012 |
| WO | WO-2012048341 A1 | 4/2012 |
| WO | WO-2012061832 A1 | 5/2012 |
| WO | WO-2012083225 A2 | 6/2012 |
| WO | WO-2012083225 A3 | 8/2012 |
| WO | WO-2012106546 A2 | 8/2012 |
| WO | WO-2012112804 A1 | 8/2012 |
| WO | WO-2012112970 A2 | 8/2012 |
| WO | WO-2012116331 A2 | 8/2012 |
| WO | WO-2012142531 A2 | 10/2012 |
| WO | WO-2012142611 A2 | 10/2012 |
| WO | WO-2012149042 A2 | 11/2012 |
| WO | WO-2012166425 A2 | 12/2012 |
| WO | WO-2012167142 A2 | 12/2012 |
| WO | WO-2013019751 A1 | 2/2013 |
| WO | WO-2013036929 A1 | 3/2013 |
| WO | WO-2013055955 A1 | 4/2013 |
| WO | WO-2013096643 A1 | 6/2013 |
| WO | WO-2013126741 A1 | 8/2013 |
| WO | WO-2013188872 A1 | 12/2013 |
| WO | WO-2014028378 A2 | 2/2014 |
| WO | WO-2014108810 A2 | 7/2014 |
| WO | WO-2014144495 A1 | 9/2014 |
| WO | WO-2014165559 A2 | 10/2014 |
| WO | WO-2015015199 A2 | 2/2015 |
| WO | WO-2015044428 A1 | 4/2015 |
| WO | WO-2015095226 A2 | 6/2015 |
| WO | WO-2015164212 A1 | 10/2015 |
| WO | WO-2015185067 A1 | 12/2015 |
| WO | WO-2015188839 A2 | 12/2015 |
| WO | WO-2016040476 A1 | 3/2016 |
| WO | WO-2016061517 A2 | 4/2016 |
| WO | WO-2016126871 A2 | 8/2016 |
| WO | WO-2016176322 A1 | 11/2016 |
| WO | WO-2017004153 A1 | 1/2017 |
| WO | WO-2017015075 A1 | 1/2017 |
| WO | WO-2017053902 A1 | 3/2017 |
| WO | WO-2017053903 A1 | 3/2017 |
| WO | WO-2017053905 A1 | 3/2017 |
| WO | WO-2017171985 A1 | 10/2017 |
| WO | WO-2017197343 A2 | 11/2017 |
| WO | WO-2018057051 A1 | 3/2018 |
| WO | WO-2018039338 A1 | 3/2018 |
| WO | WO-2018064640 A1 | 4/2018 |
| WO | WO-2018119301 A1 | 6/2018 |
| WO | WO-2018119447 A2 | 6/2018 |
| WO | WO-2018132635 A1 | 7/2018 |
| WO | WO-2018132635 A9 | 9/2018 |
| WO | WO-2018172726 A1 | 9/2018 |
| WO | WO-2018191701 A1 | 10/2018 |
| WO | WO-2018213643 A1 | 11/2018 |
| WO | WO-2018226546 A1 | 12/2018 |
| WO | WO-2018236615 A1 | 12/2018 |
| WO | WO-2019028166 A1 | 2/2019 |
| WO | WO-2019040637 A1 | 2/2019 |
| WO | WO-2019083852 A1 | 5/2019 |
| WO | WO-2019084043 A1 | 5/2019 |
| WO | WO-2019084165 A1 | 5/2019 |
| WO | WO-2019108851 A1 | 6/2019 |
| WO | WO-2019113235 A1 | 6/2019 |
| WO | WO-2019118355 A1 | 6/2019 |
| WO | WO-2019126789 A1 | 6/2019 |
| WO | WO-2019157529 A1 | 8/2019 |
| WO | WO-2019148042 A1 | 8/2019 |
| WO | WO-2019152108 A1 | 8/2019 |
| WO | WO-2019165318 A1 | 8/2019 |
| WO | WO-2019169028 A1 | 9/2019 |
| WO | WO-2019169347 A1 | 9/2019 |
| WO | WO-2019191321 A1 | 10/2019 |
| WO | WO-2019217758 A1 | 11/2019 |
| WO | WO-2020028882 A1 | 2/2020 |
| WO | WO-2020041148 A1 | 2/2020 |
| WO | WO-2020142779 A1 | 7/2020 |
| WO | WO-2020167866 | 8/2020 |
| WO | WO-2020167862 A1 | 8/2020 |

OTHER PUBLICATIONS

Adamson et al., "Production of arrays of chemically distinct nanolitre plugs via repeated splitting in microfluidic devices", Lab Chip 6(9): 1178-1186 (Sep. 2006).

(56) References Cited

OTHER PUBLICATIONS

Agasti, S.S. et al. "Photocleavable DNA barcode-antibody conjugates allow sensitive and multiplexed protein analysis in single cell" J Am Chem Soc (2012) 134(45):18499-18502.

Amini, S. et al. "Haplotype-resolved whole-genome sequencing by contiguity-preserving transposition and combinatorial indexing" Nature Genetics (2014) 46:1343-1349 doi:10.1038/ng.3119.

Anna et al.: Formation of dispersions using "flow focusing" in microchannels: Applied Physics Letters, vol. 82, No. 3, pp. 364-366 (2003).

Bakker et al. Conditional MHC class I ligands and peptide exchange technology for the human MHC gene products HLA-A1, -A3, -A11, and -B7. Proc Natl Acad Sci U S A. Mar. 11, 2008;105(10):3825-30. doi: 10.1073/pnas.0709717105. Epub Feb. 28, 2008.

Baret, et al. Surfactants in droplet-based microfluidics. Lab Chip. Feb. 7, 2012;12(3):422-33. doi: 10.1039/c1lc20582j. Epub Oct. 20, 2011.

Beer et al., On-Chip, Real-Time, Single-Copy Polymerase Chain Reaction in Picoliter Droplets, Anal. Chem., 2007, v. 79, pp. 847-8475.

Bentzen, et al. Large-scale detection of antigen-specific T cells using peptide-MHC-I multimers labeled with DNA barcodes. Nat Biotechnol. Oct. 2016;34(10):1037-1045. doi: 10.1038/nbt.3662. Epub Aug. 29, 2016.

Braeckmans et al., Scanning the Code. Modern Drug Discovery. 2003:28-32.

Brenner, et al. "In vitro cloning of complex mixtures of DNA on microbeads: physical separation of differentially expressed cDNAs." Proc Natl Acad Sci U S A. Feb. 15, 2000;97(4):1665-70.

Briggs, et al. "Tumor-infiltrating immune repertoires captures by single-cell barcoding in emulsion" with Supplementary material. bioRxiv 134841; doi: https://doi.org/10.1101/134841. Posted May 5, 2017.

Buchman GW, et al. Selective RNA amplification: a novel method using dUMP-containing primers and uracil DNA glycosylase. PCR Methods Appl. Aug. 1993; 3(1):28-31.

Burns, et al. An Integrated Nanoliter DNA Analysis Device. Science. Oct. 16, 1998;282(5388):484-7.

Burns, et al. Microfabricated structures for integrated DNA analysis. Proc Natl Acad Sci U S A. May 28, 1996; 93(11): 5556-5561.

Burns, et al. The intensification of rapid reactions in multiphase systems using slug flow in capillaries. Lab Chip. Sep. 2001;1(1):10-5. Epub Aug. 9, 2001.

Chen, et al. Chemical transfection of cells in picoliter aqueous droplets in fluorocarbon oil. Anal Chem. Nov. 15, 2011;83(22):8816-20. doi: 10.1021/ac2022794. Epub Oct. 17, 2011.

Chien et al. "Multiport flow-control system for lab-on-a-chip microfluidic devices", Fresenius J. Anal Chem, 371:106-111 (Jul. 27, 2001).

Chokkalingam, et al. Probing cellular heterogeneity in cytokine-secreting immune cells using droplet-based microfluidics. Lab Chip. Dec. 21, 2013;13(24):4740-4. doi: 10.1039/c3lc50945a.

Chu, et al. Controllable monodisperse multiple emulsions. Angew Chem Int Ed Engl. 2007;46(47):8970-4.

Clausell-Tormos et al., "Droplet-based microfluidic platforms for the encapsulation and screening of mammalian cells and multicellular organisms", Chem. Biol. 15:427-437 (2008).

Co-pending PCT/US2019/046940, filed Aug. 16, 2019.
Co-pending U.S. Appl. No. 16/454,485, filed Jun. 27, 2019.
Co-pending U.S. Appl. No. 16/575,280, filed Sep. 18, 2019.
Co-pending U.S. Appl. No. 16/434,076, filed Jun. 6, 2019.
Co-pending U.S. Appl. No. 16/434,084, filed Jun. 6, 2019.
Co-pending U.S. Appl. No. 16/434,095, filed Jun. 6, 2019.
Co-pending U.S. Appl. No. 16/434,099, filed Jun. 6, 2019.
Co-pending U.S. Appl. No. 16/434,102, filed Jun. 6, 2019.
Co-pending U.S. Appl. No. 16/434,605, filed Jun. 7, 2019.
Co-pending U.S. Appl. No. 16/435,393, filed Jun. 7, 2019.
Co-pending U.S. Appl. No. 16/530,930, filed Aug. 2, 2019.

Dahotre et al. DNA-Barcoded pMHC Tetramers for Detection of Single Antigen-Specific T Cells by Digital PCR. Anal Chem. Feb. 19, 2019;91(4):2695-2700. doi: 10.1021/acs.analchem.8b04153. Epub Jan. 30, 2019.

Damean, et al. Simultaneous measurement of reactions in microdroplets filled by concentration gradients. Lab Chip. Jun. 21, 2009;9(12):1707-13. doi: 10.1039/b821021g. Epub Mar. 19, 2009.

Drmanac et al., Sequencing by hybridization (SBH): advantages, achievements, and opportunities. Adv Biochem Eng Biotechnol. 2002;77 :75-101.

Duffy, et al. Rapid Prototyping of Microfluidic Systems in Poly(dimethylsiloxane). Anal Chem. Dec. 1, 1998;70(23):4974-84. doi: 10.1021/ac980656z.

Eastburn, et al. Ultrahigh-throughput mammalian single-cell reverse-transcriptase polymerase chain reaction in microfluidic droplets. Anal Chem. Aug. 20, 2013;85(16):8016-21. doi: 10.1021/ac402057q. Epub Aug. 8, 2013.

Esser-Kahn, et al. Triggered release from polymer capsules. Macromolecules. 2011; 44:5539-5553.

Gee et al. Antigen Identification for Orphan T Cell Receptors Expressed on Tumor-Infiltrating Lymphocytes. Cell. Jan. 25, 2018;172(3):549-563.e16. doi: 10.1016/j.cell.2017.11.043. Epub Dec. 21, 2017.

Gericke, et al. Functional cellulose beads: preparation, characterization, and applications. Chemical reviews 113.7 (2013): 4812-4836.

Guo, et al. Droplet microfluidics for high-throughput biological assays. Lab Chip. Jun. 21, 2012;12(12):2146-55. doi: 10.1039/c2lc21147e. Epub Feb. 9, 2012.

Gyarmati, et al. Reversible disulphide formation in polymer networks: a versatile functional group from synthesis to applications. European Polymer Journal. 2013; 49:1268-1286.

Han et al. Linking T-cell receptor sequence to functional phenotype at the single-cell level. Nat Biotechnol 32(7):684-692 (2014).

Hashimshony, et al. CEL-Seq: Single-Cell RNA-Seq by Multiplexed Linear Amplification. Cell Rep. Sep. 27, 2012;2(3):666-73. doi: 10.1016/j.celrep.2012.08.003. Epub Aug. 30, 2012.

Holtze, et al. Biocompatible surfactants for water-in-fluorocarbon emulsions. Lab Chip. Oct. 2008;8(10):1632-9. doi: 10.1039/b806706f. Epub Sep. 2, 2008.

Hug, et al. Measurement of the number of molecules of a single mRNA species in a complex mRNA preparation. J Theor Biol. Apr. 21, 2003;221(4):615-24.

Islam, et al. Highly multiplexed and strand-specific single-cell RNA 5' end sequencing. Nat Protoc. Apr. 5, 2012;7(5):813-28. doi: 10.1038/nprot.2012.022.

Jaitin, et al. Massively parallel single-cell RNA-seq for marker-free decomposition of tissues into cell types. Science. Feb. 14, 2014;343(6172):776-9. doi: 10.1126/science.1247651.

Jarosz, M. et al. "Using 1ng of DNA to detect haplotype phasing and gene fusions from whole exome sequencing of cancer cell lines" Cancer Res (2015) 75(suppl5):4742.

Kaper, et al. Supporting Information for "Whole-genome haplotyping by dilution, amplification, and sequencing." Proc Natl Acad Sci U S A. Apr. 2, 2013;110(14):5552-7. doi: 10.1073/pnas.1218696110. Epub Mar. 18, 2013.

Kaper, et al. Whole-genome haplotyping by dilution, amplification, and sequencing. Proc Natl Acad Sci U S A. Apr. 2, 2013;110(14):5552-7. doi: 10.1073/pnas.1218696110. Epub Mar. 18, 2013.

Kenis, et al. Microfabrication Inside Capillaries Using Multiphase Laminar Flow Patterning. Science. 1999; 285:83-85.

Kivioja, et al. Counting absolute numbers of molecules using unique molecular identifiers. Nat Methods. Nov. 20, 2011;9(1):72-4.

Klein, et al. Droplet barcoding for single-cell transcriptomics applied to embryonic stem cells. Cell. May 21, 2015; 161:1187-1201.

Kondo et al. Yeast cell-surface display—applications of molecular display. Appl Microbiol Biotechnol. Mar. 2004;64(1):28-40. Epub Jan. 10, 2004.

Korlach et al., Methods in Enzymology, Real-Time DNA Sequencing from Single Polymerase Molecules, (2010) 472:431-455.

Koster et al., "Drop-based microfluidic devices for encapsulation of single cells", Lab on a Chip the Royal Soc. of Chern. 8: 1110-1115 (2008).

(56) References Cited

OTHER PUBLICATIONS

Lagally, et al. Single-Molecule DNA Amplification and Analysis in an Integrated Microfluidic Device. Analytical Chemistry. 2001;73(3): 565-570.
Lennon et al. A scalable, fully automated process for construction of sequence-ready barcoded libraries for 454. Genome Biology 11:R15 (2010).
Macosko, et al. Highly Parallel Genome-wide Expression Profiling of Individual Cells Using Nanoliter Droplets. Cell. May 21, 2015;161(5):1202-14. doi: 10.1016/j.cell.2015.05.002.
Madl, et al. "Bioorthogonal Strategies for Engineering Extracellular matrices", Madal, Chritopher, Adv. Funct. Master. Jan. 19, 2018, vol. 28, 1706046, pp. 1-21.
Mair, et al. Injection molded microfluidic chips featuring integrated interconnects. Lab Chip. Oct. 2006;6(10):1346-54. Epub Jul. 31, 2006.
Mcshan et al. Peptide exchange on MHC-I by TAPBPR is driven by a negative allostery release cycle. Nat Chem Biol. Aug. 2018;14(8):811-820. doi: 10.1038/s41589-018-0096-2. Epub Jul. 9, 2018.
Microfluidic ChipShop. Microfluidic product catalogue. Oct 2009.
Morozov et al. Interaction of TAPBPR, a tapasin homolog, with MHC-I molecules promotes peptide editing. Proc Natl Acad Sci U S A. Feb. 23, 2016;113(8):E1006-15. doi: 10.1073/pnas. 1519894113. Epub Feb. 11, 2016.
Navin. The first five years of single-cell cancer genomics and beyond. Genome Res. Oct. 2015;25(10):1499-507. doi: 10.1101/gr. 191098.115.
Neal et al. The Basics of Artificial Antigen Presenting Cells in T Cell-Based Cancer Immunotherapies. J Immunol Res Ther. 2017;2(1):68-79. Epub Jun. 26, 2017.
Nisisako, et al. Droplet formation in a microchannel network. Lab Chip. Feb. 2002;2(1):24-6. Epub Jan. 18, 2002.
Nisisako, T. et al. "Droplet Formation in a Microchannel on PMMA Plate" Abstract. 2001 Kluwer Academic Publishers. p. 137-138.
Nisisako, T. et al., Microfluidics large-scale integration on a chip for mass production of monodisperse droplets and particles, The Royal Society of Chemistry: Lab Chip, (Nov. 23, 2007) 8:287-293.
Novak, et al. Single cell multiplex gene detection and sequencing using microfluidicallygenerated agarose emulsions. Angew Chem Int Ed Engl. Jan. 10, 2011;50(2):390-5. doi: 10.1002/anie. 201006089.
Omidfar et al. Advances in phage display technology for drug discovery. Expert Opin Drug Discov. Jun. 2015;10(6):651-69. doi: 10.1517/17460441.2015.1037738. Epub Apr. 24, 2015.
Orakdogen, N. "Novel responsive poly(N,N-dimethylaminoethyl methacrylate) gel beads: preparation, mechanical properties and pH-dependent swelling behavior" J Polym Res (2012) 19:9914.
Perrott, Jimmy. Optimization and Improvement of Emulsion PCR for the Ion Torrent Next-Generation Sequencing Platform. (2011) Thesis.
Peters, B.A. et al. Accurate whole-genome sequencing and haplotyping from 10 to 20 human cells. Nature, 487(7406):190-195 (Jul. 11, 2012).
Plunkett, et al. Chymotrypsin responsive hydrogel: application of a disulfide exchange protocol for the preparation of methacrylamide containing peptides. Biomacromolecules. Mar.-Apr. 2005;6(2):632-7.
Priest, et al. Generation of Monodisperse Gel Emulsions in a Microfluidic Device, Applied Physics Letters, 88:024106 (2006).
Pushkarev et al. "Single-molecule sequencing of an individual human genome," Nature Biotech (2009) 17:847-850.
Ramsey, J.M. "The burgeoning power of the shrinking laboratory" Nature Biotech (1999) 17:1061-1062.
Ramskold et al. (2012) "Full-length mRNA-Seq from single-cell levels of RNA and individual circulating tumor cells" Nature Biotechnology 30(8):777-782.
Roche. Using Multiplex Identifier (MID) Adaptors for the GS FLX Titanium Chemistry Basic Mid Set Genome Sequencer FLX System, Technical Bulletin 004-2009, (Apr. 1, 2009) pp. 1-7. URL:http://454.com/downloads/my454/documentation/technical-bulletins/TCB-09004 Using MultiplexIdentifierAdaptorsForTheGSFLXTitaniumSeriesChemistry-BasicMIDSet.pdf.
Rotem, et al. High-Throughput Single-Cell Labeling (Hi-SCL) for RNA-Seq Using Drop-Based Microfluidics. PLoS One. May 22, 2015;10(5):e0116328. doi: 10.1371/journal.pone.0116328. eCollection 2015.
Saikia, et al. Simultaneous multiplexed amplicon sequencing and transcriptome profiling in single cells. Nat Methods. Jan. 2019;16(1):59-62. doi: 10.1038/s41592-018-0259-9. Epub Dec. 17, 2018.
Schubert, et al. Microemulsifying fluorinated oils with mixtures of fluorinated and hydrogenated surfactants. Colloids and Surfaces A; Physicochemical and Engineering Aspects, 84(1994) 97-106.
Segaliny et al. Functional TCR T cell screening using single-cell droplet microfluidics. Lab Chip. Dec. 4, 2018;18(24):3733-3749. doi: 10.1039/c8lc00818c.
Seiffert, et al. Microfluidic fabrication of smart microgels from macromolecular precursors.Polymer. vol. 51, Issue 25, Nov. 26, 2010, pp. 5883-5889.
Seiffert, et al. Smart microgel capsules from macromolecular precursors. J Am Chem Soc. May 12, 2010;132(18):6606-9. doi: 10.1021/ja102156h.
Shah, "Fabrication of mono disperse thermosensitive microgels and gel capsules in micro fluidic devices", Soft Matter, 4:2303-2309 (2008).
Shendure, et al., Accurate Multiplex Polony Sequencing of an Evolved Bacterial Genome. Science 309.5741 (Sep. 2005): 1728-1732. XP002427180, ISSN: 0036-8075, DOI: 10.1126/SCIENCE. 1117839.
Smith, et al. Highly-multiplexed barcode sequencing: an efficient method for parallel analysis of pooled samples. Nucleic Acids Research, 38(13): e142 (2010).
Song, et al. Reactions in droplets in microfluidic channels. Angew Chem Int Ed Engl. Nov. 13, 2006;45(44):7336-56.
Thaxton, C.S. et al. "A Bio-Bar-Code Assay Based Upon Dithiothreitol Oligonucleotide Release" Anal Chem (2005) 77:8174-8178.
Theberge, et al. Microdroplets in microfluidics: an evolving platform for discoveries in chemistry and biology. Angew Chem Int Ed Engl. Aug. 9, 2010;49(34):5846-68. doi: 10.1002/anie.200906653.
Thorsen, et al. Dynamic pattern formation in a vesicle-generating microfluidic device. Physical Review Letters. American Physical Society. 2001; 86(18):4163-4166.
Toebes et al. Design and use of conditional MHC class I ligands. Nat Med. Feb. 2006;12(2):246-51. Epub Feb. 5, 2006.
Toebes et al. Generation of peptide MHC class I monomers and multimers through ligand exchange. Curr Protoc Immunol. Nov. 2009;Chapter 18:Unit 18.16. doi: 10.1002/0471142735.im1816s87.
Tonelli, et al. Perfluoropolyether functional oligomers: unusual reactivity in organic chemistry. Journal of fluorine chemistry. 2002; 118(1) 107-121.
Turchinovich, et al. "Capture and Amplification by Tailing and Switching (CATS): An Ultrasensitive Ligation-Independent Method for Generation of DNA Libraries for Deep Sequencing from Picogram Amounts of DNA and RNA." RNA Biology 11.7 (2014): 817-828. PMC. Web. Nov. 13, 2017.
Uttamapinant, et al. Fast, cell-compatible click chemistry with copper-chelating azides for biomolecular labeling.Angew. Chem. Int. End. Engl., Jun. 11, 2012: 51(24) pp. 5852-5856.
Vandormael et al. cDNA phage display for the discovery of theranostic autoantibodies in rheumatoid arthritis. Immunol Res. Feb. 2017;65(1):307-325. doi: 10.1007/s12026-016-8839-1. .
Wagner, et al. Biocompatible fluorinated polyglycerols for droplet microfluidics as an alternative to PEG-based copolymer surfactants. Lab Chip. Jan. 7, 2016;16(1):65-9. doi: 10.1039/c5lc00823a. Epub Dec. 2, 2015.
Weigl, et al. Microfluidic Diffusion-Based Separation and Detection. Science. 1999; pp. 346-347.
Williams, et al. Amplification of complex gene libraries by emulsion PCR. Nature Methods. 2006;3(7):545-50.
Wiseman, R.W. et al. "Major histocompatibility complex genotyping with massively parallel pyrosequencing" Nature Medicine (Oct. 11, 2009) 15(11):1322-1326.

(56) References Cited

OTHER PUBLICATIONS

Zhang et al. High-throughput determination of the antigen specificities of T cell receptors in single cells. Nat Biotechnol. Nov. 12, 2018. doi: 10.1038/nbt.4282. [Epub ahead of print].
Zhang, et al. One-step fabrication of supramolecular microcapsules from microfluidic droplets. Science. Feb.10, 2012;335(6069):690-4. doi: 10.1126/science.1215416.
Zheng, et al. Massively parallel digital transcriptional profiling of single cells. Nat Commun. Jan. 16, 2017;8:14049. doi: 10.1038/ncomms14049.
Zheng, X.Y. et al. "Haplotyping germline and cancer genomes with high-throughput linked-read sequencing" Nature Biotech (Feb. 1, 2016) 34(3):303-311.
Zhu, et al. Reverse transcriptase template switching: a SMART approach for full-length cDNA library construction. Biotechniques. Apr. 2001;30(4):892-7.
Amalie Kai Bentzen et al., "Large-scale detection of antigen-specific T cells using peptide-MHC-I multimers labeled with DNA barcodes", Nature Biotechnology, vo. 34, No. 10, Aug. 29, 2016 (Aug. 29, 2016), pp. 1037-1045.
Anonymous: "Assay Scheme and Configuration of Chromium (TM) Single Cell 3' v2 Libraries 1", 10X Genomics, Jul. 1, 2017 (Jul. 1, 2017).
Anonymous: "High Throughput Single Cell RNA-Seq Application Note Encapsulating single cells with barcoded beaded on the RNA-Seq chip Application Note Page", j Jul. 2017 (Jul. 1, 2017).
Cyrille L. Delley et al.., "Combined aptamer and transcriptome sequencing of single cells", bioRxiv, Dec. 3, 2017 (Dec. 3, 2017).
Evan Z. Macosko, et al., "Highly Parallel Genome-wide Expression Profiling of Individual Cells Using Nanoliter Droplets", CELL, vol. 161, No. 5, May 1, 2015 (May 1, 2015), pp. 1202-1214.
International Search Report and Written Opinion dated Jul. 17, 2019 for Corresponding International Patent Application No. PCT/US2019/017723.
Payam Shah et al., "Abseq: Ultrahigh-throughput single cell protein profiling with droplet microfluidic barcoding"., Scientific Reports, vol. 7, No. 1, Mar. 14, 2017 (Mar. 14, 2017).
Rapolas Zilionis et al., "Single-cell barcoding and sequencing using droplet microfluidics", Nature Protocols, vol. 12, No. 1, Dec. 8, 2016 (Dec. 8, 2016), pp. 44-73.
Songming Pent et al., "Sensitive, non-destructive detection and analysis of neoantigen-specific T cell populations from tumors and blood", Jul. 25, 2017 (Jul. 25, 2017).
Vanessa M. Peterson et al., "Multiplexed quantification of proteins and transcripts in single cells", Nature Biotechnology, vol. 35, No. 10, Aug. 30, 2017, (Aug. 30, 2017) , pp. 936-939.
10X Genomics, Inc. CG000153 Rev A. Chromium Single Cell DNA Reagent Kits User Guide. 2018.
10X Genomics, Inc. CG000184 Rev A. Chromium Single Cell 3' Reagent Kits v3 User Guide with Feature Barcoding Technology for CRISPR Screening. 2018.
10X Genomics, Inc. CG000185 Rev B. Chromium Single Cell 3' Reagent Kits User Guide with Feature Barcoding Technology for Cell Surface Protein. 2018.
10X Genomics, Inc. CG000208 Rev E. Chromium Next GEM Single Cell V(D)J reagent Kits v1.1 User Guide with Feature Barcode Technology for Cell Surface Protein. 2020.
10X Genomics, Inc. CG000209 Rev D. Chromium Next GEM Single Cell ATAC Reagent Kits v1.1 User Guide. 2020.
10X Genomics, Inc. CG000239 Rev B. Visium Spatial Gene Expression Reagent Kits User Guide. 2020.
10X Genomics, Inc. CG00026. Chromium Single Cell 3' Reagent Kit User Guide. 2016.
10X Genomics, Inc. LIT00003 Rev B Chromium Genome Solution Application Note. 2017.

Baret, "Surfactants in droplet-based microfluidics" Lab Chip (12(3):422-433 (2012).
Beer et al. On-Chip, Real-Time, Single-Copy Polymerase Chain Reaction in Picoliter Droplets. Anal Chem 79:8471-8475 (2007).
Caruccio N., Preparation of Next-Generation Sequencing Libraries Using Nextera Technology: Simultaneous DNA Fragmentation and Adaptor Tagging by In Vitro Transposition. Ch. 17 Methods in Microbiology 733:241-55 (2011).
Co-pending U.S. Appl. No. 16/708,214, inventors Wheeler; Tobias Daniel et al., filed Dec. 9, 2019.
Co-pending U.S. Appl. No. 16/737,762, inventors Price; Andrew D et al., filed Jan. 8, 2020.
Co-pending U.S. Appl. No. 16/737,770, inventors Belhocine; Zahara Kamila et al., filed Jan. 8, 2020.
Co-pending U.S. Appl. No. 16/789,273, inventors Maheshwari; Arundhati Shamoni et al., filed Feb. 12, 2020.
Co-pending U.S. Appl. No. 16/800,450, inventor Katherine; Pfeiffer, filed Feb. 25, 2020.
Duffy et al., Rapid Protyping of Microfluidic Systems and Polydimethylsiloxane, Anal Chem 70:4974-4984 (1998).
Ghadessy, et al. Directed evolution of polymerase function by compartmentalized self-replication. Proc Natl Acad Sci USA. 2001 ;98:4552-4557.
Granieri, Lucia. Droplet-based microfluidics and engineering of tissue plasminogen activator for biomedical applications. Ph.D. Thesis, Nov. 13, 2009 (131 pages).
Lagally, et al. Single-Molecular DNA Amplification and Analysis in an Integrated Microfluidic Device. Anal Chem. Feb. 1, 2001 ;73(3):565-70.
Macosko, et al. Highly Parallel Genome-wide Expression Profiling of Individual Cells Using Nanoliter Droplets. Cell. May 2, 20151; 161 (5):1202-14. doi: 10.1016/j.cell.2015.05.002.
McCoy, R. et al. "Illumina TruSeq Synthetic Long-Reads Empower De Novo Assembly and Resolve Complex, Highly-Repetitive Transposable Elements" PLOS (2014) 9(9):e1016689.
McDaniel, et al. Ultra-high-throughput sequencing of the immune receptor repertoire from millions of lymphocytes.Nature protocols 11.3 (2016): 429-442.
Nijman, I.J. et al. "Mutation Discovery by Targeted Genomic Enrichment of Multiplexed Barcoded Samples" Nature Methods (2010) 7:913-915.
Novak, R. et al., "Single cell multiplex gene detection and sequencing using microfluidicallygenerated agarose emulsions" Angew. Chem. Int. Ed. Engl. (2011) 50(2):390-395.
Pan, et al. Combinatorial HLA-peptide bead libraries for high throughput identification of CD8$^+$T cell specificity. J Immunol Methods. Jan. 31, 2041 ;403(1-2):72-78. doi: 10.1016/j.jim.2013.11.023. Epub Dec. 3, 2013.
Rajan, et al. Recombinant Human B Cell Repertoires Enable Screening for Rare, Specific, and Natively Paired Antibodies. Commun Biol. Jan. 2, 2018;1:5. doi: 10.1038/S42003-017-0006-2.
Reuter, J.A. et al. "Simul-seq: combined DNA and RNA sequencing for whole-genome and transcriptome profiling" Nature Methods (2016) 13(11):953-958.
Rotem, A. et al., "High-throughput single-cell labeling (Hi-SCL) for RNA-Seq using drop-based microfluidics" PLOS One (May 22, 2015) 0116328 (14 pages).
Seiffert, S. et al., "Smart microgel capsules from macromolecular precursors" J. Am. Chem. Soc. (2010) 132:6606-6609.
Shah, et al. "Fabrication of mono disperse thermosensitive microgels and gel capsules in micro fluidic devices", Soft Matter, 4:2303-2309 (2008).
Tawfik, D.S., et al., "Man-made cell-like compartments for molecular evolution," Nature Biotechnology, vol. 16, pp. 652-656 (1998).
Zhu et al. Hydrogel Droplet Microfluidics for High-Throughput Single Molecule/Cell Analysis. Accounts of Chemical Research Article ASAP. DOI: 10.1021/acs.accounts.6b00370.

Alpha  CTACACGACGCTCTTCCGATCTXXXXXXXGTXXXXXXXXN$_{10}$T$_{30}$VN
GCGAGAAGGCTAGAXXXXXXXCAXXXXXXXX Beta   CTACACGACGCTCTTCCGATCTXXXXXXXCAXXXXXXXXN$_{10}$T$_{30}$VN
GCGAGAAGGCTAGAXXXXXXXGTXXXXXXXX Gamma  CTACACGACGCTCTTCCGATCTXXXXXXXAGXXXXXXXXN$_{10}$T$_{30}$VN
GCGAGAAGGCTAGAXXXXXXXTCXXXXXXXX Delta  CTACACGACGCTCTTCCGATCTXXXXXXXTCXXXXXXXXN$_{10}$T$_{30}$VN
GCGAGAAGGCTAGAXXXXXXXAGXXXXXXXX

FIG. 14B

Alpha
GTCAGATGTGTATAAGAGACAGXXXXXXXXGTXXXXXXXN₁₀GCTTCGTACGCGAAACTAGCGT
CACATATTCTCTGTCXXXXXXCAXXXXXXX

Beta
GTCAGATGTGTATAAGAGACAGXXXXXXXXGTXXXXXXXN₁₀GCTTCGTACGCGAAACTAGCGT
CACATATTCTCTGTCXXXXXXCAXXXXXXX

Gamma
GTCAGATGTGTATAAGAGACAGXXXXXXXXGTXXXXXXXN₁₀GCTTCGTACGCGAAACTAGCGT
CACATATTCTCTGTCXXXXXXCAXXXXXXX

Delta
GTCAGATGTGTATAAGAGACAGXXXXXXXXGTXXXXXXXN₁₀GCTTCGTACGCGAAACTAGCGT
CACATATTCTCTGTCXXXXXXCAXXXXXXX

*FIG. 14C*

Assay Primers:

Splint oligo(s):

polyA-XXX → X'X'X' Analyte 1 polyA-YYY → Y'Y'Y' Analyte 2 polyA-ZZZ → Z'Z'Z' Analyte 3

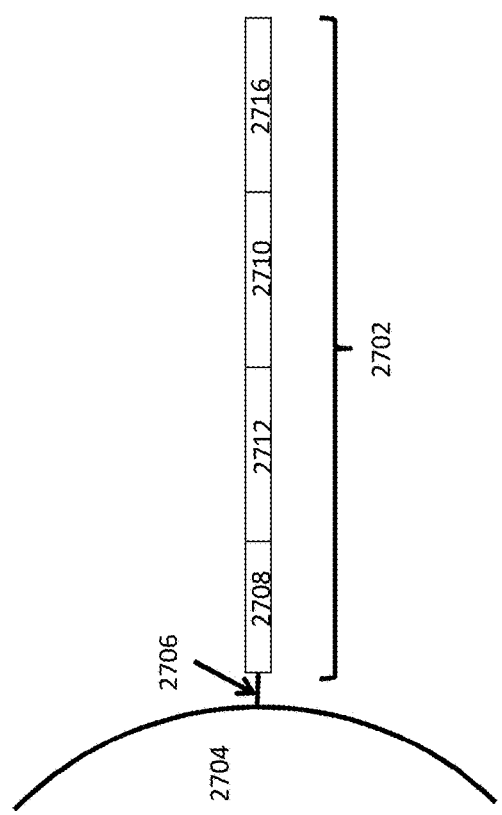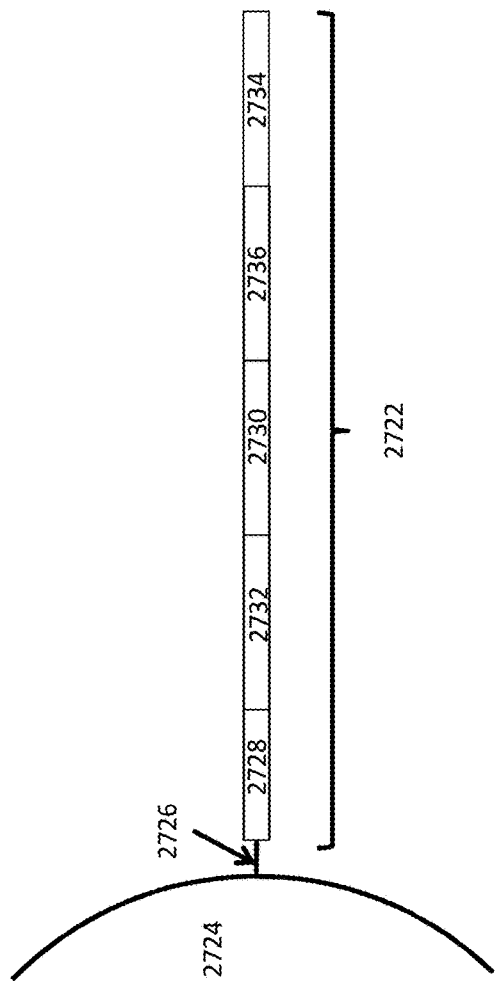

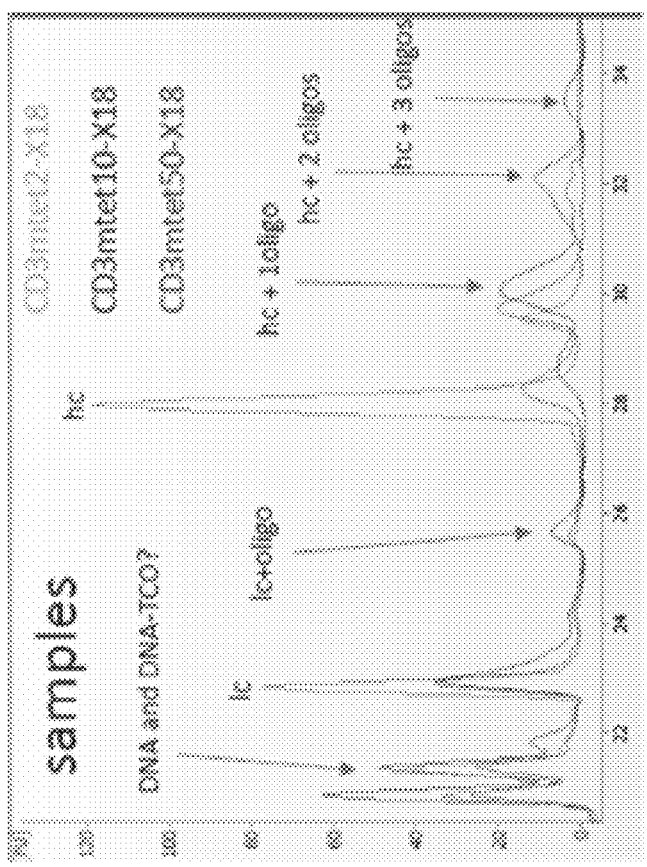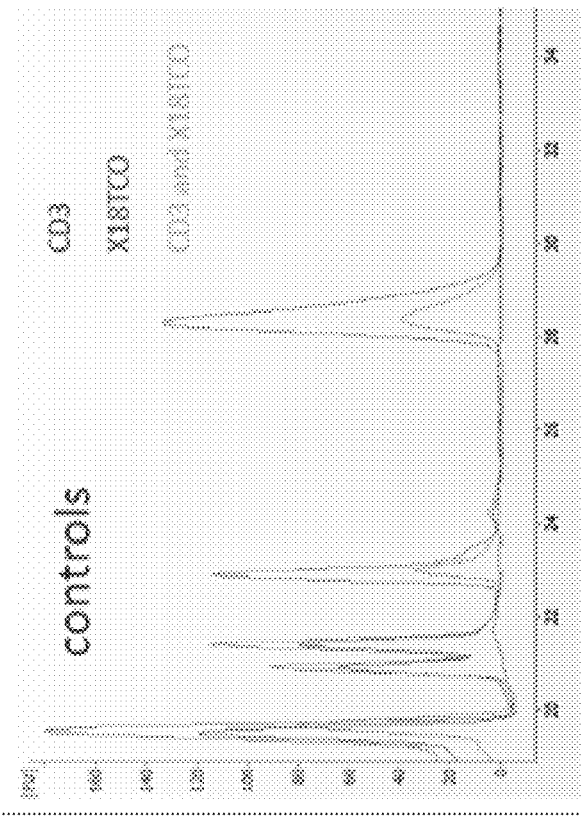
FIG. 31

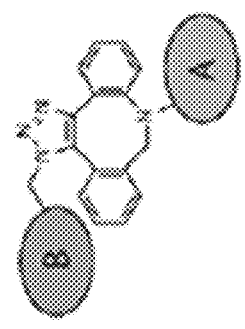
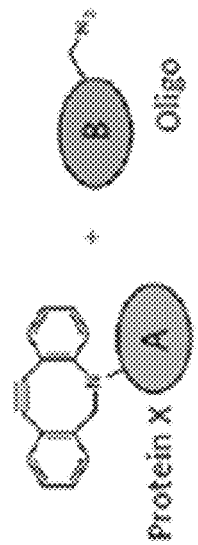
*FIG. 34A*
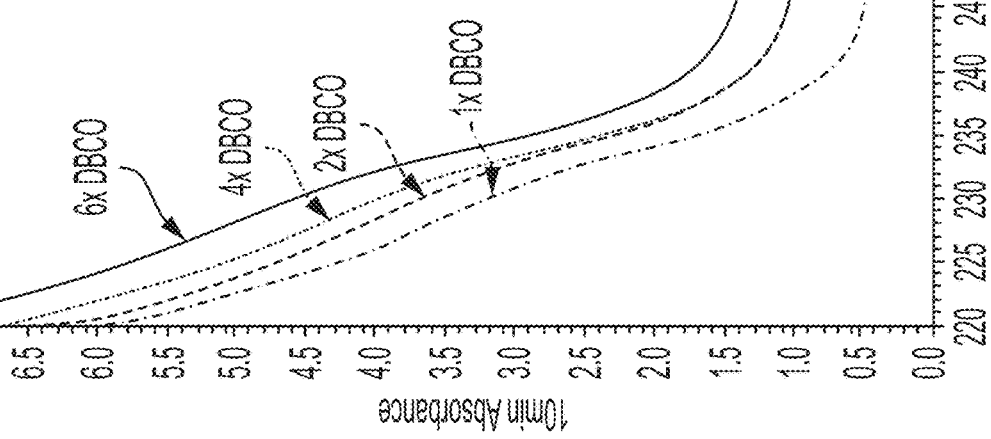
*FIG. 34B*

| MW (kDa) | Protein G | Relative Band % (Coomassie gel) | | | | | |
|---|---|---|---|---|---|---|---|
| | | 1x DBCO 1.5x oligo | 2X DBCO | | | 4x DBCO 1.5x oligo | 6x DBCO 1.5x oligo |
| | | | 1x oligo | 1.5x oligo | 2x oligo | | |
| 155.6 | | | | | | | 7.0 |
| 117.6 | | | | | | 4.6 | 20.1 |
| 85.0 | | | 2.8 | 4.6 | 6.9 | 20.3 | 21.2 |
| 70.0 | | | 1.6 | 2.9 | 4.0 | 7.7 | 5.4 |
| 58.2 | | 32.9 | 46.6 | 45.8 | 44.4 | 44.4 | 37.2 |
| 39.6 | 100 | 67.1 | 49.0 | 46.7 | 44.7 | 23.0 | 9.1 |

FIG. 36B

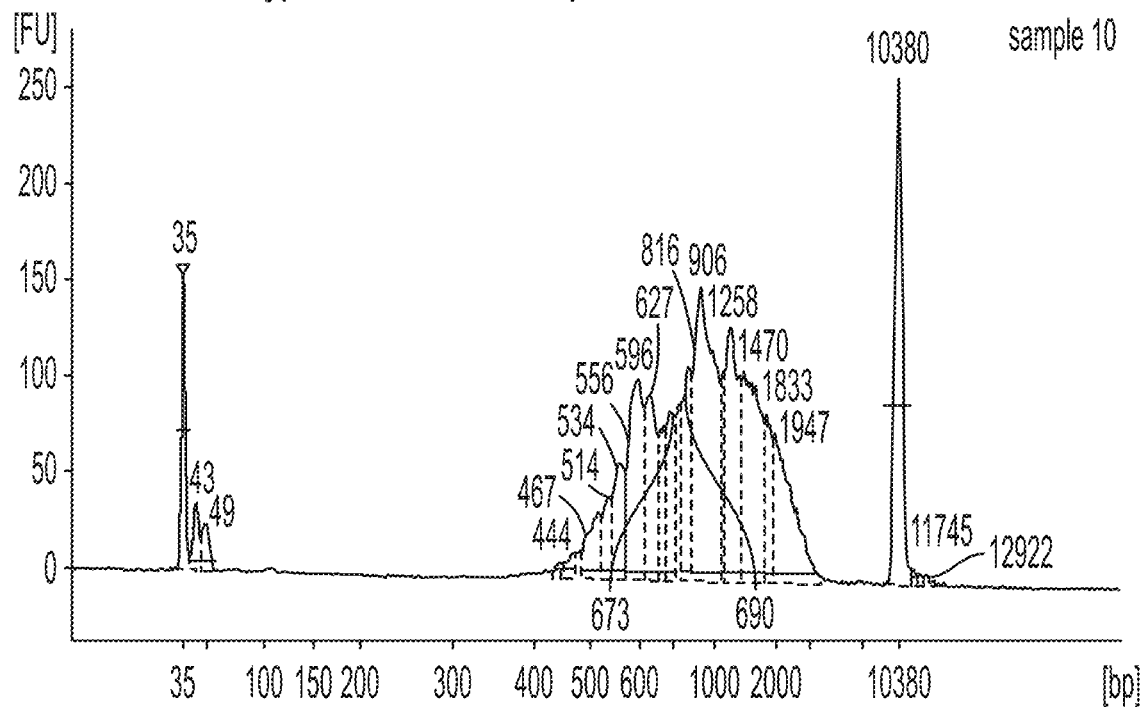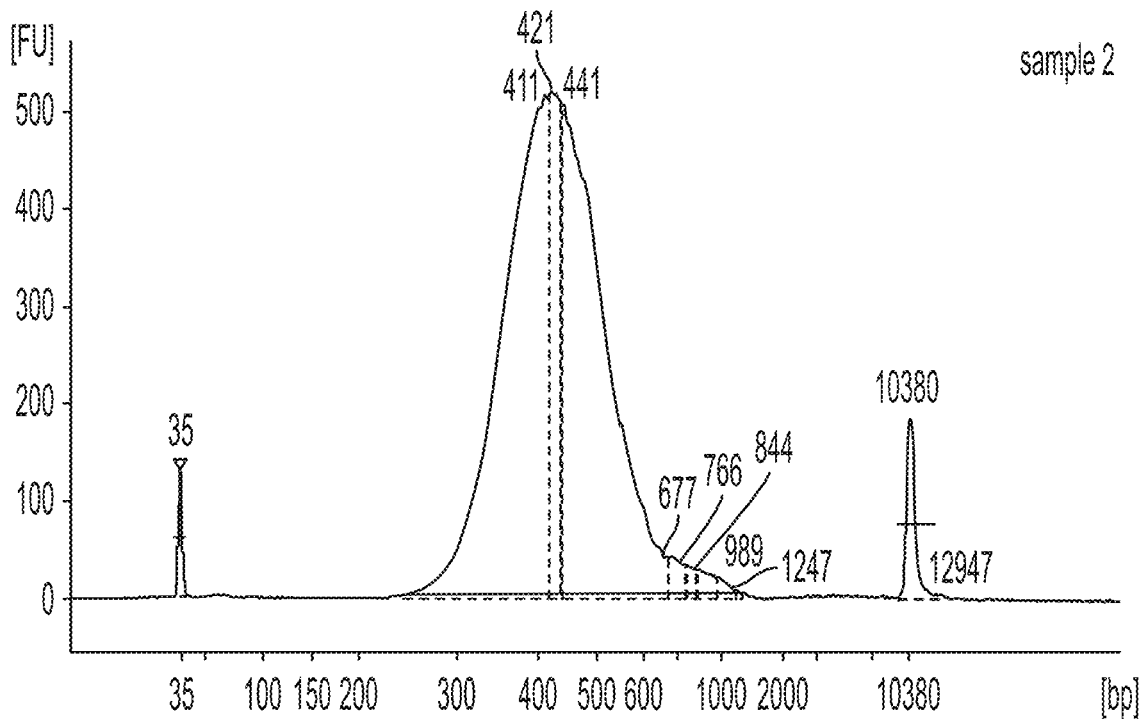
FIG. 38A

| Description | Correted Area | Product Peak Size (bp) |
|---|---|---|
| 293T Cells only | 11.0 | - |
| protG-1x DBCO-1.5x oligo + CD47Ab | 178.4 | 184 |
| protG-2x DBCO-2x oligo + CD47Ab | 120.5 | 184 |
| protG-4x DBCO-1.5x oligo + CD47Ab | 17.6 | 185 |
| protG-6x DBCO-1.5x oligo + CD47Ab | 32.4 | 184 |
| protG-TCO/mtet-10x oligo + CD47Ab | 45.6 | 183 |
| protG-oligo | 5.0 | - |

*FIG. 38C*

5' CTACACGACGCTCTTCCGATCTNNNNNNNNNNNNNNNNNNNNNNNNNNNNNNNNTTTCTTATATrGrGrG
3' AAAGAATATA C C CTAGACTGACGTGGAACCTGGCGATTTCAAC-FAM

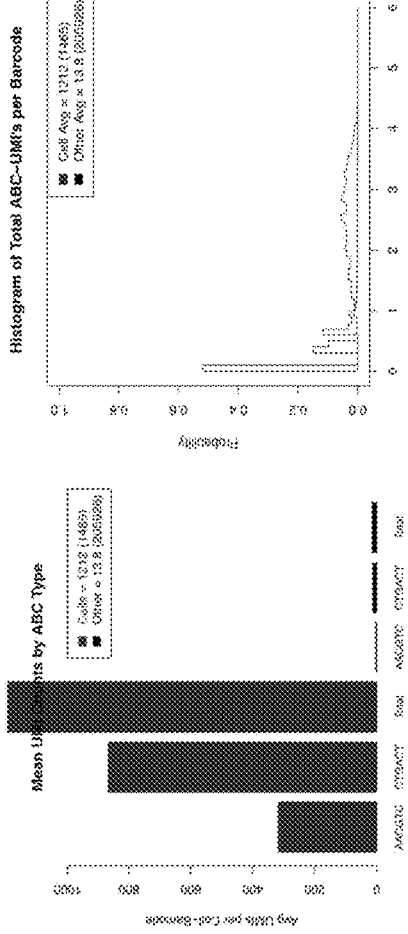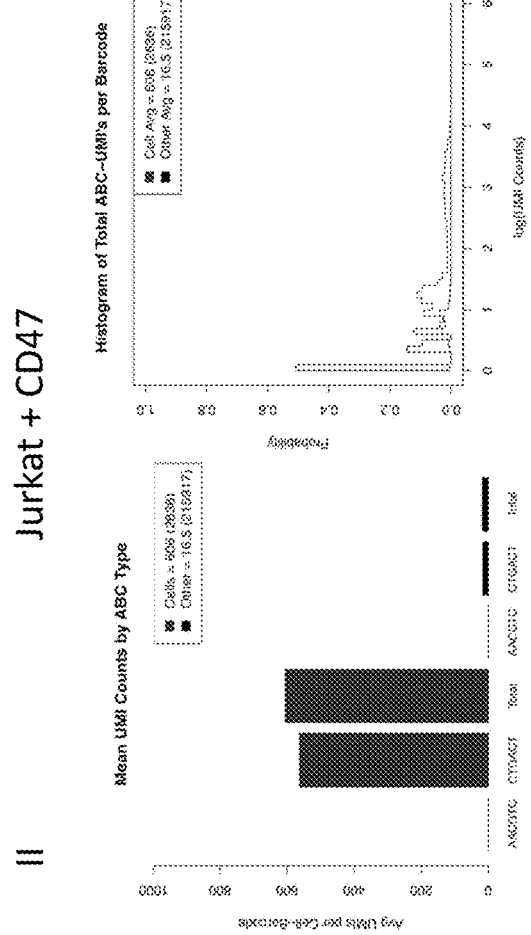
FIG. 41A

| Sample | Sample ID | Avg UMIs Per Cell | Avg UMIs Per Other | BC3 per cell | BC4 per cell | Total # of cell BCs detected in AbBC expt | # cells, SCS | # cells, AbBC topN (ncells, SCS) | AbBC topN cells ∩ SCS cells | AbBC called cells | AbBC cells ∩ SCS cells | SCS cells ∩ AbBC topN cells / SCS cells | BCAbs cells ∩ SCS cells / AbBC cells |
|---|---|---|---|---|---|---|---|---|---|---|---|---|---|
| Unbossed Jurkat + BC4 | 33600 | 4.98 | 13.9 | 686.47 | 595992 | 3818 | 1418 | 378 | 3367 | 378 | 0.27 | 0.27 | 0.11 |
| Unbossed Jurkat + BC3,4 | 33660 | 5.77 | 17.3 | 2477867 | 920883 | 3343 | 1143 | 368 | 982 | 333 | 0.32 | 0.32 | 0.34 |
| Unbossed Jurkat + BC4 | 33620 | 3.96 | 9.13 | 14740.578 | 6578 | 1559 | 1504 | 882 | 1199 | 761 | 0.57 | 0.57 | 0.64 |
| Unbossed Jurkat spike BC3/4 | 33693 | 38.3 | 14.3 | 1383 | 7133.8 | 3886 | 3983 | 103 | 6283.33 | 3570 | 0.03 | 0.03 | 0.03 |

*FIG. 41B*

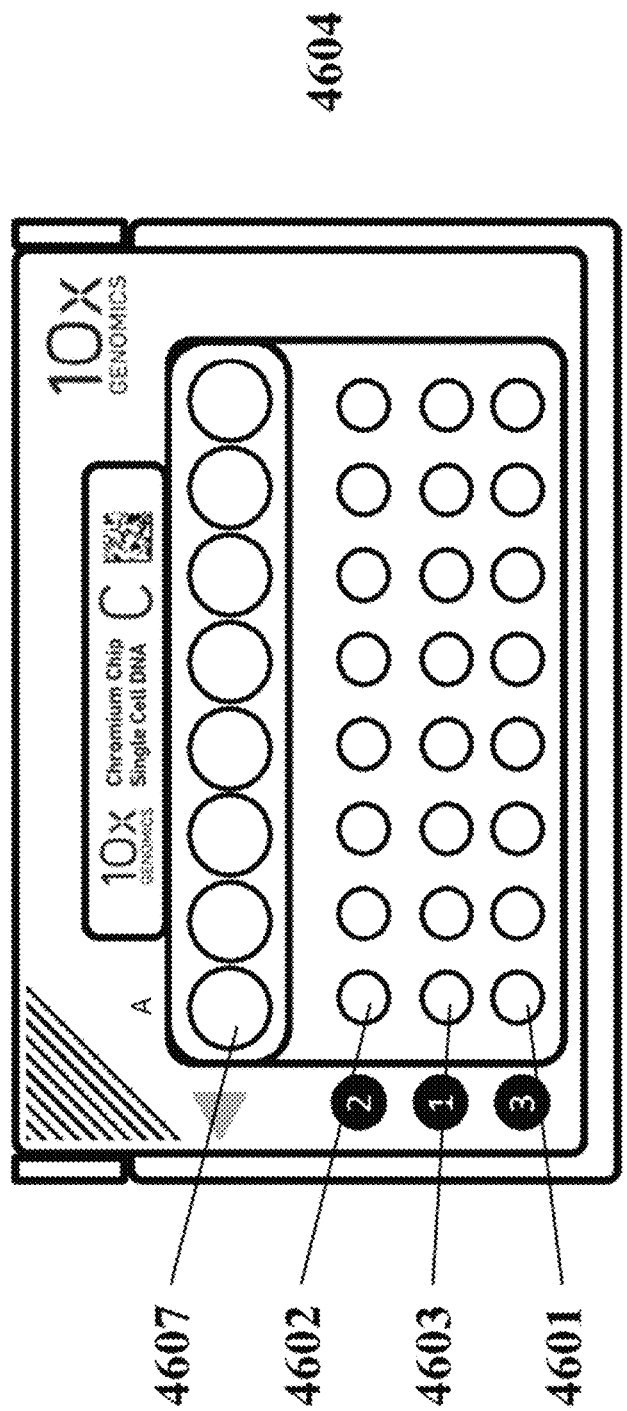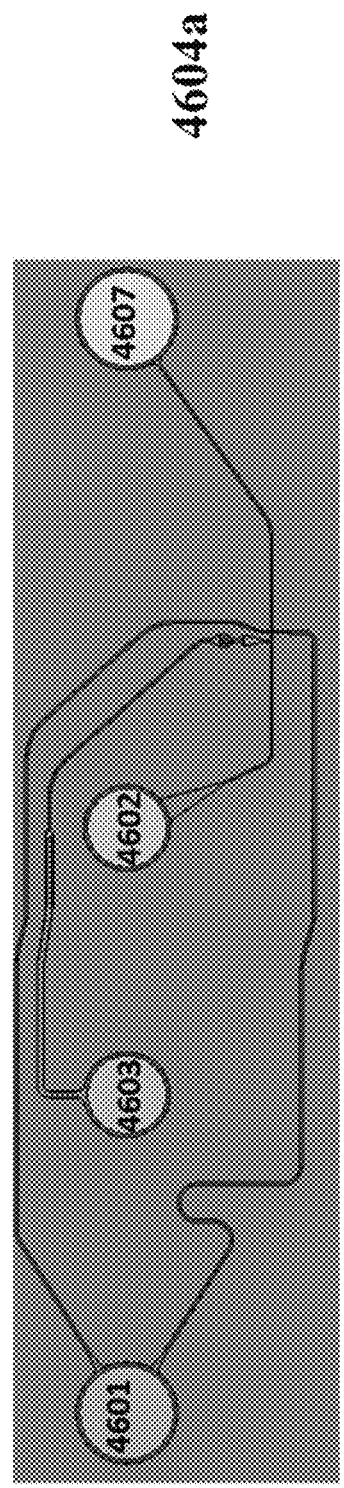
FIG. 46B

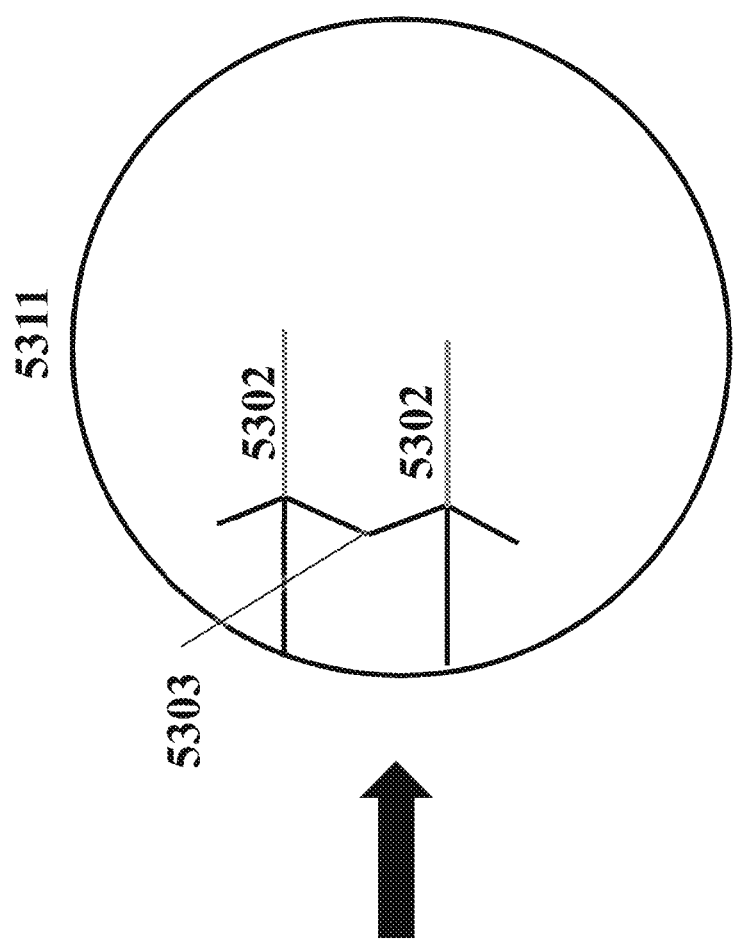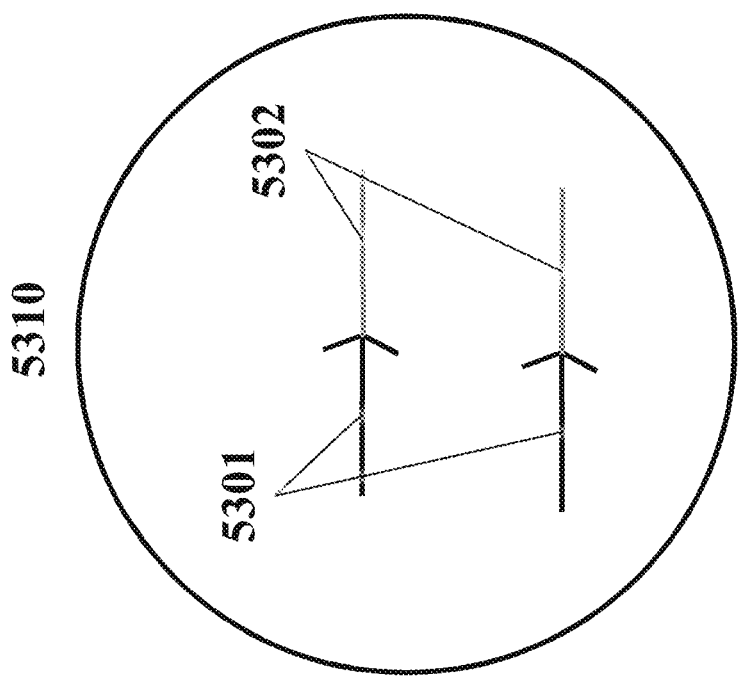
FIG. 53

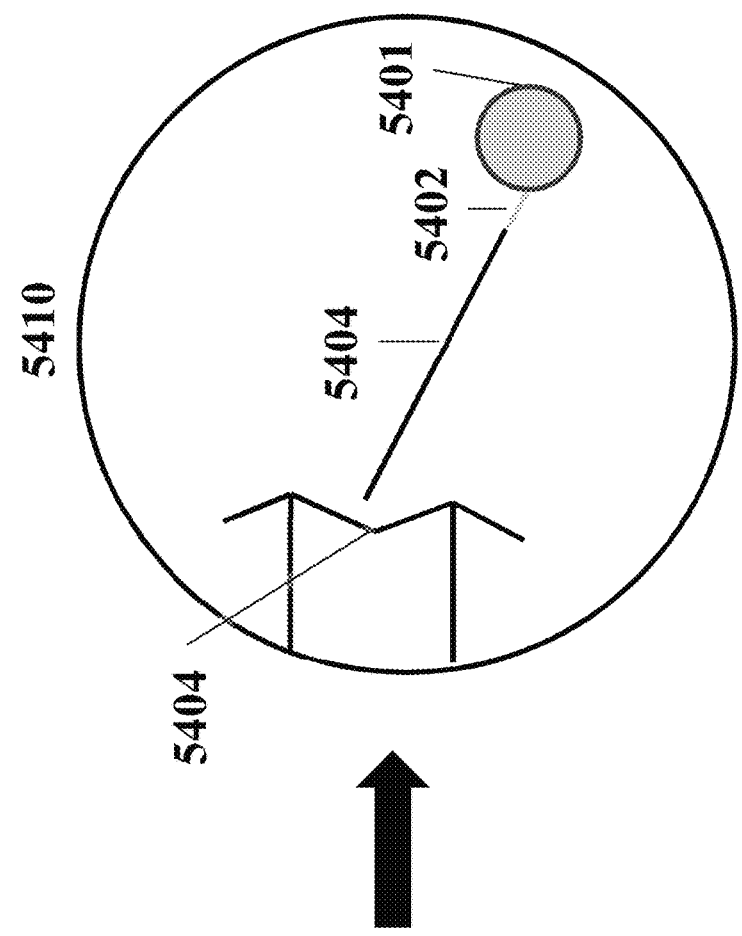
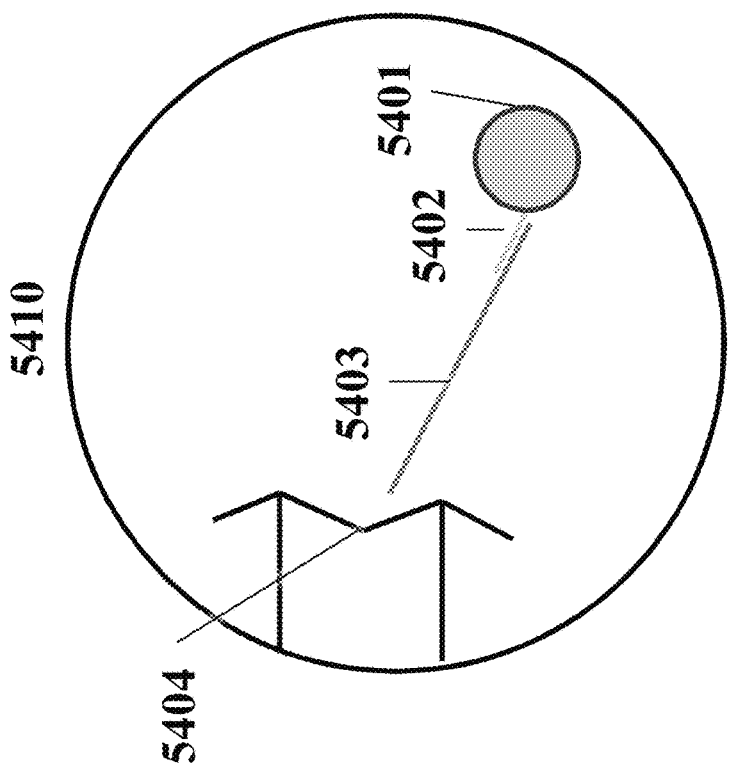
FIG. 54

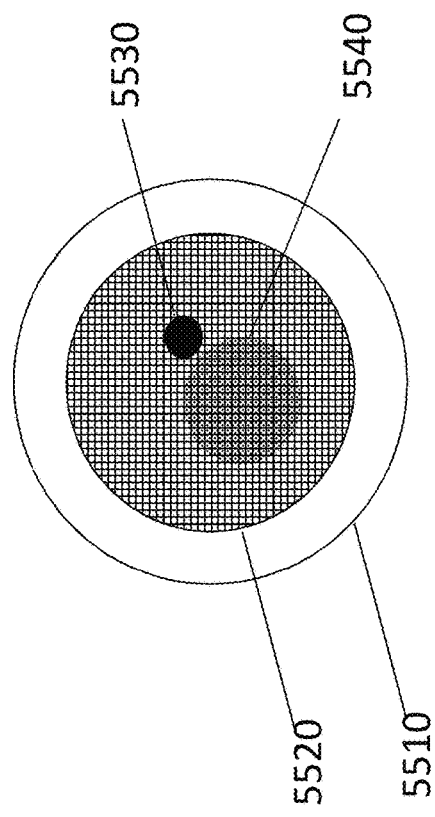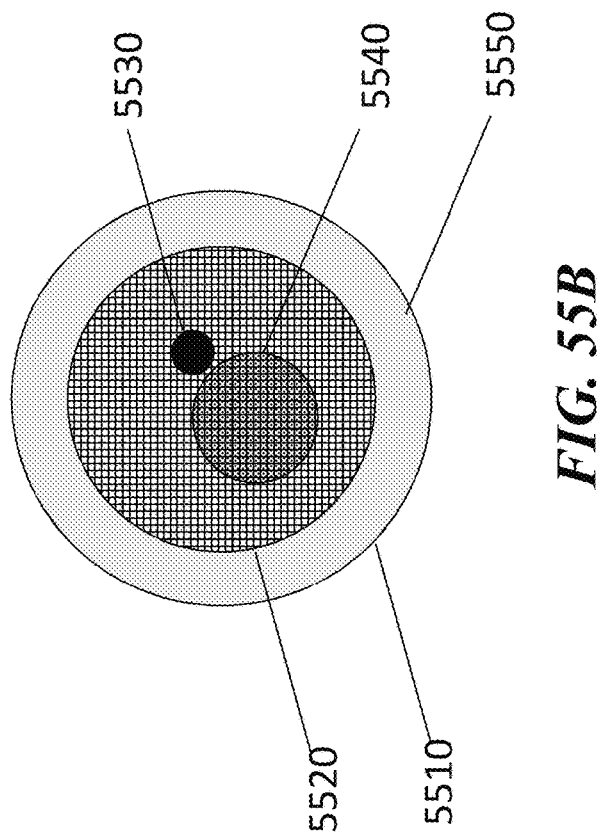
FIG. 55A
FIG. 55B

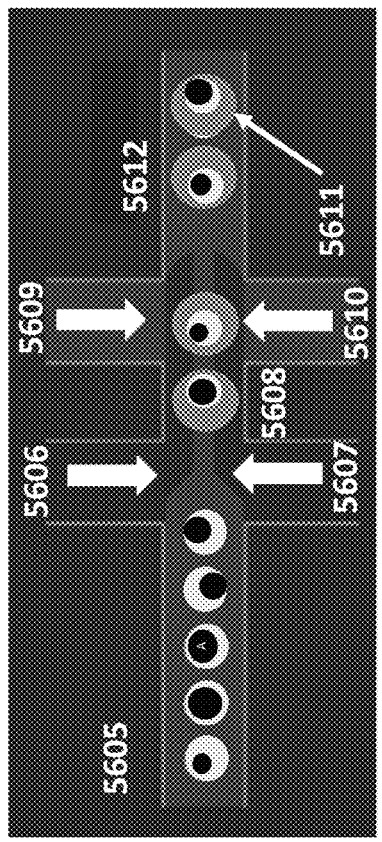
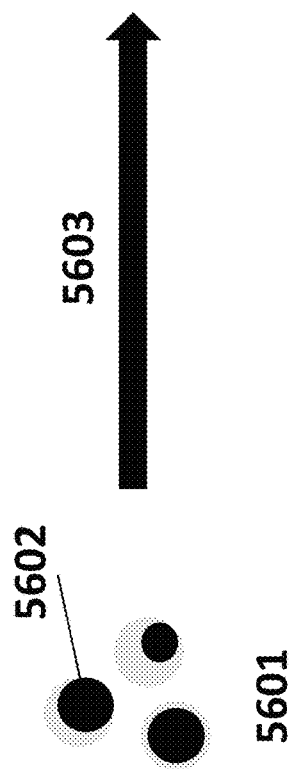
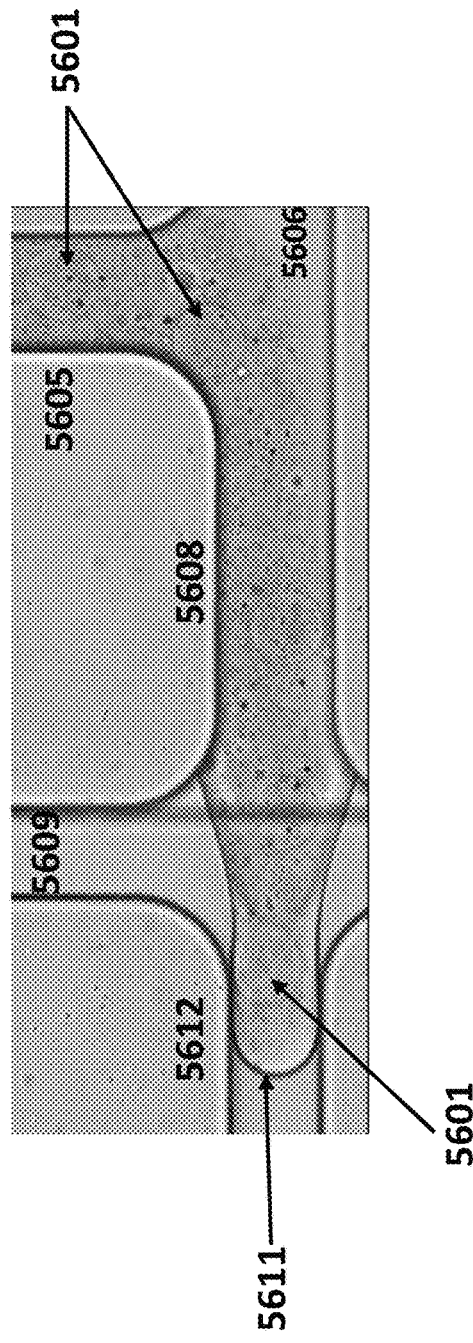
*FIG. 56A*
*FIG. 56B*

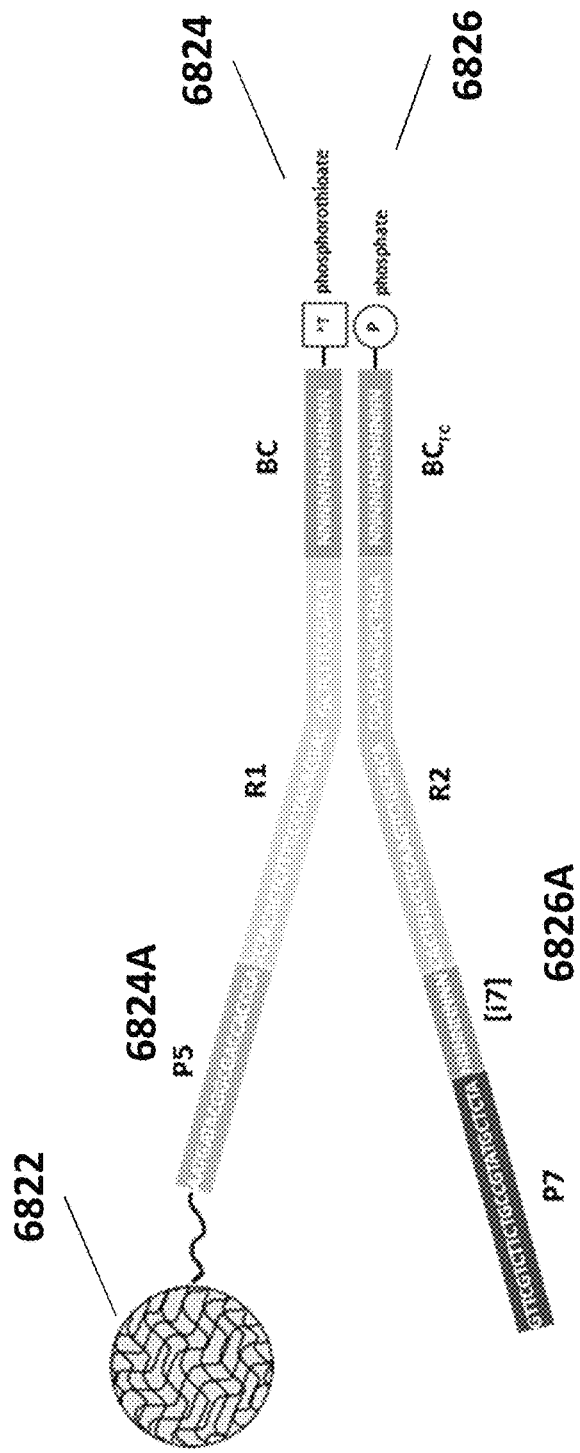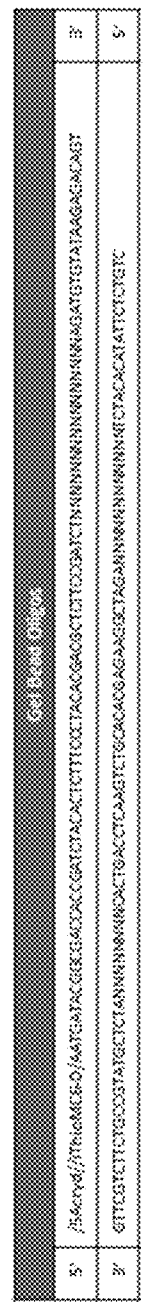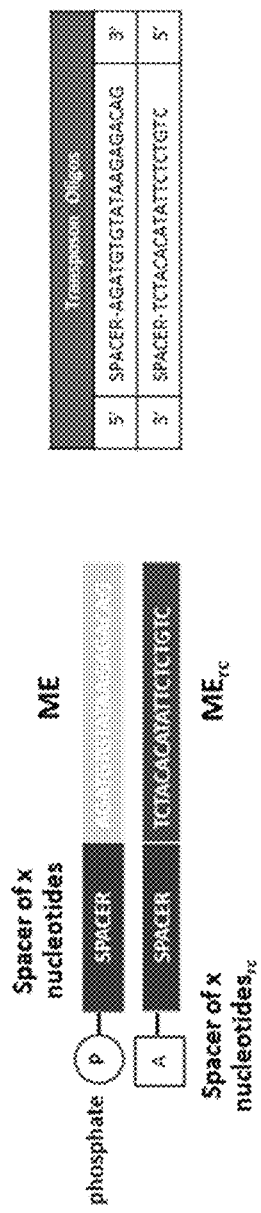
FIG. 68B

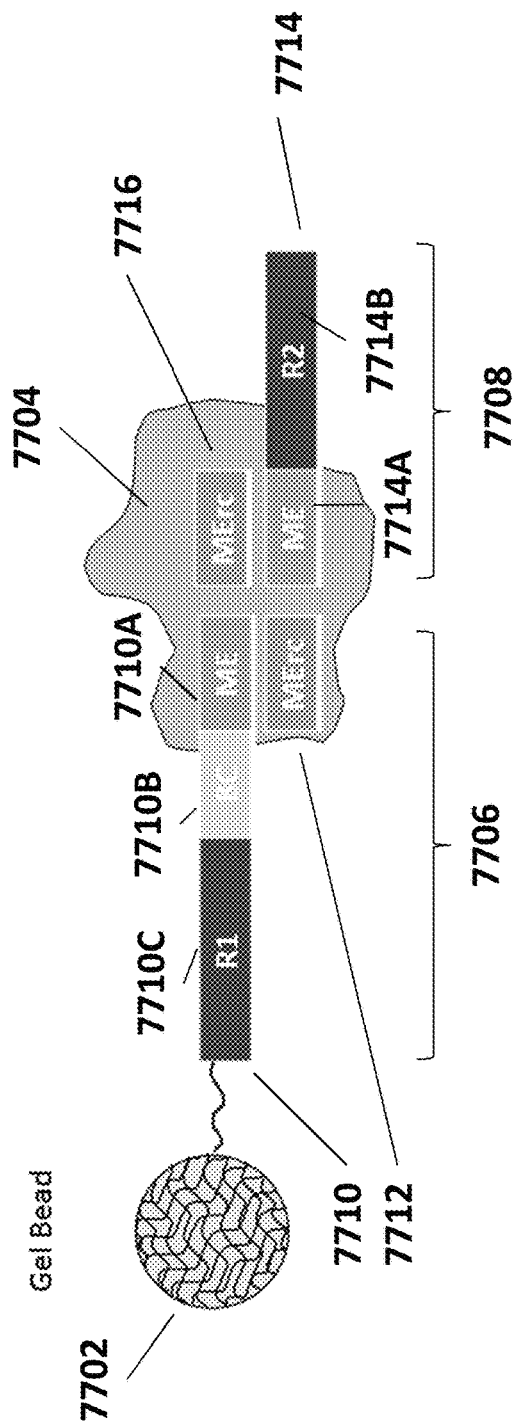
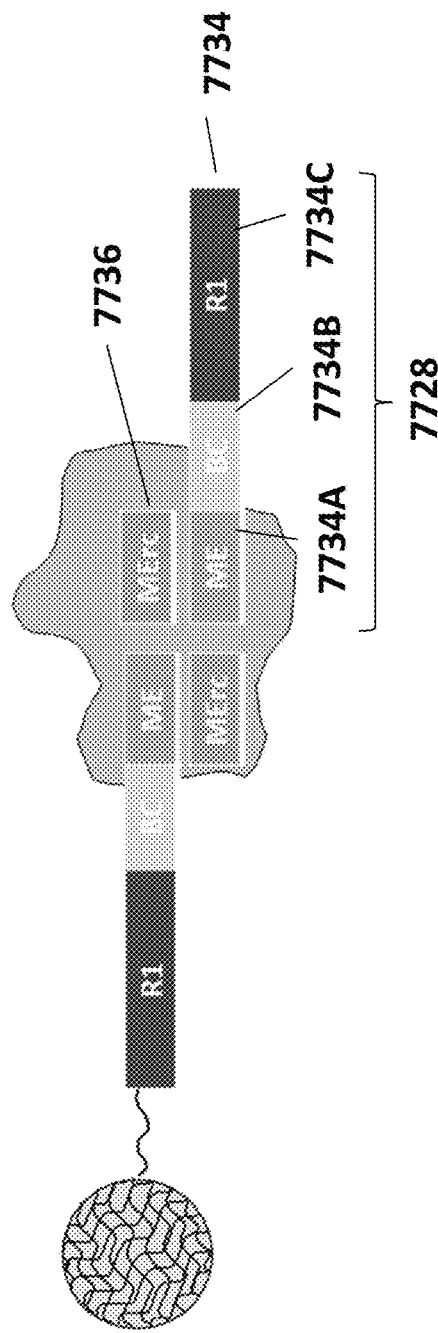
FIG. 77A
FIG. 77B

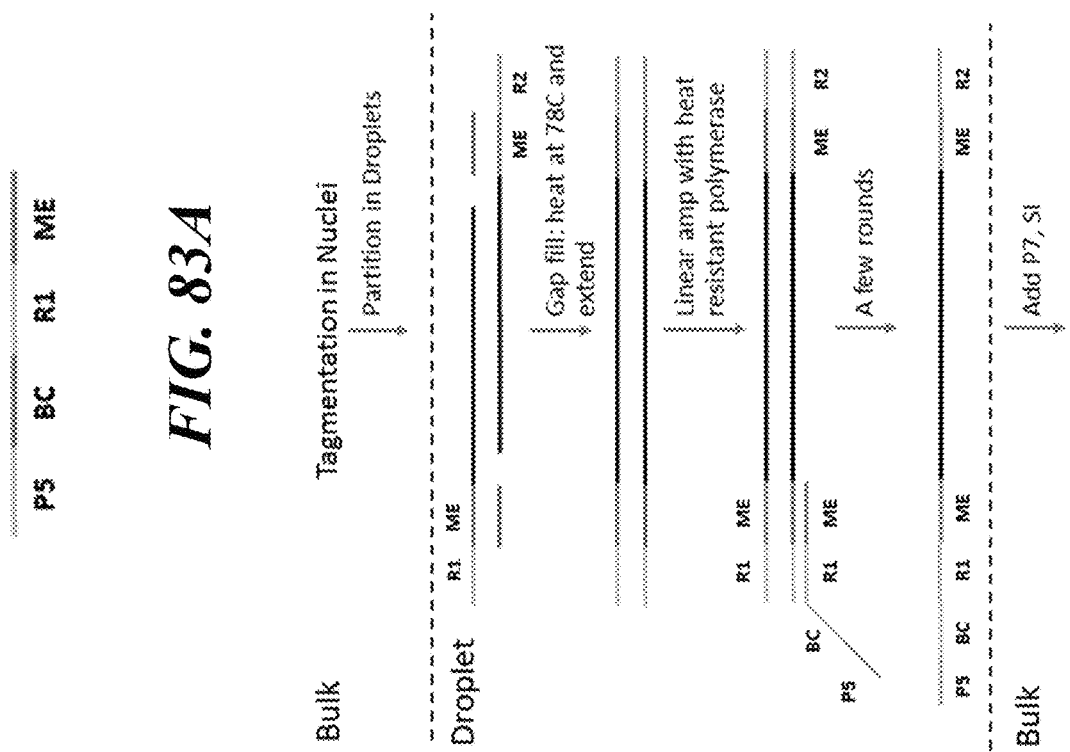

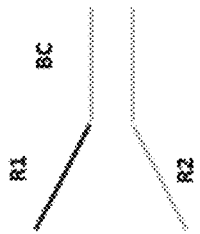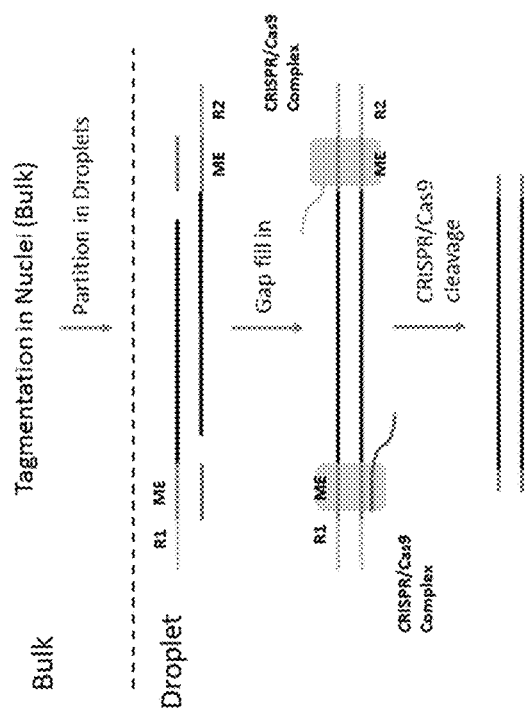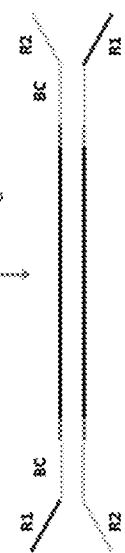
FIG. 86A
FIG. 86B

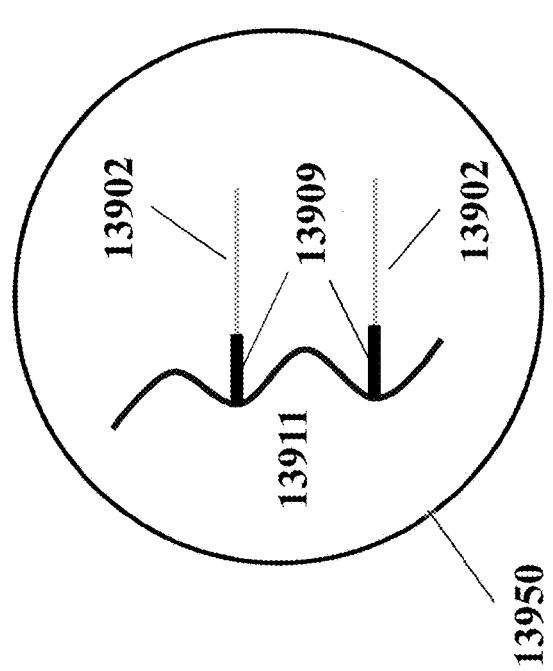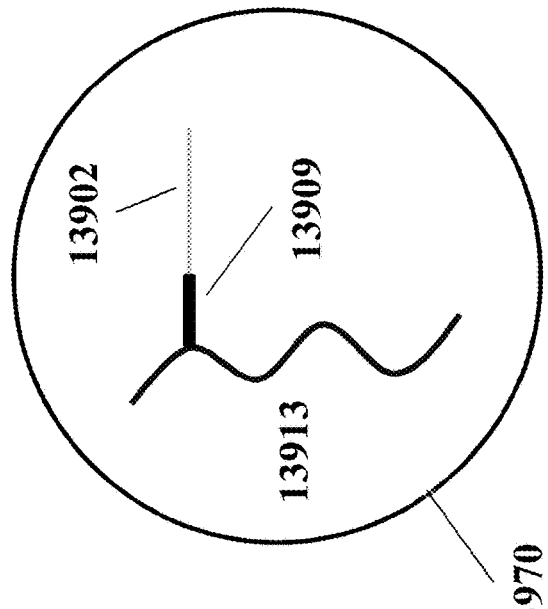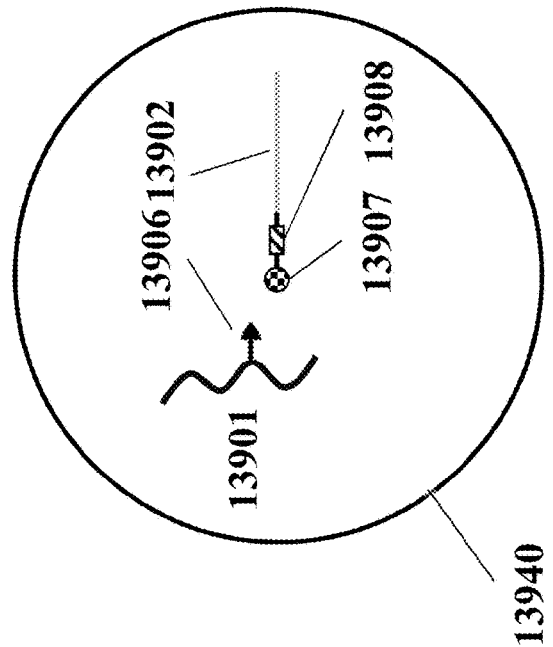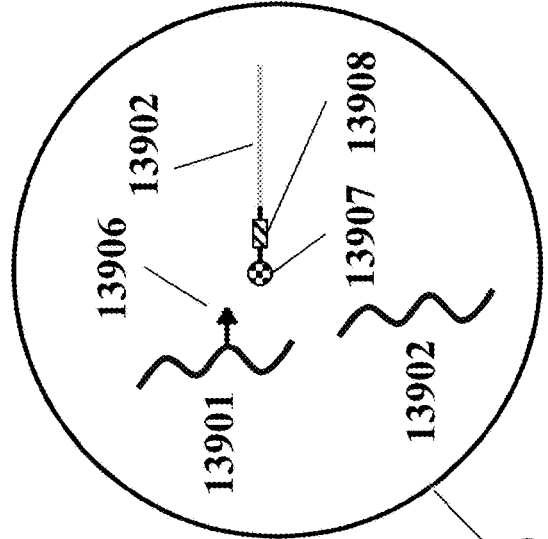
FIG. 139B

METHODS AND SYSTEMS FOR MACROMOLECULE LABELING

CROSS-REFERENCE

This application is a continuation of International Application No. PCT/US2019/17723, filed Feb. 12, 2019, which claims the benefit of U.S. Provisional Patent Application No. 62/629,602, filed Feb. 12, 2018.

SEQUENCE LISTING

The instant application contains a Sequence Listing which has been filed electronically in ASCII format and is hereby incorporated by reference in its entirety. Said ASCII copy, created on Aug. 12, 2019, is named 43487-800_306_SL.txt and is 33,397 bytes in size.

BACKGROUND

A sample may be processed for various purposes, such as detection, identification, quantitation, and characterization of a type of moiety within the sample. The sample may be a biological sample. Biological samples may be processed, such as for detection of a disease (e.g., cancer) or identification of a particular species. There are various approaches for processing samples, such as polymerase chain reaction (PCR) and sequencing.

Biological samples may be processed within various reaction environments, such as partitions. Partitions may be wells or droplets. Droplets or wells may be employed to process biological samples in a manner that enables the biological samples to be partitioned and processed separately. For example, such droplets may be fluidically isolated from other droplets, enabling accurate control of respective environments in the droplets.

Biological samples in partitions may be subjected to various processes, such as chemical processes or physical processes. Samples in partitions may be subjected to heating or cooling, or chemical reactions, such as to yield species that may be qualitatively or quantitatively processed.

SUMMARY

Recognized herein is the need for methods, compositions, and systems for analyzing multiple analytes (e.g., genomic, epigenomic, transcriptome, and/or proteomic information) from individual cells or a small population of cells. Such cells include, but are not limited to, cancer cells, fetal cells, and immune cells involved in immune responses. Provided herein are methods, compositions and systems for analyzing individual cells or a small population of cells, including the analysis and attribution of the analytes from and to these individual cells or cell populations.

Disclosed herein, in some embodiments, is a method for processing a major histocompatibility complex (MHC) molecule, comprising: (a) providing a droplet or well comprising (i) the MHC molecule and (ii) a particle having at least one peptide molecule and at least one nucleic acid molecule comprising a peptide barcode sequence coupled thereto; (b) attaching the at least one peptide molecule and the at least one nucleic acid molecule to the MHC molecule, to yield a derivative of the WIC molecule; and (c) recovering the derivative of the WIC molecule from the droplet or well. In some embodiments, the particle is a bead. In some embodiments, the bead is a gel bead. In some embodiments, the method further comprises prior to (c), releasing the peptide molecule and/or the at least one nucleic acid molecule from the particle In some embodiments, the method further comprises subsequent to (c), (1) providing an additional droplet or well comprising a cell having the derivative of the MHC molecule coupled thereto and an additional particle, which additional particle comprises at least one nucleic acid barcode molecule comprising a sample barcode sequence, and (2) using the at least one nucleic acid barcode molecule and the at least one nucleic acid molecule to generate another nucleic acid molecule that comprises the sample barcode sequence and the peptide barcode sequence, or a complement of the sample barcode sequence and the peptide barcode sequence. In some embodiments, the additional particle is an additional bead. In some embodiments, the additional bead is a gel bead. In some embodiments, the method further comprises releasing the at least one nucleic acid barcode molecule from the additional particle. In some embodiments, the method further comprises sequencing the nucleic acid molecule comprising the sample barcode sequence and the peptide barcode sequence to identify the sample barcode and the peptide barcode. In some embodiments, the method further comprises using the peptide barcode and the sample barcode to identify the WIC molecule and the cell. In some embodiments, the cell is a T-cell. In some embodiments, the MHC molecule is a MHC multimer. In some embodiments, the MHC multimer is a MHC tetramer. In some embodiments, the MHC molecule is a class I MHC molecule. In some embodiments, the MHC molecule is a class II MHC molecule.

Disclosed herein, in some embodiments, is a method for processing a major histocompatibility complex (MHC) molecule, comprising: (a) providing a droplet or well comprising (i) the MHC molecule and (ii) at least one nucleic acid molecule encoding at least one peptide; (b) translating the at least one peptide molecule from the at least one nucleic acid molecule; (c) attaching the at least one peptide molecule and the at least one nucleic acid molecule to the MHC molecule to yield a derivative of the MHC molecule; and (d) recovering the derivative of the MHC molecule from the droplet or well. In some embodiments, the at least one nucleic acid molecule is an mRNA molecule encoding the at least one peptide. In some embodiments, the at least one nucleic acid molecule is a DNA molecule encoding the at least one peptide. In some embodiments, prior to (b), the DNA molecule is transcribed in the droplet or well to yield an mRNA molecule encoding the at least one peptide. In some embodiments, the DNA molecule is attached to the MHC molecule to yield the derivative of the MHC molecule. In some embodiments, the mRNA molecule is attached to the MHC molecule to yield the derivative of the MHC molecule. In some embodiments, the nucleic acid molecule is attached to a particle. In some embodiments, the particle is a bead. In some embodiments, the bead is a gel bead. In some embodiments, the method further comprises releasing the nucleic acid molecule from the particle.

Disclosed herein, in some embodiments, is a method of generating barcoded nucleic acid fragments, comprising: (a) generating a plurality of partitions, wherein a partition of the plurality of partitions comprises: (i) a single biological particle from a plurality of biological particles, wherein the single biological particle comprises template DNA molecules, and wherein the single biological comprises a protein having attached thereto a labelling agent coupled to a nucleic acid molecule comprising a protein barcode sequence; (ii) a plurality of first barcode oligonucleotide molecules comprising a first barcode sequence; (iii) a plurality of transposon end oligonucleotide molecules comprising a transposon end sequence; (iv) a plurality of transposase molecules; and (v) a plurality of second barcode oligonucleotide molecules comprising a second barcode sequence; (b) generating a plurality of template DNA fragments by subjecting the partition to conditions sufficient to cause transposition of the transposon end oligonucleotide molecules into the template DNA with the aid of a transposase-nucleic acid complex comprising a transposase molecule from the plurality of transposase molecules and a transposon end oligonucleotide molecule from the plurality of transposon end oligonucleotide molecules; (c) generating a first barcoded nucleic acid molecule using a barcode oligonucleotide molecule from the plurality of first barcode oligonucleotide molecules and a template DNA fragment from the plurality of template DNA fragments, wherein the first barcoded nucleic acid molecule comprises the first barcode sequence; (d) generating a second barcoded nucleic acid molecule using the nucleic acid molecule coupled to the labelling agent and a barcode oligonucleotide molecule form the plurality of second barcode oligonucleotide, wherein the second barcoded nucleic acid molecule comprises the second barcode sequence and the protein barcode sequence; and (e) detecting (i) the sequence of the template DNA fragment and the first barcode sequence or a derivative thereof, and (ii) the protein barcode sequence and the second barcode sequence or a derivative thereof, thereby identifying the template DNA fragment and the protein as having originated from the single biological particle. In some embodiments, the first barcode sequence and the second barcode sequence are the same sequence. In some embodiments, the first barcode sequence is about 70% identical to the second barcode sequence. In some embodiments, the plurality of first barcode oligonucleotide molecules comprise a first capture sequence complementary to a sequence on the template DNA fragment and wherein the plurality of second barcode oligonucleotide molecules comprise a second capture sequence complementary to a sequence on the nucleic acid molecule comprising the protein barcode. In some embodiments, the first capture sequence and the second capture sequence are the same sequence. In some embodiments, the plurality of first barcode oligonucleotide molecules and the plurality of second barcode oligonucleotide molecules are identical. In some embodiments, the plurality of first barcode oligonucleotide molecules and/or the plurality of second barcode oligonucleotide molecules are attached to a particle. In some embodiments, the particle is a bead. In some embodiments, the bead is a gel bead. In some embodiments, the particle is a magnetic particle. In some embodiments, the labelling agent is an antibody. In some embodiments, the protein is a protein coupled to a surface of the single biological particle. In some embodiments, the protein is within the single biological particle. In some embodiments, the plurality of biological particles is a plurality of cells and wherein the single biological particle is a single cell. In some embodiments, the plurality of biological particles is a plurality of cell nuclei and wherein the single biological particle is a single cell nucleus. In some embodiments, the plurality of biological particles is a plurality of cell beads and wherein the single biological particle is a single cell bead. In some embodiments, the protein is a nuclear membrane protein. In some embodiments, the method further comprises subsequent to (d), recovering the first barcoded nucleic acid molecule or a derivative thereof and the second barcoded nucleic acid molecule or a derivative thereof. In some embodiments, (e) comprises sequencing (i) the first barcoded nucleic acid molecule or a derivative thereof and (ii) the second barcoded nucleic acid molecule or a derivative thereof. In some embodiments, the partition further comprises a plurality of third barcode oligonucleotide molecules comprising a third barcode sequence, wherein the single biological particle comprises a template RNA molecule and wherein the template mRNA molecule is barcoded with a barcode oligonucleotide molecule from the plurality of third barcode oligonucleotide molecules, and wherein (e) further comprises detecting a sequence of the mRNA molecule and the third barcode sequence or a derivative thereof, thereby identifying the mRNA molecule as having originated from the biological particle. In some embodiments, the plurality of third barcode oligonucleotide molecules comprises a third capture sequence complementary to a sequence on the template mRNA molecule. In some embodiments, the third capture sequence comprises a poly T sequence. In some embodiments, the first barcode sequence, the second barcode sequence, and the third barcode sequence are the same sequence. In some embodiments, the first barcode sequence and the second barcode sequence are the same sequence and wherein the third barcode sequence is about 70% identical to the first barcode sequence and the second barcode sequence. In some embodiments, the first barcode sequence, the second barcode sequence, and the third barcode sequence are about 70% identical to one another. In some embodiments, the first capture sequence and the second capture sequence are the same sequence and wherein the third capture sequence is different than the first capture sequence and the second capture sequence. In some embodiments, the plurality of first barcode oligonucleotide molecules and the plurality of second barcode oligonucleotide molecules are identical and wherein the plurality of third barcode oligonucleotide molecules are different than the first barcode oligonucleotide molecules and the second barcode oligonucleotide molecules. In some embodiments, the plurality of first barcode oligonucleotide molecules, the plurality of second barcode oligonucleotide molecules, and/or the plurality of second barcode oligonucleotide molecules are attached to a particle. In some embodiments, the particle is a bead. In some embodiments, the bead is a gel bead. In some embodiments, the particle is a magnetic particle. In some embodiments, the single biological particle comprises an analyte and wherein the partition further comprises a plurality of fourth barcode oligonucleotide molecules comprising a fourth barcode sequence, and wherein the analyte is barcoded with a barcode oligonucleotide molecule from the plurality of fourth barcode oligonucleotide molecules, and wherein (e) further comprises detecting a sequence of the fourth barcode sequence, thereby identifying the analyte as having originated from the biological particle. In some embodiments, the plurality of fourth barcode oligonucleotide molecules comprise a fourth capture sequence, wherein the fourth capture sequence is configured to hybridize to the analyte. In some embodiments, the analyte is a CRISPR ribonucleic acid (crRNA) or a single guide ribonucleic acid (sgRNA). In some embodiments, the fourth capture sequence is configured to hybridize to a nucleic acid sequence of a crRNA or a sgRNA. In some embodiments, the partition is subjected to conditions sufficient to generate the transposase-nucleic acid complex using a transposase molecule from the plurality of transposase molecules and a transposon end oligonucleotide molecule from the plurality of transposon end oligonucleotide molecules. In some embodiments, the transposase-nucleic acid complex is partitioned into the partition. In some embodiments, prior to (b), the partition is subjected to conditions sufficient to cause release of the template DNA molecules from the single biological particle. In some embodiments, the gel bead is depolymerized to release the plurality of first barcode oligonucleotide molecules and/or the plurality of second barcode oligonucleotide molecules from the gel bead. In some embodiments, the plurality of partitions further comprises a reducing agent to depolymerize the gel bead. In some embodiments, the plurality of partitions is a plurality of droplets. In some embodiments, the plurality of partitions is a plurality of wells.

Disclosed herein, in some embodiments, is a method for processing or analyzing at least two different types of components from a cell, comprising: (a) providing a plurality of cell beads, wherein a cell bead of the plurality of cell beads comprises the at least two different types of components; (b) partitioning the plurality of cell beads into a plurality of partitions, wherein upon partitioning, a partition of the plurality of partitions comprises the cell bead; and (c) processing components from each of the at least two different types of components. In some embodiments, one of the at least two different types of components is deoxyribonucleic acid. In some embodiments, the deoxyribonucleic acid is genomic deoxyribonucleic acid. In some embodiments, one of the at least two different types of components is ribonucleic acid. In some embodiments, the ribonucleic acid is messenger ribonucleic acid. In some embodiments, one of the at least two different types of components is protein. In some embodiments, the protein is cell surface protein. In some embodiments, the protein is intracellular protein. In some embodiments, one of the at least two different types of components is metabolites. In some embodiments, (a) further comprises providing a plurality of gel beads, and wherein (b) further comprises partitioning the plurality of gel beads into the plurality of partitions, wherein the partition comprises a gel bead of the plurality of gel beads, and wherein the gel bead comprises a plurality of nucleic acid barcode molecules for barcoding at least a subset of the components or derivatives thereof. In some embodiments, the processing comprises using the plurality of nucleic acid barcode molecules to barcode at least a subset of the components or derivatives thereof. In some embodiments, the processing comprises subjecting at least a subset of the components or derivatives thereof to sequencing. In some embodiments, the plurality of partitions is a plurality of wells. In some embodiments, the plurality of partitions is a plurality of droplets. In some embodiments, the method further comprises subsequent to (a), performing one or more reactions on the components. In some embodiments, the one or more reactions are selected from the group consisting of nucleic acid amplification, reverse transcription, bisulfite treatment, oxygenase treatment, enzymatic deamination, RNase treatment, proteinase treatment, tagmentation reaction, and methyltransferase treatment. In some embodiments, the one or more reactions comprise nucleic acid amplification. In some embodiments, the one or more reactions comprise reverse transcription. In some embodiments, the one or more reactions are performed outside the plurality of partitions. In some embodiments, the one or more reactions are performed in the plurality of partitions. In some embodiments, the one or more reactions are performed prior to (b). In some embodiments, the one or more reactions are performed subsequent to (b). In some embodiments, at least a subset of the at least two different types of components or derivatives thereof are attached to the cell bead. In some embodiments, the at least a subset of the at least two different types of components or derivatives thereof are attached to the cell bead via an acrydite moiety. In some embodiments, the cell beads further comprise a particle. In some embodiments, the particle is a magnetic particle. In some embodiments, the magnetic particle is a paramagnetic particle. In some embodiments, at least a subset of the at least two different types of components or derivatives thereof are attached to the particle. In some embodiments, the at least a subset of the at least two different types of components or derivatives thereof are attached to the particle via an acrydite moiety. In some embodiments, one or more reagents for processing the components are attached to the particle. In some embodiments, the one or more reagents comprise a nucleic acid molecule. In some embodiments, the nucleic acid molecule comprises a poly-T sequence. In some embodiments, the nucleic acid molecule is a poly-T primer. In some embodiments, the cell beads further comprise one or more reagents for processing the components. In some embodiments, the one or more reagents comprise a nucleic acid molecule. In some embodiments, the nucleic acid molecule comprises a poly-T sequence. In some embodiments, the nucleic acid molecule is a poly-T primer. In some embodiments, the one or more reagents are attached to the cell beads.

Disclosed herein, in some embodiments, is a method for processing or analyzing at least two different types of components from a cell, comprising: (a) providing a plurality of cells and a plurality of polymeric or gel precursors; (b) partitioning the plurality of cells and the plurality of polymeric or gel precursors into a plurality of partitions, wherein upon partitioning, a partition of the plurality of partitions comprises (i) the at least two different types of components (ii) a cell of the plurality of cells, and (iii) at least a portion of the polymeric or gel precursors; (c) subjecting the plurality of partitions to conditions sufficient to cross-link or polymerize the polymeric or gel precursors to form a plurality of cell beads; and (d) processing components from each of the at least two different types of components from the cell. In some embodiments, the method further comprises subsequent to (a), subjecting the plurality of partitions to conditions sufficient to lyse the plurality of cells, releasing the at least two different types of components into the partition. In some embodiments, (a) further comprising providing a plurality of gel beads comprising a plurality of nucleic acid barcode molecules, wherein, in (b), the partition comprises the gel bead. In some embodiments, the processing comprises using the plurality of nucleic acid barcode molecules to barcode at least a subset of the components or derivatives thereof. In some embodiments, the method further comprises subsequent to (a), performing one or more reactions on the components. In some embodiments, the method further comprises prior to (d), partitioning the cell beads into a plurality of partitions, wherein a partition of the plurality of partitions comprises a cell bead of the plurality of cell beads. In some embodiments, the method further comprises partitioning a plurality of gel beads comprising a plurality of nucleic acid barcode molecules into the plurality of partition, wherein a partition of the plurality of partitions comprises a gel bead of the plurality of gel beads.

Disclosed herein, in some embodiments, is a method for multi-analyte processing, comprising: (a) providing a partition comprising (i) a single biological particle, wherein the single biological particle comprises a first set of analytes and a second set of analytes, wherein the first set of analytes comprise ribonucleic acid (RNA) molecules, and wherein analytes of the first set of analytes and the second set of analytes are different of different types, and (ii) a bead comprising nucleic acid barcode molecules comprising barcode sequences; (b) using the nucleic acid barcode molecules to (i) barcode the RNA molecules of the first set of analytes to generate barcoded RNA molecules, and (ii) barcode analytes of the second set of analytes to generate barcoded analytes; and (c) using sequencing to (i) identify sequences of the barcoded RNA molecules or derivatives thereof to determine an RNA velocity of a subset of the RNA molecules, and (ii) sequences of the barcoded analytes or derivatives thereof. In some embodiments, the biological particle is a cell. In some embodiments, the biological particle is a cell bead. In some embodiments, the second set of analytes comprises proteins. In some embodiments, the proteins are coupled to a surface of the biological particle. In some embodiments, the second set of analytes comprises deoxyribonucleic acid (DNA) molecules. In some embodiments, the second set of analytes comprises metabolites. In some embodiments, the RNA velocity is determined by identifying an abundance of RNA spliced and unspliced sequences in the RNA molecules. In some embodiments, the RNA molecules are messenger RNA molecules. In some embodiments, the method further comprises associating the RNA velocity with the analytes. In some embodiments, the analytes are proteins from the biological particle, and wherein the RNA velocity is associated with an abundance of the proteins in the biological particle.

Disclosed herein, in some embodiments, is a method for cell lineage analysis, comprising: (a) contacting (i) a biological particle comprising a lineage tracing nucleic acid molecule and an analyte, which lineage tracing nucleic acid molecule is configured to permit the biological particle to be identified with a progenitor cell, and (ii) a plurality of nucleic acid barcode molecules comprising (1) a lineage tracing barcode molecule comprising a common barcode sequence and a lineage tracing capture sequence configured to couple to the lineage tracing nucleic acid molecule; and (2) an analyte barcode molecule comprising the common barcode sequence and an analyte capture sequence configured to couple to a nucleic acid molecule corresponding to the analyte, wherein the lineage tracing capture sequence or the analyte capture sequence lacks a poly(dT) sequence; (b) coupling (1) the lineage tracing capture sequence to the lineage tracing nucleic acid molecule and (2) the analyte capture sequence to the nucleic acid molecule corresponding to the analyte, and (c) synthesizing (1) a first nucleic acid molecule comprising the common barcode sequence and a sequence corresponding to the lineage tracing nucleic acid molecule, and (2) a second nucleic acid molecule comprising the common barcode sequence and a sequence corresponding to the nucleic acid molecule corresponding to the analyte. In some embodiments, the biological particle is a cell, a cell nucleus, or a cell bead. In some embodiments, the method further comprises sequencing (i) the first nucleic acid molecule or a derivative thereof and (ii) the second nucleic acid molecule or a derivative thereof, to identify the common barcode sequence, the sequence corresponding to the lineage tracing nucleic acid molecule, and the sequence of the nucleic acid molecule corresponding to the analyte, wherein the common barcode sequence identifies the lineage tracing nucleic acid molecule and the analyte as having originated from the biological particle. In some embodiments, the common barcode sequence comprises identical barcode sequence segments. In some embodiments, the common barcode sequence of the lineage tracing barcode molecule and the common barcode sequence of the analyte barcode molecule are identical. In some embodiments, the method further comprises co-partitioning (i) the biological particle and (ii) the plurality of nucleic acid barcode molecules into a partition. In some embodiments, the partition is an aqueous droplet in an emulsion or a well. In some embodiments, the analyte is a genomic deoxyribonucleic acid (gDNA) molecule. In some embodiments, the gDNA molecule is an enzymatically fragmented gDNA molecule. In some embodiments, the gDNA molecule comprises deaminated cytosines or oxidized 5-hydroxymethylcytosine bases. In some embodiments, the analyte is a ribonucleic acid (RNA) molecule. In some embodiments, the RNA molecule is a messenger RNA molecule (mRNA). In some embodiments, the RNA molecule is (i) a clustered regularly interspaced short palindromic (CRISPR) RNA molecule (crRNA) or (ii) a single guide RNA (sgRNA) molecule. In some embodiments, the nucleic acid molecule corresponding to the analyte is coupled to a labelling agent configured to couple to the analyte. In some embodiments, the nucleic acid molecule corresponding to the analyte comprises an analyte barcode sequence that corresponds to the analyte. In some embodiments, the nucleic acid molecule corresponding to the analyte comprises a sequence complementary to the analyte capture sequence. In some embodiments, the labelling agent is an antibody. In some embodiments, the analyte is a metabolite or a protein. In some embodiments, the plurality of nucleic acid barcode molecules is attached to a solid support. In some embodiments, the method further comprises releasing the plurality of nucleic acid barcode molecules from the solid support. In some embodiments, the solid support is a bead. In some embodiments, one or more of (a)-(c) are performed in a partition. In some embodiments, each of (a)-(c) is performed in a partition. In some embodiments, the partition is an aqueous droplet in an emulsion or a well. In some embodiments, the partition is an aqueous droplet in an emulsion or a well.

Disclosed herein, in some embodiments, is a method of analyzing chromatin, comprising: (a) providing a mixture comprising (i) a biological particle comprising (1) chromatin comprising a template deoxyribonucleic acid (DNA) and (2) a protein, and (ii) a plurality of nucleic acid barcode molecules; (b) contacting the biological particle with a labelling agent comprising a reporter oligonucleotide, wherein the labelling agent is configured to couple to the protein; (c) generating a plurality of template DNA fragments of the chromatin using a plurality of transposase complexes; (d) generating a first barcoded nucleic acid molecule using (i) a template DNA fragment of the plurality of template DNA fragments and (ii) a first nucleic acid barcode molecule of the plurality of nucleic acid barcode molecules; and (e) generating a second barcoded nucleic acid molecule using (i) the reporter oligonucleotide and (ii) a second nucleic acid barcode molecule of the plurality of nucleic acid barcode molecules. In some embodiments, a transposase complex of the plurality of transposase complexes comprises (i) a nucleic acid molecule comprising a transposon end sequence, and (ii) a transposase. In some embodiments, (i) the first nucleic acid barcode molecule comprises a barcode sequence and a first capture sequence configured to couple to a template DNA fragment of the plurality of template DNA fragments; and (ii) the second nucleic acid barcode molecule comprises the barcode sequence and a second capture sequence configured to couple to the reporter oligonucleotide. In some embodiments, (d) comprises coupling the first capture sequence to the template DNA fragment and synthesizing the first barcoded nucleic acid molecule, wherein the first barcoded nucleic acid molecule comprises the barcode sequence and a sequence of at least a portion of the template DNA fragment. In some embodiments, (e) comprises coupling the second capture sequence to the reporter oligonucleotide and synthesizing the second barcoded nucleic acid molecule, wherein the second barcoded nucleic acid molecule comprises the barcode sequence and a sequence of at least a portion of the reporter oligonucleotide. In some embodiments, the reporter oligonucleotide comprises a sequence complementary to the second capture sequence. In some embodiments, the method further comprises co-partitioning the mixture into a partition. In some embodiments, (b) or (c) is performed in the partition. In some embodiments, (b) or (c) is performed prior to the co-partitioning. In some embodiments, the partition is an aqueous droplet in an emulsion. In some embodiments, the partition is a well. In some embodiments, the biological particle is permeable to the plurality of transposase complexes and wherein the plurality of template DNA fragments is generated in the biological particle. In some embodiments, the reporter oligonucleotide further comprises an analyte barcode sequence that identifies the presence of the protein and wherein the second barcoded nucleic acid molecule comprises the analyte barcode sequence. In some embodiments, the reporter oligonucleotide comprises a unique molecule identifier (UMI) sequence. In some embodiments, the labelling agent is an antibody. In some embodiments, the protein is a cell surface protein. In some embodiments, the protein is an intracellular protein. In some embodiments, the biological particle is a cell, a cell nucleus, or a cell bead. In some embodiments, the plurality of nucleic acid barcode molecules is attached to a solid support. In some embodiments, the solid support is a bead. In some embodiments, the plurality of nucleic acid barcode molecules is releasably attached to the bead. In some embodiments, the method further comprises releasing the plurality of nucleic acid barcode molecules from the bead. In some embodiments, each of the plurality of barcode molecules are releasably attached to the bead through a labile bond. In some embodiments, the labile bond is selected from the group consisting of a thermally cleavable bond, a chemically labile bond, and a photo-sensitive bond. In some embodiments, the labile bond comprises a linkage selected from the group consisting of an ester linkage, a vicinal diol linkage, a Diels-Alder linkage, a sulfone linkage, a silyl ester linkage, a glycosidic linkage, a peptide linkage, or a phosphodiester linkage. In some embodiments, the bead is a gel bead. In some embodiments, the gel bead is degradable upon application of a stimulus. In some embodiments, the stimulus is a chemical stimulus. In some embodiments, the mixture comprises the chemical stimulus. In some embodiments, the method further comprises sequencing (i) the first barcoded nucleic acid molecule, a complement thereof, or a derivative thereof or (ii) the second barcoded nucleic acid molecule, a complement thereof, or a derivative thereof.

Disclosed herein, in some embodiments, is a method for processing or analyzing at least two analytes from a cell, comprising: (a) contacting a plurality of nucleic acid barcode molecules with a cell bead derived from the cell, wherein the cell bead comprises at least a first analyte and a second analyte, wherein the second analyte is different than the first analyte; and (b) using nucleic acid barcode molecules from the plurality of nucleic acid barcode molecules to barcode (i) a first nucleic acid molecule corresponding to the first analyte and (ii) a second nucleic acid molecule corresponding to the second analyte. In some embodiments, the plurality of nucleic acid barcode molecules comprises a (i) first nucleic acid barcode molecule comprising a common barcode sequence and a first capture sequence configured to couple to the first nucleic acid molecule corresponding to the first analyte, and (ii) a second nucleic acid barcode molecule comprising the common barcode sequence and a second capture sequence configured to couple to the second nucleic acid molecule corresponding to the second analyte. In some embodiments, (b) comprises coupling (1) the first capture sequence to the first nucleic acid molecule corresponding to the first analyte and (2) the second capture sequence to the second nucleic acid molecule corresponding to the second analyte, and synthesizing (1) a first nucleic acid molecule comprising the common barcode sequence and a sequence corresponding to the first analyte, and (2) a second nucleic acid molecule comprising the common barcode sequence and a sequence corresponding to the second analyte. In some embodiments, the first analyte is a genomic deoxyribonucleic acid (gDNA) molecule. In some embodiments, the gDNA molecule is fragmented. In some embodiments, the gDNA molecule is enzymatically fragmented. In some embodiments, the gDNA molecule comprises deaminated cytosines. In some embodiments, the gDNA molecule comprises chemically or enzymatically deaminated cytosines. In some embodiments, the gDNA molecule comprises oxidized 5-hydroxymethylcytosine bases. In some embodiments, the first analyte is a ribonucleic acid (RNA) molecule. In some embodiments, the RNA molecule is a messenger RNA molecule (mRNA). In some embodiments, the RNA molecule is (i) a clustered regularly interspaced short palindromic (CRISPR) RNA molecule (crRNA) or (ii) a single guide RNA (sgRNA) molecule. In some embodiments, the first nucleic acid molecule corresponding to the first analyte is coupled to a labelling agent configured to couple to the first analyte. In some embodiments, the first nucleic acid molecule corresponding to the first analyte comprises a first analyte barcode sequence that corresponds to the first analyte. In some embodiments, the first nucleic acid molecule corresponding to the first analyte comprises a sequence complementary to the first capture sequence. In some embodiments, the labelling agent is an antibody. In some embodiments, the first analyte is a metabolite. In some embodiments, the first analyte is a protein. In some embodiments, the protein is a cell surface protein, intracellular protein, or nuclear membrane protein. In some embodiments, the plurality of nucleic acid barcode molecules is attached to a solid support. In some embodiments, the plurality of nucleic acid barcode molecules is releasably attached to the solid support. In some embodiments, the solid support is a bead. In some embodiments, the bead is disruptable upon application of a stimulus. In some embodiments, the method further comprises prior to (a), providing a mixture comprising the cell comprising the at least two different types of analytes and a plurality of monomeric or polymeric precursors. In some embodiments, the method further comprises prior to (a), polymerizing the monomeric or polymeric precursors to form the cell bead. In some embodiments, the method further comprises prior to forming the cell bead, lysing the cell, thereby releasing the at least two different types of analytes from the cell into the mixture. In some embodiments, one of the at least two different types of analytes is a messenger ribonucleic acid (mRNA) molecule, wherein prior to (a), the mRNA molecule is subjected to a reverse transcription reaction to generate a complementary deoxyribonucleic acid (cDNA) molecule, and wherein the cell bead comprises the cDNA molecule. In some embodiments, the method further comprises co-partitioning the mixture into a partition. In some embodiments, the partition is an aqueous droplet in an emulsion. In some embodiments, the partition is a well.

In some embodiments, the method further comprises, prior to (a), crosslinking a plurality of macromolecules in the cell to form the cell bead. In some embodiments, the macromolecules are selected from the group consisting of proteins, nucleic acids, lipids, and any combination thereof. In some embodiments, the macromolecules comprise proteins. In some embodiments, the crosslinking comprises a bifunctional crosslinker. In some embodiments, the bifunctional crosslinker comprises a succinimide, aldehyde, maleimide, dicarboxylic, or diazide moiety. In some embodiments, the crosslinking comprises an alkylating agent or intercalating agent. In some embodiments, the alkylating agent is selected from the group consisting of melphalan, chlorambucil, nitrogen mustards, nitrosureas, busulfan, psoralen, and derivatives thereof.

Disclosed herein, in some embodiments, is a method for processing, comprising: (a) providing a reaction mixture comprising (i) a major histocompatibility complex (MHC) molecule, and (ii) a support having coupled thereto (1) a polypeptide and (2) a nucleic acid barcode molecule, wherein the nucleic acid barcode molecule comprises a barcode sequence that corresponds to the polypeptide, and wherein the MHC molecule is a soluble MHC molecule; and (b) subjecting the reaction mixture to conditions sufficient to couple the polypeptide and the nucleic acid barcode molecule to the MHC molecule, thereby yielding a barcoded MHC molecule. In some embodiments, the MHC molecule is coupled to a carrier. In some embodiments, the carrier is a protein or polypeptide. In some embodiments, the MHC molecule comprises biotin, wherein the carrier comprises streptavidin, and wherein the MHC is coupled to the carrier through a biotin-streptavidin interaction. In some embodiments, the carrier comprises a polymer. In some embodiments, the polymer comprises dextran. In some embodiments, in (a), the MHC molecule comprises a conditional ligand and wherein (b) comprises a peptide exchange action wherein the conditional ligand is exchanged for the polypeptide. In some embodiments, the conditional ligand is a polypeptide comprising a photo-labile amino acid, and wherein prior to (b), the conditional ligand is released from the MHC molecule upon application of a photo-stimulus. In some embodiments, the conditional ligand is covalently linked to the MHC molecule, wherein the conditional ligand is a polypeptide comprising a protease cleavage domain, and wherein prior to (b), the conditional polypeptide ligand is released from the MHC molecule upon cleavage of the protease cleavage domain by a protease. In some embodiments, the reaction mixture further comprises a molecular chaperone. In some embodiments, the molecular chaperone comprises the luminal domain of transporter associated with antigen processing (TAP)-binding protein related (TAPBPR). In some embodiments, the support is a bead. In some embodiments, the polypeptide and the nucleic acid barcode molecule are releasably attached to the bead. In some embodiments, the method further comprises releasing the polypeptide and the nucleic acid barcode molecule from the bead. In some embodiments, the bead is a gel bead. In some embodiments, the gel bead is degradable upon application of a stimulus. In some embodiments, the stimulus is a chemical stimulus. In some embodiments, the reaction mixture further comprises the chemical stimulus. In some embodiments, the method further comprises partitioning the reaction mixture into a partition. In some embodiments, the partition is an aqueous droplet in an emulsion. In some embodiments, the partition is a well. In some embodiments, the method further comprises (c) providing a plurality of partitions, including the partition, wherein at least a subset of the plurality of partitions each comprise (i) a plurality of soluble major histocompatibility complex (MHC) molecules and (ii) a given support having coupled thereto (1) a plurality of polypeptides comprising a common amino acid sequence, and (2) a plurality of nucleic acid barcode molecules comprising a common barcode sequence, wherein the barcode sequence corresponds to the common amino acid sequence, and wherein each partition of the subset of the plurality of partitions comprises a unique polypeptide and a unique barcode sequence; and (d) subjecting the plurality of partitions to conditions sufficient to, in each of the subset of the plurality partitions, couple (i) a given polypeptide of the plurality of polypeptides and (ii) a given nucleic acid barcode molecule of the plurality of nucleic acid barcode molecules to a given MHC molecule of the plurality of soluble WIC molecules to yield a plurality of barcoded MHC molecules, including the barcoded MHC molecule. In some embodiments, at least a subset of the plurality of barcoded WIC molecules are coupled to a carrier. In some embodiments, the plurality of soluble WIC molecules comprise biotin, wherein the carrier comprises streptavidin, and wherein the subset of the plurality of barcoded WIC molecules are coupled to the carrier through a biotin-streptavidin interaction. In some embodiments, the carrier comprises a dextran polymer. In some embodiments, in (c), the plurality of soluble MHC molecules comprise a conditional ligand, wherein (d) comprises a peptide exchange reaction, and wherein the conditional ligand is exchanged for a polypeptide of the plurality of polypeptides. In some embodiments, the conditional ligand is a polypeptide comprising a photo-labile amino acid, and wherein prior to (d), the conditional ligand is released from MHC molecules of the plurality of soluble WIC molecules upon application of a photo-stimulus. In some embodiments, the plurality of barcoded MHC molecules further comprise a fluorophore. In some embodiments, the plurality of partitions is plurality of aqueous droplets in an emulsion. In some embodiments, the plurality of partitions is a plurality of wells.

Disclosed herein, in some embodiments, is a method for screening an antigen, comprising: (a) contacting an immune receptor with a plurality of engineered yeast cells to yield an engineered yeast cell bound to the immune receptor, wherein the plurality of engineered yeast cells comprise (i) a complex comprising a polypeptide antigen coupled to a major histocompatibility complex (WIC) molecule; and (ii) a first nucleic acid molecule comprising a sequence encoding for the polypeptide antigen; (b) generating a plurality of partitions, wherein a partition of the plurality of partitions comprises (i) the engineered yeast cell bound to the immune receptor; and (ii) a plurality of nucleic acid barcode molecules comprising a common barcode sequence; (c) generating a second nucleic acid molecule comprising (i) a sequence corresponding to the polypeptide antigen and (ii) a sequence corresponding to the common barcode sequence. In some embodiments, in (a), the polypeptide antigen is covalently coupled to the MHC molecule. In some embodiments, in (a), the complex is displayed on the surface of the plurality of engineered yeast cells. In some embodiments, the complex further comprises a yeast cell surface anchor protein. In some embodiments, the yeast cell surface anchor protein comprises a glycosylphosphatidylinositol (GPI) anchor. In some embodiments, the yeast cell surface anchor protein is Aga2p. In some embodiments, the MHC molecule and the yeast cell surface anchor protein are a fusion protein. In some embodiments, the polypeptide antigen, the MHC molecule, and the yeast cell surface anchor protein are a fusion protein. In some embodiments, the plurality of nucleic acid barcode molecules further comprise a capture sequence and wherein the first nucleic acid molecule further comprises a sequence configured to hybridize with the capture sequence. In some embodiments, (c) comprises hybridizing the first nucleic acid molecule to a nucleic acid barcode molecule of the plurality of nucleic acid barcode molecules and performing a nucleic acid extension reaction to generate the second nucleic acid molecule. In some embodiments, (c) comprises hybridizing the first nucleic acid molecule to a nucleic acid barcode molecule of the plurality of nucleic acid barcode molecules and performing a ligation reaction to generate the second nucleic acid molecule. In some embodiments, the method further comprises sequencing the first nucleic acid molecule or derivative thereof to generate sequencing reads corresponding to the polypeptide antigen and the common barcode sequence. In some embodiments, the immune receptor is a T cell receptor. In some embodiments, (a) comprises contacting a cell comprising the immune receptor with the plurality of engineered yeast cells and wherein, in (b), the partition comprises the engineered yeast cell bound to the cell. In some embodiments, the cell is a T cell. In some embodiments, the cell comprises a messenger ribonucleic acid (mRNA) molecule encoding for the immune receptor and further comprising, prior to (b), generating a third nucleic acid molecule comprising (i) a sequence corresponding to the immune receptor and (ii) a sequence corresponding to the common barcode sequence. In some embodiments, the plurality of nucleic acid barcode molecules further comprise a capture sequence and wherein (c) comprises hybridizing the mRNA molecule to a nucleic acid barcode molecule of the plurality of nucleic acid barcode molecules and performing a nucleic acid extension reaction to generate the third nucleic acid molecule. In some embodiments, the partition further comprises a fourth nucleic acid molecule comprising a poly-T sequence, wherein the plurality of nucleic acid barcode molecules further comprise a template switching oligonucleotide (TSO) sequence, and wherein (c) comprises (i) using the fourth nucleic acid molecule and the mRNA molecule to generate a complementary deoxyribonucleic acid (cDNA) molecule comprising the sequence corresponding to the immune receptor and (ii) performing a template switching reaction using a nucleic acid barcode molecule of the plurality of nucleic acid barcode molecules to generate the third nucleic acid molecule. In some embodiments, the method further comprises (i) sequencing the first nucleic acid molecule or derivative thereof to generate sequencing reads corresponding to the polypeptide antigen and the common barcode sequence; and (ii) sequencing the third nucleic acid molecule or derivative thereof to generate sequencing reads corresponding to the immune receptor and the common barcode sequence. In some embodiments, the method further comprises using the sequencing reads corresponding to the common barcode sequence to associate the immune receptor and the polypeptide. In some embodiments, the plurality of nucleic acid barcode molecules is attached to a solid support. In some embodiments, the solid support is a bead. In some embodiments, the plurality of nucleic acid barcode molecules is releasably attached to the bead. In some embodiments, the method further comprises releasing the plurality of nucleic acid barcode molecules from the bead. In some embodiments, the bead is a gel bead. In some embodiments, the gel bead is a degradable upon application of a stimulus. In some embodiments, the stimulus is a chemical stimulus. In some embodiments, the partition comprises the chemical stimulus. In some embodiments, the plurality of partitions is a plurality of aqueous droplets in an emulsion. In some embodiments, the plurality of partitions is a plurality of wells.

Disclosed herein, in some embodiments, is a method for processing, comprising: (a) providing a reaction mixture comprising a major histocompatibility complex (MHC) molecule and a nucleic acid molecule comprising a sequence encoding a polypeptide, wherein the MHC molecule is a soluble MHC molecule; and (b) subjecting the reaction mixture to conditions sufficient to (i) generate the polypeptide from the nucleic acid molecule, and (ii) couple the polypeptide and the nucleic acid molecule to the MHC molecule, thereby yielding a labeled MHC molecule. In some embodiments, the nucleic acid molecule is a ribonucleic acid (RNA) molecule and wherein, prior to (b), the polypeptide is generated from the nucleic acid molecule by an in vitro translation reaction. In some embodiments, the nucleic acid molecule is a deoxyribonucleic acid (DNA) molecule, wherein prior to (b), the DNA molecule is transcribed to yield a messenger RNA (mRNA) molecule, and wherein the polypeptide is generated from the mRNA molecule by an in vitro translation reaction. In some embodiments, the nucleic acid molecule further comprises a T7 promoter sequence. In some embodiments, the nucleic acid molecule further comprises a capture sequence. In some embodiments, the MHC molecule is coupled to a carrier. In some embodiments, the carrier is a protein or polypeptide. In some embodiments, the carrier comprises a polymer. In some embodiments, the polymer comprises dextran. In some embodiments, the nucleic acid comprises biotin, wherein the carrier comprises streptavidin, and wherein the nucleic acid molecule is coupled to the carrier through a biotin-streptavidin interaction. In some embodiments, in (a), the MHC molecule comprises a conditional ligand and wherein (b) comprises a peptide exchange action wherein the conditional ligand is exchanged for the polypeptide. In some embodiments, the conditional polypeptide ligand is a polypeptide comprising a photo-labile amino acid, and wherein prior to (b), the conditional ligand is released from the MHC molecule upon application of a photo-stimulus. In some embodiments, the conditional ligand is covalently linked to the MHC molecule, wherein the conditional ligand is a polypeptide comprising a protease cleavage domain, and wherein prior to (b), the conditional ligand is released from the MHC molecule upon cleavage of the protease cleavage domain by a protease. In some embodiments, the reaction mixture further comprises a molecular chaperone. In some embodiments, the molecular chaperone comprises the luminal domain of transporter associated with antigen processing (TAP)-binding protein related (TAPBPR). In some embodiments, in (a), the nucleic acid molecule is attached to a support. In some embodiments, the support is a bead. In some embodiments, the nucleic acid molecule is releasably attached to the bead. In some embodiments, the method further comprises releasing the nucleic acid molecule from the bead. In some embodiments, the bead is a gel bead. In some embodiments, the gel bead is degradable upon application of a stimulus. In some embodiments, the stimulus is a chemical stimulus. In some embodiments, the reaction mixture comprises the chemical stimulus. In some embodiments, the method further comprises partitioning the reaction mixture into a partition. In some embodiments, the partition is an aqueous droplet in an emulsion. In some embodiments, the partition is a well. In some embodiments, the method further comprises: (c) providing a plurality of partitions, including the partition, wherein at least a subset of the plurality of partitions each comprises (i) a plurality of soluble MHC molecules and (ii) a plurality of nucleic acid molecules comprising a sequence encoding a common polypeptide, wherein each partition of the subset of the plurality of partitions comprises a nucleic acid molecule encoding a unique polypeptide; and (d) subjecting the plurality of partitions to conditions sufficient to, in each of the subset of the plurality partitions, (i) generate the common polypeptide from the nucleic acid molecule and (ii) couple the common polypeptide and a given nucleic acid molecule of the plurality of nucleic acid molecules to a given MHC molecule of the plurality of soluble MHC molecules to yield a plurality of labeled MHC molecules, including the labeled MHC molecule. In some embodiments, at least a subset of the plurality of labeled MHC molecules are coupled to a carrier. In some embodiments, the plurality of nucleic acid molecules comprise biotin, wherein the carrier comprises streptavidin, and wherein nucleic acid molecules of the plurality of nucleic acid molecules are coupled to the carrier through a biotin-streptavidin interaction. In some embodiments, the carrier comprises dextran.

Another aspect of the present disclosure provides a non-transitory computer readable medium comprising machine executable code that, upon execution by one or more computer processors, implements any of the methods above or elsewhere herein.

Another aspect of the present disclosure provides a system comprising one or more computer processors and computer memory coupled thereto. The computer memory comprises machine executable code that, upon execution by the one or more computer processors, implements any of the methods above or elsewhere herein.

Additional aspects and advantages of the present disclosure will become readily apparent to those skilled in this art from the following detailed description, wherein only illustrative embodiments of the present disclosure are shown and described. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

INCORPORATION BY REFERENCE

All publications, patents, and patent applications mentioned in this specification are herein incorporated by reference to the same extent as if each individual publication, patent, or patent application was specifically and individually indicated to be incorporated by reference. To the extent publications and patents or patent applications incorporated by reference contradict the disclosure contained in the specification, the specification is intended to supersede and/or take precedence over any such contradictory material.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings (also "Figure" and "FIG." herein), of which:

FIG. 12D discloses "AAAAAAAAAAAAAAAAAAAA" as SEQ ID NO: 14 and "ATCCTAGCAA" as SEQ ID NO: 15.

Figure 13A:
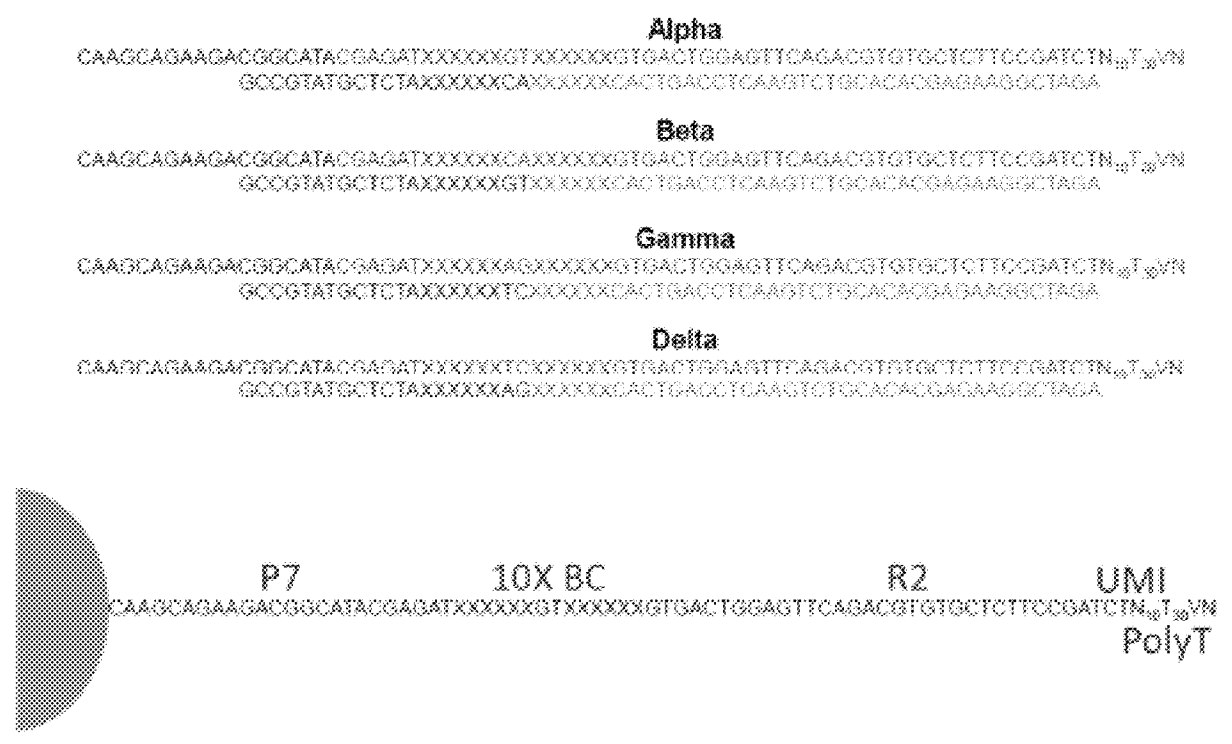
Figure 13C:
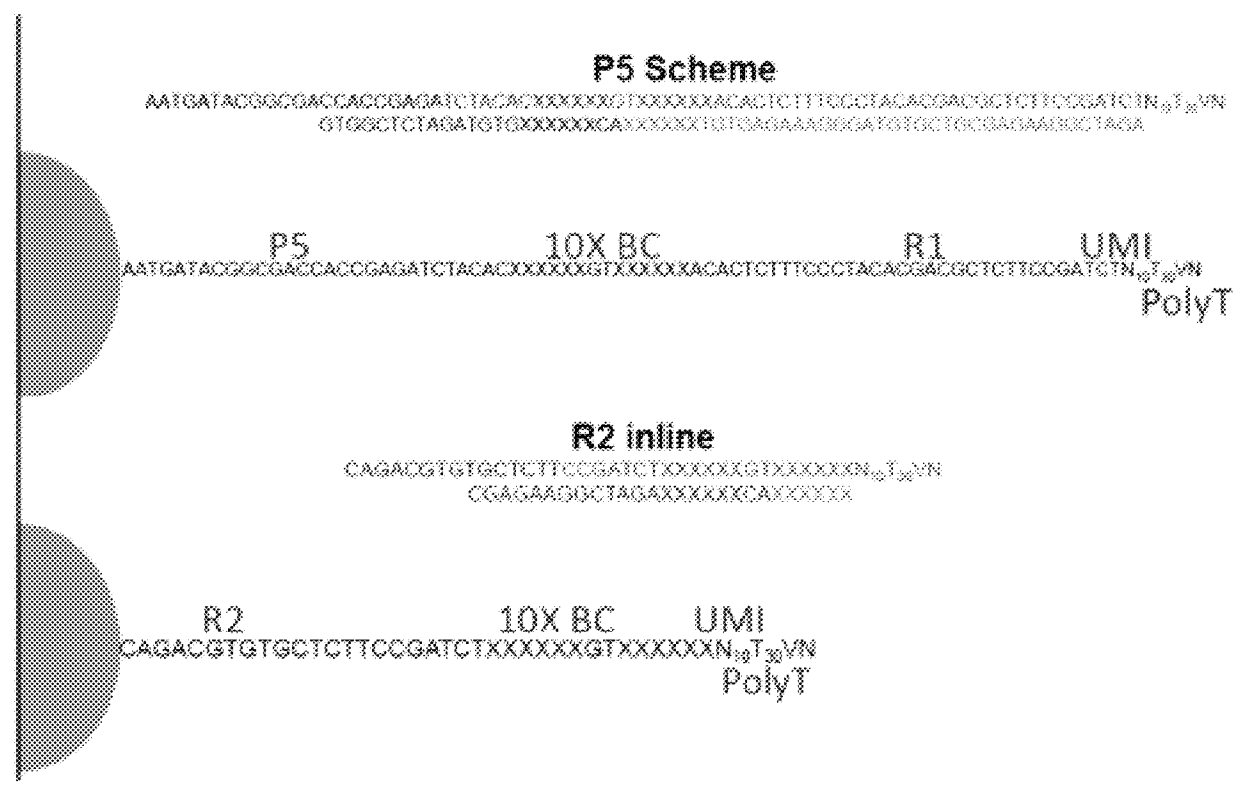
Figure 13D:
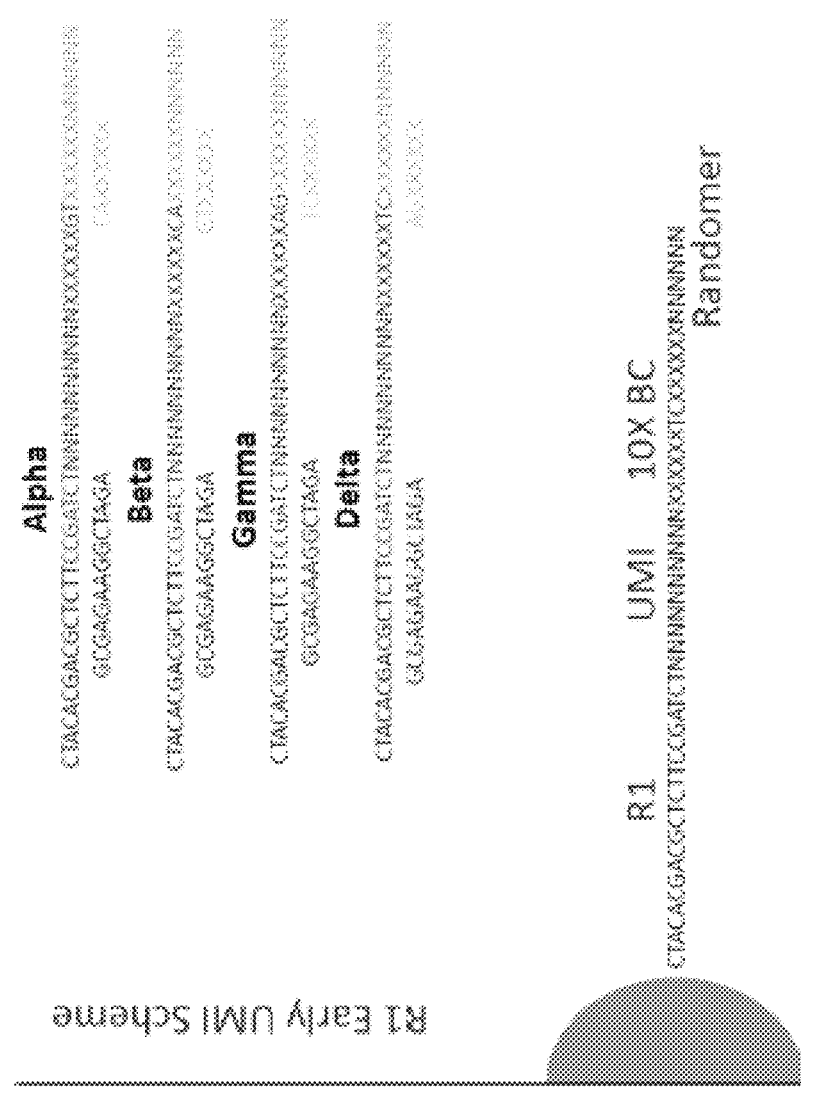

FIG. 13A shows oligonucleotides with backbones comprising P7 and R2 sequences and poly-T primers. Figure discloses SEQ ID NOS 16-23 and 16, respectively, in order of appearance.

FIG. 13C shows oligonucleotides with P5, R1, and R2 sequences and poly-T primers. Figure discloses SEQ ID NOS 32, 33, 32, 34, 35, and 34, respectively, in order of appearance.

FIG. 13D shows oligonucleotides with R1 sequences and random N-mer primers. Figure discloses SEQ ID NOS 36-38, 37, 39, 37, 40, 37, and 40, respectively, in order of appearance.

FIGS. 14B and 14C schematically depict example sequences that can be coupled to a bead. FIG. 14B discloses SEQ ID NOS 43-50, respectively, in order of appearance. FIG. 14C discloses SEQ ID NOS 51, 52, 51, 52, 51, 52, 51, and 52, respectively, in order of appearance.

FIGS. 15A-C show exemplary oligonucleotides comprising adapters and assay primers.

FIG. 15A discloses SEQ ID NOS 53 and 53, respectively, in order of appearance

FIG. 23A shows a bead coupled with an oligonucleotide comprising a target-specific primer and oligonucleotides with poly-T primers. Figure discloses SEQ ID NOS 30, 55, and 30, respectively, in order of appearance. FIG. 23B shows a bead coupled with a plurality of oligonucleotides, each of which comprises a target-specific primer. Figure discloses SEQ ID NOS 55, 55, 55, and 55, respectively, in order of appearance. FIG. 23C shows a bead coupled with a plurality of oligonucleotides, each of which comprises a target-specific primer and a plurality of oligonucleotides, each of which comprises a poly-T primer. Figure discloses SEQ ID NOS 30, 55, 55, 55, 55, and 30, respectively, in order of appearance. FIG. 23D shows a bead coupled with a plurality of oligonucleotides, each of which comprises a target-specific primer and a plurality of oligonucleotides, each of which comprises a random N-mer primer for total RNA. Figure discloses SEQ ID NOS 40, 56, 56, 56, 56, and 40, respectively, in order of appearance.

FIGS. 24A-E disclose "AAAAAAAAAAAAAAAA" as SEQ ID NO: 57.

FIGS. 27A-27B provide schematic illustrations of example barcoded oligonucleotide structures for use in analysis of RNA.

FIG. 31 shows analysis results of the CD3 protein-single-stranded DNA (ssDNA) conjugate.

FIG. 34A shows a conjugate of a functionalized antibody-binding protein and a functionalized oligonucleotide. FIG. 34B shows a relationship between a degree of dibenzocyclooctyne (DBCO) incorporation and input dibenzocyclooctyne-N-hydroxysuccinimidyl ester (DBCO-NHS) concentrations.

FIG. 36A-B depict data obtained from an example experiment described in Example 6.

FIGS. 38A-C depict data obtained from an example experiment described in Example 6.

FIG. 39A depicts sequences used in an example experiment described in Example 7. Figure discloses SEQ ID NOS 65 and 66, respectively, in order of appearance.

FIGS. 41A-B provide data obtained from an example experiment described in Example 8.

FIG. 42A discloses SEQ ID NO: 67. FIG. 42B discloses SEQ ID NOS 68 and 67, respectively, in order of appearance.

FIG. 43A shows a representative denaturing agarose gel while FIG. 43B shows a representative SDS-PAGE gel.

FIGS. 46A-C illustrate an exemplary scheme for cell bead generation and for the generation of partitions comprising cell beads and barcode beads.

FIG. 53 illustrates an example process for generating cell beads comprising complementary deoxyribonucleic acid.

FIG. 54 illustrates another example process for generating cell beads comprising complementary deoxyribonucleic acid.

FIG. 55A schematically depicts an example droplet comprising a cell bead; FIG. 55B schematically depicts an example first cell bead comprising a second cell bead.

FIGS. 56A-B schematically (FIG. 56A) and photographically (FIG. 56B) depict an example method for generating a cell bead in cell bead.

FIG. 64A illustrates a method for the in-partition transposition of sequencing adaptors into native chromatin while FIG. 64B illustrates a method for the in-bulk production of a next-generation sequencing compatible library from the fragments generated in FIG. 64A.

FIG. 65A discloses SEQ ID NOS 69-71 and 70, respectively, in order of appearance. FIG. 65B discloses SEQ ID NOS 72-74 and 73, respectively, in order of appearance.

FIG. 67A illustrates a method for the in-partition ligation of forked adaptors onto fragments of native chromatin generated by an in-partition transposition reaction. FIG. 67B illustrates a method for the in-bulk production of a next-generation sequencing compatible library from the fragments generated in FIG. 67A.

FIGS. 68A-68B illustrate additional examples of forked adaptors and transposon end sequence containing oligonucleotides. FIG. 68A discloses SEQ ID NOS 75, 76, 71, 76, 77, 78, 77, and 78, respectively, in order of appearance. FIG. 68B discloses SEQ ID NOS 79-81, 73, 77, 78, 77, and 78, respectively, in order of appearance.

FIGS. 77A-B illustrate an example of a transposase-nucleic acid complex showing a transposase, a first partially double-stranded oligonucleotide releasably attached to a gel bead, the first partially double-stranded oligonucleotide comprising a transposon end sequence, a barcode sequence, and a first primer sequence and a second partially double-stranded oligonucleotide comprising a transposon end sequence and a second primer sequence. In FIG. 77B, the first and the second primer sequence are the same.

FIG. 79A illustrates a partially double-stranded oligonucleotide releasably attached to a gel bead, the first strand comprising a transposon end sequence, a barcode sequence, and a first primer sequence and a second strand comprising a sequence complementary to the transposon end sequence. FIG. 79B illustrates a partially double-stranded oligonucleotide releasably attached to a gel bead, the first strand comprising a transposon end sequence and a barcode sequence and the second strand comprising a sequence complementary to the transposon end sequence.

FIG. 81A illustrates an exemplary transposase-nucleic acid complex showing a transposase, a first double-stranded oligonucleotide comprising a transposon end sequence and a second double-stranded oligonucleotide comprising a transposon end sequence. FIG. 81B illustrates an exemplary barcoded adaptor comprising a transposon end sequence, a barcode sequence, and a primer sequence releasably attached to a gel bead.

FIG. 82A illustrates an exemplary transposase-nucleic acid complex showing a transposase, a first double-stranded oligonucleotide comprising a transposon end sequence and a first primer sequence and a second double-stranded oligonucleotide comprising a transposon end sequence and a second primer sequence. FIG. 82B illustrates an example of a barcoded adaptor comprising an adapter sequence, a barcode sequence, and a sequence complementary to the first primer sequence. FIGS. 82C-D illustrates an example of a barcoding scheme.

FIGS. 83A-B illustrate an example of a barcode oligonucleotide and combination bulk/in-partition barcoding scheme.

FIG. 85A illustrates an example of a barcode oligonucleotide; FIG. 85B illustrates an example of a combination of bulk/in-partition barcoding scheme using CRISPR/Cas-9 mediated cleavage; FIG. 85C illustrates an example of an in-partition barcoding scheme using CRISPR/Cas-9 mediated cleavage.

FIGS. 86A-C illustrate an example of a barcoding scheme. FIG. 86A illustrates an example of a forked barcode oligonucleotide; FIG. 86B illustrates an example of a combination of bulk/in-partition barcoding scheme using CRISPR/Cas-9 mediated cleavage; FIG. 86C illustrates an example of an in-partition barcoding scheme using CRISPR/Cas-9 mediated cleavage.

FIG. 87A illustrates an example for use in amplification. FIG. 87B illustrates an example for use in ligation.

FIG. 103A shows exemplary data for COLO829 human skin melanoma cells in a population of cells while FIG. 103B shows exemplary data for breast tumor cells in a population of cells.

FIG. 104A shows exemplary data detecting a 5% mixture of MKN-45 cells while FIG. 104B shows exemplary data detecting a 1% mixture of MKN-45 cells.

Figure 110:
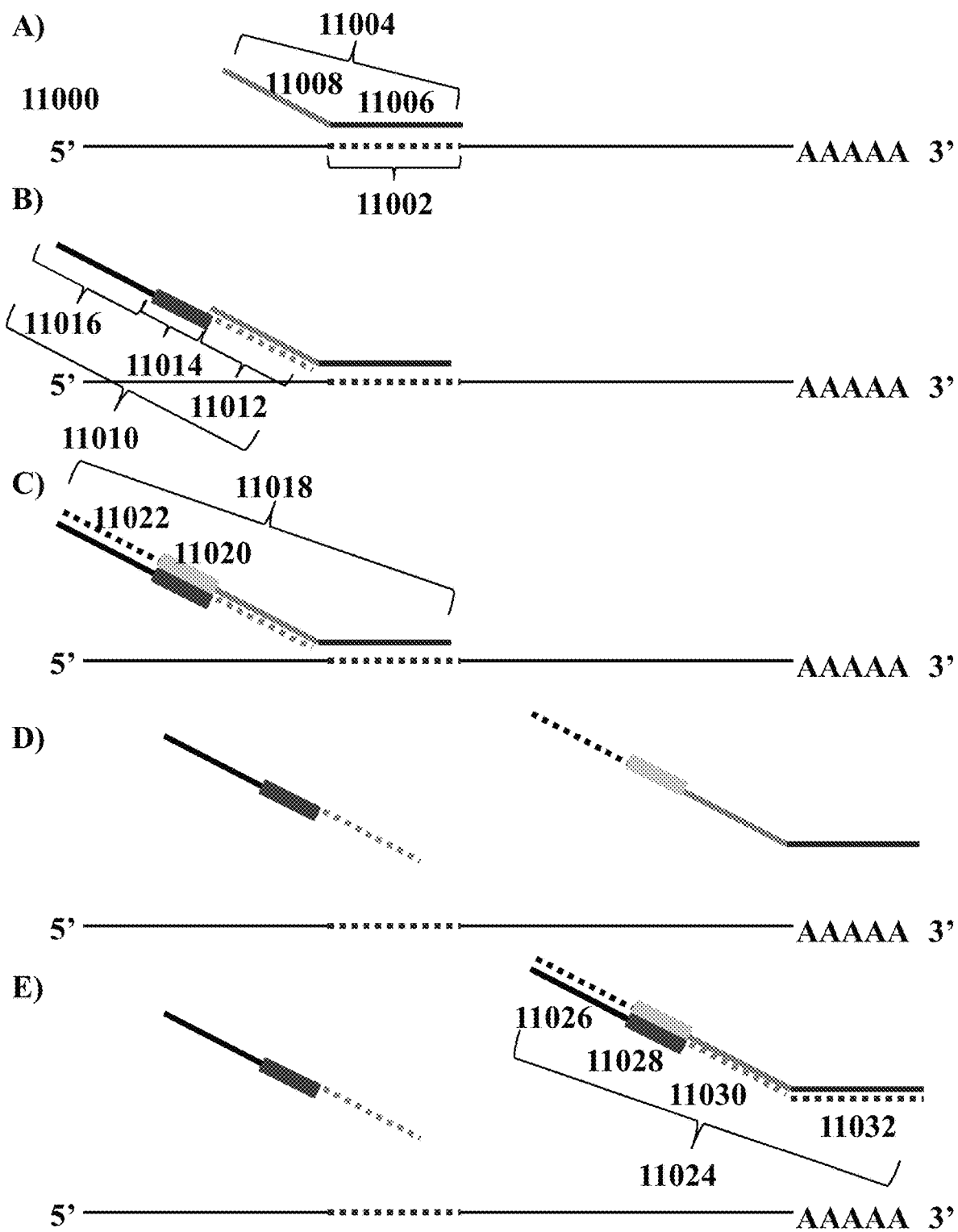

FIG. 110 schematically illustrates a method of analyzing a nucleic acid molecule. Panel 110A illustrates a probe hybridized to a nucleic acid molecule. Panel 110B illustrates a nucleic acid barcode molecule hybridized to a sequence of the probe and Panel 110C illustrates extension of the probe to an end of the nucleic acid barcode molecule. Panel 110D illustrates denaturation of an extended nucleic acid molecule from the nucleic acid barcode molecule and the nucleic acid molecule. Panel 110E illustrates amplification of the extended nucleic acid molecule.

Figure 111:
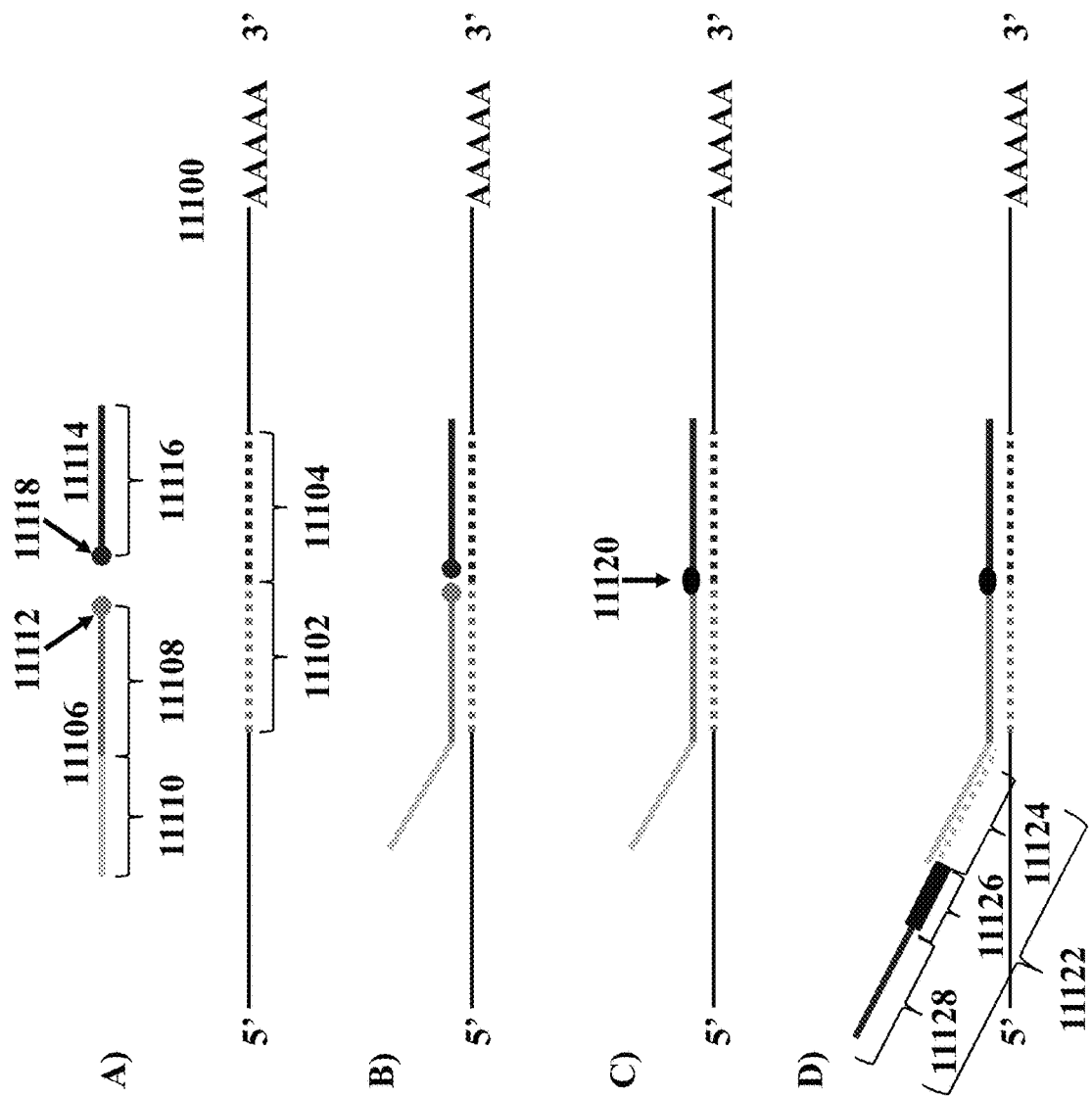

FIG. 111 schematically illustrates a method of analyzing a nucleic acid molecule. Panel 111A illustrates a nucleic acid molecule, a first probe, and a second probe, and Panel 111B illustrates a nucleic acid molecule with the first and second probes hybridized thereto. Panel 111C illustrates a probe-linked nucleic acid molecule, while Panel 111D illustrates a barcoded probe-linked nucleic acid molecule.

Figure 112:
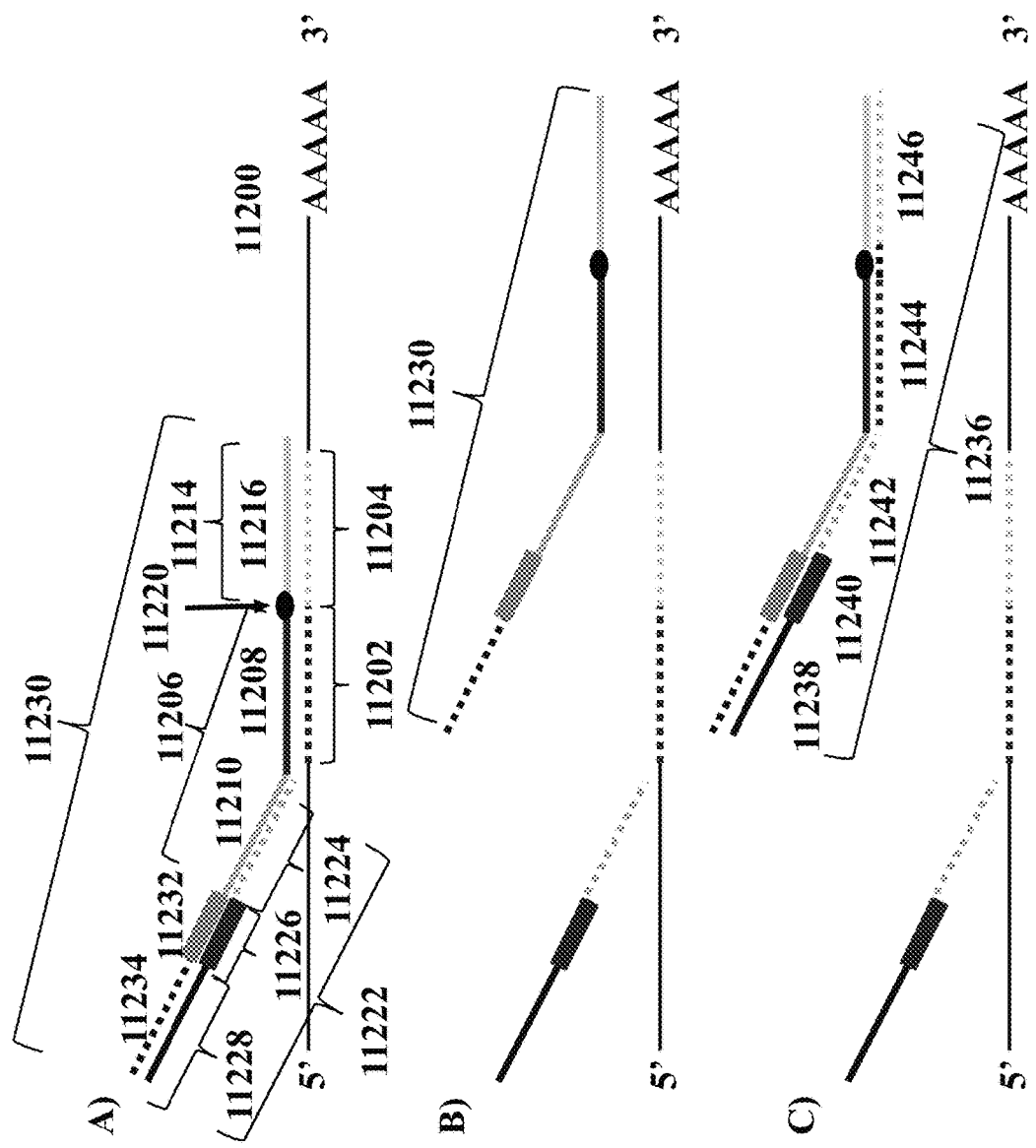

FIG. 112 schematically illustrates a method of analyzing a nucleic acid molecule. Panel 112A illustrates extension of a probe of a barcoded probe-linked nucleic acid molecule to an end of a nucleic acid barcode molecule. Panel 112B illustrates denaturation of an extended nucleic acid molecule from the nucleic acid barcode molecule and the nucleic acid molecule. Panel 112C illustrates amplification of the extended nucleic acid molecule.

Figure 113:
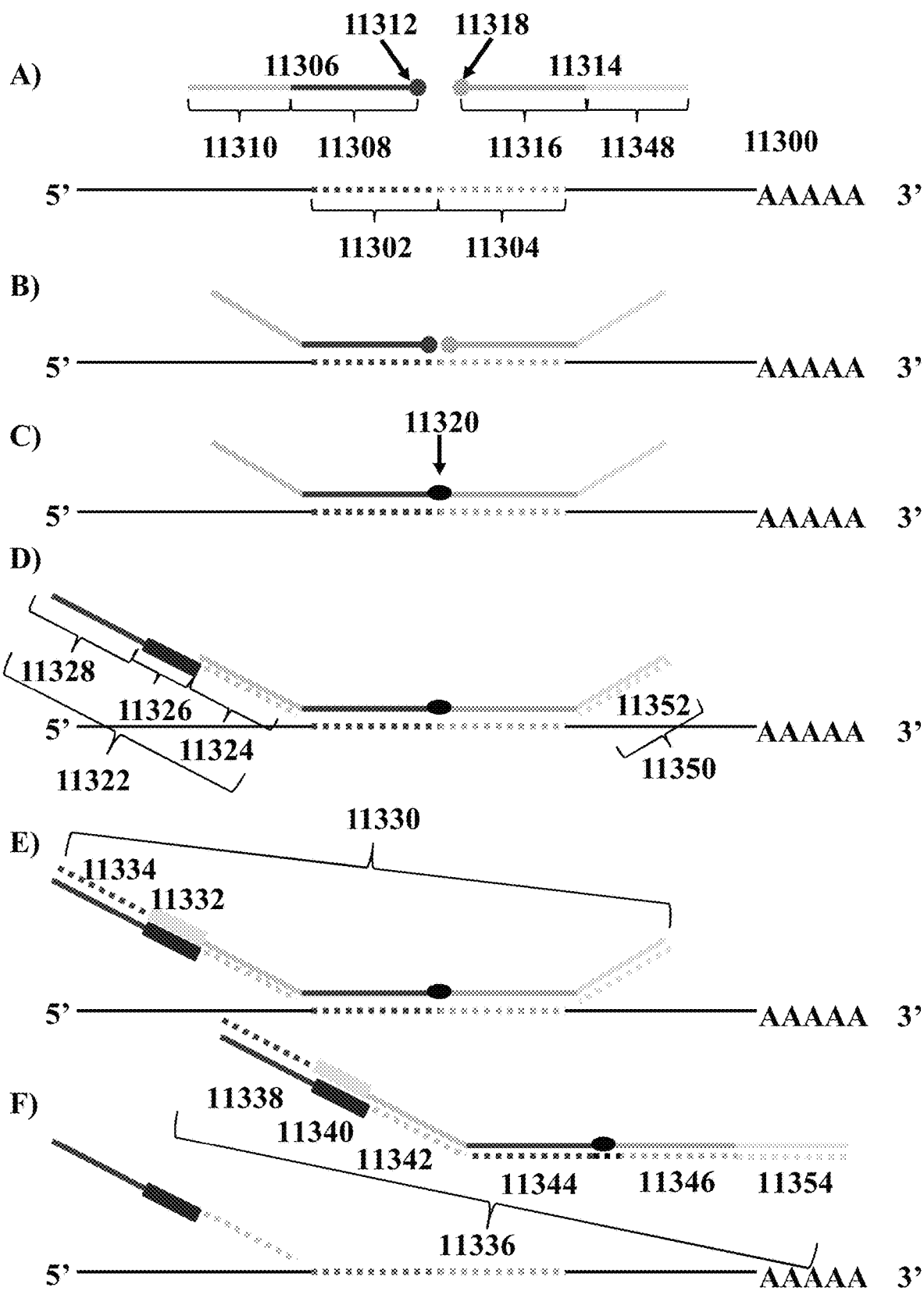

FIG. 113 schematically illustrates a method of analyzing a nucleic acid molecule. Panel 113A illustrates a nucleic acid molecule, a first probe, and a second probe, and Panel 113B illustrates a nucleic acid molecule with the first and second probes hybridized thereto. Panel 113C illustrates a probe-linked nucleic acid molecule, while Panel 113D illustrates a barcoded probe-linked nucleic acid molecule. Panel 113E illustrates extension of a probe of a barcoded probe-linked nucleic acid molecule to an end of a nucleic acid barcode molecule. Panel 113F illustrates denaturation and amplification of an extended nucleic acid molecule.

Figure 114:
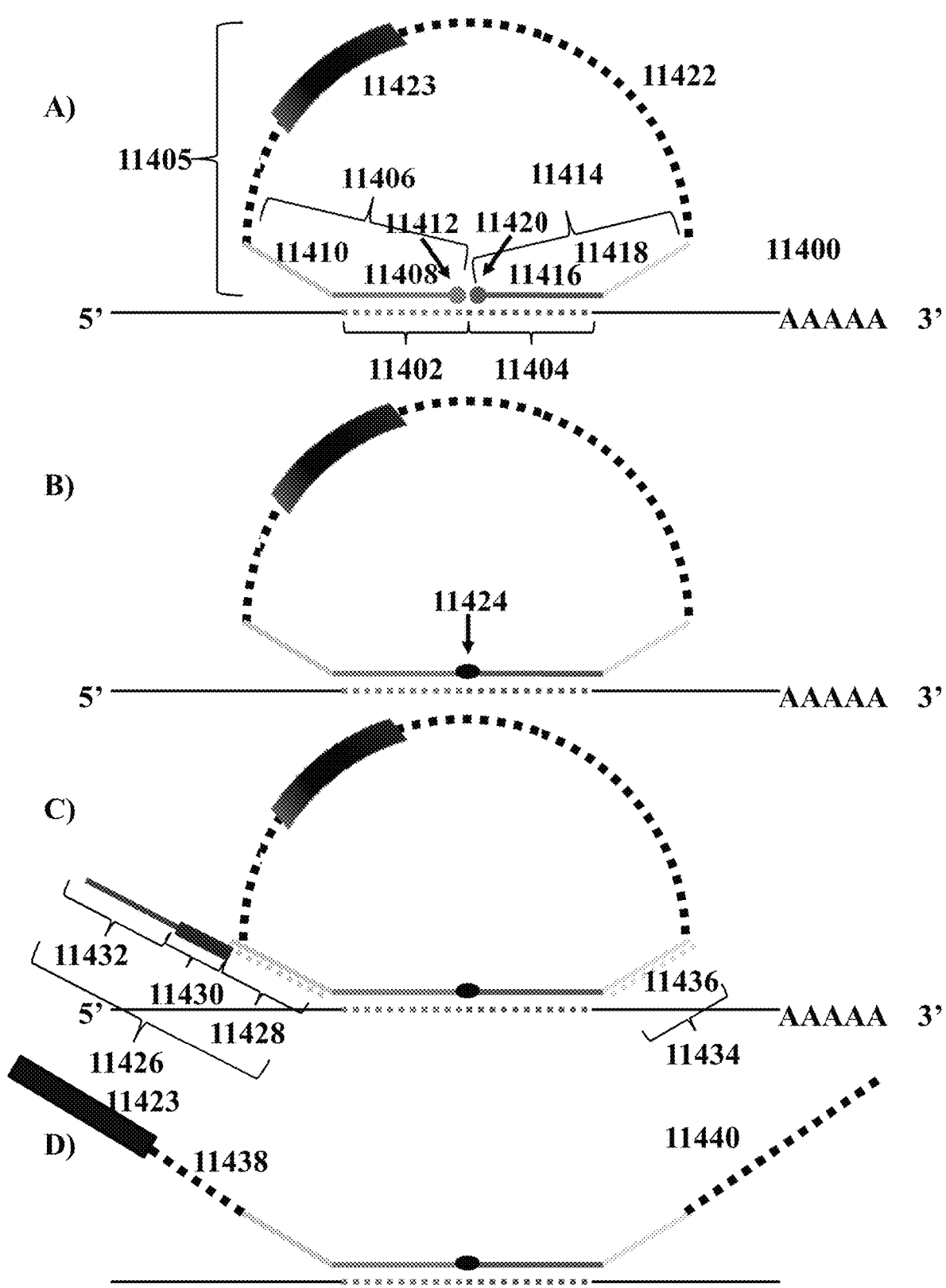

FIG. 114 schematically illustrates a method of analyzing a nucleic acid molecule using a circular probe. Panel 114A illustrates a circular probe molecule comprising first and second probe ends hybridized to a nucleic acid molecule. Panel 114B illustrates a circular probe-linked nucleic acid molecule. Panel 114C illustrates generation of a barcoded circular probe-linked nucleic acid molecule, while Panel 114D illustrates cleavage of the circular probe of the circular probe-linked nucleic acid molecule.

Figure 115:
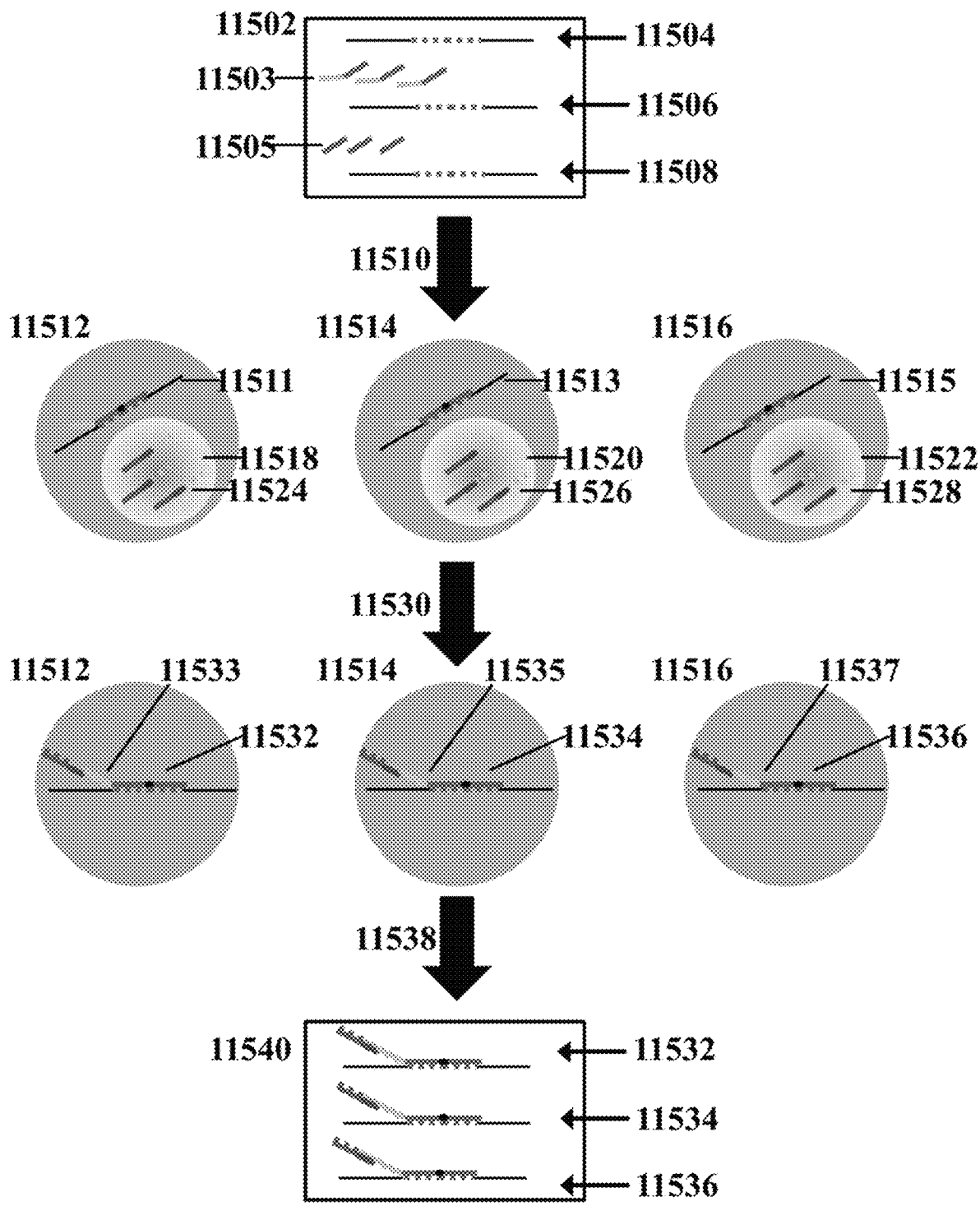

FIG. 115 shows a sample workflow for analysis of a plurality of nucleic acid molecules involving co-partitioning nucleic acid molecules with barcoded beads within droplets.

Figure 116:
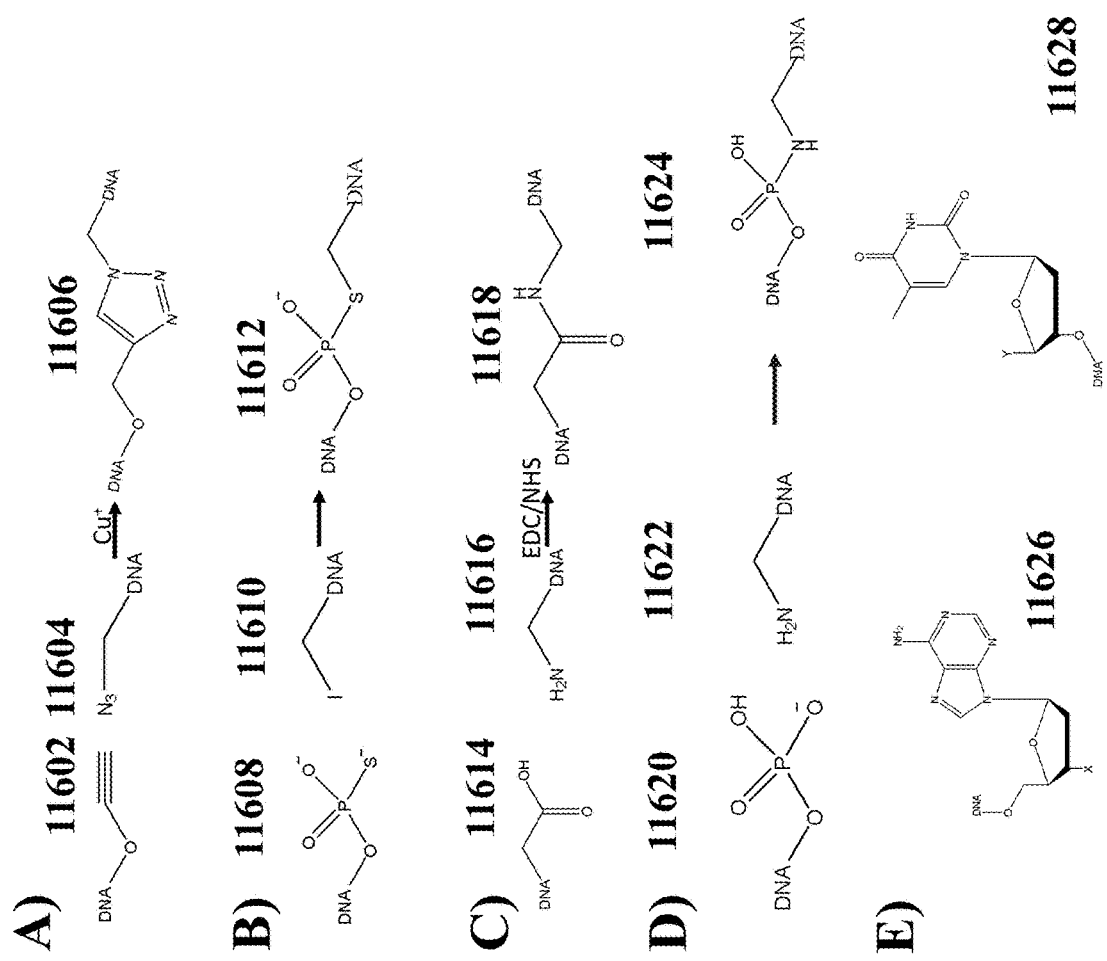

FIG. 116 shows various click chemistry approaches for nucleic acid ligation. Panel 116A illustrates a triazole bond. Panel 116B illustrates a phosphorothioate bond. Panel 116C illustrates an amide bond. Panel 116D illustrates a phosphoroamidate bond. Panel 116E illustrates a chemical comnjugation reaction of two chemical species.

Figure 117:
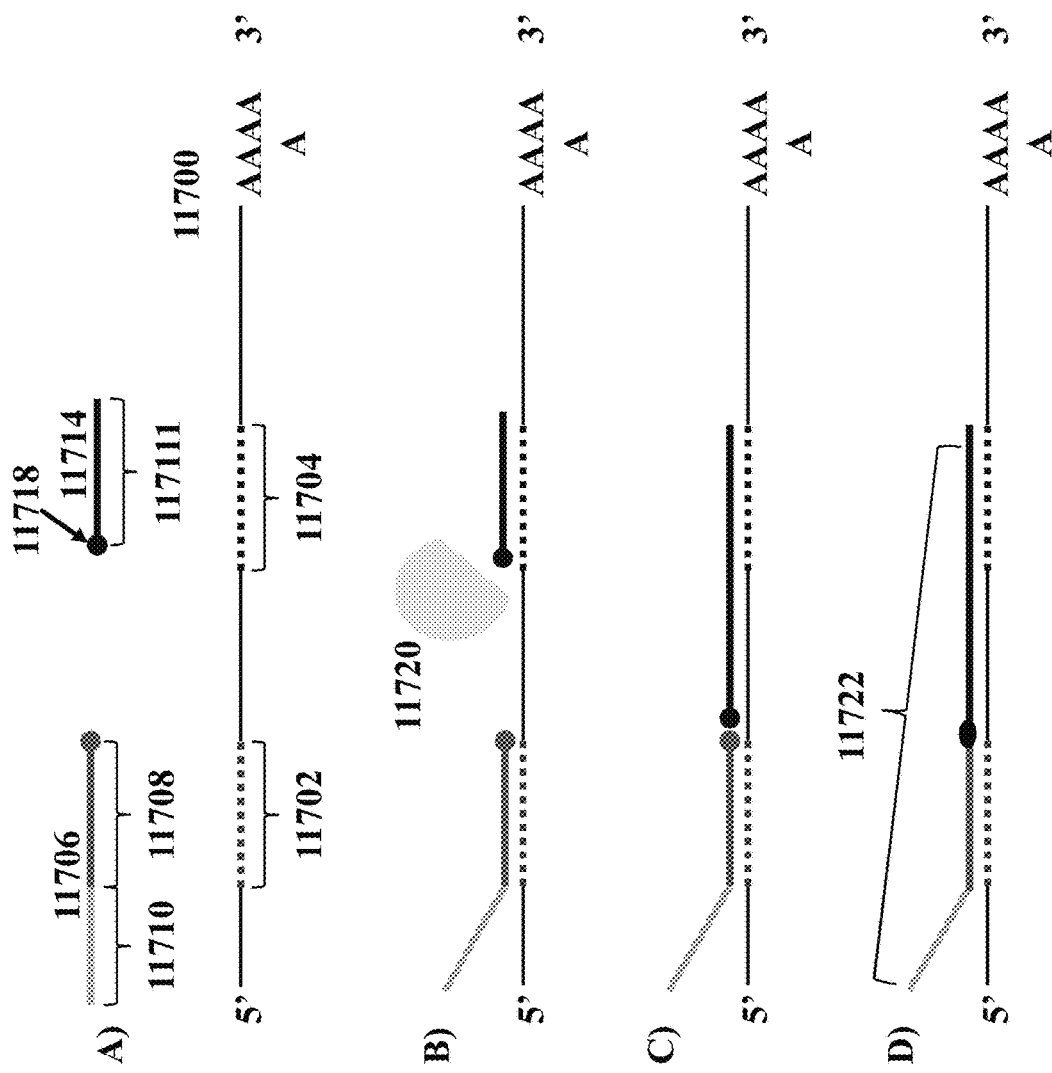

FIG. 117 shows schematically part of a method of analyzing a nucleic acid molecule. Panel 117A illustrates a nucleic acid molecule, a first probe, and a second probe, and Panel 117B illustrates a nucleic acid molecule with the first and second probes hybridized thereto and extension of the gap between probes. Panel 117C illustrates an extended nucleic acid molecule, and Panel 117D illustrates a probe-linked nucleic acid molecule.

Figure 118:
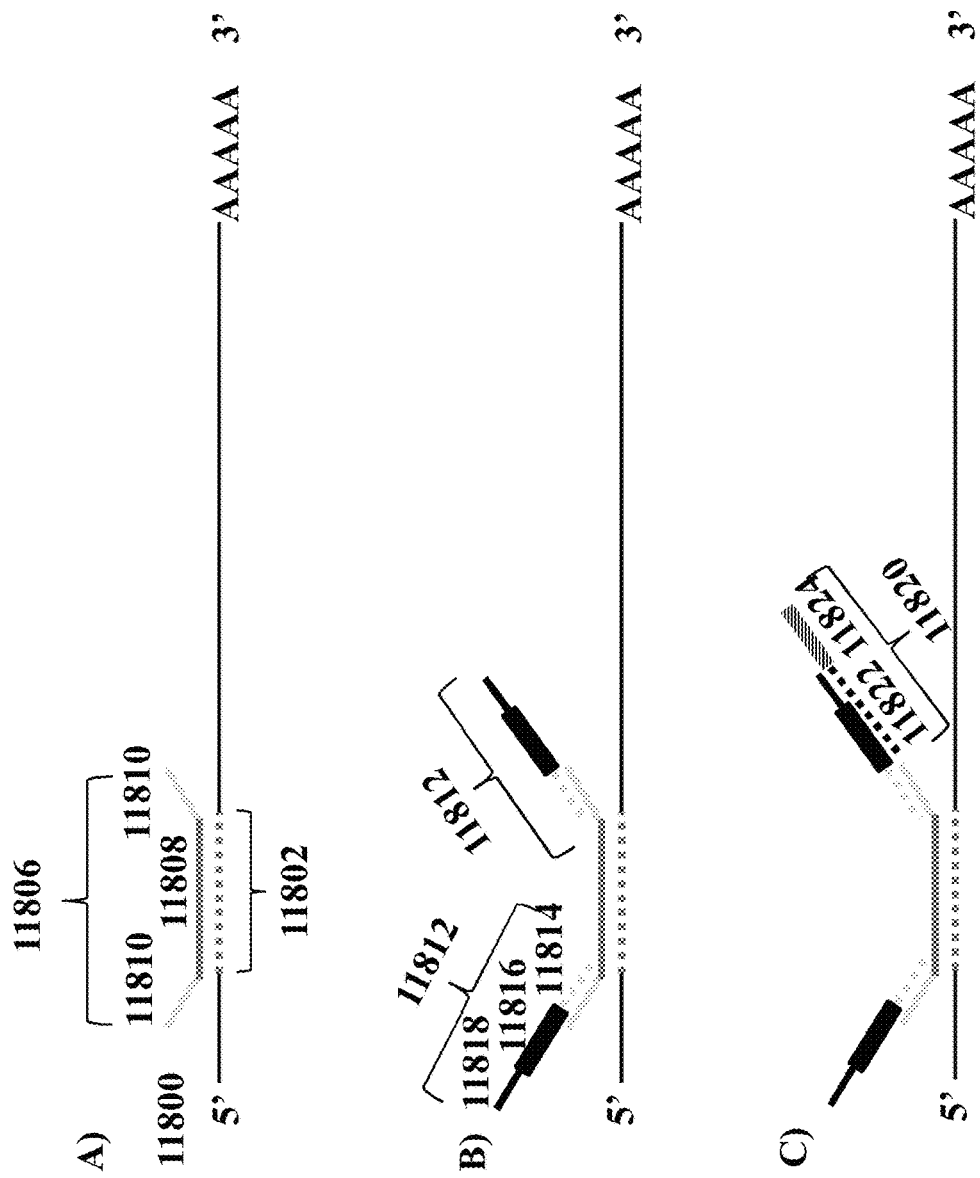

FIG. 118 illustrates schematically part of a method of analyzing a nucleic acid molecule. Panel 118A shows a nucleic acid molecule and a first probe. Panel 118B illustrates a nucleic acid molecule with the first probe hybridized thereto and a hybridization of an adaptor nucleic acid molecule to a sequence of the probe. Panel 118C illustrates hybridization of a barcode nucleic acid molecules to the adaptor nucleic acid molecule to generate a barcoded nucleic acid molecule.

Figure 119:
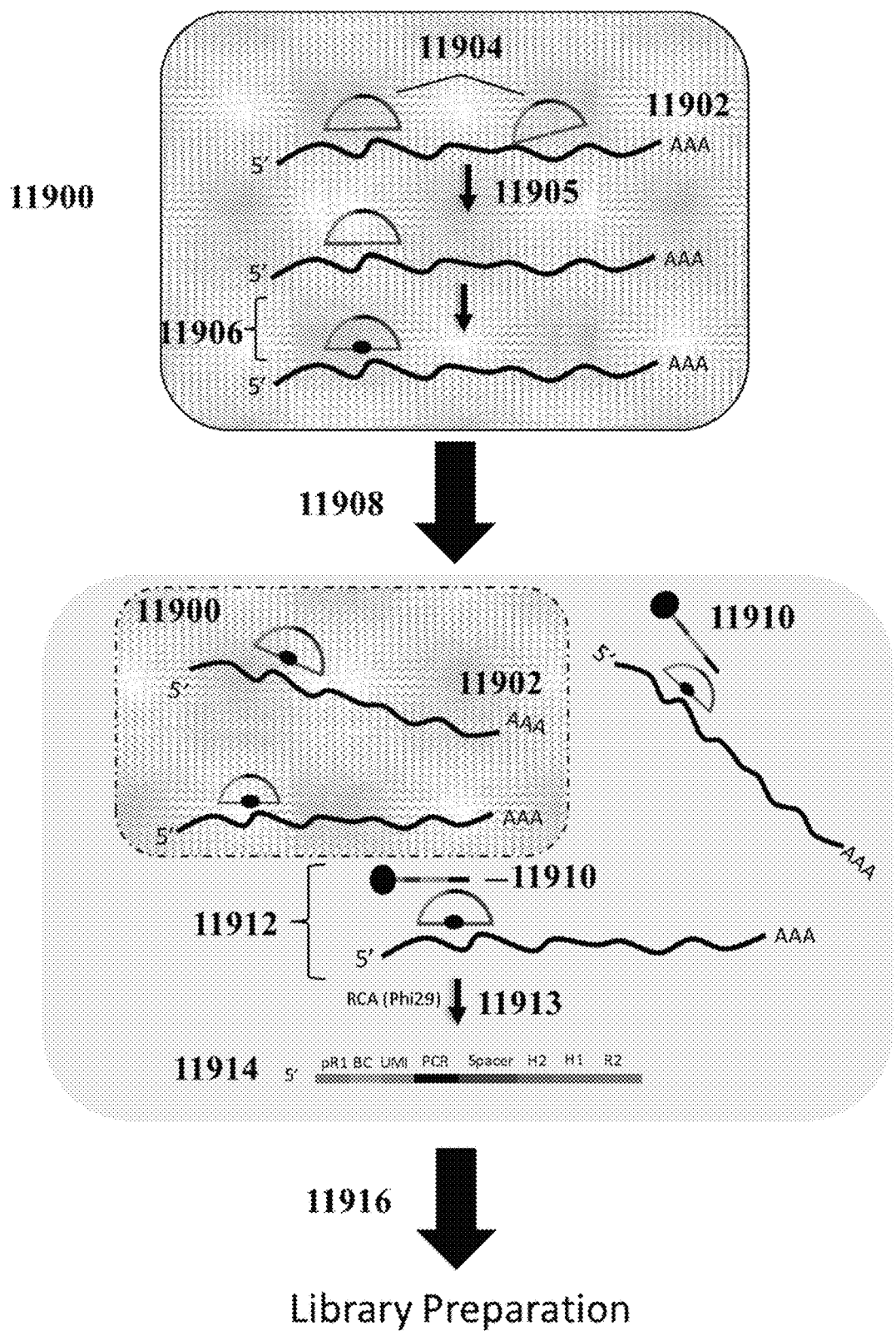

FIG. 119 schematically shows a method of analyzing a nucleic acid molecule.

Figure 120:
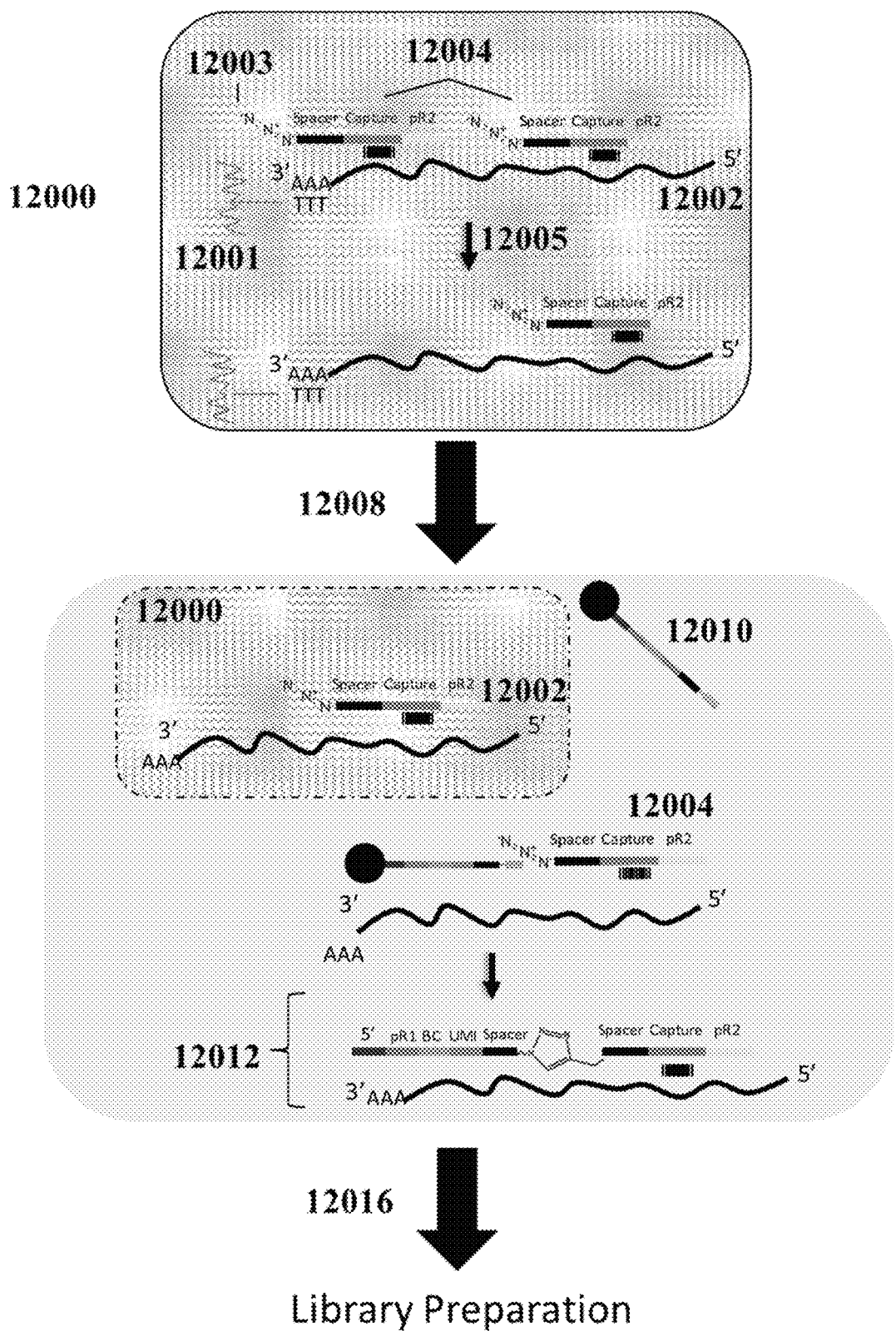

FIG. 120 schematically shows another example method of analyzing a nucleic acid molecule.

Figure 121:
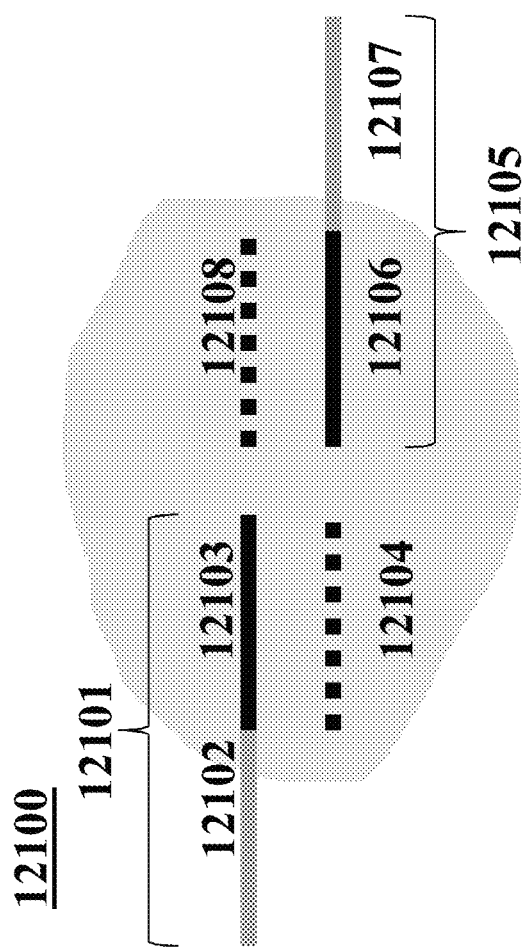

FIG. 121 illustrates a transposase-nucleic acid complex comprising a transposase, a first double-stranded oligonucleotide comprising a transposon end sequence and a first primer sequence and a second double-stranded oligonucleotide comprising a transposon end sequence and a second primer sequence.

Figure 122:
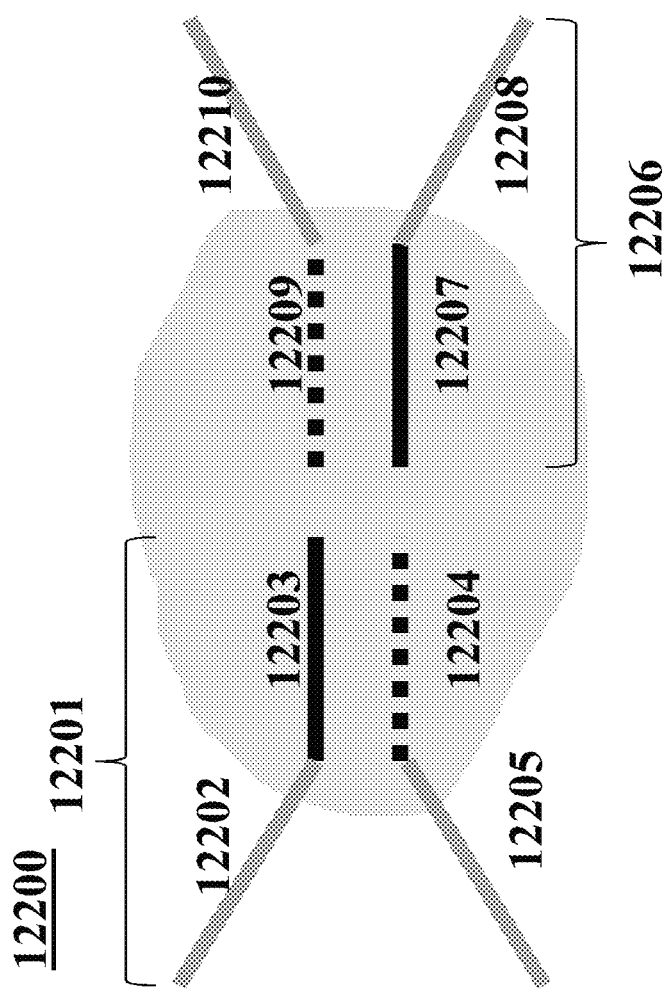

FIG. 122 illustrates a transposase-nucleic acid complex comprising a transposase, a first double-stranded oligonucleotide comprising a transposon end sequence and first and second primer sequences and a second double-stranded oligonucleotide comprising a transposon end sequence and third and fourth primer sequences.

Figure 123:
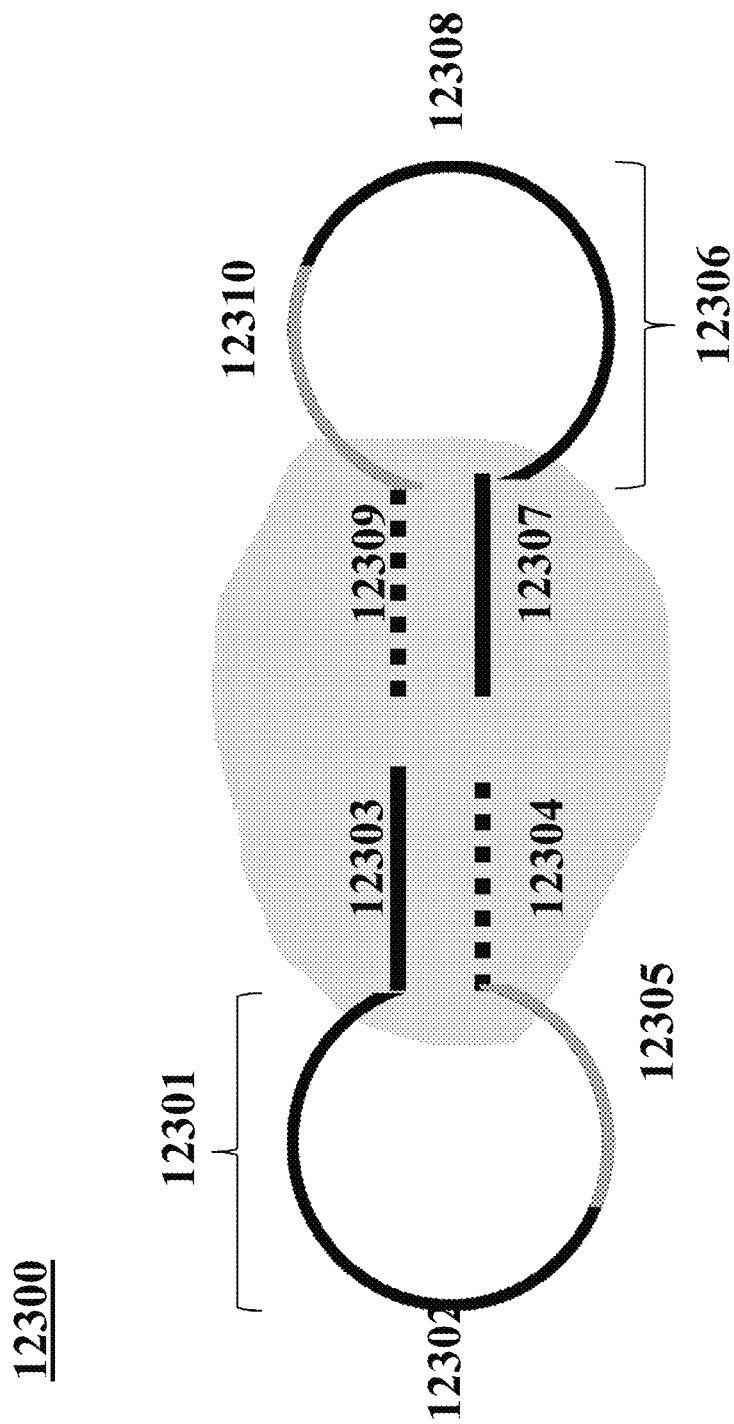

FIG. 123 illustrates a transposase-nucleic acid complex comprising a transposase, a first hairpin molecule, and a second hairpin molecule.

Figure 124:
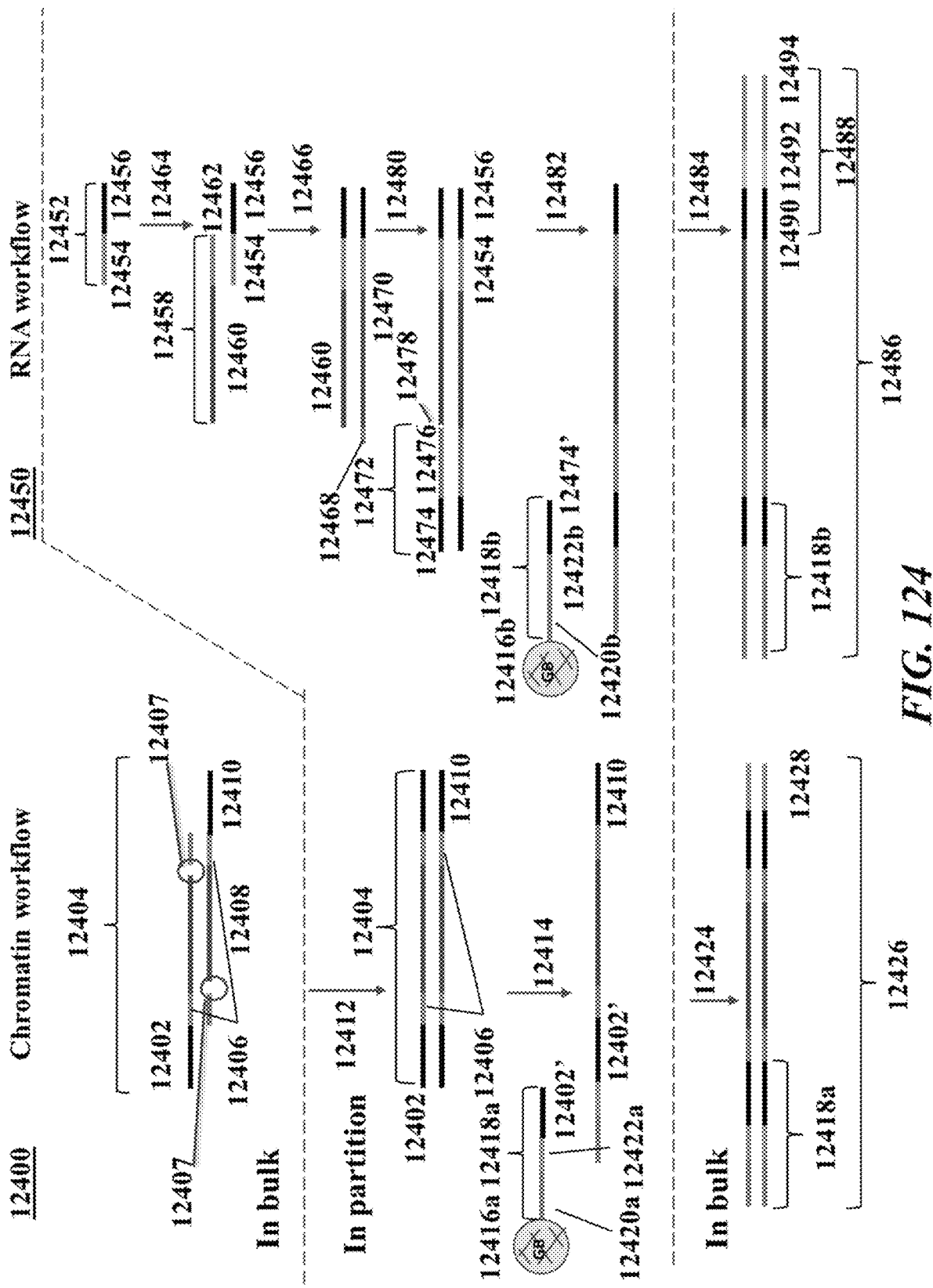

FIG. 124 illustrates a scheme for tandem ATAC ligation and RNA template switching.

Figure 125:
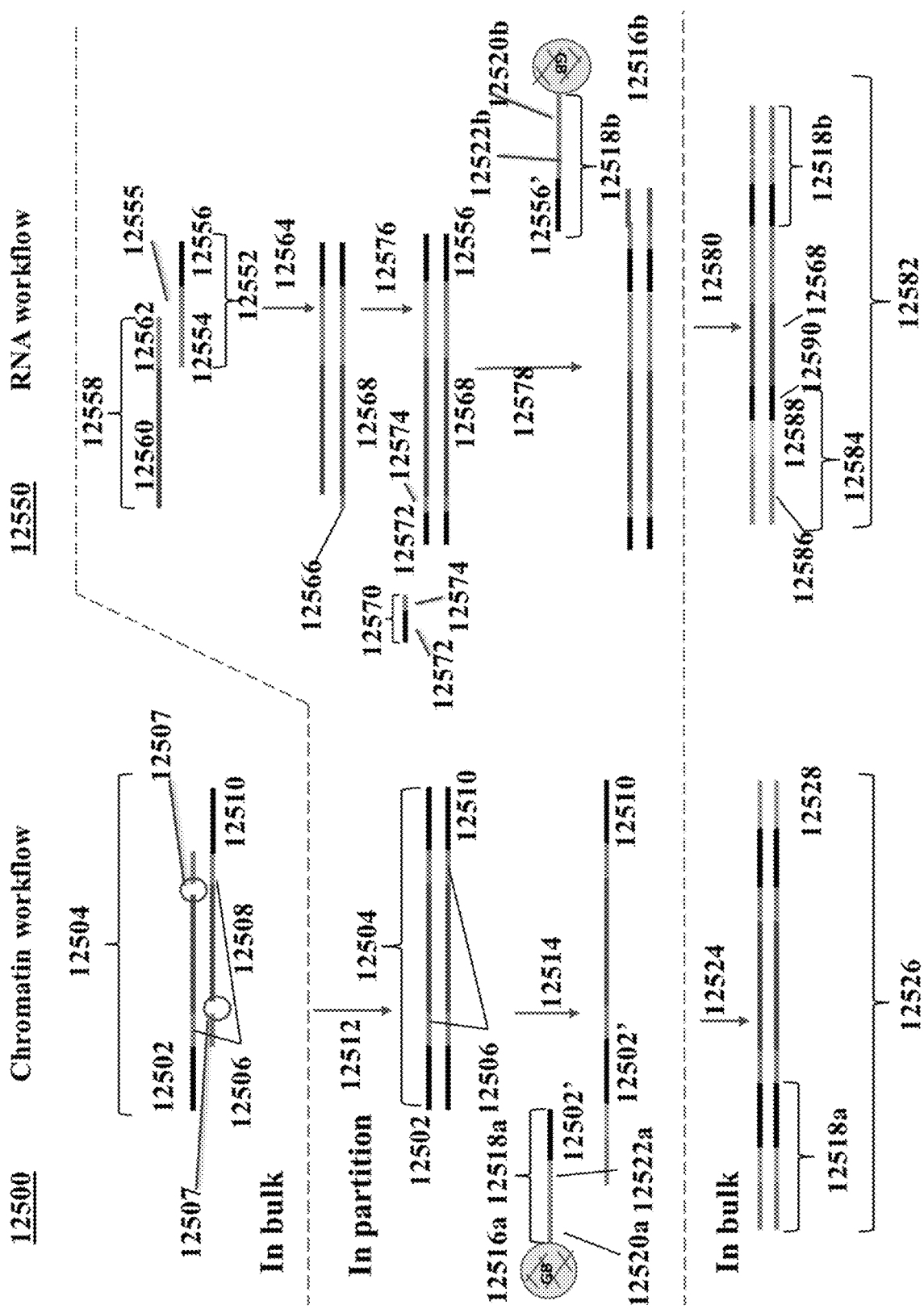

FIG. 125 illustrates an additional scheme for tandem ATAC ligation and RNA template switching.

Figure 126:
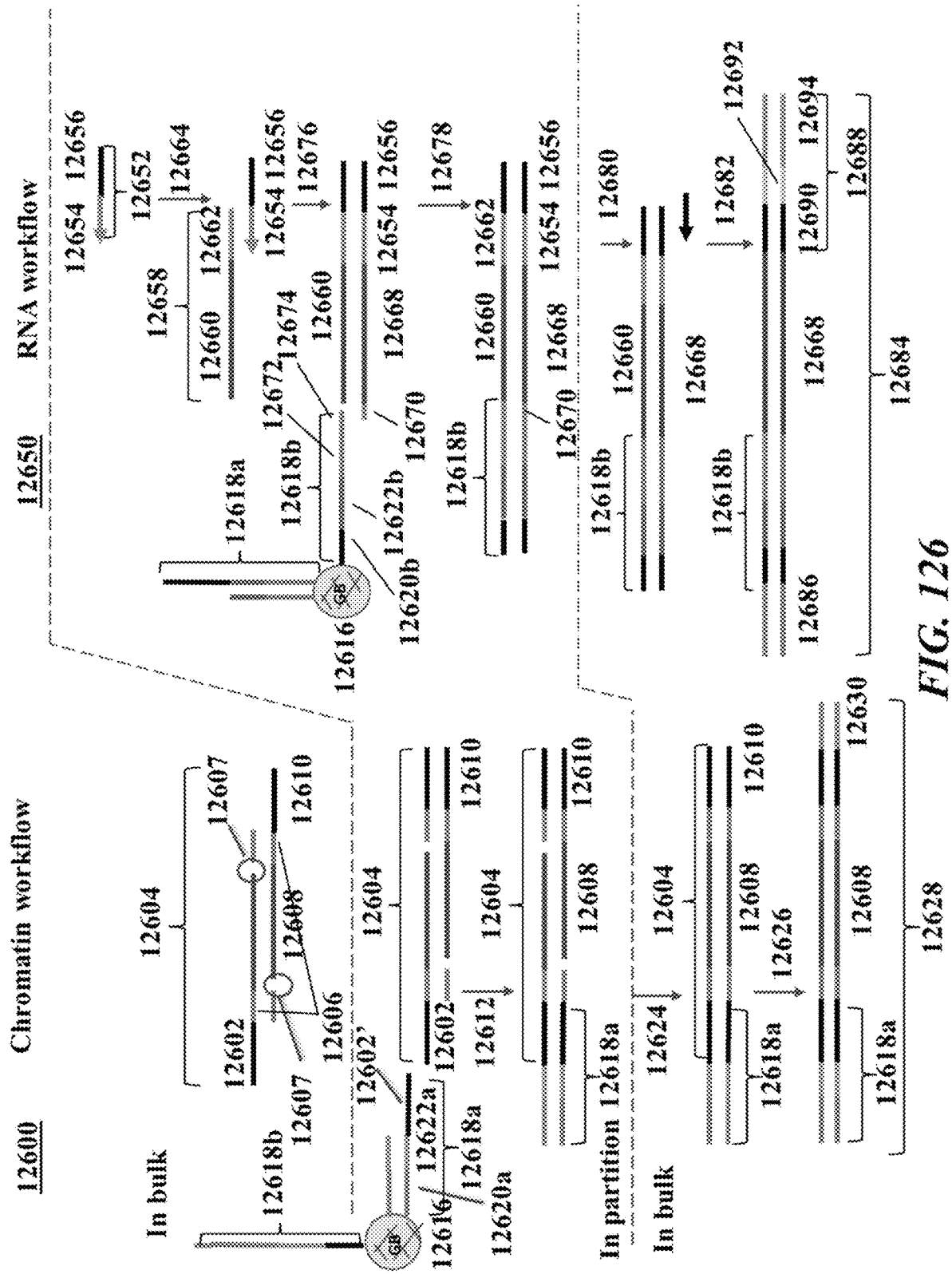

FIG. 126 illustrates an exemplary scheme for tandem ATAC ligation and RNA template switching.

Figure 127:
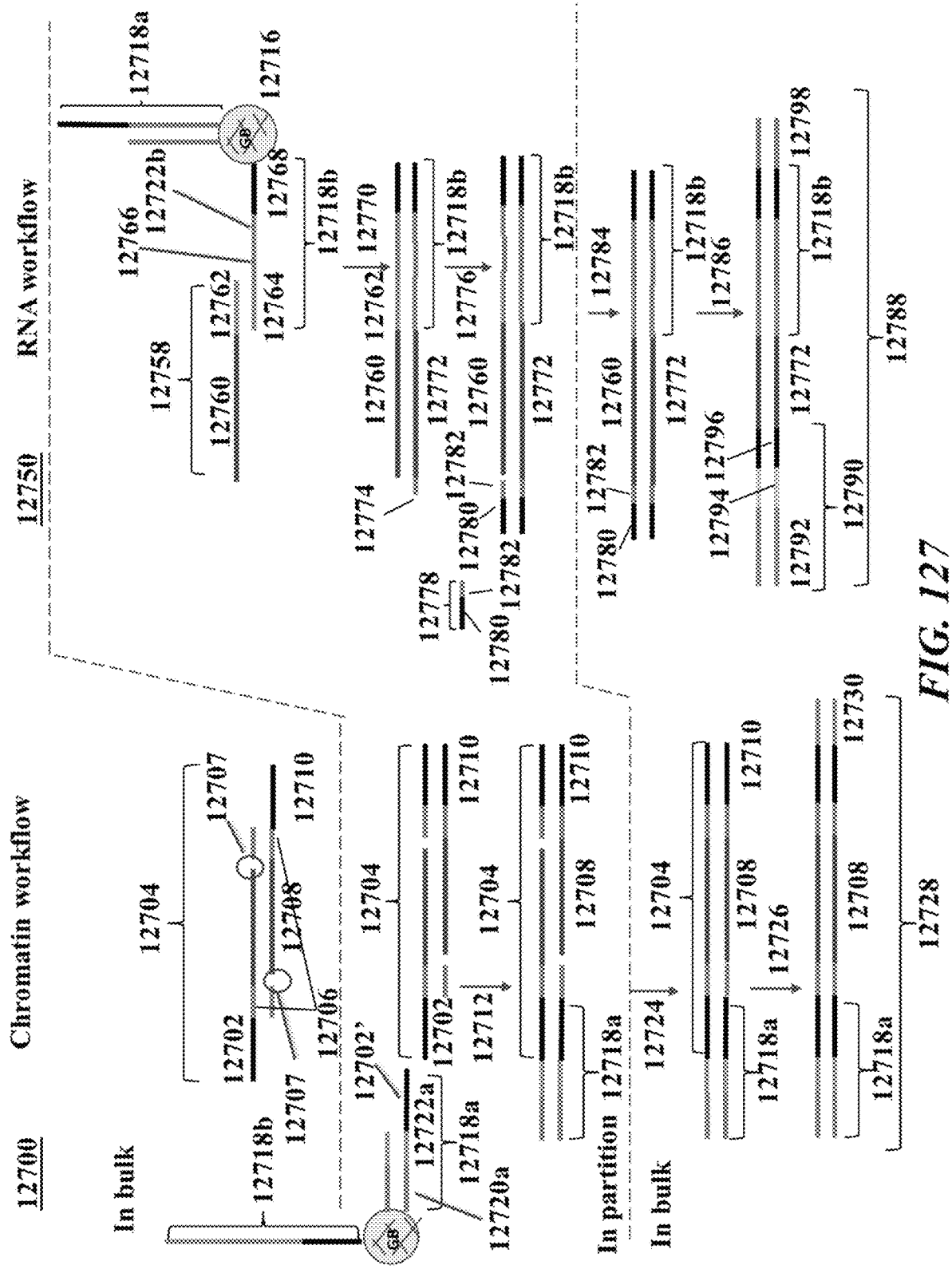

FIG. 127 illustrates an additional scheme for tandem ATAC ligation and RNA template switching.

Figure 128:
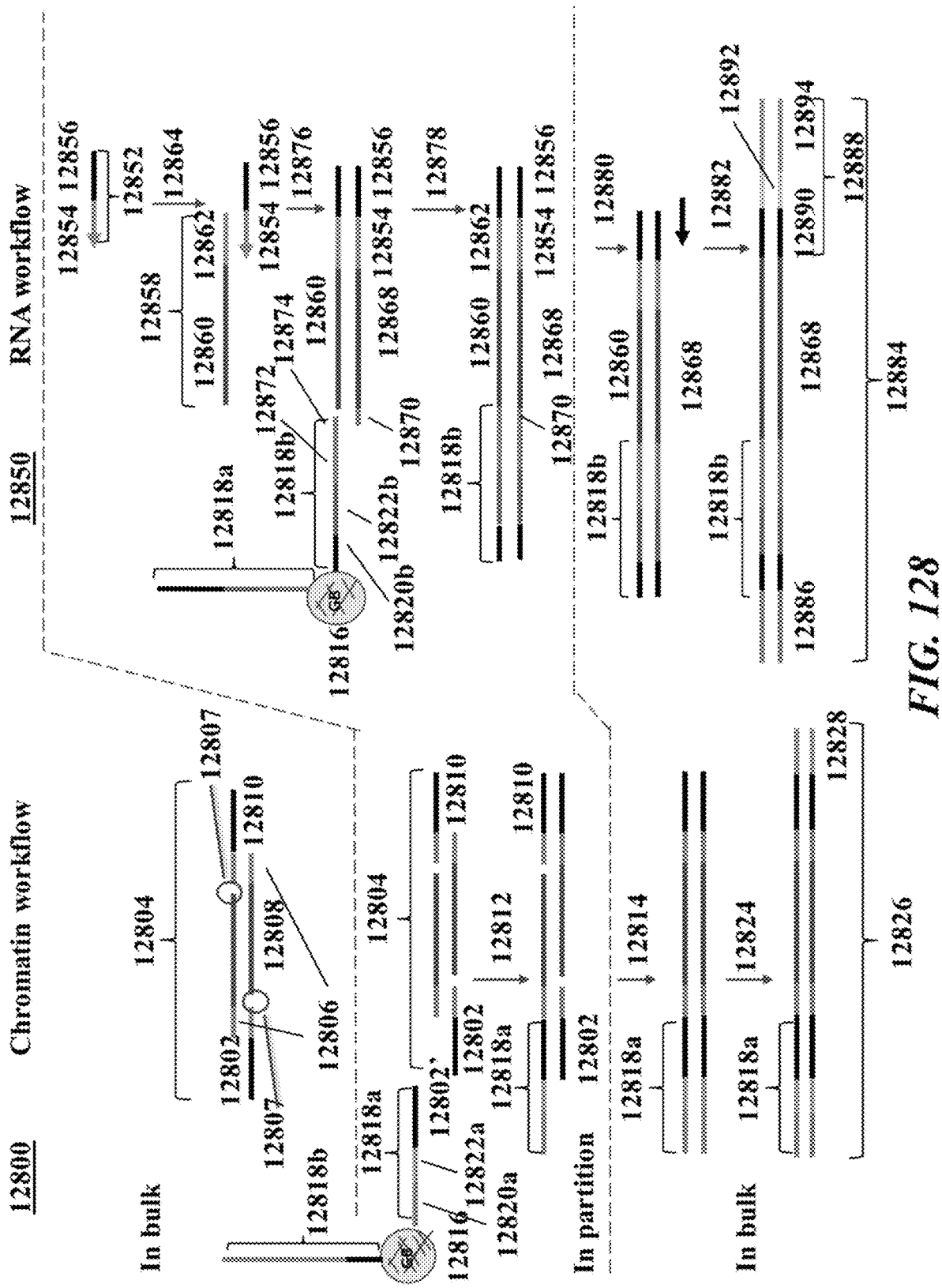

FIG. 128 illustrates an additional scheme for tandem ATAC ligation and RNA template switching.

Figure 129:
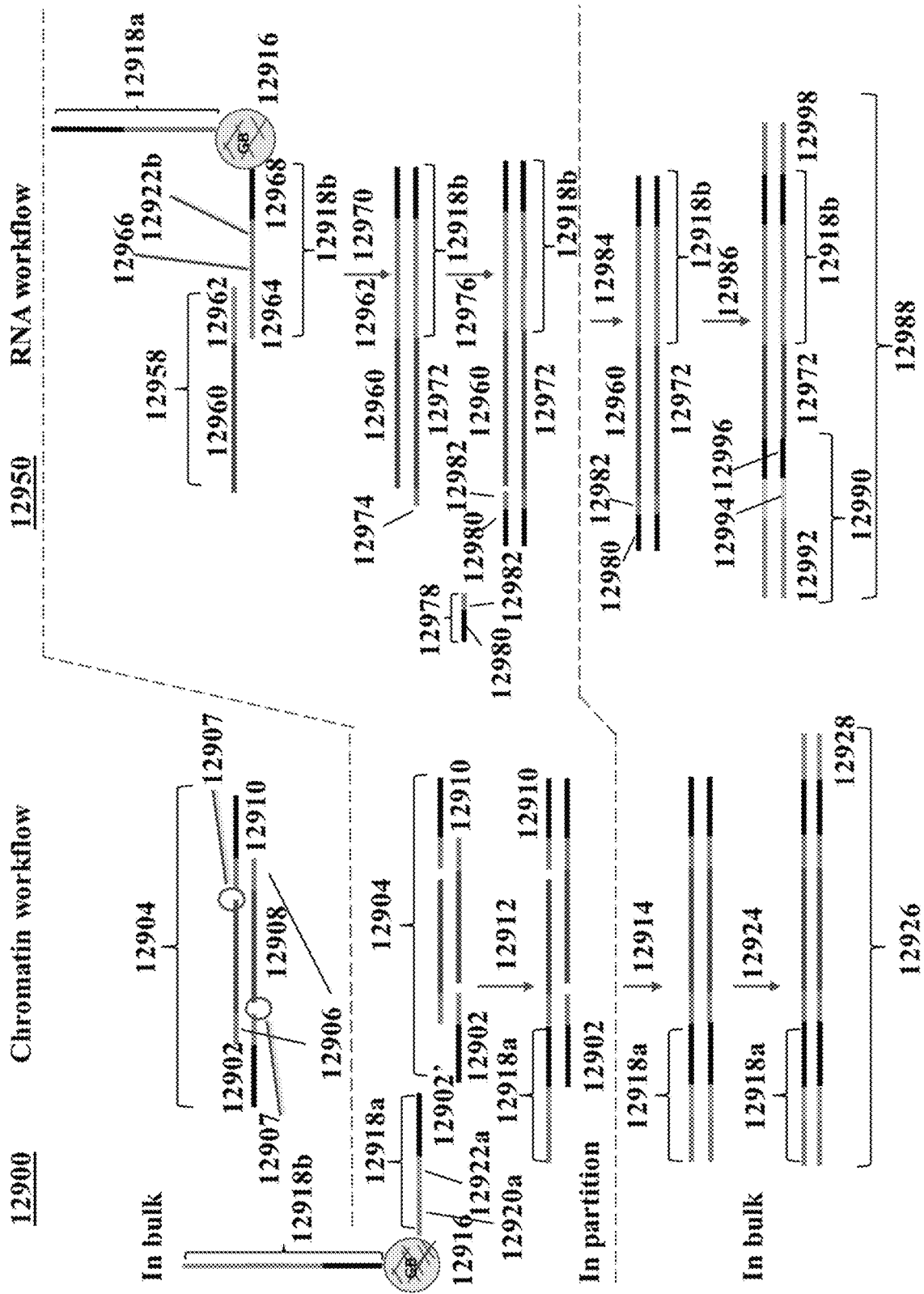

FIG. 129 illustrates an additional scheme for tandem ATAC ligation and RNA template switching.

Figure 130:
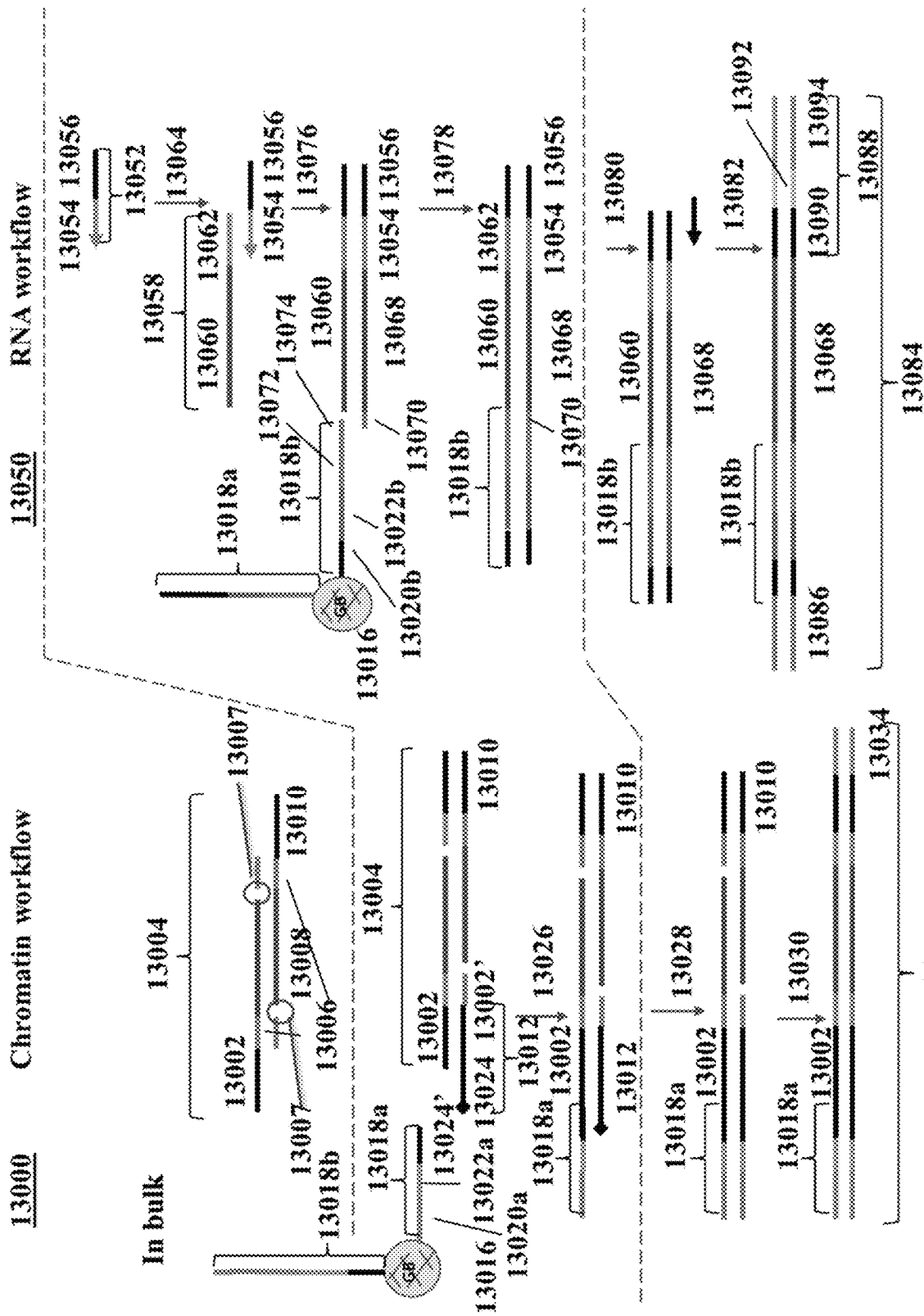

FIG. 130 illustrates an additional scheme for tandem ATAC ligation and RNA template switching.

Figure 131:
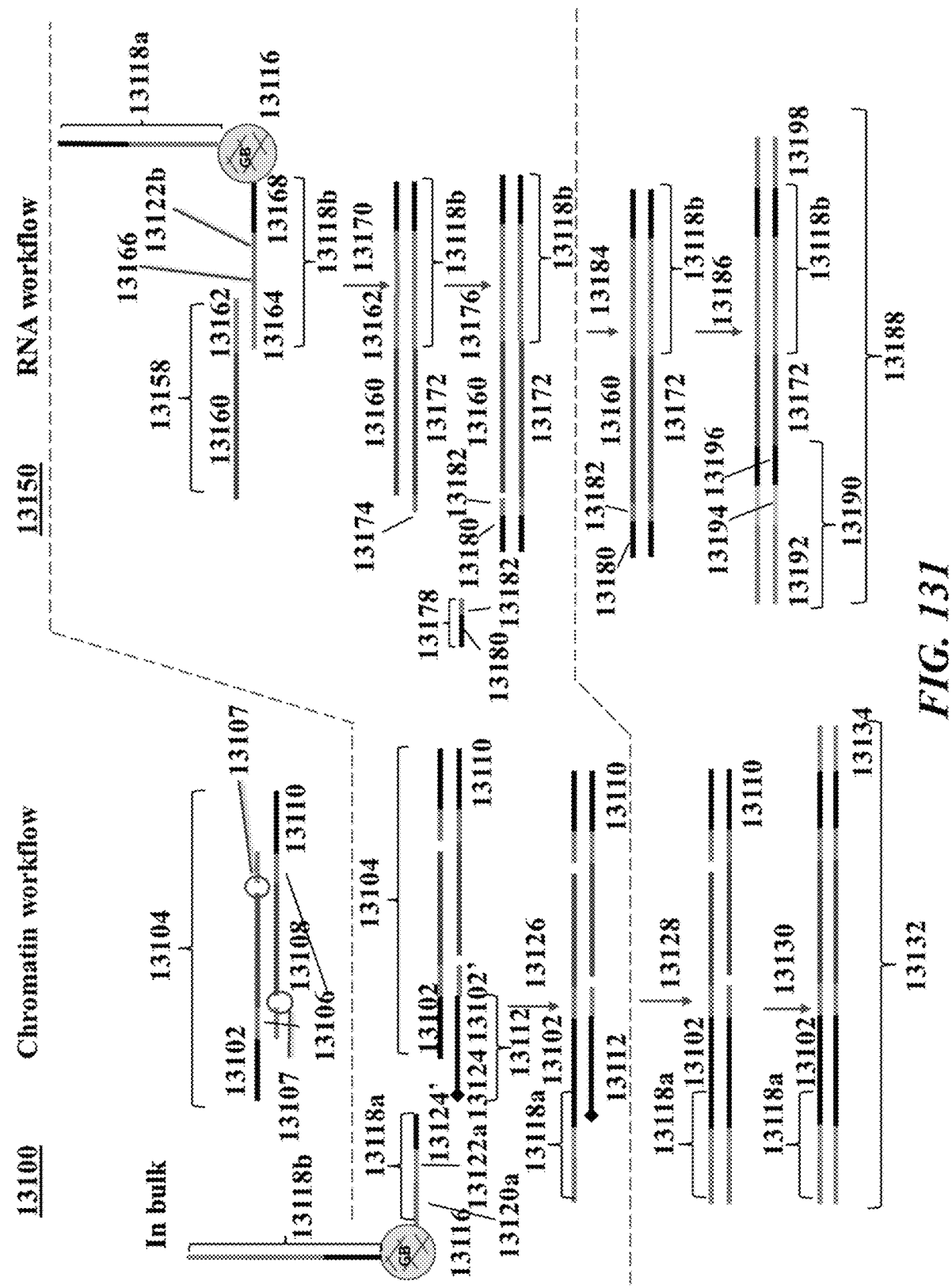

FIG. 131 illustrates an additional scheme for tandem ATAC ligation and RNA template switching.

Figure 132:
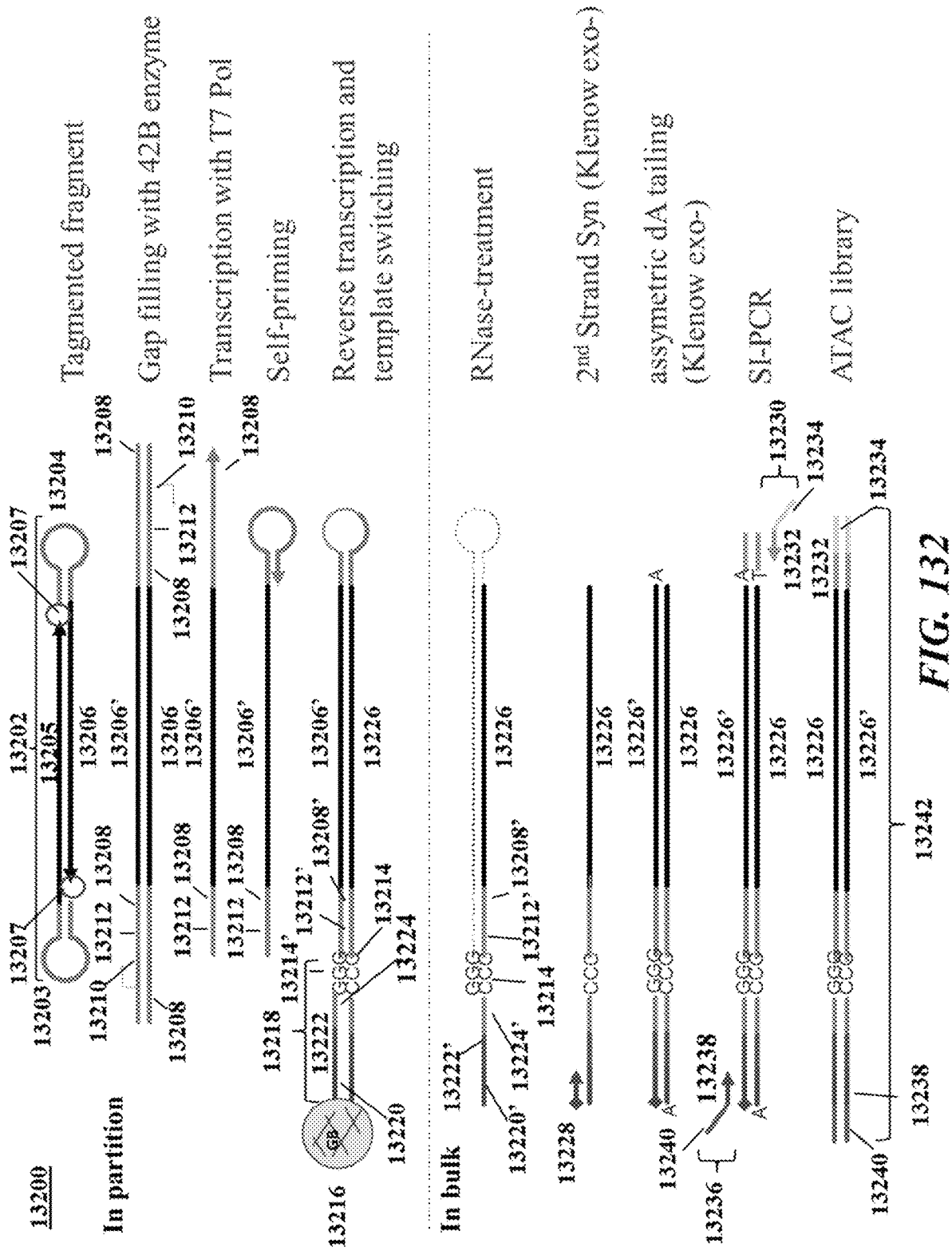

FIG. 132 illustrates a scheme for T7 mediated linear amplification.

Figure 133:
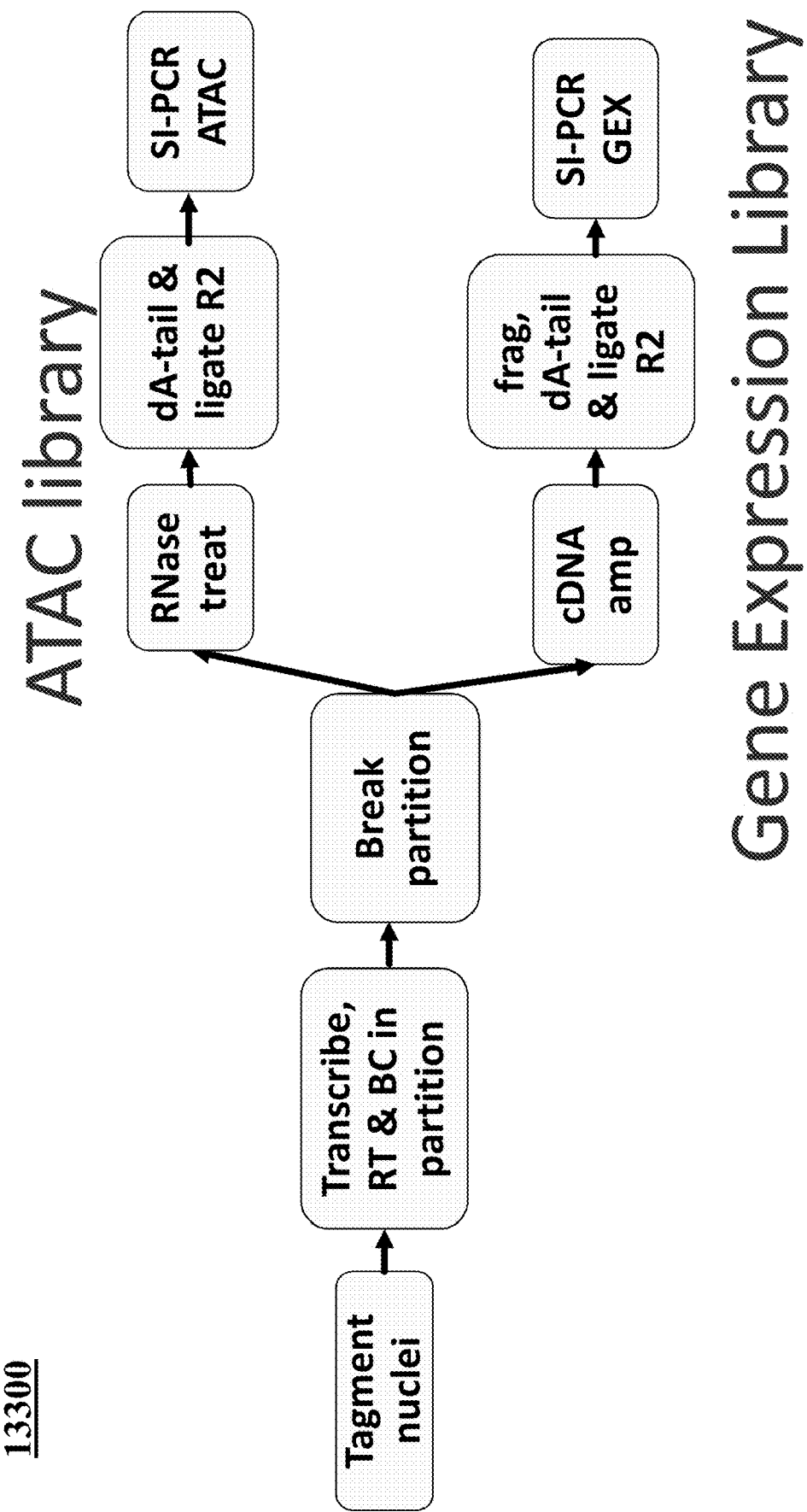

FIG. 133 shows a modified workflow T7 mediated linear amplification.

Figure 134:
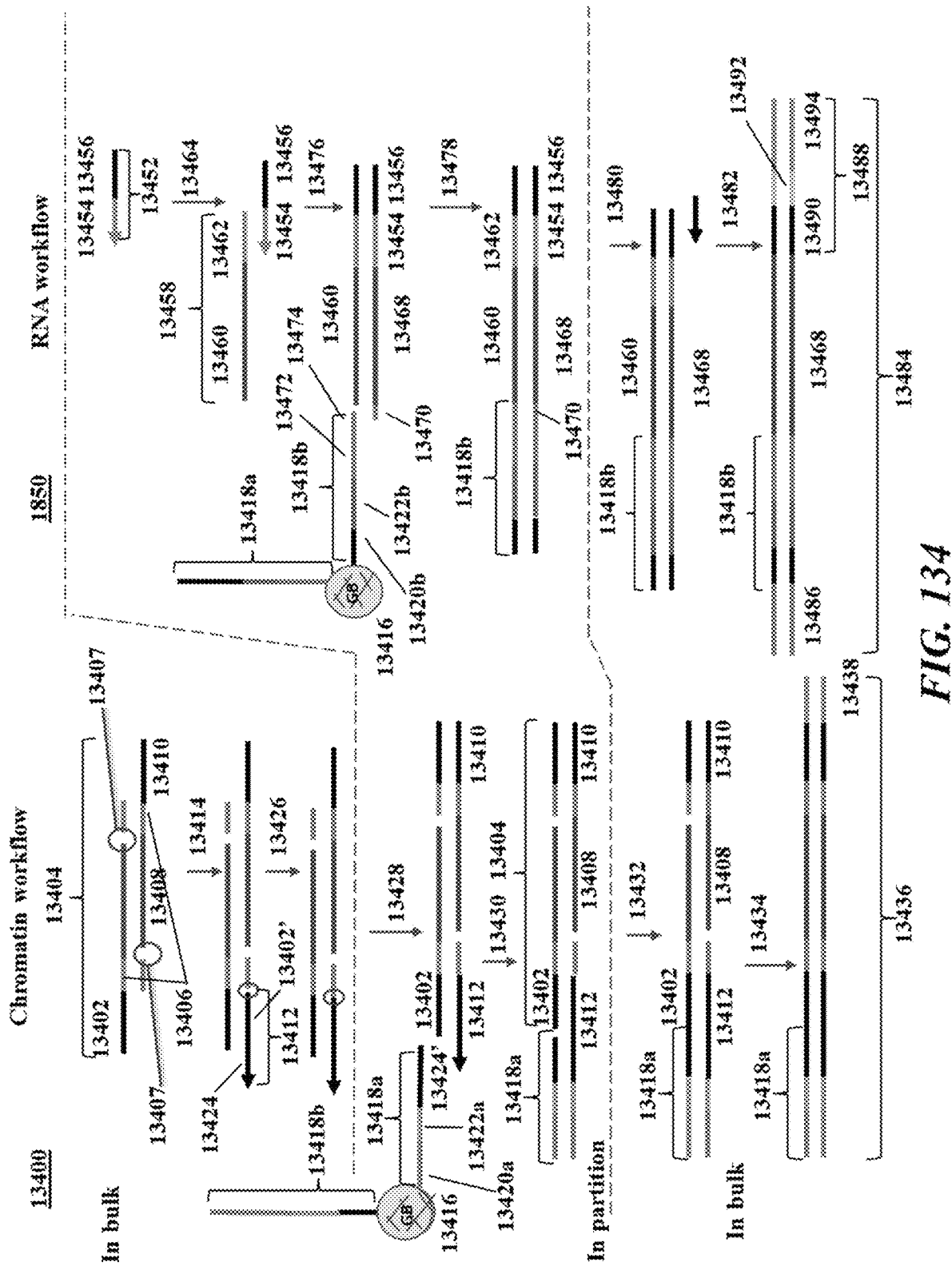

FIG. 134 illustrates a scheme for tandem ATAC and RNA processing.

Figure 135:
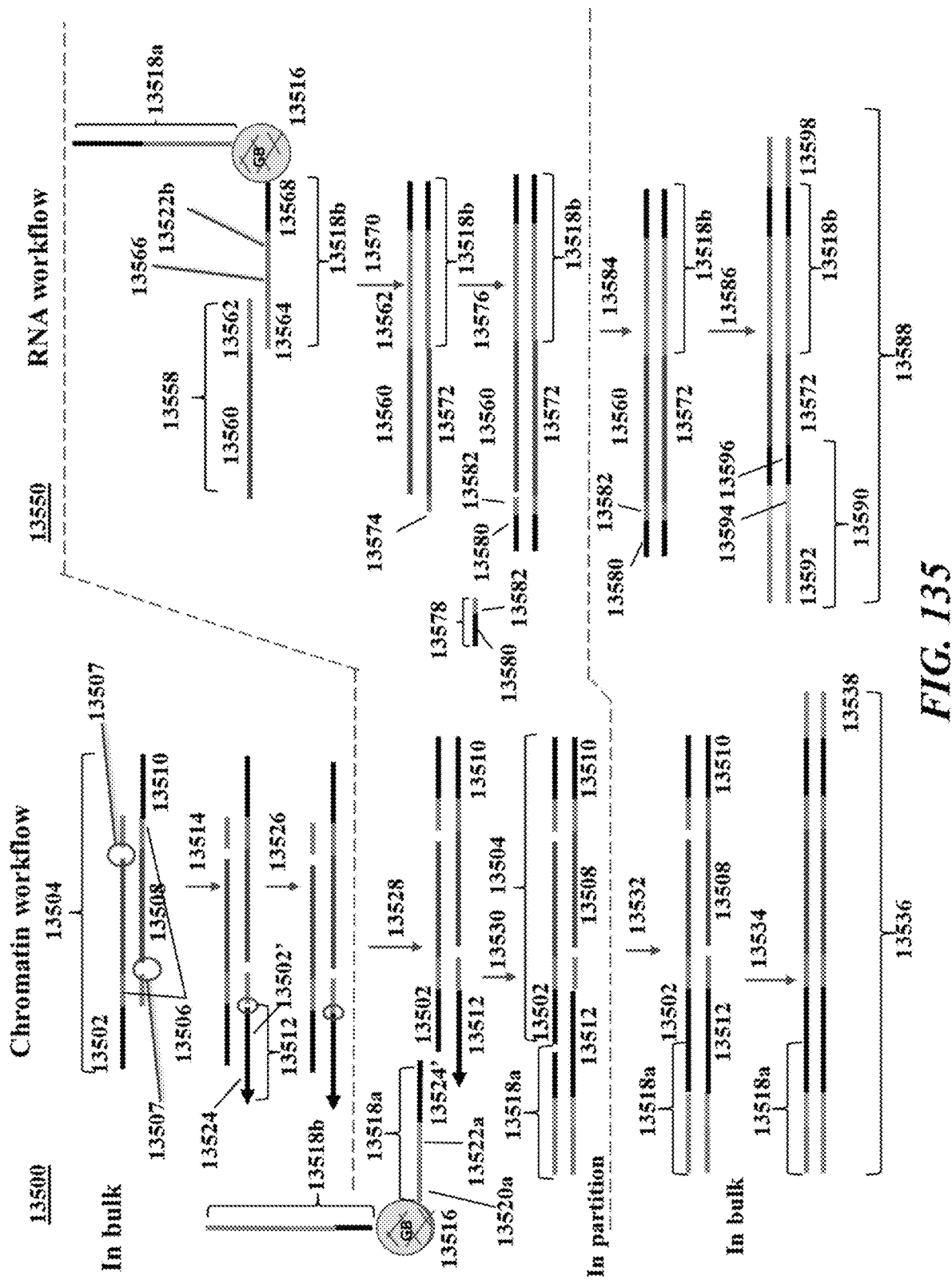

FIG. 135 illustrates a scheme for tandem ATAC and RNA processing.

Figures 136A, 136B:
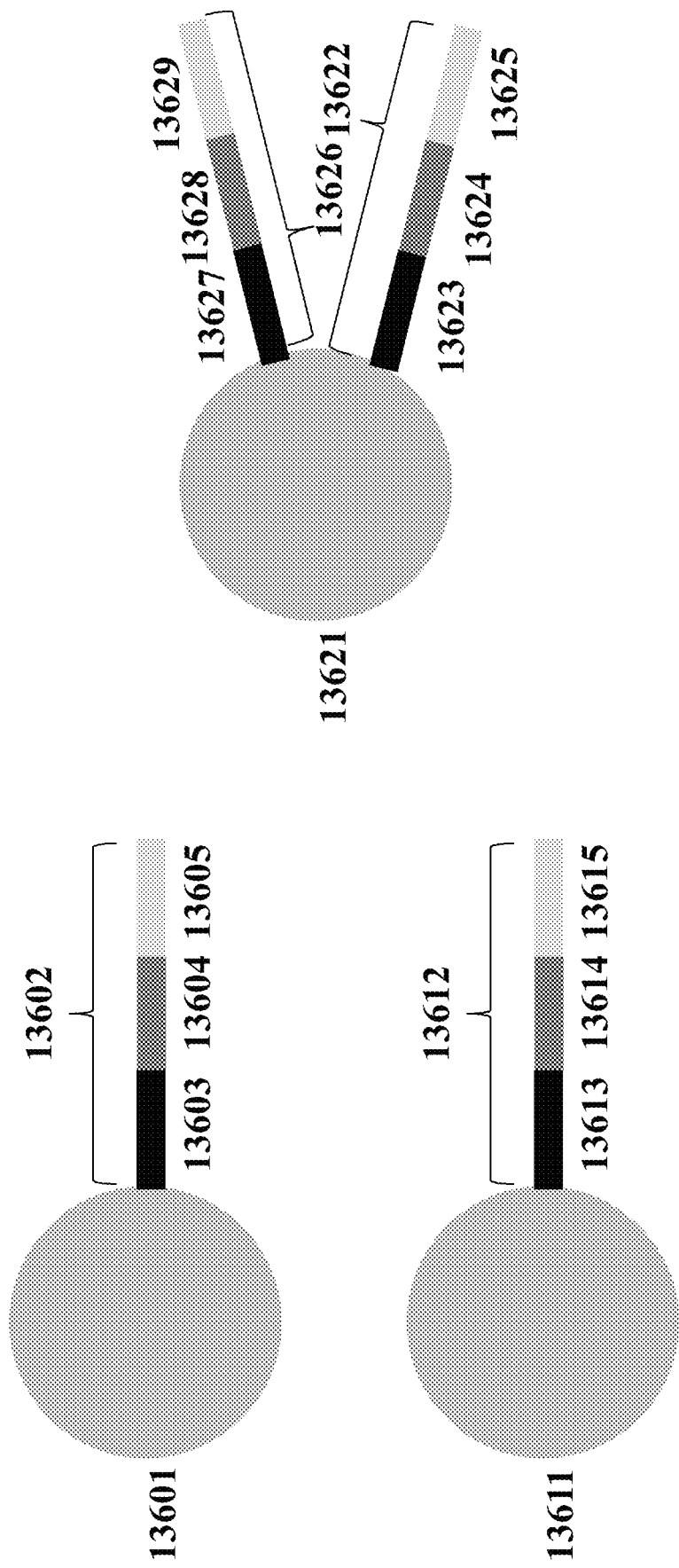

FIGS. 136A and 136B show beads for use according to the methods of the present disclosure.

Figure 137:
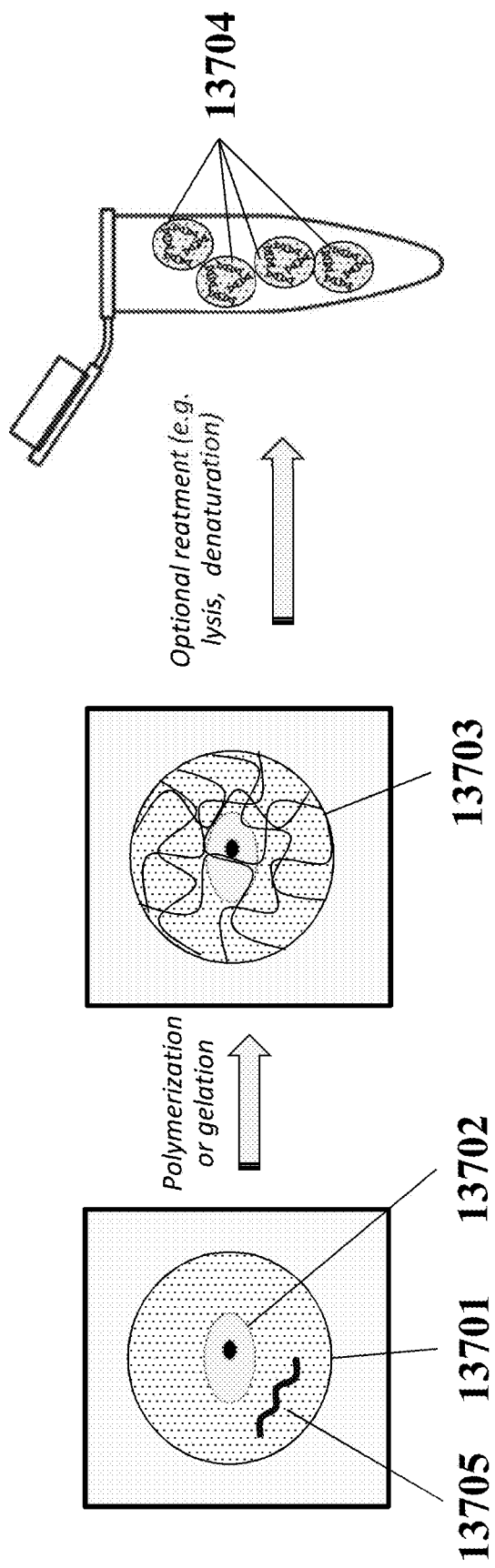

FIG. 137 illustrates an exemplary scheme for cell bead generation.

Figure 138:
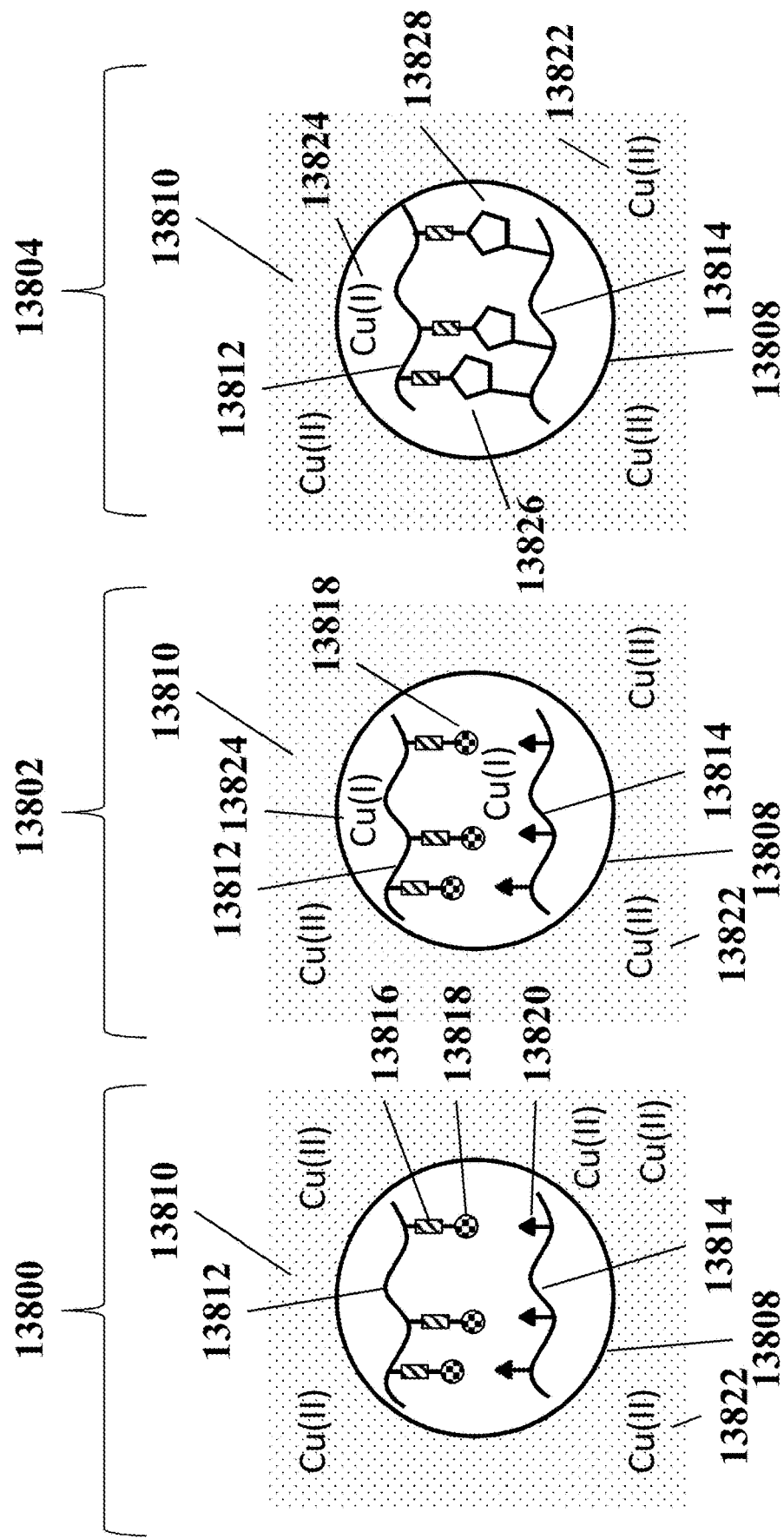

FIG. 138 illustrates an exemplary scheme for cell bead generation or functionalization using crosslinks.

Figure 139A:
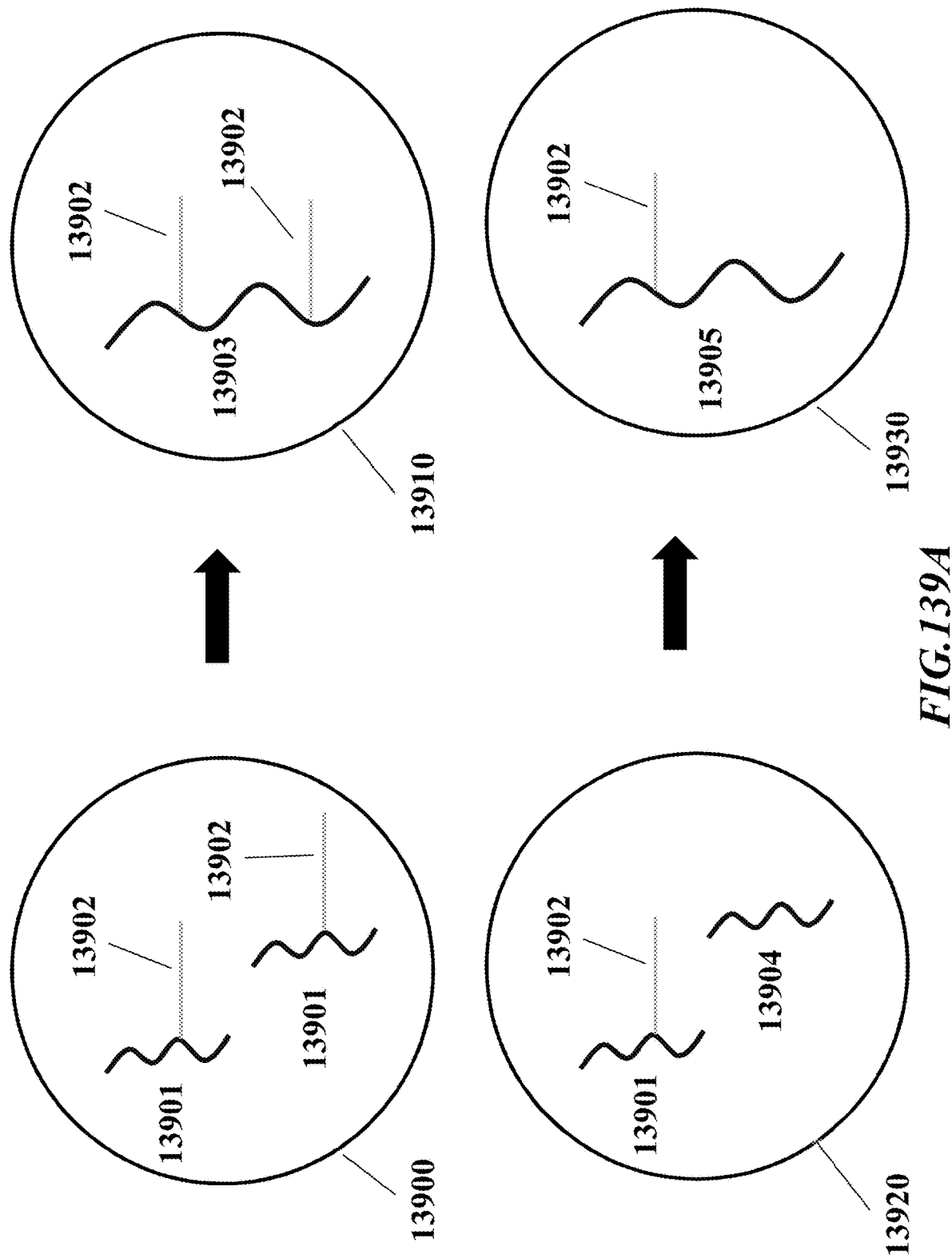

FIGS. 139A-139B illustrate exemplary schemes for polymerization or crosslinking of polymer or gel precursors to generate cell beads comprising attached nucleic acid molecules.

DETAILED DESCRIPTION

While various embodiments of the invention have been shown and described herein, it will be obvious to those skilled in the art that such embodiments are provided by way of example only. Numerous variations, changes, and substitutions may occur to those skilled in the art without departing from the invention. It should be understood that various alternatives to the embodiments of the invention described herein may be employed.

Where values are described as ranges, it will be understood that such disclosure includes the disclosure of all possible sub-ranges within such ranges, as well as specific numerical values that fall within such ranges irrespective of whether a specific numerical value or specific sub-range is expressly stated.

The term "barcode," as used herein, generally refers to a label, or identifier, that conveys or is capable of conveying information about an analyte. A barcode can be part of an analyte. A barcode can be independent of an analyte. A barcode can be a tag attached to an analyte (e.g., nucleic acid molecule) or a combination of the tag in addition to an endogenous characteristic of the analyte (e.g., size of the analyte or end sequence(s)). A barcode may be unique. Barcodes can have a variety of different formats. For example, barcodes can include: polynucleotide barcodes; random nucleic acid and/or amino acid sequences; and synthetic nucleic acid and/or amino acid sequences. A barcode can be attached to an analyte in a reversible or irreversible manner. A barcode can be added to, for example, a fragment of a deoxyribonucleic acid (DNA) or ribonucleic acid (RNA) sample before, during, and/or after sequencing of the sample. Barcodes can allow for identification and/or quantification of individual sequencing-reads.

The term "real time," as used herein, can refer to a response time of less than about 1 second, a tenth of a second, a hundredth of a second, a millisecond, or less. The response time may be greater than 1 second. In some instances, real time can refer to simultaneous or substantially simultaneous processing, detection or identification.

The term "subject," as used herein, generally refers to an animal, such as a mammal (e.g., human) or avian (e.g., bird), or other organism, such as a plant. For example, the subject can be a vertebrate, a mammal, a rodent (e.g., a mouse), a primate, a simian or a human. Animals may include, but are not limited to, farm animals, sport animals, and pets. A subject can be a healthy or asymptomatic individual, an individual that has or is suspected of having a disease (e.g., cancer) or a pre-disposition to the disease, and/or an individual that is in need of therapy or suspected of needing therapy. A subject can be a patient. A subject can be a microorganism or microbe (e.g., bacteria, fungi, archaea, viruses).

The term "genome," as used herein, generally refers to genomic information from a subject, which may be, for example, at least a portion or an entirety of a subject's hereditary information. A genome can be encoded either in DNA or in RNA. A genome can comprise coding regions (e.g., that code for proteins) as well as non-coding regions. A genome can include the sequence of all chromosomes together in an organism. For example, the human genome ordinarily has a total of 46 chromosomes. The sequence of all of these together may constitute a human genome.

The terms "adaptor(s)", "adapter(s)" and "tag(s)" may be used synonymously. An adaptor or tag can be coupled to a polynucleotide sequence to be "tagged" by any approach, including ligation, hybridization, tagmentation, or other approaches. Adaptors may also be used to refer to a nucleic acid sequence or segment, such as a functional sequence. These adaptors may comprise nucleic acid sequences that may add a function, e.g., spacer sequence, primer sequencing site, barcode sequence, unique molecular identifier sequence, etc. As used herein, "Y-adapter" and "forked adapter" may be used synonymously.

The term "sequencing," as used herein, generally refers to methods and technologies for determining the sequence of nucleotide bases in one or more polynucleotides. The polynucleotides can be, for example, nucleic acid molecules such as deoxyribonucleic acid (DNA) or ribonucleic acid (RNA), including variants or derivatives thereof (e.g., single stranded DNA). Sequencing can be performed by various systems currently available, such as, without limitation, a sequencing system by Illumina®, Pacific Biosciences (PacBio®), Oxford Nanopore®, or Life Technologies (Ion Torrent®). Alternatively or in addition, sequencing may be performed using nucleic acid amplification, polymerase chain reaction (PCR) (e.g., digital PCR, quantitative PCR, or real time PCR), or isothermal amplification. Such systems may provide a plurality of raw genetic data corresponding to the genetic information of a subject (e.g., human), as generated by the systems from a sample provided by the subject. In some examples, such systems provide sequencing reads (also "reads" herein). A read may include a string of nucleic acid bases corresponding to a sequence of a nucleic acid molecule that has been sequenced. In some situations, systems and methods provided herein may be used with proteomic information.

The term "bead," as used herein, generally refers to a particle. The bead may be a solid or semi-solid particle. The bead may be a gel bead. The gel bead may include a polymer matrix (e.g., matrix formed by polymerization or cross-linking). The polymer matrix may include one or more polymers (e.g., polymers having different functional groups or repeat units). Polymers in the polymer matrix may be randomly arranged, such as in random copolymers, and/or have ordered structures, such as in block copolymers. Cross-linking can be via covalent, ionic, or inductive, interactions, or physical entanglement. The bead may be a macromolecule. The bead may be formed of nucleic acid molecules bound together. The bead may be formed via covalent or non-covalent assembly of molecules (e.g., macromolecules), such as monomers or polymers. Such polymers or monomers may be natural or synthetic. Such polymers or monomers may be or include, for example, nucleic acid molecules (e.g., DNA or RNA). The bead may be formed of a polymeric material. The bead may be magnetic or non-magnetic. The bead may be rigid. The bead may be flexible and/or compressible. The bead may be disruptable or dissolvable. The bead may be a solid particle (e.g., a metal-based particle including but not limited to iron oxide, gold or silver) covered with a coating comprising one or more polymers. Such coating may be disruptable or dissolvable.

The term "sample," as used herein, generally refers to a biological sample of a subject. The biological sample may comprise any number of macromolecules, for example, cellular macromolecules. The sample may be a cell sample. The sample may be a cell line or cell culture sample. The sample can include one or more cells. The sample can include one or more microbes. The biological sample may be a nucleic acid sample or protein sample. The biological sample may also be a carbohydrate sample or a lipid sample. The biological sample may be derived from another sample. The sample may be a tissue sample, such as a biopsy, core biopsy, needle aspirate, or fine needle aspirate. The sample may be a fluid sample, such as a blood sample, urine sample, or saliva sample. The sample may be a skin sample. The sample may be a cheek swab. The sample may be a plasma or serum sample. The sample may be a cell-free or cell free sample. A cell-free sample may include extracellular polynucleotides. Extracellular polynucleotides may be isolated from a bodily sample that may be selected from the group consisting of blood, plasma, serum, urine, saliva, mucosal excretions, sputum, stool and tears.

The term "biological particle," as used herein, generally refers to a discrete biological system derived from a biological sample. The biological particle may be a macromolecule. The biological particle may be a small molecule. The biological particle may be a virus. The biological particle may be a cell or derivative of a cell. The biological particle may be an organelle. The biological particle may be a rare cell from a population of cells. The biological particle may be any type of cell, including without limitation prokaryotic cells, eukaryotic cells, bacterial, fungal, plant, mammalian, or other animal cell type, mycoplasmas, normal tissue cells, tumor cells, or any other cell type, whether derived from single cell or multicellular organisms. The biological particle may be a constituent of a cell. The biological particle may be or may include DNA, RNA, organelles, proteins, or any combination thereof. The biological particle may be or may include a matrix (e.g., a gel or polymer matrix) comprising a cell or one or more constituents from a cell (e.g., cell bead), such as DNA, RNA, organelles, proteins, or any combination thereof, from the cell. The biological particle may be obtained from a tissue of a subject. The biological particle may be a hardened cell. Such hardened cell may or may not include a cell wall or cell membrane. The biological particle may include one or more constituents of a cell, but may not include other constituents of the cell. An example of such constituents is a nucleus or an organelle. A cell may be a live cell. The live cell may be capable of being cultured, for example, being cultured when enclosed in a gel or polymer matrix, or cultured when comprising a gel or polymer matrix.

The term "macromolecular constituent," as used herein, generally refers to a macromolecule contained within or from a biological particle. The macromolecular constituent may comprise a nucleic acid. In some cases, the biological particle may be a macromolecule. The macromolecular constituent may comprise DNA. The macromolecular constituent may comprise RNA. The RNA may be coding or non-coding. The RNA may be messenger RNA (mRNA), ribosomal RNA (rRNA) or transfer RNA (tRNA), for example. The RNA may be a transcript. The RNA may be small RNA that are less than 200 nucleic acid bases in length, or large RNA that are greater than 200 nucleic acid bases in length. Small RNAs may include 5.8S ribosomal RNA (rRNA), 5S rRNA, transfer RNA (tRNA), microRNA (miRNA), small interfering RNA (siRNA), small nucleolar RNA (snoRNAs), Piwi-interacting RNA (piRNA), tRNA-derived small RNA (tsRNA) and small rDNA-derived RNA (srRNA). The RNA may be double-stranded RNA or single-stranded RNA. The RNA may be circular RNA. The macromolecular constituent may comprise a protein. The macromolecular constituent may comprise a peptide. The macromolecular constituent may comprise a polypeptide.

The term "molecular tag," as used herein, generally refers to a molecule capable of binding to a macromolecular constituent. The molecular tag may bind to the macromolecular constituent with high affinity. The molecular tag may bind to the macromolecular constituent with high specificity. The molecular tag may comprise a nucleotide sequence. The molecular tag may comprise a nucleic acid sequence. The nucleic acid sequence may be at least a portion or an entirety of the molecular tag. The molecular tag may be a nucleic acid molecule or may be part of a nucleic acid molecule. The molecular tag may be an oligonucleotide or a polypeptide. The molecular tag may comprise a DNA aptamer. The molecular tag may be or comprise a primer. The molecular tag may be, or comprise, a protein. The molecular tag may comprise a polypeptide. The molecular tag may be a barcode.

The term "partition," as used herein, generally, refers to a space or volume that may be suitable to contain one or more species or conduct one or more reactions. A partition may be a physical compartment, such as a droplet or well. The partition may isolate space or volume from another space or volume. The droplet may be a first phase (e.g., aqueous phase) in a second phase (e.g., oil) immiscible with the first phase. The droplet may be a first phase in a second phase that does not phase separate from the first phase, such as, for example, a capsule or liposome in an aqueous phase. A partition may comprise one or more other (inner) partitions. In some cases, a partition may be a virtual compartment that can be defined and identified by an index (e.g., indexed libraries) across multiple and/or remote physical compartments. For example, a physical compartment may comprise a plurality of virtual compartments.

The term "analyte," as used herein, generally refers to a substance or one or more constituents thereof that is capable of identification, such as by detection (e.g., detection via sequencing). Examples of analytes include, without limitation, DNA, RNA, synthetic oligonucleotides, the labelling agents described herein, antibodies, and proteins. An analyte may be a cell or one or more constituents of a cell.

Analytes may be of different types. In some examples, in a plurality of analytes, a given analyte is of a different structural or functional class from other analytes of the plurality. Examples of different types of analytes include DNA and RNA; a nucleic acid molecule and a labelling agent; a transcript and genomic nucleic acid; a plurality of nucleic acid molecules, where each nucleic acid molecule has a different function, such as a different cellular function. A sample may have a plurality of analytes of different types, such as a mixture of DNA and RNA molecules, or a mixture of nucleic acid molecules and labelling agents.

The term "epitope binding fragment" or "antibody fragment," as used herein, generally refers to a portion of a complete antibody capable of binding the same epitope as the complete antibody, albeit not necessarily to the same extent. Although multiple types of epitope binding fragments are possible, an epitope binding fragment typically comprises at least one pair of heavy and light chain variable regions (VH and VL, respectively) held together (e.g., by disulfide bonds) to preserve the antigen binding site, and does not contain all or a portion of the Fc region. Epitope binding fragments of an antibody can be obtained from a given antibody by any suitable technique (e.g., recombinant DNA technology or enzymatic or chemical cleavage of a complete antibody), and typically can be screened for specificity in the same manner in which complete antibodies are screened. In some embodiments, an epitope binding fragment comprises an F(ab')$_2$ fragment, Fab' fragment, Fab fragment, Fd fragment, or Fv fragment. In some embodiments, the term "antibody" includes antibody-derived polypeptides, such as single chain variable fragments (scFv), diabodies or other multimeric scFvs, heavy chain antibodies, single domain antibodies, or other polypeptides comprising a sufficient portion of an antibody (e.g., one or more complementarity determining regions (CDRs)) to confer specific antigen binding ability to the polypeptide.

The terms "about" or "approximately," as used herein, mean within an acceptable error range for the particular value as determined by those skilled in the art, which will depend in part on how the value is measured or determined, i.e., the limitations of the measurement system. For example, "about" can mean within 1 or more than 1 standard deviation, per the practice in the relevant field. Alternatively, "about" can mean a range of up to 20%, up to 10%, up to 5%, or up to 1% of a given value.

Systems and Methods for Sample Compartmentalization

In an aspect, the systems and methods described herein provide for the compartmentalization, depositing, or partitioning of one or more particles (e.g., biological particles, macromolecular constituents of biological particles, beads, reagents, etc.) into discrete compartments or partitions (referred to interchangeably herein as partitions), where each partition maintains separation of its own contents from the contents of other partitions. The partition can be a droplet in an emulsion. A partition may comprise one or more other partitions.

A partition may include one or more particles. A partition may include one or more types of particles. For example, a partition of the present disclosure may comprise one or more biological particles and/or macromolecular constituents thereof. A partition may comprise one or more gel beads. A partition may comprise one or more cell beads. A partition may include a single gel bead, a single cell bead, or both a single cell bead and single gel bead. A partition may include one or more reagents. Alternatively, a partition may be unoccupied. For example, a partition may not comprise a bead. A cell bead can be a biological particle and/or one or more of its macromolecular constituents encased inside of a gel or polymer matrix, such as via polymerization of a droplet containing the biological particle and precursors capable of being polymerized or gelled. Unique identifiers, such as barcodes, may be injected into the droplets previous to, subsequent to, or concurrently with droplet generation, such as via a microcapsule (e.g., bead), as described elsewhere herein. Microfluidic channel networks (e.g., on a chip) can be utilized to generate partitions as described herein. Alternative mechanisms may also be employed in the partitioning of individual biological particles, including porous membranes through which aqueous mixtures of cells are extruded into non-aqueous fluids.

The partitions can be flowable within fluid streams. The partitions may comprise, for example, micro-vesicles that have an outer barrier surrounding an inner fluid center or core. In some cases, the partitions may comprise a porous matrix that is capable of entraining and/or retaining materials within its matrix. The partitions can be droplets of a first phase within a second phase, wherein the first and second phases are immiscible. For example, the partitions can be droplets of aqueous fluid within a non-aqueous continuous phase (e.g., oil phase). In another example, the partitions can be droplets of a non-aqueous fluid within an aqueous phase. In some examples, the partitions may be provided in a water-in-oil emulsion or oil-in-water emulsion. A variety of different vessels are described in, for example, U.S. Patent Application Publication No. 2014/0155295, which is entirely incorporated herein by reference for all purposes. Emulsion systems for creating stable droplets in non-aqueous or oil continuous phases are described in, for example, U.S. Patent Application Publication No. 2010/0105112, which is entirely incorporated herein by reference for all purposes.

In the case of droplets in an emulsion, allocating individual particles to discrete partitions may in one non-limiting example be accomplished by introducing a flowing stream of particles in an aqueous fluid into a flowing stream of a non-aqueous fluid, such that droplets are generated at the junction of the two streams. Fluid properties (e.g., fluid flow rates, fluid viscosities, etc.), particle properties (e.g., volume fraction, particle size, particle concentration, etc.), microfluidic architectures (e.g., channel geometry, etc.), and other parameters may be adjusted to control the occupancy of the resulting partitions (e.g., number of biological particles per partition, number of beads per partition, etc.). For example, partition occupancy can be controlled by providing the aqueous stream at a certain concentration and/or flow rate of particles. To generate single biological particle partitions, the relative flow rates of the immiscible fluids can be selected such that, on average, the partitions may contain less than one biological particle per partition in order to ensure that those partitions that are occupied are primarily singly occupied. In some cases, partitions among a plurality of partitions may contain at most one biological particle (e.g., bead, DNA, cell or cellular material). In some embodiments, the various parameters (e.g., fluid properties, particle properties, microfluidic architectures, etc.) may be selected or adjusted such that a majority of partitions are occupied, for example, allowing for only a small percentage of unoccupied partitions. The flows and channel architectures can be controlled as to ensure a given number of singly occupied partitions, less than a certain level of unoccupied partitions and/or less than a certain level of multiply occupied partitions.

Figure 1:
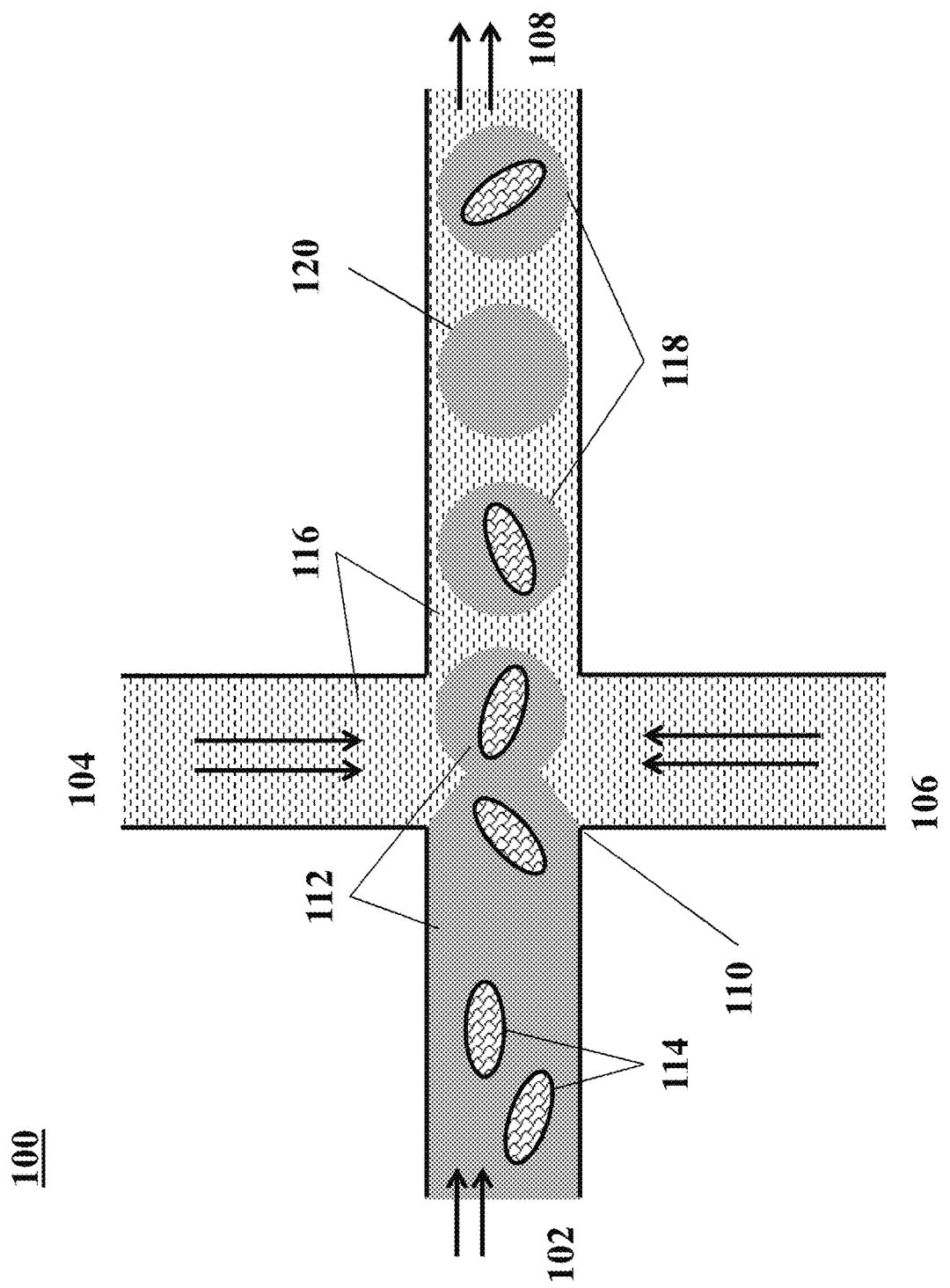
FIG. 1 shows an example of a microfluidic channel structure for partitioning individual biological particles.

FIG. 1 shows an example of a microfluidic channel structure 100 for partitioning individual biological particles. The channel structure 100 can include channel segments 102, 104, 106 and 108 communicating at a channel junction 110. In operation, a first aqueous fluid 112 that includes suspended biological particles (or cells) 114 may be transported along channel segment 102 into junction 110, while a second fluid 116 that is immiscible with the aqueous fluid 112 is delivered to the junction 110 from each of channel segments 104 and 106 to create discrete droplets 118, 120 of the first aqueous fluid 112 flowing into channel segment 108, and flowing away from junction 110. The channel segment 108 may be fluidically coupled to an outlet reservoir where the discrete droplets can be stored and/or harvested. A discrete droplet generated may include an individual biological particle 114 (such as droplets 118). A discrete droplet generated may include more than one individual biological particle 114 (not shown in FIG. 1). A discrete droplet may contain no biological particle 114 (such as droplet 120). Each discrete partition may maintain separation of its own contents (e.g., individual biological particle 114) from the contents of other partitions.

The second fluid 116 can comprise an oil, such as a fluorinated oil, that includes a fluorosurfactant for stabilizing the resulting droplets, for example, inhibiting subsequent coalescence of the resulting droplets 118, 120. Examples of particularly useful partitioning fluids and fluorosurfactants are described, for example, in U.S. Patent Application Publication No. 2010/0105112, which is entirely incorporated herein by reference for all purposes.

As will be appreciated, the channel segments described herein may be coupled to any of a variety of different fluid sources or receiving components, including reservoirs, tubing, manifolds, or fluidic components of other systems. As will be appreciated, the microfluidic channel structure 100 may have other geometries. For example, a microfluidic channel structure can have more than one channel junction. For example, a microfluidic channel structure can have 2, 3, 4, or 5 channel segments each carrying particles (e.g., biological particles, cell beads, and/or gel beads) that meet at a channel junction. Fluid may be directed to flow along one or more channels or reservoirs via one or more fluid flow units. A fluid flow unit can comprise compressors (e.g., providing positive pressure), pumps (e.g., providing negative pressure), actuators, and the like to control flow of the fluid. Fluid may also or otherwise be controlled via applied pressure differentials, centrifugal force, electrokinetic pumping, vacuum, capillary or gravity flow, or the like.

The generated droplets may comprise two subsets of droplets: (1) occupied droplets 118, containing one or more biological particles 114, and (2) unoccupied droplets 120, not containing any biological particles 114. Occupied droplets 118 may comprise singly occupied droplets (having one biological particle) and multiply occupied droplets (having more than one biological particle). As described elsewhere herein, in some cases, the majority of occupied partitions can include no more than one biological particle per occupied partition and some of the generated partitions can be unoccupied (of any biological particle). In some cases, though, some of the occupied partitions may include more than one biological particle. In some cases, the partitioning process may be controlled such that fewer than about 25% of the occupied partitions contain more than one biological particle, and in many cases, fewer than about 20% of the occupied partitions have more than one biological particle, while in some cases, fewer than about 10% or even fewer than about 5% of the occupied partitions include more than one biological particle per partition.

In some cases, it may be desirable to minimize the creation of excessive numbers of empty partitions, such as to reduce costs and/or increase efficiency. While this minimization may be achieved by providing a sufficient number of biological particles (e.g., biological particles 114) at the partitioning junction 110, such as to ensure that at least one biological particle is encapsulated in a partition, the Poissonian distribution may expectedly increase the number of partitions that include multiple biological particles. As such, where singly occupied partitions are to be obtained, at most about 95%, 90%, 85%, 80%, 75%, 70%, 65%, 60%, 55%, 50%, 45%, 40%, 35%, 30%, 25%, 20%, 15%, 10%, 5% or less of the generated partitions can be unoccupied.

In some cases, the flow of one or more of the biological particles (e.g., in channel segment 102), or other fluids directed into the partitioning junction (e.g., in channel segments 104, 106) can be controlled such that, in many cases, no more than about 50% of the generated partitions, no more than about 25% of the generated partitions, or no more than about 10% of the generated partitions are unoccupied. These flows can be controlled so as to present a non-Poissonian distribution of single-occupied partitions while providing lower levels of unoccupied partitions. The above noted ranges of unoccupied partitions can be achieved while still providing any of the single occupancy rates described above. For example, in many cases, the use of the systems and methods described herein can create resulting partitions that have multiple occupancy rates of less than about 25%, less than about 20%, less than about 15%, less than about 10%, and in many cases, less than about 5%, while having unoccupied partitions of less than about 50%, less than about 40%, less than about 30%, less than about 20%, less than about 10%, less than about 5%, or less.

Figure 2:
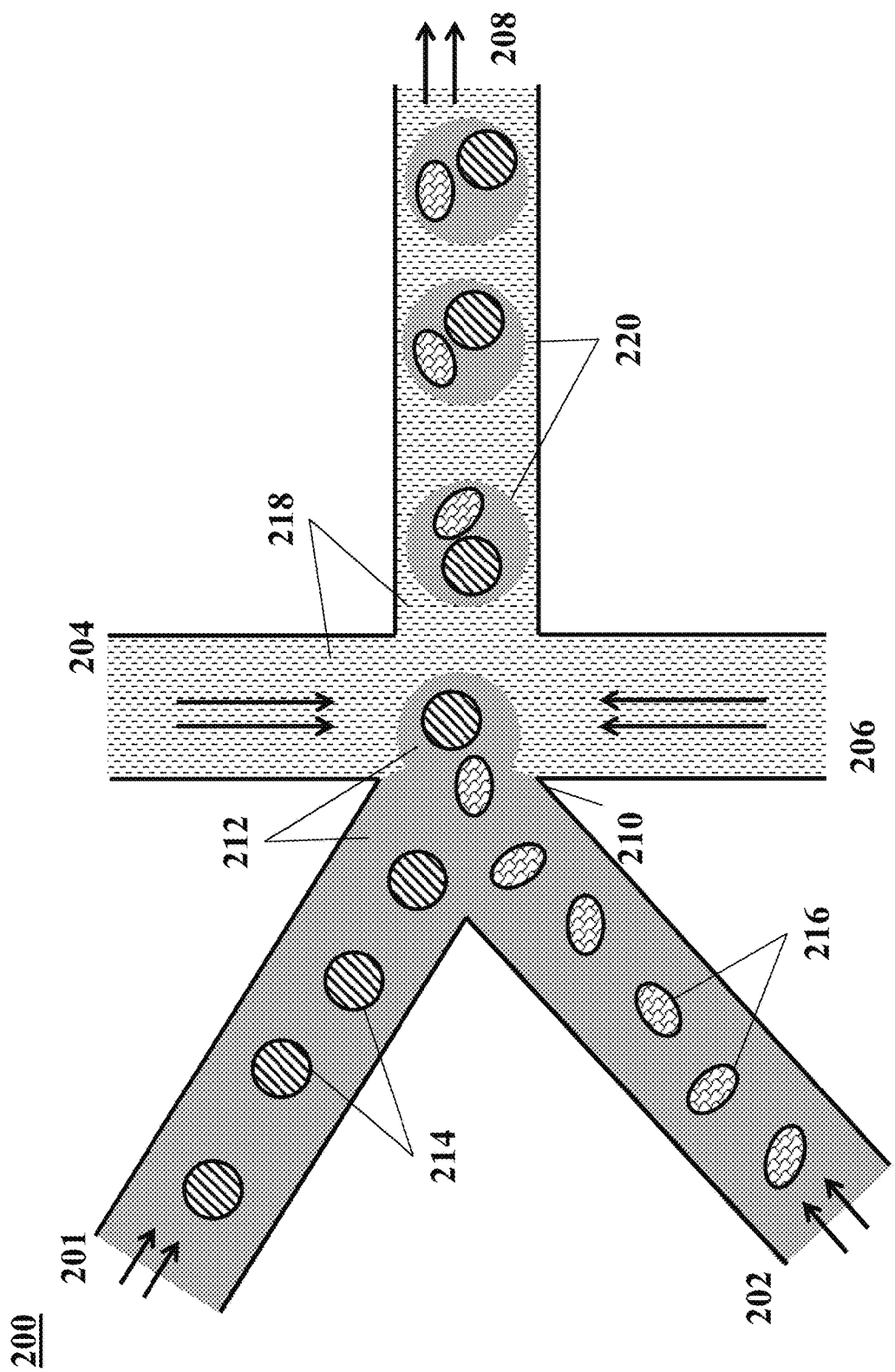
FIG. 2 shows an example of a microfluidic channel structure for delivering barcode carrying beads to droplets.

As will be appreciated, the above-described occupancy rates are also applicable to partitions that include both biological particles and additional reagents, including, but not limited to, microcapsules or beads (e.g., gel beads) carrying barcoded nucleic acid molecules (e.g., oligonucleotides) (described in relation to FIG. 2). The occupied partitions (e.g., at least about 10%, 20%, 30%, 40%, 50%, 60%, 70%, 80%, 90%, 95%, or 99% of the occupied partitions) can include both a microcapsule (e.g., bead) comprising barcoded nucleic acid molecules and a biological particle.

In another aspect, in addition to or as an alternative to droplet based partitioning, biological particles may be encapsulated within a microcapsule that comprises an outer shell, layer or porous matrix in which is entrained one or more individual biological particles or small groups of biological particles. The microcapsule may include other reagents. Encapsulation of biological particles may be performed by a variety of processes. Such processes may combine an aqueous fluid containing the biological particles with a polymeric precursor material that may be capable of being formed into a gel or other solid or semi-solid matrix upon application of a particular stimulus to the polymer precursor. Such stimuli can include, for example, thermal stimuli (e.g., either heating or cooling), photo-stimuli (e.g., through photo-curing), chemical stimuli (e.g., through cross-linking, polymerization initiation of the precursor (e.g., through added initiators)), mechanical stimuli, or any combination thereof.

Preparation of microcapsules comprising biological particles may be performed by a variety of methods. For example, air knife droplet or aerosol generators may be used to dispense droplets of precursor fluids into gelling solutions in order to form microcapsules that include individual biological particles or small groups of biological particles. Likewise, membrane based encapsulation systems may be used to generate microcapsules comprising encapsulated biological particles as described herein. Microfluidic systems of the present disclosure, such as that shown in FIG. 1, may be readily used in encapsulating cells as described herein. In particular, and with reference to FIG. 1, the aqueous fluid 112 comprising (i) the biological particles 114 and (ii) the polymer precursor material (not shown) is flowed into channel junction 110, where it is partitioned into droplets 118, 120 through the flow of non-aqueous fluid 116. In the case of encapsulation methods, non-aqueous fluid 116 may also include an initiator (not shown) to cause polymerization and/or crosslinking of the polymer precursor to form the microcapsule that includes the entrained biological particles. Examples of polymer precursor/initiator pairs include those described in U.S. Patent Application Publication No. 2014/0378345, which is entirely incorporated herein by reference for all purposes.

For example, in the case where the polymer precursor material comprises a linear polymer material, such as a linear polyacrylamide, PEG, or other linear polymeric material, the activation agent may comprise a cross-linking agent, or a chemical that activates a cross-linking agent within the formed droplets. Likewise, for polymer precursors that comprise polymerizable monomers, the activation agent may comprise a polymerization initiator. For example, in certain cases, where the polymer precursor comprises a mixture of acrylamide monomer with a N,N'-bis-(acryloyl) cystamine (BAC) comonomer, an agent such as tetraethylmethylenediamine (TEMED) may be provided within the second fluid streams 116 in channel segments 104 and 106, which can initiate the copolymerization of the acrylamide and BAC into a cross-linked polymer network, or hydrogel.

Upon contact of the second fluid stream 116 with the first fluid stream 112 at junction 110, during formation of droplets, the TEMED may diffuse from the second fluid 116 into the aqueous fluid 112 comprising the linear polyacrylamide, which will activate the crosslinking of the polyacrylamide within the droplets 118, 120, resulting in the formation of gel (e.g., hydrogel) microcapsules, as solid or semi-solid beads or particles entraining the cells 114. Although described in terms of polyacrylamide encapsulation, other 'activatable' encapsulation compositions may also be employed in the context of the methods and compositions described herein. For example, formation of alginate droplets followed by exposure to divalent metal ions (e.g., $Ca^{2+}$ ions), can be used as an encapsulation process using the described processes. Likewise, agarose droplets may also be transformed into capsules through temperature based gelling (e.g., upon cooling, etc.).

In some cases, encapsulated biological particles can be selectively releasable from the microcapsule, such as through passage of time or upon application of a particular stimulus, that degrades the microcapsule sufficiently to allow the biological particles (e.g., cell), or its other contents to be released from the microcapsule, such as into a partition (e.g., droplet). For example, in the case of the polyacrylamide polymer described above, degradation of the microcapsule may be accomplished through the introduction of an appropriate reducing agent, such as DTT or the like, to cleave disulfide bonds that cross-link the polymer matrix. See, for example, U.S. Patent Application Publication No. 2014/0378345, which is entirely incorporated herein by reference for all purposes.

The biological particle can be subjected to other conditions sufficient to polymerize or gel the precursors. The conditions sufficient to polymerize or gel the precursors may comprise exposure to heating, cooling, electromagnetic radiation, and/or light. The conditions sufficient to polymerize or gel the precursors may comprise any conditions sufficient to polymerize or gel the precursors. Following polymerization or gelling, a polymer or gel may be formed around the biological particle. The polymer or gel may be diffusively permeable to chemical or biochemical reagents. The polymer or gel may be diffusively impermeable to macromolecular constituents of the biological particle. In this manner, the polymer or gel may act to allow the biological particle to be subjected to chemical or biochemical operations while spatially confining the macromolecular constituents to a region of the droplet defined by the polymer or gel. The polymer or gel may include one or more of disulfide cross-linked polyacrylamide, agarose, alginate, polyvinyl alcohol, polyethylene glycol (PEG)-diacrylate, PEG-acrylate, PEG-thiol, PEG-azide, PEG-alkyne, other acrylates, chitosan, hyaluronic acid, collagen, fibrin, gelatin, or elastin. The polymer or gel may comprise any other polymer or gel.

The polymer or gel may be functionalized to bind to targeted analytes, such as nucleic acids, proteins, carbohydrates, lipids or other analytes. The polymer or gel may be polymerized or gelled via a passive mechanism. The polymer or gel may be stable in alkaline conditions or at elevated temperature. The polymer or gel may have mechanical properties similar to the mechanical properties of the bead. For instance, the polymer or gel may be of a similar size to the bead. The polymer or gel may have a mechanical strength (e.g. tensile strength) similar to that of the bead. The polymer or gel may be of a lower density than an oil. The polymer or gel may be of a density that is roughly similar to that of a buffer. The polymer or gel may have a tunable pore size. The pore size may be chosen to, for instance, retain denatured nucleic acids. The pore size may be chosen to maintain diffusive permeability to exogenous chemicals such as sodium hydroxide (NaOH) and/or endogenous chemicals such as inhibitors. The polymer or gel may be biocompatible. The polymer or gel may maintain or enhance cell viability. The polymer or gel may be biochemically compatible. The polymer or gel may be polymerized and/or depolymerized thermally, chemically, enzymatically, and/or optically.

The polymer may comprise poly(acrylamide-co-acrylic acid) crosslinked with disulfide linkages. The preparation of the polymer may comprise a two-step reaction. In the first activation step, poly(acrylamide-co-acrylic acid) may be exposed to an acylating agent to convert carboxylic acids to esters. For instance, the poly(acrylamide-co-acrylic acid) may be exposed to 4-(4,6-dimethoxy-1,3,5-triazin-2-yl)-4-methylmorpholinium chloride (DMTMM). The polyacrylamide-co-acrylic acid may be exposed to other salts of 4-(4,6-dimethoxy-1,3,5-triazin-2-yl)-4-methylmorpholinium. In the second cross-linking step, the ester formed in the first step may be exposed to a disulfide crosslinking agent. For instance, the ester may be exposed to cystamine (2,2'-dithiobis(ethylamine)). Following the two steps, the biological particle may be surrounded by polyacrylamide strands linked together by disulfide bridges. In this manner, the biological particle may be encased inside of or comprise a gel or matrix (e.g., polymer matrix) to form a "cell bead." A cell bead can contain biological particles (e.g., a cell) or macromolecular constituents (e.g., RNA, DNA, proteins, etc.) of biological particles. A cell bead may include a single cell or multiple cells, or a derivative of the single cell or multiple cells. For example after lysing and washing the cells, inhibitory components from cell lysates can be washed away and the macromolecular constituents can be bound as cell beads. Systems and methods disclosed herein can be applicable to both cell beads (and/or droplets or other partitions) containing biological particles and cell beads (and/or droplets or other partitions) containing macromolecular constituents of biological particles.

Encapsulated biological particles can provide certain potential advantages of being more storable and more portable than droplet-based partitioned biological particles. Furthermore, in some cases, it may be desirable to allow biological particles to incubate for a select period of time before analysis, such as in order to characterize changes in such biological particles over time, either in the presence or absence of different stimuli. In such cases, encapsulation may allow for longer incubation than partitioning in emulsion droplets, although in some cases, droplet partitioned biological particles may also be incubated for different periods of time, e.g., at least 10 seconds, at least 30 seconds, at least 1 minute, at least 5 minutes, at least 10 minutes, at least 30 minutes, at least 1 hour, at least 2 hours, at least 5 hours, or at least 10 hours or more. The encapsulation of biological particles may constitute the partitioning of the biological particles into which other reagents are co-partitioned. Alternatively or in addition, encapsulated biological particles may be readily deposited into other partitions (e.g., droplets) as described above.

Beads

A partition may comprise one or more unique identifiers, such as barcodes. Barcodes may be previously, subsequently or concurrently delivered to the partitions that hold the compartmentalized or partitioned biological particle. For example, barcodes may be injected into droplets previous to, subsequent to, or concurrently with droplet generation. The delivery of the barcodes to a particular partition allows for the later attribution of the characteristics of the individual biological particle to the particular partition. Barcodes may be delivered, for example on a nucleic acid molecule (e.g., an oligonucleotide), to a partition via any suitable mechanism. Barcoded nucleic acid molecules can be delivered to a partition via a microcapsule. A microcapsule, in some instances, can comprise a bead. Beads are described in further detail below.

In some cases, barcoded nucleic acid molecules can be initially associated with the microcapsule and then released from the microcapsule. Release of the barcoded nucleic acid molecules can be passive (e.g., by diffusion out of the microcapsule). In addition or alternatively, release from the microcapsule can be upon application of a stimulus which allows the barcoded nucleic acid nucleic acid molecules to dissociate or to be released from the microcapsule. Such stimulus may disrupt the microcapsule, an interaction that couples the barcoded nucleic acid molecules to or within the microcapsule, or both. Such stimulus can include, for example, a thermal stimulus, photo-stimulus, chemical stimulus (e.g., change in pH or use of a reducing agent(s)), a mechanical stimulus, a radiation stimulus; a biological stimulus (e.g., enzyme), or any combination thereof.

FIG. 2 shows an example of a microfluidic channel structure 200 for delivering barcode carrying beads to droplets. The channel structure 200 can include channel segments 201, 202, 204, 206 and 208 communicating at a channel junction 210. In operation, the channel segment 201 may transport an aqueous fluid 212 that includes a plurality of beads 214 (e.g., with nucleic acid molecules, oligonucleotides, molecular tags) along the channel segment 201 into junction 210. The plurality of beads 214 may be sourced from a suspension of beads. For example, the channel segment 201 may be connected to a reservoir comprising an aqueous suspension of beads 214. The channel segment 202 may transport the aqueous fluid 212 that includes a plurality of biological particles 216 along the channel segment 202 into junction 210. The plurality of biological particles 216 may be sourced from a suspension of biological particles. For example, the channel segment 202 may be connected to a reservoir comprising an aqueous suspension of biological particles 216. In some instances, the aqueous fluid 212 in either the first channel segment 201 or the second channel segment 202, or in both segments, can include one or more reagents, as further described below. A second fluid 218 that is immiscible with the aqueous fluid 212 (e.g., oil) can be delivered to the junction 210 from each of channel segments 204 and 206. Upon meeting of the aqueous fluid 212 from each of channel segments 201 and 202 and the second fluid 218 from each of channel segments 204 and 206 at the channel junction 210, the aqueous fluid 212 can be partitioned as discrete droplets 220 in the second fluid 218 and flow away from the junction 210 along channel segment 208. The channel segment 208 may deliver the discrete droplets to an outlet reservoir fluidly coupled to the channel segment 208, where they may be harvested.

As an alternative, the channel segments 201 and 202 may meet at another junction upstream of the junction 210. At such junction, beads and biological particles may form a mixture that is directed along another channel to the junction 210 to yield droplets 220. The mixture may provide the beads and biological particles in an alternating fashion, such that, for example, a droplet comprises a single bead and a single biological particle.

Beads, biological particles and droplets may flow along channels at substantially regular flow profiles (e.g., at regular flow rates). Such regular flow profiles may permit a droplet to include a single bead and a single biological particle. Such regular flow profiles may permit the droplets to have an occupancy (e.g., droplets having beads and biological particles) greater than 5%, 10%, 20%, 30%, 40%, 50%, 60%, 70%, 80%, 90%, or 95%. Such regular flow profiles and devices that may be used to provide such regular flow profiles are provided in, for example, U.S. Patent Publication No. 2015/0292988, which is entirely incorporated herein by reference.

The second fluid 218 can comprise an oil, such as a fluorinated oil, that includes a fluorosurfactant for stabilizing the resulting droplets, for example, inhibiting subsequent coalescence of the resulting droplets 220.

A discrete droplet that is generated may include an individual biological particle 216. A discrete droplet that is generated may include a barcode or other reagent carrying bead 214. A discrete droplet generated may include both an individual biological particle and a barcode carrying bead, such as droplets 220. In some instances, a discrete droplet may include more than one individual biological particle or no biological particle. In some instances, a discrete droplet may include more than one bead or no bead. A discrete droplet may be unoccupied (e.g., no beads, no biological particles).

Beneficially, a discrete droplet partitioning a biological particle and a barcode carrying bead may effectively allow the attribution of the barcode to macromolecular constituents of the biological particle within the partition. The contents of a partition may remain discrete from the contents of other partitions.

As will be appreciated, the channel segments described herein may be coupled to any of a variety of different fluid sources or receiving components, including reservoirs, tubing, manifolds, or fluidic components of other systems. As will be appreciated, the microfluidic channel structure 200 may have other geometries. For example, a microfluidic channel structure can have more than one channel junctions. For example, a microfluidic channel structure can have 2, 3, 4, or 5 channel segments each carrying beads that meet at a channel junction. Fluid may be directed flow along one or more channels or reservoirs via one or more fluid flow units. A fluid flow unit can comprise compressors (e.g., providing positive pressure), pumps (e.g., providing negative pressure), actuators, and the like to control flow of the fluid. Fluid may also or otherwise be controlled via applied pressure differentials, centrifugal force, electrokinetic pumping, vacuum, capillary or gravity flow, or the like.

A bead may be porous, non-porous, solid, semi-solid, semi-fluidic, fluidic, and/or any combination thereof. In some instances, a bead may be dissolvable, disruptable, and/or degradable. In some cases, a bead may not be degradable. In some cases, the bead may be a gel bead. A gel bead may be a hydrogel bead. A gel bead may be formed from molecular precursors, such as a polymeric or monomeric species. A semi-solid bead may be a liposomal bead. Solid beads may comprise metals including iron oxide, gold, and silver. In some cases, the bead may be a silica bead. In some cases, the bead can be rigid. In other cases, the bead may be flexible and/or compressible.

A bead may be of any suitable shape. Examples of bead shapes include, but are not limited to, spherical, non-spherical, oval, oblong, amorphous, circular, cylindrical, and variations thereof.

Beads may be of uniform size or heterogeneous size. In some cases, the diameter of a bead may be at least about 10 nanometers (nm), 100 nm, 500 nm, 1 micrometer (μm), 5 μm, 10 μm, 20 μm, 30 μm, 40 μm, 50 μm, 60 μm, 70 μm, 80 μm, 90 μm, 100 μm, 250 μm, 500 μm, 1 mm, or greater. In some cases, a bead may have a diameter of less than about 10 nm, 100 nm, 500 nm, 1μm, 5 μm, 10 μm, 20 μm, 30 μm, 40 μm, 50 μm, 60 μm, 70 μm, 80 μm, 90 μm, 100 μm, 250 μm, 500 μm, 1 mm, or less. In some cases, a bead may have a diameter in the range of about 40-75 μm, 30-75 μm, 20-75 μm, 40-85 μm, 40-95 μm, 20-100 μm, 10-100 μm, 1-100 μm, 20-250 μm, or 20-500 μm.

In certain aspects, beads can be provided as a population or plurality of beads having a relatively monodisperse size distribution. Where it may be desirable to provide relatively consistent amounts of reagents within partitions, maintaining relatively consistent bead characteristics, such as size, can contribute to the overall consistency. In particular, the beads described herein may have size distributions that have a coefficient of variation in their cross-sectional dimensions of less than 50%, less than 40%, less than 30%, less than 20%, and in some cases less than 15%, less than 10%, less than 5%, or less.

A bead may comprise natural and/or synthetic materials. For example, a bead can comprise a natural polymer, a synthetic polymer or both natural and synthetic polymers. Examples of natural polymers include proteins and sugars such as deoxyribonucleic acid, rubber, cellulose, starch (e.g., amylose, amylopectin), proteins, enzymes, polysaccharides, silks, polyhydroxyalkanoates, chitosan, dextran, collagen, carrageenan, ispaghula, acacia, agar, gelatin, shellac, sterculia gum, xanthan gum, Corn sugar gum, guar gum, gum karaya, agarose, alginic acid, alginate, or natural polymers thereof. Examples of synthetic polymers include acrylics, nylons, silicones, spandex, viscose rayon, polycarboxylic acids, polyvinyl acetate, polyacrylamide, polyacrylate, polyethylene glycol, polyurethanes, polylactic acid, silica, polystyrene, polyacrylonitrile, polybutadiene, polycarbonate, polyethylene, polyethylene terephthalate, poly(chlorotrifluoroethylene), poly(ethylene oxide), poly(ethylene terephthalate), polyethylene, polyisobutylene, poly(methyl methacrylate), poly(oxymethylene), polyformaldehyde, polypropylene, polystyrene, poly(tetrafluoroethylene), poly(vinyl acetate), poly(vinyl alcohol), poly(vinyl chloride), poly(vinylidene dichloride), poly(vinylidene difluoride), poly(vinyl fluoride) and/or combinations (e.g., co-polymers) thereof. Beads may also be formed from materials other than polymers, including lipids, micelles, ceramics, glass-ceramics, material composites, metals, other inorganic materials, and others.

In some instances, the bead may contain molecular precursors (e.g., monomers or polymers), which may form a polymer network via polymerization of the molecular precursors. In some cases, a precursor may be an already polymerized species capable of undergoing further polymerization via, for example, a chemical cross-linkage. In some cases, a precursor can comprise one or more of an acrylamide or a methacrylamide monomer, oligomer, or polymer. In some cases, the bead may comprise prepolymers, which are oligomers capable of further polymerization. For example, polyurethane beads may be prepared using prepolymers. In some cases, the bead may contain individual polymers that may be further polymerized together. In some cases, beads may be generated via polymerization of different precursors, such that they comprise mixed polymers, co-polymers, and/or block co-polymers. In some cases, the bead may comprise covalent or ionic bonds between polymeric precursors (e.g., monomers, oligomers, linear polymers), nucleic acid molecules (e.g., oligonucleotides), primers, and other entities. In some cases, the covalent bonds can be carbon-carbon bonds, thioether bonds, or carbon-heteroatom bonds.

Cross-linking may be permanent or reversible, depending upon the particular cross-linker used. Reversible cross-linking may allow for the polymer to linearize or dissociate under appropriate conditions. In some cases, reversible cross-linking may also allow for reversible attachment of a material bound to the surface of a bead. In some cases, a cross-linker may form disulfide linkages. In some cases, the chemical cross-linker forming disulfide linkages may be cystamine or a modified cystamine.

In some cases, disulfide linkages can be formed between molecular precursor units (e.g., monomers, oligomers, or linear polymers) or precursors incorporated into a bead and nucleic acid molecules (e.g., oligonucleotides). Cystamine (including modified cystamines), for example, is an organic agent comprising a disulfide bond that may be used as a crosslinker agent between individual monomeric or polymeric precursors of a bead. Polyacrylamide may be polymerized in the presence of cystamine or a species comprising cystamine (e.g., a modified cystamine) to generate polyacrylamide gel beads comprising disulfide linkages (e.g., chemically degradable beads comprising chemically-reducible cross-linkers). The disulfide linkages may permit the bead to be degraded (or dissolved) upon exposure of the bead to a reducing agent.

In some cases, chitosan, a linear polysaccharide polymer, may be crosslinked with glutaraldehyde via hydrophilic chains to form a bead. Crosslinking of chitosan polymers may be achieved by chemical reactions that are initiated by heat, pressure, change in pH, and/or radiation.

In some cases, a bead may comprise an acrydite moiety, which in certain aspects may be used to attach one or more nucleic acid molecules (e.g., barcode sequence, barcoded nucleic acid molecule, barcoded oligonucleotide, primer, or other oligonucleotide) to the bead. In some cases, an acrydite moiety can refer to an acrydite analogue generated from the reaction of acrydite with one or more species, such as, the reaction of acrydite with other monomers and cross-linkers during a polymerization reaction. Acrydite moieties may be modified to form chemical bonds with a species to be attached, such as a nucleic acid molecule (e.g., barcode sequence, barcoded nucleic acid molecule, barcoded oligonucleotide, primer, or other oligonucleotide). Acrydite moieties may be modified with thiol groups capable of forming a disulfide bond or may be modified with groups already comprising a disulfide bond. The thiol or disulfide (via disulfide exchange) may be used as an anchor point for a species to be attached or another part of the acrydite moiety may be used for attachment. In some cases, attachment can be reversible, such that when the disulfide bond is broken (e.g., in the presence of a reducing agent), the attached species is released from the bead. In other cases, an acrydite moiety can comprise a reactive hydroxyl group that may be used for attachment.

Functionalization of beads for attachment of nucleic acid molecules (e.g., oligonucleotides) may be achieved through a wide range of different approaches, including activation of chemical groups within a polymer, incorporation of active or activatable functional groups in the polymer structure, or attachment at the pre-polymer or monomer stage in bead production.

For example, precursors (e.g., monomers, cross-linkers) that are polymerized to form a bead may comprise acrydite moieties, such that when a bead is generated, the bead also comprises acrydite moieties. The acrydite moieties can be attached to a nucleic acid molecule (e.g., oligonucleotide), which may include a priming sequence (e.g., a primer for amplifying target nucleic acids, random primer, primer sequence for messenger RNA) and/or one or more barcode sequences. The one more barcode sequences may include sequences that are the same for all nucleic acid molecules coupled to a given bead and/or sequences that are different across all nucleic acid molecules coupled to the given bead. The nucleic acid molecule may be incorporated into the bead.

In some cases, the nucleic acid molecule can comprise a functional sequence, for example, for attachment to a sequencing flow cell, such as, for example, a P5 sequence for Illumina® sequencing. In some cases, the nucleic acid molecule or derivative thereof (e.g., oligonucleotide or polynucleotide generated from the nucleic acid molecule) can comprise another functional sequence, such as, for example, a P7 sequence for attachment to a sequencing flow cell for Illumina sequencing. In some cases, the nucleic acid molecule can comprise a barcode sequence. In some cases, the primer can further comprise a unique molecular identifier (UMI). In some cases, the primer can comprise an R1 primer sequence for Illumina sequencing. In some cases, the primer can comprise an R2 primer sequence for Illumina sequencing. Examples of such nucleic acid molecules (e.g., oligonucleotides, polynucleotides, etc.) and uses thereof, as may be used with compositions, devices, methods and systems of the present disclosure, are provided in U.S. Patent Pub. Nos. 2014/0378345 and 2015/0376609, each of which is entirely incorporated herein by reference.

Figure 8:
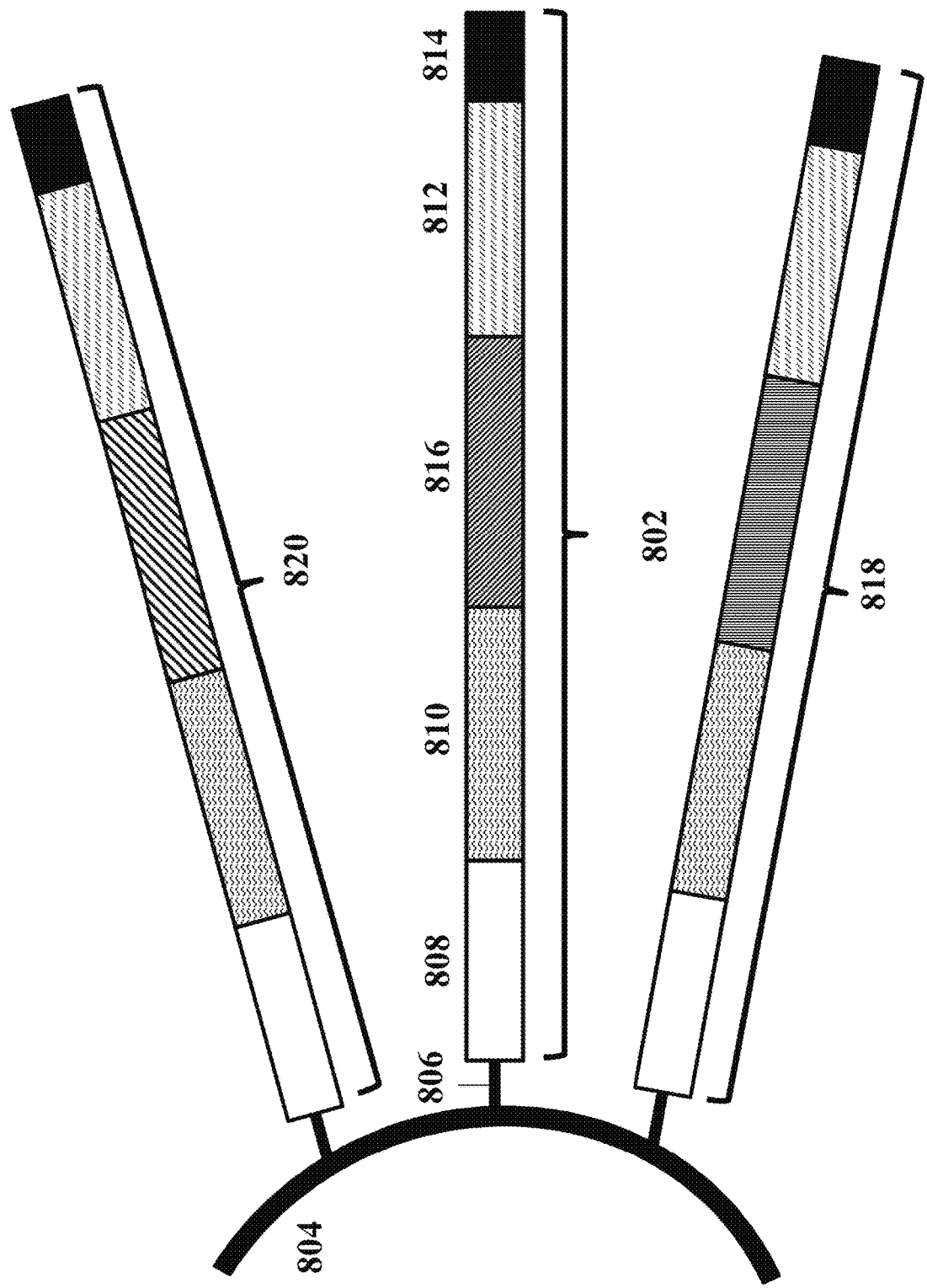
FIG. 8 illustrates an example of a barcode carrying bead.

FIG. 8 illustrates an example of a barcode carrying bead. A nucleic acid molecule 802, such as an oligonucleotide, can be coupled to a bead 804 by a releasable linkage 806, such as, for example, a disulfide linker. The same bead 804 may be coupled (e.g., via releasable linkage) to one or more other nucleic acid molecules 818, 820. The nucleic acid molecule 802 may be or comprise a barcode. As noted elsewhere herein, the structure of the barcode may comprise a number of sequence elements. The nucleic acid molecule 802 may comprise a functional sequence 808 that may be used in subsequent processing. For example, the functional sequence 808 may include one or more of a sequencer specific flow cell attachment sequence (e.g., a P5 sequence for Illumina® sequencing systems) and a sequencing primer sequence (e.g., a R1 primer for Illumina® sequencing systems). The nucleic acid molecule 802 may comprise a barcode sequence 810 for use in barcoding the sample (e.g., DNA, RNA, protein, etc.). In some cases, the barcode sequence 810 can be bead-specific such that the barcode sequence 810 is common to all nucleic acid molecules (e.g., including nucleic acid molecule 802) coupled to the same bead 804. Alternatively or in addition, the barcode sequence 810 can be partition-specific such that the barcode sequence 810 is common to all nucleic acid molecules coupled to one or more beads that are partitioned into the same partition. The nucleic acid molecule 802 may comprise a specific priming sequence 812, such as an mRNA specific priming sequence (e.g., poly-T sequence), a targeted priming sequence, and/or a random priming sequence. The nucleic acid molecule 802 may comprise an anchoring sequence 814 to ensure that the specific priming sequence 812 hybridizes at the sequence end (e.g., of the mRNA). For example, the anchoring sequence 814 can include a random short sequence of nucleotides, such as a 1-mer, 2-mer, 3-mer or longer sequence, which can ensure that a poly-T segment is more likely to hybridize at the sequence end of the poly-A tail of the mRNA.

The nucleic acid molecule 802 may comprise a unique molecular identifying sequence 816 (e.g., unique molecular identifier (UMI)). In some cases, the unique molecular identifying sequence 816 may comprise from about 5 to about 8 nucleotides. Alternatively, the unique molecular identifying sequence 816 may compress less than about 5 or more than about 8 nucleotides. The unique molecular identifying sequence 816 may be a unique sequence that varies across individual nucleic acid molecules (e.g., 802, 818, 820, etc.) coupled to a single bead (e.g., bead 804). In some cases, the unique molecular identifying sequence 816 may be a random sequence (e.g., such as a random N-mer sequence). For example, the UMI may provide a unique identifier of the starting mRNA molecule that was captured, in order to allow quantitation of the number of original expressed RNA. As will be appreciated, although FIG. 8 shows three nucleic acid molecules 802, 818, 820 coupled to the surface of the bead 804, an individual bead may be coupled to any number of individual nucleic acid molecules, for example, from one to tens to hundreds of thousands or even millions of individual nucleic acid molecules. The respective barcodes for the individual nucleic acid molecules can comprise both common sequence segments or relatively common sequence segments (e.g., 808, 810, 812, etc.) and variable or unique sequence segments (e.g., 816) between different individual nucleic acid molecules coupled to the same bead.

In operation, a biological particle (e.g., cell, DNA, RNA, etc.) can be co-partitioned along with a barcode bearing bead 804. The barcoded nucleic acid molecules 802, 818, 820 can be released from the bead 804 in the partition. By way of example, in the context of analyzing sample RNA, the poly-T segment (e.g., 812) of one of the released nucleic acid molecules (e.g., 802) can hybridize to the poly-A tail of a mRNA molecule. Reverse transcription may result in a cDNA transcript of the mRNA, but which transcript includes each of the sequence segments 808, 810, 816 of the nucleic acid molecule 802. Because the nucleic acid molecule 802 comprises an anchoring sequence 814, it will more likely hybridize to and prime reverse transcription at the sequence end of the poly-A tail of the mRNA. Within any given partition, all of the cDNA transcripts of the individual mRNA molecules may include a common barcode sequence segment 810. However, the transcripts made from the different mRNA molecules within a given partition may vary at the unique molecular identifying sequence 812 segment (e.g., UMI segment). Beneficially, even following any subsequent amplification of the contents of a given partition, the number of different UMIs can be indicative of the quantity of mRNA originating from a given partition, and thus from the biological particle (e.g., cell). As noted above, the transcripts can be amplified, cleaned up and sequenced to identify the sequence of the cDNA transcript of the mRNA, as well as to sequence the barcode segment and the UMI segment. While a poly-T primer sequence is described, other targeted or random priming sequences may also be used in priming the reverse transcription reaction. Likewise, although described as releasing the barcoded oligonucleotides into the partition, in some cases, the nucleic acid molecules bound to the bead (e.g., gel bead) may be used to hybridize and capture the mRNA on the solid phase of the bead, for example, in order to facilitate the separation of the RNA from other cell contents.

In some cases, precursors comprising a functional group that is reactive or capable of being activated such that it becomes reactive can be polymerized with other precursors to generate gel beads comprising the activated or activatable functional group. The functional group may then be used to attach additional species (e.g., disulfide linkers, primers, other oligonucleotides, etc.) to the gel beads. For example, some precursors comprising a carboxylic acid (COOH) group can co-polymerize with other precursors to form a gel bead that also comprises a COOH functional group. In some cases, acrylic acid (a species comprising free COOH groups), acrylamide, and bis(acryloyl)cystamine can be co-polymerized together to generate a gel bead comprising free COOH groups. The COOH groups of the gel bead can be activated (e.g., via 1-Ethyl-3-(3-dimethylaminopropyl)carbodiimide (EDC) and N-Hydroxysuccinimide (NETS) or 4-(4,6-Dimethoxy-1,3,5-triazin-2-yl)-4-methylmorpholinium chloride (DMTMM)) such that they are reactive (e.g., reactive to amine functional groups where EDC/NHS or DMTMM are used for activation). The activated COOH groups can then react with an appropriate species (e.g., a species comprising an amine functional group where the carboxylic acid groups are activated to be reactive with an amine functional group) comprising a moiety to be linked to the bead.

Beads comprising disulfide linkages in their polymeric network may be functionalized with additional species via reduction of some of the disulfide linkages to free thiols. The disulfide linkages may be reduced via, for example, the action of a reducing agent (e.g., DTT, TCEP, etc.) to generate free thiol groups, without dissolution of the bead. Free thiols of the beads can then react with free thiols of a species or a species comprising another disulfide bond (e.g., via thiol-disulfide exchange) such that the species can be linked to the beads (e.g., via a generated disulfide bond). In some cases, free thiols of the beads may react with any other suitable group. For example, free thiols of the beads may react with species comprising an acrydite moiety. The free thiol groups of the beads can react with the acrydite via Michael addition chemistry, such that the species comprising the acrydite is linked to the bead. In some cases, uncontrolled reactions can be prevented by inclusion of a thiol capping agent such as N-ethylmalieamide or iodoacetate.

Activation of disulfide linkages within a bead can be controlled such that only a small number of disulfide linkages are activated. Control may be exerted, for example, by controlling the concentration of a reducing agent used to generate free thiol groups and/or concentration of reagents used to form disulfide bonds in bead polymerization. In some cases, a low concentration (e.g., molecules of reducing agent:gel bead ratios of less than or equal to about 1:100,000,000,000, less than or equal to about 1:10,000,000,000, less than or equal to about 1:1,000,000,000, less than or equal to about 1:100,000,000, less than or equal to about 1:10,000,000, less than or equal to about 1:1,000,000, less than or equal to about 1:100,000, less than or equal to about 1:10,000) of reducing agent may be used for reduction. Controlling the number of disulfide linkages that are reduced to free thiols may be useful in ensuring bead structural integrity during functionalization. In some cases, optically-active agents, such as fluorescent dyes may be coupled to beads via free thiol groups of the beads and used to quantify the number of free thiols present in a bead and/or track a bead.

In some cases, addition of moieties to a gel bead after gel bead formation may be advantageous. For example, addition of an oligonucleotide (e.g., barcoded oligonucleotide) after gel bead formation may avoid loss of the species during chain transfer termination that can occur during polymerization. Moreover, smaller precursors (e.g., monomers or cross linkers that do not comprise side chain groups and linked moieties) may be used for polymerization and can be minimally hindered from growing chain ends due to viscous effects. In some cases, functionalization after gel bead synthesis can minimize exposure of species (e.g., oligonucleotides) to be loaded with potentially damaging agents (e.g., free radicals) and/or chemical environments. In some cases, the generated gel may possess an upper critical solution temperature (UCST) that can permit temperature driven swelling and collapse of a bead. Such functionality may aid in oligonucleotide (e.g., a primer) infiltration into the bead during subsequent functionalization of the bead with the oligonucleotide. Post-production functionalization may also be useful in controlling loading ratios of species in beads, such that, for example, the variability in loading ratio is minimized. Species loading may also be performed in a batch process such that a plurality of beads can be functionalized with the species in a single batch.

A bead injected or otherwise introduced into a partition may comprise releasably, cleavably, or reversibly attached barcodes. A bead injected or otherwise introduced into a partition may comprise activatable barcodes. A bead injected or otherwise introduced into a partition may be degradable, disruptable, or dissolvable beads.

Barcodes can be releasably, cleavably or reversibly attached to the beads such that barcodes can be released or be releasable through cleavage of a linkage between the barcode molecule and the bead, or released through degradation of the underlying bead itself, allowing the barcodes to be accessed or be accessible by other reagents, or both. In non-limiting examples, cleavage may be achieved through reduction of di-sulfide bonds, use of restriction enzymes, photo-activated cleavage, or cleavage via other types of stimuli (e.g., chemical, thermal, pH, enzymatic, etc.) and/or reactions, such as described elsewhere herein. Releasable barcodes may sometimes be referred to as being activatable, in that they are available for reaction once released. Thus, for example, an activatable barcode may be activated by releasing the barcode from a bead (or other suitable type of partition described herein). Other activatable configurations are also envisioned in the context of the described methods and systems.

In addition to, or as an alternative to the cleavable linkages between the beads and the associated molecules, such as barcode containing nucleic acid molecules (e.g., barcoded oligonucleotides), the beads may be degradable, disruptable, or dissolvable spontaneously or upon exposure to one or more stimuli (e.g., temperature changes, pH changes, exposure to particular chemical species or phase, exposure to light, reducing agent, etc.). In some cases, a bead may be dissolvable, such that material components of the beads are solubilized when exposed to a particular chemical species or an environmental change, such as a change temperature or a change in pH. In some cases, a gel bead can be degraded or dissolved at elevated temperature and/or in basic conditions. In some cases, a bead may be thermally degradable such that when the bead is exposed to an appropriate change in temperature (e.g., heat), the bead degrades. Degradation or dissolution of a bead bound to a species (e.g., a nucleic acid molecule, e.g., barcoded oligonucleotide) may result in release of the species from the bead.

As will be appreciated from the above disclosure, the degradation of a bead may refer to the disassociation of a bound or entrained species from a bead, both with and without structurally degrading the physical bead itself. For example, the degradation of the bead may involve cleavage of a cleavable linkage via one or more species and/or methods described elsewhere herein. In another example, entrained species may be released from beads through osmotic pressure differences due to, for example, changing chemical environments. By way of example, alteration of bead pore sizes due to osmotic pressure differences can generally occur without structural degradation of the bead itself. In some cases, an increase in pore size due to osmotic swelling of a bead can permit the release of entrained species within the bead. In other cases, osmotic shrinking of a bead may cause a bead to better retain an entrained species due to pore size contraction.

A degradable bead may be introduced into a partition, such as a droplet of an emulsion or a well, such that the bead degrades within the partition and any associated species (e.g., oligonucleotides) are released within the droplet when the appropriate stimulus is applied. The free species (e.g., oligonucleotides, nucleic acid molecules) may interact with other reagents contained in the partition. For example, a polyacrylamide bead comprising cystamine and linked, via a disulfide bond, to a barcode sequence, may be combined with a reducing agent within a droplet of a water-in-oil emulsion. Within the droplet, the reducing agent can break the various disulfide bonds, resulting in bead degradation and release of the barcode sequence into the aqueous, inner environment of the droplet. In another example, heating of a droplet comprising a bead-bound barcode sequence in basic solution may also result in bead degradation and release of the attached barcode sequence into the aqueous, inner environment of the droplet.

Any suitable number of molecular tag molecules (e.g., primer, barcoded oligonucleotide) can be associated with a bead such that, upon release from the bead, the molecular tag molecules (e.g., primer, e.g., barcoded oligonucleotide) are present in the partition at a pre-defined concentration. Such pre-defined concentration may be selected to facilitate certain reactions for generating a sequencing library, e.g., amplification, within the partition. In some cases, the pre-defined concentration of the primer can be limited by the process of producing nucleic acid molecule (e.g., oligonucleotide) bearing beads.

In some cases, beads can be non-covalently loaded with one or more reagents. The beads can be non-covalently loaded by, for instance, subjecting the beads to conditions sufficient to swell the beads, allowing sufficient time for the reagents to diffuse into the interiors of the beads, and subjecting the beads to conditions sufficient to de-swell the beads. The swelling of the beads may be accomplished, for instance, by placing the beads in a thermodynamically favorable solvent, subjecting the beads to a higher or lower temperature, subjecting the beads to a higher or lower ion concentration, and/or subjecting the beads to an electric field. The swelling of the beads may be accomplished by various swelling methods. The de-swelling of the beads may be accomplished, for instance, by transferring the beads in a thermodynamically unfavorable solvent, subjecting the beads to lower or high temperatures, subjecting the beads to a lower or higher ion concentration, and/or removing an electric field. The de-swelling of the beads may be accomplished by various de-swelling methods. Transferring the beads may cause pores in the bead to shrink. The shrinking may then hinder reagents within the beads from diffusing out of the interiors of the beads. The hindrance may be due to steric interactions between the reagents and the interiors of the beads. The transfer may be accomplished microfluidically. For instance, the transfer may be achieved by moving the beads from one co-flowing solvent stream to a different co-flowing solvent stream. The swellability and/or pore size of the beads may be adjusted by changing the polymer composition of the bead.

In some cases, an acrydite moiety linked to a precursor, another species linked to a precursor, or a precursor itself can comprise a labile bond, such as chemically, thermally, or photo-sensitive bond e.g., disulfide bond, UV sensitive bond, or the like. Once acrydite moieties or other moieties comprising a labile bond are incorporated into a bead, the bead may also comprise the labile bond. The labile bond may be, for example, useful in reversibly linking (e.g., covalently linking) species (e.g., barcodes, primers, etc.) to a bead. In some cases, a thermally labile bond may include a nucleic acid hybridization based attachment, e.g., where an oligonucleotide is hybridized to a complementary sequence that is attached to the bead, such that thermal melting of the hybrid releases the oligonucleotide, e.g., a barcode containing sequence, from the bead or microcapsule.

The addition of multiple types of labile bonds to a gel bead may result in the generation of a bead capable of responding to varied stimuli. Each type of labile bond may be sensitive to an associated stimulus (e.g., chemical stimulus, light, temperature, enzymatic, etc.) such that release of species attached to a bead via each labile bond may be controlled by the application of the appropriate stimulus. Such functionality may be useful in controlled release of species from a gel bead. In some cases, another species comprising a labile bond may be linked to a gel bead after gel bead formation via, for example, an activated functional group of the gel bead as described above. As will be appreciated, barcodes that are releasably, cleavably or reversibly attached to the beads described herein include barcodes that are released or releasable through cleavage of a linkage between the barcode molecule and the bead, or that are released through degradation of the underlying bead itself, allowing the barcodes to be accessed or accessible by other reagents, or both.

The barcodes that are releasable as described herein may sometimes be referred to as being activatable, in that they are available for reaction once released. Thus, for example, an activatable barcode may be activated by releasing the barcode from a bead (or other suitable type of partition described herein). Other activatable configurations are also envisioned in the context of the described methods and systems.

In addition to thermally cleavable bonds, disulfide bonds and UV sensitive bonds, other non-limiting examples of labile bonds that may be coupled to a precursor or bead include an ester linkage (e.g., cleavable with an acid, a base, or hydroxylamine), a vicinal diol linkage (e.g., cleavable via sodium periodate), a Diels-Alder linkage (e.g., cleavable via heat), a sulfone linkage (e.g., cleavable via a base), a silyl ether linkage (e.g., cleavable via an acid), a glycosidic linkage (e.g., cleavable via an amylase), a peptide linkage (e.g., cleavable via a protease), or a phosphodiester linkage (e.g., cleavable via a nuclease (e.g., DNAase)). A bond may be cleavable via other nucleic acid molecule targeting enzymes, such as restriction enzymes (e.g., restriction endonucleases), as described further below.

Species may be encapsulated in beads during bead generation (e.g., during polymerization of precursors). Such species may or may not participate in polymerization. Such species may be entered into polymerization reaction mixtures such that generated beads comprise the species upon bead formation. In some cases, such species may be added to the gel beads after formation. Such species may include, for example, nucleic acid molecules (e.g., oligonucleotides), reagents for a nucleic acid amplification reaction (e.g., primers, polymerases, dNTPs, co-factors (e.g., ionic co-factors), buffers) including those described herein, reagents for enzymatic reactions (e.g., enzymes, co-factors, substrates, buffers), reagents for nucleic acid modification reactions such as polymerization, ligation, or digestion, and/or reagents for template preparation (e.g., tagmentation) for one or more sequencing platforms (e.g., Nextera® for Illumina®). Such species may include one or more enzymes described herein, including without limitation, polymerase, reverse transcriptase, restriction enzymes (e.g., endonuclease), transposase, ligase, proteinase K, DNAse, etc. Such species may include one or more reagents described elsewhere herein (e.g., lysis agents, inhibitors, inactivating agents, chelating agents, stimulus). Trapping of such species may be controlled by the polymer network density generated during polymerization of precursors, control of ionic charge within the gel bead (e.g., via ionic species linked to polymerized species), or by the release of other species. Encapsulated species may be released from a bead upon bead degradation and/or by application of a stimulus capable of releasing the species from the bead. Alternatively or in addition, species may be partitioned in a partition (e.g., droplet) during or subsequent to partition formation. Such species may include, without limitation, the abovementioned species that may also be encapsulated in a bead.

A degradable bead may comprise one or more species with a labile bond such that, when the bead/species is exposed to the appropriate stimuli, the bond is broken and the bead degrades. The labile bond may be a chemical bond (e.g., covalent bond, ionic bond) or may be another type of physical interaction (e.g., van der Waals interactions, dipole-dipole interactions, etc.). In some cases, a crosslinker used to generate a bead may comprise a labile bond. Upon exposure to the appropriate conditions, the labile bond can be broken and the bead degraded. For example, upon exposure of a polyacrylamide gel bead comprising cystamine crosslinkers to a reducing agent, the disulfide bonds of the cystamine can be broken and the bead degraded.

A degradable bead may be useful in more quickly releasing an attached species (e.g., a nucleic acid molecule, a barcode sequence, a primer, etc) from the bead when the appropriate stimulus is applied to the bead as compared to a bead that does not degrade. For example, for a species bound to an inner surface of a porous bead or in the case of an encapsulated species, the species may have greater mobility and accessibility to other species in solution upon degradation of the bead. In some cases, a species may also be attached to a degradable bead via a degradable linker (e.g., disulfide linker). The degradable linker may respond to the same stimuli as the degradable bead or the two degradable species may respond to different stimuli. For example, a barcode sequence may be attached, via a disulfide bond, to a polyacrylamide bead comprising cystamine. Upon exposure of the barcoded-bead to a reducing agent, the bead degrades and the barcode sequence is released upon breakage of both the disulfide linkage between the barcode sequence and the bead and the disulfide linkages of the cystamine in the bead.

As will be appreciated from the above disclosure, while referred to as degradation of a bead, in many instances as noted above, that degradation may refer to the disassociation of a bound or entrained species from a bead, both with and without structurally degrading the physical bead itself. For example, entrained species may be released from beads through osmotic pressure differences due to, for example, changing chemical environments. By way of example, alteration of bead pore sizes due to osmotic pressure differences can generally occur without structural degradation of the bead itself. In some cases, an increase in pore size due to osmotic swelling of a bead can permit the release of entrained species within the bead. In other cases, osmotic shrinking of a bead may cause a bead to better retain an entrained species due to pore size contraction.

Where degradable beads are provided, it may be beneficial to avoid exposing such beads to the stimulus or stimuli that cause such degradation prior to a given time, in order to, for example, avoid premature bead degradation and issues that arise from such degradation, including for example poor flow characteristics and aggregation. By way of example, where beads comprise reducible cross-linking groups, such as disulfide groups, it will be desirable to avoid contacting such beads with reducing agents, e.g., DTT or other disulfide cleaving reagents. In such cases, treatment to the beads described herein will, in some cases be provided free of reducing agents, such as DTT. Because reducing agents are often provided in commercial enzyme preparations, it may be desirable to provide reducing agent free (or DTT free) enzyme preparations in treating the beads described herein. Examples of such enzymes include, e.g., polymerase enzyme preparations, reverse transcriptase enzyme preparations, ligase enzyme preparations, as well as many other enzyme preparations that may be used to treat the beads described herein. The terms "reducing agent free" or "DTT free" preparations can refer to a preparation having less than about 1/10th, less than about 1/50th, or even less than about 1/100th of the lower ranges for such materials used in degrading the beads. For example, for DTT, the reducing agent free preparation can have less than about 0.01 millimolar (mM), 0.005 mM, 0.001 mM DTT, 0.0005 mM DTT, or even less than about 0.0001 mM DTT. In many cases, the amount of DTT can be undetectable.

Numerous chemical triggers may be used to trigger the degradation of beads. Examples of these chemical changes may include, but are not limited to pH-mediated changes to the integrity of a component within the bead, degradation of a component of a bead via cleavage of cross-linked bonds, and depolymerization of a component of a bead.

In some embodiments, a bead may be formed from materials that comprise degradable chemical crosslinkers, such as BAC or cystamine. Degradation of such degradable crosslinkers may be accomplished through a number of mechanisms. In some examples, a bead may be contacted with a chemical degrading agent that may induce oxidation, reduction or other chemical changes. For example, a chemical degrading agent may be a reducing agent, such as dithiothreitol (DTT). Additional examples of reducing agents may include β-mercaptoethanol, (2S)-2-amino-1,4-dimercaptobutane (dithiobutylamine or DTBA), tris(2-carboxyethyl) phosphine (TCEP), or combinations thereof. A reducing agent may degrade the disulfide bonds formed between gel precursors forming the bead, and thus, degrade the bead. In other cases, a change in pH of a solution, such as an increase in pH, may trigger degradation of a bead. In other cases, exposure to an aqueous solution, such as water, may trigger hydrolytic degradation, and thus degradation of the bead. In some cases, any combination of stimuli may trigger degradation of a bead. For example, a change in pH may enable a chemical agent (e.g., DTT) to become an effective reducing agent.

Beads may also be induced to release their contents upon the application of a thermal stimulus. A change in temperature can cause a variety of changes to a bead. For example, heat can cause a solid bead to liquefy. A change in heat may cause melting of a bead such that a portion of the bead degrades. In other cases, heat may increase the internal pressure of the bead components such that the bead ruptures or explodes. Heat may also act upon heat-sensitive polymers used as materials to construct beads.

Any suitable agent may degrade beads. In some embodiments, changes in temperature or pH may be used to degrade thermo-sensitive or pH-sensitive bonds within beads. In some embodiments, chemical degrading agents may be used to degrade chemical bonds within beads by oxidation, reduction or other chemical changes. For example, a chemical degrading agent may be a reducing agent, such as DTT, wherein DTT may degrade the disulfide bonds formed between a crosslinker and gel precursors, thus degrading the bead. In some embodiments, a reducing agent may be added to degrade the bead, which may or may not cause the bead to release its contents. Examples of reducing agents may include dithiothreitol (DTT), β-mercaptoethanol, (2S)-2-amino-1,4-dimercaptobutane (dithiobutylamine or DTBA), tris(2-carboxyethyl) phosphine (TCEP), or combinations thereof. The reducing agent may be present at a concentration of about 0.1 mM, 0.5 mM, 1 mM, 5 mM, 10 mM. The reducing agent may be present at a concentration of at least about 0.1 mM, 0.5 mM, 1 mM, 5 mM, 10 mM, or greater than 10 mM. The reducing agent may be present at concentration of at most about 10 mM, 5 mM, 1 mM, 0.5 mM, 0.1 mM, or less.

Any suitable number of molecular tag molecules (e.g., primer, barcoded oligonucleotide) can be associated with a bead such that, upon release from the bead, the molecular tag molecules (e.g., primer, e.g., barcoded oligonucleotide) are present in the partition at a pre-defined concentration. Such pre-defined concentration may be selected to facilitate certain reactions for generating a sequencing library, e.g., amplification, within the partition. In some cases, the pre-defined concentration of the primer can be limited by the process of producing oligonucleotide bearing beads.

Although FIG. 1 and FIG. 2 have been described in terms of providing substantially singly occupied partitions, above, in certain cases, it may be desirable to provide multiply occupied partitions, e.g., containing two, three, four or more cells and/or microcapsules (e.g., beads) comprising barcoded nucleic acid molecules (e.g., oligonucleotides) within a single partition. Accordingly, as noted above, the flow characteristics of the biological particle and/or bead containing fluids and partitioning fluids may be controlled to provide for such multiply occupied partitions. In particular, the flow parameters may be controlled to provide a given occupancy rate at greater than about 50% of the partitions, greater than about 75%, and in some cases greater than about 80%, 90%, 95%, or higher.

In some cases, additional microcapsules can be used to deliver additional reagents to a partition. In such cases, it may be advantageous to introduce different beads into a common channel or droplet generation junction, from different bead sources (e.g., containing different associated reagents) through different channel inlets into such common channel or droplet generation junction (e.g., junction 210). In such cases, the flow and frequency of the different beads into the channel or junction may be controlled to provide for a certain ratio of microcapsules from each source, while ensuring a given pairing or combination of such beads into a partition with a given number of biological particles (e.g., one biological particle and one bead per partition).

The partitions described herein may comprise small volumes, for example, less than about 10 microliters (μL), 5 μL, 1 μL, 900 picoliters (pL), 800 pL, 700 pL, 600 pL, 500 pL, 400 pL, 300 pL, 200 pL, 100 pL, 50 pL, 20 pL, 10 pL, 1 pL, 500 nanoliters (nL), 100 nL, 50 nL, or less.

For example, in the case of droplet based partitions, the droplets may have overall volumes that are less than about 1000 pL, 900 pL, 800 pL, 700 pL, 600 pL, 500 pL, 400 pL, 300 pL, 200 pL, 100 pL, 50 pL, 20 pL, 10 pL, 1 pL, or less. Where co-partitioned with microcapsules, it will be appreciated that the sample fluid volume, e.g., including co-partitioned biological particles and/or beads, within the partitions may be less than about 90% of the above described volumes, less than about 80%, less than about 70%, less than about 60%, less than about 50%, less than about 40%, less than about 30%, less than about 20%, or less than about 10% of the above described volumes.

As is described elsewhere herein, partitioning species may generate a population or plurality of partitions. In such cases, any suitable number of partitions can be generated or otherwise provided. For example, at least about 1,000 partitions, at least about 5,000 partitions, at least about 10,000 partitions, at least about 50,000 partitions, at least about 100,000 partitions, at least about 500,000 partitions, at least about 1,000,000 partitions, at least about 5,000,000 partitions at least about 10,000,000 partitions, at least about 50,000,000 partitions, at least about 100,000,000 partitions, at least about 500,000,000 partitions, at least about 1,000,000,000 partitions, or more partitions can be generated or otherwise provided. Moreover, the plurality of partitions may comprise both unoccupied partitions (e.g., empty partitions) and occupied partitions.

Reagents

In accordance with certain aspects, biological particles may be partitioned along with lysis reagents in order to release the contents of the biological particles within the partition. In such cases, the lysis agents can be contacted with the biological particle suspension concurrently with, or immediately prior to, the introduction of the biological particles into the partitioning junction/droplet generation zone (e.g., junction 210), such as through an additional channel or channels upstream of the channel junction. In accordance with other aspects, additionally or alternatively, biological particles may be partitioned along with other reagents, as will be described further below.

Figure 3:
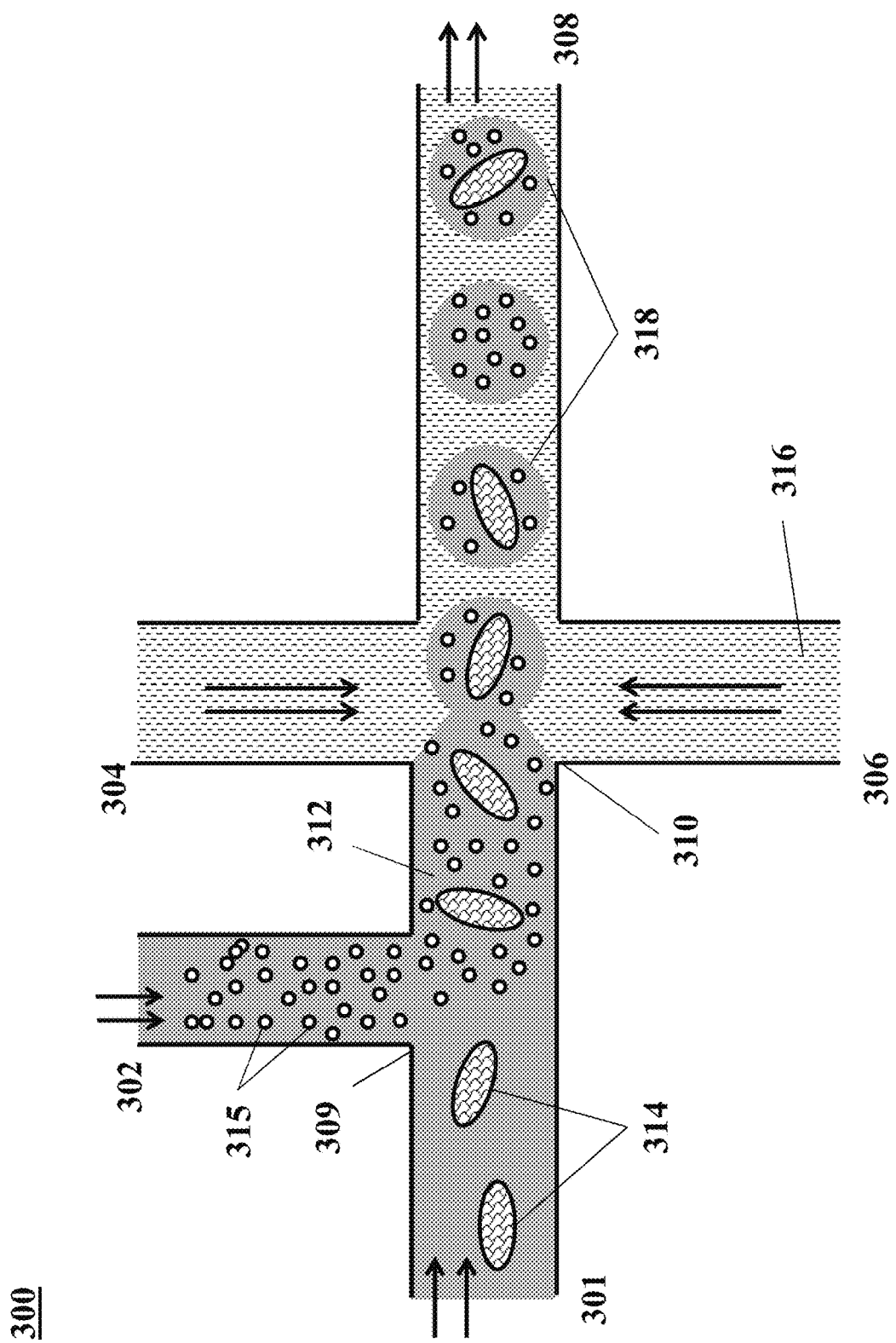
FIG. 3 shows an example of a microfluidic channel structure for co-partitioning biological particles and reagents.

FIG. 3 shows an example of a microfluidic channel structure 300 for co-partitioning biological particles and reagents. The channel structure 300 can include channel segments 301, 302, 304, 306 and 308. Channel segments 301 and 302 communicate at a first channel junction 309. Channel segments 302, 304, 306, and 308 communicate at a second channel junction 310.

In an example operation, the channel segment 301 may transport an aqueous fluid 312 that includes a plurality of biological particles 314 along the channel segment 301 into the second junction 310. As an alternative or in addition to, channel segment 301 may transport beads (e.g., gel beads). The beads may comprise barcode molecules.

For example, the channel segment 301 may be connected to a reservoir comprising an aqueous suspension of biological particles 314. Upstream of, and immediately prior to reaching, the second junction 310, the channel segment 301 may meet the channel segment 302 at the first junction 309. The channel segment 302 may transport a plurality of reagents 315 (e.g., lysis agents) suspended in the aqueous fluid 312 along the channel segment 302 into the first junction 309. For example, the channel segment 302 may be connected to a reservoir comprising the reagents 315. After the first junction 309, the aqueous fluid 312 in the channel segment 301 can carry both the biological particles 314 and the reagents 315 towards the second junction 310. In some instances, the aqueous fluid 312 in the channel segment 301 can include one or more reagents, which can be the same or different reagents as the reagents 315. A second fluid 316 that is immiscible with the aqueous fluid 312 (e.g., oil) can be delivered to the second junction 310 from each of channel segments 304 and 306. Upon meeting of the aqueous fluid 312 from the channel segment 301 and the second fluid 316 from each of channel segments 304 and 306 at the second channel junction 310, the aqueous fluid 312 can be partitioned as discrete droplets 318 in the second fluid 316 and flow away from the second junction 310 along channel segment 308. The channel segment 308 may deliver the discrete droplets 318 to an outlet reservoir fluidly coupled to the channel segment 308, where they may be harvested.

The second fluid 316 can comprise an oil, such as a fluorinated oil, that includes a fluorosurfactant for stabilizing the resulting droplets, for example, inhibiting subsequent coalescence of the resulting droplets 318.

A discrete droplet generated may include an individual biological particle 314 and/or one or more reagents 315. In some instances, a discrete droplet generated may include a barcode carrying bead (not shown), such as via other microfluidics structures described elsewhere herein. In some instances, a discrete droplet may be unoccupied (e.g., no reagents, no biological particles).

Beneficially, when lysis reagents and biological particles are co-partitioned, the lysis reagents can facilitate the release of the contents of the biological particles within the partition. The contents released in a partition may remain discrete from the contents of other partitions.

As will be appreciated, the channel segments described herein may be coupled to any of a variety of different fluid sources or receiving components, including reservoirs, tubing, manifolds, or fluidic components of other systems. As will be appreciated, the microfluidic channel structure 300 may have other geometries. For example, a microfluidic channel structure can have more than two channel junctions. For example, a microfluidic channel structure can have 2, 3, 4, 5 channel segments or more each carrying the same or different types of beads, reagents, and/or biological particles that meet at a channel junction. Fluid flow in each channel segment may be controlled to control the partitioning of the different elements into droplets. Fluid may be directed flow along one or more channels or reservoirs via one or more fluid flow units. A fluid flow unit can comprise compressors (e.g., providing positive pressure), pumps (e.g., providing negative pressure), actuators, and the like to control flow of the fluid. Fluid may also or otherwise be controlled via applied pressure differentials, centrifugal force, electrokinetic pumping, vacuum, capillary or gravity flow, or the like.

Examples of lysis agents include bioactive reagents, such as lysis enzymes that are used for lysis of different cell types, e.g., gram positive or negative bacteria, plants, yeast, mammalian, etc., such as lysozymes, achromopeptidase, lysostaphin, labiase, kitalase, lyticase, and a variety of other lysis enzymes available from, e.g., Sigma-Aldrich, Inc. (St Louis, Mo.), as well as other commercially available lysis enzymes. Other lysis agents may additionally or alternatively be co-partitioned with the biological particles to cause the release of the biological particles's contents into the partitions. For example, in some cases, surfactant-based lysis solutions may be used to lyse cells, although these may be less desirable for emulsion based systems where the surfactants can interfere with stable emulsions. In some cases, lysis solutions may include non-ionic surfactants such as, for example, TritonX-100 and Tween 20. In some cases, lysis solutions may include ionic surfactants such as, for example, sarcosyl and sodium dodecyl sulfate (SDS). Electroporation, thermal, acoustic or mechanical cellular disruption may also be used in certain cases, e.g., non-emulsion based partitioning such as encapsulation of biological particles that may be in addition to or in place of droplet partitioning, where any pore size of the encapsulate is sufficiently small to retain nucleic acid fragments of a given size, following cellular disruption.

Alternatively or in addition to the lysis agents co-partitioned with the biological particles described above, other reagents can also be co-partitioned with the biological particles, including, for example, DNase and RNase inactivating agents or inhibitors, such as proteinase K, chelating agents, such as EDTA, and other reagents employed in removing or otherwise reducing negative activity or impact of different cell lysate components on subsequent processing of nucleic acids. In addition, in the case of encapsulated biological particles, the biological particles may be exposed to an appropriate stimulus to release the biological particles or their contents from a co-partitioned microcapsule. For example, in some cases, a chemical stimulus may be co-partitioned along with an encapsulated biological particle to allow for the degradation of the microcapsule and release of the cell or its contents into the larger partition. In some cases, this stimulus may be the same as the stimulus described elsewhere herein for release of nucleic acid molecules (e.g., oligonucleotides) from their respective microcapsule (e.g., bead). In alternative aspects, this may be a different and non-overlapping stimulus, in order to allow an encapsulated biological particle to be released into a partition at a different time from the release of nucleic acid molecules into the same partition.

Additional reagents may also be co-partitioned with the biological particles, such as endonucleases to fragment a biological particle's DNA, DNA polymerase enzymes and dNTPs used to amplify the biological particle's nucleic acid fragments and to attach the barcode molecular tags to the amplified fragments. Other enzymes may be co-partitioned, including without limitation, polymerase, transposase, ligase, proteinase K, DNAse, etc. Additional reagents may also include reverse transcriptase enzymes, including enzymes with terminal transferase activity, primers and oligonucleotides, and switch oligonucleotides (also referred to herein as "switch oligos" or "template switching oligonucleotides") which can be used for template switching. In some cases, template switching can be used to increase the length of a cDNA. In some cases, template switching can be used to append a predefined nucleic acid sequence to the cDNA. In an example of template switching, cDNA can be generated from reverse transcription of a template, e.g., cellular mRNA, where a reverse transcriptase with terminal transferase activity can add additional nucleotides, e.g., polyC, to the cDNA in a template independent manner. Switch oligos can include sequences complementary to the additional nucleotides, e.g., polyG. The additional nucleotides (e.g., polyC) on the cDNA can hybridize to the additional nucleotides (e.g., polyG) on the switch oligo, whereby the switch oligo can be used by the reverse transcriptase as template to further extend the cDNA. Template switching oligonucleotides may comprise a hybridization region and a template region. The hybridization region can comprise any sequence capable of hybridizing to the target. In some cases, as previously described, the hybridization region comprises a series of G bases to complement the overhanging C bases at the 3' end of a cDNA molecule. The series of G bases may comprise 1 G base, 2 G bases, 3 G bases, 4 G bases, 5 G bases or more than 5 G bases. The template sequence can comprise any sequence to be incorporated into the cDNA. In some cases, the template region comprises at least 1 (e.g., at least 2, 3, 4, 5 or more) tag sequences and/or functional sequences. Switch oligos may comprise deoxyribonucleic acids; ribonucleic acids; modified nucleic acids including 2-Aminopurine, 2,6-Diaminopurine (2-Amino-dA), inverted dT, 5-Methyl dC, 2'-deoxyInosine, Super T (5-hydroxybutynl-2'-deoxyuridine), Super G (8-aza-7-deazaguanosine), locked nucleic acids (LNAs), unlocked nucleic acids (UNAs, e.g., UNA-A, UNA-U, UNA-C, UNA-G), Iso-dG, Iso-dC, 2' Fluoro bases (e.g., Fluoro C, Fluoro U, Fluoro A, and Fluoro G), or any combination.

In some cases, the length of a switch oligo may be at least about 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249 or 250 nucleotides or longer.

In some cases, the length of a switch oligo may be at most about 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249 or 250 nucleotides.

Once the contents of the cells are released into their respective partitions, the macromolecular components (e.g., macromolecular constituents of biological particles, such as RNA, DNA, or proteins) contained therein may be further processed within the partitions. In accordance with the methods and systems described herein, the macromolecular component contents of individual biological particles can be provided with unique identifiers such that, upon characterization of those macromolecular components they may be attributed as having been derived from the same biological particle or particles. The ability to attribute characteristics to individual biological particles or groups of biological particles is provided by the assignment of unique identifiers specifically to an individual biological particle or groups of biological particles. Unique identifiers, e.g., in the form of nucleic acid barcodes can be assigned or associated with individual biological particles or populations of biological particles, in order to tag or label the biological particle's macromolecular components (and as a result, its characteristics) with the unique identifiers. These unique identifiers can then be used to attribute the biological particle's components and characteristics to an individual biological particle or group of biological particles.

In some aspects, this is performed by co-partitioning the individual biological particle or groups of biological particles with the unique identifiers, such as described above (with reference to FIG. 2). In some aspects, the unique identifiers are provided in the form of nucleic acid molecules (e.g., oligonucleotides) that comprise nucleic acid barcode sequences that may be attached to or otherwise associated with the nucleic acid contents of individual biological particle, or to other components of the biological particle, and particularly to fragments of those nucleic acids. The nucleic acid molecules are partitioned such that as between nucleic acid molecules in a given partition, the nucleic acid barcode sequences contained therein are the same, but as between different partitions, the nucleic acid molecule can, and do have differing barcode sequences, or at least represent a large number of different barcode sequences across all of the partitions in a given analysis. In some aspects, only one nucleic acid barcode sequence can be associated with a given partition, although in some cases, two or more different barcode sequences may be present.

The nucleic acid barcode sequences can include from about 6 to about 20 or more nucleotides within the sequence of the nucleic acid molecules (e.g., oligonucleotides). The nucleic acid barcode sequences can include from about 6 to about 20, 30, 40, 50, 60, 70, 80, 90, 100 or more nucleotides. In some cases, the length of a barcode sequence may be about 6, 7, 8, 9, 10, 11, 12, 13, 14, 15, 16, 17, 18, 19, 20 nucleotides or longer. In some cases, the length of a barcode sequence may be at least about 6, 7, 8, 9, 10, 11, 12, 13, 14, 15, 16, 17, 18, 19, 20 nucleotides or longer. In some cases, the length of a barcode sequence may be at most about 6, 7, 8, 9, 10, 11, 12, 13, 14, 15, 16, 17, 18, 19, 20 nucleotides or shorter. These nucleotides may be completely contiguous, i.e., in a single stretch of adjacent nucleotides, or they may be separated into two or more separate subsequences that are separated by 1 or more nucleotides. In some cases, separated barcode subsequences can be from about 4 to about 16 nucleotides in length. In some cases, the barcode subsequence may be about 4, 5, 6, 7, 8, 9, 10, 11, 12, 13, 14, 15, 16 nucleotides or longer. In some cases, the barcode subsequence may be at least about 4, 5, 6, 7, 8, 9, 10, 11, 12, 13, 14, 15, 16 nucleotides or longer. In some cases, the barcode subsequence may be at most about 4, 5, 6, 7, 8, 9, 10, 11, 12, 13, 14, 15, 16 nucleotides or shorter.

The co-partitioned nucleic acid molecules can also comprise other functional sequences useful in the processing of the nucleic acids from the co-partitioned biological particles. These sequences include, e.g., targeted or random/universal amplification primer sequences for amplifying the genomic DNA from the individual biological particles within the partitions while attaching the associated barcode sequences, sequencing primers or primer recognition sites, hybridization or probing sequences, e.g., for identification of presence of the sequences or for pulling down barcoded nucleic acids, or any of a number of other potential functional sequences. Other mechanisms of co-partitioning oligonucleotides may also be employed, including, e.g., coalescence of two or more droplets, where one droplet contains oligonucleotides, or microdispensing of oligonucleotides into partitions, e.g., droplets within microfluidic systems.

In an example, microcapsules, such as beads, are provided that each include large numbers of the above described barcoded nucleic acid molecules (e.g., barcoded oligonucleotides) releasably attached to the beads, where all of the nucleic acid molecules attached to a particular bead will include the same nucleic acid barcode sequence, but where a large number of diverse barcode sequences are represented across the population of beads used. In some embodiments, hydrogel beads, e.g., comprising polyacrylamide polymer matrices, are used as a solid support and delivery vehicle for the nucleic acid molecules into the partitions, as they are capable of carrying large numbers of nucleic acid molecules, and may be configured to release those nucleic acid molecules upon exposure to a particular stimulus, as described elsewhere herein. In some cases, the population of beads provides a diverse barcode sequence library that includes at least about 1,000 different barcode sequences, at least about 5,000 different barcode sequences, at least about 10,000 different barcode sequences, at least about 50,000 different barcode sequences, at least about 100,000 different barcode sequences, at least about 1,000,000 different barcode sequences, at least about 5,000,000 different barcode sequences, or at least about 10,000,000 different barcode sequences, or more. Additionally, each bead can be provided with large numbers of nucleic acid (e.g., oligonucleotide) molecules attached. In particular, the number of molecules of nucleic acid molecules including the barcode sequence on an individual bead can be at least about 1,000 nucleic acid molecules, at least about 5,000 nucleic acid molecules, at least about 10,000 nucleic acid molecules, at least about 50,000 nucleic acid molecules, at least about 100,000 nucleic acid molecules, at least about 500,000 nucleic acids, at least about 1,000,000 nucleic acid molecules, at least about 5,000,000 nucleic acid molecules, at least about 10,000,000 nucleic acid molecules, at least about 50,000,000 nucleic acid molecules, at least about 100,000,000 nucleic acid molecules, at least about 250,000,000 nucleic acid molecules and in some cases at least about 1 billion nucleic acid molecules, or more. Nucleic acid molecules of a given bead can include identical (or common) barcode sequences, different barcode sequences, or a combination of both. Nucleic acid molecules of a given bead can include multiple sets of nucleic acid molecules. Nucleic acid molecules of a given set can include identical barcode sequences. The identical barcode sequences can be different from barcode sequences of nucleic acid molecules of another set.

Moreover, when the population of beads is partitioned, the resulting population of partitions can also include a diverse barcode library that includes at least about 1,000 different barcode sequences, at least about 5,000 different barcode sequences, at least about 10,000 different barcode sequences, at least at least about 50,000 different barcode sequences, at least about 100,000 different barcode sequences, at least about 1,000,000 different barcode sequences, at least about 5,000,000 different barcode sequences, or at least about 10,000,000 different barcode sequences. Additionally, each partition of the population can include at least about 1,000 nucleic acid molecules, at least about 5,000 nucleic acid molecules, at least about 10,000 nucleic acid molecules, at least about 50,000 nucleic acid molecules, at least about 100,000 nucleic acid molecules, at least about 500,000 nucleic acids, at least about 1,000,000 nucleic acid molecules, at least about 5,000,000 nucleic acid molecules, at least about 10,000,000 nucleic acid molecules, at least about 50,000,000 nucleic acid molecules, at least about 100,000,000 nucleic acid molecules, at least about 250,000,000 nucleic acid molecules and in some cases at least about 1 billion nucleic acid molecules.

In some cases, it may be desirable to incorporate multiple different barcodes within a given partition, either attached to a single or multiple beads within the partition. For example, in some cases, a mixed, but known set of barcode sequences may provide greater assurance of identification in the subsequent processing, e.g., by providing a stronger address or attribution of the barcodes to a given partition, as a duplicate or independent confirmation of the output from a given partition.

The nucleic acid molecules (e.g., oligonucleotides) are releasable from the beads upon the application of a particular stimulus to the beads. In some cases, the stimulus may be a photo-stimulus, e.g., through cleavage of a photo-labile linkage that releases the nucleic acid molecules. In other cases, a thermal stimulus may be used, where elevation of the temperature of the beads environment will result in cleavage of a linkage or other release of the nucleic acid molecules form the beads. In still other cases, a chemical stimulus can be used that cleaves a linkage of the nucleic acid molecules to the beads, or otherwise results in release of the nucleic acid molecules from the beads. In one case, such compositions include the polyacrylamide matrices described above for encapsulation of biological particles, and may be degraded for release of the attached nucleic acid molecules through exposure to a reducing agent, such as DTT.

In some aspects, provided are systems and methods for controlled partitioning. Droplet size may be controlled by adjusting certain geometric features in channel architecture (e.g., microfluidics channel architecture). For example, an expansion angle, width, and/or length of a channel may be adjusted to control droplet size.

Figure 4:
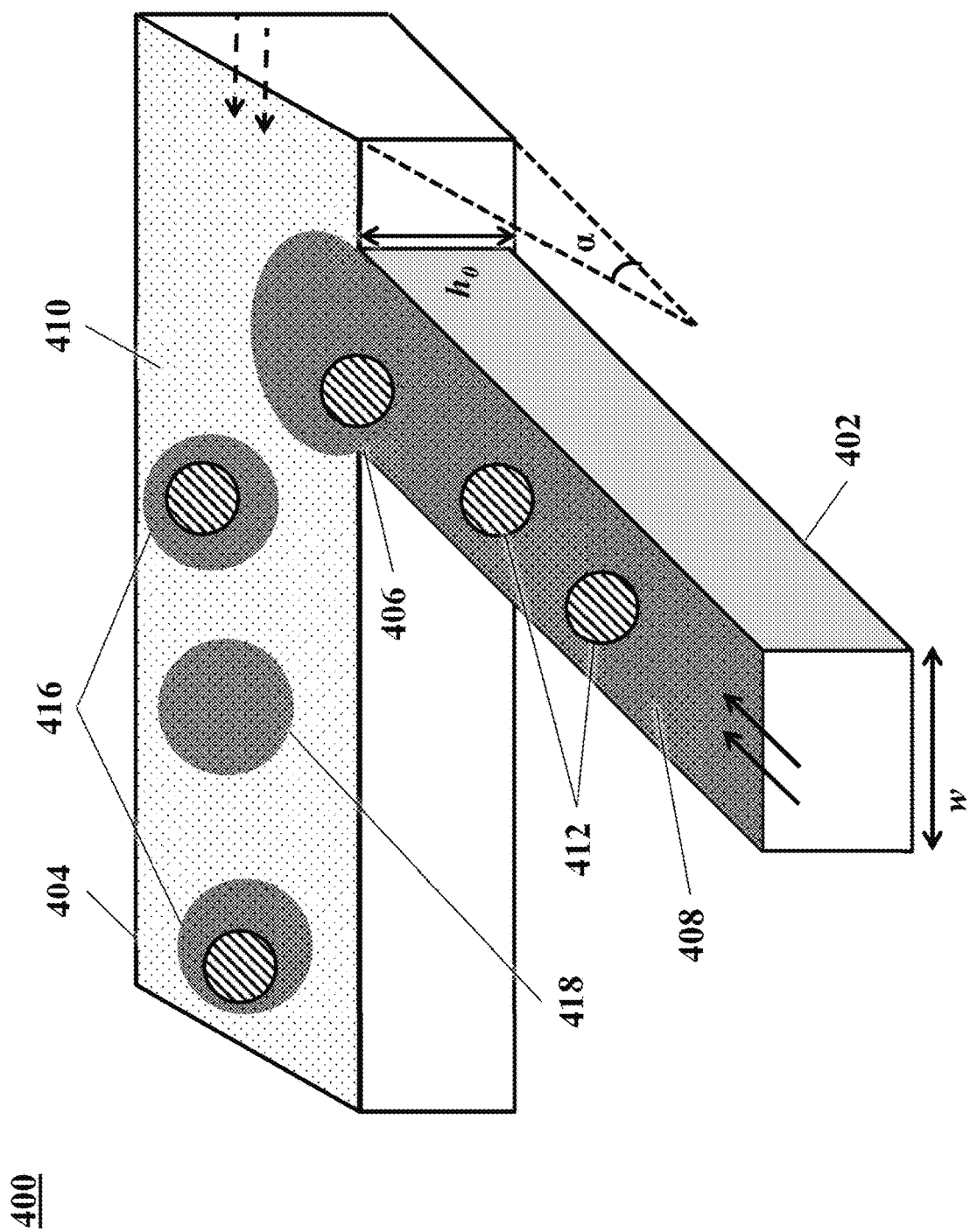
FIG. 4 shows an example of a microfluidic channel structure for the controlled partitioning of beads into discrete droplets.

FIG. 4 shows an example of a microfluidic channel structure for the controlled partitioning of beads into discrete droplets. A channel structure 400 can include a channel segment 402 communicating at a channel junction 406 (or intersection) with a reservoir 404. The reservoir 404 can be a chamber. Any reference to "reservoir," as used herein, can also refer to a "chamber." In operation, an aqueous fluid 408 that includes suspended beads 412 may be transported along the channel segment 402 into the junction 406 to meet a second fluid 410 that is immiscible with the aqueous fluid 408 in the reservoir 404 to create droplets 416, 418 of the aqueous fluid 408 flowing into the reservoir 404. At the junction 406 where the aqueous fluid 408 and the second fluid 410 meet, droplets can form based on factors such as the hydrodynamic forces at the junction 406, flow rates of the two fluids 408, 410, fluid properties, and certain geometric parameters (e.g., w, $h_0$, $\alpha$, etc.) of the channel structure 400. A plurality of droplets can be collected in the reservoir 404 by continuously injecting the aqueous fluid 408 from the channel segment 402 through the junction 406.

A discrete droplet generated may include a bead (e.g., as in occupied droplets 416). Alternatively, a discrete droplet generated may include more than one bead. Alternatively, a discrete droplet generated may not include any beads (e.g., as in unoccupied droplet 418). In some instances, a discrete droplet generated may contain one or more biological particles, as described elsewhere herein. In some instances, a discrete droplet generated may comprise one or more reagents, as described elsewhere herein.

In some instances, the aqueous fluid 408 can have a substantially uniform concentration or frequency of beads 412. The beads 412 can be introduced into the channel segment 402 from a separate channel (not shown in FIG. 4). The frequency of beads 412 in the channel segment 402 may be controlled by controlling the frequency in which the beads 412 are introduced into the channel segment 402 and/or the relative flow rates of the fluids in the channel segment 402 and the separate channel. In some instances, the beads can be introduced into the channel segment 402 from a plurality of different channels, and the frequency controlled accordingly.

In some instances, the aqueous fluid 408 in the channel segment 402 can comprise biological particles (e.g., described with reference to FIGS. 1 and 2). In some instances, the aqueous fluid 408 can have a substantially uniform concentration or frequency of biological particles. As with the beads, the biological particles can be introduced into the channel segment 402 from a separate channel. The frequency or concentration of the biological particles in the aqueous fluid 408 in the channel segment 402 may be controlled by controlling the frequency in which the biological particles are introduced into the channel segment 402 and/or the relative flow rates of the fluids in the channel segment 402 and the separate channel. In some instances, the biological particles can be introduced into the channel segment 402 from a plurality of different channels, and the frequency controlled accordingly. In some instances, a first separate channel can introduce beads and a second separate channel can introduce biological particles into the channel segment 402. The first separate channel introducing the beads may be upstream or downstream of the second separate channel introducing the biological particles.

The second fluid 410 can comprise an oil, such as a fluorinated oil, that includes a fluorosurfactant for stabilizing the resulting droplets, for example, inhibiting subsequent coalescence of the resulting droplets.

In some instances, the second fluid 410 may not be subjected to and/or directed to any flow in or out of the reservoir 404. For example, the second fluid 410 may be substantially stationary in the reservoir 404. In some instances, the second fluid 410 may be subjected to flow within the reservoir 404, but not in or out of the reservoir 404, such as via application of pressure to the reservoir 404 and/or as affected by the incoming flow of the aqueous fluid 408 at the junction 406. Alternatively, the second fluid 410 may be subjected and/or directed to flow in or out of the reservoir 404. For example, the reservoir 404 can be a channel directing the second fluid 410 from upstream to downstream, transporting the generated droplets.

The channel structure 400 at or near the junction 406 may have certain geometric features that at least partly determine the sizes of the droplets formed by the channel structure 400. The channel segment 402 can have a height, $h_0$ and width, w, at or near the junction 406. By way of example, the channel segment 402 can comprise a rectangular cross-section that leads to a reservoir 404 having a wider cross-section (such as in width or diameter). Alternatively, the cross-section of the channel segment 402 can be other shapes, such as a circular shape, trapezoidal shape, polygonal shape, or any other shapes. The top and bottom walls of the reservoir 404 at or near the junction 406 can be inclined at an expansion angle, $\alpha$. The expansion angle, $\alpha$, allows the tongue (portion of the aqueous fluid 408 leaving channel segment 402 at junction 406 and entering the reservoir 404 before droplet formation) to increase in depth and facilitate decrease in curvature of the intermediately formed droplet. Droplet size may decrease with increasing expansion angle. The resulting droplet radius, $R_d$, may be predicted by the following equation for the aforementioned geometric parameters of $h_0$, w, and $\alpha$:

$$R_d \approx 0.44\left(1 + 2.2\sqrt{\tan\alpha}\,\frac{w}{h_0}\right)\frac{h_0}{\sqrt{\tan\alpha}}$$

By way of example, for a channel structure with w=21 μm, h=21 μm, and α=3°, the predicted droplet size is 121 μm. In another example, for a channel structure with w=25 μm, h=25 μm, and α=5°, the predicted droplet size is 123 μm. In another example, for a channel structure with w=28 μm, h=28 μm, and α=7°, the predicted droplet size is 124 μm.

In some instances, the expansion angle, α, may be between a range of from about 0.5° to about 4°, from about 0.1° to about 10°, or from about 0° to about 90°. For example, the expansion angle can be at least about 0.01°, 0.1°, 0.2°, 0.3°, 0.4°, 0.5°, 0.6°, 0.7°, 0.8°, 0.9°, 1°, 2°, 3°, 4°, 5°, 6°, 7°, 8°, 9°, 10°, 15°, 20°, 25°, 30°, 35°, 40°, 45°, 50°, 55°, 60°, 65°, 70°, 75°, 80°, 85°, or higher. In some instances, the expansion angle can be at most about 89°, 88°, 87°, 86°, 85°, 84°, 83°, 82°, 81°, 80°, 75°, 70°, 65°, 60°, 55°, 50°, 45°, 40°, 35°, 30°, 25°, 20°, 15°, 10°, 9°, 8°, 7°, 6°, 5°, 4°, 3°, 2°, 1°, 0.1°, 0.01°, or less. In some instances, the width, w, can be between a range of from about 100 micrometers (μm) to about 500 μm. In some instances, the width, w, can be between a range of from about 10 μm to about 200 μm. Alternatively, the width can be less than about 10 μm. Alternatively, the width can be greater than about 500 μm. In some instances, the flow rate of the aqueous fluid 408 entering the junction 406 can be between about 0.04 microliters (μL)/minute (min) and about 40 μL/min. In some instances, the flow rate of the aqueous fluid 408 entering the junction 406 can be between about 0.01 microliters (μL)/minute (min) and about 100 μL/min. Alternatively, the flow rate of the aqueous fluid 408 entering the junction 406 can be less than about 0.01 μL/min. Alternatively, the flow rate of the aqueous fluid 408 entering the junction 406 can be greater than about 40 μL/min, such as 45 μL/min, 50 μL/min, 55 μL/min, 60 μL/min, 65 μL/min, 70 μL/min, 75 μL/min, 80 μL/min, 85 μL/min, 90 μL/min, 95 μL/min, 100 μL/min, 110 μL/min, 120 μL/min, 130 μL/min, 140 μL/min, 150 μL/min, or greater. At lower flow rates, such as flow rates of about less than or equal to 10 microliters/minute, the droplet radius may not be dependent on the flow rate of the aqueous fluid 408 entering the junction 406.

In some instances, at least about 50% of the droplets generated can have uniform size. In some instances, at least about 55%, 60%, 65%, 70%, 75%, 80%, 85%, 90%, 95%, 96%, 97%, 98%, 99%, or greater of the droplets generated can have uniform size. Alternatively, less than about 50% of the droplets generated can have uniform size.

The throughput of droplet generation can be increased by increasing the points of generation, such as increasing the number of junctions (e.g., junction 406) between aqueous fluid 408 channel segments (e.g., channel segment 402) and the reservoir 404. Alternatively or in addition, the throughput of droplet generation can be increased by increasing the flow rate of the aqueous fluid 408 in the channel segment 402.

Figure 5:
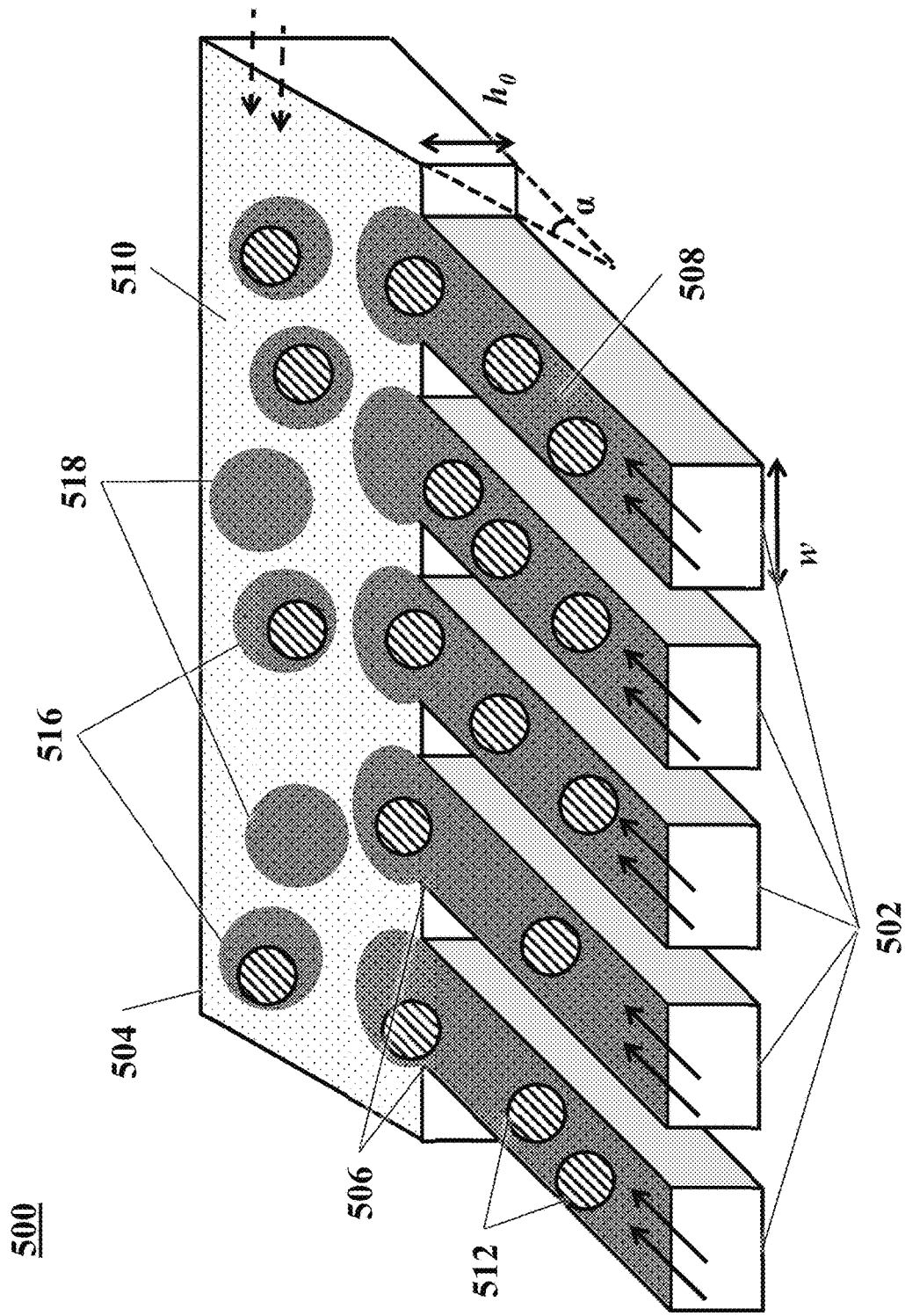
FIG. 5 shows an example of a microfluidic channel structure for increased droplet generation throughput.

FIG. 5 shows an example of a microfluidic channel structure for increased droplet generation throughput. A microfluidic channel structure 500 can comprise a plurality of channel segments 502 and a reservoir 504. Each of the plurality of channel segments 502 may be in fluid communication with the reservoir 504. The channel structure 500 can comprise a plurality of channel junctions 506 between the plurality of channel segments 502 and the reservoir 504. Each channel junction can be a point of droplet generation. The channel segment 402 from the channel structure 400 in FIG. 4 and any description to the components thereof may correspond to a given channel segment of the plurality of channel segments 502 in channel structure 500 and any description to the corresponding components thereof. The reservoir 404 from the channel structure 400 and any description to the components thereof may correspond to the reservoir 504 from the channel structure 500 and any description to the corresponding components thereof.

Each channel segment of the plurality of channel segments 502 may comprise an aqueous fluid 508 that includes suspended beads 512. The reservoir 504 may comprise a second fluid 510 that is immiscible with the aqueous fluid 508. In some instances, the second fluid 510 may not be subjected to and/or directed to any flow in or out of the reservoir 504. For example, the second fluid 510 may be substantially stationary in the reservoir 504. In some instances, the second fluid 510 may be subjected to flow within the reservoir 504, but not in or out of the reservoir 504, such as via application of pressure to the reservoir 504 and/or as affected by the incoming flow of the aqueous fluid 508 at the junctions. Alternatively, the second fluid 510 may be subjected and/or directed to flow in or out of the reservoir 504. For example, the reservoir 504 can be a channel directing the second fluid 510 from upstream to downstream, transporting the generated droplets.

In operation, the aqueous fluid 508 that includes suspended beads 512 may be transported along the plurality of channel segments 502 into the plurality of junctions 506 to meet the second fluid 510 in the reservoir 504 to create droplets 516, 518. A droplet may form from each channel segment at each corresponding junction with the reservoir 504. At the junction where the aqueous fluid 508 and the second fluid 510 meet, droplets can form based on factors such as the hydrodynamic forces at the junction, flow rates of the two fluids 508, 510, fluid properties, and certain geometric parameters (e.g., w, $h_0$, α, etc.) of the channel structure 500, as described elsewhere herein. A plurality of droplets can be collected in the reservoir 504 by continuously injecting the aqueous fluid 508 from the plurality of channel segments 502 through the plurality of junctions 506. Throughput may significantly increase with the parallel channel configuration of channel structure 500. For example, a channel structure having five inlet channel segments comprising the aqueous fluid 508 may generate droplets five times as frequently than a channel structure having one inlet channel segment, provided that the fluid flow rate in the channel segments are substantially the same. The fluid flow rate in the different inlet channel segments may or may not be substantially the same. A channel structure may have as many parallel channel segments as is practical and allowed for the size of the reservoir. For example, the channel structure may have at least about 2, 3, 4, 5, 6, 7, 8, 9, 10, 20, 30, 40, 50, 60, 70, 80, 90, 100, 150, 500, 250, 300, 350, 400, 450, 500, 600, 700, 800, 900, 1000, 1500, 5000 or more parallel or substantially parallel channel segments.

The geometric parameters, w, $h_0$, and α, may or may not be uniform for each of the channel segments in the plurality of channel segments 502. For example, each channel segment may have the same or different widths at or near its respective channel junction with the reservoir 504. For example, each channel segment may have the same or different height at or near its respective channel junction with the reservoir 504. In another example, the reservoir 504 may have the same or different expansion angle at the different channel junctions with the plurality of channel segments 502. When the geometric parameters are uniform, beneficially, droplet size may also be controlled to be uniform even with the increased throughput. In some instances, when it is desirable to have a different distribution of droplet sizes, the geometric parameters for the plurality of channel segments 502 may be varied accordingly.

In some instances, at least about 50% of the droplets generated can have uniform size. In some instances, at least about 55%, 60%, 65%, 70%, 75%, 80%, 85%, 90%, 95%, 96%, 97%, 98%, 99%, or greater of the droplets generated can have uniform size. Alternatively, less than about 50% of the droplets generated can have uniform size.

Figure 6:
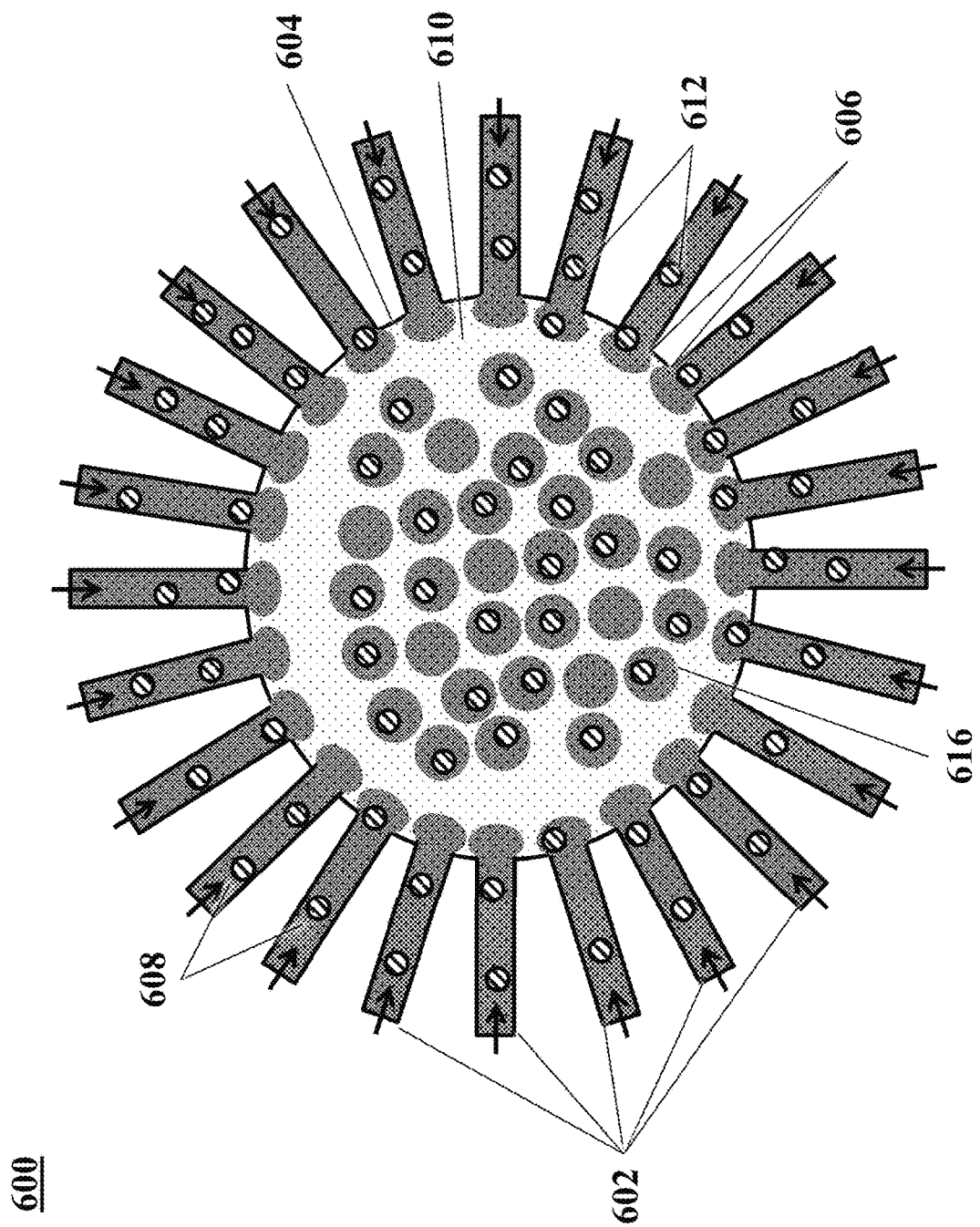
FIG. 6 shows another example of a microfluidic channel structure for increased droplet generation throughput.

FIG. 6 shows another example of a microfluidic channel structure for increased droplet generation throughput. A microfluidic channel structure 600 can comprise a plurality of channel segments 602 arranged generally circularly around the perimeter of a reservoir 604. Each of the plurality of channel segments 602 may be in fluid communication with the reservoir 604. The channel structure 600 can comprise a plurality of channel junctions 606 between the plurality of channel segments 602 and the reservoir 604. Each channel junction can be a point of droplet generation. The channel segment 402 from the channel structure 400 in FIG. 2 and any description to the components thereof may correspond to a given channel segment of the plurality of channel segments 602 in channel structure 600 and any description to the corresponding components thereof. The reservoir 404 from the channel structure 400 and any description to the components thereof may correspond to the reservoir 604 from the channel structure 600 and any description to the corresponding components thereof.

Each channel segment of the plurality of channel segments 602 may comprise an aqueous fluid 608 that includes suspended beads 612. The reservoir 604 may comprise a second fluid 610 that is immiscible with the aqueous fluid 608. In some instances, the second fluid 610 may not be subjected to and/or directed to any flow in or out of the reservoir 604. For example, the second fluid 610 may be substantially stationary in the reservoir 604. In some instances, the second fluid 610 may be subjected to flow within the reservoir 604, but not in or out of the reservoir 604, such as via application of pressure to the reservoir 604 and/or as affected by the incoming flow of the aqueous fluid 608 at the junctions. Alternatively, the second fluid 610 may be subjected and/or directed to flow in or out of the reservoir 604. For example, the reservoir 604 can be a channel directing the second fluid 610 from upstream to downstream, transporting the generated droplets.

In operation, the aqueous fluid 608 that includes suspended beads 612 may be transported along the plurality of channel segments 602 into the plurality of junctions 606 to meet the second fluid 610 in the reservoir 604 to create a plurality of droplets 616. A droplet may form from each channel segment at each corresponding junction with the reservoir 604. At the junction where the aqueous fluid 608 and the second fluid 610 meet, droplets can form based on factors such as the hydrodynamic forces at the junction, flow rates of the two fluids 608, 610, fluid properties, and certain geometric parameters (e.g., widths and heights of the channel segments 602, expansion angle of the reservoir 604, etc.) of the channel structure 600, as described elsewhere herein. A plurality of droplets can be collected in the reservoir 604 by continuously injecting the aqueous fluid 608 from the plurality of channel segments 602 through the plurality of junctions 606. Throughput may significantly increase with the substantially parallel channel configuration of the channel structure 600. A channel structure may have as many substantially parallel channel segments as is practical and allowed for by the size of the reservoir. For example, the channel structure may have at least about 2, 3, 4, 5, 6, 7, 8, 9, 10, 20, 30, 40, 50, 60, 70, 80, 90, 100, 150, 200, 250, 300, 350, 400, 450, 500, 600, 700, 800, 900, 1000, 1500, 5000 or more parallel or substantially parallel channel segments. The plurality of channel segments may be substantially evenly spaced apart, for example, around an edge or perimeter of the reservoir. Alternatively, the spacing of the plurality of channel segments may be uneven.

The reservoir 604 may have an expansion angle, α (not shown in FIG. 6) at or near each channel junction. Each channel segment of the plurality of channel segments 602 may have a width, w, and a height, $h_0$, at or near the channel junction. The geometric parameters, w, $h_0$, and α, may or may not be uniform for each of the channel segments in the plurality of channel segments 602. For example, each channel segment may have the same or different widths at or near its respective channel junction with the reservoir 604. For example, each channel segment may have the same or different height at or near its respective channel junction with the reservoir 604.

The reservoir 604 may have the same or different expansion angle at the different channel junctions with the plurality of channel segments 602. For example, a circular reservoir (as shown in FIG. 6) may have a conical, dome-like, or hemispherical ceiling (e.g., top wall) to provide the same or substantially same expansion angle for each channel segments 602 at or near the plurality of channel junctions 606. When the geometric parameters are uniform, beneficially, resulting droplet size may be controlled to be uniform even with the increased throughput. In some instances, when it is desirable to have a different distribution of droplet sizes, the geometric parameters for the plurality of channel segments 602 may be varied accordingly.

In some instances, at least about 50% of the droplets generated can have uniform size. In some instances, at least about 55%, 60%, 65%, 70%, 75%, 80%, 85%, 90%, 95%, 96%, 97%, 98%, 99%, or greater of the droplets generated can have uniform size. Alternatively, less than about 50% of the droplets generated can have uniform size. The beads and/or biological particle injected into the droplets may or may not have uniform size.

Figure 7A:
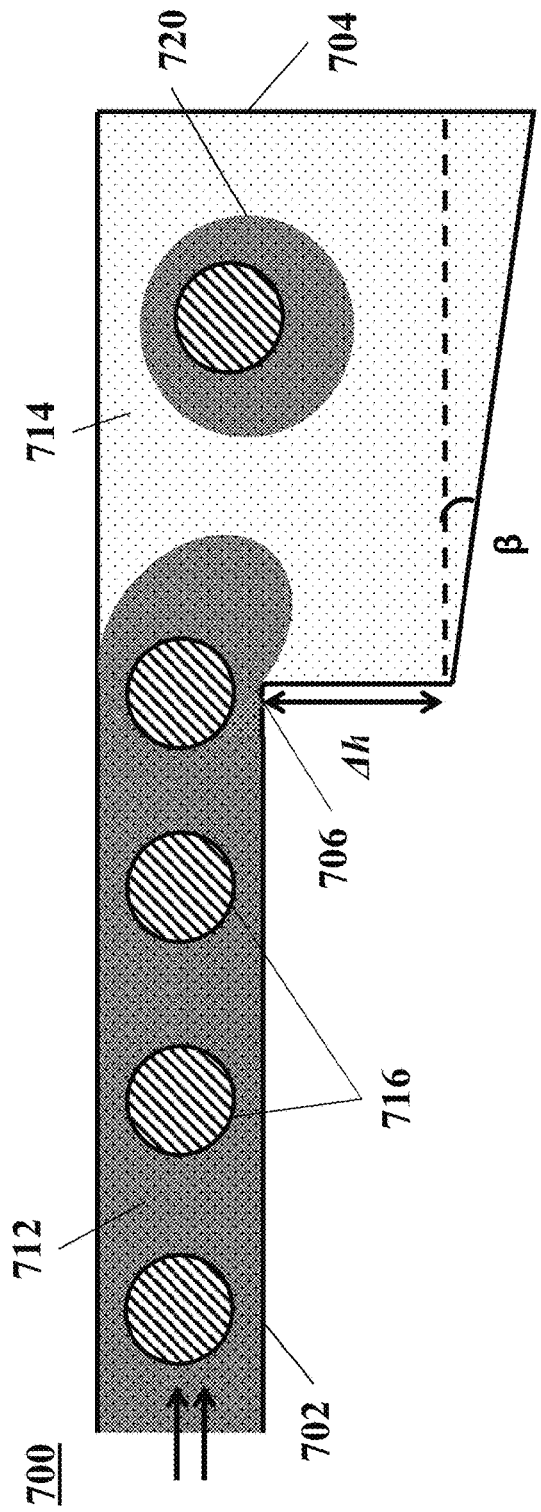
FIG. 7A shows a cross-section view of another example of a microfluidic channel structure with a geometric feature for controlled partitioning.
Figure 7B:
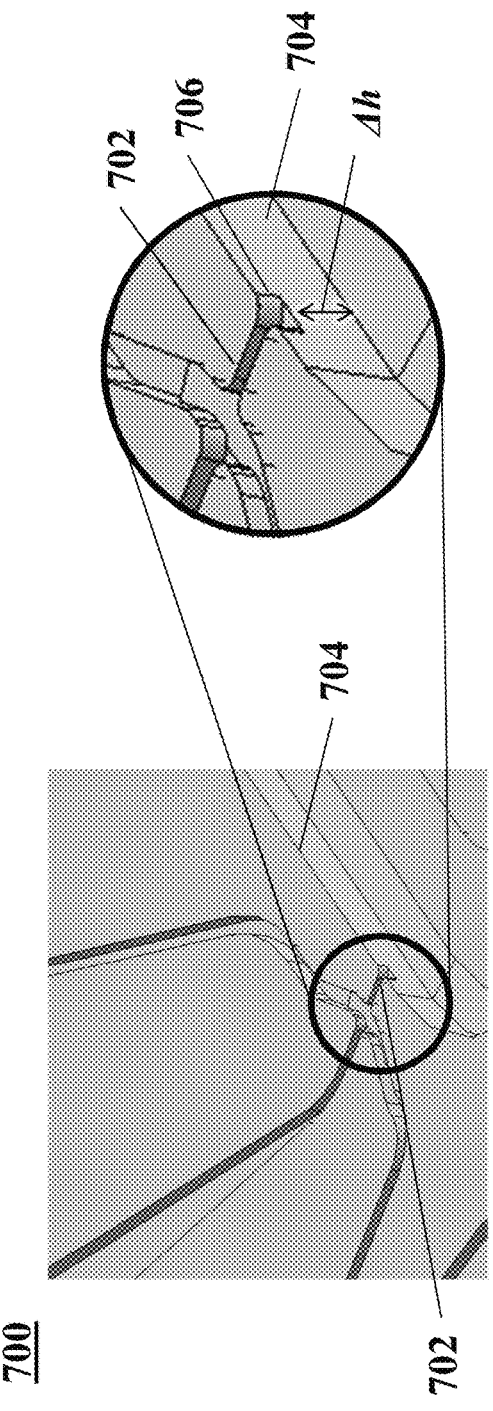
FIG. 7B shows a perspective view of the channel structure of FIG. 7A.

FIG. 7A shows a cross-section view of another example of a microfluidic channel structure with a geometric feature for controlled partitioning. A channel structure 700 can include a channel segment 702 communicating at a channel junction 706 (or intersection) with a reservoir 704. In some instances, the channel structure 700 and one or more of its components can correspond to the channel structure 100 and one or more of its components. FIG. 7B shows a perspective view of the channel structure 700 of FIG. 7A.

An aqueous fluid 712 comprising a plurality of particles 716 may be transported along the channel segment 702 into the junction 706 to meet a second fluid 714 (e.g., oil, etc.) that is immiscible with the aqueous fluid 712 in the reservoir 704 to create droplets 720 of the aqueous fluid 712 flowing into the reservoir 704. At the junction 706 where the aqueous fluid 712 and the second fluid 714 meet, droplets can form based on factors such as the hydrodynamic forces at the junction 706, relative flow rates of the two fluids 712, 714, fluid properties, and certain geometric parameters (e.g., Δh, etc.) of the channel structure 700. A plurality of droplets can be collected in the reservoir 704 by continuously injecting the aqueous fluid 712 from the channel segment 702 at the junction 706.

A discrete droplet generated may comprise one or more particles of the plurality of particles 716. As described elsewhere herein, a particle may be any particle, such as a bead, cell bead, gel bead, biological particle, macromolecular constituents of biological particle, or other particles. Alternatively, a discrete droplet generated may not include any particles.

In some instances, the aqueous fluid 712 can have a substantially uniform concentration or frequency of particles 716. As described elsewhere herein (e.g., with reference to FIG. 4), the particles 716 (e.g., beads) can be introduced into the channel segment 702 from a separate channel (not shown in FIG. 7). The frequency of particles 716 in the channel segment 702 may be controlled by controlling the frequency in which the particles 716 are introduced into the channel segment 702 and/or the relative flow rates of the fluids in the channel segment 702 and the separate channel. In some instances, the particles 716 can be introduced into the channel segment 702 from a plurality of different channels, and the frequency controlled accordingly. In some instances, different particles may be introduced via separate channels. For example, a first separate channel can introduce beads and a second separate channel can introduce biological particles into the channel segment 702. The first separate channel introducing the beads may be upstream or downstream of the second separate channel introducing the biological particles.

In some instances, the second fluid 714 may not be subjected to and/or directed to any flow in or out of the reservoir 704. For example, the second fluid 714 may be substantially stationary in the reservoir 704. In some instances, the second fluid 714 may be subjected to flow within the reservoir 704, but not in or out of the reservoir 704, such as via application of pressure to the reservoir 704 and/or as affected by the incoming flow of the aqueous fluid 712 at the junction 706. Alternatively, the second fluid 714 may be subjected and/or directed to flow in or out of the reservoir 704. For example, the reservoir 704 can be a channel directing the second fluid 714 from upstream to downstream, transporting the generated droplets.

The channel structure 700 at or near the junction 706 may have certain geometric features that at least partly determine the sizes and/or shapes of the droplets formed by the channel structure 700. The channel segment 702 can have a first cross-section height, $h_1$, and the reservoir 704 can have a second cross-section height, $h_2$. The first cross-section height, $h_1$, and the second cross-section height, $h_2$, may be different, such that at the junction 706, there is a height difference of $\Delta h$. The second cross-section height, $h_2$, may be greater than the first cross-section height, $h_1$. In some instances, the reservoir may thereafter gradually increase in cross-section height, for example, the more distant it is from the junction 706. In some instances, the cross-section height of the reservoir may increase in accordance with expansion angle, $\beta$, at or near the junction 706. The height difference, $\Delta h$, and/or expansion angle, $\beta$, can allow the tongue (portion of the aqueous fluid 712 leaving channel segment 702 at junction 706 and entering the reservoir 704 before droplet formation) to increase in depth and facilitate decrease in curvature of the intermediately formed droplet. For example, droplet size may decrease with increasing height difference and/or increasing expansion angle.

The height difference, $\Delta h$, can be at least about 1 μm. Alternatively, the height difference can be at least about 1, 2, 3, 4, 5, 6, 7, 8, 9, 10, 11, 12, 13, 14, 15, 16, 17, 18, 19, 20, 25, 30, 35, 40, 45, 50, 60, 70, 80, 90, 100, 200, 300, 400, 500 μm or more. Alternatively, the height difference can be at most about 500, 400, 300, 200, 100, 90, 80, 70, 60, 50, 45, 40, 35, 30, 25, 20, 19, 18, 17, 16, 15, 14, 13, 12, 11, 10, 9, 8, 7, 6, 5, 4, 3, 2, 1 μm or less. In some instances, the expansion angle, $\beta$, may be between a range of from about 0.5° to about 4°, from about 0.1° to about 10°, or from about 0° to about 90°. For example, the expansion angle can be at least about 0.01°, 0.1°, 0.2°, 0.3°, 0.4°, 0.5°, 0.6°, 0.7°, 0.8°, 0.9°, 1°, 2°, 3°, 4°, 5°, 6°, 7°, 8°, 9°, 10°, 15°, 20°, 25°, 30°, 35°, 40°, 45°, 50°, 55°, 60°, 65°, 70°, 75°, 80°, 85°, or higher. In some instances, the expansion angle can be at most about 89°, 88°, 87°, 86°, 85°, 84°, 83°, 82°, 81°, 80°, 75°, 70°, 65°, 60°, 55°, 50°, 45°, 40°, 35°, 30°, 25°, 20°, 15°, 10°, 9°, 8°, 7°, 6°, 5°, 4°, 3°, 2°, 1°, 0.1°, 0.01°, or less.

In some instances, the flow rate of the aqueous fluid 712 entering the junction 706 can be between about 0.04 microliters (μL)/minute (min) and about 40 μL/min. In some instances, the flow rate of the aqueous fluid 712 entering the junction 706 can be between about 0.01 microliters (μL)/minute (min) and about 100 μL/min. Alternatively, the flow rate of the aqueous fluid 712 entering the junction 706 can be less than about 0.01 μL/min. Alternatively, the flow rate of the aqueous fluid 712 entering the junction 706 can be greater than about 40 μL/min, such as 45 μL/min, 50 μL/min, 55 μL/min, 60 μL/min, 65 μL/min, 70 μL/min, 75 μL/min, 80 μL/min, 85 μL/min, 90 μL/min, 95 μL/min, 100 μL/min, 110 μL/min, 120 μL/min, 130 μL/min, 140 μL/min, 150 μL/min, or greater. At lower flow rates, such as flow rates of about less than or equal to 10 microliters/minute, the droplet radius may not be dependent on the flow rate of the aqueous fluid 712 entering the junction 706. The second fluid 714 may be stationary, or substantially stationary, in the reservoir 704. Alternatively, the second fluid 714 may be flowing, such as at the above flow rates described for the aqueous fluid 712.

In some instances, at least about 50% of the droplets generated can have uniform size. In some instances, at least about 55%, 60%, 65%, 70%, 75%, 80%, 85%, 90%, 95%, 96%, 97%, 98%, 99%, or greater of the droplets generated can have uniform size. Alternatively, less than about 50% of the droplets generated can have uniform size.

While FIGS. 7A and 7B illustrate the height difference, $\Delta h$, being abrupt at the junction 706 (e.g., a step increase), the height difference may increase gradually (e.g., from about 0 μm to a maximum height difference). Alternatively, the height difference may decrease gradually (e.g., taper) from a maximum height difference. A gradual increase or decrease in height difference, as used herein, may refer to a continuous incremental increase or decrease in height difference, wherein an angle between any one differential segment of a height profile and an immediately adjacent differential segment of the height profile is greater than 90°. For example, at the junction 706, a bottom wall of the channel and a bottom wall of the reservoir can meet at an angle greater than 90°. Alternatively or in addition, a top wall (e.g., ceiling) of the channel and a top wall (e.g., ceiling) of the reservoir can meet an angle greater than 90°. A gradual increase or decrease may be linear or non-linear (e.g., exponential, sinusoidal, etc.). Alternatively or in addition, the height difference may variably increase and/or decrease linearly or non-linearly. While FIGS. 7A and 7B illustrate the expanding reservoir cross-section height as linear (e.g., constant expansion angle, $\beta$), the cross-section height may expand non-linearly. For example, the reservoir may be defined at least partially by a dome-like (e.g., hemispherical) shape having variable expansion angles. The cross-section height may expand in any shape.

The channel networks, e.g., as described above or elsewhere herein, can be fluidly coupled to appropriate fluidic components. For example, the inlet channel segments are fluidly coupled to appropriate sources of the materials they are to deliver to a channel junction. These sources may include any of a variety of different fluidic components, from simple reservoirs defined in or connected to a body structure of a microfluidic device, to fluid conduits that deliver fluids from off-device sources, manifolds, fluid flow units (e.g., actuators, pumps, compressors) or the like. Likewise, the outlet channel segment (e.g., channel segment 208, reservoir 604, etc.) may be fluidly coupled to a receiving vessel or conduit for the partitioned cells for subsequent processing. Again, this may be a reservoir defined in the body of a microfluidic device, or it may be a fluidic conduit for delivering the partitioned cells to a subsequent process operation, instrument or component.

The methods and systems described herein may be used to greatly increase the efficiency of single cell applications and/or other applications receiving droplet-based input. For example, following the sorting of occupied cells and/or appropriately-sized cells, subsequent operations that can be performed can include generation of amplification products, purification (e.g., via solid phase reversible immobilization (SPRI)), further processing (e.g., shearing, ligation of functional sequences, and subsequent amplification (e.g., via PCR)). These operations may occur in bulk (e.g., outside the partition). In the case where a partition is a droplet in an emulsion, the emulsion can be broken and the contents of the droplet pooled for additional operations. Additional reagents that may be co-partitioned along with the barcode bearing bead may include oligonucleotides to block ribosomal RNA (rRNA) and nucleases to digest genomic DNA from cells. Alternatively, rRNA removal agents may be applied during additional processing operations. The configuration of the constructs generated by such a method can help minimize (or avoid) sequencing of the poly-T sequence during sequencing and/or sequence the 5' end of a polynucleotide sequence. The amplification products, for example, first amplification products and/or second amplification products, may be subject to sequencing for sequence analysis. In some cases, amplification may be performed using the Partial Hairpin Amplification for Sequencing (PHASE) method.

A variety of applications require the evaluation of the presence and quantification of different biological particle or organism types within a population of biological particles, including, for example, microbiome analysis and characterization, environmental testing, food safety testing, epidemiological analysis, e.g., in tracing contamination or the like.

Computer Systems

Figure 9:
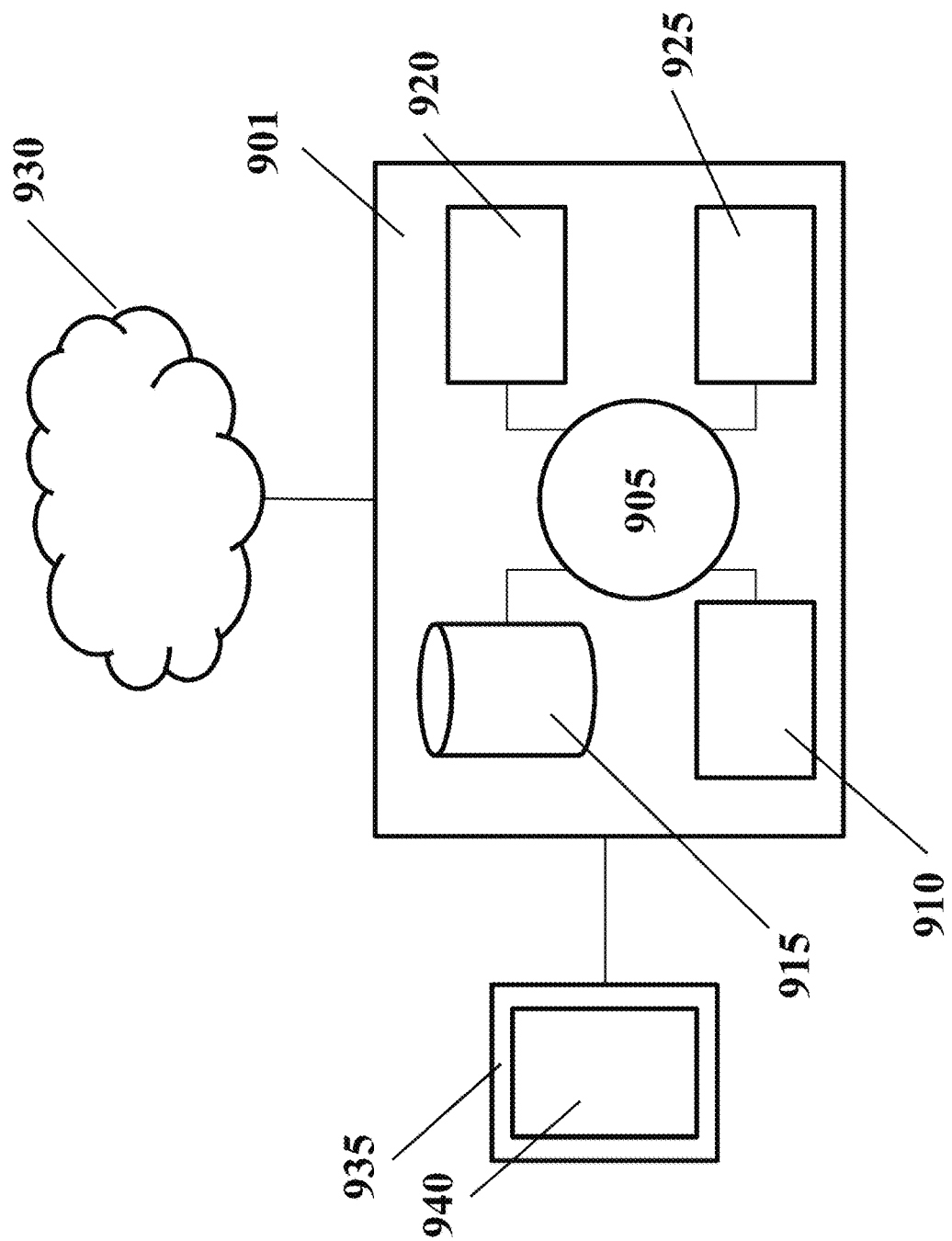
FIG. 9 shows a computer system that is programmed or otherwise configured to implement methods provided herein.

The present disclosure provides computer systems that are programmed to implement methods of the disclosure. FIG. 9 shows a computer system 901 that is programmed or otherwise configured to, for example, (i) control a microfluidics system (e.g., fluid flow), (ii) sort occupied droplets from unoccupied droplets, (iii) polymerize droplets, (iv) perform sequencing applications, (v) generate and maintain a library of analytes; and/or (vi) analyze sequencing results. The computer system 901 can regulate various aspects of the present disclosure, such as, for example, regulating fluid flow rate in one or more channels in a microfluidic structure, regulating polymerization application units, etc. The computer system 901 can be an electronic device of a user or a computer system that is remotely located with respect to the electronic device. The electronic device can be a mobile electronic device.

The computer system 901 includes a central processing unit (CPU, also "processor" and "computer processor" herein) 905, which can be a single core or multi core processor, or a plurality of processors for parallel processing. The computer system 901 also includes memory or memory location 910 (e.g., random-access memory, read-only memory, flash memory), electronic storage unit 915 (e.g., hard disk), communication interface 920 (e.g., network adapter) for communicating with one or more other systems, and peripheral devices 925, such as cache, other memory, data storage and/or electronic display adapters. The memory 910, storage unit 915, interface 920 and peripheral devices 925 are in communication with the CPU 905 through a communication bus (solid lines), such as a motherboard. The storage unit 915 can be a data storage unit (or data repository) for storing data. The computer system 901 can be operatively coupled to a computer network ("network") 930 with the aid of the communication interface 920. The network 930 can be the Internet, an internet and/or extranet, or an intranet and/or extranet that is in communication with the Internet. The network 930 in some cases is a telecommunication and/or data network. The network 930 can include one or more computer servers, which can enable distributed computing, such as cloud computing. The network 930, in some cases with the aid of the computer system 901, can implement a peer-to-peer network, which may enable devices coupled to the computer system 901 to behave as a client or a server.

The CPU 905 can execute a sequence of machine-readable instructions, which can be embodied in a program or software. The instructions may be stored in a memory location, such as the memory 910. The instructions can be directed to the CPU 905, which can subsequently program or otherwise configure the CPU 905 to implement methods of the present disclosure. Examples of operations performed by the CPU 905 can include fetch, decode, execute, and writeback.

The CPU 905 can be part of a circuit, such as an integrated circuit. One or more other components of the system 901 can be included in the circuit. In some cases, the circuit is an application specific integrated circuit (ASIC).

The storage unit 915 can store files, such as drivers, libraries and saved programs. The storage unit 915 can store user data, e.g., user preferences and user programs. The computer system 901 in some cases can include one or more additional data storage units that are external to the computer system 901, such as located on a remote server that is in communication with the computer system 901 through an intranet or the Internet.

The computer system 901 can communicate with one or more remote computer systems through the network 930. For instance, the computer system 901 can communicate with a remote computer system of a user (e.g., operator). Examples of remote computer systems include personal computers (e.g., portable PC), slate or tablet PC's (e.g., Apple® iPad, Samsung® Galaxy Tab), telephones, Smart phones (e.g., Apple® iPhone, Android-enabled device, Blackberry®), or personal digital assistants. The user can access the computer system 901 via the network 930.

Methods as described herein can be implemented by way of machine (e.g., computer processor) executable code stored on an electronic storage location of the computer system 901, such as, for example, on the memory 910 or electronic storage unit 915. The machine executable or machine readable code can be provided in the form of software. During use, the code can be executed by the processor 905. In some cases, the code can be retrieved from the storage unit 915 and stored on the memory 910 for ready access by the processor 905. In some situations, the electronic storage unit 915 can be precluded, and machine-executable instructions are stored on memory 910.

The code can be pre-compiled and configured for use with a machine having a processor adapted to execute the code, or can be compiled during runtime. The code can be supplied in a programming language that can be selected to enable the code to execute in a pre-compiled or as-compiled fashion.

Aspects of the systems and methods provided herein, such as the computer system 901, can be embodied in programming. Various aspects of the technology may be thought of as "products" or "articles of manufacture" typically in the form of machine (or processor) executable code and/or associated data that is carried on or embodied in a type of machine readable medium. Machine-executable code can be stored on an electronic storage unit, such as memory (e.g., read-only memory, random-access memory, flash memory) or a hard disk. "Storage" type media can include any or all of the tangible memory of the computers, processors or the like, or associated modules thereof, such as various semiconductor memories, tape drives, disk drives and the like, which may provide non-transitory storage at any time for the software programming. All or portions of the software may at times be communicated through the Internet or various other telecommunication networks. Such communications, for example, may enable loading of the software from one computer or processor into another, for example, from a management server or host computer into the computer platform of an application server. Thus, another type of media that may bear the software elements includes optical, electrical and electromagnetic waves, such as used across physical interfaces between local devices, through wired and optical landline networks and over various air-links. The physical elements that carry such waves, such as wired or wireless links, optical links or the like, also may be considered as media bearing the software. As used herein, unless restricted to non-transitory, tangible "storage" media, terms such as computer or machine "readable medium" refer to any medium that participates in providing instructions to a processor for execution.

Hence, a machine readable medium, such as computer-executable code, may take many forms, including but not limited to, a tangible storage medium, a carrier wave medium or physical transmission medium. Non-volatile storage media include, for example, optical or magnetic disks, such as any of the storage devices in any computer(s) or the like, such as may be used to implement the databases, etc. shown in the drawings. Volatile storage media include dynamic memory, such as main memory of such a computer platform. Tangible transmission media include coaxial cables; copper wire and fiber optics, including the wires that comprise a bus within a computer system. Carrier-wave transmission media may take the form of electric or electromagnetic signals, or acoustic or light waves such as those generated during radio frequency (RF) and infrared (IR) data communications. Common forms of computer-readable media therefore include for example: a floppy disk, a flexible disk, hard disk, magnetic tape, any other magnetic medium, a CD-ROM, DVD or DVD-ROM, any other optical medium, punch cards paper tape, any other physical storage medium with patterns of holes, a RAM, a ROM, a PROM and EPROM, a FLASH-EPROM, any other memory chip or cartridge, a carrier wave transporting data or instructions, cables or links transporting such a carrier wave, or any other medium from which a computer may read programming code and/or data. Many of these forms of computer readable media may be involved in carrying one or more sequences of one or more instructions to a processor for execution.

The computer system 901 can include or be in communication with an electronic display 935 that comprises a user interface (UI) 940 for providing, for example, e.g., results of sequencing analysis. Examples of UIs include, without limitation, a graphical user interface (GUI) and web-based user interface.

Methods and systems of the present disclosure can be implemented by way of one or more algorithms. An algorithm can be implemented by way of software upon execution by the central processing unit 905. The algorithm can, for example, perform sequencing, analyze sequencing results, or associate sequencing results as arising from the same cell.

Devices, systems, compositions and methods of the present disclosure may be used for various applications, such as, for example, processing a single analyte (e.g., RNA, DNA, or protein) or multiple analytes (e.g., DNA and RNA, DNA and protein, RNA and protein, or RNA, DNA and protein) from a single cell. For example, a biological particle (e.g., a cell or cell bead) is partitioned in a partition (e.g., droplet), and multiple analytes from the biological particle are processed for subsequent processing. The multiple analytes may be from the single cell. This may enable, for example, simultaneous proteomic, transcriptomic and genomic analysis of the cell.

Characterization, Analysis, and Detection of Multiple Analytes

Disclosed herein, in some embodiments, are compositions, methods, and systems useful in the analysis of multiple analytes in a single cell or cell population. Examples of analytes include, without limitation, DNA (e.g., genomic DNA or cDNA), epigenetic information (e.g., accessible chromatin, DNA methylation), RNA (e.g., mRNA, CRISPR guide RNAs), synthetic oligonucleotides (e.g., DNA transgenes), and proteins (e.g., intracellular proteins, cell surface proteins, nuclear membrane proteins, extracellular matrix proteins). In some embodiments, the compositions, methods, and systems disclosed herein identify the cell that the analytes originated from.

An analyte may be a cell or one or more constituents of a cell. An analyte can be a protein (e.g., surface-bound protein, internal protein, extracellular matrix protein, etc.). An analyte can be a cellular metabolite (e.g., alcohol, amino acid, nucleotide, antioxidant, organic acid, polyol, vitamin, cofactor, etc.). An analyte can be any constituent of a cell, such as a small molecule, large molecule, macromolecule, or organelle. An analyte can be a nucleic acid (e.g., deoxyribonucleic acid, ribonucleic acid, modified nucleic acid, synthetic nucleic acid). An analyte can be a molecule (e.g., RNA molecule) introduced into a cell using gene or transcription perturbation method (e.g., CRISPR crRNA or sgRNA, TALEN, zinc finger nuclease, antisense oligonucleotide, siRNA, shRNA, miRNA, etc.). An analyte can be a biological particle. The analyte can be a targeted analyte, such as having binding specificity that is specifically captured and analyzed (e.g., using an antibody specific for an antigen). The analyte can be a non-targeted analyte that is non-specifically captured and analyzed. Multiple types of analytes can be processed and measured from a single cell. One or more of a protein, a metabolite, and/or one or more nucleic acids (e.g., DNA, RNA) can be processed from the same single cell, as described herein. During processing, one or more reactions can be performed on one or more analytes. Examples of reactions can include, for example, tagmentation, bisulfite treatment, oxygenase treatment, enzymatic deamination, RNase treatment, proteinase treatment, and methyltransferase treatment. Reactions may be performed so as to modify an analyte for analysis. For example, bisulfite treatment may be performed on genomic DNA (gDNA), in order to assess a methylation profile of gDNA from a cell. Alternatively or in addition, methyltransferase treatment may be performed on gDNA, in some cases followed by proteinase K treatment, in order to assess chromatin accessibility of gDNA from a cell. A tagmentation reaction may be performed on gDNA or cell nuclei isolated from cells in the presence of a transposase, in order to assess open chromatin structure of the gDNA or cell nuclei. Multiple types of analytes (e.g., protein, metabolites, DNA, RNA, lipids, small molecules) may be processed in various ways, in order to obtain multiple types of information from a single cell (e.g., methylation profile, expression profile, genetic profile, epigenetic profile, proteomic profile, metabolomics profile, microbiome profile, pharmacological profile, etc.).

The single cell compositions, methods, and systems described herein can be utilized for a wide variety of applications, including analysis of specific individual cells, analysis of different cell types within populations of differing cell types, analysis and characterization of large populations of cells for environmental, human health, epidemiological, forensic, or any of a wide variety of different applications.

In addition to characterizing individual cells or cell subpopulations from larger populations, the processes and systems described herein may also be used to characterize individual cells as a way to provide an overall profile of a cellular, or other organismal population. A variety of applications require the evaluation of the presence and quantification of different cell or organism types within a population of cells, including, for example, microbiome analysis and characterization, environmental testing, food safety testing, epidemiological analysis, e.g., in tracing contamination or the like. In particular, the analysis processes described above may be used to individually characterize, sequence, and/or identify large numbers of individual cells within a population. This characterization may then be used to assemble an overall profile of the originating population, which can provide important prognostic and diagnostic information.

For example, shifts in human microbiomes, including, e.g., gut, buccal, epidermal microbiomes, etc., have been identified as being both diagnostic and prognostic of different conditions or general states of health. Using the single cell analysis methods and systems described herein, one can again, characterize, sequence and identify individual cells in an overall population, and identify shifts within that population that may be indicative of diagnostic ally relevant factors. By way of example, measuring the abundance of host DNA in a sample (e.g., stool sample) has been used as an accurate biomarker of Crohn's disease in humans (See, e.g., U.S. Pat. No. 9,873,914). By way of another example, sequencing of bacterial 16S ribosomal RNA genes has been used as a highly accurate method for taxonomic classification of bacteria. Using the targeted amplification and sequencing processes described above can provide identification of individual cells within a population of cells. One may further quantify the numbers of different cells within a population to identify current states or shifts in states over time. See, e.g., Morgan et al, PLoS Comput. Biol., Ch. 12, December 2012, 8(12):e1002808, and Ram et al., Syst. Biol. Reprod. Med., June 2011, 57(3):162-170, each of which is entirely incorporated herein by reference for all purposes. Likewise, identification and diagnosis of infection or potential infection may also benefit from the single cell analyses described herein, e.g., to identify microbial species present in large mixes of other cells or other biological material, cells and/or nucleic acids, including the environments described above, as well as any other diagnostically relevant environments, e.g., cerebrospinal fluid, blood, fecal or intestinal samples, or the like.

The foregoing analyses may also be particularly useful in the characterization of potential drug resistance of different cells or pathogens, e.g., cancer cells, bacterial pathogens, etc., through the analysis of distribution and profiling of different resistance markers/mutations across cell populations in a given sample. Additionally, characterization of shifts in these markers/mutations across populations of cells over time can provide valuable insight into the progression, alteration, prevention, and treatment of a variety of diseases characterized by such drug resistance issues.

Although described in terms of cells, it will be appreciated that any of a variety of individual biological organisms, or components of organisms are encompassed within this description, including, for example, cells, viruses, organelles, cellular inclusions, vesicles, or the like. Additionally, where referring to cells, it will be appreciated that such reference includes any type of cell, including without limitation prokaryotic cells, eukaryotic cells, bacterial, fungal, plant, mammalian, or other animal cell types, mycoplasmas, normal tissue cells, tumor cells, or any other cell type, whether derived from single cell or multicellular organisms.

Similarly, analysis of different environmental samples to profile the microbial organisms, viruses, or other biological contaminants that are present within such samples, can provide important information about disease epidemiology A particularly valuable application of the single cell analysis processes described herein is in the sequencing and characterization of a diseased cell. A diseased cell can have altered metabolic properties, gene expression, protein expression, and/or morphologic features. Examples of diseases include inflammatory disorders, metabolic disorders, nervous system disorders, and cancer.

Of particular interest are cancer cells. In particular, conventional analytical techniques, including the ensemble sequencing processes alluded to above, are not highly adept at picking small variations in genomic make-up of cancer cells, particularly where those exist in a sea of normal tissue cells. Further, even as between tumor cells, wide variations can exist and can be masked by the ensemble approaches to sequencing (See, e.g., Patel, et al., Single-cell RNA-seq highlights intratumoral heterogeneity in primary glioblastoma, Science DOI: 10.1126/science.1254257 (Published online Jun. 12, 2014). Cancer cells may be derived from solid tumors, hematological malignancies, cell lines, or obtained as circulating tumor cells, and subjected to the partitioning processes described above. Upon analysis, one can identify individual cell sequences as deriving from a single cell or small group of cells, and distinguish those over normal tissue cell sequences.

Where cancer cells are to be analyzed, primer sequences useful in any of the various operations for attaching barcode sequences and/or amplification reactions may comprise gene specific sequences which target genes or regions of genes associated with or suspected of being associated with cancer. For example, this can include genes or regions of genes where the presence of mutations (e.g., insertions, deletions, polymorphisms, copy number variations, and gene fusions) associated with a cancerous condition are suspected to be present in a cell population.

As with cancer cell analysis, the analysis and diagnosis of fetal health or abnormality through the analysis of fetal cells is a difficult task using conventional techniques. In particular, in the absence of relatively invasive procedures, such as amniocentesis obtaining fetal cell samples can employ harvesting those cells from the maternal circulation. As will be appreciated, such circulating fetal cells make up an extremely small fraction of the overall cellular population of that circulation. As a result complex analyses are performed in order to characterize what of the obtained data is likely derived from fetal cells as opposed to maternal cells. By employing the single cell characterization methods and systems described herein, however, one can attribute genetic make up to individual cells, and categorize those cells as maternal or fetal based upon their respective genetic make-up. Further, the genetic sequence of fetal cells may be used to identify any of a number of genetic disorders, including, e.g., aneuploidy such as Down syndrome, Edwards syndrome, and Patau syndrome. Further, the cell surface features of fetal cells may be used to identify any of a number of disorders or diseases.

Also of interest are immune cells. The methods, compositions, and systems disclosed herein can be utilized for sequence analysis of the immune repertoire, including genomic, proteomic, and cell surface features. Analysis of information underlying the immune repertoire can provide a significant improvement in understanding the status and function of the immune system. By way of example, determining the status (e.g., negative or positive) of minimal residue disease (MRD) in a multiple myeloma (MM) patient following autologous stem cell transplantation is considered a predictor of MRD in the MM patient (See, e.g., U.S. Patent Publication 2018/0156784).

Non-limiting examples of immune cells which can be analyzed utilizing the methods described herein include B cells, T cells (e.g., cytotoxic T cells, natural killer T cells, regulatory T cells, and T helper cells), natural killer cells, cytokine induced killer (CIK) cells; myeloid cells, such as granulocytes (basophil granulocytes, eosinophil granulocytes, neutrophil granulocytes/hypersegmented neutrophils), monocytes/macrophages, mast cell, thrombocytes/megakaryocytes, and dendritic cells. In some embodiments, individual T cells are analyzed using the methods disclosed herein. In some embodiments, individual B cells are analyzed using the methods disclosed herein.

Disclosed herein, in some embodiments, are compositions, methods, and systems useful in the analysis of multiple analytes in a single cell or cell population. Examples of analytes include, without limitation, DNA (e.g., genomic DNA), epigenetic information (e.g., accessible chromatin or DNA methylation), RNA (e.g., mRNA or CRISPR guide RNAs), synthetic oligonucleotides (e.g., DNA transgenes), and proteins (e.g., intracellular proteins, cell surface proteins or features, extracellular matrix proteins, or nuclear membrane proteins). An analyte may be a cell or one or more constituents of a cell.

Analytes may be of different types. In some examples, in a plurality of analytes, a given analyte is of a different structural or functional class from other analytes of the plurality. Examples of different types of analytes include DNA and RNA; a nucleic acid molecule and a protein/labelling agent; a transcript and genomic nucleic acid; a plurality of nucleic acid molecules, where each nucleic acid molecule has a different function, such as a different cellular function. A sample may have a plurality of analytes of different types, such as a mixture of DNA and RNA molecules, or a mixture of nucleic acid molecules and proteins.

The labelling agents described herein may include, but are not limited to, an antibody or antibody fragment, a cell surface receptor binding molecule, a cell surface protein, a receptor ligand, a small molecule, a bi-specific antibody, a bi-specific T-cell engager, a T-cell receptor engager, a B-cell receptor engager, a pro-body, ribozyme, a monobody, an affimer, a darpin, and a protein scaffold. The labelling agents may have binding affinity for one or more analytes (e.g., proteins). The labelling agents may have binding affinity for one or more proteins based on the presence or absence of one or more posttranslational modifications, such as phosphorylation, glycosylation, ubiquitination, methylation, or acetylation. For example, a labelling agent (e.g., an antibody or antibody fragment) may have binding affinity for a protein when phosphorylated at one or more specific sites (e.g., may be a phosphospecific antibody). The labelling agents may be coupled, through the coupling approaches as described herein, to a reporter oligonucleotide comprising a nucleic acid barcode sequence that permits identification of the labelling agent, as described herein. In some embodiments, the nucleic acid barcode sequence coupled to the labelling agent comprises a unique molecular identifier (UMI) sequence segment, as described herein. The labelling agents described herein may also include fatty acids, cholesterol, or other cell membrane intercalating agents that can be used to associate DNA barcodes with an analyte. In some embodiments, the labelling agent is a lipid-displaying molecule (e.g., a CD1d protein or polypeptide) that can be utilized to label analytes such as cell receptors specific for the displayed lipid.

In some embodiments, the labelling agent is a small molecule binding agent (e.g., biotin, folic acid, or any suitable chemical entities capable of binding or interacting with a protein, DNA, or other biomolecule). Small molecule binding agents can be barcoded by chemical linkage to oligonucleotide barcodes for use as primary labelling agents or can be unlabeled with the analyte detected by a secondary barcoded labelling agent that binds or interacts with the primary unlabeled small molecule.

In some embodiments, the labelling agent is an aptamer. Aptamers are single stranded oligonucleotides that fold into a 3-D shape and are capable of binding small molecules such as toxins, antibiotics, heavy metals, and proteins. In some embodiments, aptamers utilized as labelling agents are directly or indirectly coupled with a barcode, e.g., directly in the aptamer sequence or indirectly through hybridization, ligation, or functionalization of the aptamer (e.g., with biotin).

The labelling agents described herein may not interact directly with the analyte, but rather function as a secondary labelling agent. For example, a first agent that does not comprise a barcode oligonucleotide (e.g., a primary antibody) may bind or couple to an analyte (e.g., a cell surface feature) and a secondary labelling agent (e.g., a secondary antibody or antibody binding protein) comprising a barcode oligonucleotide becomes associated or coupled to the analyte through interaction with the primary antibody. Exemplary affinities for the secondary antibody include, but are not limited to fluorophores (e.g., anti-phycoerythrin) and species-binding antibodies (e.g., goat, anti-mouse secondary antibody). In some embodiments, the labelling agent comprising the barcode oligonucleotide interacts with the analyte through a tertiary, quaternary, or larger interaction.

Multiple types of the labelling agents described herein may be used simultaneously to characterize an analyte (e.g., a primary labelling agent and secondary labelling agent, a barcoded antibody and a barcoded MHC, mRNA display together with fatty acid labelling).

In some embodiments, the analytes (e.g., a cell comprising a labelling agent bound to a cell surface receptor) can be physically sorted. Physical cell sorting can be paired with a variety of approaches, such as associating a fluorophore or other detectable molecule (radioactive molecule, etc) with a labelling agents and/or display techniques discussed herein. Cells can then be physically sorted by flow cytometry such that only cells with desired phenotypes are partitioned for analyte characterization. For example, a non-barcoded PE-streptavidin (fluorescent) can be used to created a fluorescent and barcoded MHC multimer as described herein. A T-cell sample would be incubated with the fluorescent and barcoded MHC multimer and then sorted with flow cytometry to isolate the subset of T cells with TCR receptors which have affinity for the MHC-peptide(s). These cells are then partitioned and sequenced as generally described herein resulting in cells that are enriched for clones which effectively bind to the MHC-peptide labelling reagent.

In some embodiments, a protein or peptide used in a binding or interaction assay to characterize or detect an analyte may not comprise a physical label but can instead be associated with sequence-based information useful in identifying the protein or peptide. In some cases, a protein or peptide can be displayed on a surface for a binding assay or an interaction assay. The protein or peptide, in some embodiments, can be displayed on a cell surface using cell surface display systems. In some cases, a protein or peptide displayed on a surface for a binding assay is the analyte to be characterized. In other cases, the analyte to be characterized is the interacting or binding partner of the protein or peptide displayed on a surface. In some instances, the protein or peptide displayed on a surface and the interacting or binding partner of the displayed protein or peptide are both the analytes to be characterized.

Cell surface display systems can express a protein or peptide on the surface of prokaryotic or eukaryotic cells (e.g., bacteria, yeast, insect, and mammalian cells). The protein or peptide can, for example, be coupled to a protein present at a cell surface and, by association with the cellular protein, can be displayed at the surface of the cell. Typically, the genetic information encoding the peptide or protein for display can be introduced into the cell (e.g., bacteria, yeast, insect, or mammalian cell) in the form of a polynucleotide element, such as a plasmid. Any suitable delivery method can be used for introducing a polynucleotide element, e.g., plasmid, into a cell. Non-limiting examples of delivery methods include, for example, viral or bacteriophage infection, transfection, conjugation, protoplast fusion, lipofection, electroporation, calcium phosphate precipitation polyethyleneimine (PEI)-mediated transfection, DEAE-dextran mediated transfection, liposome-mediated transfection, particle gun technology, calcium phosphate precipitation, direct microinjection, use of cell permeable peptides, and nanoparticle mediated nucleic acid delivery. Conventional viral and non-viral based gene transfer methods can be used. Non-viral vector delivery systems can include DNA plasmids, RNA, naked nucleic acid, and nucleic acid complexed with a delivery vehicle, such as a liposome. Viral vector delivery systems can include DNA and RNA viruses, which can have either episomal or integrated genomes after delivery to the cell. Methods of non-viral delivery of nucleic acids can include lipofection, nucleofection, microinjection, biolistics, virosomes, liposomes, immunoliposomes, polycation or lipid:nucleic acid conjugates, naked DNA, artificial virions, and agent-enhanced uptake of DNA. Cationic and neutral lipids that are suitable for efficient receptor-recognition lipofection of polynucleotides can be used. The preparation of lipid:nucleic acid complexes, including targeted liposomes such as immunolipid complexes, can be used. In some cases, expressing the peptide or protein comprises editing a cell genome via an integrase, recombinase, or Cas protein.

The cell can use the exogenous genetic information to produce the protein or peptide to be displayed. The genetic information (e.g., sequence-based information) can later be interrogated, for example by sequencing analysis, to determine the identity of a protein or peptide (e.g., amino acid sequence) identified in a binding assay or an interaction assay.

In an example, the coding sequence of a protein or peptide of interest can be linked to the coding sequence of a yeast cell wall protein. A non-limiting example of such a yeast protein is Aga2p which is used by yeast to mediate cell-cell contacts during yeast cell mating. The protein or peptide of interest can be tethered to the yeast cell wall protein, allowing the protein or peptide of interest to be displayed on the yeast cell surface. The protein or peptide displayed on the yeast cell surface can then be subjected to binding or interaction assays, and binding interactions of the protein or peptide can be studied by capturing the DNA or RNA sequence encoding the recombinantly displayed protein or peptide. In some cases, the DNA or RNA sequence can comprise a barcode sequence which specifically identifies the displayed protein or peptide. Similar systems are available for bacteria, insect cells, and mammalian cells. In cases where the protein or peptide binds to a cell or a component of a cell, information about the cell (e.g., transcriptome analysis, genome analysis, etc.) can also be obtained using methods disclosed herein.

In some cases, a library of cell-surface displayed proteins (e.g, yeast displayed) generated according to embodiments herein can be subjected to binding or interaction assays to identify proteins or peptides having certain properties of interest, for example, binding specificity, binding affinity, and biological activity. The library can include a plurality of proteins or peptides having different amino acid sequences displayed on a cell surface. Each member of the library can have unique biochemical or biophysical properties which can be analyzed by screening the library.

In some cases, the surface is not a cell surface. Non-limiting examples of technologies that do not utilize cells include phage display, mRNA display, and ribosome display. A protein of interest can be displayed, for example, on a phage by inserting the protein coding sequence into a phage coat protein gene. When the phage DNA is expressed as phage proteins, it can display the protein of interest on the surface of the phage, and package the corresponding DNA inside the phage capsid. The protein displayed on phage can then be subjected to binding or interaction assays, and binding interactions of the protein can then be studied by sequencing the phage DNA or mRNAs or by secondary labelling of the phage. In some cases, the phage DNA or mRNA includes a barcode sequence which is useful in identifying the protein of interest. In cases where the protein binds to a cell or a component of a cell, information about the cell (e.g., transcriptome analysis, genome analysis, etc.) can also be obtained using methods disclosed herein.

In some cases, a library of phage displayed proteins generated according to embodiments herein can be subjected to binding or interaction assays to identify proteins or peptides having certain properties of interest, for example, binding specificity, binding affinity, and biological activity. The library can include a plurality of proteins or peptides having different amino acid sequences displayed on phage.

Each member of the library can have unique biochemical or biophysical properties which can be analyzed by screening the library.

In some embodiments, a protein of interested is produced by mRNA display for binding or interaction assays. In mRNA display, a translated protein can be associated with its coding mRNA via a linkage, e.g., a puromycin linkage. The protein of interest, linked to its coding mRNA, can then be subjected to binding or interaction assays, and binding interactions of the protein of interest can be studied by sequencing the coding mRNA, or a derivative thereof (e.g., cDNA transcript) linked to the protein. In some cases, the coding mRNA may be linked to a barcode sequence which can be used to identify the protein of interest. In cases where the protein binds to a cell or a component of a cell, information about the cell (e.g., transcriptome analysis, genome analysis, etc.) can also be obtained using methods disclosed herein.

In some cases, a library of mRNA displayed proteins generated according to embodiments herein can be subjected to binding or interaction assays to identify proteins or peptides having certain properties of interest, for example, binding specificity, binding affinity, and biological activity. The library can include a plurality of proteins or peptides having different amino acid sequences, each linked to its corresponding mRNA. Each member of the library can have unique biochemical or biophysical properties which can be analyzed by screening the library.

In some embodiments, a protein of interest is produced by ribosome display for binding or interaction assays. In ribosome display, the translated protein can be associated with its coding mRNA and a ribosome. The protein of interest, linked to its coding mRNA and a ribosome, can then be subjected to binding or interaction assays, and binding interactions of the protein can then be studied by sequencing the coding mRNA, or a derivative thereof (e.g., cDNA transcript) associated with the protein. In some cases, the coding mRNA may be linked to a barcode sequence which can be used to identify the protein of interest. In cases where the protein binds to a cell or a component of a cell, information about the cell (e.g., transcriptome analysis, genome analysis, etc.) can also be obtained using methods disclosed herein.

In some cases, a library of ribosome displayed proteins generated according to embodiments herein can be subjected to binding or interaction assays to identify proteins or peptides having certain properties of interest, for example, binding specificity, binding activity, and biological activity. The library can include a plurality of ribosome-displayed proteins or peptides having different amino acid sequences. Each member of the library can have unique biochemical or biophysical properties which can be analyzed by screening the library.

Figure 11A:
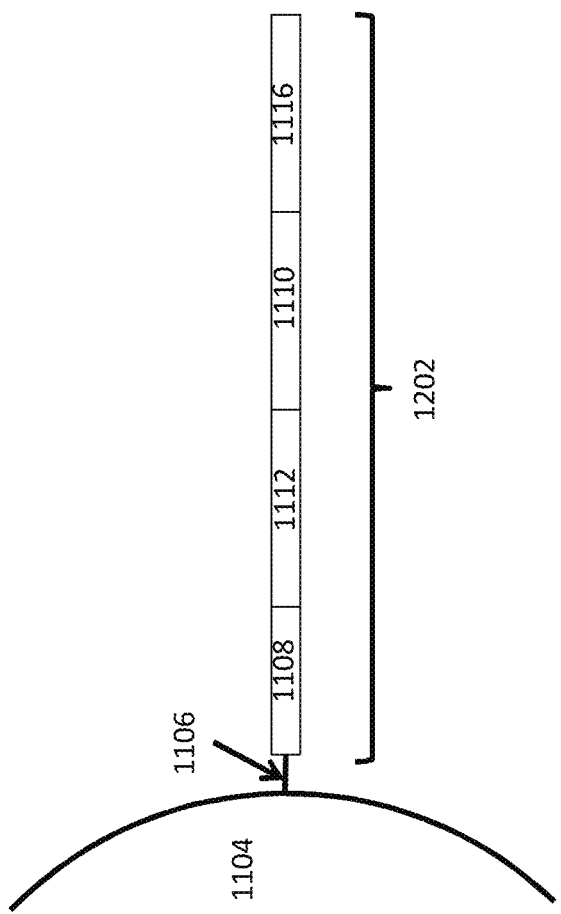
FIG. 11A provides a schematic illustration of an example barcoded oligonucleotide structure.
Figure 11B:
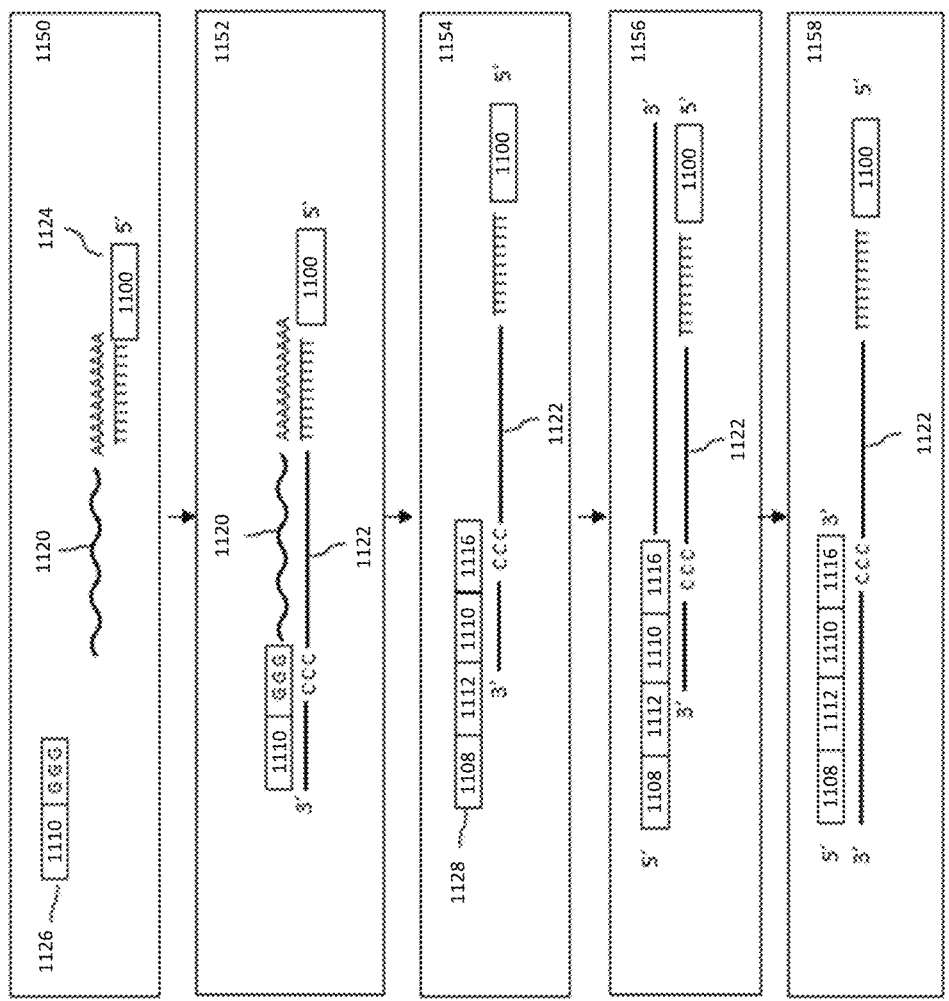
FIG. 11B shows-example operations for performing RNA analysis. Figure discloses "AAAAAAAAAAA" as SEQ ID NO: 12 and "TTTTTTTTTTT" as SEQ ID NO: 13.
Figure 12A:
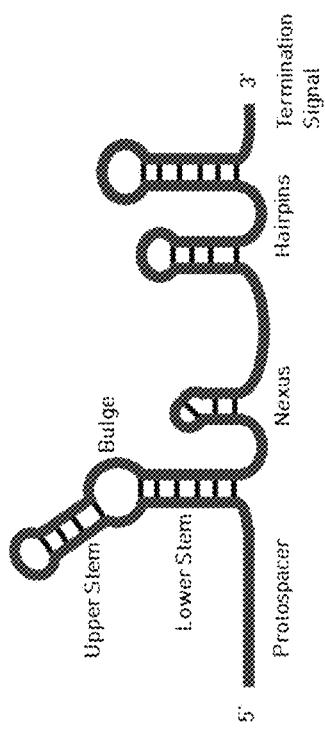
FIGS. 12A-D schematically depict an example barcoding scheme of CRISPR guide RNAs.
Figure 12B:
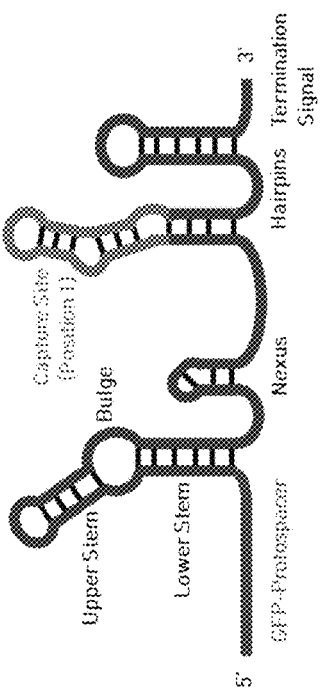
Figure 12C:
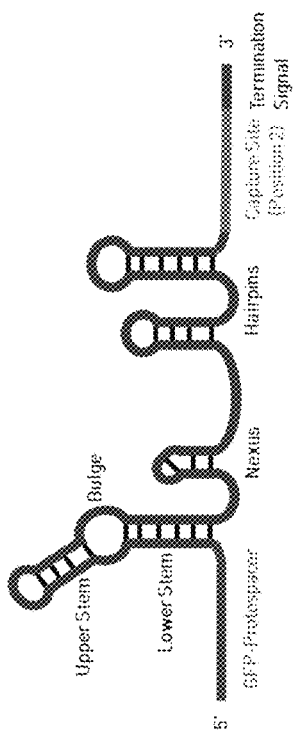
Figure 12D:
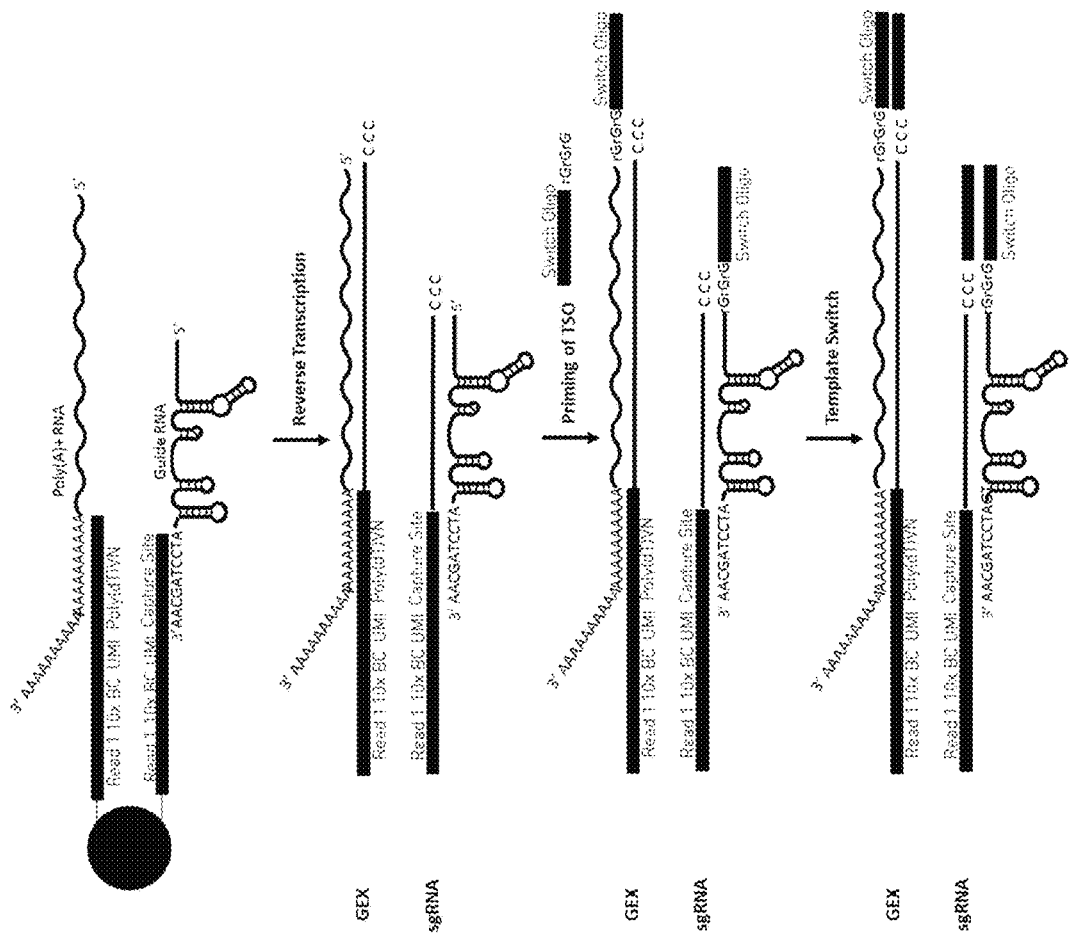
Figure 13B:
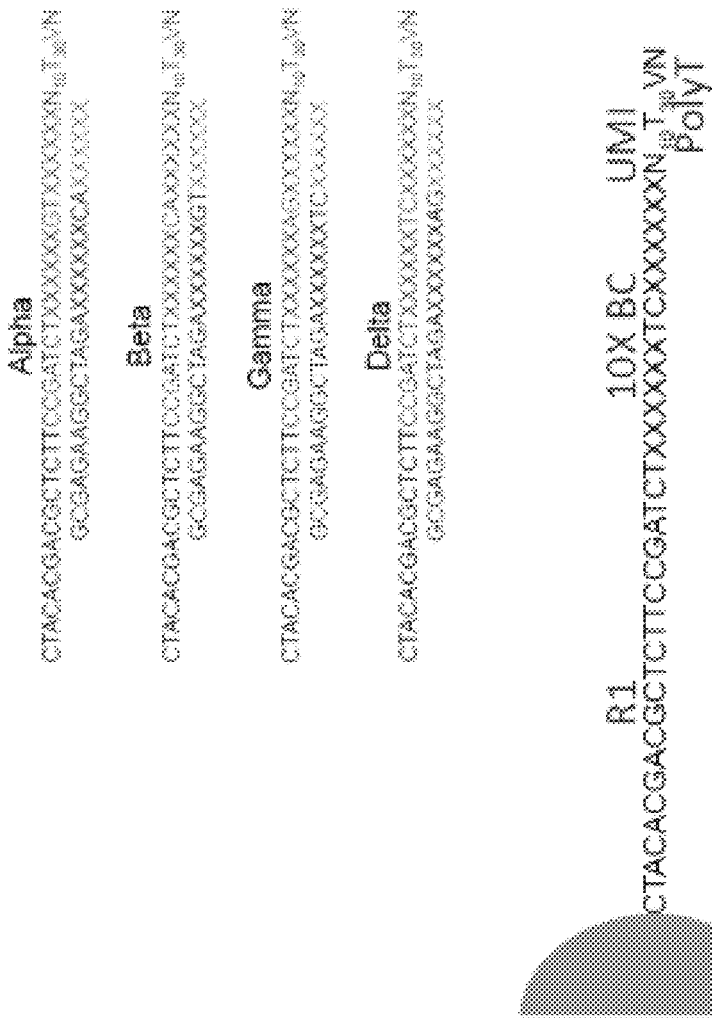
FIG. 13B shows oligonucleotides with backbones comprising R1 sequences and poly-T primers. Figure discloses SEQ ID NOS 24-31 and 30, respectively, in order of appearance.

In an example, a method for using displayed proteins in a binding or interaction assay may comprise one or more of the following operations. A sample comprising immune cells (e.g., blood or a fraction thereof), preferably B cells, are mixed with a population displayed proteins (e.g., yeast-surface displayed, mammalian cell surface displayed, phage displayed, ribosome displayed, mRNA displayed, etc.) and incubated to allow for the immune cells and displayed proteins to interact. In some cases, the immune cell is a B cell and the B cell receptor (BCR) binds to a displayed protein. A B cell receptor can bind to a folded or unfolded polypeptide. The immune cells and displayed proteins can be partitioned such that bound BCR and displayed proteins are co-partitioned into the same partition (e.g., droplet, well, microwell, tube, etc.). Each of the partitions can also include a gel bead comprising one or more types of oligonucleotides. The oligonucleotide(s) attached to the bead can comprise a plurality of sequence elements useful for generating amplification products according to embodiments herein. For example, the oligonucleotide can comprise a barcode sequence (e.g., a partition specific barcode sequence), a unique molecular identifier sequence (UMI), and hybridization sequences (e.g., for primer extension). Within a partition, the immune cell can be lysed. If the protein display method employed includes a cell, e.g., a yeast cell or a mammalian cell, the display cell may also be lysed within the partition. For individual pairs of interacting B cells and displayed proteins, the identity of the protein (e.g., amino acid sequence) and identity of the B cell receptor (BCR) (e.g., receptor sequence) can be determined by sequencing nucleic acids derived therefrom. The coding mRNA of proteins of interest can be obtained and translated into a corresponding amino acid sequence. In cases where a barcode sequence is used, the polynucleotide sequence of the barcode itself can serve as an identifier. The sequence of the BCR can be obtained, for example, according methods as illustrated in FIGS. 11A-B. Partition specific barcode sequences can be used to label and identify amplification products originating from common partitions (e.g., co-partitioned B cells and displayed proteins).

The methods described herein may compartmentalize (e.g., partition) the analysis of individual cells or small populations of cells, including e.g., cell surface features, proteins, and nucleic acids of individual cells or small groups of cells, and then allow that analysis to be attributed back to the individual cell or small group of cells from which the cell surface features, proteins, and nucleic acids were derived. This can be accomplished regardless of whether the cell population represents a 50/50 mix of cell types, a 90/10 mix of cell types, or virtually any ratio of cell types, as well as a complete heterogeneous mix of different cell types, or any mixture between these. Differing cell types may include cells from different tissue types of an individual or the same tissue type from different individuals, or biological organisms such as microorganisms from differing genera, species, strains, variants, or any combination of any or all of the foregoing. For example, differing cell types may include normal and tumor tissue from an individual, various cell types obtained from a human subject such as a variety of immune cells (e.g., B cells, T cells, and the like), multiple different bacterial species, strains and/or variants from environmental, forensic, microbiome or other samples, or any of a variety of other mixtures of cell types.

Unique identifiers, e.g., barcodes, may be previously, subsequently, or concurrently delivered to the partitions that hold the compartmentalized or partitioned cells, in order to allow for the later attribution of the characteristics of the individual cells to the particular compartment. Further, unique identifiers, e.g., barcodes, may be coupled to the analytes and previously, subsequently, or concurrently delivered to the partitions that hold the compartmentalized or partitioned cells, in order to allow for the later attribution of the characteristics of the individual cells to the particular compartment. Barcodes may be delivered, for example on an oligonucleotide, to a partition via any suitable mechanism (e.g., attached to a gel bead as described herein). In accordance with the methods and systems described herein, analytes of individual cells can be provided with unique identifiers such that, upon characterization of those analytes they may be attributed as having been derived from the same cell or cells. The ability to attribute characteristics to individual cells or groups of cells is provided by the assignment of unique identifiers specifically to an individual cell or groups of cells. Unique identifiers, e.g., in the form of nucleic acid barcodes can be assigned or associated with individual cells or populations of cells, in order to tag or label the cell's components (and as a result, its characteristics) with the unique identifiers. These unique identifiers can then be used to attribute the cell's components and characteristics to an individual cell or group of cells. In some aspects, this is carried out by co-partitioning the individual cells or groups of cells with the unique identifiers. In some aspects, the unique identifiers are provided in the form of oligonucleotides (also referred to herein as capture oligonucleotides or reporter oligonucleotides) that comprise nucleic acid barcode sequences that may be attached to or otherwise associated with the nucleic acid contents of individual cells, or to other components of the cells, and particularly to fragments of those nucleic acids. The oligonucleotides may be partitioned such that as between oligonucleotides in a given partition, the nucleic acid barcode sequences contained therein are the same, but as between different partitions, the oligonucleotides can, and do have differing barcode sequences, or at least represent a large number of different barcode sequences across all of the partitions in a given analysis. In some aspects, only one nucleic acid barcode sequence can be associated with a given partition, although in some cases, two or more different barcode sequences may be present.

In some embodiments, a given partition comprises a plurality of oligonucleotides comprising a barcode sequence, wherein said plurality of oligonucleotides are identical, and wherein said plurality of oligonucleotides are capable of coupling to two or more analytes (e.g., an mRNA molecule and an adapter sequence of a labelling agent). In some embodiments, a given partition comprises (a) a first plurality of oligonucleotides comprising a first barcode sequence; and (b) a second plurality of oligonucleotides comprising a second barcode sequence; wherein said first plurality of oligonucleotides are capable of coupling to a first analyte (e.g., gDNA, processed gDNA (e.g., ATAC-seq, DNase-seq, MNase-seq, etc.) and wherein said second plurality of oligonucleotides are capable of coupling to a second analyte (e.g., mRNA). In some embodiments, said first plurality of oligonucleotides comprise a first capture sequence (e.g., a random N-mer or ATAC-seq oligonucleotide as disclosed herein) and said second plurality of oligonucleotides comprise a second capture sequence (e.g., a poly-T sequence). In some embodiments, the first barcode sequence and the second barcode sequence are identical. In some embodiments, the first barcode sequence and the second barcode sequence are at least about 70%, at least about 71%, at least about 72%, at least about 73%, at least about 74%, at least about 75%, at least about 76%, at least about 77%, at least about 78%, at least about 79%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, or at least about 99% identical. In some embodiments, the first barcode sequence and the second barcode sequence are about 70%, about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, or about 99% identical.

In other embodiments, a given partition comprises (a) a first plurality of oligonucleotides comprising a first barcode sequence; and (b) a second plurality of oligonucleotides comprising a second barcode sequence; wherein said first plurality of oligonucleotides are capable of coupling to a first analyte (e.g., a first adapter sequence present in, e.g., a CRISPR sgRNA molecule) and wherein said second plurality of oligonucleotides are capable of coupling to at least two additional analytes (e.g., an mRNA molecule and an adapter sequence of a labelling agent oligonucleotide, e.g., a barcoded antibody). In some embodiments, said first plurality of oligonucleotides comprise a first capture sequence (e.g., a sequence complementary to an adapter sequence present in, e.g., a CRISPR sgRNA molecule) and said second plurality of oligonucleotides comprise a second capture sequence (e.g., a rGrGrG sequence complementary to a CCC sequence of a labelling agent oligonucleotide and a CCC sequence present on the 5' end of a cDNA molecule). In some embodiments, the first barcode sequence and the second barcode sequence are identical. In some embodiments, the first barcode sequence and the second barcode sequence are at least about 70%, at least about 71%, at least about 72%, at least about 73%, at least about 74%, at least about 75%, at least about 76%, at least about 77%, at least about 78%, at least about 79%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, or at least about 99% identical. In some embodiments, the first barcode sequence and the second barcode sequence are about 70%, about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, or about 99% identical.

In some embodiments, a given partition comprises (a) a first plurality of oligonucleotides comprising a first barcode sequence; (b) a second plurality of oligonucleotides comprising a second barcode sequence; and (c) a third plurality of oligonucleotides comprising a third barcode sequence; wherein said first plurality of oligonucleotides are capable of coupling to a first analyte (e.g., gDNA, processed gDNA (e.g., ATAC-seq, DNase-seq, MNase-seq, etc.), wherein said second plurality of oligonucleotides are capable of coupling to a second analyte (e.g., mRNA), and wherein said third plurality of oligonucleotides are capable of coupling to a third analyte (e.g., an adapter sequence of a labelling agent oligonucleotide, e.g., a barcoded antibody). In some embodiments, said first plurality of oligonucleotides comprise a first capture sequence (e.g., a random N-mer or ATAC-seq oligonucleotide as disclosed herein), said second plurality of oligonucleotides comprise a second capture sequence (e.g., a poly-T sequence), and said third plurality of oligonucleotides comprise a third capture sequence (e.g., a sequence complementary to an adapter sequence of a labelling agent oligonucleotide, e.g., barcoded antibody). In some embodiments, the first barcode sequence, the second barcode sequence, and the third barcode sequence are identical. In some embodiments, the first barcode sequence, the second barcode sequence, and the third barcode sequence are at least about 70%, at least about 71%, at least about 72%, at least about 73%, at least about 74%, at least about 75%, at least about 76%, at least about 77%, at least about 78%, at least about 79%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, or at least about 99% identical. In some embodiments, the first barcode sequence, the second barcode sequence, and the third barcode sequence are about 70%, about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, or about 99% identical.

In some embodiments, a given partition comprises (a) a first plurality of oligonucleotides comprising a first barcode sequence; (b) a second plurality of oligonucleotides comprising a second barcode sequence; and (c) a third plurality of oligonucleotides comprising a third barcode sequence; wherein said first plurality of oligonucleotides are capable of coupling to a first analyte (e.g., gDNA, processed gDNA (e.g., ATAC-seq, DNase-seq, MNase-seq, etc.), wherein said second plurality of oligonucleotides are capable of coupling to a second analyte (e.g., mRNA), and wherein said third plurality of oligonucleotides are capable of coupling to at least two additional analytes (e.g., an mRNA molecule and an adapter sequence of a labelling agent oligonucleotide, e.g., a barcoded antibody). In some embodiments, said first plurality of oligonucleotides comprise a first capture sequence (e.g., a random N-mer or ATAC-seq oligonucleotide as disclosed herein), said second plurality of oligonucleotides comprise a second capture sequence (e.g., a poly-T sequence), and said third plurality of oligonucleotides comprise a third capture sequence (e.g., a rGrGrG sequence complementary to a CCC sequence of a labelling agent oligonucleotide and a CCC sequence present on the 5' end of a cDNA molecule). In some embodiments, the first barcode sequence, the second barcode sequence, and the third barcode sequence are identical. In some embodiments, the first barcode sequence, the second barcode sequence, and the third barcode sequence are at least about 70%, at least about 71%, at least about 72%, at least about 73%, at least about 74%, at least about 75%, at least about 76%, at least about 77%, at least about 78%, at least about 79%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, or at least about 99% identical. In some embodiments, the first barcode sequence, the second barcode sequence, and the third barcode sequence are about 70%, about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, or about 99% identical.

In some embodiments, a given partition comprises (a) a first plurality of oligonucleotides comprising a first barcode sequence and a first capture sequence; (b) a second plurality of oligonucleotides comprising a second barcode sequence and a second capture sequence; (c) a third plurality of oligonucleotides comprising a third barcode sequence and a third capture sequence; and (d) a fourth plurality of oligonucleotides comprising a fourth barcode sequence and a fourth capture sequence wherein said first plurality of oligonucleotides are capable of coupling to a first analyte (e.g., gDNA, processed gDNA (e.g., ATAC-seq, DNase-seq, MNase-seq, etc.), wherein said second plurality of oligonucleotides are capable of coupling to a second analyte (e.g., mRNA), wherein said third plurality of oligonucleotides are capable of coupling to a third analyte (e.g., an adapter sequence of a labelling agent oligonucleotide, e.g., a barcoded antibody), and wherein said fourth plurality of oligonucleotides are capable of coupling to a fourth analyte (e.g., a first adapter sequence present in, e.g., a CRISPR sgRNA molecule). In other embodiments, a given partition comprises (a) a first plurality of oligonucleotides comprising a first barcode sequence and a first capture sequence; (b) a second plurality of oligonucleotides comprising a second barcode sequence and a second capture sequence; (c) a third plurality of oligonucleotides comprising a third barcode sequence and a third capture sequence; and (d) a fourth plurality of oligonucleotides comprising a fourth barcode sequence and a fourth capture sequence; wherein said first plurality of oligonucleotides are capable of coupling to a first analyte, wherein said second plurality of oligonucleotides are capable of coupling to a second analyte, wherein said third plurality of oligonucleotides are capable of coupling to a third analyte, and wherein said fourth plurality of oligonucleotides are capable of coupling to at least two or more analytes. In some embodiments, the first barcode sequence, the second barcode sequence, the third barcode sequence, and the fourth barcode sequence are identical. In some embodiments, the first barcode sequence, the second barcode sequence, the third barcode sequence, and the fourth barcode sequence are at least about 70%, at least about 71%, at least about 72%, at least about 73%, at least about 74%, at least about 75%, at least about 76%, at least about 77%, at least about 78%, at least about 79%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, or at least about 99% identical. In some embodiments, the first barcode sequence, the second barcode sequence, and the third barcode sequence are about 70%, about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, or about 99% identical.

As described herein, the bead may comprise a gel bead. Further, as described herein, the bead may comprise a diverse library of capture oligonucleotides (e.g., barcoded oligonucleotides capable of coupling to an analyte). In some instances, the bead may comprise at least about 1,000 copies of a capture oligonucleotide, at least about 10,000 copies of a capture oligonucleotide, at least about 100,000 copies of a capture oligonucleotide, at least about 100,000 copies of a capture oligonucleotide, at least about 1,000,000 copies of a capture oligonucleotide, at least about 5,000,000 copies of a capture oligonucleotide, or at least about 10,000,000 copies of a capture oligonucleotide. In some instances, the bead may comprise at least about 1,000 copies of diverse capture oligonucleotides, at least about 10,000 copies of diverse capture oligonucleotides, at least about 100,000 copies of diverse capture oligonucleotides, at least about 100,000 copies of diverse capture oligonucleotides, at least about 1,00,000 copies of diverse capture oligonucleotides, at least about 5,000,000 copies of diverse capture oligonucleotides, or at least about 10,000,000 copies of diverse capture oligonucleotides. In some instances, and as described herein, releasing capture oligonucleotides from the bead may comprise subjecting the bead to a stimulus that degrades the bead. In some instances, as described herein, releasing capture oligonucleotides from the bead may comprise subjecting the bead to a chemical stimulus that degrades the bead.

A solid support (e.g., a bead) may comprise different types of capture oligonucleotides for analyzing both intrinsic and extrinsic information of a cell. For example, a solid support may comprise one or more of the following: 1) a capture oligonucleotide comprising a primer that binds to one or more endogenous nucleic acids in the cell; 2) a capture oligonucleotide comprising a primer that binds to one or more exogenous nucleic acids in the cell, e.g., nucleic acids from a microorganism (e.g., a virus, a bacterium) that infects the cell, nucleic acids introduced into the cell (e.g., such as plasmids or nucleic acid derived therefrom), nucleic acids for gene editing (e.g., CRISPR-related RNA such as crRNA, guide RNA); 3) a capture oligonucleotide comprising a primer that binds to a barcode (e.g., a barcode of a nucleic acid, of a protein, or of a cell); and 4) a capture oligonucleotide comprising a sequence (e.g., a primer) that binds to a protein, e.g., an exogenous protein expressed in the cell, an protein from a microorganism (e.g., a virus, a bacterium) that infects the cell, or an binding partner for a protein of the cell (e.g., an antigen for an immune cell receptor).

Figure 10A:
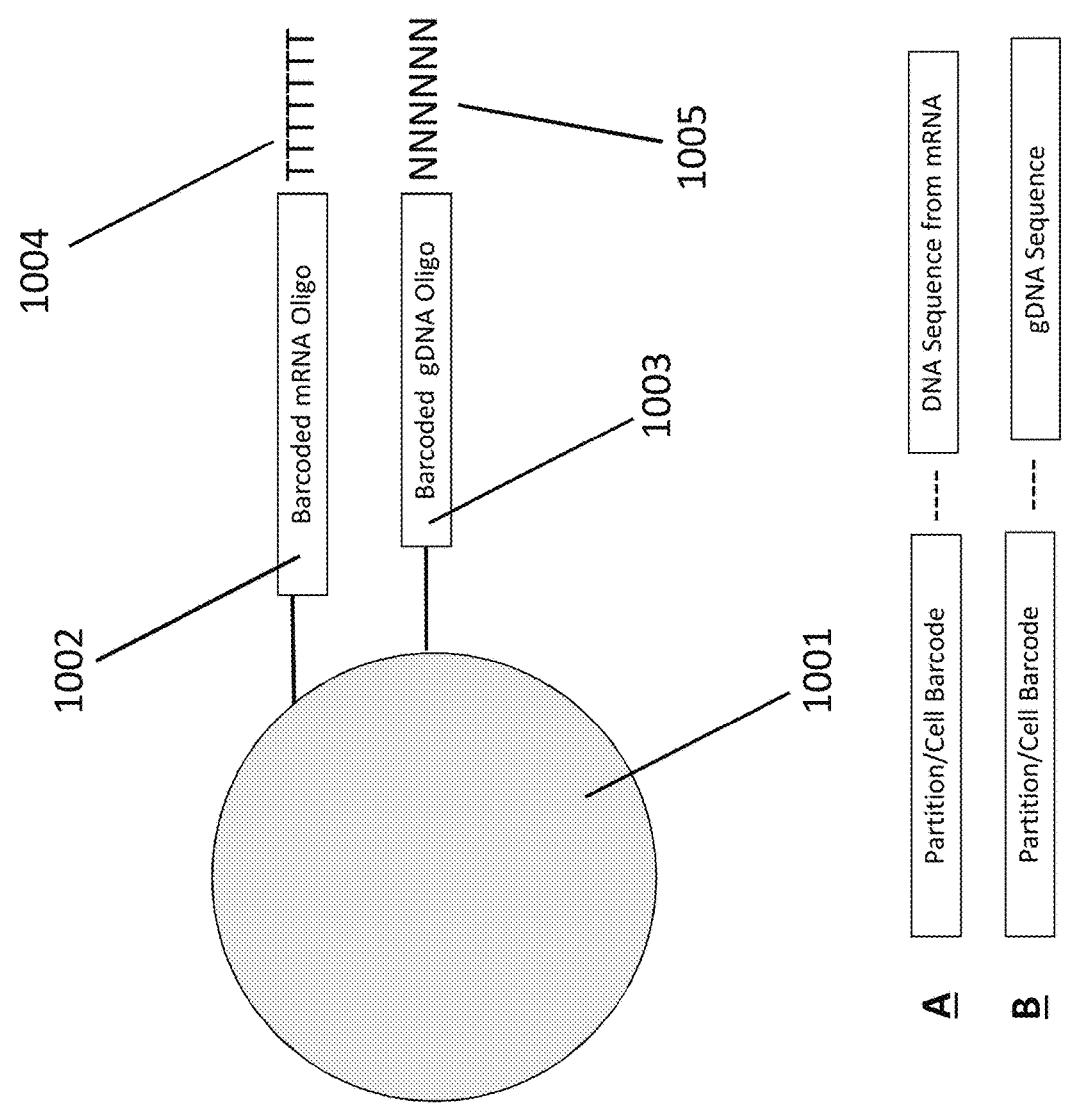
FIGS. 10A-G schematically depict components of example multi-assay schemes described herein.

In an example, schematically depicted in FIG. 10A, a partition (e.g., a droplet, a well or any other type of partition described herein) comprises a bead 1001, which is coupled (e.g., reversibly coupled) to barcoded oligonucleotides 1002 and 1003. The bead 1001 and barcoded oligonucleotides 1002 and 1003 are schematically depicted in FIG. 10A. Barcoded oligonucleotide 1002 comprises a first nucleic acid barcode sequence and a poly-T priming sequence 1004 that can hybridize with the poly-A tail of an mRNA transcript. Barcoded oligonucleotide 1002 may also comprise a UMI sequence that can uniquely identify a given transcript. Barcoded oligonucleotide 1003 comprises a second nucleic acid barcode sequence and a random N-mer priming sequence 1005 that is capable of randomly hybridizing with gDNA. In this configuration, barcoded oligonucleotides 1002 and 1003 comprise the same nucleic acid barcode sequence, which permits association of downstream sequencing reads with the partition. In some cases, though, the first nucleic acid barcode sequence and the second nucleic acid barcode sequence are different.

The partition also comprises a cell (not shown) and lysis agents that aid in releasing nucleic acids from the cell and can also include an agent (e.g., a reducing agent) that can degrade the bead and/or break a covalent linkage between the barcoded oligonucleotides 1002 and 1003 and bead 1001, releasing them into the partition. The released barcoded oligonucleotide 1002 can hybridize with mRNA released from the cell and the released barcoded oligonucleotide 1003 can hybridize with gDNA released from the cell. Barcoded constructs A and B can then be generated for each of the mRNA and barcoded oligonucleotide 1023 as described elsewhere herein, such as via the action of a polymerase (and/or reverse transcriptase) and/or primer extension. Barcoded construct A can comprises a sequence corresponding to the original barcode sequence from the bead and a sequence corresponding to a transcript from the cell. Barcoded construct B can comprise a sequence corresponding to the original barcode sequence from the bead and a sequence corresponding to genomic DNA from the cell. The barcoded constructs can then be released/removed from the partition and, in some cases, further processed to add any additional sequences. The resulting constructs are then sequenced, sequencing data processed, and the results used to characterize the mRNA and the gDNA from the cell. Analysis can be completed, for example, as described elsewhere herein. The information received from the characterization can then be used in a subsequent analysis of another cell in a partition. Moreover, barcoded oligonucleotides 1002 and 1003 can be designed to prime any particular type of nucleic acid, including those that are not derived from a cell. Moreover, the priming sequences shown in FIG. 10A are for example purposes only and are not meant to be limiting.

In various aspects, the first analyte may be a nucleic acid molecule (e.g., deoxyribonucleic acid (e.g., gDNA) or ribonucleic acid (e.g., mRNA)) and the second analyte a labelling agent capable of coupling to a cell surface feature. In such a case, the first individual barcode molecule may comprise a priming sequence capable of hybridizing to the nucleic acid molecule and may also include a UMI sequence. Moreover, the second individual barcode molecule may comprise a priming sequence capable of hybridizing with a third nucleic acid molecule coupled to the labelling agent. As noted elsewhere herein, this third nucleic acid molecule can include a barcode sequence that identifies the labelling agent. It may also include a UMI sequence. The labelling agent can be any suitable labelling agent described herein, and may be targeted to any suitable cell surface feature to which it can selectively bind. Non-limiting examples of such cell surface features are provided elsewhere herein. Furthermore, in some cases, the partition comprises a cell having the cell surface feature and, in some cases, may comprise only one cell. In other cases, a partition comprises a cell (e.g., a single cell) having one or more labelling agents coupled to a cell surface feature of the cell.

Figure 10B:
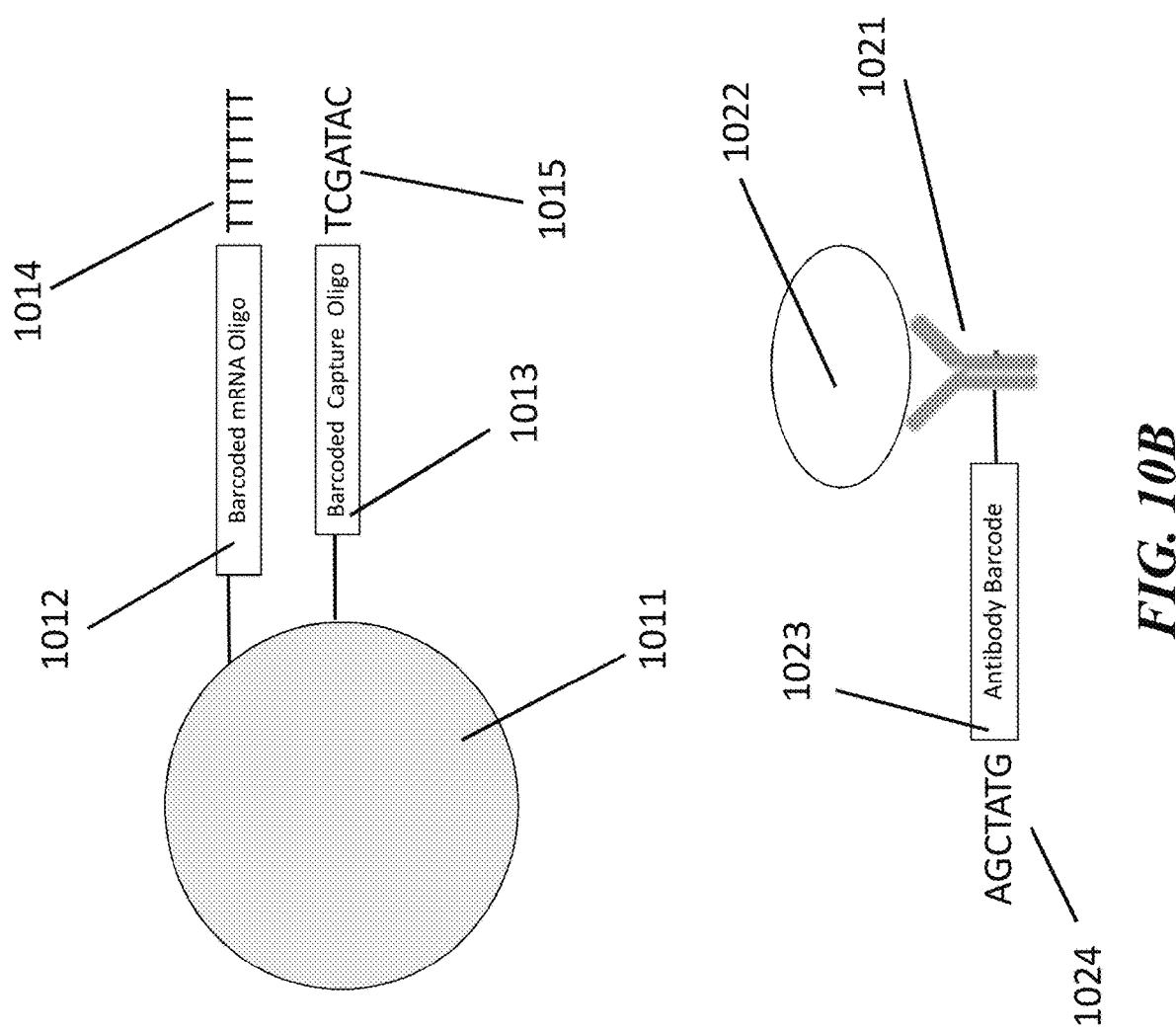

In an example, schematically depicted in FIG. 10B, a partition (e.g., a droplet, a well, a microcapsule, or any other type of partition described herein) comprises a bead 1011, which is coupled (e.g., reversibly coupled) to barcoded oligonucleotides 1012 and 1013. The bead 1011 and barcoded oligonucleotides 1012 and 1013 are schematically depicted in FIG. 10B. Barcoded oligonucleotide 1012 comprises a first nucleic acid barcode sequence and a poly-T priming sequence 1014 that can hybridize with the poly-A tail of an mRNA transcript. Barcoded oligonucleotide 1012 may also comprise a UMI sequence that can uniquely identify a given transcript. Barcoded oligonucleotide 1013 comprises a second nucleic acid barcode sequence and a targeted priming sequence that is capable of specifically hybridizing with a barcoded oligonucleotide 1023 via a complementary portion 1024 of barcoded oligonucleotide 1023 coupled to an antibody 1021 that is bound to the surface of a cell 1022. Barcoded oligonucleotide 1023 comprises a barcode sequence that uniquely identifies the antibody 1021 (and thus, the particular cell surface feature to which it is bound). In this configuration, barcoded oligonucleotides 1012 and 1013 comprise the same nucleic acid barcode sequence, which permit downstream association of barcoded nucleic acids with the partition. In some cases, though, the first nucleic acid barcode sequence and the second nucleic acid barcode sequence are different. Furthermore, barcoded labelling agents, including antibodies, may be produced by any suitable route, including via example coupling schemes described elsewhere herein.

Figure 10C:
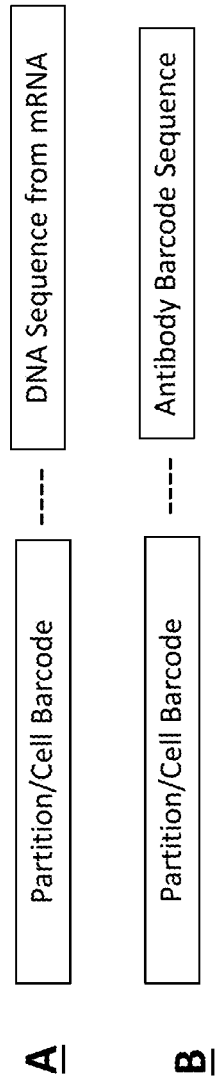

As shown in FIG. 10B, the partition also comprises cell 1022, lysis agents that aid in releasing nucleic acids from the cell 1022 and can also include an agent (e.g., a reducing agent) that can degrade the bead and/or break a covalent linkage between the barcoded oligonucleotides 1012 and 1013 and bead 1011, releasing them into the partition. The released barcoded oligonucleotide 1012 can hybridize with mRNA released from the cell and the released barcoded oligonucleotide 1013 can hybridize with barcoded oligonucleotide 1023. Barcoded constructs A and B (FIG. 10C) can then be generated for each of the mRNA and barcoded oligonucleotide 1023 as described elsewhere herein, such as via the action of a polymerase (and/or reverse transcriptase) and/or primer extension. Barcoded construct A may comprise a sequence corresponding to the original barcode sequence from the bead and a sequence corresponding to a transcript from the cell. Barcoded construct B may comprise a sequence corresponding to the original barcode sequence from the bead and an additional sequence corresponding to the barcode sequence coupled to the labelling agent. The barcoded constructs can then be released/removed from the partition and, in some cases, further processed to add any additional sequences. The resulting constructs are then sequenced, sequencing data processed, and the results used to characterize the mRNA and cell surface feature of the cell. Analysis, for example, can be completed as described elsewhere herein. The information received from the characterization can then be used in a subsequent analysis of another cell in a partition. In some cases, the partition comprises only one cell. Moreover, the priming sequences shown in FIG. 10B are for example purposes only and are not meant to be limiting. In addition, the schemes shown in FIGS. 10A-B may also be used for concurrent analysis of other analytes disclosed herein, including, but not limited to: (a) genomic DNA and cell surface features (e.g., using the labelling agents described herein); (b) mRNA and a lineage tracing construct; (c) mRNA and cell methylation status; (d) mRNA and accessible chromatin (e.g., ATAC-seq, DNase-seq, and/or MNase-seq); (e) mRNA and cell surface or intracellular proteins and/or metabolites (e.g., using the labelling agents described herein); (f) a barcoded labelling agent (e.g., the MHC multimers described herein) and a V(D)J sequence of an immune cell receptor (e.g., T-cell receptor); and (g) mRNA and a perturbation agent (e.g., a CRISPR crRNA/sgRNA, TALEN, zinc finger nuclease, and/or antisense oligonucleotide as described herein).

Furthermore, in various aspects, the first analyte may comprise a nucleic acid molecule with a nucleic acid sequence (mRNA, complementary DNA derived from reverse transcription of mRNA) encoding at least a portion of a V(D)J sequence of an immune cell receptor (e.g., a TCR or BCR). Accordingly, a first barcode molecule may comprise a priming sequence that can prime such a nucleic acid sequence, as is described elsewhere herein. In some cases, the nucleic acid molecule with a nucleic acid sequence encoding at least a portion of a V(D)J sequence of an immune cell receptor is cDNA first generated from reverse transcription of the corresponding mRNA, using a poly-T containing primer. The cDNA that is generated can then be barcoded using a primer, comprising a barcode sequence (and optionally, a UMI sequence) that hybridizes with at least a portion of the cDNA that is generated. In some cases, a template switching oligonucleotide in conjunction a terminal transferase or a reverse transcriptase having terminal transferase activity may be employed to generate a priming region on the cDNA to which a barcoded primer can hybridize during cDNA generation. Terminal transferase activity can, for example, add a poly-C tail to a 3' end of the cDNA such that the template switching oligonucleotide can bind via a poly-G priming sequence and the 3' end of the cDNA can be further extended. The original mRNA template and template switching oligonucleotide can then be denatured from the cDNA and the barcoded primer comprising a sequence complementary to at least a portion of the generated priming region on the cDNA can then hybridize with the cDNA and a barcoded construct comprising the barcode sequence (and any optional UMI sequence) and a complement of the cDNA generated. Additional methods and compositions suitable for barcoding cDNA generated from mRNA transcripts including those encoding V(D)J regions of an immune cell receptor and/or barcoding methods and composition including a template switch oligonucleotide are described in PCT Patent Application PCT/US2017/057269 filed Oct. 18, 2017 and U.S. patent application Ser. No. 15/825,740, filed Nov. 29, 2017, both of which applications are herein incorporated by reference in their entireties. In one example, the scheme described elsewhere herein and schematically depicted in FIG. 11A-B may be used for V(D)J analysis.

V(D)J analysis may also be completed with the use of one or more labelling agents that bind to particular surface features of immune cells and are associated with barcode sequences as described elsewhere herein. In some cases, the one or more labelling agents comprise an MHC or MHC multimer as described herein.

Moreover, in various aspects, the first analyte may comprise a nucleic acid capable of functioning as a component of a gene editing reaction, such as, for example, clustered regularly interspaced short palindromic repeats (CRISPR)-based gene editing. Accordingly, the first barcode molecule may comprise a priming sequence that can prime such a nucleic acid sequence as is described elsewhere herein (e.g., a sequence specific to the CRISPR RNA (crRNA) or single guide RNA (sgRNA) or an adapter sequence engineered into a crRNA or sgRNA).

While the examples described with respect to FIGS. 10A and 10B involve the analysis of two different types of analytes, these examples are not meant to be limiting. Any suitable number of analytes may be evaluated. Accordingly, in various aspects, there may be at least about 2, at least about 3, at least about 4, at least about 5, at least about 6, at least about 7, at least about 8, at least about 9, at least about 10, at least about 11, at least about 12, at least about 13, at least about 14, at least about 15, at least about 20, at least about 25, at least about 30, at least about 40, at least about 50, at least about 100 or more different analytes present in a partition, that can be subject to barcoded sequencing analysis. Higher number, multi-assay analysis can be completed by including primer species (one or more of which may be barcoded) that are capable of generating barcoded constructs and capable of specifically hybridizing with a particular analyte or oligonucleotide coupled to a labelling agent that is itself coupled to a particular analyte in the partition and subjecting the partition to suitable conditions for barcoding.

Figure 10D:
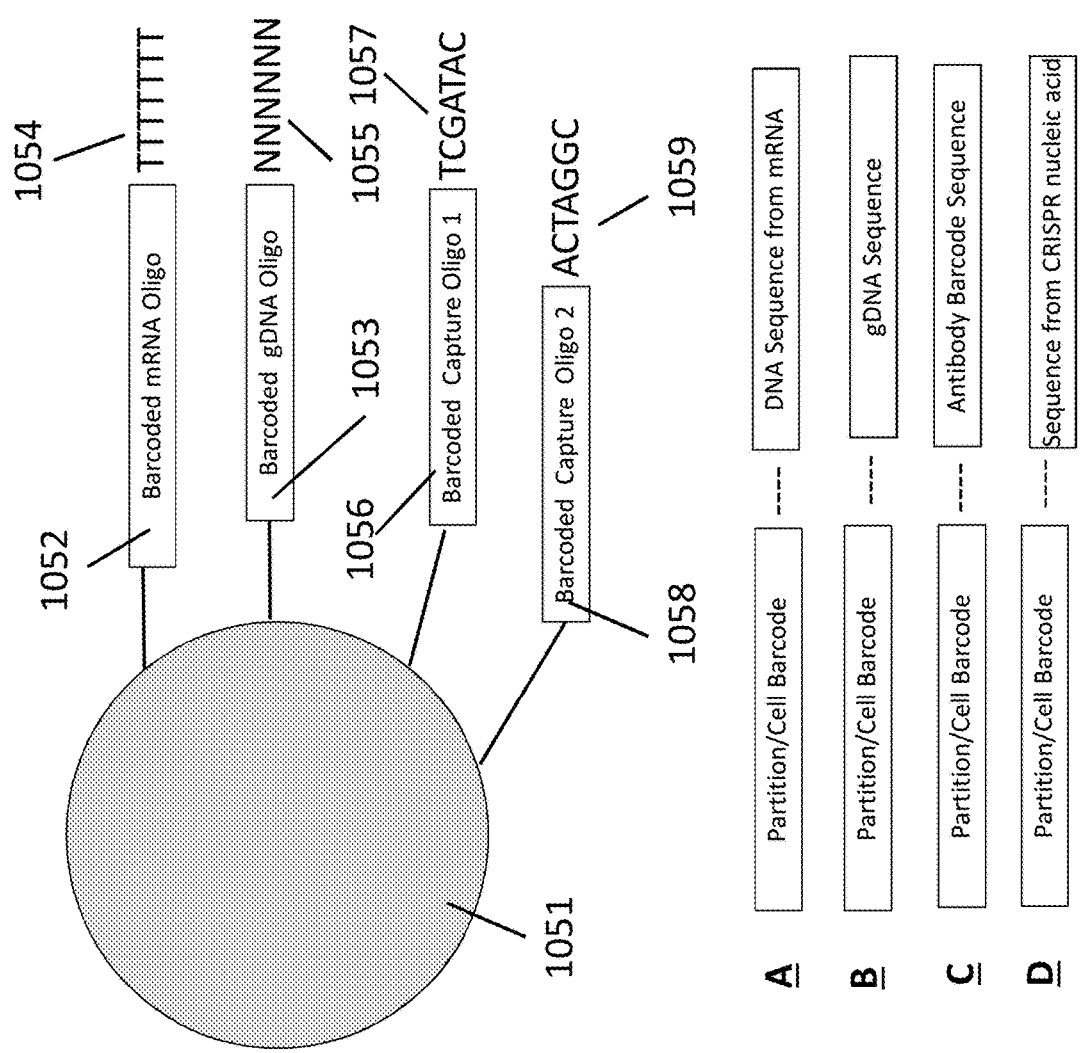

An example reagent for multi-assay analysis is schematically depicted in FIG. 10D. As shown in FIG. 10D, a partition can include a bead 1051 that is coupled to barcoded primers that can each participate in an assay of a different analyte. The bead 1051 is coupled (e.g., reversibly coupled) to a barcoded oligonucleotide 1052 that comprises a poly-T priming sequence 1054 for mRNA analysis and is also coupled (e.g., reversibly coupled) to barcoded oligonucleotide 1053 that comprises a random N-mer priming sequence 1055 for gDNA analysis. Moreover, bead 1051 is also coupled (e.g., reversibly coupled) to a barcoded oligonucleotide 1056 that can specifically bind an oligonucleotide coupled to a labelling agent (e.g., an antibody), via its targeted priming sequence 1057. Bead 1051 is also coupled to a barcoded oligonucleotide 1058 that can specifically bind a nucleic acid molecule that can function in a CRISPR assay (e.g., CRISPR/Cas9), via its targeted priming sequence 1059. In this example, each of the various barcoded primers comprises the same barcode sequence. Each barcoded oligonucleotide can be released from the bead 1051 within the partition and subject to conditions suitable for analysis of its respective analyte. In some cases, one or more of the analytes is associated with or derived from a cell, which itself, may be in the partition. In some cases, the partition comprises only one cell. Barcoded constructs A, B, C and D can be generated as described elsewhere herein and analyzed. Barcoded construct A may comprise a sequence corresponding to the barcode sequence from the bead and a DNA sequence corresponding to a target mRNA. Barcoded construct B may comprise a sequence corresponding to the barcode sequence from the bead and a sequence corresponding to genomic DNA. Barcoded construct C comprises a sequence corresponding to the barcode sequence from the bead and a sequence corresponding to barcode sequence associated with an antibody labelling agent. Barcoded construct D comprises a sequence corresponding to the barcode sequence from the bead and a sequence corresponding to a CRISPR nucleic acid (which, in some embodiments, also comprises a barcode sequence). Each construct can be analyzed via sequencing and the results associated with the given cell from which the various analytes originated. While only four different barcoded constructs are shown in FIG. 10D, barcoded (or even non-barcoded) constructs can be tailored for analyses of any given analyte associated with a nucleic acid and capable of binding with such a construct. For example, the schemes shown in FIG. 10D may also be used for concurrent analysis of other analytes disclosed herein, including, but not limited to: (a) mRNA, a lineage tracing construct, cell surface or intracellular proteins and metabolites (e.g., using the labelling agents described herein), and gDNA; (b) mRNA, accessible chromatin (e.g., ATAC-seq, DNase-seq, and/or MNase-seq) cell surface or intracellular proteins and metabolites (e.g., using the labelling agents described herein), and a perturbation agent (e.g., a CRISPR crRNA/sgRNA, TALEN, zinc finger nuclease, and/or antisense oligonucleotide as described herein); (c) mRNA, cell surface or intracellular proteins and/or metabolites (e.g., using the labelling agents described herein), a barcoded labelling agent (e.g., the MHC multimers described herein), and a V(D)J sequence of an immune cell receptor (e.g., T-cell receptor).

For example, a partition can include a bead (e.g., a gel bead) that is coupled (e.g., reversibly coupled) to barcoded oligonucleotides that can participate in an assay of at least two different analytes. See FIG. 10A for an exemplary bead coupled to a barcoded oligonucleotide 1002 that comprises a poly-T priming sequence 1004 for mRNA analysis and a barcoded oligonucleotide 1003 that comprises a random N-mer priming sequence 1005 for gDNA analysis. See FIG. 10B for an exemplary bead coupled to a barcoded oligonucleotide 1012 that comprise a poly-T priming sequence 1014 for mRNA analysis and a barcoded oligonucleotide 1013 that comprises a capture sequence 1015 that can specifically bind an oligonucleotide coupled to a labelling agent (e.g., an antibody), via its targeted priming sequence 1024.

Additional exemplary assays for measuring at least two different analytes include a bead coupled to a barcoded oligonucleotide (e.g., 1002) that comprises a poly-T priming sequence (e.g., 1004) for mRNA analysis and a barcoded oligonucleotide (e.g., 1058) that comprises a capture sequence 1059 that can specifically bind a perturbation agent (e.g., a nucleic acid molecule that can function in a CRISPR assay (e.g., CRISPR/Cas9), via its targeted priming sequence (see, e.g., FIGS. 12A-D)). Further exemplary assays for measuring at least two different analytes include a bead coupled to a barcoded oligonucleotide (e.g., 1013) that comprises a capture sequence (e.g., 1015) that can specifically bind an oligonucleotide coupled to a labelling agent (e.g., an antibody), via its targeted priming sequence (e.g., 1024) and a barcoded oligonucleotide (e.g., 1003) that comprises a random N-mer priming sequence (e.g., 1005) for gDNA analysis. Additional exemplary assays for measuring at least two different analytes include a bead coupled a barcoded oligonucleotide (e.g., 1013) that comprises a capture sequence (e.g., 1015) that can specifically bind an oligonucleotide coupled to a labelling agent (e.g., an antibody), via its targeted priming sequence (e.g., 1024) and a barcoded oligonucleotide (e.g., 1058) that comprises a capture sequence (e.g., 1059) that can specifically bind a nucleic acid molecule that can function in a CRISPR assay (e.g., CRISPR/Cas9), via its targeted priming sequence (see, e.g., FIGS. 12A-D). Further exemplary assays for measuring at least two different analytes include a bead coupled a barcoded oligonucleotide (e.g., 1003) that comprises a random N-mer priming sequence (e.g., 1005) for gDNA analysis and a barcoded oligonucleotide (e.g., 1058) that comprises a capture sequence (e.g., 1059) that can specifically bind a nucleic acid molecule that can function in a CRISPR assay (e.g., CRISPR/Cas9), via its targeted priming sequence (see, e.g., FIGS. 12A-D).

Figure 10E:
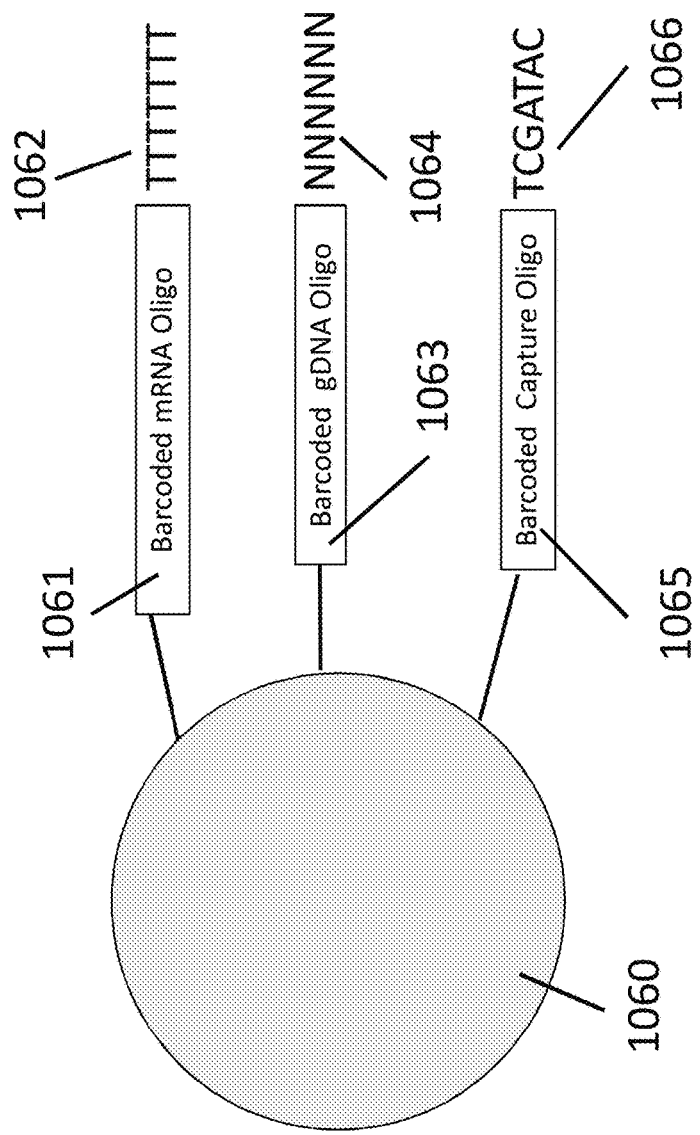
Figure 10F:
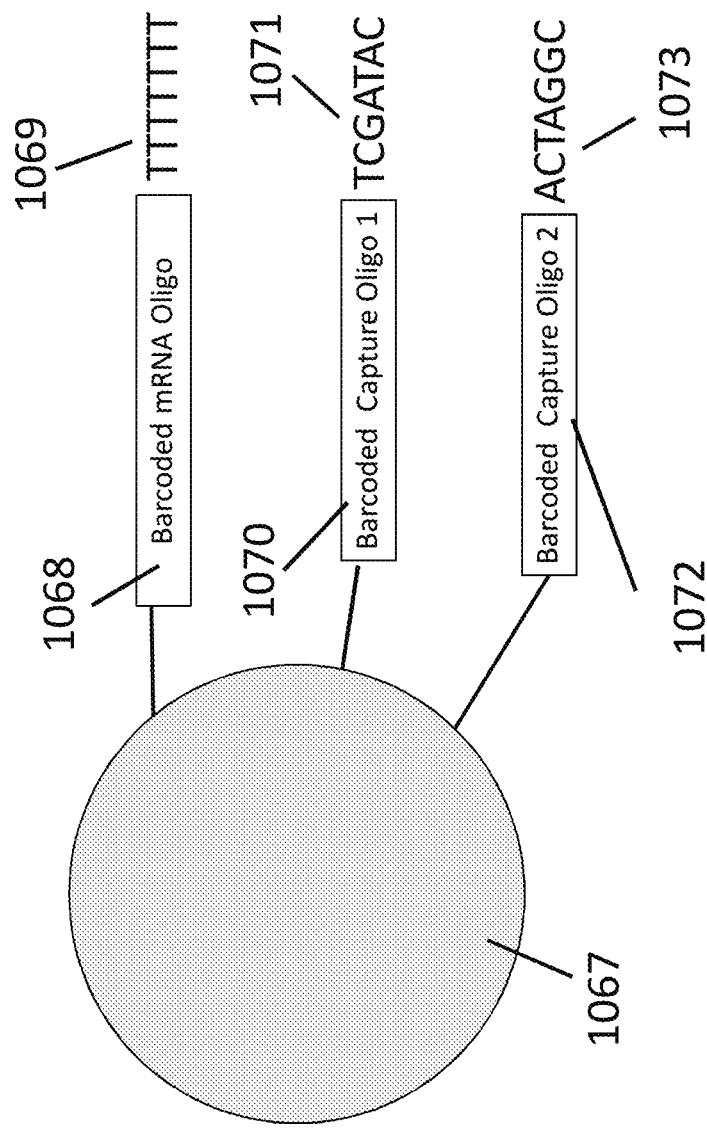

For example, a partition can include a bead (e.g., a gel bead) that is coupled (e.g., reversibly coupled) to barcoded oligonucleotides that can participate in an assay of at least three different analytes. See FIG. 10E for an exemplary bead 1060 coupled to a barcoded oligonucleotide 1061 that comprises a poly-T priming sequence 1062 for mRNA analysis; a barcoded oligonucleotide 1063 that comprises a random N-mer priming sequence 1064 for gDNA analysis; and a barcoded oligonucleotide 1065 that comprises a capture sequence 1066 that can specifically bind an oligonucleotide coupled to a labelling agent (e.g., an antibody), via its targeted priming sequence (e.g., 1024). See FIG. 10F for an exemplary bead 1067 coupled to a barcoded oligonucleotide 1061 that comprises a poly-T priming sequence 1062 for mRNA analysis; a barcoded oligonucleotide 1065 that comprises a capture sequence 1066 that can specifically bind an oligonucleotide coupled to a labelling agent (e.g., an antibody), via its targeted priming sequence (e.g., 1024); and a barcoded oligonucleotide 1072 that comprises a capture sequence 1073 that can specifically bind a nucleic acid molecule that can function in a CRISPR assay (e.g., CRISPR/Cas9), via its targeted priming sequence (see, e.g., FIGS. 12A-D).

Additional exemplary assays for measuring at least three different analytes include a bead coupled to a barcoded oligonucleotide (e.g., 1061) that comprises a poly-T priming sequence (e.g., 1062) for mRNA analysis; a barcoded oligonucleotide (e.g., 1063) that comprises a random N-mer priming sequence (e.g., 1064) for gDNA analysis; and a barcoded oligonucleotide (e.g., 1072) that comprises a capture sequence (e.g., 1073) that can specifically bind a nucleic acid molecule that can function in a CRISPR assay (e.g., CRISPR/Cas9), via its targeted priming sequence (see, e.g., FIGS. 12A-D). In addition, the schemes shown in FIGS. 10E-F may also be used for concurrent analysis of other analytes disclosed herein, including, but not limited to: (a) mRNA, a lineage tracing construct, and cell surface or intracellular proteins and metabolites (e.g., using the labelling agents described herein); (b) mRNA, accessible chromatin (e.g., ATAC-seq, DNase-seq, and/or MNase-seq), and cell surface or intracellular proteins and metabolites (e.g., using the labelling agents described herein); (c) mRNA, cell surface or intracellular proteins and metabolites (e.g., using the labelling agents described herein), and a perturbation agent (e.g., a CRISPR crRNA/sgRNA, TALEN, zinc finger nuclease, and/or antisense oligonucleotide as described herein); (d) mRNA, a barcoded labelling agent (e.g., the MHC multimers described herein), and a V(D)J sequence of an immune cell receptor (e.g., T-cell receptor); (e) cell surface or intracellular proteins and/or metabolites (e.g., using the labelling agents described herein), a barcoded labelling agent (e.g., the MHC multimers described herein), and a V(D)J sequence of an immune cell receptor (e.g., T-cell receptor); and (f) methylation status, mRNA, and cell surface or intracellular proteins and/or metabolites (e.g., using the labelling agents described herein).

A capture oligonucleotide (e.g., a barcoded oligonucleotide capable of coupling to an analyte) or a labelling agent may comprise a backbone. The backbone may comprise one or more of the following elements: a sequencer primer, a barcode, and a UMI. In addition to the backbone, the oligonucleotide may also comprise a primer as described herein, e.g., a poly-T primer, a random N-mer primer, and/or a target-specific capture primer. Examples of oligonucleotides comprising various backbones and primer sequences are shown in FIGS. 13A-13D.

Figure 14A:
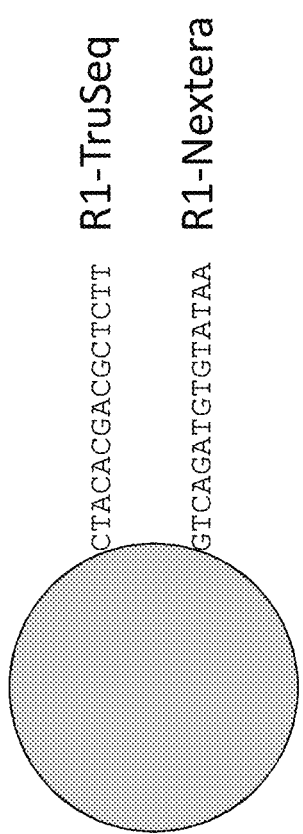
FIG. 14A schematically depicts an example bead comprising oligonucleotides having two different functional sequences. Figure discloses SEQ ID NOS 41 and 42, respectively, in order of appearance.

In some cases, barcoded oligonucleotides are coupled to beads and beads may comprise oligonucleotides having a first type functional sequence at a given position and oligonucleotides having a second, different type of functional sequence at the given position. An example is depicted in FIG. 14A. As shown in FIG. 14A, a bead may be coupled to oligonucleotides comprising a TruSeq functional sequence and also to oligonucleotides comprising a Nextera functional sequence. Onto each of these sequences additional sequences can be added to generate a full oligonucleotide also comprising a nucleic acid barcode sequence, an optional UMI sequence and a priming sequence. Attachment of these sequences can be via ligation (including via splint ligation as is described in U.S. Patent Publication No. 20140378345, which is herein incorporated by reference in its entirety) or any other suitable route. Sequences of example barcoded oligonucleotides comprising a TruSeq functional group are shown in FIG. 14B and sequences of example barcoded oligonucleotides comprising a Nextera functional group are shown in FIG. 14C. Each of the example barcoded oligonucleotides shown in FIG. 14B and FIG. 14C (top sequence for each construct) are shown hybridized with splint sequences (bottom sequence for each construct) that can be helpful in constructing complete barcoded oligonucleotides.

In some embodiments, an oligonucleotide comprising a capture sequence (e.g., a barcoded oligonucleotide capable of coupling to an analyte) or an oligonucleotide labelling agent (e.g., a barcoded antibody) may comprise modifications that render it non-extendable by a polymerase. When binding to a nucleic acid in a sample for a primer extension reaction, the oligonucleotide may serve as a template, not a primer. When the oligonucleotide also comprises a barcode (e.g., the oligonucleotide is a reporter oligonucleotide), such design may increase the efficiency of molecular barcoding by increasing the affinity between the oligonucleotide and the unbarcoded sample nucleic acids, and eliminate the potential formation of adaptor artifacts. In some cases, the oligonucleotide may comprise a random N-mer sequence that is capped with modifications that render it non-extendable by a polymerase. In some cases, the composition of the random N-mer sequence may be designed to maximize the binding efficiency to free, unbarcoded ssDNA molecules. The design may include a random sequence composition with a higher GC content, a partial random sequence with fixed G or C at specific positions, the use of guanosines, the use of locked nucleic acids, or any combination thereof.

A modification for blocking primer extension by a polymerase may be a carbon spacer group of different lengths or a dideoxynucleotide. In some cases, the modification may be an abasic site that has an apurine or apyrimidine structure, a base analog, or an analogue of a phosphate backbone, such as a backbone of N-(2-aminoethyl)-glycine linked by amide bonds, tetrahydrofuran, or 1',2'-Dideoxyribose. The modification may also be a uracil base, 2'OMe modified RNA, C3-18 spacers (e.g., structures with 3-18 consecutive carbon atoms, such as C3 spacer), ethylene glycol multimer spacers (e.g., spacer 18 (hexa-ethyleneglycol spacer), biotin, dideoxynucleotide triphosphate, ethylene glycol, amine, or phosphate.

Species (e.g., oligonucleotides comprising barcodes) attached to a solid support (e.g., a bead) may comprise a U-excising element that allows the species to release from the bead. In some cases, the U-excising element may comprise a single-stranded DNA (ssDNA) sequence that contains at least one uracil. The species may be attached to a solid support via the ssDNA sequence. The species may be released by a combination of uracil-DNA glycosylase (e.g., to remove the uracil) and an endonuclease (e.g., to induce an ssDNA break). If the endonuclease generates a 5' phosphate group from the cleavage, then additional enzyme treatment may be included in downstream processing to eliminate the phosphate group, e.g., prior to ligation of additional sequencing handle elements, e.g., Illumina full P5 sequence, partial P5 sequence, full R1 sequence, and/or partial R1 sequence.

An oligonucleotide comprising a capture sequence or a labelling agent may be a splint oligonucleotide. A splint oligonucleotide may comprise two or more different primers. The primers may have different functions. For example, a splint oligonucleotide may comprise two or more of the following: a poly-T primer, a random N-mer primer, and a target-specific primer.

Figure 15A:
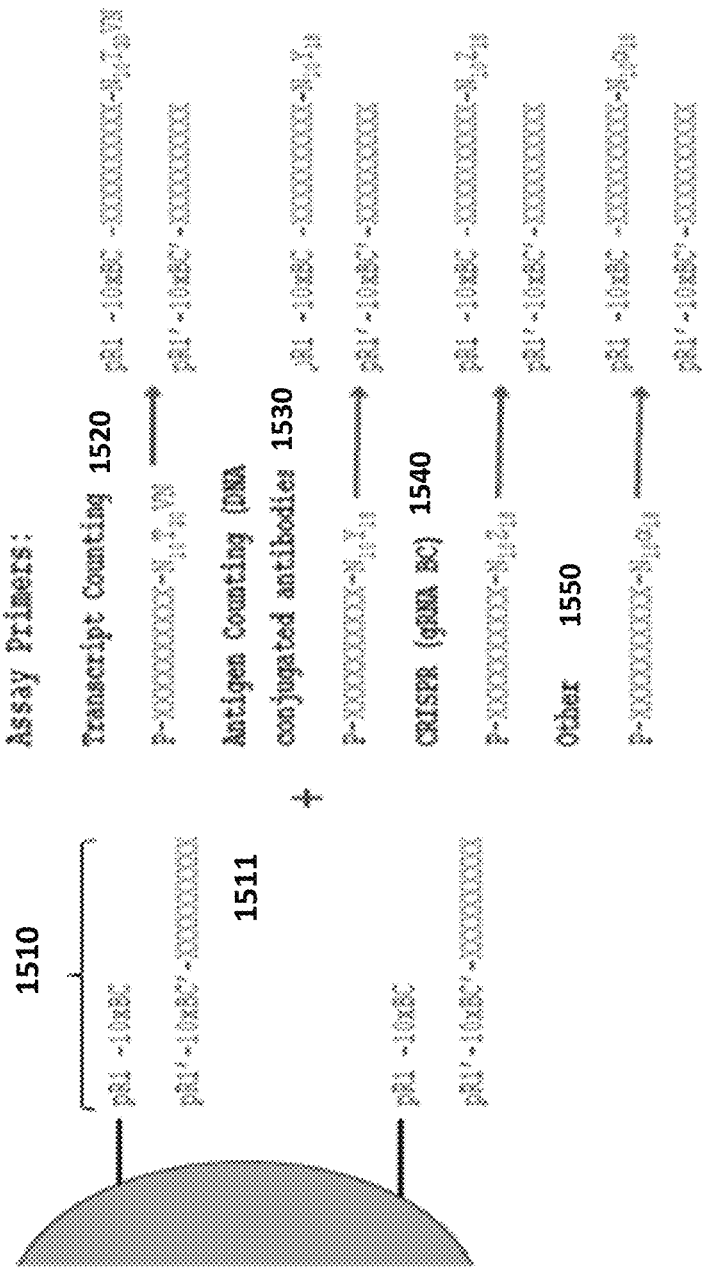
Figure 15B:
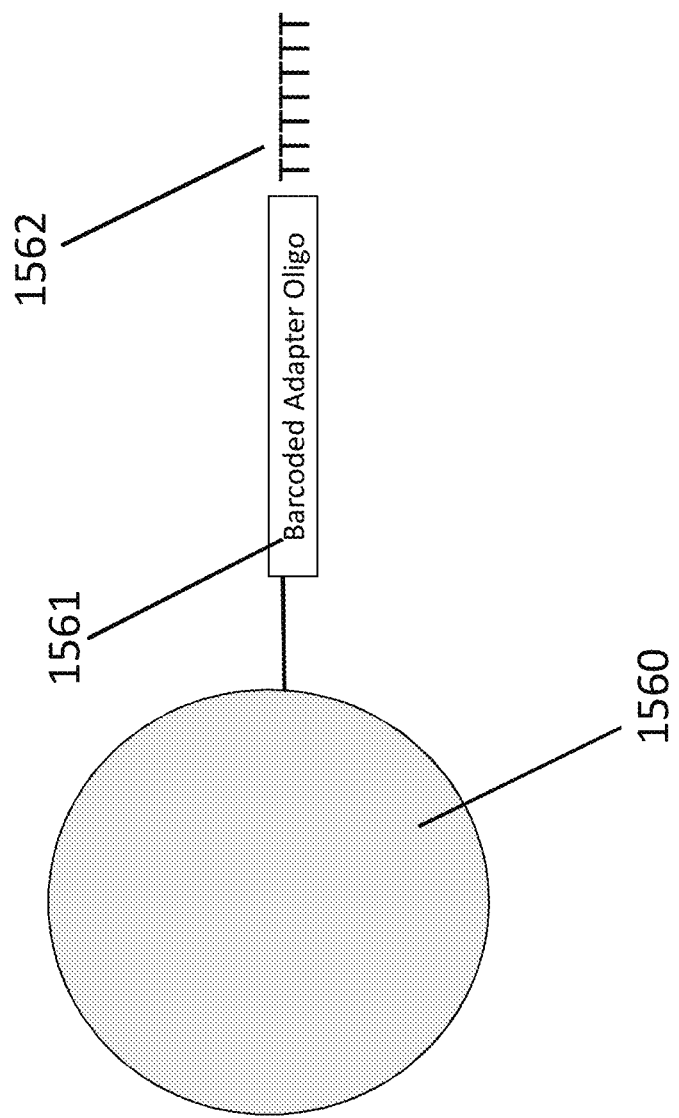

An oligonucleotide comprising a capture sequence (e.g., a barcoded oligonucleotide capable of coupling to an analyte) or an oligonucleotide labelling agent (e.g., a barcoded antibody) may comprise an oligonucleotide sequence that is capable of binding or ligating to an assay primer. The adapter may allow the capture oligonucleotide or the oligonucleotide labelling agent to be attached to any suitable assay primers and used in any suitable assays. The assay primer may comprise a priming region and a sequence that is capable of binding or ligating to the adapter. In some cases, the adapter may be a non-specific primer (e.g., a 5' overhang) and the assay primer may comprise a 3' overhang that can be ligated to the 5' overhang. The priming region on the assay primer may be any primer described herein, e.g., a poly-T primer, a random N-mer primer, a target-specific primer, or a labelling agent capture sequence. FIG. 15A shows exemplary adapters and assay primers. Oligonucleotide 1510 comprises an adapter 1511, which is a 5' overhang comprising 10 nucleotides. The adapter 1511 can be ligated to the assay primers, each of which comprises a 3' overhang comprising 10 nucleotides that complementary to the 5' overhang of adapter 1511. The capture oligonucleotide may be used in any assay by attaching to the assay primer designed for that assay. FIG. 15B shows exemplary adapters and assay primers that allows the capture oligonucleotide or the labelling agent oligonucleotide to be attached to any suitable assay primers and used in any suitable assays. Barcoded adapter oligonucleotide 1561 is attached to a bead 1560, such as a gel bead, and comprises a poly(dT) sequence 1562. The barcoded oligonucleotide 1561 comprising a poly-T sequence 1562 as depicted in FIG. 15B can be used to assay multiple analytes as generally described herein (e.g., the analyte comprises a poly-A sequence or is coupled to or otherwise is associated with a labelling agent comprising a poly-A sequence). For example, in some embodiments, a single bead 1560 (e.g., a gel bead) comprising barcoded oligonucleotide 1561 comprising a poly-T sequence 1562 is partitioned with a single cell (or cell bead) coupled to one or more labelling agents capable of coupling to an analyte (e.g., a barcoded antibody), wherein the labelling agent comprises an oligonucleotide comprising a poly-A sequence and a peptide barcode sequence that identifies the labelling agent. The aforementioned single cell is then lysed and mRNA molecules released from the single cell and the poly-A containing labelling agent oligonucleotide both hybridize to the poly-T sequence 1562 of barcoded oligonucleotide 1561 and are processed (e.g., by reverse transcription) to add the barcode sequence from the barcoded adapter 1561. After further processing and sequencing as generally described elsewhere herein, the peptide barcode sequence can be used to identify the analyte and the barcode sequence of barcoded adapter 1561 can be used to associate mRNA transcripts and the analyte as having arisen from the same cell. FIG. 15C shows exemplary splint oligos comprising a poly-A sequence that facilitates coupling to the barcoded adapter oligonucleotide 1561 and a second sequence (shown as "XXX", "YYY", and "ZZZ") that facilitates coupling with an assay primer. Assay primers comprise a sequence complementary to the splint oligo second sequence (shown as "X'X'X'", "Y'Y'Y'", and "Z'Z'Z'") and an assay-specific sequence that determines assay primer functionality (e.g., a poly-T primer, a random N-mer primer, a target-specific primer, or a labelling agent capture sequence as described herein).

Figure 16:
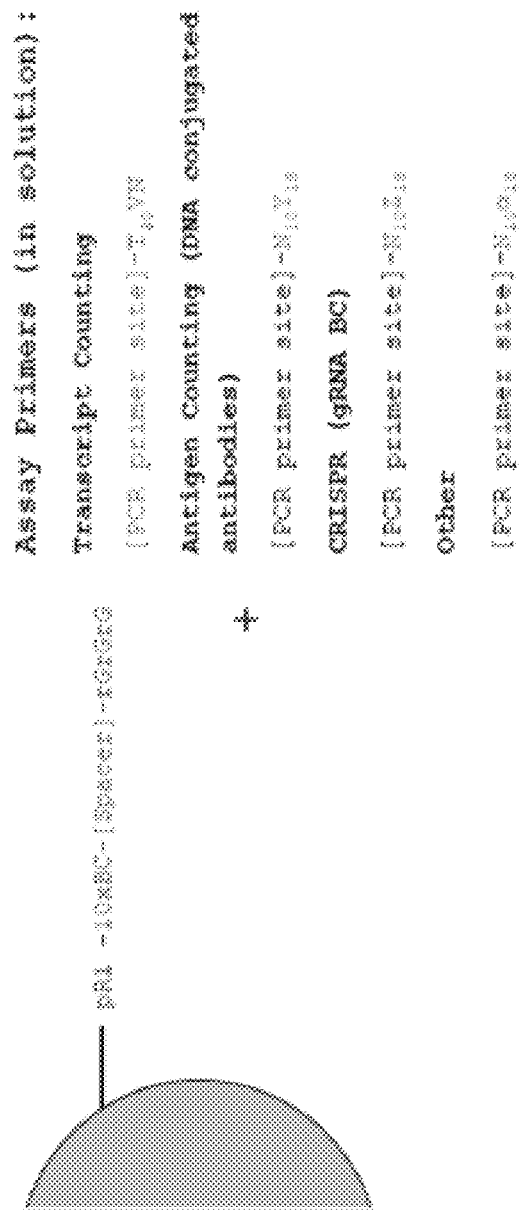
FIG. 16 shows an oligonucleotide with an adapter comprising a switch oligonucleotide. Figure discloses SEQ ID NO: 54.

In some cases, the barcoded adapter comprises a switch oligo, e.g., with a 3' end 3rG. FIG. 16 shows a bead (such as a gel bead) comprising a barcoded adapter oligonucleotide functionalized with a 3rG sequence that enables template switching (e.g., reverse transcriptase template switching), but is not specific for any particular assay. Assay primers added to the reaction determine the particular assay by binding to targeted molecules and are extended by a reverse transcriptase enzyme/polymerase followed by template switching onto the barcoded adapter oligonucleotide to incorporate the barcode and other functional sequences. The priming region determines the assay and, in some embodiments, comprises a poly-T sequence for mRNA analysis, random primers for gDNA analysis, or a capture sequence that can bind a nucleic acid molecule coupled to a labelling agent (e.g., an antibody) or a nucleic acid molecule that can function in a CRISPR assay (e.g., CRISPR/Cas9) via a targeted priming sequence.

In some embodiments, the analytes (e.g., genomic, epigenomic, proteomic, and cell surface information) of cells characterized by the methods and systems described herein may be sequenced individually. In some embodiments, the cellular analytes characterized by the methods and systems described herein may be pooled and sequenced together. In some embodiments, the cellular analytes characterized by the methods and systems described herein may be sequenced sequentially (e.g., cell surface information characterized first, then proteomic and genomic information).

A microcapsule (e.g., a gel bead) entrapping one or more magnetic particles may be used in the methods described herein. In some instances, the magnetic particles do not diffuse out of the microcapsule until the microcapsule is dissolved. The microcapsule may comprise an oligonucleotide comprising a DNA primer. For example, the DNA primer may be a genomic DNA primer. The DNA primer may bind to DNA molecules from a cell. The DNA primer may be used to amplify and/or sequence DNA molecules from a cell. DNA primers may be entrapped and/or bound to the microcapsule and released when the microcapsule is dissolved.

The magnetic particles entrapped within the microcapsule may comprise an oligonucleotide comprising a capture sequence complementary to a sequence present on an analyte (e.g., an adapter sequence present on a labelling agent, e.g., a barcoded antibody, as described herein).

Figure 17A:
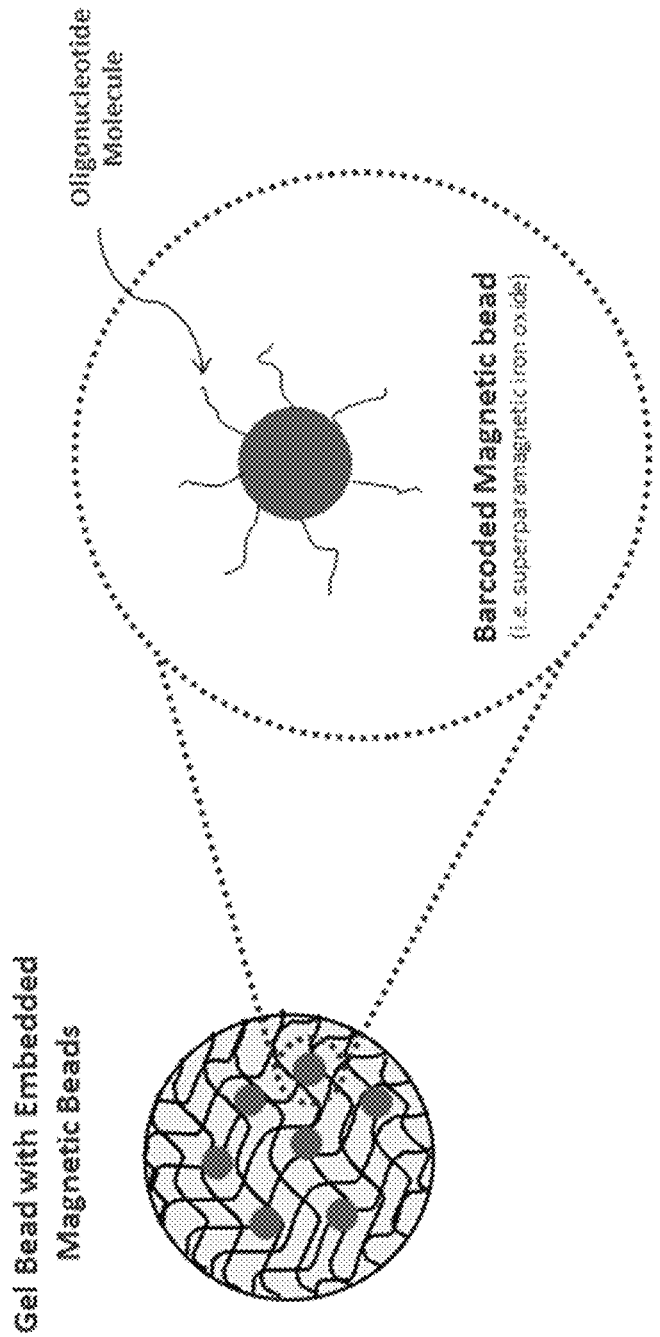
FIG. 17A shows a microcapsule with a barcoded magnetic particle entrapped.
Figure 17B:
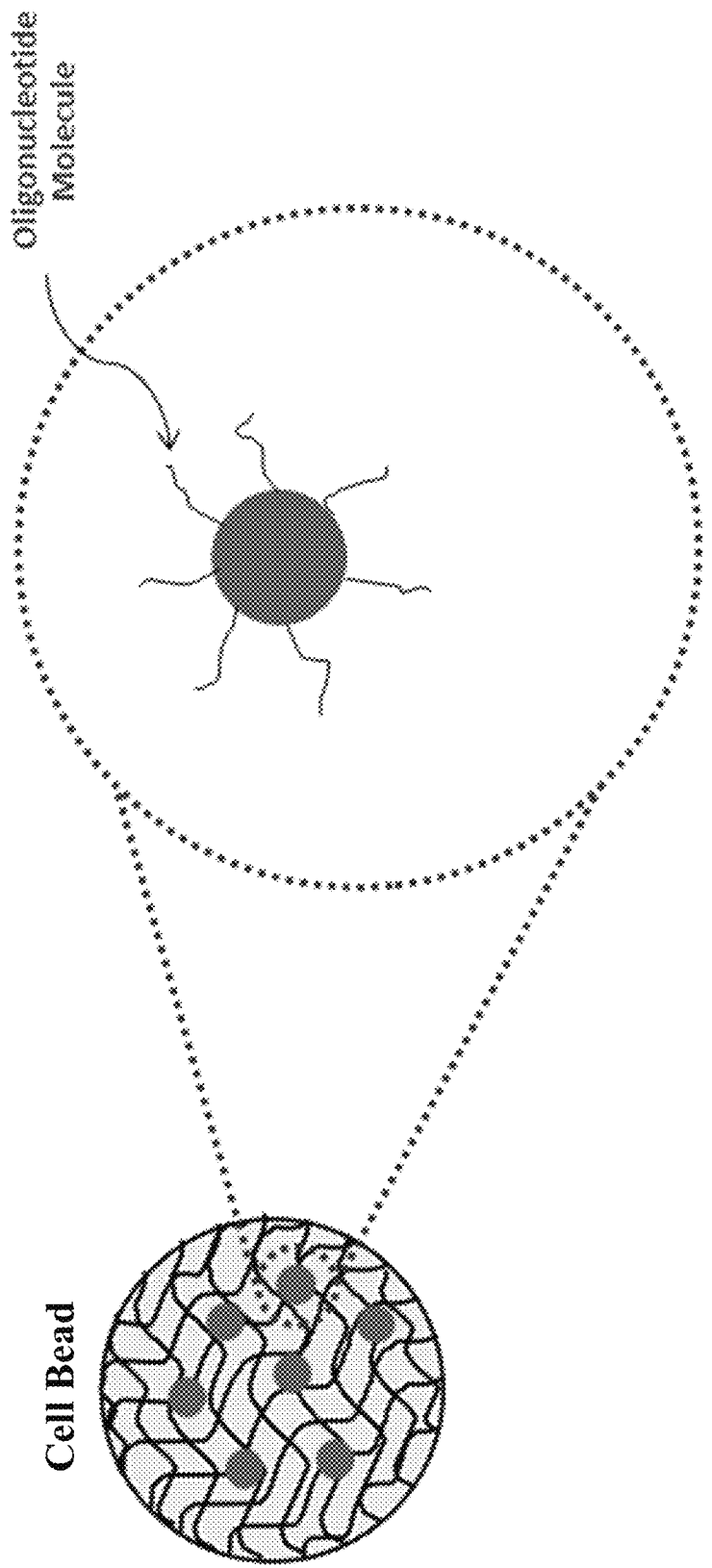
FIG. 17B shows a cell bead comprising a magnetic particle attached to an oligonucleotide.

The magnetic particles entrapped within the microcapsule may comprise an oligonucleotide comprising an RNA primer. The RNA primer may bind to RNA molecules from a cell. In some cases, the RNA primer is an mRNA primer that binds to the mRNA molecules from the cell. For example, the mRNA primer may comprise a poly-T sequence that binds to the poly-A sequence of the mRNA molecules from the cell. FIG. 17A shows a microcapsule (e.g. gel bead) with a barcoded magnetic particle entrapped. FIG. 17B shows a cell bead with a barcoded magnetic particle entrapped.

The magnetic particles may be made from materials such as iron oxide (e.g., superparamagnetic iron oxide), ferromagnetic, ferrimagnetic, or paramagnetic materials. Ferromagnetic materials may be strongly susceptible to magnetic fields and capable of retaining magnetic properties when the field can be removed. Ferromagnetic materials include, but are not limited to, iron, cobalt, nickel, alloys thereof, and combinations thereof. Other ferromagnetic rare earth metals or alloys thereof can also be used to make the magnetic particles.

The oligonucleotides on both the microcapsule and the magnetic particle may comprise the same barcode sequence. The barcode sequence may allow matching the information (e.g., sequence reads) of DNA and RNA from the same cell.

In some cases, the microcapsule may also contain one or more reagents for analyzing cells. For example, the microcapsule may contain a lysis agent. When the microcapsule is dissolved, the lysis agent may be released and lyse the cell in the same partition with the microcapsule.

In some cases, the microcapsule may be a gel bead. An example method for making a gel bead with one or more magnetic particles may comprise one or more of the following operations: 1) Magnetic particles are added to the aqueous phase of the material for making the gel beads, e.g., the gel beads monomer mixture; 2) The gel beads are made using a microfluidic approach, e.g., by forming droplets that polymerize to form the gel beads. When the droplets polymerize, the magnetic particles are entrapped within; 3) The same barcode sequence is added to the gel bead and the magnetic particles entrapped within, e.g., using dual ligation strategy.

Once a partition is generated to include a cell, a microcapsule, and a magnetic particle entrapped in the microcapsule, the partition may be incubated with one or more reagents (e.g., a lysis agent) to lyse the cell and dissolve the microcapsule. The incubation may be performed on a microfluidic chip device, e.g., with a delay line device as described in Frenz et al., Reliable microfluidic on-chip incubation of droplets in delay-lines. Lab Chip. 2009 May 21; 9(10):1344-8, which is incorporated herein by reference in its entirety. After the incubation, the partition may be collected and placed in a container e.g., a strip tube or plate.

The incubation may be performed for a period that allows sufficient time for the cell to lyse and the magnetic particles to be released from the microcapsule. The incubation time may also allow sufficient binding of the RNA primers on the magnetic particles with the RNA molecules from the cell. In some cases, the incubation time may be from 1 minute to 100 minutes, from 5 minutes to 50 minutes, from 10 minutes to 30 minutes, or from 10 minutes to 20 minutes.

Figure 18:
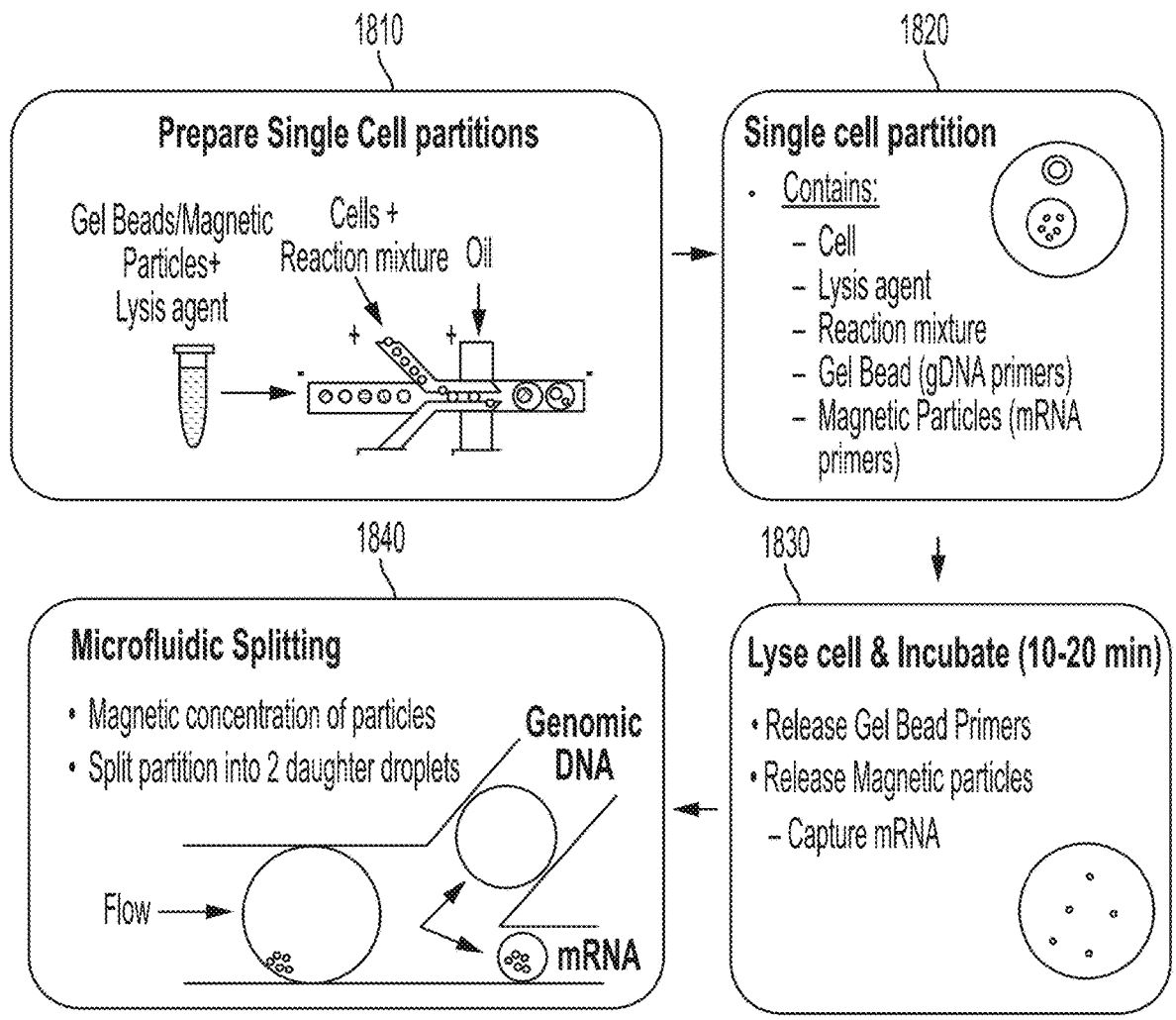
FIG. 18 shows a method for parallel sequencing of DNA molecules and RNA molecules in a cell.

One or more RNA molecules bound to the RNA primers on the magnetic particles may be separated from other components in the partition. The separation may be performed by concentrating the magnetic particles. The magnetic particles may be concentrated by a magnetic field. The separation may be performed on a microfluidic device, e.g., a device as described in Gao et al., Wash-free magnetic immunoassay of the PSA cancer marker using SERS and droplet microfluidics, Lab Chip, 2016, 16, 1022-1029; Brouzes et al., Rapid and continuous magnetic separation in droplet microfluidic devices. Lab Chip. 2015 Feb. 7; 15(3): 908-19; or Lombardi et al., Droplet microfluidics with magnetic beads: a new tool to investigate drug-protein interactions. Anal Bioanal Chem. 2011 January; 399(1):347-52, which are incorporated herein by reference in their entireties. In some cases, the one or more RNA molecules may be separated from DNA molecules. The separated RNA molecules and DNA molecules from a single cell may be analyzed using approaches described herein, e.g., sequencing, to determine a characteristic of the cell. FIG. 18 shows a method for parallel sequencing DNA (e.g., genomic DNA) and RNA (e.g., mRNA) in a cell. In operation 1810, single cell partitions are prepared by mixing gel beads with magnetic particles, cells and reaction reagents, e.g., a lysis agent. Droplets are generated from the mixture. A single droplet 1820 contains one cell, a gel bead with magnetic particles, and reaction reagents. The gel bead has genomic DNA primers and the magnetic particles have mRNA primers. The gel bead and the magnetic particles in the partition have the same barcode sequence. In 1830, the gel bead is dissolved to release the magnetic particles and genomic DNA primers. The cell is also lysed to release the genomic DNA molecules and mRNA molecules. The mRNA molecules are captured on the magnetic particles by binding with the mRNA primers. In operation 1840, on a microfluidic device, the partition split into two daughter droplets. The magnetic particles with the captured mRNA molecules are collected in only one of the daughter droplets, thus being separated from other components, e.g., genomic DNA in the other daughter droplet. Thus, the genomic DNA molecules and mRNA molecules from a single cell are separated and may be used for further analysis. The scheme shown in FIGS. 17-18 may also be used for concurrent analysis of other analytes as disclosed herein. For example, a capture oligonucleotide specific for an analyte (e.g., poly-T for mRNA, a capture sequence capable of coupling to a labelling agent oligonucleotide, etc.) may be coupled to magnetic beads while capture oligonucleotides specific for one or more other analytes can be attached to the gel bead. In some embodiments, a first plurality of magnetic particles may be coupled to a capture oligonucleotide specific for one analyte (e.g., poly-T for mRNA), a second plurality of magnetic particles may be coupled to a capture oligonucleotide specific for another analyte (e.g., a capture sequence capable of coupling to a labelling agent oligonucleotide), and a capture oligonucleotides specific for a third analyte (e.g., gDNA) can be attached to the gel bead.

Characterization, Analysis, and Detection of Cell Surface Features

Disclosed herein, in some embodiments, are compositions, methods, and systems useful in the analysis of multiple analytes in a single cell or cell population. Examples of analytes include, without limitation, DNA (e.g., genomic DNA), epigenetic information (e.g., accessible chromatin or DNA methylation), RNA (e.g., mRNA or CRISPR guide RNAs), synthetic oligonucleotides (e.g., DNA transgenes), and proteins (e.g., intracellular proteins, cell surface proteins or features, extracellular matrix proteins, or nuclear membrane proteins). Examples of intracellular protein analytes include, but are not limited to, transcription factors, histone proteins, kinases, phosphatases, cytoskeletal proteins (e.g., actin, tubulin), polymerases, nucleases, and ribosomal proteins. An analyte may be a cell or one or more constituents of a cell.

In some embodiments, a cell surface protein (or cell surface feature) is one of the analytes characterized by the compositions, methods, and systems disclosed herein. To facilitate the analysis of cell surface proteins, additional agents may also be co-partitioned with the cells, such as one or more labelling agents as described herein capable of binding to one or more cell surface features of the cell(s).

Cell surface features may comprise a receptor, an antigen, a surface protein, a transmembrane protein, a cluster of differentiation protein, a protein channel, a protein pump, a carrier protein, a phospholipid, a glycoprotein, a glycolipid, a cell-cell interaction protein complex, an antigen-presenting complex, a major histocompatibility complex, an engineered T-cell receptor, a T-cell receptor, a B-cell receptor, a chimeric antigen receptor, an extracellular matrix protein, a posttranslational modification (e.g., phosphorylation, glycosylation, ubiquitination, nitrosylation, methylation, acetylation or lipidation) state of a cell surface protein, a gap junction, and an adherens junction.

In some cases, the labelling agent and/or the reporter oligonucleotide may be delivered into the cell, e.g., by transfection (e.g., using transfectamine, cationic polymers, calcium phosphate or electroporation), by transduction (e.g., using a bacteriophage or recombinant viral vector), by mechanical delivery (e.g., magnetic beads), by lipid (e.g., 1,2-Dioleoyl-sn-glycero-3-phosphocholine (DOPC)), or by transporter proteins. A labelling agent and/or reporter oligonucleotide may be delivered into a cell using exosomes. For example, a first cell may be generated that releases exosomes comprising a labelling agent and/or reporter oligonucleotide. A labelling agent may be attached to an exosome membrane. A labelling agent may be contained within the cytosol of an exosome. Released exosomes may be harvested and provided to a second cell, thereby delivering the labelling agent and/or reporter oligonucleotide into the second cell. A labelling agent may be releasable from an exosome membrane before, during, or after delivery into a cell. In other cases, the cell is permeabilized to allow the labelling agent to couple with intracellular cellular constituents (such as intracellular proteins, metabolites and nuclear membrane proteins). Following intracellular delivery, labelling agents and reporter oligonucleotides may be used to analyze intracellular constituents as described herein.

In one example process, a sample is provided that contains cells that are to be analyzed and characterized as to their cell surface features. Also provided is at least one labelling agent, such as a library of labelling agents, capable of binding to a cell surface feature of interest. A labelling agent may include, but is not limited to, an antibody, or an epitope binding fragment thereof, a cell surface receptor binding molecule, a receptor ligand, a small molecule, a bi-specific antibody, a bi-specific T-cell engager, a T-cell receptor engager, a B-cell receptor engager, a pro-body, an aptamer, a monobody, an affimer, a darpin, and a protein scaffold, or any combination thereof. The labelling agents can include a reporter oligonucleotide that is indicative of the cell surface feature to which the binding group binds. In particular, a labelling agent that is specific to one type of cell surface feature may have coupled thereto a first reporter oligonucleotide, while a labelling agent that is specific to a different cell surface feature may have a different reporter oligonucleotide coupled thereto. In some aspects, these reporter oligonucleotides may comprise nucleic acid barcode sequences that permit identification of the labelling agent which the reporter oligonucleotide is coupled to. The selection of oligonucleotides as the reporter may provide advantages of being able to generate significant diversity in terms of sequence, while also being readily attachable to most biomolecules, e.g., antibodies, etc., as well as being readily detected, e.g., using sequencing or array technologies. In some embodiments, the labelling agents may include reporter oligonucleotides attached to them. Thus, a first labelling agent, e.g., an antibody to a first cell surface feature, may have associated with it a reporter oligonucleotide that has a first nucleic acid sequence. Different labelling agents, e.g., antibodies having binding affinity for other, different cell surface features, may have associated therewith reporter oligonucleotides that comprise different nucleic acid sequences, e.g., having a partially or completely different nucleic acid sequence. In some cases, for each type of cell surface feature labelling agent, e.g., antibody or antibody fragment, the reporter oligonucleotide sequence may be known and readily identifiable as being associated with the known cell surface feature labelling agent. These reporter oligonucleotides may be directly coupled to the labelling agent, or they may be attached to a bead, molecular lattice, e.g., a linear, globular, cross-linked, or other polymer, or other framework that is attached or otherwise associated with the labelling agent, which allows attachment of multiple reporter oligonucleotides to a single labelling agent.

In the case of multiple reporter oligonucleotides coupled to a single labelling agent, such reporter oligonucleotides can comprise the same sequence, or a particular labelling agent may include a known set of reporter oligonucleotide sequences. As between different labelling agents, e.g., specific for different cell surface features, the reporter oligonucleotides may be different and attributable to the particular labelling agent.

Figure 19:
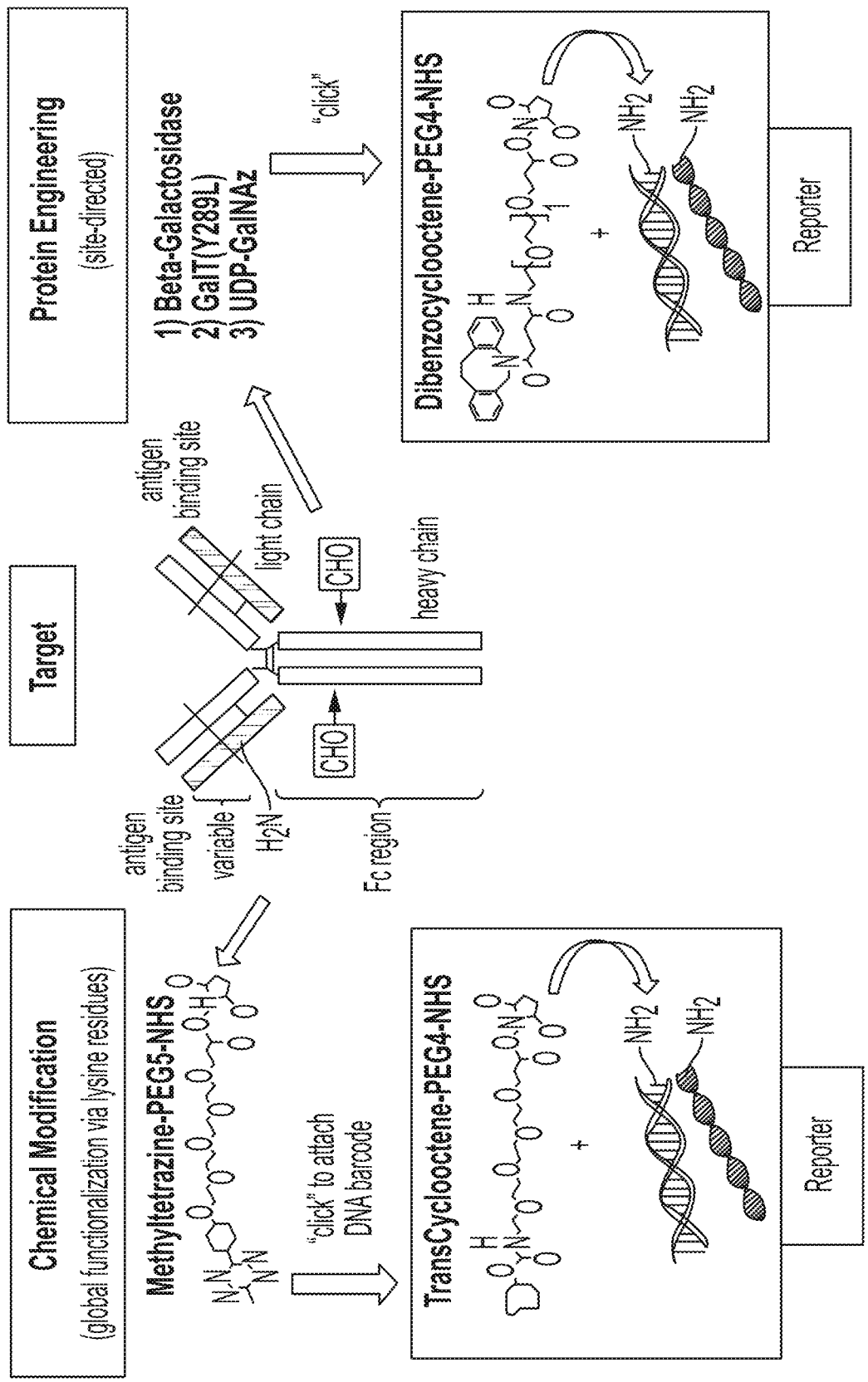
FIG. 19 shows various approaches for making antibody-reporter oligonucleotide conjugates.

Attachment (coupling) of the reporter oligonucleotides to the labelling agents may be achieved through any of a variety of direct or indirect, covalent or non-covalent associations or attachments. For example, in the case of oligonucleotide reporter oligonucleotides associated with antibody based labelling agents, such oligonucleotides may be covalently attached to a portion of an antibody or antibody fragment using chemical conjugation techniques (e.g., Lightning-Link® antibody labelling kits available from Innova Biosciences), as well as other non-covalent attachment mechanisms, e.g., using biotinylated antibodies and oligonucleotides (or beads that include one or more biotinylated linker, coupled to oligonucleotides) with an avidin or streptavidin linker. Antibody and oligonucleotide biotinylation techniques are available. See, e.g., Fang, et al., "Fluoride-Cleavable Biotinylation Phosphoramidite for 5'-end-Labelling and Affinity Purification of Synthetic Oligonucleotides," Nucleic Acids Res. Jan. 15, 2003; 31(2): 708-715, which is entirely incorporated herein by reference for all purposes. Likewise, protein and peptide biotinylation techniques have been developed and are readily available. See, e.g., U.S. Pat. No. 6,265,552, which is entirely incorporated herein by reference for all purposes. Furthermore, click reaction chemistry such as a Methyltetrazine-PEG5-NHS Ester reaction, a TCO-PEG4-NHS Ester reaction, or the like, may be used to couple reporter oligonucleotides to labelling agents. The reactive moiety on the labelling agent may also include amine for targeting aldehydes, amine for targeting maleimide (e.g., free thiols), azide for targeting click chemistry compounds (e.g., alkynes), biotin for targeting streptavidin, phosphates for targeting EDC, which in turn targets active ester (e.g., $NH_2$). The reactive moiety on the protein probe may be a chemical compound or group that binds to the reactive moiety on the labelling agent. Example strategies to conjugate the protein probe to the labelling agent include using of commercial kits (e.g., Solulink, Thunder link), conjugation of mild reduction of hinge region and maleimide labelling, stain-promoted click chemistry reaction to labeled amides (e.g., copper-free), and conjugation of periodate oxidation of sugar chain and amine conjugation. In the cases where the protein probe is an antibody, the antibody may be modified for conjugating the reporter oligonucleotide. For example, the antibody may be glycosylated with a substrate-permissive mutant of $\beta$-1,4-galactosyltransferase, GalT (Y289L) and azide-bearing uridine diphosphate-N-acetylgalactosamine analog uridine diphosphate-GalNAz. The modified antibody may be conjugated with a reporter oligonucleotide with a dibenzocyclooctyne-PEG4-NHS group. FIG. 19 shows example strategies for antibody-reporter oligonucleotide conjugation. In some cases, some strategy (e.g., COOH activation (e.g., EDC) and homobifunctional cross linkers) may be avoided to prevent the protein probes from conjugating to themselves.

Figure 20:
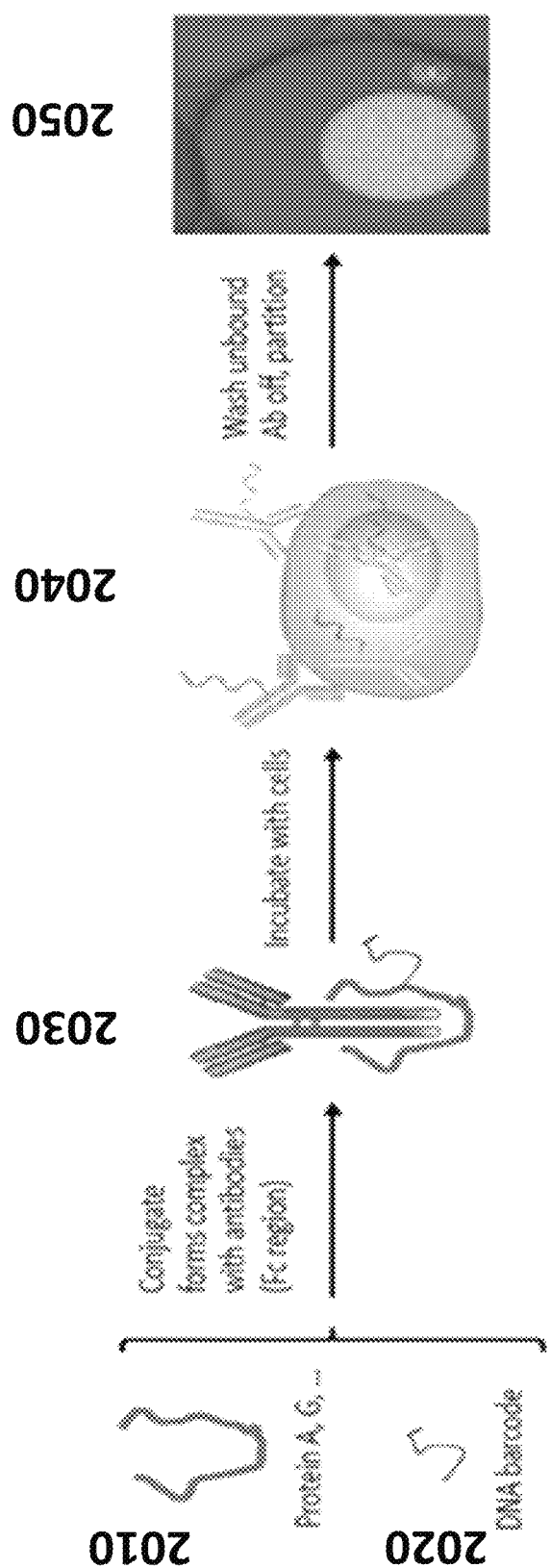
FIG. 20 shows a workflow for conjugating a DNA barcode on an antibody using an antibody-binding protein.

In the case that the labelling agent is a primary antibody, a reporter oligonucleotide may be coupled to the labelling agent through a secondary antibody coupling interaction. In some cases, a reporter oligonucleotide may be associated (e.g., covalently linked such as conjugated or non-covalently bound through a binding interaction) to an antibody via an antibody-binding protein. For example, a reporter oligonucleotide and an antibody-binding protein may form a complex. The complex may bind to a respective antibody through the antibody-binding protein. FIG. 20 shows an example workflow for associating a nucleic acid (e.g., DNA) barcode on an antibody using an antibody-binding protein. An antibody binding protein 2010, e.g., Protein A or Protein G, and an oligonucleotide comprising a nucleic acid (e.g., DNA) barcode 2020 are conjugated to the Fc region of an antibody, forming a complex 2030 comprising the antibody, the antibody-binding protein 2010, and the DNA barcode 2020. The complex 2030 is incubated with cells and unbound antibody is washed out. When the complex 2030 binds to a cell, the complex and the cell are partitioned into a droplet for further analysis.

An antibody-binding protein may have fast adsorption kinetics, slow desorption kinetics, and/or a low binding equilibrium constant. Any methods for adding chemical functionality to peptides or proteins may be used. Some methods may include attaching a reporter oligonucleotide to specific amino acids or chemical groups (e.g., chemical groups present in multiple types of proteins) on the antibody-binding protein. The conjugation of antibody-binding proteins and oligonucleotides may be performed using methods for forming antibody-nucleic acid conjugation described herein, e.g., using click chemistry. Dissociation of the antibody-binding protein/oligonucleotide complexes may be prevented by crosslinking (e.g., using a crosslinker such as formaldehyde), protein engineering, or adding the protein-binding proteins in excess.

Examples of antibody-binding proteins include proteins that bind to the constant (Fc) region of antibodies, such as Protein A, Protein G, Protein L, or fragments thereof. Other binding proteins (e.g., streptavidin) may be expressed as fusion proteins with antibody-binding proteins, and used to associate oligonucleotides (e.g., by binding of biotinylated oligonucleotides to a streptavidin-Protein A fusion protein). Other antibody-binding proteins or domains may provide additional binding affinity for various antibody classes. In some cases, the antibody-binding protein may be an antibody, e.g., a secondary antibody for the antibody targeting the sample. The secondary antibody may comprise an oligonucleotide described here, e.g., an oligonucleotide with a barcode and a poly-A or poly T terminated sequence.

The antibody-binding proteins may be engineered to introduce additional functionalities. Antibody-binding proteins may be engineered to contain amino acids with functional groups amenable to conjugation with oligonucleotide. For example, the antibody-binding proteins may naturally have or be engineered to have cysteine residues, e.g., for controlling stoichiometry and/or attachment location of the oligonucleotides. The antibody-binding proteins may be engineered to have non-natural amino acid residues, e.g., for targeted crosslinking of binding proteins and antibodies. The antibody-binding proteins may be engineered to have tags, e.g., fluorescent tags (e.g., by fusing with a fluorescent protein such as green fluorescence protein (GFP), red fluorescence protein (RFP), yellow fluorescence protein (YFP)) and/or affinity tags for purification and visualization. The fluorescent tags and/or the affinity tags may be cleavable. In some cases, the antigen-binding protein may be engineered to have one or more (e.g., only one) barcode attachment sites per protein.

Also provided herein are kits comprising antibody-binding proteins conjugated with reporter oligonucleotides, e.g., in well plates. Antibody for an assay may be incubated with the antibody-binding proteins conjugated with reporter oligonucleotides at a specified concentration without interfering with the antibody's binding site and/or without the need for any chemistry to be carried out in the customer's hands to conjugate the reporter oligonucleotide to the antibody.

The reporter oligonucleotides may be provided having any of a range of different lengths, depending upon the diversity of reporter oligonucleotides suitable for a given analysis, the sequence detection scheme employed, and the like. In some cases, these reporter oligonucleotides can be greater than or equal to about 5 nucleotides in length, greater than or equal to about 10 nucleotides in length, greater than or equal to about 5, 10, 20, 30, 40, 50, 60, 70, 80, 90, 100, 120, 150, 200 or 250 nucleotides in length. In some cases, these reporter oligonucleotides may be less than or equal to about 250, 200, 180, 150, 120, 100, 90, 80, 70, 60, 50, 40, 30, 20, 10 or 5 nucleotides in length. In some cases, the reporter oligonucleotides may be selected to provide barcoded products that are already sized, and otherwise configured to be analyzed on a sequencing system. For example, these sequences may be provided at a length that ideally creates sequenceable products of a suitable length for particular sequencing systems. Likewise, these reporter oligonucleotides may include additional sequence elements, in addition to the reporter sequence, such as sequencer attachment sequences, sequencing primer sequences, amplification primer sequences, or the complements to any of these.

In operation, a cell-containing sample may be incubated with the labelling agents and their associated reporter oligonucleotides, for any of the cell surface features to be analyzed. Following incubation, the cells may be washed to remove unbound labelling agents. Following washing, the cells may be partitioned into separate partitions, e.g., droplets, along with the barcode carrying beads described above, where each partition includes a limited number of cells, e.g., a single cell. Upon releasing of the barcodes (or capture oligonucleotides) from the beads, they may prime the amplification and barcoding of the reporter oligonucleotides coupled to the labelling agents. The barcoded replicates of the reporter oligonucleotides may additionally include functional sequences, such as primer sequences, attachment sequences or the like.

In the methods described herein, in some instances, the cell is bound to at least one labelling agent. In some instances, the labelling agent may comprise at least two of the same labelling agent. In some instances, the labelling agent may comprise at least two different labelling agents. In some instances, the cell may be bound to at least about 5 different labelling agents, at least about 10 different labelling agents, at least about 50 different labelling agents, at least about 100 different labelling agents, at least about 500 different labelling agents, at least about 1,000 different labelling agents, at least about 5,000 different labelling agents, at least about 10,000 different labelling agents, or at least about 50,000 different labelling agents. In some instances, the cell may be bound to between about 2 and 5 different labelling agents, between about 5 and 10 different labelling agents, between about 10 and 100 different labelling agents, between about 100 and 500 different labelling agents, between about 500 and 1,000 different labelling agents, between about 1,000 and 5,000 different labelling agents, between about 5,000 and 10,000 different labelling agents, between about 10,000 and 50,000 different labelling agents, or between about 2 and 50,000 different labelling agents, or any range in-between. In some instances, operation 2030 of method 2000 may comprise determining an identity of at least a subset of the different labelling agents.

The barcoded reporter oligonucleotides may then subjected to sequence analysis to identify which reporter oligonucleotides were bound to the cells (i.e., cell surface features) within the partitions. Further, by also sequencing the associated barcode sequence, one can identify that a given cell surface feature likely came from the same cell as other, different cell surface features, whose reporter sequences include the same barcode sequence, i.e., they were derived from the same partition.

In some embodiments, capture oligonucleotides within the partition may interact with the reporter oligonucleotides coupled to labelling agents bound to cell surface features and lead to the synthesizing of a nucleic acid molecule as described herein, where the synthesized nucleic acid molecule may comprise at least a portion of the nucleic acid barcode sequence(s), or complement(s) thereof, that comprise the reporter oligonucleotide, or the capture oligonucleotide, or both. These synthesized nucleic acid molecules may then be subjected to amplification and sequencing, as described herein.

In some embodiments, more than one labelling agent may be bound to a single cell surface feature, and proximity between the labelling agents may allow the 3' ends of the reporter oligonucleotides coupled thereto to hybridize (wherein this hybridization is discouraged by the melting temperature when unbound in solution). By an extension reaction as described herein, a nucleic acid molecule may be synthesized, amplified, and subjected to sequencing, as described herein.

Based upon the reporter oligonucleotides that emanate from an individual partition based upon the presence of the barcode sequence, one may then create a cell surface feature profile of individual cells from a population of cells. Profiles of individual cells or populations of cells may be compared to profiles from other cells, e.g., 'normal' cells, to identify variations in cell surface features, which may provide diagnostically relevant information. In particular, these profiles may be particularly useful in the diagnosis of a variety of disorders that are characterized by variations in cell surface receptors, such as cancer and other disorders.

In some examples, the cell surface features to be analyzed may be posttranslational modification states of one or more cell surface proteins. In this case, labelling agents may be specific for cell surface proteins based on a given state of posttranslational modification (e.g., phosphorylation, glycosylation, ubiquitination, nitrosylation, methylation, acetylation or lipidation), such that a cell surface feature profile may comprise posttranslational modification information of one or more proteins.

Figure 21:
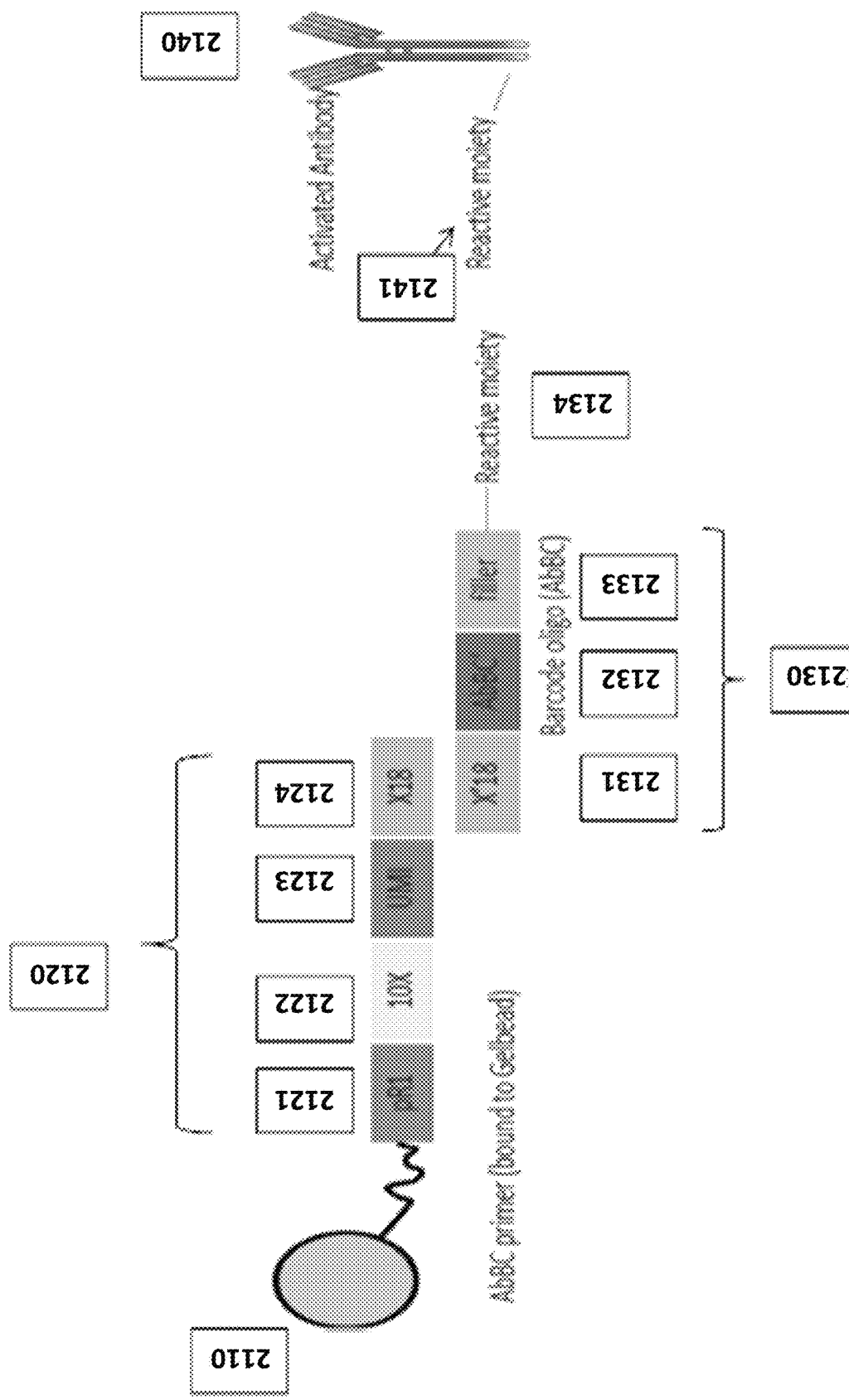
FIG. 21 shows an antibody-reporter oligonucleotide conjugation.

FIG. 21 shows example reagents used in the methods. A capture oligonucleotide 2120 is coupled to a bead 2110. The capture oligonucleotide comprises a barcode sequence 2122 and a UMI 2123. The capture oligonucleotide also comprises an oligonucleotide sequence 2124 that allows binding to the labelling agent 2130. The labelling agent 2130 comprises an oligonucleotide 2131 for binding to the capture oligonucleotide. The labelling agent 2130 also comprises a barcode 2132 that allows identifying the antibody it is coupled to. The labelling agent 2130 further comprises a reactive moiety 2134 that allows the labelling agent to couple with an antibody 2140.

Figure 22:
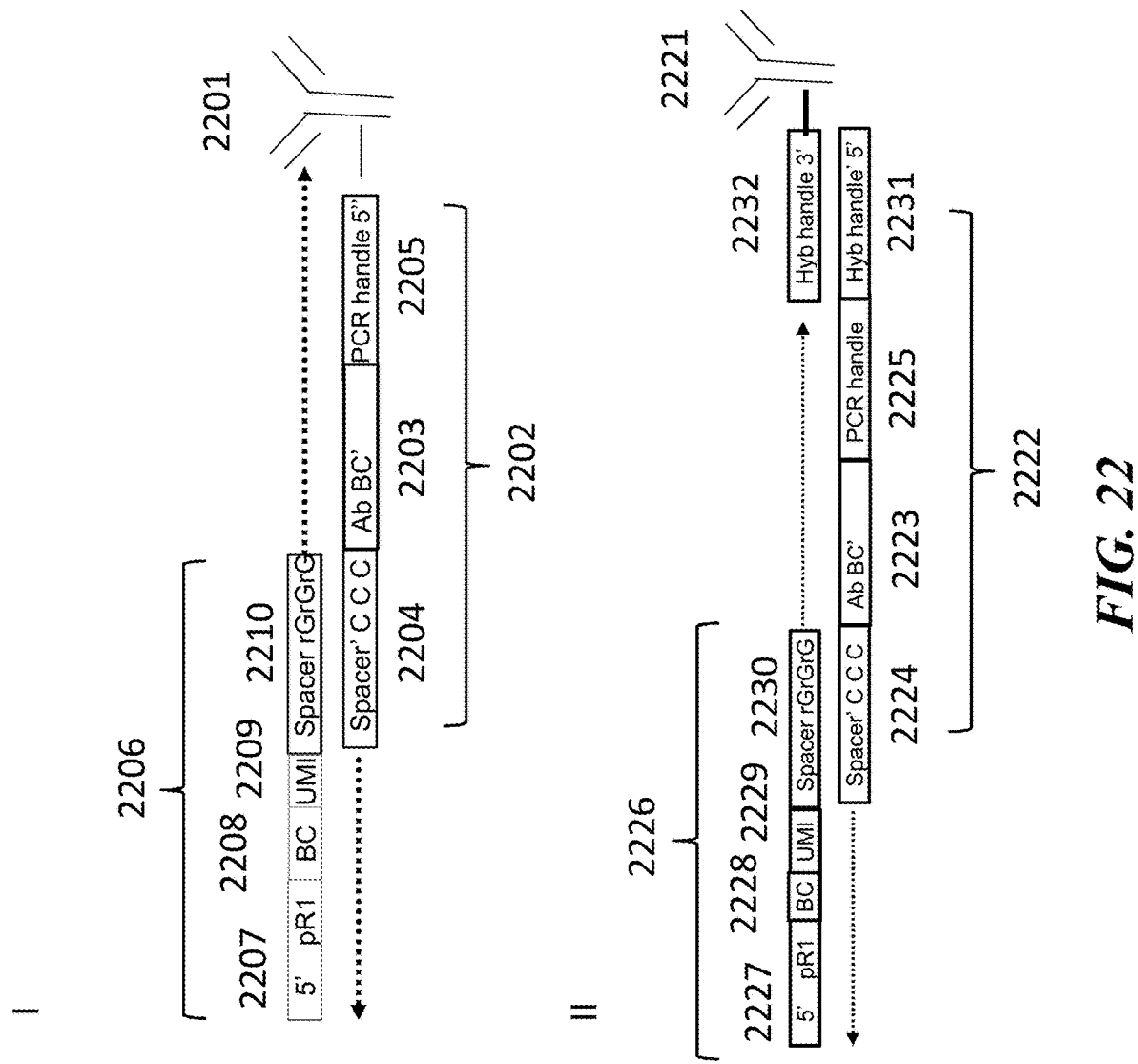
FIG. 22 schematically depicts example extension schemes to link barcodes.

An additional example of reagents and schemes suitable for analysis of barcoded labelling agents is shown in panels I and II of FIG. 22. As shown in FIG. 22 (panel I), a labelling agent (e.g., antibody, an MHC moiety) 2201 is directly (e.g., covalently bound, bound via a protein-protein interaction, such as with Protein G) coupled to an oligonucleotide 2202 comprising a barcode sequence 2203 that identifies the label agent 2201. Oligonucleotide 2202 also includes additional sequences (sequence 2204 comprising a reverse complement of a template switch oligo and sequence 2205 comprising a PCR handle) suitable for downstream reactions. FIG. 22 (panel I) also shows an additional oligonucleotide 2206 (e.g., which may have been released from a bead as described elsewhere herein) comprising a barcode sequence 2208, a UMI sequence 2209 and additional sequences (sequence 2207 comprising a sequencing read primer binding site 'pR1' and sequence 2210 comprising a template switch oligo) suitable for downstream reactions. During analysis, the labelling agent is bound to its target cell surface feature and the rGrGrG sequence of sequence 2210 hybridizes with sequence 2204 and both oligonucleotides 2202 and 2206 are extended via the action of a polymerizing enzyme (e.g., a reverse transcriptase, a polymerase), where oligonucleotide 2206 then comprises complement sequences to oligonucleotide 2202 at its 3' end. These constructs can then be optionally processed as described elsewhere herein and subject to sequencing to, for example, identify the target cell surface feature (via the complementary barcode sequence generated from oligonucleotide 2202) and associate it with the cell, identified by the barcode sequence of oligonucleotide 2206.

In another example, shown in FIG. 22 (panel II), a labelling agent (e.g., antibody) 2221 is indirectly (e.g., via hybridization) coupled to an oligonucleotide 2222 comprising a barcode sequence 2223 that identifies the label agent 2221. Labelling agent 2221 is directly (e.g., covalently bound, bound via a protein-protein interaction, such as with Protein G) coupled to a hybridization oligonucleotide 2232 that hybridizes with sequence 2231 of oligonucleotide 2222. Hybridization of oligonucleotide 2232 to oligonucleotide 2231 couples label agent 2221 to oligonucleotide 2222. Oligonucleotide 2222 also includes additional sequences (sequence 2224 comprising a reverse complement of a template switch oligo and sequence 2225 comprising a PCR handle) suitable for downstream reactions. FIG. 22 (panel II) also shows an additional oligonucleotide 2226 (e.g., which may have been released from a bead as described elsewhere herein) comprising a barcode sequence 2228, a UMI sequence 2229 and additional sequences (sequence 2227 comprising a sequencing read primer binding site 'pR1' and sequence 2220 comprising a template switch oligo) suitable for downstream reactions. During analysis, the labelling agent is bound to its target cell surface feature and the rGrGrG sequence of sequence 2220 hybridizes with sequence 2224 and both oligonucleotides 2222 and 2226 are extended via the action of a polymerizing enzyme (e.g., a reverse transcriptase, a polymerase), where oligonucleotide 2226 then comprises complement sequences to oligonucleotide 2222 at its 3' end. These constructs can then be optionally processed as described elsewhere herein and subject to sequencing to, for example, identify the target cell surface feature (via the complementary barcode sequence generated from oligonucleotide 2222) and associate it with the cell, identified by the barcode sequence of oligonucleotide 2226.

Characterization, Analysis, and Detection of RNA Molecules

Disclosed herein, in some embodiments, are compositions, methods, and systems useful in the analysis of multiple analytes in a single cell or cell population. Examples of analytes include, without limitation, DNA (e.g., genomic DNA), epigenetic information (e.g., accessible chromatin or DNA methylation), RNA (e.g., mRNA or CRISPR guide RNAs), synthetic oligonucleotides (e.g., DNA transgenes), and proteins (e.g., intracellular proteins, cell surface proteins, extracellular matrix proteins, or nuclear membrane proteins). Examples of intracellular protein analytes include, but are not limited to, transcription factors, histone proteins, kinases, phosphatases, cytoskeletal proteins (e.g., actin, tubulin), polymerases, nucleases, and ribosomal proteins. An analyte may be a cell or one or more constituents of a cell. In some embodiments, an RNA molecule (e.g., mRNA or miRNA) is one of the analytes characterized by the compositions, methods, and systems disclosed herein.

The single cell analysis methods described herein may also be useful in the analysis of gene expression, both in terms of identification of RNA transcripts and their quantitation. In particular, using the single cell level analysis methods described herein, one can isolate and analyze the RNA transcripts present in individual cells, populations of cells, or subsets of populations of cells. In particular, in some cases, the barcode oligonucleotides may be configured to prime, replicate and consequently yield barcoded fragments of RNA from individual cells. For example, in some cases, the barcode oligonucleotides may include mRNA specific priming sequences, e.g., poly-T primer segments that allow priming and replication of mRNA in a reverse transcription reaction or other targeted priming sequences. Alternatively or additionally, random RNA priming may be carried out using random N-mer primer segments of the barcode oligonucleotides.

A capture oligonucleotide (e.g., a primer for RNA-seq applications) may be a target-specific primer. A target-specific primer may bind to a specific sequence in a RNA molecule or a DNA molecule (e.g., complementary DNA (cDNA) from RNA, or endogenous DNA from a cell). For example, the target-specific sequence may be a sequence that is not in the poly-A tail of an RNA molecule or its cDNA. In some cases, the target-specific primer may bind to RNA molecules such as mRNA molecules or non-coding RNA molecules, e.g., rRNA, tRNA, siRNA, piRNA, snoRNA, snRNA, exRNA or miRNA molecules. In some cases, the target-specific primer may bind to RNA molecules introduced to a cell. In some cases, the RNA molecules introduced to a cell may be RNA molecules (or RNA molecules introduced into a cell through one or more DNA constructs) used in gene editing methods (e.g., CRISPR RNA (crRNA) or single guide RNA (sgRNA), TALEN, zinc finger nuclease, or antisense oligonucleotide). For example, the target-specific primer may bind to crRNA or sgRNA for identifying the crRNA/sgRNA introduced to a cell and/or determining the effect of the crRNA/sgRNA on the transcriptome of the cell. In some cases, the target-specific primer may be used to determine copy numbers of disease (e.g., cancer)-related genes while simultaneously analyzing the rest of the transcriptome. In other cases, the target-specific primer may be used to analyze RNA molecules from pathogens infecting the cell, e.g., for distinguishing pathogen infected cells from non-pathogen infected cells and/or determining how the pathogen alters the cells transcriptome. In some cases, a target-specific primer may bind to DNA molecules, e.g., endogenous DNA molecules from a cell, or synthetic DNA molecules. For example, in some instances, a target-specific primer may bind to a barcode, e.g., a barcode of a cell (e.g., inside a cell or on the surface of a cell), a barcode of a protein (e.g., an antibody barcode), or a barcode of a nucleic acid (e.g., a CRISPR barcode).

Figures 23A, 23B:
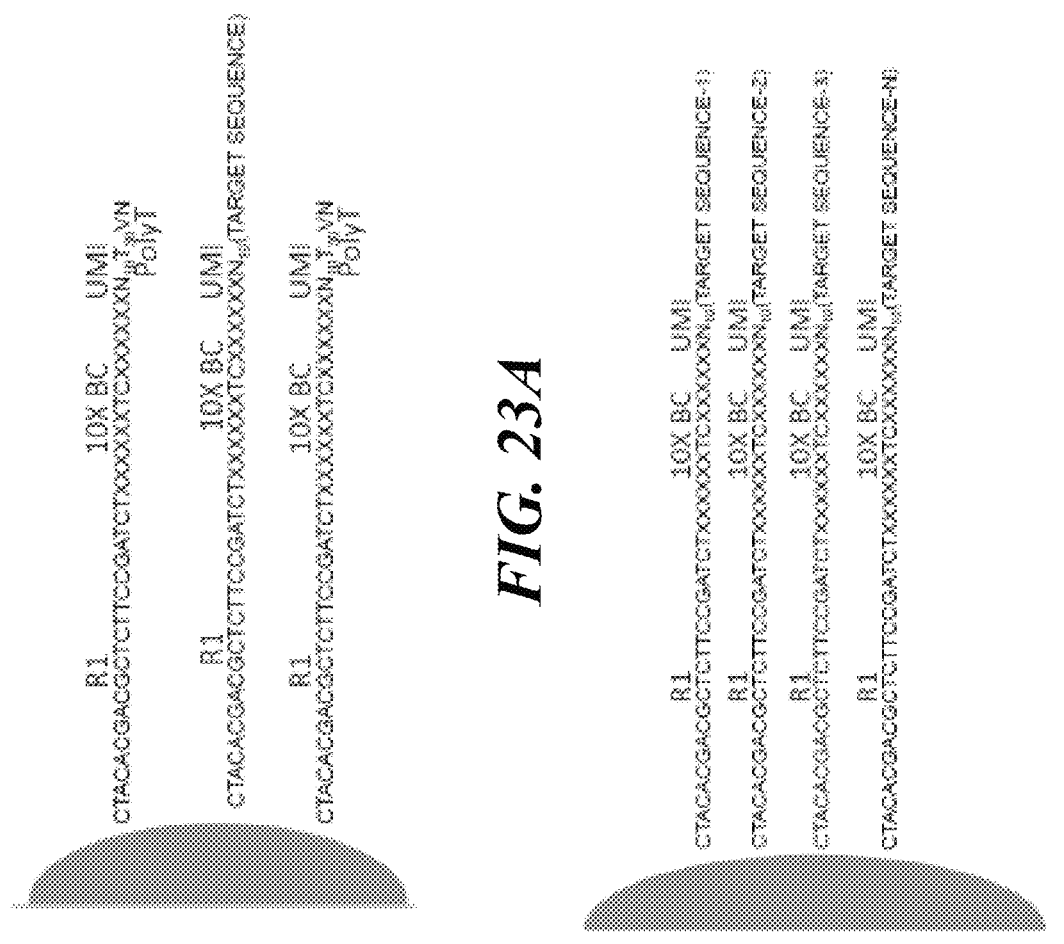
Figures 23C, 23D:
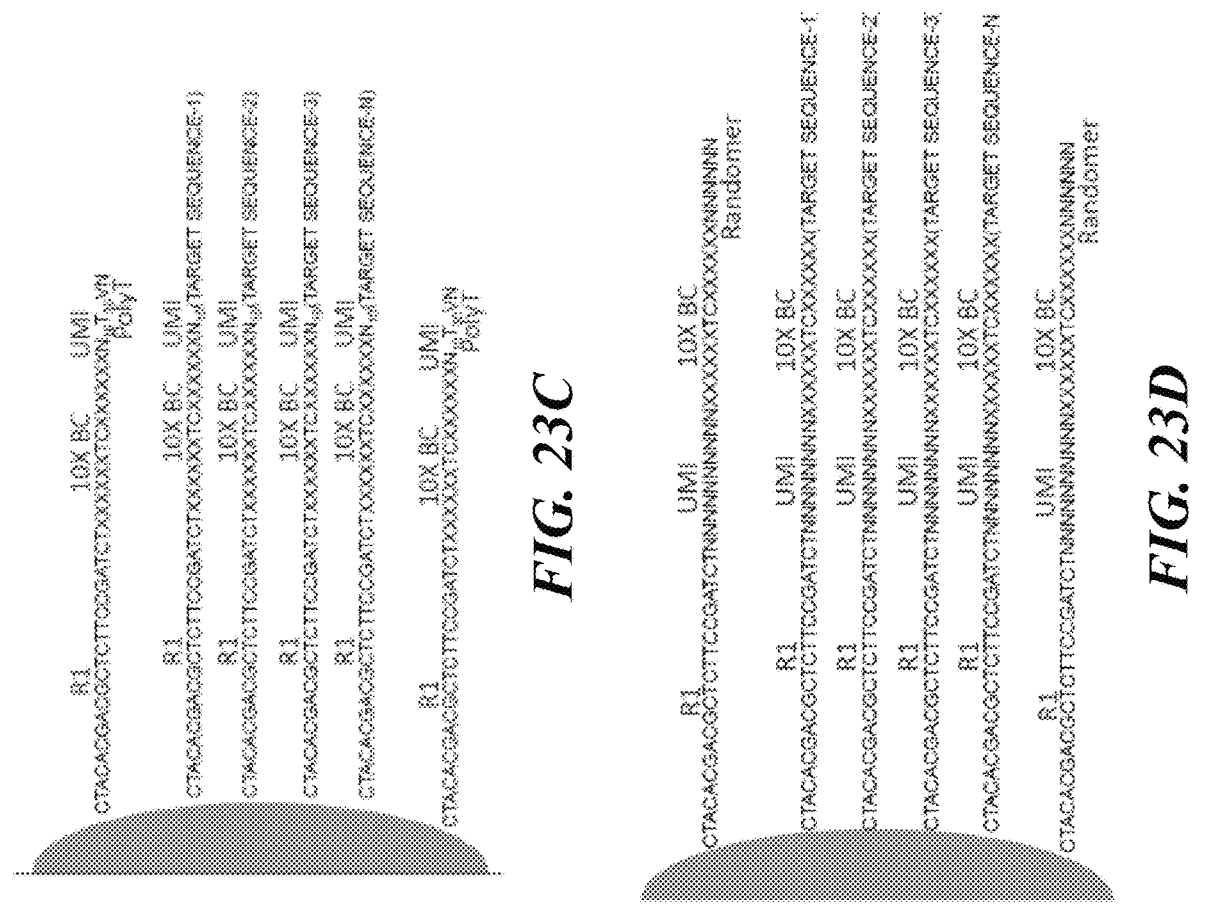

A target-specific primer may be combined with one or more barcodes, one or more UMIs, one or more poly-T primers for mRNA, and/or one or more random N-mer primers (randomers) for total RNA in the same or different oligonucleotides. In some cases, a bead disclosed herein may comprise an oligonucleotide with a target-specific primer and one or more oligonucleotides with a poly-T primer, e.g., as shown in FIG. 23A. In some cases, a bead may have a plurality of oligonucleotides, each of which comprises a target-specific primer, e.g., as shown in FIG. 23B. In some cases, a bead may have a plurality of oligonucleotides, each of which comprises a target-specific primer and a plurality of oligonucleotides, each of which comprises a poly-T primer, e.g., as shown in FIG. 23C. In some cases, a bead may have a plurality of oligonucleotides, each of which comprises a target-specific primer and a plurality of oligonucleotides, each of which comprises a random N-mer primer for total RNA, e.g., as shown in FIG. 23D.

On a bead, the ratio of oligonucleotides with target-specific primers (including capture sequences capable of coupling to labelling agent oligonucleotides) to oligonucleotides with non-specific primers (e.g., poly-T or random N-mer) may be adjusted to match the needs of a specific application. In some cases, at least 0.1%, 1%, 5%, 10%, 20%, 30%, 40%, 50%, 60%, 70%, 80%, 90%, 95%, 99%, or 100% of the oligonucleotides on a bead may comprise target-specific primers. In some cases, at least 0.1%, 1%, 5%, 10%, 20%, 30%, 40%, 50%, 60%, 70%, 80%, 90%, 95%, 99%, or 100% of the oligonucleotides on a bead may comprise non-specific (e.g., poly-T or random N-mer) primers. The oligonucleotide may be made by attaching (e.g., by ligation) one or more oligonucleotide backbones on a bead and then attaching (e.g., by ligation) one or more primer sequences to the backbones.

Figure 24A:
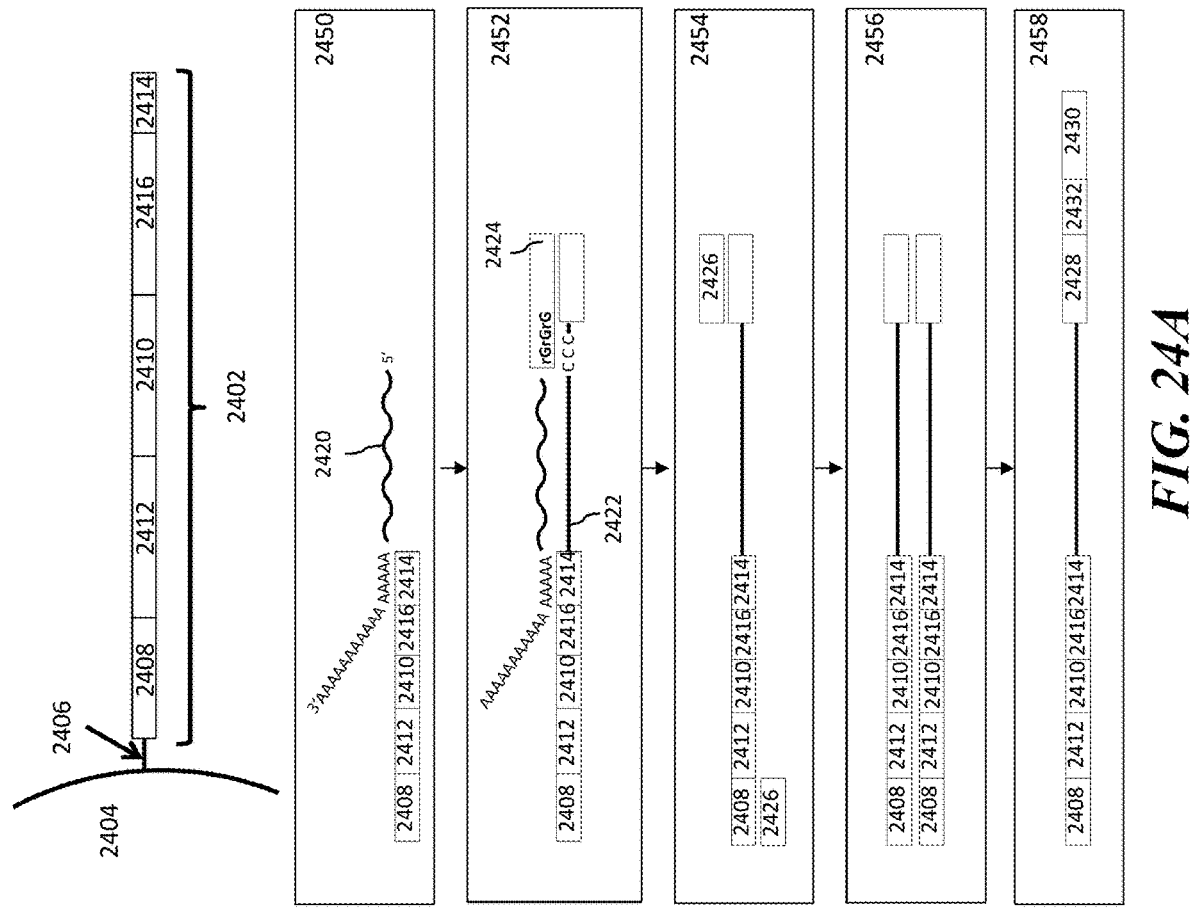
FIGS. 24A-E provide schematic illustrations of example barcoded oligonucleotide structures for use in analysis of RNA and example operations for performing RNA analysis.

An additional example of a barcode oligonucleotide for use in RNA analysis, including messenger RNA (mRNA, including mRNA obtained from a cell) analysis, is shown in FIG. 24A. As shown, the overall oligonucleotide 2402 can be coupled to a bead 2404 by a releasable linkage 2406, such as a disulfide linker. The oligonucleotide may include functional sequences that are used in subsequent processing, such as functional sequence 2408, which may include a sequencer specific flow cell attachment sequence, e.g., a P5 sequence for Illumina sequencing systems, as well as functional sequence 2410, which may include sequencing primer sequences, e.g., a R1 primer binding site for Illumina sequencing systems. A barcode sequence 2412 is included within the structure for use in barcoding the sample RNA. An RNA specific (e.g., mRNA specific) priming sequence, such as poly-T sequence 2414 is also included in the oligonucleotide structure. An anchoring sequence segment (not shown) may be included to ensure that the poly-T sequence hybridizes at the sequence end of the mRNA. An additional sequence segment 2416 may be provided within the oligonucleotide sequence. This additional sequence can provide a unique molecular identifier (UMI) sequence segment, e.g., as a random N-mer sequence that varies across individual oligonucleotides coupled to a single bead, whereas barcode sequence 2412 can be constant among oligonucleotides tethered to an individual bead. As described elsewhere herein, this unique sequence can serve to provide a unique identifier of the starting mRNA molecule that was captured, in order to allow quantitation of the number of original expressed RNA, e.g., mRNA counting. As will be appreciated, although shown as a single oligonucleotide tethered to the surface of a bead, individual beads can include tens to hundreds of thousands or millions of individual oligonucleotide molecules (e.g., at least about 10,000, 50,000, 100,000, 500,000, 1,000,000 or 10,000,000 oligonucleotide molecules), where the barcode segment can be constant or relatively constant for a given bead, but where the variable or unique sequence segment will vary across an individual bead.

In an example method of cellular RNA (e.g., mRNA) analysis and in reference to FIG. 24A, a cell is co-partitioned along with a barcode bearing bead, switch oligo 2424, and other reagents such as reverse transcriptase, a reducing agent and dNTPs into a partition (e.g., a droplet in an emulsion). In operation 2450, the cell is lysed while the barcoded oligonucleotides 2402 are released from the bead (e.g., via the action of the reducing agent) and the poly-T segment 2414 of the released barcode oligonucleotide then hybridizes to the poly-A tail of mRNA 2420 that is released from the cell. Next, in operation 2452 the poly-T segment 2414 is extended in a reverse transcription reaction using the mRNA as a template to produce a cDNA 2422 complementary to the mRNA and also includes each of the sequence segments 2408, 2412, 2410, 2416 and 2414 of the barcode oligonucleotide. Terminal transferase activity of the reverse transcriptase can add additional bases to the cDNA (e.g., polyC). The switch oligo 2424 may then hybridize with the additional bases added to the cDNA and facilitate template switching. A sequence complementary to the switch oligo sequence can then be incorporated into the cDNA 2422 via extension of the cDNA 2422 using the switch oligo 2424 as a template. Within any given partition, all of the cDNAs of the individual mRNA molecules will include a common barcode sequence segment 2412. However, by including the unique random N-mer sequence 2416, the transcripts made from different mRNA molecules within a given partition will vary at this unique sequence. As described elsewhere herein, this provides a quantitation feature that can be identifiable even following any subsequent amplification of the contents of a given partition, e.g., the number of unique segments associated with a common barcode can be indicative of the quantity of mRNA originating from a single partition, and thus, a single cell. Following operation 2452, the cDNA 2422 is then amplified with primers 2426 (e.g., PCR primers) in operation 2454. Next, the amplified product is then purified (e.g., via solid phase reversible immobilization (SPRI)) in operation 2456. At operation 2458, the amplified product is then sheared, ligated to additional functional sequences, and further amplified (e.g., via PCR). The functional sequences may include a sequencer specific flow cell attachment sequence 2430, e.g., a P7 sequence for Illumina sequencing systems, as well as functional sequence 2428, which may include a sequencing primer binding site, e.g., for a R2 primer for Illumina sequencing systems, as well as functional sequence 2432, which may include a sample index, e.g., an i7 sample index sequence for Illumina sequencing systems. In some cases, operations 2450 and 2452 can occur in the partition, while operations 2454, 2456 and 2458 can occur in bulk solution (e.g., in a pooled mixture outside of the partition). In the case where a partition is a droplet in an emulsion, the emulsion can be broken and the contents of the droplet pooled in order to complete operations 2454, 2456 and 2458. In some cases, operation 2454 may be completed in the partition. In some cases, barcode oligonucleotides may be digested with exonucleases after the emulsion is broken. Exonuclease activity can be inhibited by ethylenediaminetetraacetic acid (EDTA) following primer digestion. Although described in terms of specific sequence references used for certain sequencing systems, e.g., Illumina systems, it will be understood that the reference to these sequences is for illustration purposes only, and the methods described herein may be configured for use with other sequencing systems incorporating specific priming, attachment, index, and other operational sequences used in those systems, e.g., systems available from Ion Torrent, Oxford Nanopore, Genia, Pacific Biosciences, Complete Genomics, and the like.

In an alternative example of a barcode oligonucleotide for use in RNA (e.g., cellular RNA) analysis as shown in FIG. 24A, functional sequence 2408 may be a P7 sequence and functional sequence 2410 may be a R2 primer binding site. Moreover, the functional sequence 2430 may be a P5 sequence, functional sequence 2428 may be a R1 primer binding site, and functional sequence 2432 may be an i5 sample index sequence for Illumina sequencing systems. The configuration of the constructs generated by such a barcode oligonucleotide can help minimize (or avoid) sequencing of the poly-T sequence during sequencing.

Figure 24B:
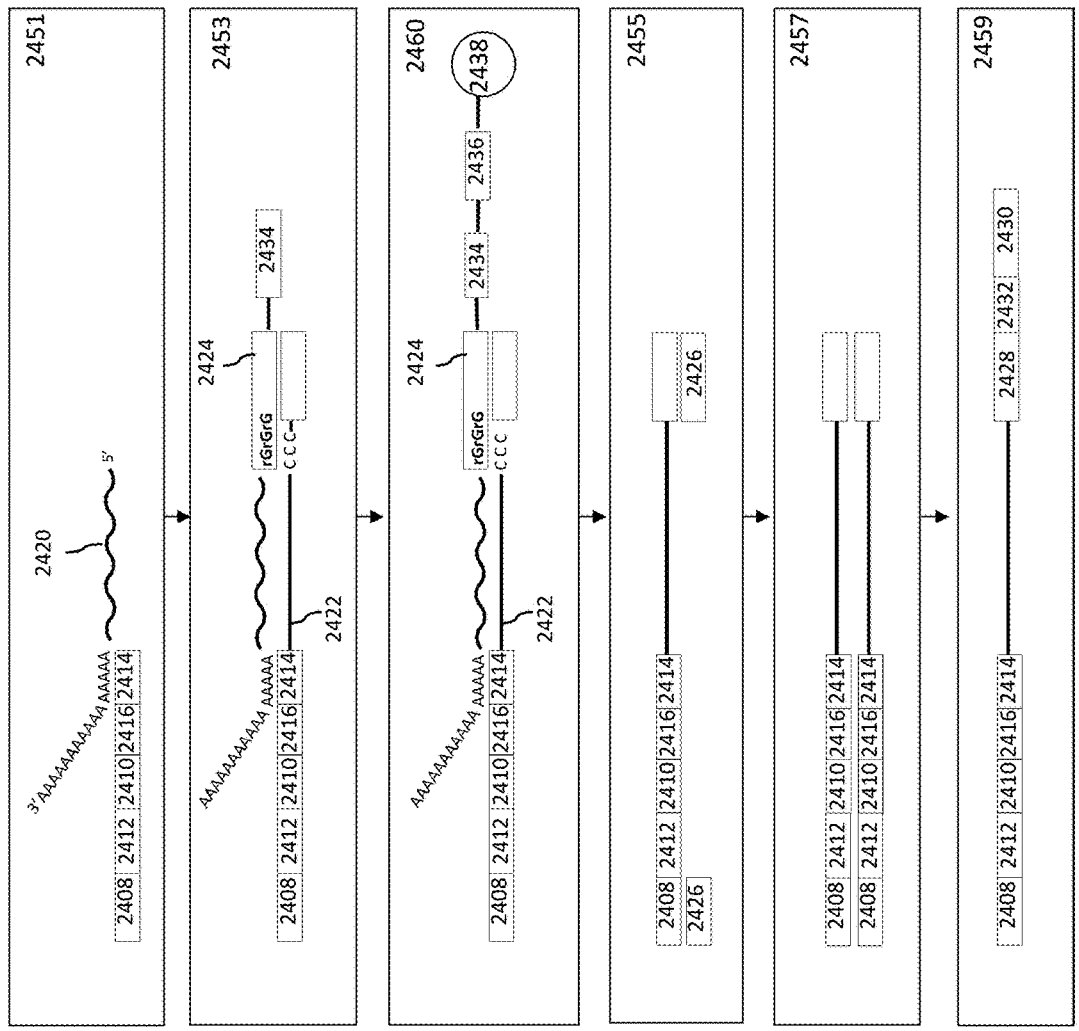

Shown in FIG. 24B is another example method for RNA analysis, including cellular mRNA analysis. In this method, the switch oligo 2424 is co-partitioned with the individual cell and barcoded bead along with reagents such as reverse transcriptase, a reducing agent and dNTPs into a partition (e.g., a droplet in an emulsion). The switch oligo 2424 may be labeled with an additional tag 2434, e.g., biotin. In operation 2451, the cell is lysed while the barcoded oligonucleotides 2402 (e.g., as shown in FIG. 24A) are released from the bead (e.g., via the action of the reducing agent). In some cases, sequence 2408 is a P7 sequence and sequence 2410 is a R2 primer binding site. In other cases, sequence 2408 is a P5 sequence and sequence 2410 is a R1 primer binding site. Next, the poly-T segment 2414 of the released barcode oligonucleotide hybridizes to the poly-A tail of mRNA 2420 that is released from the cell. In operation 2453, the poly-T segment 2414 is then extended in a reverse transcription reaction using the mRNA as a template to produce a cDNA 2422 complementary to the mRNA and also includes each of the sequence segments 2408, 2412, 2410, 2416 and 2414 of the barcode oligonucleotide. Terminal transferase activity of the reverse transcriptase can add additional bases to the cDNA (e.g., polyC). The switch oligo 2424 may then hybridize with the cDNA and facilitate template switching. A sequence complementary to the switch oligo sequence can then be incorporated into the cDNA 2422 via extension of the cDNA 2422 using the switch oligo 2424 as a template. Next, an isolation operation 2460 can be used to isolate the cDNA 2422 from the reagents and oligonucleotides in the partition. The additional tag 2434, e.g., biotin, can be contacted with an interacting tag 2436, e.g., streptavidin, which may be attached to a magnetic bead 2438. At operation 2460 the cDNA can be isolated with a pull-down operation (e.g., via magnetic separation, centrifugation) before amplification (e.g., via PCR) in operation 2455, followed by purification (e.g., via solid phase reversible immobilization (SPRI)) in operation 2457 and further processing (shearing, ligation of sequences 2428, 2432 and 2430 and subsequent amplification (e.g., via PCR)) in operation 2459. In some cases where sequence 2408 is a P7 sequence and sequence 2410 is a R2 primer binding site, sequence 2430 is a P5 sequence and sequence 2428 is a R1 primer binding site and sequence 2432 is an i5 sample index sequence. In some cases where sequence 2408 is a P5 sequence and sequence 2410 is a R1 primer binding site, sequence 2430 is a P7 sequence and sequence 2428 is a R2 primer binding site and sequence 2432 is an i7 sample index sequence. In some cases, as shown, operations 2451 and 2453 can occur in the partition, while operations 2460, 2455, 2457 and 2459 can occur in bulk solution (e.g., in a pooled mixture outside of the partition). In the case where a partition is a droplet in an emulsion, the emulsion can be broken and the contents of the droplet pooled in order to complete operation 2460. The operations 2455, 2457, and 2459 can then be carried out following operation 2460 after the transcripts are pooled for processing.

Figure 24C:
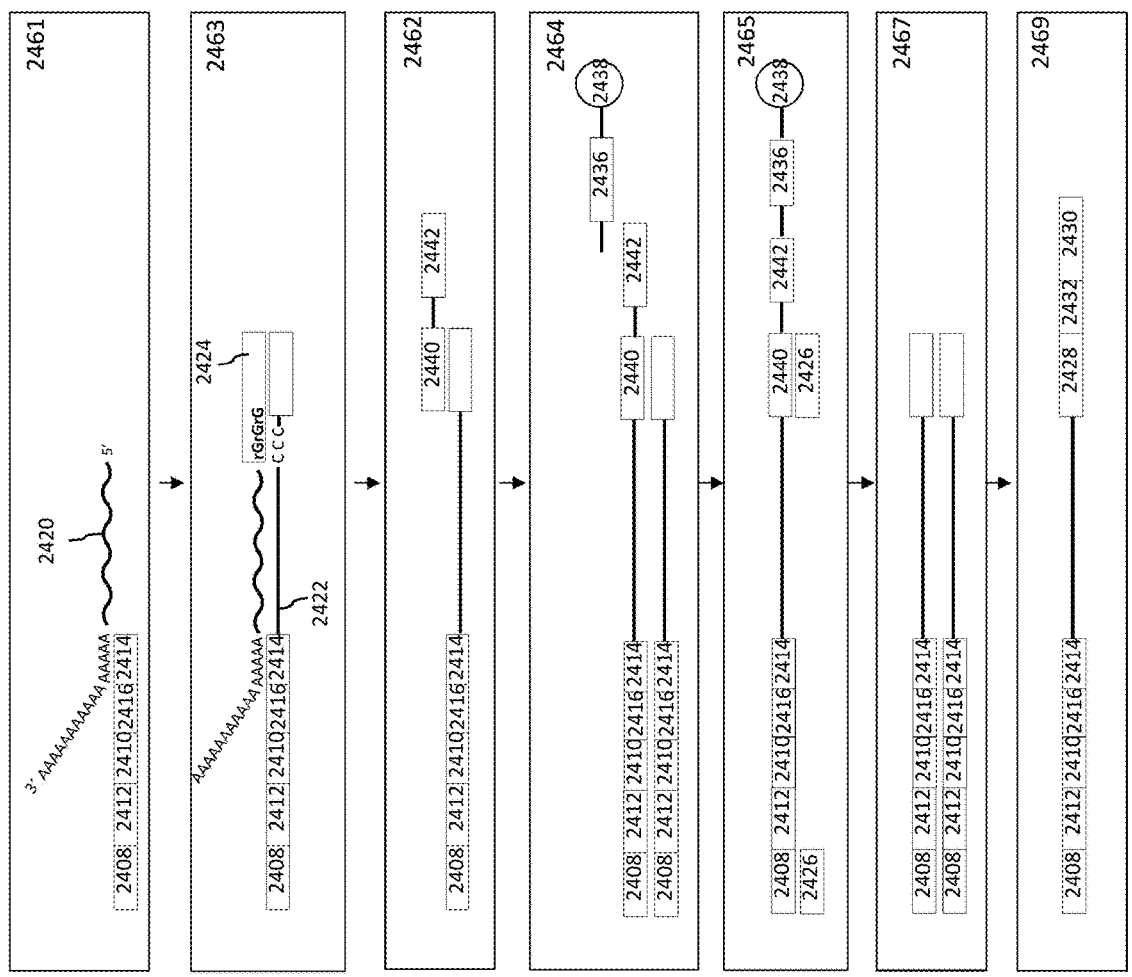

Shown in FIG. 24C is another example method for RNA analysis, including cellular mRNA analysis. In this method, the switch oligo 2424 is co-partitioned with the individual cell and barcoded bead along with reagents such as reverse transcriptase, a reducing agent and dNTPs in a partition (e.g., a droplet in an emulsion). In operation 2461, the cell is lysed while the barcoded oligonucleotides 2402 (e.g., as shown in FIG. 24A) are released from the bead (e.g., via the action of the reducing agent). In some cases, sequence 2408 is a P7 sequence and sequence 2410 is a R2 primer binding site. In other cases, sequence 2408 is a P5 sequence and sequence 2410 is a R1 primer binding site. Next, the poly-T segment 2414 of the released barcode oligonucleotide then hybridizes to the poly-A tail of mRNA 2420 that is released from the cell. Next, in operation 2463 the poly-T segment 2414 is then extended in a reverse transcription reaction using the mRNA as a template to produce a cDNA 2422 complementary to the mRNA and also includes each of the sequence segments 2408, 2412, 2410, 2416 and 2414 of the barcode oligonucleotide. Terminal transferase activity of the reverse transcriptase can add additional bases to the cDNA (e.g., polyC). The switch oligo 2424 may then hybridize with the cDNA and facilitate template switching. A sequence complementary to the switch oligo sequence can then be incorporated into the cDNA 2422 via extension of the cDNA 2422 using the switch oligo 2424 as a template. Following operation 2461 and operation 2463, mRNA 2420 and cDNA 2422 are denatured in operation 2462. At operation 2464, a second strand is extended from a primer 2440 having an additional tag 2442, e.g., biotin, and hybridized to the cDNA 2422. Also in operation 2464, the biotin labeled second strand can be contacted with an interacting tag 2436, e.g., streptavidin, which may be attached to a magnetic bead 2438. The cDNA can be isolated with a pull-down operation (e.g., via magnetic separation, centrifugation) before amplification (e.g., via polymerase chain reaction (PCR)) in operation 2465, followed by purification (e.g., via solid phase reversible immobilization (SPRI)) in operation 2467 and further processing (shearing, ligation of sequences 2428, 2432 and 2430 and subsequent amplification (e.g., via PCR)) in operation 2469. In some cases where sequence 2408 is a P7 sequence and sequence 2410 is a R2 primer binding site, sequence 2430 is a P5 sequence and sequence 2428 is a R1 primer binding site and sequence 2432 is an i5 sample index sequence. In some cases where sequence 2408 is a P5 sequence and sequence 2410 is a R1 primer binding site, sequence 2430 is a P7 sequence and sequence 2428 is a R2 primer binding site and sequence 2432 is an i7 sample index sequence. In some cases, operations 2461 and 2463 can occur in the partition, while operations 2462, 2464, 2465, 2467, and 2469 can occur in bulk (e.g., outside the partition). In the case where a partition is a droplet in an emulsion, the emulsion can be broken and the contents of the droplet pooled in order to complete operations 2462, 2464, 2465, 2467 and 2469.

Figure 24D:
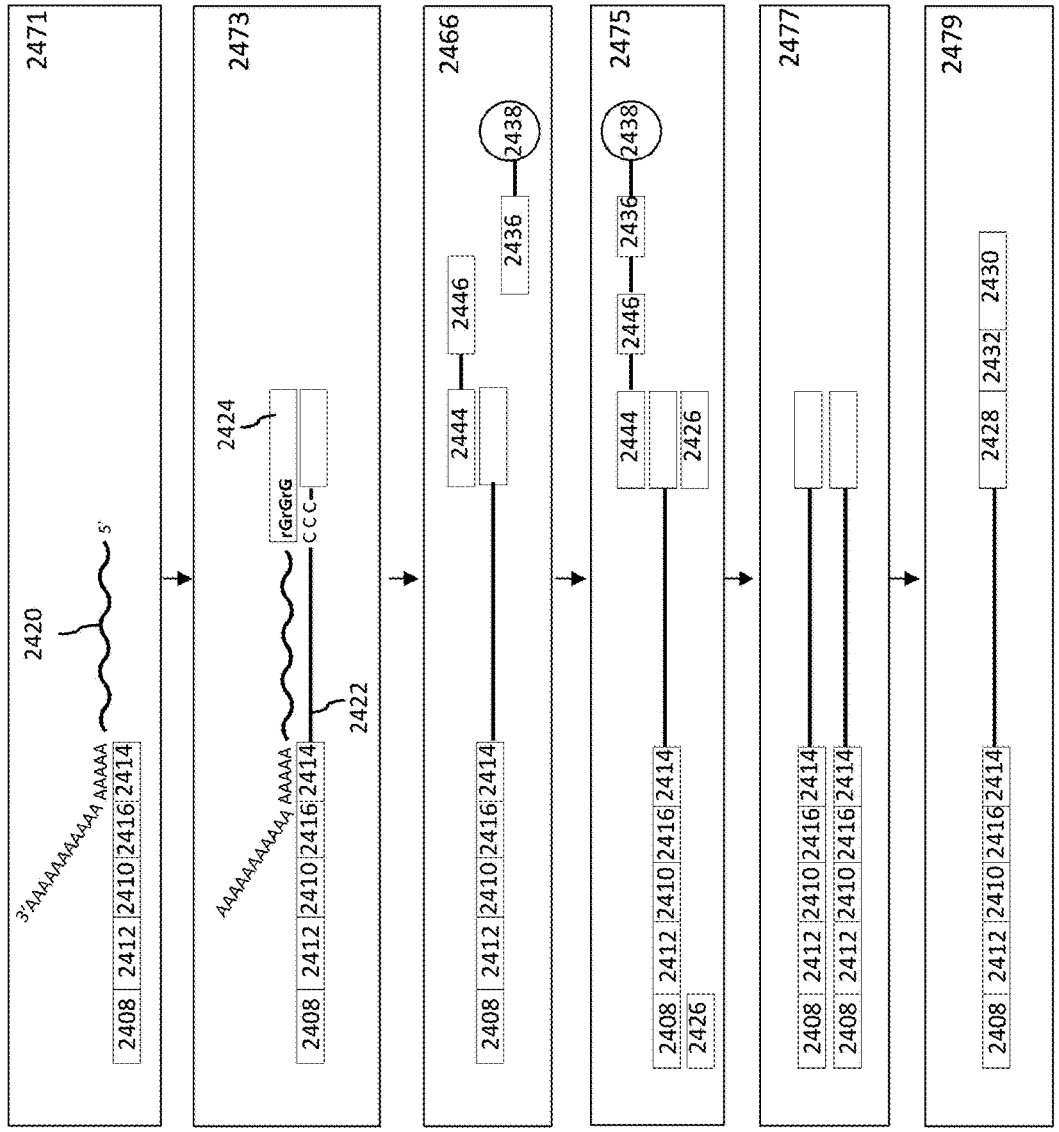

Shown in FIG. 24D is another example method for RNA analysis, including cellular mRNA analysis. In this method, the switch oligo 2424 is co-partitioned with the individual cell and barcoded bead along with reagents such as reverse transcriptase, a reducing agent and dNTPs. In operation 2471, the cell is lysed while the barcoded oligonucleotides 2402 (e.g., as shown in FIG. 24A) are released from the bead (e.g., via the action of the reducing agent). In some cases, sequence 2408 is a P7 sequence and sequence 2410 is a R2 primer binding site. In other cases, sequence 2408 is a P5 sequence and sequence 2410 is a R1 primer binding site. Next the poly-T segment 2414 of the released barcode oligonucleotide then hybridizes to the poly-A tail of mRNA 2420 that is released from the cell. Next in operation 2473, the poly-T segment 2414 is then extended in a reverse transcription reaction using the mRNA as a template to produce a cDNA 2422 complementary to the mRNA and also includes each of the sequence segments 2408, 2412, 2410, 2416 and 2414 of the barcode oligonucleotide. Terminal transferase activity of the reverse transcriptase can add additional bases to the cDNA (e.g., polyC). The switch oligo 2424 may then hybridize with the cDNA and facilitate template switching. A sequence complementary to the switch oligo sequence can then be incorporated into the cDNA 2422 via extension of the cDNA 2422 using the switch oligo 2424 as a template. In operation 2466, the mRNA 2420, cDNA 2422 and switch oligo 2424 can be denatured, and the cDNA 2422 can be hybridized with a capture oligonucleotide 2444 labeled with an additional tag 2446, e.g., biotin. In this operation, the biotin-labeled capture oligonucleotide 2444, which is hybridized to the cDNA, can be contacted with an interacting tag 2436, e.g., streptavidin, which may be attached to a magnetic bead 2438. Following separation from other species (e.g., excess barcoded oligonucleotides) using a pull-down operation (e.g., via magnetic separation, centrifugation), the cDNA can be amplified (e.g., via PCR) with primers 2426 at operation 2475, followed by purification (e.g., via solid phase reversible immobilization (SPRI)) in operation 2477 and further processing (shearing, ligation of sequences 2428, 2432 and 2430 and subsequent amplification (e.g., via PCR)) in operation 2479. In some cases where sequence 2408 is a P7 sequence and sequence 2410 is a R2 primer binding site, sequence 2430 is a P5 sequence and sequence 2428 is a R1 primer binding site and sequence 2432 is an i5 sample index sequence. In other cases where sequence 2408 is a P5 sequence and sequence 2410 is a R1 primer binding site, sequence 2430 is a P7 sequence and sequence 2428 is a R2 primer binding site and sequence 2432 is an i7 sample index sequence. In some cases, operations 2471 and 2473 can occur in the partition, while operations 2466, 2475, 2477 (purification), and 2479 can occur in bulk (e.g., outside the partition). In the case where a partition is a droplet in an emulsion, the emulsion can be broken and the contents of the droplet pooled in order to complete operations 2466, 2475, 2477 and 2479.

Figure 24E:
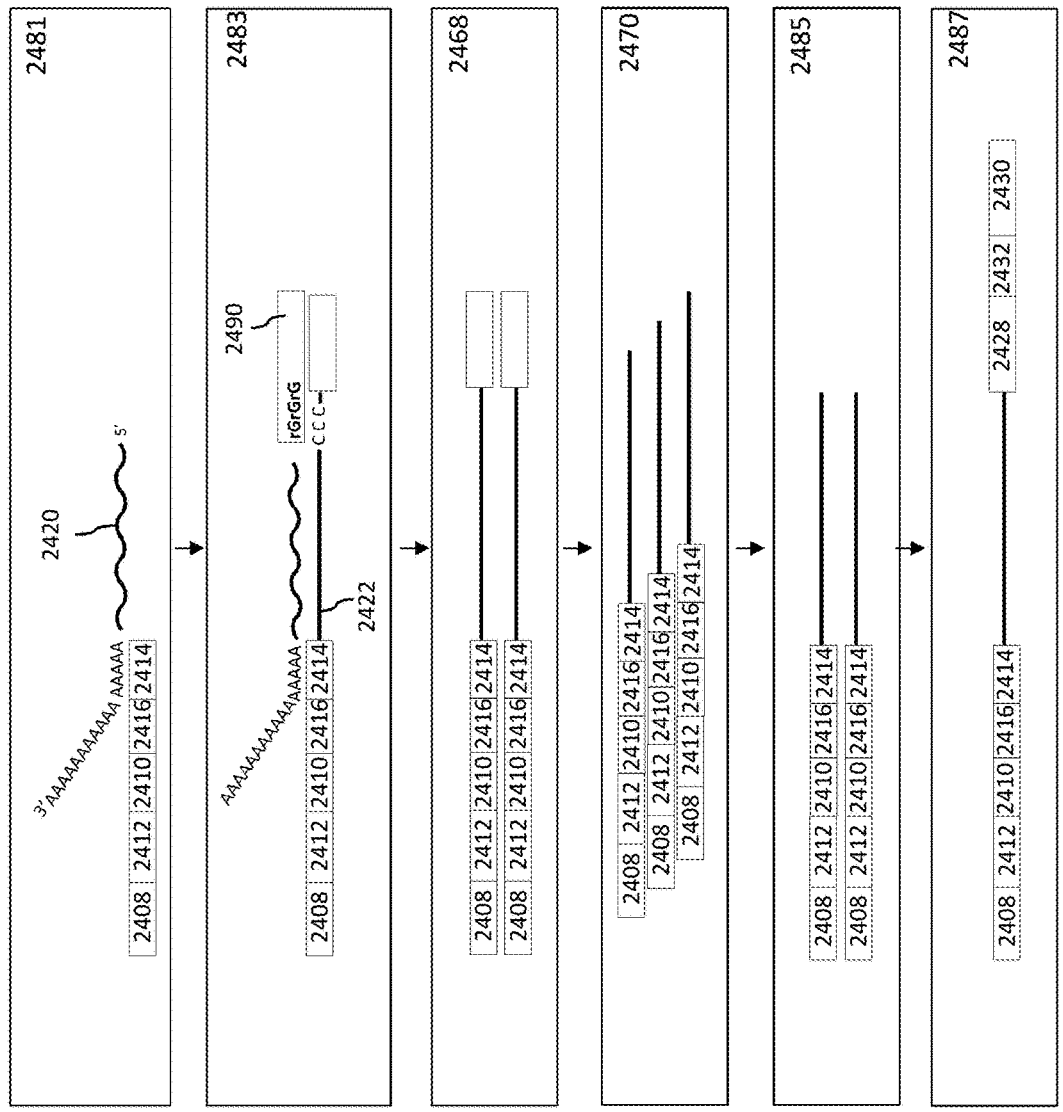

Shown in FIG. 24E is another example method for RNA analysis, including cellular RNA analysis. In this method, an individual cell is co-partitioned along with a barcode bearing bead, a switch oligo 2490, and other reagents such as reverse transcriptase, a reducing agent, and dNTPs into a partition (e.g., a droplet in an emulsion). In operation 2481, the cell is lysed while the barcoded oligonucleotides (e.g., 2402 as shown in FIG. 24A) are released from the bead (e.g., via the action of the reducing agent). In some cases, sequence 2408 is a P7 sequence and sequence 2410 is a R2 primer binding site. In other cases, sequence 2408 is a P5 sequence and sequence 2410 is a R1 primer binding site. Next, the poly-T segment of the released barcode oligonucleotide then hybridizes to the poly-A tail of mRNA 2420 released from the cell. Next at operation 2483, the poly-T segment is then extended in a reverse transcription reaction to produce a cDNA 2422 complementary to the mRNA and also includes each of the sequence segments 2408, 2412, 2410, 2416 and 2414 of the barcode oligonucleotide. Terminal transferase activity of the reverse transcriptase can add additional bases to the cDNA (e.g., polyC). The switch oligo 2490 may then hybridize with the cDNA and facilitate template switching. A sequence complementary to the switch oligo sequence and including a T7 promoter sequence, can be incorporated into the cDNA 2422. At operation 2468, a second strand is synthesized and at operation 2470 the T7 promoter sequence can be used by T7 polymerase to produce RNA transcripts in in vitro transcription. At operation 2485 the RNA transcripts can be purified (e.g., via solid phase reversible immobilization (SPRI)), reverse transcribed to form DNA transcripts, and a second strand can be synthesized for each of the DNA transcripts. In some cases, prior to purification, the RNA transcripts can be contacted with a DNase (e.g., DNAase I) to break down residual DNA. At operation 2487 the DNA transcripts are then fragmented and ligated to additional functional sequences, such as sequences 2428, 2432 and 2430 and, in some cases, further amplified (e.g., via PCR). In some cases where sequence 2408 is a P7 sequence and sequence 2410 is a R2 primer binding site, sequence 2430 is a P5 sequence and sequence 2428 is a R1 primer binding site and sequence 2432 is an i5 sample index sequence. In some cases where sequence 2408 is a P5 sequence and sequence 2410 is a R1 primer binding site, sequence 2430 is a P7 sequence and sequence 2428 is a R2 primer binding site and sequence 2432 is an i7 sample index sequence. In some cases, prior to removing a portion of the DNA transcripts, the DNA transcripts can be contacted with an RNase to break down residual RNA. In some cases, operations 2481 and 2483 can occur in the partition, while operations 2468, 2470, 2485 and 2487 can occur in bulk (e.g., outside the partition). In the case where a partition is a droplet in an emulsion, the emulsion can be broken and the contents of the droplet pooled in order to complete operations 2468, 2470, 2485 and 2487.

Figure 25:
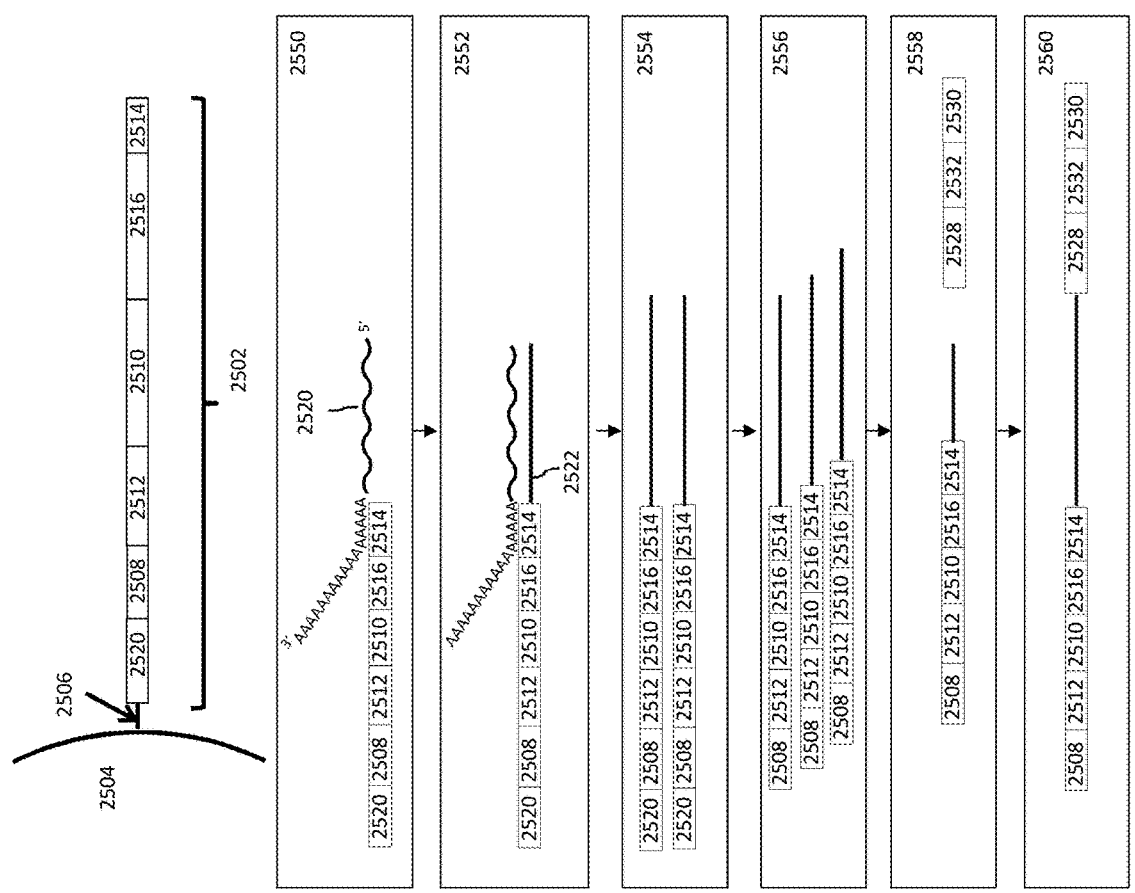
FIG. 25 provides a schematic illustration of example barcoded oligonucleotide structure for use in example analysis of RNA and use of a sequence for in vitro transcription. Figure discloses "AAAAAAAAAAAAAAAA" as SEQ ID NO: 57.

Another example of a barcode oligonucleotide for use in RNA analysis, including messenger RNA (mRNA, including mRNA obtained from a cell) analysis is shown in FIG. 25. As shown, the overall oligonucleotide 2502 is coupled to a bead 2504 by a releasable linkage 2506, such as a disulfide linker. The oligonucleotide may include functional sequences that are used in subsequent processing, such as functional sequence 2508, which may include a sequencer specific flow cell attachment sequence, e.g., a P7 sequence, as well as functional sequence 2510, which may include sequencing primer sequences, e.g., a R2 primer binding site. A barcode sequence 2512 is included within the structure for use in barcoding the sample RNA. An RNA specific (e.g., mRNA specific) priming sequence, such as poly-T sequence 2514 may be included in the oligonucleotide structure. An anchoring sequence segment (not shown) may be included to ensure that the poly-T sequence hybridizes at the sequence end of the mRNA. An additional sequence segment 2516 may be provided within the oligonucleotide sequence. This additional sequence can provide a unique molecular identifier (UMI) sequence segment, as described elsewhere herein. An additional functional sequence 2520 may be included for in vitro transcription, e.g., a T7 RNA polymerase promoter sequence. As will be appreciated, although shown as a single oligonucleotide tethered to the surface of a bead, individual beads can include tens to hundreds of thousands or millions of individual oligonucleotide molecules (e.g., at least about 10,000, 50,000, 100,000, 500,000, 1,000,000 or 10,000,000 oligonucleotide molecules), where the barcode segment can be constant or relatively constant for a given bead, but where the variable or unique sequence segment will vary across an individual bead.

In an example method of cellular RNA analysis and in reference to FIG. 25, a cell is co-partitioned along with a barcode bearing bead, and other reagents such as reverse transcriptase, reducing agent and dNTPs into a partition (e.g., a droplet in an emulsion). In operation 2550, the cell is lysed while the barcoded oligonucleotides 2502 are released (e.g., via the action of the reducing agent) from the bead, and the poly-T segment 2514 of the released barcode oligonucleotide then hybridizes to the poly-A tail of mRNA 2520. Next at operation 2552, the poly-T segment is then extended in a reverse transcription reaction using the mRNA as template to produce a cDNA 2522 of the mRNA and also includes each of the sequence segments 2520, 2508, 2512, 2510, 2516, and 2514 of the barcode oligonucleotide. Within any given partition, all of the cDNAs of the individual mRNA molecules will include a common barcode sequence segment 2512. However, by including the unique random N-mer sequence, the transcripts made from different mRNA molecules within a given partition will vary at this unique sequence. As described elsewhere herein, this provides a quantitation feature that can be identifiable even following any subsequent amplification of the contents of a given partition, e.g., the number of unique segments associated with a common barcode can be indicative of the quantity of mRNA originating from a single partition, and thus, a single cell. At operation 2554 a second strand is synthesized and at operation 2556 the T7 promoter sequence can be used by T7 polymerase to produce RNA transcripts in in vitro transcription. At operation 2558 the transcripts are fragmented (e.g., sheared), ligated to additional functional sequences, and reverse transcribed. The functional sequences may include a sequencer specific flow cell attachment sequence 2530, e.g., a P5 sequence, as well as functional sequence 2528, which may include sequencing primers, e.g., a R1 primer binding sequence, as well as functional sequence 2532, which may include a sample index, e.g., an i5 sample index sequence. At operation 2560 the RNA transcripts can be reverse transcribed to DNA, the DNA amplified (e.g., via PCR), and sequenced to identify the sequence of the cDNA of the mRNA, as well as to sequence the barcode segment and the unique sequence segment. In some cases, operations 2550 and 2552 can occur in the partition, while operations 2554, 2556, 2558 and 2560 can occur in bulk (e.g., outside the partition). In the case where a partition is a droplet in an emulsion, the emulsion can be broken and the contents of the droplet pooled in order to complete operations 2554, 2556, 2558 and 2560.

In an alternative example of a barcode oligonucleotide for use in RNA (e.g., cellular RNA) analysis as shown in FIG. 25, functional sequence 2508 may be a P5 sequence and functional sequence 2510 may be a R1 primer binding site. Moreover, the functional sequence 2530 may be a P7 sequence, functional sequence 2528 may be a R2 primer binding site, and functional sequence 2532 may be an i7 sample index sequence.

Figure 26:
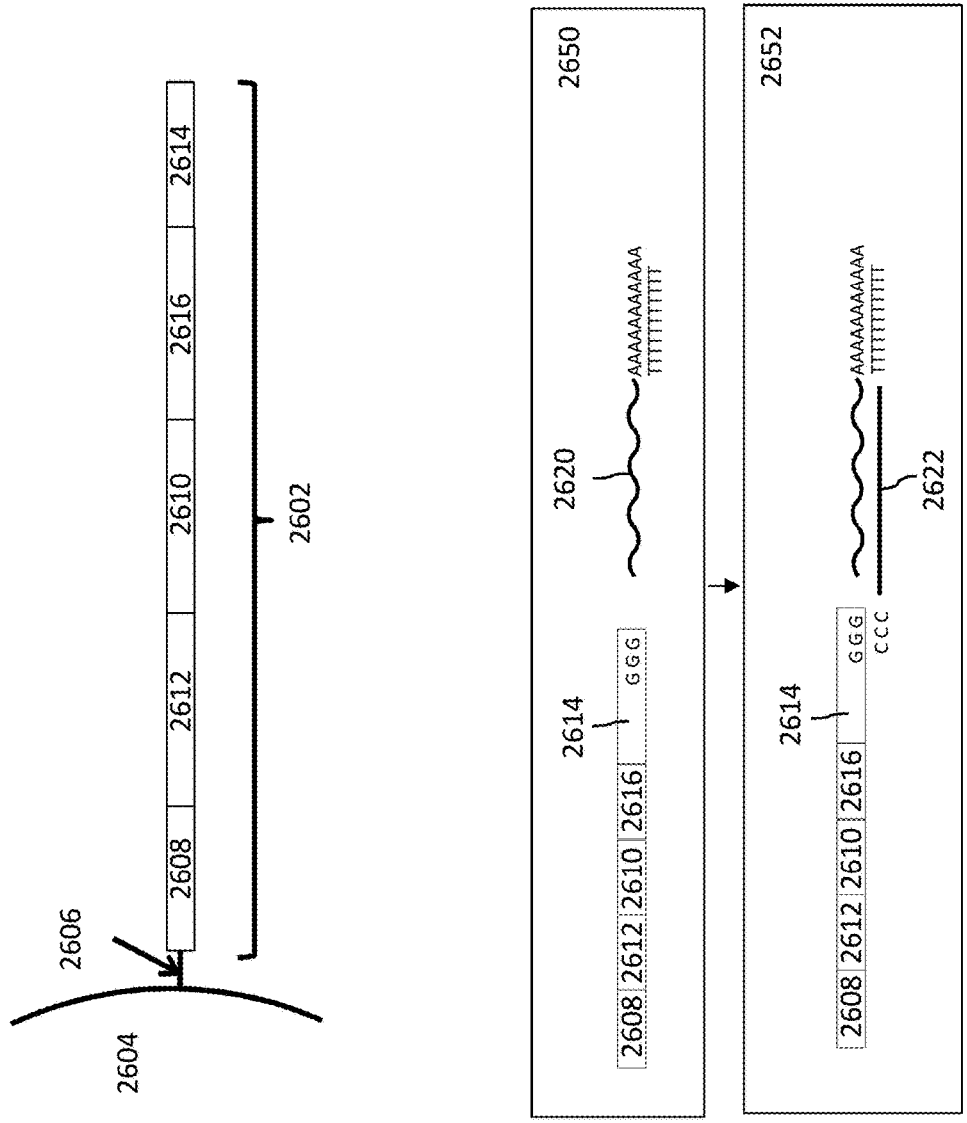
FIG. 26 provides a schematic illustration of an example barcoded oligonucleotide structure for use in analysis of RNA and example operations for performing RNA analysis. Figure discloses "AAAAAAAAAA" as SEQ ID NO: 12 and "TTTTTTTTTT" as SEQ ID NO: 13.

An additional example of a barcode oligonucleotide for use in RNA analysis, including messenger RNA (mRNA, including mRNA obtained from a cell) analysis is shown in FIG. 26. As shown, the overall oligonucleotide 2602 is coupled to a bead 2604 by a releasable linkage 2606, such as a disulfide linker. The oligonucleotide may include functional sequences that are used in subsequent processing, such as functional sequence 2608, which may include a sequencer specific flow cell attachment sequence, e.g., a P5 sequence, as well as functional sequence 2610, which may include sequencing primer sequences, e.g., a R1 primer binding site. In some cases, sequence 2608 is a P7 sequence and sequence 2610 is a R2 primer binding site. A barcode sequence 2612 is included within the structure for use in barcoding the sample RNA. An additional sequence segment 2616 may be provided within the oligonucleotide sequence. In some cases, this additional sequence can provide a unique molecular identifier (UMI) sequence segment, as described elsewhere herein. An additional sequence 2614 may be included to facilitate template switching, e.g., polyG. As will be appreciated, although shown as a single oligonucleotide tethered to the surface of a bead, individual beads can include tens to hundreds of thousands or millions of individual oligonucleotide molecules (e.g., at least about 10,000, 50,000, 100,000, 500,000, 1,000,000 or 10,000,000 oligonucleotide molecules), where the barcode segment can be constant or relatively constant for a given bead, but where the variable or unique sequence segment will vary across an individual bead.

In an example method of cellular mRNA analysis and in reference to FIG. 26, a cell is co-partitioned along with a microcapsule (e.g., bead bearing a barcoded oligonucleotide), polyT sequence, and other reagents such as a DNA polymerase, a reverse transcriptase, oligonucleotide primers, dNTPs, and reducing agent into a partition (e.g., a droplet in an emulsion). The partition can serve as a reaction volume. As described elsewhere herein, the partition serving as the reaction volume can comprise a container or vessel such as a well, a microwell, vial, a tube, through ports in nanoarray substrates, or micro-vesicles having an outer barrier surrounding an inner fluid center or core, emulsion, or a droplet. In some embodiments, the partition comprises a droplet of aqueous fluid within a non-aqueous continuous phase, e.g., an oil phase. Within the partition, the cell can be lysed and the barcoded oligonucleotides can be released from the bead (e.g., via the action of the reducing agent or other stimulus). Cell lysis and release of the barcoded oligonucleotides from the microcapsule may occur simultaneously in the partition (e.g., a droplet in an emulsion) or the reaction volume. In some embodiments, cell lysis precedes release of the barcoded oligonucleotides from the microcapsule. In some embodiments, release of the barcoded oligonucleotides from the microcapsule precedes cell lysis.

Subsequent to cell lysis and the release of barcoded oligonucleotides from the microcapsule, the reaction volume can be subjected to an amplification reaction to generate an amplification product. In an example amplification reaction, the polyT sequence hybridizes to the polyA tail of mRNA 2620 released from the cell as illustrated in operation 2650. Next, in operation 2652, the polyT sequence is then extended in a reverse transcription reaction using the mRNA as a template to produce a cDNA 2622 complementary to the mRNA. Terminal transferase activity of the reverse transcriptase can add additional bases to the cDNA (e.g., polyC) in a template independent manner. The additional bases added to the cDNA, e.g., polyC, can then hybridize with 2614 of the barcoded oligonucleotide. This can facilitate template switching and a sequence complementary to the barcoded oligonucleotide can be incorporated into the cDNA. In various embodiments, the barcoded oligonucleotide does not hybridize to the template polynucleotide.

The barcoded oligonucleotide, upon release from the microcapsule, can be present in the reaction volume at any suitable concentration. In some embodiments, the barcoded oligonucleotide is present in the reaction volume at a concentration of about 0.2 µM, 0.3 µM, 0.4 µM, 0.5 µM, 1 µM, 5 µM, 10 µM, 15 µM, 20 µM, 25 µM, 30 µM, 35 µM, 40 µM, 50 µM, 100 µM, 150 µM, 200 µM, 250 µM, 300 µM, 400 µM, or 500 µM. In some embodiments, the barcoded oligonucleotide is present in the reaction volume at a concentration of at least about 0.2 µM, 0.3 µM, 0.4 µM, 0.5 µM, 1 µM, 5 µM, 10 µM, 15 µM, 20 µM, 25 µM, 30 µM, 35 µM, 40 µM, 50 µM, 100 µM, 150 µM, 200 µM, 250 µM, 300 µM, 400 µM, 500 µM or greater. In some embodiments, the barcoded oligonucleotide is present in the reaction volume at a concentration of at most about 0.2 µM, 0.3 µM, 0.4 µM, 0.5 µM, 1 µM, 5 µM, 10 µM, 15 µM, 20 µM, 25 µM, 30 µM, 35 µM, 40 µM, 50 µM, 100 µM, 150 µM, 200 µM, 250 µM, 300 µM, 400 µM, or 500 µM.

The transcripts can be further processed (e.g., amplified, portions removed, additional sequences added, etc.) and characterized as described elsewhere herein. In some embodiments, the transcripts are sequenced directly. In some embodiments, the transcripts are further processed (e.g., portions removed, additional sequences added, etc) and then sequenced. In some embodiments, the reaction volume is subjected to a second amplification reaction to generate an additional amplification product. The transcripts or first amplification products can be used as the template for the second amplification reaction. In some embodiments, primers for the second amplification reaction comprise the barcoded oligonucleotide and polyT sequence. In some embodiments, primers for the second amplification reaction comprise additional primers co-partitioned with the cell. In some embodiments, these additional amplification products are sequenced directly. In some embodiments, these additional amplification products are further processed (e.g., portions removed, additional sequences added, etc) and then sequenced. The configuration of the amplification products (e.g., first amplification products and second amplification products) generated by such a method can help minimize (or avoid) sequencing of the poly-T sequence during sequencing.

An additional example of a barcode oligonucleotide for use in RNA analysis, including cellular RNA analysis is shown in FIG. 27A. As shown, the overall oligonucleotide 2702 is coupled to a bead 2704 by a releasable linkage 2706, such as a disulfide linker. The oligonucleotide may include functional sequences that are used in subsequent processing, such as functional sequence 2708, which may include a sequencer specific flow cell attachment sequence, e.g., a P5 sequence, as well as functional sequence 2710, which may include sequencing primer sequences, e.g., a R1 primer binding site. In some cases, sequence 2708 is a P7 sequence and sequence 2710 is a R2 primer binding site. A barcode sequence 2712 is included within the structure for use in barcoding the sample RNA. An additional sequence segment 2716 may be provided within the oligonucleotide sequence. In some cases, this additional sequence can provide a unique molecular identifier (UMI) sequence segment, as described elsewhere herein. As will be appreciated, although shown as a single oligonucleotide tethered to the surface of a bead, individual beads can include tens to hundreds of thousands or millions of individual oligonucleotide molecules (e.g., at least about 10,000, 50,000, 100,000, 500,000, 1,000,000 or 10,000,000 oligonucleotide molecules), where the barcode segment can be constant or relatively constant for a given bead, but where the variable or unique sequence segment will vary across an individual bead. In an example method of cellular RNA analysis using this barcode, a cell is co-partitioned along with a barcode bearing bead and other reagents such as RNA ligase and a reducing agent into a partition (e.g., a droplet in an emulsion). The cell is lysed while the barcoded oligonucleotides are released (e.g., via the action of the reducing agent) from the bead. The barcoded oligonucleotides can then be ligated to the 5' end of mRNA transcripts while in the partitions by RNA ligase. Subsequent operations may include purification (e.g., via solid phase reversible immobilization (SPRI)) and further processing (shearing, ligation of functional sequences, and subsequent amplification (e.g., via PCR)), and these operations may occur in bulk (e.g., outside the partition). In the case where a partition is a droplet in an emulsion, the emulsion can be broken and the contents of the droplet pooled for the additional operations.

Provided herein are methods that may allow for barcoding of a nucleic acid molecule (e.g., a ribonucleic acid (RNA) molecule) within a partition without performing reverse transcription. The nucleic acid molecule barcoded may be a targeted nucleic acid molecule. Such a method may involve attaching a probe to the nucleic acid molecule, and subsequently attaching a nucleic acid barcode molecule comprising a barcode sequence to the probe. For example, the nucleic acid barcode molecule may attach to an overhanging sequence of the probe or to the end of the probe. Extension from an end of the probe to an end of the nucleic acid barcode molecule may form an extended nucleic acid molecule comprising both a sequence complementary to the barcode sequence and a sequence complementary to a target region of the nucleic acid molecule. The extended nucleic acid molecule may then be denatured from the nucleic acid barcode molecule and the nucleic acid molecule and duplicated. This method may avoid the use of reverse transcription, which may be highly error prone. One or more processes of the method may be carried out within a partition such as a droplet or well.

The present disclosure also provides a method of processing a sample that provides a barcoded nucleic acid molecule having linked probe molecules attached thereto. The method may comprise one or more ligation-mediated reactions. The method may comprise providing a sample comprising a nucleic acid molecule (e.g., an RNA molecule) having adjacent first and second target regions; a first probe having a first probe sequence that is complementary to the first target region and a second probe sequence; and a second probe having a third probe sequence that is complementary to the second target region. The first and third probe sequences may also comprise first and second reactive moieties, respectively. Upon hybridization of the first probe sequence of the first probe to the first target region of the nucleic acid molecule, and hybridization of the third probe sequence of the second probe to the second target region of the nucleic acid molecule, the reactive moieties may be adjacent to one another. Subsequent reaction between the adjacent reactive moieties under sufficient conditions may link the first and second probes to yield a probe-linked nucleic acid molecule. The probe-linked nucleic acid molecule may also be referred to as a probe-ligated nucleic acid molecule. The probe-linked nucleic acid molecule may then be barcoded with a barcode sequence of a nucleic acid barcode molecule to provide a barcoded probe-linked nucleic acid molecule. Barcoding may be achieved by hybridizing a binding sequence of the nucleic acid barcode molecule to the second probe sequence of the first probe of the probe-linked nucleic acid molecule. The barcoded probe linked-nucleic acid molecule may be subjected to amplification reactions to yield an amplified product comprising the first and second target regions and the barcode sequence or sequences complementary to these sequences. Accordingly, the method may provide amplified products without the use of reverse transcription. One or more processes may be performed within a partition such as a droplet or well.

Further provided herein are methods of processing a sample that provides a barcoded nucleic acid molecule having linked probe molecules attached thereto. The method may comprise one or more nucleic acid reactions. The method may comprise providing a sample comprising a nucleic acid molecule (e.g., an RNA molecule) having adjacent or non-adjacent first and second target regions; a first probe having a first probe sequence that is complementary to the first target region and a second probe sequence; and a second probe having a third probe sequence that is complementary to the second target region. The third probe sequence may be known or degenerate (i.e., randomly generated). The first and third probe sequences may also comprise first and second reactive moieties, respectively. Where the nucleic acid molecule has non-adjacent first and second target regions, the nucleic acid molecule may comprise one or more gap regions between the first and second target regions. Upon hybridization of the first probe sequence of the first probe to the first target region of the nucleic acid molecule, and the third probe sequence of the second probe to the second target region of the nucleic acid molecule, the reactive moieties may be adjacent or non-adjacent to one another. Subsequent reaction between the adjacent or non-adjacent probes may generate a probe-linked nucleic acid molecule. The probe-linked nucleic acid molecule may also be referred to as a probe-ligated nucleic acid molecule. The probe-linked nucleic acid molecule may then be barcoded with a barcode sequence of a nucleic acid barcode molecule to provide a barcoded probe-linked nucleic acid molecule. Barcoding may be achieved by hybridizing a binding sequence of the nucleic acid barcode molecule to the second probe sequence of the first probe of the probe-linked nucleic acid molecule. Barcoding may also be achieved by hybridizing a binding sequence of a barcode nucleic acid molecule to a nucleic acid adaptor sequence, where the nucleic acid adaptor sequence comprises a binding sequence that can hybridize to one or more nucleic acid probes. The barcoded probe linked-nucleic acid molecule may be subjected to amplification reactions to yield an amplified product comprising the first and second target regions and the barcode sequence or sequences complementary to these sequences. Accordingly, the method may provide amplified products without the use of reverse transcription. One or more processes may be performed within a cell bead and/or a partition, such as a droplet or well.

In an aspect, the present disclosure provides a method comprising providing a sample comprising a nucleic acid molecule (e.g., a ribonucleic acid (RNA) molecule) comprising a target region and a probe comprising (i) a first probe sequence complementary to the sequence of the target region of the nucleic acid molecule and (ii) a second probe sequence; attaching (e.g., hybridizing) the first probe sequence of the probe to the target region of the nucleic acid molecule; providing a nucleic acid barcode molecule comprising (i) a first binding sequence that is complementary to the second probe sequence, (ii) a barcode sequence, and (iii) a second binding sequence; attaching (e.g., hybridizing) the first binding sequence of the nucleic acid barcode molecule to the second probe sequence of the probe; extending the probe from an end of the second probe sequence to an end of the second binding sequence of the nucleic acid barcode molecule to form an extended nucleic acid molecule comprising both a sequence complementary to the barcode sequence and a sequence complementary to the target region of the nucleic acid molecule; denaturing the extended nucleic acid molecule from the nucleic acid barcode molecule and the target region of the nucleic acid molecule to regenerate the nucleic acid barcode molecule and the nucleic acid molecule; and duplicating the extended nucleic acid molecule. The extended nucleic acid molecule may be further amplified (e.g., using polymerase chain reactions (PCR) or linear amplification, as described herein) to facilitate the detection of the extended nucleic acid molecule or a complement thereof (e.g., an amplified product) by, e.g., sequencing.

The methods described herein may facilitate gene expression profiling with single cell resolution using, for example, chemical ligation-mediated barcoding, amplification, and sequencing. The methods described herein may allow for gene expression analysis while avoiding the use of specialized imaging equipment and reverse transcription, which may be highly error prone and inefficient. For example, the methods may be used to analyze a pre-determined panel of target genes in a population of single cells in a sensitive and accurate manner. In some cases, the nucleic acid molecule analyzed by the methods described herein may be a fusion gene (e.g., a hybrid gene generated via translocation, interstitial deletion, or chromosomal inversion).

The nucleic acid molecule analyzed by the methods described herein may be a single-stranded or a double-stranded nucleic acid molecule. A double-stranded nucleic acid molecule may be completely or partially denatured to provide access to a target region (e.g., a target sequence) of a strand of the nucleic acid molecule. Denaturation may be achieved by, for example, adjusting the temperature or pH of a solution comprising the nucleic acid molecule; using a chemical agent such as formamide, guanidine, sodium salicylate, dimethyl sulfoxide, propylene glycol, urea, or an alkaline agent (e.g., NaOH); or using mechanical agitation (e.g., centrifuging or vortexing a solution including the nucleic acid molecule).

The nucleic acid molecule may be an RNA molecule. The RNA molecule may be, for example, a transfer RNA (tRNA) molecule, ribosomal RNA (rRNA) molecule, mitochondrial RNA (mtRNA) molecule, messenger RNA (mRNA) molecule, non-coding RNA molecule, synthetic RNA molecule, or another type of RNA molecule. For example, the RNA molecule may be an mRNA molecule. In some cases, the nucleic acid molecule may be a viral or pathogenic RNA. In some cases, the nucleic acid molecule may be a synthetic nucleic acid molecule previously introduced into or onto a cell. For example, the nucleic acid molecule may comprise a plurality of barcode sequences, and two or more barcode sequences may be target regions of the nucleic acid molecule.

The nucleic acid molecule (e.g., RNA molecule) may comprise one or more features selected from the group consisting of a 5' cap structure, an untranslated region (UTR), a 5' triphosphate moiety, a 5' hydroxyl moiety, a Kozak sequence, a Shine-Dalgarno sequence, a coding sequence, a codon, an intron, an exon, an open reading frame, a regulatory sequence, an enhancer sequence, a silencer sequence, a promoter sequence, and a poly(A) sequence (e.g., a poly(A) tail). For example, the nucleic acid molecule may comprise one or more features selected from the group consisting of a 5' cap structure, an untranslated region (UTR), a Kozak sequence, a Shine-Dalgarno sequence, a coding sequence, and a poly(A) sequence (e.g., a poly(A) tail).

Features of the nucleic acid molecule may have any useful characteristics. A 5' cap structure may comprise one or more nucleoside moieties joined by a linker such as a triphosphate (ppp) linker. A 5' cap structure may comprise naturally occurring nucleoside and/or non-naturally occurring (e.g., modified) nucleosides. For example, a 5' cap structure may comprise a guanine moiety or a modified (e.g., alkylated, reduced, or oxidized) guanine moiety such as a 7-methylguanylate ($m^7G$) cap. Examples of 5' cap structures include, but are not limited to, $m^7GpppG$, $m^7Gpppm^7G$, $m^7GpppA$, $m^7GpppC$, $GpppG$, $m^{2,7}GpppG$, $m^{2,2,7}GpppG$, and anti-reverse cap analogs such as $m^{7,2'Ome}GpppG$, $m^{7,2'd}GpppG$, $m^{7,3'Ome}GpppG$, and $m^{7,3'd}GpppG$. An untranslated region (UTR) may be a 5' UTR or a 3' UTR. A UTR may include any number of nucleotides. For example, a UTR may comprise at least 3, 5, 7, 10, 20, 30, 40, 50, 60, 70, 80, 90, 100, or more nucleotides. In some cases, a UTR may comprise fewer than 20 nucleotides. In other cases, a UTR may comprise at least 100 nucleotides, such as more than 200, 300, 400, 500, 600, 700, 800, 900, or 1000 nucleotides. Similarly, a coding sequence may include any number of nucleotides, such as at least 3, 5, 10, 20, 30, 40, 50, 60, 70, 80, 90, 100, or more nucleotides. A UTR, coding sequence, or other sequence of a nucleic acid molecule may have any nucleotide or base content or arrangement. For example, a sequence of a nucleic acid molecule may comprise any number or concentration of guanine, cytosine, uracil, and adenine bases. A nucleic acid molecule may also include non-naturally occurring (e.g., modified) nucleosides. A modified nucleoside may comprise one or more modifications (e.g., alkylations, hydroxylation, oxidation, or other modification) in its nucleobase and/or sugar moieties.

The nucleic acid molecule may comprise one or more target regions. In some cases, a target region may correspond to a gene or a portion thereof. Each region may have the same or different sequences. For example, the nucleic acid molecule may comprise two target regions having the same sequence located at different positions along a strand of the nucleic acid molecule. Alternatively, the nucleic acid molecule may comprise two or more target regions having different sequences. Different target regions may be interrogated by different probes. Target regions may be located adjacent to one another or may be spatially separated along a strand of the nucleic acid molecule. As used herein with regard to two entities, "adjacent," may mean that the entities directly next to one other (e.g., contiguous) or in proximity to one another. For example, a first target region may be directly next to a second target region (e.g., having no other entity disposed between the first and second target regions) or in proximity to a second target region (e.g., having an intervening sequence or molecule between the first and second target regions). In some cases, a double-stranded nucleic acid molecule may comprise a target region in each strand that may be the same or different. For a nucleic acid molecule comprising multiple target regions, the methods described herein may be performed for one or more target regions at a time. For example, a single target region of the multiple target regions may be analyzed (e.g., as described herein) or two or more target regions may be analyzed at the same time. Analyzing two or more target regions may involve providing two or more probes, where a first probe has a sequence that is complementary to the first target region, a second probe has a sequence that is complementary to the second target region, etc. Each probe may further comprise one or more additional sequences (e.g., additional probe sequences, unique molecular identifiers (UMIs), or other sequences) that are different from one another such that each probe may bind to a different nucleic acid barcode molecule. In another example, where two target regions are non-adjacent, a first target region and a second target region may be separated by one or more gap regions disposed between the first target region and the second target region.

A target region of the nucleic acid molecule may have one or more useful characteristics. For example, a target region may have any useful length, base content, sequence, melting point, or other characteristic. A target region may comprise, for example, at least 10 bases, such as at least 20, 25, 30, 35, 40, 45, 50, 60, 65, 70, 75, 80, 85, 90, 95, 100, 110, 120, 130, 140, 150, 160, 170, 180, 190, 200, 250, 300, 350, 400, 450, 500, or more bases. A target region may have any useful base content and any useful sequence and combination of bases. For example, a target region may comprise one or more adenine, thymine, uracil, cytosine, and/or guanine bases (e.g., natural or canonical bases). A target region may also comprise one or more derivatives or modified versions of a natural or canonical base, such as an oxidized, alkylated (e.g., methylated), hydroxylated, or otherwise modified base. Similarly, a target region may comprise ribose or deoxyribose moieties and phosphate moieties or derivatives or modified versions thereof.

A target region of the nucleic acid molecule may comprise one or more sequences or features, or portions thereof, of the nucleic acid molecule. For example, a target region may comprise all or a portion of a UTR (e.g., a 3' UTR or a 5' UTR), a Kozak sequence, a Shine-Dalgarno sequence, a coding sequence, a polyA sequence, a cap structure, an intron, an exon, or any other sequence or feature of the nucleic acid molecule.

The nucleic acid molecule (e.g., RNA molecule, such as an mRNA molecule) of a sample may be included within a cell. For example, the sample may comprise a cell comprising the nucleic acid molecule. The cell may comprise additional nucleic acid molecules that may be the same as or different from the nucleic acid molecule of interest. In some cases, the sample may comprise a plurality of cells, and each cell may contain one or more nucleic acid molecules. The cell may be, for example, a human cell, an animal cell, or a plant cell. In some cases, the cell may be derived from a tissue or fluid, as described herein. The cell may be a prokaryotic cell or a eukaryotic cell. The cell may be a lymphocyte such as a B cell or T cell.

Access to a nucleic acid molecule included in a cell may be provided by lysing or permeabilizing the cell. Lysing the cell may release the nucleic acid molecule contained therein from the cell. A cell may be lysed using a lysis agent such as a bioactive agent. A bioactive agent useful for lysing a cell may be, for example, an enzyme (e.g., as described herein). An enzyme used to lyse a cell may or may not be capable of carrying out additional functions such as degrading, extending, reverse transcribing, or otherwise altering a nucleic acid molecule. Alternatively, an ionic or non-ionic surfactant such as TritonX-100, Tween 20, sarcosyl, or sodium dodecyl sulfate may be used to lyse a cell. Cell lysis may also be achieved using a cellular disruption method such as an electroporation or a thermal, acoustic, or mechanical disruption method. Alternatively, a cell may be permeabilized to provide access to a nucleic acid molecule included therein. Permeabilization may involve partially or completely dissolving or disrupting a cell membrane or a portion thereof. Permeabilization may be achieved by, for example, contacting a cell membrane with an organic solvent (e.g., methanol) or a detergent such as Triton X-100 or NP-40.

A nucleic acid molecule or a derivative thereof (e.g., a probe-linked nucleic acid molecule, a nucleic acid molecule having one or more probes hybridized thereto, a barcoded probe-linked nucleic acid molecule, or an extended nucleic acid molecule or complement thereof) or a cell comprising the nucleic acid molecule or a derivative thereof (e.g., a cell bead) may be partitioned within a partition such as a well or droplet, e.g., as described herein. One or more reagents may be co-partitioned with a nucleic acid molecule or a derivative thereof or a cell comprising the nucleic acid molecule or a derivative thereof. For example, a nucleic acid molecule or a derivative thereof or a cell comprising the nucleic acid molecule or a derivative thereof may be co-partitioned with one or more reagents selected from the group consisting of lysis agents or buffers, permeabilizing agents, enzymes (e.g., enzymes capable of digesting one or more RNA molecules, extending one or more nucleic acid molecules, reverse transcribing an RNA molecule, permeabilizing or lysing a cell, or carrying out other actions), fluorophores, oligonucleotides, primers, probes, barcodes, nucleic acid barcode molecules (e.g., nucleic acid barcode molecules comprising one or more barcode sequences), buffers, deoxynucleotide triphosphates, detergents, reducing agents, chelating agents, oxidizing agents, nanoparticles, beads, and antibodies. In some cases, a nucleic acid molecule or a derivative thereof, or a cell comprising the nucleic acid molecule or a derivative thereof (e.g., a cell bead), may be co-partitioned with one or more reagents selected from the group consisting of temperature-sensitive enzymes, pH-sensitive enzymes, light-sensitive enzymes, reverse transcriptases, proteases, transposases, ligase, polymerases, restriction enzymes, nucleases, protease inhibitors, exonucleases, and nuclease inhibitors. For example, a nucleic acid molecule or a derivative thereof or a cell comprising the nucleic acid molecule or a derivative thereof may be co-partitioned with a polymerase and nucleotide molecules. Partitioning a nucleic acid molecule or a derivative thereof or a cell comprising the nucleic acid molecule or a derivative thereof and one or more reagents may comprise flowing a first phase comprising an aqueous fluid, the cell, and the one or more reagents and a second phase comprising a fluid that is immiscible with the aqueous fluid toward a junction. Upon interaction of the first and second phases, a discrete droplet of the first phase comprising the nucleic acid molecule or a derivative thereof or a cell comprising the nucleic acid molecule or a derivative thereof (e.g., a cell bead) and the one or more reagents may be formed. In some cases, the partition may comprise a single cell. The cell may be lysed or permeabilized within the partition (e.g., droplet) to provide access to the nucleic acid molecule of the cell.

In some embodiments, the cell may be lysed within the cell bead, and a subset of the intracellular contents may associate with the bead. In some cases, the cell bead may comprise thioacrydite-modified nucleic acid molecules that can hybridize with nucleic acids from the cell. For example, a poly-T nucleic acid sequence may be thioacrydite-modified and bound to the cell bead matrix. Upon cell lysis, the cellular nucleic acids (e.g., mRNA) may hybridize with the poly-T sequence. The retained intracellular contents may be released, for example, by addition of a reducing agent, e.g., DTT, TCEP, etc. The release may occur at any convenient step, such as before or after partitioning.

One or more processes may be carried out within a partition. For example, one or more processes selected from the group consisting of lysis, permeabilization, denaturation, hybridization, extension, duplication, and amplification of one or more components of a sample comprising the nucleic acid molecule may be performed within a partition. In some cases, multiple processes are carried out within a partition. The nucleic acid molecule or a cell comprising the nucleic acid molecule, may be co-partitioned with one or more reagents (e.g., as described herein) at any useful stage of the method. For example, the nucleic acid molecule contained within a cell may be co-partitioned with a probe and one or more additional reagents prior to hybridization of the probe with the target region of the nucleic acid molecule. Similarly, the nucleic acid molecule or a cell comprising the nucleic acid molecule may be released from a partition at any useful stage of the method. For example, the nucleic acid molecule or a cell comprising the nucleic acid molecule may be released from the partition subsequent to hybridization of a binding sequence of a nucleic acid barcode molecule to a sequence of a probe hybridized to the target region of the nucleic acid molecule. Alternatively, the nucleic acid molecule or a cell comprising the nucleic acid molecule, and/or another component of the sample comprising the same, may be released from the partition subsequent to denaturation of a complexed extended nucleic acid molecule that comprises a sequence complementary to the barcode sequence of a nucleic acid barcode molecule and a sequence complementary to the target region of the nucleic acid molecule. Duplication and/or amplification of the extended nucleic acid molecule may then be carried out within a solution. In some cases, the solution may comprise additional extended nucleic acid molecules generated through the same process carried out in different partitions. Each extended nucleic acid molecule may comprise a different barcode sequence or a sequence complementary to a different barcode sequence. In this instance, the solution may be a pooled mixture comprising the contents of two or more partitions (e.g., droplets).

Hybridization of a probe sequence of a probe to a target region of the nucleic acid molecule may be performed within or outside of a partition. In some cases, hybridization may be preceded by denaturation of a double-stranded nucleic acid molecule to provide a single-stranded nucleic acid molecule or by lysis or permeabilization of a cell. The sequence of the probe that is complementary to the target region may be situated at an end of the probe. Alternatively, this sequence may be disposed between other sequences such that when the probe sequence is hybridized to the target region, additional probe sequences extend beyond the hybridized sequence in multiple directions. The probe sequence that hybridizes to the target region of the nucleic acid molecule may be of the same or different length as the target region. For example, the probe sequence may be shorter than the target region and may only hybridize to a portion of the target region. Alternatively, the probe sequence may be longer than the target region and may hybridize to the entirety of the target region and extend beyond the target region in one or more directions. In addition to a probe sequence complementary to a target region of the nucleic acid molecule, the probe may comprise one or more additional probe sequences. For example, the probe may comprise the probe sequence complementary to the target region and a second probe sequence. The second probe sequence may have any useful length and other characteristics. The probe may comprise one or more additional sequences, such as one or more barcode sequences or unique molecule identifier (UMI) sequences. In some cases, one or more probe sequences of the probe may comprise a detectable moiety such as a fluorophore or a fluorescent moiety.

A probe sequence of the probe may be capable of hybridizing with a sequence of a nucleic acid barcode molecule. A nucleic acid barcode molecule may comprise a first binding sequence that is complementary to a probe sequence of the probe (e.g., a second probe sequence), a barcode sequence, and a second binding sequence. A nucleic acid barcode molecule may also comprise one or more additional functional sequences selected from the group consisting of primer sequences, primer annealing sequences, and immobilization sequences. The binding sequences may have any useful length and other characteristics. In some cases, the binding sequence that is complementary to a probe sequence of the probe may be the same length as the probe sequence. Alternatively, the binding sequence may be a different length of the probe sequence. For example, the binding sequence may be shorter than the probe sequence and may only hybridize to a portion of the probe sequence. Alternatively, the binding sequence may be longer than the probe sequence and may hybridize to the entirety of the probe sequence and extend beyond the probe sequence in one or more directions.

The barcode sequence of a nucleic acid barcode molecule may have any useful length and other characteristics (e.g., as described herein). The nucleic acid barcode molecule may be attached to a bead such as a gel bead (e.g., as described herein). The bead may be co-partitioned with the nucleic acid molecule or the cell comprising the nucleic acid molecule. The bead may comprise a plurality of nucleic acid barcode molecules that may be the same or different. The bead may comprise at least 10,000 nucleic acid barcode molecules attached thereto. For example, the bead may comprise at least 100,000, 1,000,000, or 10,000,000 nucleic acid barcode molecules attached thereto. In some cases, each nucleic acid barcode molecule of the plurality of nucleic acid barcode molecules may comprise a common barcode sequence. The nucleic acid barcode molecules may further comprise an additional barcode sequence that may be different for each nucleic acid barcode molecule attached to the bead. The plurality of nucleic acid barcode molecules may be releasably attached to the bead. The plurality of nucleic acid barcode molecules may be releasable from the bead upon application of a stimulus. Such a stimulus may be selected from the group consisting of a thermal stimulus, a photo stimulus, a biological stimulus, and a chemical stimulus. For example, the stimulus may be a reducing agent such as dithiothreitol Application of a stimulus may result in one or more of (i) cleavage of a linkage between nucleic acid barcode molecules of the plurality of nucleic acid barcode molecules and the bead, and (ii) degradation or dissolution of the bead to release nucleic acid barcode molecules of the plurality of nucleic acid barcode molecules from the bead. In some cases, one or more nucleic acid barcode molecules may be released from the bead prior to hybridization of a binding sequence of a nucleic acid barcode molecule to a probe sequence of the probe hybridized to the nucleic acid molecule of interest. The one or more nucleic acid barcode molecules may be released from the bead within a partition including the bead and the nucleic acid molecule (or a cell comprising the nucleic acid molecule) and the probe. Releasing may take place before, after, or during hybridization of a probe sequence to a target region of the nucleic acid molecule.

Following hybridization of a binding sequence of the nucleic acid barcode molecule to a probe sequence of the probe hybridized to the target region of the nucleic acid molecule, the probe may be extended from an end of the probe to an end of the nucleic acid barcode molecule. Extension may comprise the use of an enzyme (e.g., a polymerase) to add one or more nucleotides to the end of the probe. Extension may provide an extended nucleic acid molecule comprising sequences complementary to the target region of the nucleic acid molecule of interest, the barcode sequence, and one or more additional sequences of the nucleic acid barcode molecule such as one or more binding sequences. Appropriate conditions and or chemical agents (e.g., as described herein) may then be applied to denature the extended nucleic acid molecule from the nucleic acid barcode molecule and the target nucleic acid molecule. The nucleic acid barcode molecule and the target nucleic acid molecule may then undergo further analysis. For example, a second probe that may be identical to the first probe and comprise a probe sequence that is complementary to the target region of the nucleic acid molecule may hybridize to the target region, and the nucleic acid barcode molecule may hybridize to an additional probe sequence of the second probe. In some cases, hybridization of the nucleic acid barcode molecule to the probe may precede hybridization of the probe to the target region of the nucleic acid molecule. The extended nucleic acid molecule that has been released from the nucleic acid barcode molecule and the target nucleic acid molecule may be duplicated or amplified by, for example, one or more amplification reactions. The amplification reactions may comprise polymerase chain reactions (PCR) and may involve the use of one or more primers or polymerases. The extension, denaturation, and/or amplification processes may take place within a partition. Alternatively, materials may be released from a partition prior to extension, denaturation, or amplification. For example, materials may be released from a partition between the extension and denaturation processes. Denaturation may then take place within a solution comprising the extended nucleic acid molecule, nucleic acid barcode molecule, and target nucleic acid molecule. Alternatively, materials may be released from a partition subsequent to denaturation and prior to amplification. In some cases, the extended nucleic acid molecule may be duplicated or amplified within a partition to provide an amplified product. The extended nucleic acid molecule, or a complement thereof (e.g., an amplified product), may be detected via sequencing (e.g., as described herein).

FIG. 110 schematically illustrates a method of analyzing a nucleic acid molecule. Panel 110A shows a nucleic acid molecule 11000 comprising a target region 11002. Nucleic acid molecule 11000 is an mRNA molecule comprising a polyA sequence at its 3' end. Probe 11004 comprises probe sequences 11006 and 11008. Probe sequence 11006 has a sequence complementary to target region 11002 of nucleic acid molecule 11000 and hybridizes thereto. Panel 110B shows nucleic acid barcode molecule 11010 comprising binding sequences 11012 and 11016 and barcode sequence 11014. Binding sequence 11012 has a sequence complementary to probe sequence 11008 and hybridizes thereto. Panel 110C shows extension of probe 11004 from an end of probe sequence 11008 to the end of nucleic acid barcode molecule 11010 to which it is hybridized. Extension results in the generation of extended nucleic acid molecule 11018, which comprises probe sequences 11006 and 11008; sequence 11020, which is complementary to barcode sequence 11014; and sequence 11022, which is complementary to binding sequence 11016. Panel 110D shows denaturation of extended nucleic acid molecule 11018 from nucleic acid molecule 11000 and nucleic acid barcode molecule 11010. Panel 110E shows duplication or amplification of extended nucleic acid molecule 11018 to generate amplified product 11024. Amplified product 11024 comprises sequence 11026, which is complementary to sequence 11022 and the same or substantially the same as binding sequence 11016 of nucleic acid barcode molecule 11010; sequence 11028, which is complementary to sequence 11020 and the same or substantially the same as barcode sequence 11014 of nucleic acid barcode molecule 11010; sequence 11030, which is complementary to probe sequence 11008 and the same or substantially the same as binding sequence 11012 of nucleic acid barcode molecule 11010; and sequence 11032, which is complementary to probe sequence 11006 and the same or substantially the same as target region 11002 of nucleic acid molecule 11000.

In some cases, reverse transcription may be performed to provide complementary deoxyribonucleic acid (cDNA) molecules, as described herein. However, the presently disclosed method may provide for duplication of a target region of an mRNA molecule of interest without the need for reverse transcription, which may be highly prone to error. Accordingly, the presently disclosed method may be useful in transcriptome analysis methods.

The presently disclosed method may be applied to a single nucleic acid molecule or a plurality of nucleic acid molecules. A method of analyzing a sample comprising a nucleic acid molecule may comprise providing a plurality of nucleic acid molecules (e.g., RNA molecules), where each nucleic acid molecule comprises a target region, and a plurality of probes. In some cases, the target region of nucleic acid molecules of the plurality of nucleic acid molecules may comprise the same sequence. The plurality of probes may each comprise a first probe sequence complementary to the sequence of a target region of a nucleic acid molecule of the plurality of nucleic acid molecules as well as a second probe sequence. One or more probes may comprise the same first probe sequence. A first probe sequence of a probe of the plurality of probes may be hybridized to a target region of a nucleic acid molecule of the plurality of nucleic acid molecules. A binding sequence of a nucleic acid barcode molecule of a plurality of nucleic acid barcode molecules may hybridize to the second probe sequence of a probe of the plurality of probes that is hybridized to a target region of a nucleic acid molecule of a plurality of nucleic acid molecules. Each nucleic acid barcode molecule of the plurality of nucleic acid barcode molecules may comprise a barcode sequence and a second binding sequence. The barcode sequence of each nucleic acid barcode molecule of the plurality of nucleic acid barcode molecules may be the same or different. Following hybridization of a binding sequence of a nucleic acid barcode molecule of the plurality of nucleic acid barcode molecules to a probe sequence of a probe of the plurality of probes that is hybridized to a target region of a nucleic acid molecule of the plurality of nucleic acid molecules, each probe of the plurality of hybridized probes may then be extended from an end of the probe to an end of the nucleic acid barcode molecule to which it is hybridized (e.g., an end of the second binding sequence of the nucleic acid barcode molecule). A plurality of extended nucleic acid molecules may thereby be created, where each extended nucleic acid molecule of the plurality of extended nucleic acid molecules comprises a sequence complementary to a target region of a nucleic acid molecule of the plurality of nucleic acid molecules and a sequence complementary to a barcode sequence of a nucleic acid barcode molecule of the plurality of nucleic acid barcode molecules.

In some cases, one or more processes described above may be performed within a partition. For example, each nucleic acid molecule of the plurality of nucleic acid molecules may be provided within a different partition. This may be achieved by partitioning a plurality of cells comprising the plurality of nucleic acid molecules within a plurality of separate partitions, where each cell comprises a target nucleic acid molecule and each partition of a plurality of different partitions of the plurality of separate partitions comprises a single cell. Access to a target nucleic acid molecule contained within a cell in a partition may be provided by lysing or permeabilizing the cell (e.g., as described herein). Nucleic acid barcode molecules provided within each partition of the plurality of different partitions of the plurality of separate partitions may be provided attached to beads. For example, each partition of the plurality of different partitions of the plurality of separate partitions may comprise a bead comprising a plurality of nucleic acid barcode molecules attached thereto (e.g., as described herein). The plurality of nucleic acid barcode molecules attached to each bead may comprise a different barcode sequence, such that each partition of the plurality of different partitions of the plurality of separate partitions comprises a different barcode sequence. Upon release of components from the plurality of different partitions of the plurality of separate partitions (e.g., following extension of each probe), each extended nucleic acid molecule may comprise a sequence complementary to a different barcode sequence, such that each extended nucleic acid molecule can be traced to a given partition and, in some cases, a given cell.

Chemical Ligation Methods

In another aspect, the present disclosure provides a method comprising providing a sample comprising a nucleic acid molecule (e.g., a ribonucleic acid (RNA) molecule) having a first target region and a second target region. The first target region may be adjacent to the second target region a first probe and a second probe. The first probe may comprise a first probe sequence and a second probe sequence, where the first probe sequence of the first probe is complementary to the first target region of the nucleic acid molecule. The second probe may comprise a third probe sequence that is complementary to the second target region of the nucleic acid molecule. The first probe sequence may also comprise a first reactive moiety, and the third probe sequence may comprise a second reactive moiety. The sample may be subjected to conditions sufficient to hybridize (i) the first probe sequence of the first probe to the first target region of the nucleic acid molecule and (ii) the third probe sequence of the second probe to the second target region of the nucleic acid molecule such that the first reactive moiety of the first probe sequence is adjacent to the second reactive moiety of the third probe sequence. The reactive moieties may then be subjected to conditions sufficient to cause them to react to yield a probe-linked nucleic acid molecule comprising the first probe linked to the second probe. The probe-linked nucleic acid molecule may then be barcoded (e.g., within a partition) to provide a barcoded probe-linked nucleic acid molecule. Barcoding may comprise hybridizing a binding sequence of a nucleic acid barcode molecule to the second probe sequence of the first probe. The first probe of the barcoded probe-linked nucleic acid molecule may subsequently be extended from an end of the first probe to an end of the nucleic acid barcode molecule to which it is hybridized to provide an extended nucleic acid molecule. The extended nucleic acid barcode molecule may comprise the first probe, the second probe, a sequence complementary to the barcode sequence of the nucleic acid barcode molecule, and a sequence complementary to another sequence (e.g., another binding sequence) of the nucleic acid barcode molecule. The extended nucleic acid molecule may be denatured from the nucleic acid barcode molecule and the nucleic acid molecule of interest and then duplicated or amplified (e.g., using polymerase chain reactions (PCR) or linear amplification) to facilitate detection of the extended nucleic acid molecule or a complement thereof (e.g., an amplified product) by, e.g., sequencing.

The methods described herein may facilitate gene expression profiling with single cell resolution using, for example, chemical ligation-mediated barcoding, amplification, and sequencing. The methods described herein may allow for gene expression analysis while avoiding the use of enzymatic ligation, specialized imaging equipment, and reverse transcription, which may be highly error prone and inefficient. For example, the methods may be used to analyze a pre-determined panel of target genes in a population of single cells in a sensitive and accurate manner. In some cases, the nucleic acid molecule analyzed by the methods described herein may be a fusion gene (e.g., a hybrid gene generated via translocation, interstitial deletion, or chromosomal inversion).

The nucleic acid molecule analyzed by the method may be a single-stranded or double-stranded nucleic acid molecule (e.g., as described herein). The nucleic acid molecule may be an RNA molecule such as an mRNA molecule. In some cases, the nucleic acid molecule may be a viral or pathogenic RNA. In some cases, the nucleic acid molecule may be a synthetic nucleic acid molecule previously introduced into or onto a cell. For example, the nucleic acid molecule may comprise a plurality of barcode sequences, and two or more barcode sequences may be target regions of the nucleic acid molecule.

The nucleic acid molecule (e.g., mRNA molecule) may comprise one or more features selected from the group consisting of a 5' cap structure, an untranslated region (UTR), a 5' triphosphate moiety, a 5' hydroxyl moiety, a Kozak sequence, a Shine-Dalgarno sequence, a coding sequence, a codon, an intron, an exon, an open reading frame, a regulatory sequence, an enhancer sequence, a silencer sequence, a promoter sequence, and a poly(A) sequence (e.g., a poly(A) tail). Features of the nucleic acid molecule may have any useful characteristics. Additional details of nucleic acid molecules are provided in the preceding section.

The nucleic acid molecule may comprise two or more target regions. In some cases, a target region may correspond to a gene or a portion thereof. Each region may have the same or different sequences. For example, the nucleic acid molecule may comprise two target regions having the same sequence located at adjacent positions along a strand of the nucleic acid molecule. Alternatively, the nucleic acid molecule may comprise two or more target regions having different sequences at adjacent positions along a strand of the nucleic acid molecule. As used herein with regard to two entities, "adjacent," may mean that the entities directly next to one other (e.g., contiguous) or in proximity to one another. For example, a first target region may be directly next to a second target region (e.g., having no other entity disposed between the first and second target regions) or in proximity to a second target region (e.g., having an intervening sequence or molecule between the first and second target regions). In some cases, the nucleic acid molecule may comprise additional target regions disposed at different locations along the same or a different strand of the nucleic acid molecule. For example, a double-stranded nucleic acid molecule may comprise one or more target regions in each strand that may be the same or different. Different target regions may be interrogated by different probes. For example, a first target region may be interrogated by a first probe having a first probe sequence that is complementary to the first target region, and a second target region may be interrogated by a second probe having a second probe sequence that is complementary to the second target region. One or both probes may further comprise one or more additional sequences (e.g., additional probe sequences, unique molecular identifiers (UMIs), or other sequences). For example, the first probe may further comprise a second probe sequence. The second probe sequence of the first probe may undergo hybridization with a binding sequence of a nucleic acid barcode molecule. The second probe may also comprise an additional probe sequence. This sequence may be different from the second barcode sequence of the first probe so that the first and second probes may hybridize to different nucleic acid barcode molecules.

The target regions of the nucleic acid molecule may have any useful characteristics (e.g., as described in the preceding section).

The nucleic acid molecule (e.g., RNA molecule, such as an mRNA molecule) of a sample may be included within a cell (e.g., as described in the preceding section). For example, the sample may comprise a cell comprising the nucleic acid molecule that may be, for example, a human cell, an animal cell, or a plant cell. Access to a nucleic acid molecule included in a cell may be provided by lysing or permeabilizing the cell (e.g., as described in the preceding section).

Hybridization of a probe sequence of a probe to a target region of the nucleic acid molecule may be performed within or outside of a cell, partition, and/or container. In some cases, a cell may be lysed within a cell bead and a subset of the intracellular contents (e.g., mRNA) may be retained in the cell bead, as described elsewhere herein. In such cases, hybridization of a probe sequence of a probe to a target region of the nucleic acid may occur prior to partitioning. In some cases, hybridization may be preceded by denaturation of a double-stranded nucleic acid molecule to provide a single-stranded nucleic acid molecule or by lysis or permeabilization of a cell. The sequence of a probe that is complementary to a target region may be situated at an end of the probe. Alternatively, this sequence may be disposed between other sequences such that when the probe sequence is hybridized to a target region, additional probe sequences extend beyond the hybridized sequence in multiple directions. A probe sequence that hybridizes to a target region of the nucleic acid molecule may be of the same or different length as the target region. For example, a probe sequence may be shorter than a target region and may only hybridize to a portion of the target region. Alternatively, a probe sequence may be longer than a target region and may hybridize to the entirety of the target region and extend beyond the target region in one or more directions. In addition to a probe sequence complementary to a target region of the nucleic acid molecule, a probe may comprise one or more additional probe sequences. For example, a probe may comprise a probe sequence complementary to a target region and a second probe sequence. The second probe sequence may have any useful length and other characteristics. In an example, the first probe comprises a first probe sequence capable of hybridizing to the first target region of the nucleic acid molecule of interest and a second probe sequence, and the second probe comprises a third probe sequence capable of hybridizing to the second target region of the nucleic acid molecule of interest. In some cases, the second probe may further comprise a fourth binding sequence. Both the first probe and the second probe may comprise one or more additional sequences, such as one or more barcode sequences or unique molecule identifier (UMI) sequences. In some cases, one or more probe sequences of a probe may comprise a detectable moiety such as a fluorophore or a fluorescent moiety.

A probe may comprise a reactive moiety. For example, a probe sequence of a first probe capable of hybridizing to a first target region of a nucleic acid molecule may comprise a first reactive moiety, and a probe sequence of a second probe capable of hybridizing to a second target region of the nucleic acid molecule may comprise a second reactive moiety. When the first and second probes are hybridized to the first and second target regions of the nucleic acid molecule, the first and second reactive moieties may be adjacent to one another. A reactive moiety of a probe may be selected from the non-limiting group consisting of azides, alkynes, nitrones (e.g., 1,3-nitrones), strained alkenes (e.g., trans-cycloalkenes such as cyclooctenes or oxanorbornadiene), tetrazines, tetrazoles, iodides, thioates (e.g., phosphorothioate), acids, amines, and phosphates. For example, the first reactive moiety of a first probe may comprise an azide moiety, and a second reactive moiety of a second probe may comprise an alkyne moiety. The first and second reactive moieties may react to form a linking moiety. A reaction between the first and second reactive moieties may be, for example, a cycloaddition reaction such as a strain-promoted azide-alkyne cycloaddition, a copper-catalyzed azide-alkyne cycloaddition, a strain-promoted alkyne-nitrone cycloaddition, a Diels-Alder reaction, a [3+2] cycloaddition, a [4+2] cycloaddition, or a [4+1] cycloaddition; a thiol-ene reaction; a nucleophilic substation reaction; or another reaction. In some cases, reaction between the first and second reactive moieties may yield a triazole moiety or an isoxazoline moiety. A reaction between the first and second reactive moieties may involve subjecting the reactive moieties to suitable conditions such as a suitable temperature, pH, or pressure and providing one or more reagents or catalysts for the reaction. For example, a reaction between the first and second reactive moieties may be catalyzed by a copper catalyst, a ruthenium catalyst, or a strained species such as a difluorooctyne, dibenzylcyclooctyne, or biarylazacyclooctynone. Reaction between a first reactive moiety of a first probe sequence of a first probe hybridized to a first target region of the nucleic acid molecule and a second reactive moiety of a third probe sequence of a second probe hybridized to a second target region of the nucleic acid molecule may link the first probe and the second probe to provide a probe-linked nucleic acid molecule. Upon linking, the first and second probes may be considered ligated. Accordingly, reaction of the first and second reactive moieties may comprise a chemical ligation reaction such as a copper-catalyzed 5' azide to 3' alkyne "click" chemistry reaction to form a triazole linkage between two probes. In other non-limiting examples, an iodide moiety may be chemically ligated to a phosphorothioate moiety to form a phosphorothioate bond, an acid may be ligated to an amine to form an amide bond, and/or a phosphate and amine may be ligated to form a phosphoramidate bond. FIG. 116 illustrates examples of "click" chemistry reactions. Panel 116A shows a chemical ligation reaction of an alkyne moiety 11602 and an azide moiety 11604 reacting under copper-mediated cycloaddition to form a triazole linkage 11606. Panel 116B shows a chemical ligation reaction of a phosphorothioate group 11608 with an iodide group 11610 to form a phosphorothioate linkage 11612. Panel 116C shows a chemical ligation reaction of an acid 11614 and amine 11616 to form an amide linkage 11618. Panel 116D shows a chemical ligation reaction of a phosphate moiety 11620 and an amine moiety 11622 to form a phosphoramidate linkage 11624. Panel 116E shows a conjugation reaction of two species of 11626 and 11628.

In some instances, the first and second probes are hybridized to the first and second target regions of the nucleic acid molecule, and the first and second reactive moieties may be adjacent to one another. In some cases, the probes do not comprise reactive moieties and may be subjected to a nucleic acid reaction, providing a probe-linked nucleic acid molecule. For example, the probes may be subjected to an enzymatic ligation reaction, using a ligase (e.g., SplintR ligase and/or T4 ligase). Following the enzymatic ligation reaction, the first and second probes may be considered ligated. In one embodiment, the first and second probes are both present in a linear nucleic acid molecule. In another embodiment, the linear nucleic acid molecule is a molecular inversion probe.

In other instances, the first and second probes are hybridized to the first and second target regions of the nucleic acid molecule, and the first and second reactive moieties may not be adjacent to one another (e.g., comprise a gap region between the first and second probes). The first probe and the second probe may be positioned on (i.e., hybridized to) the nucleic acid molecule (e.g., mRNA) one or more nucleotides apart. For example, the first probe and the second probe may be spaced at least about 2, 3, 4, 5, 6, 7, 8, 9, 10, 11, 12, 13, 14, 15, 16, 17, 18, 19, 20, 30, 40, 50, 60, 70, 80, 90, 100, 200, 300, 400, 500, 700, 700, 800, 900, 1000 or more nucleotides apart. In some embodiments, the non-adjacent first and second probes may be ligated to form a probe-linked nucleic acid molecule. The probes may be subjected to an enzymatic ligation reaction, using a ligase, e.g., SplintR ligases, T4 ligases, Mu polymerase, PBCV1 enzymes, and/or any combinations, derivatives, and variants thereof. In some embodiments, ribonucleotides are ligated between the first and second probes. In some embodiments, deoxyribonucleotides are ligated between the first and second probes. In one embodiment, the first and second probes are both present in a linear nucleic acid molecule. In another embodiment, the linear nucleic acid molecule may form a circularized nucleic acid molecule upon hybridization to target regions. The circularized nucleic acid molecule may then be subjected to conditions sufficient for ligation of its ends to form a circular probe-linked nucleic acid molecule.

A probe sequence of a probe (e.g., a probe of a probe-linked nucleic acid molecule) may be capable of hybridizing with a sequence (e.g., binding sequence) of a nucleic acid barcode molecule. A nucleic acid barcode molecule may comprise a first binding sequence that is complementary to a probe sequence of a probe (e.g., a second probe sequence), a barcode sequence, and a second binding sequence. In some cases, the binding sequence may be known and may bind to a target of interest (e.g., mRNA encoding a gene of interest). In some cases, the binding sequence may be degenerate (i.e., randomly generated). Employing degenerate or known sequences may be used in whole transcriptome analysis or for targeted RNA sequencing, respectively. A nucleic acid barcode molecule may also comprise one or more additional functional sequences selected from the group consisting of primer sequences, primer annealing sequences, and immobilization sequences. The binding sequences may have any useful length and other characteristics. In some cases, the binding sequence that is complementary to a probe sequence of a probe may be the same length as the probe sequence. Alternatively, the binding sequence may be a different length of the probe sequence. For example, the binding sequence may be shorter than the probe sequence and may only hybridize to a portion of the probe sequence. Alternatively, the binding sequence may be longer than the probe sequence and may hybridize to the entirety of the probe sequence and extend beyond the probe sequence in one or more directions.

In some cases, a first probe with a first probe sequence capable of hybridizing with a first target region of the nucleic acid molecule may comprise a second probe sequence capable of hybridizing with a sequence of a nucleic acid barcode molecule, and a second probe capable of hybridizing with a second target region of the nucleic acid molecule may not comprise a sequence capable of hybridizing with a nucleic acid barcode molecule. In other cases, the second probe may also comprise a probe sequence capable of hybridizing with a sequence of a nucleic acid barcode molecule. The first nucleic acid barcode molecule to which a first probe hybridizes may be different from a second nucleic acid barcode molecule to which a second probe hybridizes. For example, the first and second nucleic acid barcode molecules may comprise one or more different binding sequences and/or different barcode sequences.

In some cases, a first probe with a first probe sequence capable of hybridizing with a first target region of the nucleic acid molecule may comprise a second probe sequence capable of hybridizing with a first sequence of a nucleic acid adaptor molecule. The nucleic acid adaptor molecule may comprise this first sequence and a second sequence that can hybridize with a first sequence of a nucleic acid barcode molecule. The nucleic acid adaptor molecule may also comprise a third sequence such as a primer region for downstream PCR, a barcode sequence, etc. The nucleic acid adaptor molecule may have any combination and derivatives or variants of the abovementioned sequences.

The barcode sequence of a nucleic acid barcode molecule may have any useful length and other characteristics (e.g., as described herein). The nucleic acid barcode molecule may be attached to a bead such as a gel bead (e.g., as described herein). The bead may be co-partitioned with the nucleic acid molecule or the cell comprising the nucleic acid molecule. The bead may comprise a plurality of nucleic acid barcode molecules that may be the same or different. The bead may comprise at least 10,000 nucleic acid barcode molecules attached thereto. For example, the bead may comprise at least 100,000, 1,000,000, or 10,000,000 nucleic acid barcode molecules attached thereto. In some cases, each nucleic acid barcode molecule of the plurality of nucleic acid barcode molecules may comprise a common barcode sequence. The nucleic acid barcode molecules may further comprise an additional barcode sequence that may be different for each nucleic acid barcode molecule attached to the bead. The plurality of nucleic acid barcode molecules may be releasably attached to the bead. The plurality of nucleic acid barcode molecules may be releasable from the bead upon application of a stimulus. Such a stimulus may be selected from the group consisting of a thermal stimulus, a photo stimulus, and a chemical stimulus. For example, the stimulus may be a reducing agent such as dithiothreitol. Application of a stimulus may result in one or more of (i) cleavage of a linkage between nucleic acid barcode molecules of the plurality of nucleic acid barcode molecules and the bead, and (ii) degradation or dissolution of the bead to release nucleic acid barcode molecules of the plurality of nucleic acid barcode molecules from the bead. In some cases, one or more nucleic acid barcode molecules may be released from the bead prior to hybridization of a binding sequence of a nucleic acid barcode molecule to a probe sequence of the probe hybridized to the nucleic acid molecule of interest. The one or more nucleic acid barcode molecules may be released from the bead within a partition including the bead and the nucleic acid molecule (or a cell comprising the nucleic acid molecule) and the probe. Releasing may take place before, after, or during hybridization of a probe sequence to a target region of the nucleic acid molecule.

FIG. 111 schematically illustrates a method of analyzing a nucleic acid molecule. Panel 111A shows a nucleic acid molecule 11100 comprising adjacent target regions 11102 and 11104. Nucleic acid molecule 11100 is an mRNA molecule comprising a polyA sequence at its 3' end. Probe 11106 comprises probe sequences 11108 and 11110 and probe 11114 comprises probe sequence 11116. Probe sequence 11108 of probe 11106 is complementary to target region 11102 and comprises reactive moiety 11112. Similarly, probe sequence 11116 of probe 11114 is complementary to target region 11104 and comprises reactive moiety 11118. Panel 111B shows probe sequence 11108 of probe 11106 hybridized to target region 11102 and probe sequence 11116 of probe 11114 hybridized to target region 11104. Reactive moiety 11112 of probe 11106 and reactive moiety 11118 of probe 11114 are adjacent to one another. Panel 111C shows linking moiety 11120 produced through a reaction of reactive moieties 11112 and 11118. Linked probes 11106 and 11114 together with nucleic acid molecule 11100 comprise a probe-linked nucleic acid molecule. Panel 111D shows hybridization of binding sequence 11124 of nucleic acid barcode molecule 11122 to probe sequence 11110 of probe 11106. Hybridization of these moieties yields a barcoded probe-linked nucleic acid molecule. Nucleic acid barcode molecule 11122 further comprises barcode sequence 11126 and binding sequence 11128. In some cases, probe 11114 may comprise an additional probe sequence 11117 (not shown). Probe sequence 11117 may hybridize to another nucleic acid barcode molecule or primer with comprising a sequence complementary to probe sequence 11117. In some cases, moieties 11112 and 11118 may not be reactive and can be ligated using an enzyme (e.g., SplintR, T4 ligase).

Following hybridization of a binding sequence of the nucleic acid barcode molecule to a probe sequence of a probe hybridized to a target region of the nucleic acid molecule, the probe may be extended from an end of the probe to an end of the nucleic acid barcode molecule. Extension may comprise the use of an enzyme (e.g., a polymerase) to add one or more nucleotides to the end of the probe. Extension may provide an extended nucleic acid molecule comprising sequences complementary to the first and second target regions of the nucleic acid molecule of interest, the barcode sequence, and one or more additional sequences of the nucleic acid barcode molecule such as one or more binding sequences. Appropriate conditions and or chemical agents (e.g., as described herein) may then be applied to denature the extended nucleic acid molecule from the nucleic acid barcode molecule and the target nucleic acid molecule. The nucleic acid barcode molecule and the target nucleic acid molecule may then undergo further analysis. For example, another set of probes may hybridize to the target regions of the nucleic acid molecule, and the nucleic acid barcode molecule may hybridize to a probe sequence of one of the additional probes. In some cases, hybridization of the nucleic acid barcode molecule to the first probe may precede hybridization of the first and second probes to the target region of the nucleic acid molecule. The extended nucleic acid molecule that has been released from the nucleic acid barcode molecule and the target nucleic acid molecule may be duplicated or amplified by, for example, one or more amplification reactions. The amplification reactions may comprise polymerase chain reactions (PCR) and may involve the use of one or more primers or polymerases. The extended nucleic acid molecule, or a complement thereof, may be detected via sequencing (e.g., as described herein).

FIG. 112 schematically illustrates a method of analyzing a nucleic acid molecule. Panel 112A shows extension of linked probes of a probe-linked nucleic acid molecule. mRNA molecule 11200 of the probe-linked nucleic acid molecule comprises adjacent target regions 11202 and 11204. Probe 11206 comprises probe sequence 11208 hybridized to target region 11202 and probe sequence 11210, while probe 11214 comprises probe sequence 11216 hybridized to target region 11204. Probes 11206 and 11214 are linked (e.g., ligated) via linking moiety or enzymatic ligation 11220. Binding sequence 11224 of nucleic acid barcode molecule 11222 is hybridized to probe sequence 11210 of probe 11206. Nucleic acid barcode molecule 11222 further comprises barcode sequence 11226 and binding sequence 11228. Extended nucleic acid molecule 11230 is hybridized to both mRNA molecule 11200 and nucleic acid barcode molecule 11222 and comprises probe sequences 11216, 11208, and 11210; a sequence 11232 that is complementary to barcode sequence 11226 of nucleic acid barcode molecule 11222; and a sequence 11234 that is complementary to binding sequence 11228 of nucleic acid barcode molecule 11222. Panel 112B shows denaturation of extended nucleic acid molecule 11230 from mRNA molecule 11200 and nucleic acid barcode molecule 11222. Panel 112C shows duplication or amplification of extended nucleic acid molecule 11230 to generate amplified product 11236. Amplified product 11236 comprises sequence 11238, which is complementary to sequence 11234 and the same or substantially the same as binding sequence 11228 of nucleic acid barcode molecule 11222; sequence 11240, which is complementary to sequence 11232 and the same or substantially the same as barcode sequence 11226 of nucleic acid barcode molecule 11222; sequence 11242, which is complementary to probe sequence 11210 and the same or substantially the same as binding sequence 11224 of nucleic acid barcode molecule 11222; sequence 11244, which is complementary to probe sequence 11208 and the same or substantially the same as target region 11202 of mRNA molecule 11200; and sequence 11246, which is complementary to probe sequence 11216 and the same or substantially the same as target region 11204 of mRNA molecule 11200.

In some cases, a first probe molecule used for analyzing a nucleic acid molecule comprises a first probe sequence and a second probe sequence, and a second probe molecule used for analyzing the nucleic acid molecule comprises a third probe sequence and a fourth probe sequence. FIG. 113 schematically illustrate a method of analyzing a nucleic acid molecule using such first and second probe molecules. Panel 113A shows a nucleic acid molecule 11300 comprising adjacent target regions 11302 and 11304. Nucleic acid molecule 11300 is an mRNA molecule comprising a polyA sequence at its 3' end. Probe 11306 comprises probe sequences 11308 and 11310 and probe 11314 comprises probe sequences 11316 and 11348. Probe sequence 11308 of probe 11306 is complementary to target region 11302 and comprises reactive moiety 11312. Similarly, probe sequence 11316 of probe 11314 is complementary to target region 11304 and comprises reactive moiety 11318. Panel 113B shows probe sequence 11308 of probe 11306 hybridized to target region 11302 and probe sequence 11316 of probe 11314 hybridized to target region 11304. Reactive moiety 11312 of probe 11306 and reactive moiety 11318 of probe 11314 are adjacent to one another. Panel 113C shows linking moiety 11320 produced through a reaction of reactive moieties 113113 and 11318. In some cases, moieties 11312 and 11318 are ligated using click chemistry, and in other cases, an enzyme (e.g., SplintR, T4 ligase) may be used. Linked probes 11306 and 11314 together with nucleic acid molecule 11300 comprise a probe-linked nucleic acid molecule. Panel 113D shows hybridization of binding sequence 11324 of nucleic acid barcode molecule 11322 to probe sequence 11310 of probe 11306 and hybridization of binding sequence 11352 of nucleic acid binding molecule 11350 to probe sequence 11348 of probe 11314. Hybridization of these moieties yields a barcoded probe-linked nucleic acid molecule. Nucleic acid barcode molecule 11322 further comprises barcode sequence 11326 and binding sequence 11328. Panel 113E shows extension of linked probes of the probe-linked nucleic acid molecule to form extended nucleic acid molecule 11330, which is hybridized to mRNA molecule 11300, nucleic acid binding molecule 11350, and nucleic acid barcode molecule 11322 and comprises probe sequences 11348, 11316, 11308, and 11310; a sequence 11332 that is complementary to barcode sequence 11326 of nucleic acid barcode molecule 11322; and a sequence 11334 that is complementary to binding sequence 11328 of nucleic acid barcode molecule 11322. Extended nucleic acid molecule 11330 may subsequently be decoupled (e.g., denatured) from mRNA molecule 11300 and subjected to one or more amplification or duplication reactions, as shown in Panel 113F. Amplification or duplication of extended nucleic acid molecule 11330 results in the generation of amplified product 11336, which comprises sequence 11338, which is complementary to sequence 11334 and the same or substantially the same as binding sequence 11328 of nucleic acid barcode molecule 11322; sequence 11340, which is complementary to sequence 11332 and the same or substantially the same as barcode sequence 11326 of nucleic acid barcode molecule 11322; sequence 11342, which is complementary to probe sequence 11310 and the same or substantially the same as binding sequence 11324 of nucleic acid barcode molecule 11322; sequence 11344, which is complementary to probe sequence 11308 and the same or substantially the same as target region 11302 of mRNA molecule 11300; sequence 11346, which is complementary to probe sequence 11316 and the same or substantially the same as target region 11304 of mRNA molecule 11300, and sequence 11354, which is complementary to probe sequence 11348 and the same or substantially the same as binding sequence 11352 of nucleic acid binding molecule 11350. In some cases, nucleic acid binding molecule 11350 and/or nucleic acid barcode molecule 11322 may further comprise one or more additional sequences such as a barcode sequence, unique molecular identifier (UMI), or other sequence. Amplification of extended nucleic acid molecule 11330 may comprise denaturing extended nucleic acid molecule 11330 from mRNA molecule 11300 and extending binding sequence 11352 to the end of sequence 11334 to generate amplified product 11336. Alternatively, or in addition, amplification of extended nucleic acid molecule 11330 may comprise denaturing extended nucleic acid molecule 11330 from mRNA molecule 11300 and extending nucleic acid barcode molecule 11322 to the end of probe sequence 11348 of probe 11314 to generate amplified product 11336. In either case, the denaturing and extending process may occur simultaneously. The two stands of amplified product 11336 may subsequently be separated by, for example, denaturing the double-stranded nucleic acid molecule to regenerate extended nucleic acid molecule 11330 and its complement. Amplification may then be repeated one or more times to, for example, generate a detectable species.

FIG. 117 schematically illustrates a method of ligating non-adjacent probes to form a probe-linked nucleic acid molecule. Panel 117A shows a nucleic acid molecule 11700 comprising non-adjacent target regions 11702 and 11704. Nucleic acid molecule 11700 is an mRNA molecule comprising a polyA sequence at its 3' end. Probe 11706 comprises probe sequences 11708 and 11710 and probe 11714 comprises probe sequences 117117 and 11718. Probe sequence 11708 of probe 11706 is complementary to target region 11702. Similarly, probe sequence 11716 of probe 11714 is complementary to target region 11704 and comprises a moiety 11718 onto which a polymerase may bind. Panel 117B shows probe sequence 11708 of probe 11706 hybridized to target region 11702 and probe sequence 11716 of probe 11714 hybridized to target region 11704. A polymerase 11720, such as Mu polymerase or DNA polymerase, extends probe 117117 by adding complementary ribonucleotides (e.g., ribonucleoside tri-phosphate (rNTP)) or deoxyribonucleotides (e.g., deoxyribonucleotide triphosphate (dNTP)), respectively. Panel 117C shows probes 11706 and extended probe 11714 as adjacent to one another. Panel 117D shows a ligation reaction of probe 11706 and extended probe 11714. Ligation may occur enzymatically, for example, by using a T4RNA ligase or a PBCV1 ligase, to form a probe-linked nucleic acid molecule 11722. Downstream analysis may subsequently be performed, such as barcoding and amplification, similar to as shown in Panels 113D-F in FIG. 113.

FIG. 118 schematically shows an alternative method barcoding nucleic acid probes using adaptor nucleic acid molecules. Panel 118A shows a nucleic acid molecule 11800 comprising a target region 11802. Nucleic acid molecule 11800 is an mRNA molecule comprising a polyA sequence at its 3' end. Probe 11806 comprises probe sequences 11808 and adaptor sequences 11810. Probe sequence 11808 of probe 11806 is complementary to target region 11802. Panel 118B shows probe sequence 11808 of probe 11806 hybridized to target region 11802. An adaptor nucleic acid molecule 11812 comprises a sequence 11814 that hybridizes with the adaptor sequence 11810 of the nucleic acid probe 11806, and modular sequences 11816, 11818. Modular sequences 11816, 11818 may comprise, for example, a PCR primer sequence, a barcode, a constant sequence, and/or any variants or derivatives thereof. Panel 118C schematically shows a method of barcoding the probe nucleic acid 11806. A barcode nucleic acid molecule 11820 comprises a hybridization sequence 11822 that hybridizes with the adaptor nucleic acid molecule 11812 and a barcode sequence 11824. Hybridization of the barcode nucleic acid molecule may occur prior to or during partitioning. Following hybridization, other nucleic acid reactions may be performed, such as extension using DNA polymerase, to generate double-stranded, barcoded, nucleic acid probes (not shown). Subsequent amplification, cleanup of primers, and sequencing may be performed.

In some cases, probe molecules that attach to the same target nucleic acid molecule may be linked to one another. For example, a single probe molecule (e.g., a probe nucleic acid molecule) may comprise (i) a first probe moiety at a first end that comprises a sequence complementary to a first target region of a nucleic acid molecule and (ii) a second probe moiety at a second end that comprises a sequence complementary to a second target region of the nucleic acid molecule that is adjacent to the first target region. A single probe molecule may comprise additional sequences, such as a sequencing primer binding site, or a primer site for downstream analysis, e.g., rolling circle amplification. Upon hybridization of the first and second probe moieties to the target nucleic acid molecule, the first and second probe moieties may be adjacent and the probe molecule and target nucleic acid molecule may form a circular nucleic acid product. The circular nucleic acid product may then be subjected to conditions sufficient for ligation of the nucleic acid product, forming a circular probe-linked nucleic acid molecule. Hybridization kinetics of a circular nucleic acid product may be substantially different from those of a corresponding linear product involving two disconnected probes. In some cases, the use of a single probe molecule comprising two probe moieties may result in enhanced sensitivity of a target region of a nucleic acid molecule. For example, the use of a single probe molecule comprising two probe moieties may result in an increased number of target nucleic acid molecules having two probe moieties attached thereto relative to the use of two disconnected probes. Circularization of nucleic acid moieties may also facilitate removal of unwanted nucleic acid species and unhybridized probes by permitting the use of exonucleases without affecting ligation products. In some cases, unwanted nucleic acid species and unhybridized probes may be removed from a solution or partition including a circular nucleic acid product subsequent to its formation. For example, a circular nucleic acid product may be formed in a solution, and unwanted and unhybridized materials removed from the solution prior to barcoding or other processing. In such an example, the circular nucleic acid product may then be partitioned with one of more materials including one or more nucleic acid barcode molecules (e.g., coupled to a bead, as described herein) or nucleic acid binding molecules to undergo further processing. Alternatively, a circular nucleic acid product may be formed within a partition and hybridize with a nucleic acid barcode molecule and/or nucleic acid binding molecule within the partition to generate a barcoded circular nucleic acid product. The barcoded circular nucleic acid product may then be released from the partition to undergo further processing. A circular nucleic acid product may be opened at any useful time. For example, the circular nucleic acid product may be open following removal of unwanted and unhybridized materials. Alternatively, the circular nucleic acid product may be opened subsequent to hybridization of a nucleic acid barcode molecule and/or nucleic acid binding molecule to the circular nucleic acid product to generate a barcoded circular nucleic acid product. In some cases, a circular nucleic acid product may be amplified by rolling circle amplification (RCA) prior or subsequent to partitioning of the circular nucleic acid product. The use of RCA may increase efficiency of a barcoding process by generating multiple targets from the same original ligation event. An RCA product may be less susceptible to loss prior to partitioning due to its large size. An RCA product may be digested within a partition prior to a barcoding process by hybridization of a complementary probe and a restriction enzyme or other targeted endonuclease. RCA may be used in combination with or as an alternative to PCR.

FIG. 114 schematically illustrates an example of nucleic acid molecule analysis involving a circular nucleic acid product. Panel A shows probe molecule 11405 comprising probe moiety 11406 at a first end and probe moiety 11414 at a second end. Probe moieties 11406 and 11414 are linked by linking sequence 11422. Linking sequence 11422 may comprise one or more nucleic acid sequences and/or other moieties (amino acids, peptides, proteins, PEG moieties, hydrocarbon chains, or other linkers). In some instances, linking sequence 11422 may also comprise primer sequence 11423 that may comprise a PCR primer, a spacer, a sequencing primer-binding sequence, and any combinations or derivatives thereof. Probe moiety 11406 comprises probe sequence 11410 and probe sequence 11408, which has a sequence complementary to target region 11402 of nucleic acid molecule 11400. Similarly, probe moiety 11414 comprises probe sequence 11418 and probe sequence 11416, which has a sequence complementary to target region 11404 of nucleic acid molecule 11400. Probe moiety 11408 may comprise reactive moiety 11412, and probe moiety 11416 may comprise reactive moiety 11420. When probe moieties 11406 and 11414 are hybridized to nucleic acid molecule 11400, reactive moieties 11412 and 11420 may be adjacent. Panel 114B shows ligation (e.g., click chemistry, enzymatic ligation) of reactive moieties 11412 and 11420 to form linking moiety 11424. Ligation of reactive moieties 11412 and 11420 closes the circle of the circular nucleic acid product comprising probe molecule 11405. As described elsewhere herein, linking moiety 11424 may comprise a triazole moiety generated by reaction of an alkyne moiety and an azide moiety. The ligation reaction of reactive moieties 11412 and 11420 may involve the use of a catalyst such as a copper species or a strained alkene and may take place within or outside of a partition. Panel 114C shows hybridization of sequence 11428 of nucleic acid barcode molecule 11426 to probe sequence 11410 of probe molecule 11405 and hybridization of sequence 11436 of nucleic acid binding molecule 11434 to probe sequence 11418 of probe molecule 11405. These hybridization processes may take place within partitions (e.g., as described herein) and may precede rolling circle amplification and/or opening of the circular nucleic acid product. Alternatively, the circular nucleic acid product may be opened to provide a linear nucleic acid product comprising sequences 11438, 11410, 11408, 11416, 11418, and 11440 prior to hybridization of a nucleic acid barcode molecule and/or a nucleic acid binding molecule, as shown in Panel 114D.

In some cases, reverse transcription may be performed to provide complementary deoxyribonucleic acid (cDNA) molecules, as described herein. However, the presently disclosed method may provide for duplication of a target region of an mRNA molecule of interest without the need for reverse transcription, which may be highly prone to error. Accordingly, the presently disclosed method may be useful in transcriptome analysis methods.

One or more processes of the presently disclosed method may be carried out within a partition (e.g., as described herein). For example, one or more processes selected from the group consisting of lysis, permeabilization, denaturation, hybridization, extension, duplication, and amplification of one or more components of a sample comprising the nucleic acid molecule may be performed within a partition. In some cases, multiple processes are carried out within a partition.

The nucleic acid molecule or a derivative thereof (e.g., a probe-linked nucleic acid molecule, a nucleic acid molecule having one or more probes hybridized thereto, a barcoded probe-linked nucleic acid molecule, or an extended nucleic acid molecule or complement thereof) or a cell comprising the nucleic acid molecule or a derivative thereof (e.g., a cell bead), as well as additional components (e.g., probes, nucleic acid barcode molecules, and reagents), may be provided within a partition. In some cases, the probes may be hybridized to the target regions of the nucleic acid molecule and linked or ligated to one another inside a partition. Alternatively, the probes may be hybridized to the target regions of the nucleic acid molecule and linked or ligated to one another outside of a partition. For example, the nucleic acid molecule or a cell comprising the nucleic acid molecule may be provided in a container other than a partition and undergo hybridization of the probes within the initial container or another container that is not a partition. In some cases, a cell may be permeabilized (e.g., as described herein) to provide access to the nucleic acid molecule of interest therein and hybridization of the probes to the target regions of the nucleic acid molecule of interest may take place within the cell. Ligation of the probes hybridized to the target regions of the nucleic acid molecule may then be initiated (e.g., under suitable conditions and through introduction of an appropriate catalyst) to provide a probe-linked nucleic acid molecule. For example, reaction between a first probe comprising an azide moiety and a second probe comprising an alkyne moiety may be catalyzed by a copper catalyst. Excess probes and catalyst may then be washed away and the cell may be partitioned (e.g., as described herein) for further analysis and processing. In another example, ligation of the hybridized probes may take place within a partition. Extension, denaturation, and/or amplification processes may also take place within a partition.

The nucleic acid molecule or a derivative thereof (e.g., a probe-linked nucleic acid molecule, a nucleic acid molecule having one or more probes hybridized thereto, a barcoded probe-linked nucleic acid molecule, or an extended nucleic acid molecule or complement thereof) or the cell comprising the nucleic acid molecule or a derivative thereof (e.g., a cell bead) may be co-partitioned with one or more reagents (e.g., as described herein) at any useful stage of the method. For example, the nucleic acid molecule or a derivative thereof contained within a cell may be co-partitioned with one or more reagents following generation of the probe-linked nucleic acid molecule. Similarly, the nucleic acid molecule or a derivative thereof or a cell comprising the nucleic acid molecule or a derivative thereof may be released from a partition at any useful stage of the method. For example, the nucleic acid molecule or a derivative thereof or a cell comprising the nucleic acid molecule or a derivative thereof may be released from the partition subsequent to hybridization of a binding sequence of a nucleic acid barcode molecule to a probe-linked nucleic acid molecule (e.g., to a sequence of a probe hybridized to the target region of the nucleic acid molecule) to provide a barcoded probe-linked nucleic acid molecule. In another example, release from the partition may take place subsequent to extension of the barcoded probe-linked nucleic acid molecule to provide an extended nucleic acid molecule that comprises a sequence complementary to the barcode sequence of a nucleic acid barcode molecule and one or more sequences complementary to one or more target regions of the nucleic acid molecule. Alternatively, the nucleic acid molecule or a derivative thereof or a cell comprising the nucleic acid molecule or a derivative thereof may be released from a partition subsequent to denaturation of an extended nucleic acid molecule from the nucleic acid molecule and the nucleic acid barcode molecule. Duplication and/or amplification of the extended nucleic acid molecule may then be carried out within a solution. In some cases, such a solution may comprise additional extended nucleic acid molecules and/or complements thereof generated through the same process carried out in different partitions. Each extended nucleic acid molecule or complement thereof (e.g., amplified product) may comprise a different barcode sequence or a sequence complementary to a different barcode sequence. In this instance, the solution may be a pooled mixture comprising the contents of two or more partitions (e.g., droplets).

One or more additional components such as one or more reagents may be co-partitioned with a nucleic acid molecule or derivative thereof or a cell comprising a nucleic acid molecule or a derivative thereof (e.g., as described in the preceding section).

In some cases, the methods described herein may be used to facilitate gene expression analysis. For example, a target nucleic acid molecule comprising a hybrid gene may be contacted by a plurality of different probes. One or more probes of the plurality of probes may have a sequence complementary to a first portion of the hybrid gene (e.g., a first target region), and one or more probes of the plurality of probes may have a sequence complementary to a second portion of the hybrid gene (e.g., a second target region) in proximity to the first portion of the hybrid gene. The two probes may each comprise a reactive moiety such that, upon hybridization to the hybrid gene and exposure to appropriate reaction conditions, the two probes may ligate to one another. The solution including the probe-ligated hybrid gene may undergo processing to remove unhybridized probes and may be partitioned with one or more reagents including one or more nucleic acid barcode molecules. A nucleic acid barcode molecule included within the partition including the probe-ligated hybrid gene may have a sequence complementary to a sequence of a probe hybridized to the hybrid gene and may hybridize thereto to generate a barcoded probe-ligated hybrid gene. Subsequent extension and amplification may take place within or outside of the partition. Following amplification to generate an amplified product comprising sequences of portions of the hybrid gene, or complements thereof, the amplified product may be detected using sequencing. Resultant sequence reads may be used to determine the components of the hybrid gene.

The presently disclosed method may be applied to a single nucleic acid molecule or a plurality of nucleic acid molecules. A method of analyzing a sample comprising a nucleic acid molecule may comprise providing a plurality of nucleic acid molecules (e.g., RNA molecules), where each nucleic acid molecule comprises a first target region and a second target region, a plurality of first probes, and a plurality of second probes. In some cases, one or more target regions of nucleic acid molecules of the plurality of nucleic acid molecules may comprise the same sequence. The first and second target regions of a nucleic acid molecule of the plurality of nucleic acid molecules may be adjacent to one another. The plurality of first probes may each comprise a first probe sequence complementary to the sequence of a first target region of a nucleic acid molecule of the plurality of nucleic acid molecules as well as a second probe sequence. A first probe sequence of a first probe of the plurality of first probes may comprise a first reactive moiety. One or more first probes of the plurality of first probes may comprise the same first probe sequence and/or the same second probe sequence. The plurality of second probes may each comprise a third probe sequence complementary to the sequence of a second target region of a nucleic acid molecule of the plurality of nucleic acid molecules. The plurality of second probes may further comprise a fourth probe sequence. A third probe sequence of a second probe of the plurality of second probes may comprise a second reactive moiety. One or more probes of the second probes of the plurality of second probes may comprise the same third probe sequence and/or, if present, the same fourth probe sequence. A first probe sequence of a first probe of the plurality of first probes may hybridize to first target region of a nucleic acid molecule of the plurality of nucleic acid molecules. A third probe sequence of a second probe of the plurality of second probes may hybridize to the second target region of a nucleic acid molecule of the plurality of nucleic acid molecules. The first and third probe sequences hybridized to the first and second target regions, respectively, of a nucleic acid molecule of the plurality of nucleic acid molecules may be adjacent to one another such that a first reactive moiety of the first probe sequence is adjacent to a second reactive moiety of the third probe sequence. The first and second reactive moieties of the first and second probes hybridized to nucleic acid molecules of the plurality of nucleic acid molecules may react to provide a plurality of probe-linked nucleic acid molecules. A binding sequence of a nucleic acid barcode molecule of a plurality of nucleic acid barcode molecules may hybridize to the second probe sequence of a first probe of the plurality of first probes that is hybridized to a first target region of a nucleic acid molecule of a plurality of nucleic acid molecules or a probe-linked nucleic acid molecule of the plurality of probe-linked nucleic acid molecules. Each nucleic acid barcode molecule of the plurality of nucleic acid barcode molecules may comprise a barcode sequence and a second binding sequence. The barcode sequence of each nucleic acid barcode molecule of the plurality of nucleic acid barcode molecules may be the same or different. Following hybridization of a binding sequence of a nucleic acid barcode molecule of the plurality of nucleic acid barcode molecules to a second probe sequence of a first probe of the plurality of first probes that is hybridized to a first target region of a nucleic acid molecule of the plurality of nucleic acid molecules or a probe-linked nucleic acid molecule of the plurality of probe-linked nucleic acid molecules, each first probe of the plurality of hybridized probes may then be extended from an end of the probe to an end of the nucleic acid barcode molecule to which it is hybridized (e.g., an end of the second binding sequence of the nucleic acid barcode molecule). A plurality of extended nucleic acid molecules may thereby be created, where each extended nucleic acid molecule of the plurality of extended nucleic acid molecules comprises a sequence complementary to the first target region of a nucleic acid molecule of the plurality of nucleic acid molecules, a sequence complementary to the second target region of a nucleic acid molecule of the plurality of nucleic acid molecules, a second probe sequence of a first probe of the plurality of first probes, a sequence complementary to a barcode sequence of a nucleic acid barcode molecule of the plurality of nucleic acid barcode molecules, and one or more sequences complementary to one or more additional sequences (e.g., binding or barcode sequences) of a nucleic acid barcode molecule of the plurality of nucleic acid barcode molecules.

In some cases, one or more processes described above may be performed within a partition. For example, each nucleic acid molecule of the plurality of nucleic acid molecules may be provided within a different partition. This may be achieved by partitioning a plurality of cells comprising the plurality of nucleic acid molecules within a plurality of separate partitions, where each cell comprises a target nucleic acid molecule and each partition of a plurality of different partitions of the plurality of separate partitions comprises a single cell. The plurality of cells may be partitioned prior or subsequent to hybridization of probes to target regions of the nucleic acid molecules of interest included therein and linking of the probes to provide probe-linked nucleic acid molecules. Access to a target nucleic acid molecule or derivative thereof (e.g., as described herein) contained within a cell in a partition may be provided by lysing or permeabilizing the cell (e.g., as described herein). Nucleic acid barcode molecules provided within each partition of the plurality of different partitions of the plurality of separate partitions may be provided attached to beads. For example, each partition of the plurality of different partitions of the plurality of separate partitions may comprise a bead comprising a plurality of nucleic acid barcode molecules attached thereto (e.g., as described herein). The plurality of nucleic acid barcode molecules attached to each bead may comprise a different barcode sequence, such that each partition of the plurality of different partitions of the plurality of separate partitions comprises a different barcode sequence. Upon release of components from the plurality of different partitions of the plurality of separate partitions (e.g., following extension of each probe), each extended nucleic acid molecule may comprise a sequence complementary to a different barcode sequence, such that each extended nucleic acid molecule can be traced to a given partition and, in some cases, a given cell.

FIG. 115 illustrates a sample workflow for a method of analyzing a plurality of nucleic acid molecules comprising chemical-ligation mediated amplification. Nucleic acid molecules 11504, 11506, and 11508 are provided within container 11502. Each nucleic acid molecule comprises a first target region and a second target region indicated by dashed lines. The first target regions of each nucleic acid molecule may be the same or different. Similarly, the second target regions of each nucleic acid molecule may be the same or different. A plurality of first probes 11503 and a plurality of second probes 11505 may be provided in container 11502. First probes of the plurality of first probes 11503 may comprise a first probe sequence that is complementary to the first target region of nucleic acid molecule 11504, 11506, and/or 11508 and a second probe sequence. First probe sequences of the plurality of first probes 11503 may comprise a first reactive moiety. Second probes of the plurality of second probes 11505 may comprise a third probe sequence that is complementary to the second target region of nucleic acid molecule 11504, 11506, and/or 11508. Third probe sequences of the plurality of second probes 11505 may comprise a second reactive moiety. A first probe sequence of first probes of the plurality of first probes 11503 may hybridize to the first target regions of nucleic acid molecules 11504, 11506, and 11508. Similarly, a second probe sequence of second probes of the plurality of second probes 11505 may hybridize to the second target regions of nucleic acid molecules 11504, 11506, and 11508. The first and second reactive moieties of the first and third probe sequences may then react to provide probe-linked nucleic acid molecules 11511, 11513, and 11515.

In process 11510, probe-linked nucleic acid molecules 11511, 11513, and 11515 may be co-partitioned with beads 11518, 11520, and 11522 into separate droplets 11512, 11514, and 11516 such that each droplet includes a single probe-linked nucleic acid molecule and a single bead. Each bead may comprise a plurality of nucleic acid barcode molecules attached thereto. Bead 11518 comprises nucleic acid barcode molecule 11524, bead 11520 comprises nucleic acid barcode molecule 11526, and bead 11522 comprises nucleic acid barcode molecule 11528. Nucleic acid barcode molecules 11524, 11526, and 11528 each comprise first and second binding sequences and a barcode sequence. The barcode sequences of nucleic acid barcode molecules 11524, 11526, and 11528 are different such that each droplet comprises a different barcode sequence.

In process 11530, nucleic acid barcode molecules 11524, 11526, and 11528 are released from their respective beads (e.g., by application of a stimulus that degrades or dissolves the bead) within their respective droplets. A binding sequence of nucleic acid barcode molecules 11524, 11526, and 11528 hybridizes to the second probe sequence of probe-linked nucleic acid molecules 11511, 11513, and 11515, respectively, to provide a barcoded probe-linked nucleic acid molecule within each droplet. The barcoded probe-linked nucleic acid molecule within each droplet then undergoes extension to provide complexed extended nucleic acid molecules 11532, 11534, and 11536 comprising extended nucleic acid molecules 11533, 11535, and 11537.

Extended nucleic acid molecules 11533, 11535, and 11537 comprise sequences complementary to a barcode sequence and the sequences of the target regions of the nucleic acid molecule from which they derive. For example, extended nucleic acid molecule 11533 comprises sequences complementary to the sequences of the target regions of nucleic acid molecule 11504 and a sequence complementary to the barcode sequence of nucleic acid barcode molecule 11524.

In process 11538, the contents of droplets 11512, 11514, and 11516 are pooled to provide a pooled mixture 11540 comprising complexed extended nucleic acid molecules 11532, 11534, and 11536. Complexed extended nucleic acid molecules 11532, 11534, and 11536 may then be denatured from the nucleic acid molecule and nucleic acid barcode molecule to which they are hybridized to provide extended nucleic acid molecules 11533, 11535, and 11537. Extended nucleic acid molecules 11533, 11535, and 11537 may then be amplified to provide amplified products corresponding to each extended nucleic acid molecule. The amplified products will comprise sequences that are the same or substantially the same as the barcode sequence and sequences of the target regions of the nucleic acid molecule from which they derive. For example, the amplified product corresponding to extended nucleic acid molecule 11533 comprises sequences that are the same or substantially the same as the sequences of the target regions of nucleic acid molecule 11504 and a sequence that is the same or substantially the same as the barcode sequence of nucleic acid barcode molecule 11524. Because each extended nucleic acid molecule and each amplified product comprises a different barcode sequence or complement thereof, the extended nucleic acid molecules and amplified products can be traced back to particular nucleic acid molecules and, in some cases, to particular cells. This barcoding method may therefore facilitate rapid analysis of nucleic acid molecules through, for example, sequencing without the need for reverse transcription.

In one aspect, the present invention provides methods of analysis that target specific sequences (e.g., RNA sequences) with a molecular inversion probe. In one embodiment, the molecular inversion probe can form a circularized nucleic acid molecule upon hybridization to target specific sequences.

FIG. 119 illustrates an example workflow for a method of analyzing a plurality of nucleic acid molecules comprising enzymatic ligation-mediated amplification. 11900 is a fixed and permeabilized cell comprising nucleic acid molecules 11902. Each nucleic acid molecule 11902 comprises a first target region and a second target region. The first target regions of each nucleic acid molecule may be the same or different. Similarly, the second target regions of each nucleic acid molecule may be the same or different. The first and second target regions of each nucleic acid molecule may be adjacent to one another. A plurality of first probes 11904 comprising first and second probe sequences that hybridize with the first and second target regions, respectively, may be introduced into the cell 11900. The probes 11904 can be provided as linear molecules and may comprise adapter sequences such as a PCR primer region, a sequencing site primer region, and/or a spacer region, as described elsewhere herein. The first probe sequence of the plurality of probes 11904 may hybridize to the first target regions of nucleic acid molecules 11902. Upon hybridization of the probes to the target regions, a circularized nucleic acid molecule may be formed. Similarly, the second probe sequence of the plurality of probes 11904 may hybridize to the second target regions of nucleic acid molecules 11902. In some cases, the first probe sequence and the second target probe sequence are adjacent to each other. In some cases, they are non-adjacent and may be ligated using polymerases, e.g., Mu polymerase, as described elsewhere herein. In some cases, the first and second probe sequences of probes 11904 comprise reactive moieties. Following hybridization, excess, unhybridized probes may be removed via a wash step 11905. The first and second probe sequences may then be connected via introduction of enzymes (e.g., polymerases, ligases) or through a chemical reaction (e.g., click chemistry of reactive moieties), generating a probe-linked nucleic acid molecule 11906.

In process 11908, probe-linked nucleic acid molecules 11906 within cell 11900 may be co-partitioned with barcode nucleic acid molecules 11910. The barcode nucleic acid molecules may comprise adaptor regions including, but not limited to, a unique molecular identifier sequence, a PCR primer sequence, a spacer sequence, and sequencing site primer region. The barcode nucleic acid molecules may be attached to beads (not shown). Each bead may comprise a plurality of nucleic acid barcode molecules attached thereto. A binding sequence of nucleic acid barcode molecule 11910 hybridizes to a sequence of the probe 11904 of the probe-linked nucleic acid molecules 11906, to provide a barcoded probe-linked nucleic acid molecule 11912. The barcoded probe-linked nucleic acid molecule 11912 then undergoes a nucleic acid reaction 11913 such as amplification, e.g., Phi29-based rolling circle amplification, to provide barcoded amplicons of interest 11914, which comprise sequences complementary to the sequences of the target regions of nucleic acid molecule 11902, a sequence complementary to the barcode sequence of nucleic acid barcode molecule 11910, and any adaptor sequences of probe 11904.

In process 11916, the contents of the one or more partitions are pooled. Barcoded amplicons of interest 11914 may then be subjected to conditions sufficient for library preparation. In some cases, the barcoded amplicons of interest may be subjected to nucleic acid reactions, such as amplification (e.g., PCR). The amplified products will comprise sequences that are the same or substantially the same as the barcode sequence and sequences of the target regions of the nucleic acid molecule from which they derive. The amplified products can be traced back to particular nucleic acid molecules and, in some cases, to particular cells. This barcoding method may therefore facilitate rapid analysis of nucleic acid molecules through, for example, sequencing without the need for reverse transcription.

FIG. 120 illustrates an example workflow for a method of analyzing a plurality of nucleic acid molecules comprising chemical ligation-mediated amplification of nucleic acids in cell beads. 12000 is a cell bead comprising dissolvable nucleic acid molecule capture moieties 12001. These moieties may be thioacrydite-conjugated nucleic acid molecules that are bound to the gel bead matrix. Within the cell bead are nucleic acid molecules 12002, which comprise a target region. A plurality of first probes 12004 comprising a probe sequence that hybridizes with the target region, respectively, may be introduced into the cell bead 12000. The probes 12004 may additionally comprise adapter sequences such as a PCR primer region, a sequencing site primer region, and/or a spacer region, as described elsewhere herein. The probes 12004 may also comprise a reactive moiety 12003. Following hybridization, excess, unhybridized probes may be removed via a wash step 12005.

In process 12008, the cell bead 12000 comprising nucleic acid molecules 12002 is co-partitioned with barcode nucleic acid molecules 12010 which comprise a reactive moiety. The partition comprises conditions sufficient to release the nucleic acid molecules 12002 from the cell bead matrix. In some cases, a reducing agent such as DTT may be used to release the nucleic acid molecules from the cell bead into the partition. The barcode nucleic acid molecules may be attached to beads (not shown). Each bead may comprise a plurality of nucleic acid barcode molecules attached thereto. The partition may comprise conditions sufficient to release the nucleic acid barcode molecules from the beads into the partition. The barcode nucleic acid molecule 12010 may associate with the probe 12004 that is hybridized to the nucleic acid molecule 12002. The barcode nucleic acid molecule 12010 and the probe 12004 may then be ligated, e.g., via click chemistry of the reactive moieties on the barcode nucleic acid molecule and the reactive moiety on the probe 12004, to provide a barcoded, probe-linked nucleic acid molecule 12012. Reaction yield may be enhanced by incorporating splint nucleic acid sequences that hybridize with the spacer adapter sequences. For example, the barcode nucleic acid molecule 12010 may comprise a sequence (e.g., overhang sequence, not shown) that may hybridize with an adapter sequence (e.g., spacer sequence) on the probe 12004. Following hybridization, the reactive moieties on the barcode nucleic acid molecule 12010 and the reactive moiety on the probe 12004 may be ligated to provide a barcoded, probe-linked nucleic acid molecule. In other non-limiting examples, the barcode nucleic acid molecule 12010 may be partially double-stranded and comprise a sequence (e.g., overhang sequence) to form a splint nucleic acid sequence that can partially hybridize with the probe 12004 and be ligated to provide a barcoded, probe-linked nucleic acid molecule that is partially double-stranded.

In process 12016, the contents of the one or more partitions are pooled. The barcoded probe-linked nucleic acid molecules 12012 may then be subjected to conditions sufficient for library preparation. In some cases, the barcoded probe-linked nucleic acid molecules are cleaned up. In a non-limiting example of cleanup, samples may be enriched or purified via a magnetic-based pulldown assay of the of nucleic acid molecules. In some cases, the cleanup process may allow for size selection of nucleic acid molecules. In some cases, the probe-linked nucleic acid molecules may be and subjected to nucleic acid reactions, such as amplification (e.g., PCR). The amplified products will comprise sequences that are the same or substantially the same as the barcode sequence and sequences of the target regions of the nucleic acid molecule from which they derive. The amplified products can be traced back to particular nucleic acid molecules and, in some cases, to particular cells. This barcoding method may therefore facilitate rapid analysis of nucleic acid molecules through, for example, sequencing without the need for reverse transcription.

An additional example of a barcode oligonucleotide for use in RNA analysis, including cellular RNA analysis is shown in FIG. 27B. As shown, the overall oligonucleotide 2722 is coupled to a bead 2724 by a releasable linkage 2726, such as a disulfide linker. The oligonucleotide may include functional sequences that are used in subsequent processing, such as functional sequence 2728, which may include a sequencer specific flow cell attachment sequence, e.g., a P5 sequence, as well as functional sequence 2730, which may include sequencing primer sequences, e.g., a R1 primer binding site. In some cases, sequence 2728 is a P7 sequence and sequence 2730 is a R2 primer binding site. A barcode sequence 2732 is included within the structure for use in barcoding the sample RNA. A priming sequence 2734 (e.g., a random priming sequence) can also be included in the oligonucleotide structure, e.g., a random hexamer. An additional sequence segment 2736 may be provided within the oligonucleotide sequence. In some cases, this additional sequence provides a unique molecular identifier (UMI) sequence segment, as described elsewhere herein. As will be appreciated, although shown as a single oligonucleotide tethered to the surface of a bead, individual beads can include tens to hundreds of thousands or millions of individual oligonucleotide molecules (e.g., at least about 10,000, 50,000, 100,000, 500,000, 1,000,000 or 10,000,000 oligonucleotide molecules), where the barcode segment can be constant or relatively constant for a given bead, but where the variable or unique sequence segment will vary across an individual bead. In an example method of cellular mRNA analysis using the barcode oligonucleotide of FIG. 27B, a cell is co-partitioned along with a barcode bearing bead and additional reagents such as reverse transcriptase, a reducing agent and dNTPs into a partition (e.g., a droplet in an emulsion). The cell is lysed while the barcoded oligonucleotides are released from the bead (e.g., via the action of the reducing agent). In some cases, sequence 2728 is a P7 sequence and sequence 2730 is a R2 primer binding site. In other cases, sequence 2728 is a P5 sequence and sequence 2730 is a R1 primer binding site. The priming sequence 2734 of random hexamers can randomly hybridize cellular mRNA. The random hexamer sequence can then be extended in a reverse transcription reaction using mRNA from the cell as a template to produce a cDNA complementary to the mRNA and also includes each of the sequence segments 2728, 2732, 2730, 2736, and 2734 of the barcode oligonucleotide. Subsequent operations may include purification (e.g., via solid phase reversible immobilization (SPRI)), further processing (shearing, ligation of functional sequences, and subsequent amplification (e.g., via PCR)), and these operations may occur in bulk (e.g., outside the partition). In the case where a partition is a droplet in an emulsion, the emulsion can be broken and the contents of the droplet pooled for additional operations. Additional reagents that may be co-partitioned along with the barcode bearing bead may include oligonucleotides to block ribosomal RNA (rRNA) and nucleases to digest genomic DNA and cDNA from cells. Alternatively, rRNA removal agents may be applied during additional processing operations. The configuration of the constructs generated by such a method can help minimize (or avoid) sequencing of the poly-T sequence during sequencing.

The single cell analysis methods described herein may also be useful in the analysis of the whole transcriptome. Referring back to the barcode of FIG. 27B, the priming sequence 2734 may be a random N-mer. In some cases, sequence 2728 is a P7 sequence and sequence 2730 is a R2 primer binding site. In other cases, sequence 2728 is a P5 sequence and sequence 2730 is a R1 primer binding site. In an example method of whole transcriptome analysis using this barcode, the individual cell is co-partitioned along with a barcode bearing bead, poly-T sequence, and other reagents such as reverse transcriptase, polymerase, a reducing agent and dNTPs into a partition (e.g., droplet in an emulsion). In an operation of this method, the cell is lysed while the barcoded oligonucleotides are released from the bead (e.g., via the action of the reducing agent) and the poly-T sequence hybridizes to the poly-A tail of cellular mRNA. In a reverse transcription reaction using the mRNA as template, cDNAs of cellular mRNA can be produced. The RNA can then be degraded with an RNase. The priming sequence 2734 in the barcoded oligonucleotide can then randomly hybridize to the cDNAs. The oligonucleotides can be extended using polymerase enzymes and other extension reagents co-partitioned with the bead and cell to generate amplification products (e.g., barcoded fragments). The barcoded nucleic acid fragments may, in some cases subjected to further processing (e.g., amplification, addition of additional sequences, clean up processes, etc. as described elsewhere herein) characterized, e.g., through sequence analysis. In this operation, sequencing signals can come from full length RNA.

In an example method, the barcode sequence can be appended to the 3' end of the template polynucleotide sequence (e.g., mRNA). Such configuration may be useful, for example, if the sequence the 3' end of the template polynucleotide is to be analyzed. In some embodiments, the barcode sequence can be appended to the 5' end of a template polynucleotide sequence (e.g., mRNA). Such configuration may be useful, for example, if the sequence at the 5' end of the template polynucleotide is to be analyzed. In some embodiments, a barcode sequence can be appended to both the 3' end and the 5' end of a template polynucleotide sequence (e.g., mRNA). Such configuration may be useful, for example, if sequence at both the 5' end of and the 3' end of the template polynucleotide is to be analyzed.

In another aspect, a partition comprises a cell co-partitioned with a primer having a sequence towards a 3' end that hybridizes to the template polynucleotide, a template switching oligonucleotide having a first predefined sequence towards a 5' end, and a microcapsule, such as a bead, having barcoded oligonucleotides releasably coupled thereto. In some embodiments, the oligonucleotides coupled to the bead include barcode sequences that are identical (e.g., all oligonucleotides sharing the same barcode sequence). In some aspects, the oligonucleotides coupled to the beads additionally include unique molecular identifier (UMI) sequence segments (e.g., all oligonucleotides having different unique molecular identifier sequences).

FIG. 11A shows a barcoded oligonucleotide coupled to a bead. As shown, the overall oligonucleotide 1102 is coupled to a bead 1104 by a releasable linkage 1106, such as a disulfide linker. The oligonucleotide may include functional sequences that are useful for subsequent processing, such as functional sequence 1108, which may include a sequencer specific flow cell attachment sequence, e.g., a P5 sequence, as well as functional sequence 1110, which may include sequencing primer sequences, e.g., a R1 primer binding site. In some cases, sequence 1108 is a P7 sequence and sequence 1110 is a R2 primer binding site. A barcode sequence 1112 can be included within the structure for use in barcoding the template polynucleotide. The functional sequences may be selected for compatibility with a variety of different sequencing systems, e.g., 454 Sequencing, Ion Torrent Proton or PGM, Illumina X10, etc., and the requirements thereof. In some cases, the barcode sequence 1112, functional sequences 1108 (e.g., flow cell attachment sequence) and 1110 (e.g., sequencing primer sequences) may be common to all of the oligonucleotides attached to a given bead. The barcoded oligonucleotide can also comprise a sequence 1116 to facilitate template switching (e.g., a polyG sequence). In some cases, the additional sequence provides a unique molecular identifier (UMI) sequence segment, as described elsewhere herein.

Although shown as a single oligonucleotide tethered to the surface of a bead, individual beads can include tens to hundreds of thousands or millions of individual oligonucleotide molecules (e.g., at least about 10,000, 50,000, 100,000, 500,000, 1,000,000 or 10,000,000 oligonucleotide molecules), where the barcode sequence can be constant or relatively constant for a given bead.

In an example method of cellular polynucleotide analysis using the barcode oligonucleotide of FIG. 11A, a cell is co-partitioned along with a bead bearing a barcoded oligonucleotide and additional reagents such as reverse transcriptase, primers, oligonucleotides (e.g., template switching oligonucleotides), dNTPs, and reducing agent into a partition (e.g., a droplet in an emulsion). Within the partition, the cell can be lysed to yield a plurality of template polynucleotides (e.g., DNA such as genomic DNA, RNA such as mRNA, etc). In some cases, the cell is lysed using lysis reagents that are co-partitioned with the cell.

Where the bead is a degradable or disruptable bead, the barcoded oligonucleotide can be released from the bead following the application of stimulus as previously described. Following release from the bead, the barcoded oligonucleotide can be present in the partition at any suitable concentration. In some embodiments, the barcoded oligonucleotide is present in the partition at a concentration that is suitable for generating a sufficient yield of amplification products for downstream processing and analysis, including, but not limited to, sequencing adaptor attachment and sequencing analysis. In some embodiments, the concentration of the barcoded oligonucleotide is limited by the loading capacity of the barcode bearing bead, or the amount of oligonucleotides deliverable by the bead.

The template switching oligonucleotide, which can be co-partitioned with the cell, bead bearing barcoded oligonucleotides, etc, can be present in the partition at any suitable concentration. In some embodiments, the template switching oligonucleotide is present in the partition at a concentration that is suitable for efficient template switching during an amplification reaction. The concentration of the template switching oligonucleotide can be dependent on the reagents used for droplet generation. In some embodiments, the template switching oligonucleotide is among a plurality of template switching oligonucleotides.

In some embodiments, the barcoded oligonucleotide and template switching oligonucleotide are present in the partition at similar concentrations. In some embodiments, the barcoded oligonucleotide and template switching oligonucleotides may be present in proportions reflective of the amount of amplification products to be generated using each oligonucleotide. In some embodiments, the template switching oligonucleotide is present in the partition at a greater concentration than the barcoded oligonucleotide. This difference in concentration can be due to limitations on the capacity of the barcode bearing bead. In some embodiments, the concentration of the template switching oligonucleotide in the reaction volume is at least 2, 5, 10, 20, 50, 100, or 200 times that of the concentration of the barcoded oligonucleotide in the same reaction volume when the barcoded oligonucleotide is free in the partition (e.g., not attached to the bead).

As illustrated in FIGS. 11A-B, a reaction mixture comprising a template polynucleotide from a cell 1120 and (i) the primer 1124 having a sequence towards a 3' end that hybridizes to the template polynucleotide (e.g., polyT) and (ii) a template switching oligonucleotide 1126 that comprises a first predefined sequence 1110 towards a 5' end can be subjected to an amplification reaction to yield a first amplification product. In some cases, the template polynucleotide is an mRNA with a polyA tail and the primer that hybridizes to the template polynucleotide comprises a polyT sequence towards a 3' end, which is complementary to the polyA segment. The first predefined sequence can comprise at least one of an adaptor sequence, a barcode sequence, a unique molecular identifier (UMI) sequence, a primer binding site, and a sequencing primer binding site or any combination thereof. In some cases, the first predefined sequence 1110 is a sequence that can be common to all partitions of a plurality of partitions. For example, the first predefined sequence may comprise a flow cell attachment sequence, an amplification primer binding site, or a sequencing primer binding site and the first amplification reaction facilitates the attachment the predefined sequence to the template polynucleotide from the cell. In some embodiments, the first predefined sequence comprises a primer binding site. In some embodiments, the first predefined sequence comprises a sequencing primer binding site. As illustrated in operation 1150, the sequence towards a 3' end (e.g., polyT) of the primer 1124 hybridizes to the template polynucleotide 1120. In a first amplification reaction, extension reaction reagents, e.g., reverse transcriptase, nucleoside triphosphates, co-factors (e.g., Mg2+ or Mn2+), that are also co-partitioned, can extend the primer 1124 sequence using the cell's nucleic acid as a template, to produce a transcript, e.g., cDNA, 1122 having a fragment complementary to the strand of the cell's nucleic acid to which the primer annealed. In some cases, the reverse transcriptase has terminal transferase activity and the reverse transcriptase adds additional nucleotides, e.g., polyC, to the cDNA in a template independent manner. As illustrated in operation 1152, the template switching oligonucleotide 1126, for example a template switching oligonucleotide which includes a polyG sequence, can hybridize to the cDNA 1122 and facilitate template switching in the first amplification reaction. The transcript, therefore, may comprise the sequence of the primer 1124, a sequence complementary to the template polynucleotide from the cell, and a sequence complementary to the template switching oligonucleotide.

Among a plurality of partitions, each partition containing one or more cells or no cells, the primer and template switching oligonucleotide may be universal to all partitions. Where analysis of mRNA is conducted, for example, the primer may comprise at least a polyT segment capable of hybridizing and priming an extension reaction from the polyA segment of an mRNA. Where analysis of a variety of polynucleotides is conducted, the primer may comprise a random sequence capable of hybridizing to and priming extension reactions randomly on various polynucleotide templates. As template switching can occur with the use of an enzyme having terminal transferase activity, a template switching oligonucleotide having a sequence capable of hybridizing to the appended bases can be used for template switching in manner that is independent of the sequence of the polynucleotide templates to be analyzed. In some embodiments, the template switching oligonucleotide can comprise a first predefined sequence towards a 5' end that does not specifically hybridize to the template. In some embodiments, analysis of particular genes is conducted. In such cases, the primer may comprise a gene specific sequence capable of hybridizing to and priming extension reactions from templates comprising specific genes. In some embodiments, multiple genes are analyzed and a primer is among a plurality of primers. Each of the plurality of primers may have a sequence for a particular gene of interest.

Subsequent to the first amplification reaction, the first amplification product or transcript can be subjected to a second amplification reaction to generate a second amplification product. In some cases, additional sequences (e.g., functional sequences such as flow cell attachment sequence, sequencing primer binding sequences, barcode sequences, etc) are to be attached. The first and second amplification reactions can be performed in the same volume, such as for example in a droplet. In some cases, the first amplification product is subjected to a second amplification reaction in the presence of a barcoded oligonucleotide to generate a second amplification product having a barcode sequence. The barcode sequence can be unique to a partition, that is, each partition has a unique barcode sequence. The barcoded oligonucleotide may comprise a sequence of at least a segment of the template switching oligonucleotide and at least a second predefined sequence. The segment of the template switching oligonucleotide on the barcoded oligonucleotide can facilitate hybridization of the barcoded oligonucleotide to the transcript, e.g., cDNA, to facilitate the generation of a second amplification product. In addition to a barcode sequence, the barcoded oligonucleotide may comprise a second defined sequence such as at least one of an adaptor sequence, a unique molecular identifier (UMI) sequence, a primer binding site, and a sequencing primer binding site or any combination thereof.

In some embodiments, the second amplification reaction uses the first amplification product as a template and the barcoded oligonucleotide as a primer. As illustrated in operation 1154, the segment of the template switching oligonucleotide on the barcoded oligonucleotide 1128 can hybridize to the portion of the cDNA or complementary fragment 1122 having a sequence complementary to the template switching oligonucleotide or that which was copied from the template switching oligonucleotide. In the second amplification reaction, extension reaction reagents, e.g., polymerase, nucleoside triphosphates, co-factors (e.g., Mg2+ or Mn2+), that are also co-partitioned, can extend the primer sequence using the first amplification product as template as illustrated in operation 1156. The second amplification product can comprise a second predefined sequence (e.g., 1108, 1112, and 1110), a sequence of a segment of the template polynucleotide (e.g., mRNA), and a sequence complementary to the primer (e.g., 1124).

In some embodiments, the second amplification product uses the barcoded oligonucleotide as a template and at least a portion of the first amplification product as a primer. As illustrated in operation 1154, the segment of the first amplification product (e.g., cDNA) having a sequence complementary to the template switching oligonucleotide can hybridize to the segment of the barcoded oligonucleotide comprising a sequence of at least a segment of the template switching oligonucleotide. In the second amplification reaction, extension reaction reagents, e.g., polymerase, nucleoside triphosphates, co-factors (e.g., Mg2+ or Mn2+), that are also co-partitioned, can extend the primer sequence (e.g., first amplification product) using the barcoded oligonucleotide as template as illustrated in operation 1158. The second amplification product may comprise the sequence of the primer (e.g., 1124), a sequence which is complementary to the sequence of the template polynucleotide (e.g., mRNA), and a sequence complementary to the second predefined sequence (e.g., 1108, 1112, and 1110).

In some embodiments, the second amplification reaction is performed subsequent to the first amplification reaction in the presence of an intervening purification operation. An intervening purification operation can be used, for example, to purify the template (e.g., first amplification product) from excess reagents, including excess primers such as template switching oligonucleotides. In some embodiments, the amplification reaction is performed in the absence of an intervening purification operation. In certain embodiments, an intervening purification operation is not performed so that all sample preparation is performed in a same reaction volume. In the absence of an intervening purification operation, the template switching oligonucleotide may compete with barcoded oligonucleotide in the second amplification reaction as the barcoded oligonucleotide comprises at least a segment of the template switching oligonucleotide. Competition between the template switching oligonucleotide and barcoded oligonucleotide in the second amplification reaction to generate additional amplification product may result in a second amplification product lacking a barcode sequence. In some embodiments, the template switching oligonucleotide may out-compete the barcoded oligonucleotide in the second amplification reaction if the template switching oligonucleotide is present at a higher concentration in the reaction volume than the barcoded oligonucleotide. Various approaches can be utilized to favor the use of the barcoded oligonucleotide in the second amplification reaction to generate amplification products having a barcode sequence in situations where the barcoded oligonucleotide is present at a lower concentration than the template switching oligonucleotide in the reaction volume.

In some embodiments, the template switching oligonucleotide is not available for primer extension during the second amplification reaction. In some embodiments, the template switching oligonucleotide is degraded prior to the second amplification reaction. In some embodiments, the template switching oligonucleotide is degraded during the second amplification reaction. The template switching oligonucleotide may comprise ribonucleic acids (RNA). A template switching oligonucleotide comprising RNA can be degraded, for example, by elevated temperatures or alkaline conditions. In some embodiments, the template switching oligonucleotide comprises at least 10%, 15%, 20%, 25%, 30%, 35%, 40%, 45%, 50%, 55%, 60%, 65%, 70%, 75%, 80%, 85%, 90%, or 95% RNA. In some embodiments, the template switching oligonucleotide comprises 100% RNA. In some embodiments, a first reaction rate of the second amplification reaction using the barcoded oligonucleotide is greater than a second reaction rate of the second amplification using the template switching oligonucleotide.

In some embodiments, the barcoded oligonucleotide can hybridize to the first amplification product at a higher annealing temperature as compared to the template switching oligonucleotide. For example, the first amplification product and the barcoded oligonucleotide can have a higher melting temperature as compared to a melting temperature of the first amplification product and the template switching oligonucleotide. In such cases, the second amplification reaction may be performed with an annealing temperature at which the barcoded oligonucleotide is able to hybridize to the first amplification product and initiation primer extension and at which the template switching oligonucleotide is unable to hybridize to the first amplification product and initiate primer extension. In some embodiments, the primer annealing temperature of the second amplification reaction is at least about 0.5° C., 1° C., 2° C., 3° C., 4° C., 5° C., 6° C., 7° C., 8° C., 9° C., 10° C. or greater than a primer annealing temperature of the first amplification reaction. The difference in melting temperatures can result from the presence of modified nucleotides in the template switching oligonucleotide. In some embodiment, the template switching oligonucleotide comprises at least about 10%, 15%, 20%, 25%, 30%, 35%, 40%, 45%, 50%, 55%, 60%, 65%, 70%, 75%, 80%, 85%, 90%, or 95% modified nucleotides. In some embodiments, the template switching oligonucleotide comprises 100% modified oligonucleotides. In some embodiments, the difference in melting temperature can be the result of the presence of modified nucleotides in the barcoded oligonucleotide. In some embodiment, the barcoded oligonucleotide comprises at least 10%, 15%, 20%, 25%, 30%, 35%, 40%, 45%, 50%, 55%, 60%, 65%, 70%, 75%, 80%, 85%, 90%, or 95% modified nucleotides. In some embodiments, the barcoded oligonucleotide comprises 100% modified oligonucleotides. Modified nucleotides include, but are not limited to, 2-Aminopurine, 2,6-Diaminopurine (2-Amino-dA), inverted dT, 5-Methyl dC, 2'-deoxyInosine, Super T (5-hydroxybutynl-2'-deoxyuridine), Super G (8-aza-7-deazaguanosine), locked nucleic acids (LNAs), unlocked nucleic acids (UNAs, e.g., UNA-A, UNA-U, UNA-C, UNA-G), Iso-dG, Iso-dC, and 2' Fluoro bases (e.g., Fluoro C, Fluoro U, Fluoro A, and Fluoro G).

In various embodiments, the first amplification reaction is facilitated using an enzyme comprising polymerase activity. For example, the first amplification reaction can be facilitated by a DNA-dependent polymerase or a reverse-transcriptase (e.g., RNA dependent). In some embodiments, the first amplification reaction comprises polymerase chain reaction. In some embodiments, the first amplification reaction comprises reverse transcription. In various embodiments, the second amplification reaction is facilitated using an enzyme comprising polymerase activity. For example, the second amplification reaction can be facilitated by a DNA-dependent polymerase. In some embodiments, the second amplification reaction comprises polymerase chain reaction.

Also provided herein are methods for barcoding toward both a 5' end and a 3' end of template nucleic acid molecules (e.g., mRNA). Such methods may combine certain barcoding methods described herein to provide a template nucleic acid sequence comprising a barcode sequence on both a 5' end and a 3' end. In one example, a plurality of mRNA molecules derived from a single cell may be co-partitioned with a bead comprising a first set of barcode molecules and a second set of barcode molecules. The first set of barcode molecules may comprise an RNA specific (e.g., mRNA specific) priming sequence, such as poly-T sequence, along with a barcode sequence and, in some cases, additional sequences as disclosed herein. The second set of barcode molecules may comprise a sequence configured to facilitate template switching (e.g., a polyG sequence), along with a barcode sequence and, in some cases, additional sequences as disclosed herein. A partition comprising the bead and mRNA molecules may further comprise a template switching oligonucleotide, a primer comprising a poly-T sequence, and extension reaction reagents (e.g., reverse transcriptase, nucleoside triphosphates, co-factors (e.g., Mg2+ or Mn2+), etc.). The first and second sets of barcode molecules, together with the primer, template switching oligonucleotide, and extension reaction reagents, can be used to generate cDNA from the mRNA molecules using the barcoding methods described herein, wherein a subset of the cDNA molecules comprise a barcode sequence on the 5' end and a subset of the cDNA molecules comprise a barcode sequence on the 3' end. In some instances, a subset of the cDNA molecules comprise a barcode sequence on the 3' end and a barcode sequence on the 5' end. cDNA molecules can be subjected to sequencing, thereby generating sequences corresponding to the mRNA molecules that comprise a barcode sequence at both the 5' and 3' ends. Generating such sequences may be useful in, for example, analyzing both ends of an mRNA sequence derived from a single cell.

Following the generation of amplification products, subsequent operations may include purification (e.g., via solid phase reversible immobilization (SPRI)), further processing (e.g., shearing, ligation of functional sequences, and subsequent amplification (e.g., via PCR)). These operations may occur in bulk (e.g., outside the partition). In the case where a partition is a droplet in an emulsion, the emulsion can be broken and the contents of the droplet pooled for additional operations. Additional reagents that may be co-partitioned along with the barcode bearing bead may include oligonucleotides to block ribosomal RNA (rRNA) and nucleases to digest genomic DNA from cells. Alternatively, rRNA removal agents may be applied during additional processing operations. The configuration of the constructs generated by such a method can help minimize (or avoid) sequencing of the poly-T sequence during sequencing and/or sequence the 5' end of a polynucleotide sequence. The amplification products, for example first amplification products and/or second amplification products, may be subject to sequencing for sequence analysis.

Although operations with various barcode designs have been discussed individually, individual beads can include barcode oligonucleotides of various designs for simultaneous use.

The methods described herein may be used for capturing, processing, barcoding, and/or sequencing RNA for the purposes of determining an RNA velocity from one or more single cells. An RNA velocity may be determined by sequencing RNA (e.g., mRNA) from a cell. An RNA velocity may be determined by analyzing sequencing reads to determine the abundance of spliced and unspliced RNA in a cell, which may be used to calculate an RNA velocity. Alternatively or in addition, spliced and/or unspliced RNA may be measured via targeted amplification of a given RNA of interest (e.g., a gene transcript) to determine an RNA velocity. An RNA velocity may be related to the rate at which mRNA is being transcribed. An RNA velocity may be determined for one or more genes from a cell, or for an entire cell (e.g., an entire transcriptome of a cell). An RNA velocity may be positive when gene transcription is being increased, and may be negative when gene transcription is being decreased. Measuring an RNA velocity from a cell may be useful in, for example, determining the rates of change in RNA expression during mammalian development (e.g., fetal development, stem cell development, etc.).

RNA from a cell may be barcoded, as described herein, and sequenced to identify RNA from a single cell. Sequences can be analyzed to determine an RNA velocity for at least a subset of RNA from each single cell of a plurality of cells. RNA from a cell may be barcoded together with additional analytes from the cell (e.g., DNA, proteins, metabolites, molecules introduced into a cell, etc.) or derivatives thereof. Barcoding of one or more analytes from a cell is described in further detail herein. Sequences from RNA and/or one or more additional analytes may be identified and used to determine an RNA velocity. An RNA velocity may be associated with information obtained from identifying and/or sequencing one or more additional analytes from a cell. For example, an RNA velocity may be associated with an abundance of proteins from a cell. This may be useful in, for example, measuring the rate at which a change in gene expression results in a change in levels of spliced RNA protein from that gene. An RNA velocity may be associated with genetic information from a cell (e.g., one or more genetic mutations). This may be useful in, for example, identifying how a given genetic mutation impacts RNA velocity during of development. An RNA velocity may be associated with epigenetic (e.g., methylation) information from a cell. This may be useful in, for example, determining how a methylation pattern impacts RNA velocity during development.

In one aspect, the present invention provides a method of nucleic acid processing comprising analysis of RNA velocity. In one embodiment, the method comprises the step of co-partitioning a cell-derived particle (or a cell) and a bead in a partition, wherein said bead comprises a plurality of barcode oligonucleotide molecules each comprising a barcode sequence. The method may further comprise capturing a messenger ribonucleic acid (mRNA) molecule and/or a pre-mRNA molecule from the cell-derived particle (or cell) using the bead, wherein the capturing occurs via a barcode oligonucleotide molecule of said plurality of barcode oligonucleotide molecules from the bead. The method may further comprise conducting a nucleic acid reaction with said mRNA molecule (and/or pre-mRNA molecule), or a derivative thereof, to yield a plurality of barcoded nucleic acid products. In one embodiment, the method comprises removing the bead from the partition prior to conducting the nucleic acid reaction. In another embodiment, the method comprises conducting the nucleic acid reaction within the partition. In another embodiment, the cell-derived particle is a cell nucleus.

In another embodiment, the captured mRNA molecule (and/or pre-mRNA molecule) comprises an intron or a spliced region. In some embodiments, the intron comprises an exon/intron boundary. The exon/intron boundary is indicative of a newly transcribed mRNA molecule (or a pre-mRNA molecule). In one embodiment, the spliced region comprises an exon/exon boundary. The exon/exon boundary is indicative of a spliced mRNA molecule or a spliced mRNA molecule within the nucleus of the cell. In another embodiment, the exon/exon boundary is indicative of the absence of an un-spliced mRNA molecule (or pre-mRNA molecule).

In other embodiments, the barcode oligonucleotide molecule further comprises a capture region for mRNA molecules from the cell-derived particles (or cell). The capture region may comprise a poly(dT) sequence and/or a sequence that is complementary to a splice site consensus sequence. In one embodiment, the splice site consensus sequence comprises a 3' splice site consensus sequence and/or a 5' splice site consensus sequence. In other embodiments, the splice site consensus sequence is a sequence recognized by a spliceosome as a substrate.

In one aspect, the present invention provides the combined analysis of RNA velocity and chromatin accessibility in the same cell from a plurality of cells. An analysis of RNA velocity provides information about the abundance of both spliced and un-spliced RNA molecules, which estimates short-term changes in transcription, and an analysis of chromatin accessibility provides information on longer term changes in transcription and transcript abundance. The methods described herein provide a more reliable and extensive estimation of changes in RNA transcription as well as linkage information between chromatin accessibility and RNA transcription. In one embodiment, the present invention provides a method of nucleic acid processing comprising analysis of RNA velocity and chromatin accessibility within the same cell of a plurality of cells. In one embodiment, the analysis of chromatin accessibility comprises a transposase-based method as described herein. In other embodiments, the analysis of chromatin accessibility comprises detecting accessible region(s) within the chromatin that correspond to transcription regulatory elements including, without limitation, one or more of a cis-regulatory element, a trans-regulatory element, a promoter, and an enhancer. In another embodiment, the enhancer is proximal or distal to a promoter region. In one other embodiment, the method of nucleic acid processing comprises detecting the current state of RNA transcription within a cell via RNA velocity analysis and detecting regions of accessible chromatin for RNA transcription via chromatin accessibility analysis. In another embodiment, a detected region of accessible chromatin in a cell for RNA transcription corresponds to an mRNA (or a pre-mRNA) molecule detected via RNA velocity analysis. In other embodiments, a detected region of accessible chromatin in a cell for RNA transcription (i) corresponds to a spliced mRNA molecule, (ii) corresponds to an un-spliced mRNA molecule (or pre-mRNA), or (iii) does not correspond to a molecule according to (i) or (ii). In yet other embodiments, detected regions of accessible chromatin in a cell for RNA transcription comprise (i) regions that correspond to a spliced mRNA molecule, (ii) regions that correspond to an un-spliced mRNA molecule (or pre-mRNA), (iii) regions that do not correspond to a molecule according to (i) or (ii), and combinations thereof. In one other aspect, one or more steps of the combined analysis may be achieved in partitions as further described herein. For instance, the barcoding of analyte(s) may be performed in partitions. In another embodiment, the processing of chromatin and/or mRNA may involve steps outside of a partition including, without limitation, further nucleic acid reactions with barcoded analyte molecules (e.g., amplification of barcoded analyte molecules).

Antigen Library Screening

Disclosed herein, in some embodiments, are compositions, methods, and systems useful in the analysis of multiple analytes in a single cell or cell population. Examples of analytes include, without limitation, DNA (e.g., genomic DNA), epigenetic information (e.g., accessible chromatin or DNA methylation), RNA (e.g., mRNA or CRISPR guide RNAs), synthetic oligonucleotides (e.g., DNA transgenes), and proteins (e.g., intracellular proteins, cell surface proteins, extracellular matrix proteins, or nuclear membrane proteins). Examples of intracellular protein analytes include, but are not limited to, transcription factors, histone proteins, kinases, phosphatases, cytoskeletal proteins (e.g., actin, tubulin), polymerases, nucleases, and ribosomal proteins. An analyte may be a cell or one or more constituents of a cell. In some embodiments, the ability of a receptor (e.g., TCR or BCR) to bind an antigen is one of the analytes characterized by the compositions, methods, and systems disclosed herein.

Immune cells express various adaptive immunological receptors relating to immune function, such as T cell receptors (TCRs) and B cell receptors (BCRs). T cell receptors and B cell receptors play a part in the immune response by specifically recognizing and binding to antigens and aiding in their destruction.

The T cell receptor, or TCR, is a molecule found on the surface of T cells that is generally responsible for recognizing fragments of antigen as peptides bound to major histocompatibility complex (MHC) molecules. The TCR is generally a heterodimer of two chains, each of which is a member of the immunoglobulin superfamily, possessing an N-terminal variable (V) domain, and a C terminal constant domain. In humans, in 95% of T cells the TCR consists of an alpha (α) and beta (β) chain, whereas in 5% of T cells the TCR consists of gamma and delta (γ/δ) chains. This ratio can change during ontogeny and in diseased states as well as in different species. When the TCR engages with antigenic peptide and MHC (peptide/MHC or pMHC), the T lymphocyte is activated through signal transduction.

Each of the two chains of a TCR contains multiple copies of gene segments—a variable 'V' gene segment, a diversity 'D' gene segment, and a joining 'J' gene segment. The TCR alpha chain (TCRa) is generated by recombination of V and J segments, while the beta chain (TCRb) is generated by recombination of V, D, and J segments. Similarly, generation of the TCR gamma chain involves recombination of V and J gene segments, while generation of the TCR delta chain occurs by recombination of V, D, and J gene segments. The intersection of these specific regions (V and J for the alpha or gamma chain, or V, D and J for the beta or delta chain) corresponds to the CDR3 region that is important for antigen-MHC recognition. Complementarity determining regions (e.g., CDR1, CDR2, and CDR3), or hypervariable regions, are sequences in the variable domains of antigen receptors (e.g., T cell receptor and immunoglobulin) that can complement an antigen. Most of the diversity of CDRs is found in CDR3, with the diversity being generated by somatic recombination events during the development of T lymphocytes. A unique nucleotide sequence that arises during the gene arrangement process can be referred to as a clonotype.

The B cell receptor, or BCR, is a molecule found on the surface of B cells. The antigen binding portion of a BCR is composed of a membrane-bound antibody that, like most antibodies (e.g., immunoglobulins), has a unique and randomly determined antigen-binding site. The antigen binding portion of a BCR includes membrane-bound immunoglobulin molecule of one isotype (e.g., IgD, IgM, IgA, IgG, or IgE). When a B cell is activated by its first encounter with a cognate antigen, the cell proliferates and differentiates to generate a population of antibody-secreting plasma B cells and memory B cells. The various immunoglobulin isotypes differ in their biological features, structure, target specificity and distribution. A variety of molecular mechanisms exist to generate initial diversity, including genetic recombination at multiple sites.

The BCR is composed of two genes IgH and IgK (or IgL) coding for antibody heavy and light chains. Immunoglobulins are formed by recombination among gene segments, sequence diversification at the junctions of these segments, and point mutations throughout the gene. Each heavy chain gene contains multiple copies of three different gene segments—a variable 'V' gene segment, a diversity 'D' gene segment, and a joining 'J' gene segment. Each light chain gene contains multiple copies of two different gene segments for the variable region of the protein—a variable 'V' gene segment and a joining 'J' gene segment. The recombination can generate a molecule with one of each of the V, D, and J segments. Furthermore, several bases may be deleted and others added (called N and P nucleotides) at each of the two junctions, thereby generating further diversity. After B cell activation, a process of affinity maturation through somatic hypermutation occurs. In this process progeny cells of the activated B cells accumulate distinct somatic mutations throughout the gene with higher mutation concentration in the CDR regions leading to the generation of antibodies with higher affinity to the antigens. In addition to somatic hypermutation activated B cells undergo the process of isotype switching. Antibodies with the same variable segments can have different forms (isotypes) depending on the constant segment. Whereas all naïve B cells express IgM (or IgD), activated B cells mostly express IgG but also IgM, IgA and IgE. This expression switching from IgM (and/or IgD) to IgG, IgA, or IgE occurs through a recombination event causing one cell to specialize in producing a specific isotype. A unique nucleotide sequence that arises during the gene arrangement process can similarly be referred to as a clonotype.

In some embodiments, the methods, compositions and systems disclosed herein are utilized to analyze the various sequences of TCRs and BCRs from immune cells, for example various clonotypes. In some embodiments, methods, compositions and systems disclosed herein are used to analyze the sequence of a TCR alpha chain, a TCR beta chain, a TCR delta chain, a TCR gamma chain, or any fragment thereof (e.g., variable regions including VDJ or VJ regions, constant regions, transmembrane regions, fragments thereof, combinations thereof, and combinations of fragments thereof). In some embodiments, methods, compositions and systems disclosed herein are used to analyze the sequence of a B cell receptor heavy chain, B cell receptor light chain, or any fragment thereof (e.g., variable regions including VDJ or VJ regions, constant regions, transmembrane regions, fragments thereof, combinations thereof, and combinations of fragments thereof).

Where immune cells are to be analyzed, primer sequences useful in any of the various operations for attaching barcode sequences and/or amplification reactions may comprise gene specific sequences which target genes or regions of genes of immune cell proteins, for example immune receptors. Such gene sequences include, but are not limited to, sequences of various T cell receptor alpha variable genes (TRAV genes), T cell receptor alpha joining genes (TRAJ genes), T cell receptor alpha constant genes (TRAC genes), T cell receptor beta variable genes (TRBV genes), T cell receptor beta diversity genes (TRBD genes), T cell receptor beta joining genes (TRBJ genes), T cell receptor beta constant genes (TRBC genes), T cell receptor gamma variable genes (TRGV genes), T cell receptor gamma joining genes (TRGJ genes), T cell receptor gamma constant genes (TRGC genes), T cell receptor delta variable genes (TRDV genes), T cell receptor delta diversity genes (TRDD genes), T cell receptor delta joining genes (TRDJ genes), and T cell receptor delta constant genes (TRDC genes).

MHCs (e.g., a soluble MHC monomer molecule), including full or partial MHC-peptides, may be used as labelling agents that are coupled to oligonucleotides that comprise a barcode sequence that identifies its associated MHC (and, thus, for example, the MHC's TCR binding partner). In some cases, MHCs are used to analyze one or more cell-surface features of a T-cell, such as a TCR. In some cases, multiple MHCs are associated together in a larger complex (MHC multi-mer) to improve binding affinity of MHCs to TCRs via multiple ligand binding synergies.

Figure 28A:
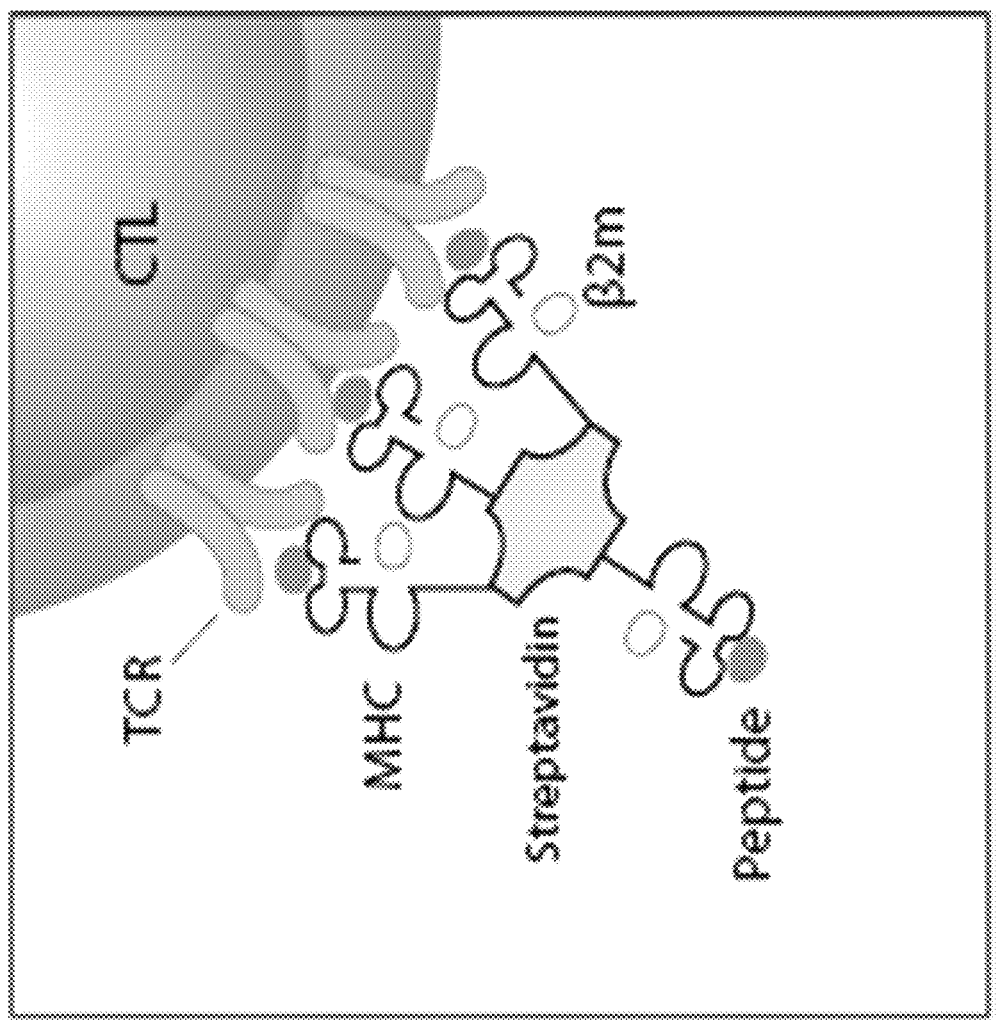
FIGS. 28A-C schematically depict an example barcoding scheme that includes major histocompatibility complexes.

For example, as shown in FIG. 28A, pMHCs can individually be associated with biotin and bound to a streptavidin moiety such that the streptavidin moiety comprises multiple pMHC moieties. Each of these moieties can bind to a TCR such that the streptavidin binds to the target T-cell via multiple MCH/TCR binding interactions. These multiple interactions synergize and can substantially improve binding affinity. Such improved affinity can improve labelling of T-cells and also reduce the likelihood that labels will dissociate from T-cell surfaces.

Figure 28B:
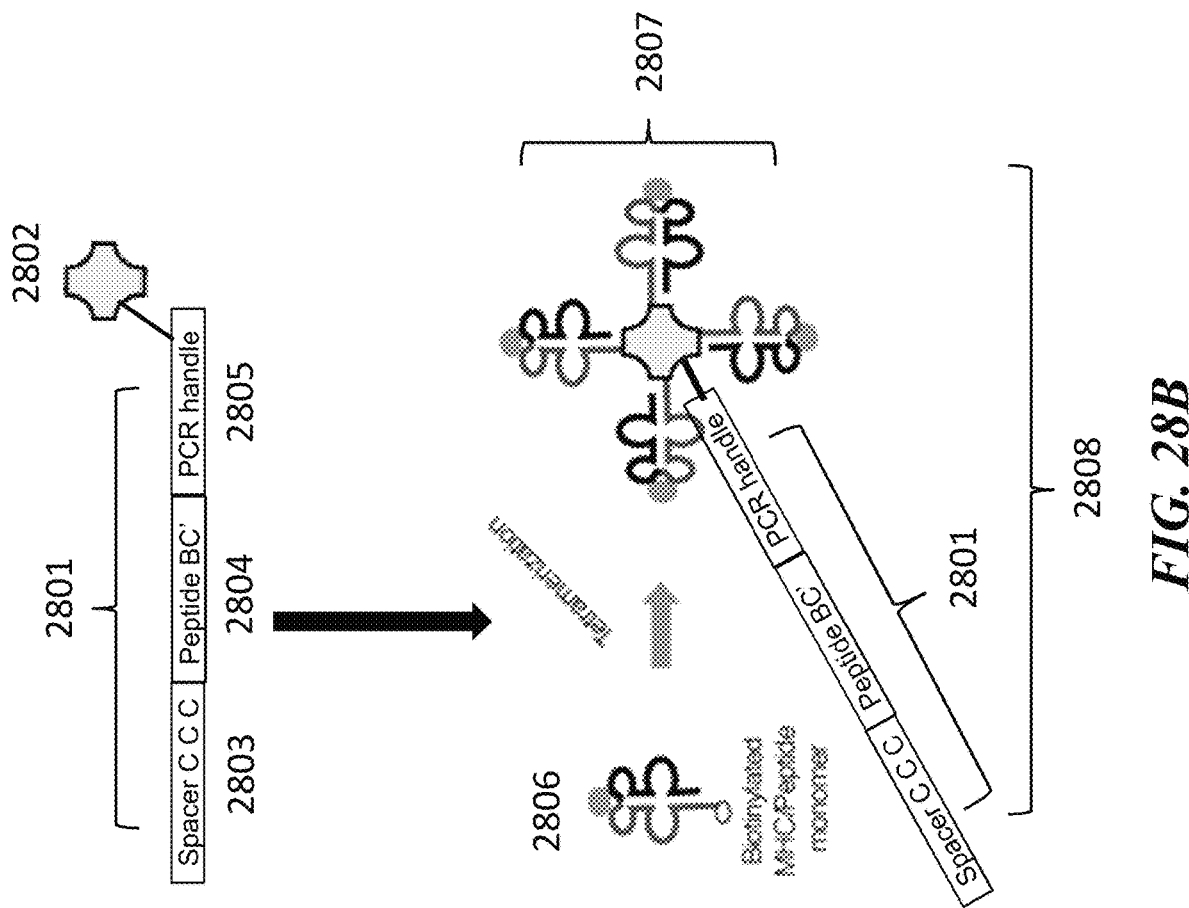
Figure 28C:
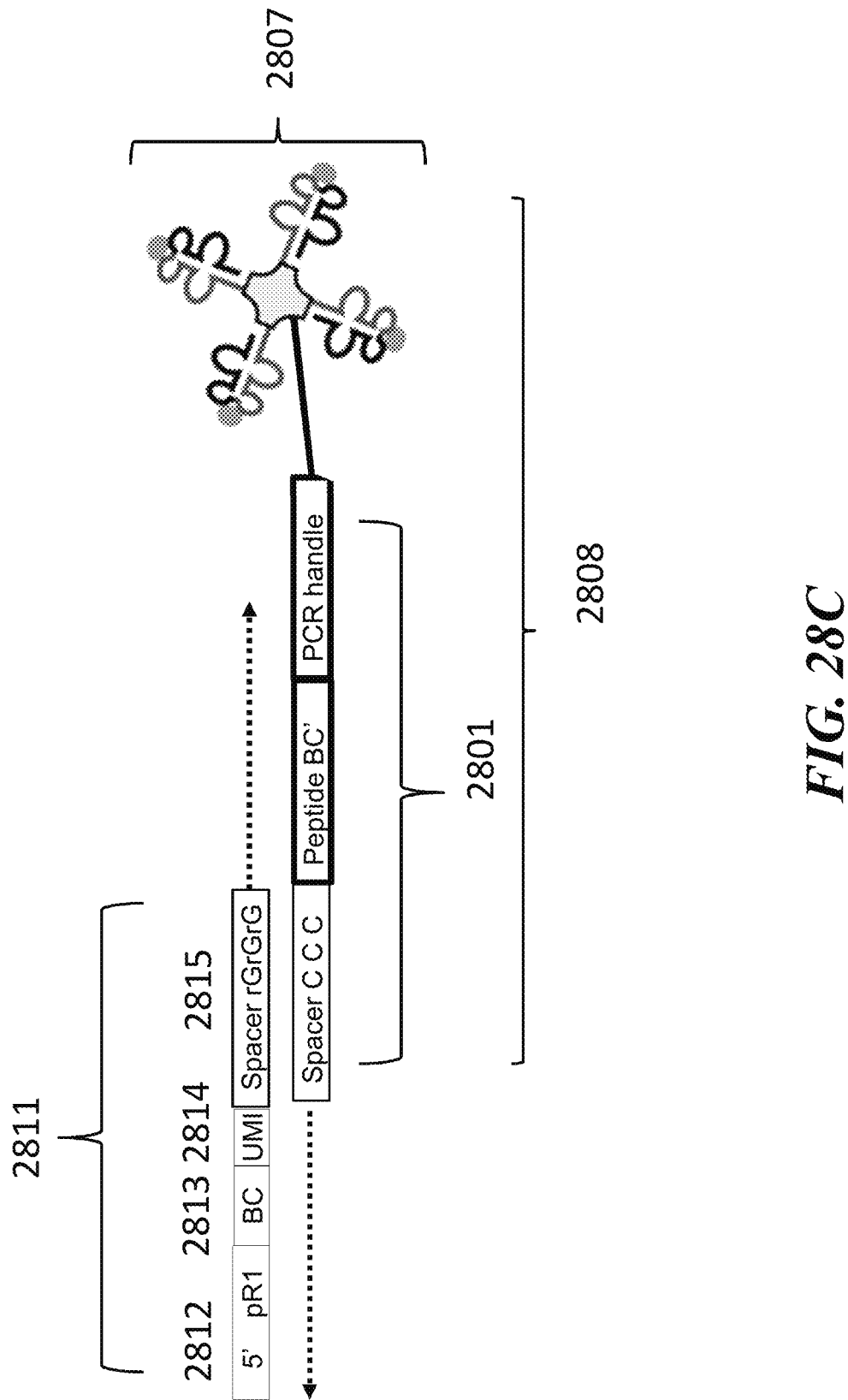

As shown in FIG. 28B and continuing with this example, a barcoded oligonucleotide 2801 can be modified with streptavidin 2802 and contacted with multiple molecules of biotinylated MHC 2806 (such as a pMHC) such that the biotinylated MHC 2806 molecules are coupled with the streptavidin conjugated barcoded oligonucleotide 2801. The result is a barcoded MHC multimer complex 2808. As shown in FIG. 28B, the oligonucleotide 2801 barcode sequence 2802 can identify the MHC 2804 as its associated label and also includes optional functional sequences such as sequences for hybridization with other oligonucleotides (e.g., sequence 2803 comprising a 'Spacer C C C' and sequence 2805 comprising a 'Spacer PCR handle'). As shown in FIG. 28C, one example oligonucleotide is oligonucleotide 2811 that comprises a complementary sequence 2815 (e.g., rGrGrG corresponding to C C C), a barcode sequence 2813 and other functional sequences, such as, for example, a UMI 2814, an adapter sequence 2812 (e.g., comprising a sequencing primer sequence (e.g., R1 or a partial R1 ("pR1")), a flow cell attachment sequence (e.g., P5 or P7 or partial sequences thereof)), etc. In some cases, oligonucleotide 2811 may at first be associated with a bead (e.g., a gel bead) and released from the bead. In any case, though, oligonucleotide 2811 can hybridize with oligonucleotide 2801 of the MHC-oligonucleotide complex 2808. The hybridized oligonucleotides 2811 and 2801 can then be extended in primer extension reactions such that constructs comprising sequences that correspond to each of the two barcode sequences 2813 and 2804 are generated. In some cases, one or both of these corresponding sequences may be a complement of the original sequence in oligonucleotide 2811 or 2801. In other embodiments, nucleic acid molecules 2811 and 2801 are configured (e.g., 2801 and/or 2811 are partially double stranded with compatible overhangs) such that 2811 and 2801 are ligated together. The resulting constructs can be optionally further processed (e.g., to add any additional sequences and/or for clean-up) and subjected to sequencing. As described elsewhere herein, a sequence derived from barcode sequence 2813 may be used to identify a partition or a cell within a partition and the sequence derived from barcode sequence 2804 may be used to identify the particular peptide MHC complex 2807 bound on the surface of the cell (e.g., when using MHC-peptide libraries for screening immune cells or immune cell populations). To determine the sequence of the TCR bound to the MHC-oligonucleotide complex 2808 (see, e.g., FIG. 28A), the T cell can be lysed to release T cell mRNA transcripts and the V(D)J sequence(s) of the TCR determined using, e.g., oligonucleotide 2811 and the schemes described elsewhere herein (see, e.g., FIG. 11A-B and accompanying text). After processing and sequencing as generally described elsewhere herein, the sequence derived from peptide barcode 2804 may be used to identify the peptide MHC complex 2807 bound on the surface of the cell while cellular barcode sequence 2813 may be used to associate a TCR and a peptide MHC complex as arising from the same partition.

Furthermore, while the example shown in FIG. 28B and FIG. 28C shows streptavidin directly coupled to its oligonucleotide, the streptavidin may also be coupled to a hybridization oligonucleotide which then hybridizes with the identifying barcoded oligonucleotide, similar to the example scheme shown in FIG. 22 (panel II) and described elsewhere herein.

A variety of methods can be employed to generate barcoded MHC monomers and barcoded MHC multimer complexes, non-limiting examples of which are described herein. For example, disclosed herein, in some embodiments, are methods for generating barcoded MHC molecules, comprising: (a) providing a reaction mixture comprising (i) a major histocompatibility complex (MHC) molecule, and (ii) a support having coupled thereto (1) a polypeptide of interest (e.g., an antigenic polypeptide) and (2) a nucleic acid barcode molecule, wherein the nucleic acid barcode molecule comprises a barcode sequence that corresponds to the polypeptide, and wherein the MHC molecule is a soluble MHC molecule (e.g., lacking the transmembrane domain and cytoplasmic domains); and (b) subjecting the reaction mixture to conditions sufficient to couple the polypeptide and the nucleic acid barcode molecule to the MHC molecule, thereby yielding a barcoded MHC molecule. Here, the identity of the pMHC complex can be determined by detecting the nucleic acid barcode molecule (e.g., through nucleic acid sequencing, hybridization, PCR, digital PCR, etc.). The MHC molecules can be composed of MHC class I, class II, CD1, or other MHC-like molecules. The MHC molecule may comprise any suitable MHC allele (e.g., any suitable HLA allele).

The WIC molecules may be of any suitable configuration, for example, monomers, dimers, trimers, tetramer, pentamers, hexamers, etc. While examples are provided herein, MHC multimers may be assembled by any of a variety of suitable techniques. In some instances, the WIC molecule (e.g., soluble MHC monomer) is provided coupled to a carrier. For example, the WIC molecule may be coupled to a protein or polypeptide carrier. In some instances, the protein or polypeptide is streptavidin or a biotin-binding portion thereof. The WIC molecule(s) may be directly coupled to the carrier or indirectly bound to the carrier. The MHC molecule(s) may be covalently coupled to the carrier (e.g., chemically coupled or part of a fusion protein). In some embodiments, the WIC molecule is bound to the carrier through a biotin moiety (e.g., WIC tetramers—MBL International Corp., BioLegend®). For example, an WIC molecule may be conjugated to a biotin molecule and be coupled to a streptavidin carrier. In some instances, multiple WIC molecules are coupled to a common carrier (e.g., an MHC multimer). In some embodiments, an MHC multimer is an WIC pentamer. For example, five WIC molecules can be connected via flexible linkers to a coiled-coil multimerization domain. In some embodiments, the carrier comprises a polymer. For example, the carrier may be a dextran polymer (e.g., MHC Dextramer®—Immunudex). In some instances, the MHC molecule(s) are coupled to the polymer carrier through one or more functional groups of the polymer. For example, in some instances, the polymer (e.g., a dextran polymer) comprises streptavidin and a biotinylated MHC molecule is indirectly coupled to the polymer carrier through a biotin-streptavidin interaction. In some instances, the carrier can comprise additional molecules, such as a fluorophore. In some instances, the MHC molecule may be coupled to the carrier prior to the barcoding reaction (i.e., an MHC-carrier molecule is provided in the reaction mixture). In some instances, the WIC molecule may be coupled to the carrier after antigenic polypeptide loading and barcoding.

In some instances, MHC molecules (such as recombinant soluble WIC monomers) that do not associate with a peptide ligand can be unstable. Thus, in some embodiments, prior to antigenic polypeptide loading and barcoding, the MHC molecule(s) (e.g., MHC monomers or multimers, such as tetramers and dextramers) comprise a conditional ligand to aid in WIC stability (e.g., a placeholder polypeptide to be substituted by the antigenic polypeptide of interest). The conditional ligand may be replaced by a polypeptide of interest (e.g., an antigenic polypeptide) through a peptide exchange reaction. In some embodiments, the conditional ligand is a polypeptide comprising a protease cleavage domain configured to facilitate cleavage and release of the conditional ligand. In other embodiments, the conditional ligand is a polypeptide comprising a modification configured to facilitate cleavage of the conditional ligand. Any suitable modification may be utilized in the conditional ligands described herein, including periodate-sensitive linkers, such as linkers comprising a vicinal diol moiety or α,γ-diamino-β-hydroxybutanoic acid (DAHB) (see, e.g., Leriche G, et al, Cleavable linkers in chemical biology; Bioorg Med Chem. 2012 Jan. 15; 20(2):571-82). In some embodiments, the conditional ligand is a polypeptide comprising a photo-labile amino acid that is released from the WIC molecule upon application of a photo-stimulus (e.g., UV light). Any suitable photolabile amino acid may be utilized in the conditional ligands described herein, including, e.g., 2-nitrophenyl-based compounds, such as 3-amino-3-(2-nitro)phenyl-propionic acid (see, e.g., Toebes M, et al., Design and use of conditional WIC class I ligands; Nat Med. 2006 February; 12(2):246-51). For example, in some embodiments, a reaction mixture is provided comprising (a) at least one soluble WIC molecule comprising a conditional polypeptide ligand comprising at least one photolabile amino acid; and (b) a bead (e.g., a gel bead) comprising, releasably attached thereto: (i) polypeptides composing a common amino acid sequence; and (ii) nucleic acid barcode molecules comprising a common barcode sequence corresponding to the antigenic polypeptide. The reaction mixture is then exposed to UV-light such that the photolabile amino acid in the conditional ligand is cleaved, thereby releasing the conditional ligand from the WIC molecule. The bead-bound polypeptides and nucleic acid barcode molecules are released from the bead (e.g., the gel bead) as described elsewhere herein (e.g., a chemical reagent in the reaction mixture, such as a reducing agent to cleave disulfide bonds). The bead-bound polypeptides and the nucleic acid barcode molecules can be released prior to, concurrent with, or subsequent to release of the conditional ligand. The released polypeptides and nucleic acid barcode molecules then may be used with the MHC molecule(s) to generate a barcoded pMHC complex.

In some embodiments, the conditional ligand is covalently linked to the MHC molecule (e.g., is a fusion protein). For example, the conditional ligand may be a polypeptide covalently linked to the WIC molecule, wherein the polypeptide comprises a protease cleavage domain configured to release the conditional ligand upon protease treatment. In some instances, the conditional ligand is a polypeptide covalently linked to the MHC molecule, wherein the polypeptide comprises a thrombin cleavage domain, and wherein the conditional ligand is released from the WIC molecule upon thrombin treatment.

In some instances, e.g., prior to polypeptide loading and barcoding, the MHC molecule is provided in a reaction mixture with a molecular chaperone. In some embodiments, the molecular chaperone is provided along with an empty MHC (e.g., not loaded with peptide). In other embodiments, the molecular chaperone is provided along with an MHC molecule comprising a conditional ligand. In some embodiments, the molecular chaperone comprises the luminal domain of transporter associated with antigen processing (TAP)-binding protein related (TAPBPR). See, e.g., Morozov G, et al, Interaction of TAPBPR, a tapasin homolog, with MHC-I molecules promotes peptide editing; Proc Natl Acad Sci USA. 2016 Feb. 23; 113(8):E1006-15; and McShan A C, et al, Peptide exchange on MHC-I by TAPBPR is driven by a negative allostery release cycle; Nat Chem Biol. 2018 August; 14(8):811-820.

Disclosed herein, in some embodiments, are methods for generating barcoded MHC molecules, comprising: (a) providing a reaction mixture comprising (i) a major histocompatibility complex (MHC) molecule, and (ii) a support having coupled thereto (1) a polypeptide of interest (e.g., an antigenic polypeptide) and (2) a nucleic acid barcode molecule, wherein the nucleic acid barcode molecule comprises a barcode sequence that corresponds to the polypeptide, and wherein the MHC molecule is a soluble MHC molecule; and (b) subjecting the reaction mixture to conditions sufficient to couple the polypeptide and the nucleic acid barcode molecule to the MHC molecule, thereby yielding a barcoded MHC molecule. In some instances, the support is a bead (e.g., a single bead). The polypeptide and the nucleic acid barcode molecule may be releasably attached to the bead, wherein the polypeptide and the nucleic acid barcode molecule are released from the bead. In some embodiments the bead is a gel bead. In some instances, the gel bead is a degradable gel bead, wherein the gel bead is degradable upon application of a stimulus as described elsewhere herein. In some embodiments, the reaction mixture is partitioned into a partition, such as a partition amongst a plurality of partitions. In some instances, disclosed herein, are methods comprising: (a) providing a plurality of partitions (such as a droplet in an emulsion or a well of, e.g., a micro/nanowell array), wherein at least a subset of the plurality of partitions each comprise (i) a plurality of soluble major histocompatibility complex (MHC) molecules and (ii) a support having coupled thereto (1) a plurality of polypeptides comprising a common amino acid sequence, and (2) a plurality of nucleic acid barcode molecules comprising a common barcode sequence, wherein the barcode sequence corresponds to the common amino acid sequence, and wherein each partition of the subset of the plurality of partitions comprises a unique polypeptide and a unique barcode sequence; and (b) subjecting the plurality of partitions to conditions sufficient to, in each of the subset of the plurality partitions, couple (i) a polypeptide of the plurality of polypeptides and (ii) a nucleic acid barcode molecule of the plurality of nucleic acid barcode molecules to a MHC molecule of the plurality of soluble MHC molecules to yield a plurality of barcoded MHC molecules. Thus, these methods enable the high throughput generation of diverse libraries of unique pMHC complexes, wherein the identity of the polypeptide in the pMHC complexes can be readily determined by the nucleic acid barcode sequence (e.g., by nucleic acid sequencing).

Peptides to be complexed with MHC molecules can be of any suitable length. Peptide length can be selected for optimal loading into the peptide binding groove. In some cases, peptides are at least 5, 6, 7, 8, 9, 10, 11, 12, 13, 14, 15, 16, 17, 18, 19, 20, 21, 22, 23, 24, 25, 26, 27, 28, 29, or 30 amino acids in length. In some cases, peptides are at most about 35, 34, 33, 32, 31, 30, 29, 28, 27, 26, 25, 24, 23, 22, 21, 20, 19, 18, 17, 16, 15, 14, 13, 12, 11, 10, 9, 8, 7, 6, or 5 amino acids in length. In some cases, peptides are between about 5 and 35, between about 6 and 34, between about 7 and 33, between about 8 and 32, between about 9 and 31, between about 10 and 30, between about 11 and 29, between about 12 and 28, between about 13 and 27, between about 14 and 26, between about 15 and 25, between about 16 and 24, between about 17 and 23, or between about 18 and 22 amino acids in length.

In some cases, peptides to be used with MHC class I molecules are between about 6 to 12 amino acids in length, e.g., between about 7 to 11 amino acids in length, or between about 8 to 10 amino acids in length. In some cases, peptides to be used with MHC class II molecules are between about 5 to 35 amino acids in length, between about 10 to 30 amino acids in length, or between about 15 to 25 amino acids in length. In some cases, peptides are between about 13 to 25 amino acids in length.

Barcode-containing oligonucleotides (e.g., in a partition) may be coupled to MHC monomer and multimer complexes by a variety of mechanisms, including, but not limited to covalent and non-covalent interactions. In some instances, the nucleic acid barcode molecule(s) are directly conjugated to an MHC molecule (e.g., MHC monomer or MHC multimer). In other instances, the MHC molecule is coupled to a carrier (e.g., a biotinylated MHC molecule coupled to a streptavidin carrier), thereby coupling the nucleic acid barcode molecules to the MHC molecule through the carrier. For example, the nucleic acid barcode molecule(s) can be chemically linked to the MHC molecule and/or carrier. In another example, a pair of binding molecules can be utilized to couple the nucleic acid barcode molecule(s) to the MHC molecule or carrier. For example, the nucleic acid barcode molecule(s) may be linked to one member of a binding pair and the other member of the binding pair is linked to the MHC multimer and/or carrier. In some cases, the nucleic acid barcode molecule(s) comprise a subsequence having sequence complementary to an oligonucleotide coupled to the MHC molecule and/or carrier and the subsequence hybridizes to the oligonucleotide coupled to the MHC molecule and/or carrier, thereby coupling the nucleic acid barcode molecule(s) to the MHC molecule. Nucleic acid barcode molecules may be conjugated to MHC molecules and/or carrier molecules through any suitable method, such as chemical conjugation methods described elsewhere herein (e.g., LightningLink® chemistry, reaction of functional groups such as thiols, amines, click chemistry moieties, etc.). The nucleic acid barcode molecules, MHC molecules, and/or carrier molecules may comprise functional groups/modifications (e.g., thiols, amines, click chemistry moieties, biotin, etc.) configured to facilitate coupling of barcode molecules to MHC and/or carrier molecules. For example, in some instances, the nucleic acid barcode molecules comprise a biotin moiety and are coupled to a MHC molecule (e.g., a biotinylated MHC molecule) through a common streptavidin carrier.

In some cases, loading of a peptide into a peptide binding groove of a MHC molecule (e.g., a MHC multimer) occurs prior to coupling of a barcode-containing oligonucleotide to the MHC molecule. In some cases, loading of a peptide into a peptide binding groove of an MHC molecule occurs subsequent to coupling of a barcode-containing oligonucleotide to the MHC molecule. In some cases, loading of a peptide into a peptide binding groove of an MHC molecule occurs simultaneously with coupling of a barcode-containing oligonucleotide to the MHC molecule.

While the use of supports (such as beads, e.g., gel beads) is described herein, a plurality of substrates can be employed to supply peptides and barcode-containing oligonucleotides to a partition. Peptides and barcode-containing oligonucleotides can be supplied to a partition, for example by nanoparticles, liposomes, and polymerosomes. Peptides and barcode-containing oligonucleotides can be coupled to nanoparticles formed from a variety of materials. Peptides and oligonucleotides can be embedded in and/or attached to the surface of nanoparticles comprising natural materials or derivatives (e.g., chitosan, dextrane, gelatin, alginates, starches, silica, metal), dendrimers (e.g., branched polymers), fullerenes, and polymers (e.g., polylactic acid, poly(cyano)acrylates, polyethyleinemine, block copolymers, and polycaprolactone). Peptides and oligonucleotides can also be encapsulated in and/or integrated into the membrane of a liposome or polymerosome.

A partition can refer to any apparatus or mechanism by which a substance can be fractionated, for example to separate one fraction from another. A partition may be, for example, a well, a microwell, a droplet, a test tube, a spot, or any other means of sequestering one fraction of a sample from another. In certain embodiments, a partition comprises a droplet in an emulsion. In other embodiments, a partition comprises a well, such as a well in a microwell/nanowell array. Partitioning may be performed, for example, using microfluidics, dilution, dispensing, and the like.

In some cases, a method of generating barcoded MHC complexes employs in vitro transcription and/or translation. Using in vitro systems, sometimes referred to as cell-free systems, proteins can be produced outside of a cell. The biological machinery, e.g., polymerase, ribosomes, aminoacyl-tRNA synthetases, translation initiation and elongation factors, nucleases, etc., can be harvested from bacteria (e.g., E. coli), insect cells (e.g., Sf9 and Sf21), yeast, mammalian cells (e.g., rabbit reticulocytes), and/or wheat germ extracts and these components can be used for transcription and/or translation in vitro. Reaction solutions comprising the biological machinery, DNA template, amino acids, and other necessary supplements can be incubated together to facilitate the in vitro transcription of mRNA and/or in vitro translation of protein from mRNA. Advantages of cell-free protein synthesis include direct access to and control of the translation environment, which may be advantageous for the optimization of protein production and incorporation of non-natural amino acids, amino acid analogues, modified amino acids, etc.

For example, disclosed herein, in some embodiments, are methods for generating barcoded MHC molecules, comprising: (a) providing a reaction mixture comprising a major histocompatibility complex (MHC) molecule and a nucleic acid molecule comprising a sequence encoding a polypeptide of interest (e.g., an antigenic polypeptide), wherein the MHC molecule is a soluble MHC molecule (e.g., lacking the transmembrane domain and cytoplasmic domains); and (b) subjecting the reaction mixture to conditions sufficient to (i) generate the polypeptide from the nucleic acid molecule, and (ii) couple the polypeptide and the nucleic acid molecule to the MHC molecule, thereby yielding a barcoded MHC molecule. In some instances, the reaction mixture is partitioned into a partition, such as a partition amongst a plurality of partitions (such as a droplet in an emulsion or a well of, e.g., a micro/nanowell array).

Also disclosed herein, in some embodiments, are methods for generating labeled MHC molecules, comprising: (a) providing a plurality of partitions, wherein at least a subset of the plurality of partitions each comprise (i) a plurality of soluble MHC molecules and (ii) a plurality of nucleic acid molecules comprising a sequence encoding a common polypeptide, wherein each partition of the subset of the plurality of partitions comprises a nucleic acid molecule encoding a unique polypeptide; and (b) subjecting the plurality of partitions to conditions sufficient to, in each of the subset of the plurality partitions, (i) generate the common polypeptide from the nucleic acid molecule and (ii) couple the common polypeptide and a nucleic acid molecule of the plurality of nucleic acid molecules to a MHC molecule of the plurality of soluble MHC molecules to yield a plurality of labeled MHC molecules. Here, the nucleic acid molecule encoding for the polypeptide (and/or a proxy for the polypeptide, such as a barcode sequence) can be detected (e.g., through nucleic acid sequencing, hybridization, PCR, digital PCR, etc.) to determine the identity of the pMHC complex. The reaction mixture (e.g., in a partition amongst a plurality of partitions) may comprise the necessary reagents and biological machinery for in vitro transcription and translation. In vitro transcription within the reaction mixture yields an mRNA molecule using the polynucleotide as a template. In vitro translation of the mRNA molecule yields the peptide encoded by the polynucleotide sequence. The peptide can then be loaded into the peptide binding groove of an MHC molecule. The MHC molecule, e.g., an MHC monomer or multimer, may be supplied to the reaction mixture following in vitro transcription and translation or is optionally present in the reaction mixture prior to and/or during in vitro transcription and translation.

In some instances, the nucleic acid molecule comprising a sequence encoding the polypeptide to be loaded into an MHC molecule is an RNA molecule and the polypeptide is generated from the RNA using in vitro translation reaction. In other instances, the nucleic acid molecule comprising a sequence encoding the polypeptide to be loaded into an MHC molecule is a DNA molecule, wherein an RNA encoding the polypeptide is generated using an in vitro transcription reaction and the polypeptide is generated from the RNA using in vitro translation reaction. The nucleic acid molecule encoding the peptide can comprise one or more sequence elements configured to facilitate in vitro transcription and/or translation, for example a promoter sequence (such as a T7 promoter sequence) and open reading frame for the polypeptide. In some cases, the open reading frame can serve to identify the polypeptide. The nucleic acid molecule can also include a barcode element which can serve as a specific label or identifier for the polypeptide sequence as well as other functional sequences, such as, for example, a primer sequence, a capture sequence (e.g., a sequence complementary to a sequence on, e.g., a barcoded bead), an adapter sequence (e.g., comprising a sequencing primer sequence (e.g., R1 or a partial R1 ("pR1")), a flow cell attachment sequence (e.g., P5 or P7 or partial sequences thereof)), etc. The plurality of nucleic acid molecules comprising the sequence encoding the polypeptide of interest may be single-stranded molecules. The plurality of nucleic acid molecules comprising the sequence encoding the polypeptide of interest may be double-stranded molecules. The nucleic acid molecules comprising the sequence encoding the polypeptide of interest may be partially double-stranded molecules. In some instances, the MHC molecule (e.g., MHC monomer or MHC multimer) is coupled to a carrier as described elsewhere herein (e.g., protein or polypeptide carrier, such a streptavidin, or a polymer backbone, such as dextran). As described previously, the MHC molecule may be directly coupled to the carrier or indirectly bound to the carrier. The MHC molecule may be covalently coupled to the carrier (e.g., chemically coupled or part of a fusion protein). The MHC molecules may be attached to a carrier and the plurality of nucleic acid molecules comprising the sequence encoding the polypeptide may be coupled to said carrier. For example, in some embodiments, the MHC molecules (e.g., biotinylated MHC molecules) are attached to a streptavidin carrier, the plurality of nucleic acid molecules comprising the sequence encoding the polypeptide of interest comprise a biotin moiety, and wherein the nucleic acid molecule are coupled to said carrier through a biotin-streptavidin interaction.

In some instances, the MHC molecule comprises a conditional ligand as previously described, wherein the conditional ligand is exchanged for the polypeptide in a peptide exchange reaction. As described elsewhere herein, the conditional ligand may be a polypeptide comprising a protease cleavage domain configured to facilitate cleavage and release of the conditional ligand, a polypeptide comprising a modification configured to facilitate cleavage of the conditional ligand (e.g., a periodate-sensitive linker), a polypeptide comprising a photo-labile amino acid (e.g., 2-nitrophenyl-based compounds such as 3-amino-3-(2-nitro)phenyl-propionic acid), or a polypeptide covalently linked to the MHC molecule, wherein the polypeptide comprises a protease (e.g., thrombin) cleavage domain configured to release the conditional ligand upon protease treatment. In some instances, as also described elsewhere herein, the MHC molecule is provided in the reaction mixture (e.g., a partition) with a molecular chaperone. The molecular chaperone (e.g., TAPBR) may be provided along with an empty MHC (e.g., not loaded with peptide) or with an MHC molecule comprising a conditional ligand.

In some instances, the plurality of nucleic acid molecules comprising the sequence encoding the polypeptide of interest is provided to the reaction mixture (e.g., partition) attached to a support. In some instances, the support is a bead (e.g., a single bead). The polypeptide encoding nucleic acid molecules may be releasably attached to the bead and released from the bead. The polypeptide encoding nucleic acid molecules may be released from the bead prior to, concurrent with, or subsequent to in vitro transcription and/or translation steps. In some embodiments the bead is a gel bead. In some instances, the gel bead is a degradable gel bead, wherein the gel bead is degradable upon application of a stimulus as described elsewhere herein.

In some cases, the nucleic acid molecule encoding the polypeptide of interest is coupled to the WIC molecule and/or carrier. The nucleic acid molecule can be coupled to a MHC multimer by a variety of mechanisms as previously described, including, but not limited to covalent and non-covalent interactions. For example, the polypeptide encoding nucleic acid molecules can be chemically linked to the WIC molecule and/or carrier (e.g., using Lightning-Link® chemistry, reaction of functional groups such as thiols, amines, click chemistry moieties, etc.). As such, the polypeptide encoding nucleic acid molecules, WIC molecules, and/or carrier molecules may comprise functional groups/modifications configured to facilitate coupling of barcode molecules to WIC and/or carrier molecules. In another example, a pair of binding molecules couples the nucleic acid molecule encoding the polypeptide to the WIC molecule and/or carrier. For example, the nucleic acid molecule encoding the polypeptide may be linked to one member of a binding pair and the other member of the binding pair can be linked to the MHC molecule and/or carrier. In some cases, the nucleic acid molecule encoding the polypeptide comprises a subsequence having sequence complementary to an oligonucleotide coupled to the WIC multimer and the subsequence hybridizes to the oligonucleotide coupled to the WIC multimer, thereby coupling the polypeptide-encoding nucleic acid to the MHC molecule and/or carrier.

In some cases, loading of a peptide into a peptide binding groove of a WIC molecule (e.g. in a multimer) occurs prior to coupling of a polypeptide-encoding nucleic acid to the WIC molecule. In some cases, loading of a peptide into a peptide binding groove of a MHC molecule occurs subsequent to coupling of the polypeptide-encoding nucleic acid to the multimer. In some cases, loading of a peptide into a peptide binding groove of a WIC molecule occurs simultaneously the coupling of a polypeptide-encoding nucleic acid to the WIC molecule.

Figure 60:
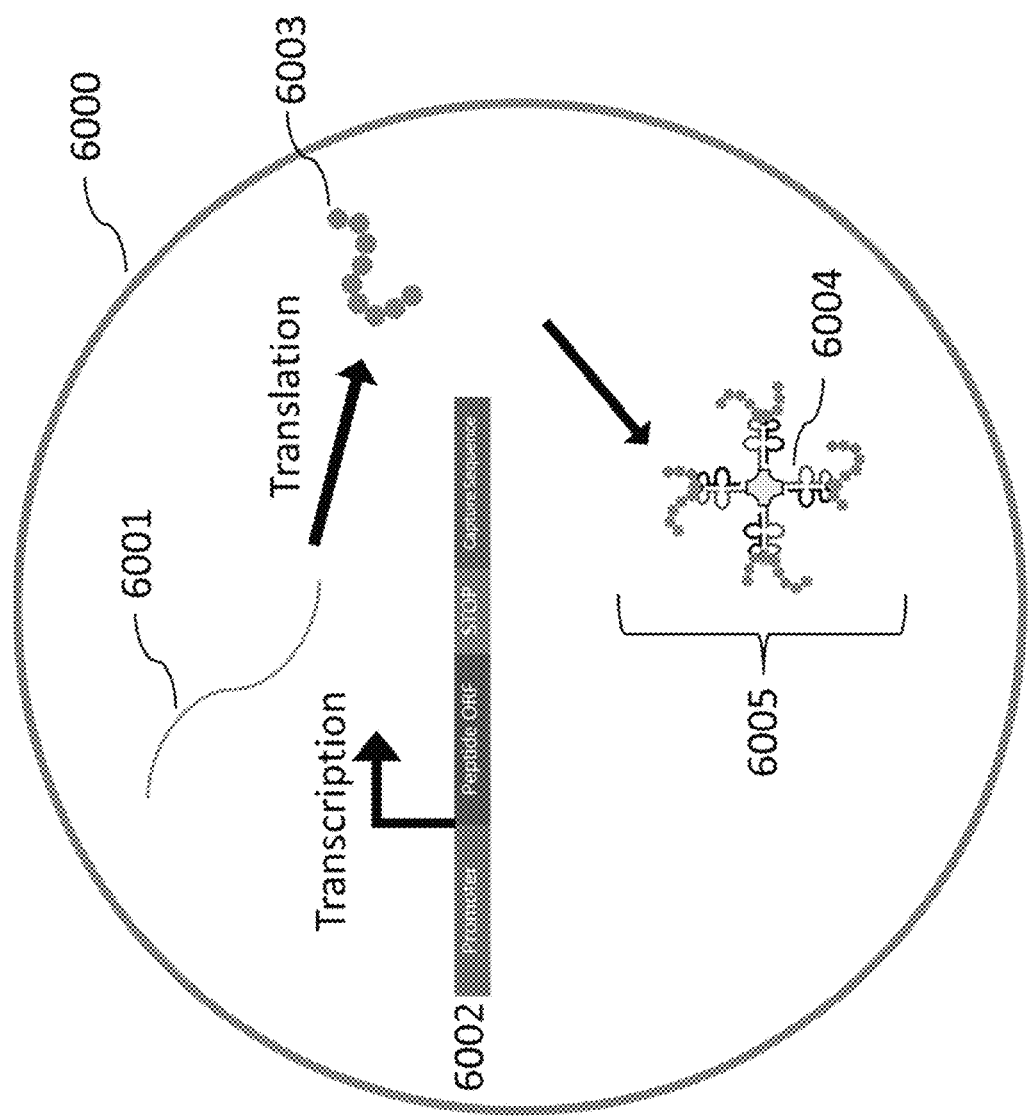
FIG. 60 illustrates the in-partition generation of MHC multimer complexes using in vitro transcription and in vitro translation.
Figure 105:
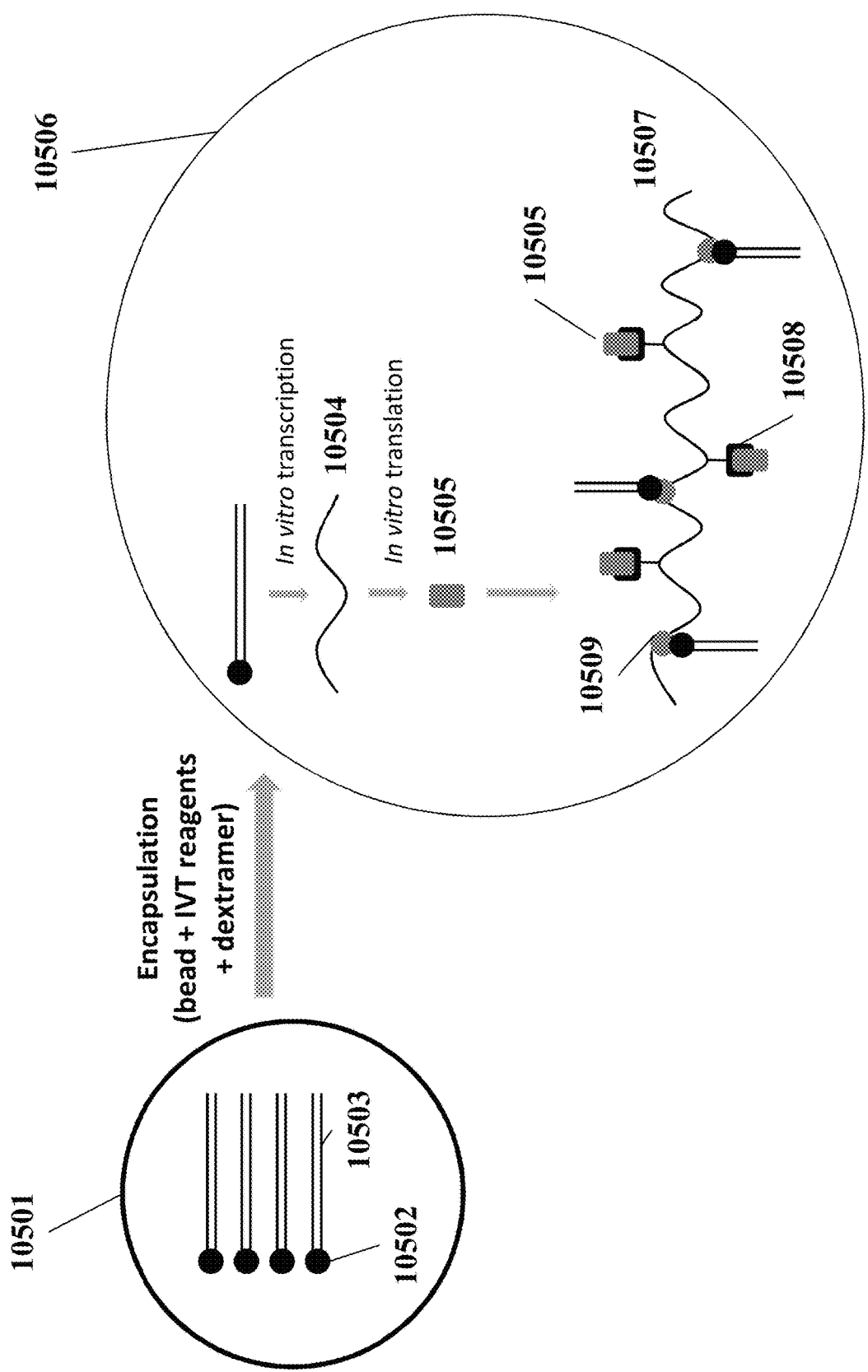
FIG. 105 illustrates an example method of dextramer display.

In some embodiments, labeled MHC-peptide multimer complexes are produced by in vitro transcription and/or in vitro translation as previously described (see, e.g., FIG. 60 describing MHC tetramers and FIG. 105 describing dextramer display). In dextramer display, a translated peptide (e.g., a polypeptide antigen) may be associated (e.g., directly or indirectly associated) with its coding nucleic acid (e.g., a biotin-labeled DNA construct) molecule via a polymer backbone (e.g., a linear or branched, functionalized dextran polymer). A dextran backbone may be functionalized such that translated peptide molecules and peptide-coding nucleic acid molecules can be attached (e.g., covalently and/or non-covalently linked) to the dextran backbone to generate a dextramer display. In some cases, a dextran backbone may be functionalized with WIC molecules and streptavidin moieties. For example, the MHC molecules may be covalently coupled to dextran backbone, which comprises free streptavidin moieties to which a biotinylated polypeptide encoding nucleic acid molecule can be coupled. Biotinylated WIC molecules may also be coupled to streptavidin moieties on a dextran backbone, which may also comprise additional free streptavidin moieties to bind a biotinylated polypeptide encoding nucleic acid molecule. For example, using a streptavidin-containing dextran backbone, biotinylated WIC molecules may be provided at limiting concentrations such that the WIC molecules attach to the backbone, but still comprise empty streptavidin sites. Alternatively, biotinylated WIC molecules may be attached to the dextran backbone, and additional streptavidin sites (e.g., for biotinylated nucleic acid molecule attachment) may be added to the MHC-conjugated dextramer. A translated peptide may then bind to such an WIC molecule linked to the dextramer to produce a labeled MHC-peptide multimer complex. Thus, dextramers functionalized with MHC-peptide complexes and peptide-coding nucleic acid (e.g., DNA) molecules can be used in binding assays, for example, with TCRs or with cells comprising TCRs (such as a T cell). The peptide sequence of an interacting pair can be determined from the peptide-coding nucleic acid (e.g., DNA) molecules linked to the dextramers, and the identity of the TCR that may be bound to the MHC-peptide complex of a dextramer can be obtained by characterizing the TCR gene(s) or derivatives thereof as described elsewhere herein.

A method for generating a MHC-peptide library comprising nucleic acid barcodes (e.g., DNA or RNA molecules) may comprise one or more of the following operations. A plurality of nucleic acid molecules coding for a plurality of different peptide sequences (e.g., a select number of peptide sequences or a large number of peptide sequences for semi-random or completely random library generation) may be labeled with a binding group, such as biotin. In some cases, the nucleic acid molecules are DNA molecules and comprise, in addition to a sequence coding for a peptide, a barcode or identifier sequence. Alternatively, a nucleic acid sequence coding for a peptide may be used as an identifier or barcode sequence. A plurality of copies of a first labeled nucleic acid molecule may be linked (e.g., covalently or non-covalently linked) to a first bead (e.g., a first gel bead). A plurality of copies of a second labeled nucleic acid molecule may be linked (e.g., covalently or non-covalently linked) to a second bead (e.g., a second gel bead). Thus, a plurality of beads (e.g., a plurality of gel beads) may be generated, wherein each bead may be linked (e.g., covalently or non-covalently linked) to a plurality of copies of a specific nucleic acid molecule coding for a specific peptide. A binding moiety-labeled nucleic acid molecule (e.g., biotinylated molecule) may be releasably attached to a bead (e.g., through a labile bond, such as a disulfide bond) as described elsewhere herein. A plurality of functionalized beads (e.g., beads having nucleic acid molecules attached thereto) may be partitioned into a plurality of droplets (e.g., a plurality of emulsion droplets) wherein at least one droplet of the plurality of droplets may comprise: (1) a bead comprising one or more copies of a nucleic acid molecule (e.g., a DNA template for a peptide); (2) a biological machinery, e.g., polymerase, ribosomes, aminoacyl-tRNA synthetases, translation initiation and elongation factors, nucleases, etc., that may be used for in vitro transcription and/or translation; and (3) one or more MHC molecules coupled to a carrier (e.g., streptavidin) as described elsewhere herein (e.g., biotinylated MHC-streptavidin multimers, MHC dextramers) In vitro transcription and/or translation of the nucleic acid molecules may be performed in the plurality of droplets resulting in the generation of peptides inside the plurality of droplets. The generated peptides may be loaded into peptide binding grooves of MHC molecules (e.g., MHC monomers or MHC multimers, such as MHC-streptavidin tetramers and dextramers). In some cases, MHC molecules are pre-loaded with a conditional ligand as described herein, which is replaced by a generated peptide. Binding-moiety (e.g., biotin) labeled nucleic acid molecules (e.g., those not bound to any bead) may bind to streptavidin moieties linked to the carrier. Hence, in the at least one droplet of the plurality of droplets peptide-MHC molecules may be generated that are linked to one or more nucleic acid molecules (e.g., those comprising coding sequences and/or barcode sequences). The plurality of droplets (e.g., plurality of emulsion droplets) may be broken and, in some cases, a quenching step is performed. Quenching may be performed by adding, e.g., biotin molecules to the mixture to occupy any remaining streptavidin sites (e.g., those not bound to any biotin-labeled nucleic acid molecule) on the carrier (e.g., to prevent cross-reaction of dextramers and nucleic acid molecules from different partitions). Emulsion breaking and quenching may be performed simultaneously. The peptide-MHC complexes may be purified (e.g., separated or isolated) from the mixture (e.g., the emulsion) using any suitable purification technique, e.g., size-exclusion or affinity chromatography. The peptide-MHC complexes may be pooled to generate a MHC-peptide library suitable for screening, e.g., TCRs and cells comprising TCRs.

In some cases, loading of a peptide into a peptide binding groove of an MHC molecule occurs prior to linking of a peptide encoding oligonucleotide (e.g., DNA) to a MHC-carrier complex (e.g., dextramer comprising free streptavidin sites). In some cases, loading of a peptide into a peptide binding groove of a MHC molecule occurs subsequent to coupling of a peptide encoding oligonucleotide (e.g., DNA) to a MHC-carrier complex. In some cases, loading of a peptide into a peptide binding groove of a nMHC molecule occurs simultaneously with coupling of a peptide encoding oligonucleotide (e.g., DNA) to a MHC-carrier complex.

A method for generating MHC-peptide libraries may comprise two or more partitioning steps. For example, a method for generating MHC-peptide libraries may comprise a first partitioning step comprising generating a first plurality of emulsion droplets for performing a first reaction or set of reactions, and a second step comprising generating a second plurality of emulsion droplets for performing a second reaction or set of reactions. In some cases, the first reaction performed in the first plurality of emulsion droplets is in vitro transcription of a DNA construct (e.g., a DNA construct encoding a peptide or protein) that yields a corresponding mRNA molecule. In some cases, the second reaction performed in the second plurality of emulsion droplets is in vitro translation of an mRNA molecule into a peptide or protein. Loading of the generated peptides into peptide binding grooves of MHC molecules may occur subsequent to in vitro translation in the second plurality of emulsion droplets.

In another example, a plurality of MHC-peptide complexes displayed on a surface (e.g., a surface of a cell, a particle, or a polymer) can be used as a labelling agent. In some cases, the surface is a cell surface and MHC-peptide complexes are presented using cell surface display systems. Cell surface display systems can be used to express a protein or polypeptide on the surface of prokaryotic and eukaryotic cells (e.g., bacteria, yeast, insect, and mammalian cells). In some embodiments, the genetic information encoding the MHC-peptide complex for display is introduced into a cell (e.g., bacteria, yeast, insect, or mammalian cell) in the form of a polynucleotide element, e.g. plasmid. The polynucleotide element can be introduced into a cell using any suitable delivery method, examples of which are provided elsewhere herein.

The cell can use the exogenous genetic information to produce the MHC-peptide complex to be displayed. For example, the coding sequence a MHC-peptide complex can be linked to the coding sequence of a yeast cell wall protein. The MHC-peptide complex can then be tethered to the yeast cell wall protein, allowing the MHC-peptide complex to be displayed on the yeast cell surface. The displayed MHC-peptide complex can then be subjected to binding or interaction assays, and binding interactions of the MHC-peptide complex can then be studied by capturing the DNA or RNA sequence encoding the recombinantly displayed protein. In some cases, the DNA or RNA sequence can comprise a barcode sequence which specifically identifies the displayed MHC-peptide complex. Similar systems are available for bacteria, insect cells, and mammalian cells. In cases where the MHC-peptide complex binds to a cell or a component of a cell (e.g., a cellular receptor, e.g., T cell receptor), information about the cell (e.g., transcriptome analysis, genome analysis, etc.) can also be obtained using methods disclosed herein.

Disclosed herein, in some embodiments, are methods for screening an antigen, comprising: (a) contacting an immune receptor with a plurality of engineered yeast cells to yield an engineered yeast cell bound to the immune receptor, wherein the plurality of engineered yeast cells comprise (i) a complex comprising a polypeptide (e.g., an antigenic polypeptide) coupled to a major histocompatibility complex (MHC) molecule; and (ii) a first nucleic acid molecule comprising a sequence encoding for the polypeptide antigen; (b) generating a plurality of partitions, wherein a partition of the plurality of partitions comprises (i) the engineered yeast cell bound to the immune receptor; and (ii) a plurality of nucleic acid barcode molecules comprising a common barcode sequence; (c) generating a second nucleic acid molecule comprising (i) a sequence corresponding to the polypeptide antigen and (ii) a sequence corresponding to the common barcode sequence. The plurality of partitions may be a plurality of aqueous droplets in an emulsion. The plurality of partitions may be a plurality of wells, such as wells in a micro/nanowell array.

In some instances, the engineered yeast may comprise at least one exogenous nucleic acid molecule comprising one or more sequences encoding for a MHC molecule (such as a specific HLA allele) and a sequence encoding for a polypeptide antigen. The MHC-peptide complex may be encoded for and expressed as a single chain fusion protein wherein the polypeptide is covalently coupled to the MHC molecule. See, e.g., Gee M H, et al, Antigen Identification for Orphan T Cell Receptors Expressed on Tumor-Infiltrating Lymphocytes; Cell. 2018 Jan. 25; 172(3):549-563.e16. In some instances, the yeast are lysed in the partition to release polypeptide encoding nucleic acids corresponding to the pMHC complex. In some embodiments, the engineered yeast cells comprise one or more mutations in one or more cell wall proteins and/or cell wall biogenesis proteins, wherein the mutations are configured to facilitate yeast cell wall lysis. For example, in some instances, the engineered yeast comprises one or more mutations in one or more of the PDE2, SRB1/PSA1, and/or PKC1 genes. See, e.g., Zhang N, et al, Genetically controlled cell lysis in the yeast *Saccharomyces cerevisiae*; Biotechnol Bioeng. 1999 Sep. 5; 64(5): 607-15.

The peptide-MHC complex (covalently linked or non-covalently linked) may be displayed on the surface of the engineered yeast cells. For example, the engineered yeast may be configured (e.g., using recombinant fusion protein) to express a pMHC complex coupled to a domain of a yeast cell surface anchor protein such that the pMHC is displayed on the surface of the engineered yeast cell. See, e.g., Andreu C, et al, Yeast arming systems: pros and cons of different protein anchors and other elements required for display; Appl Microbiol Biotechnol. 2018 March; 102(6):2543-2561. The MHC molecule may be coupled (e.g. as a fusion protein) to the N-terminus of a yeast cell surface anchor protein. The MHC molecule may be coupled (e.g. as a fusion protein) to the C-terminus of a yeast cell surface anchor protein. The MHC molecule may be coupled (e.g. as a fusion protein) to an endogenous or native yeast cell surface anchor protein. The MHC molecule may be coupled (e.g. as a fusion protein) to an exogenous or non-native yeast cell surface anchor protein. In some embodiments, the engineered yeast is configured to express a MHC complex (e.g., a pMHC) coupled (e.g., as a fusion protein) to a yeast cell surface anchor protein comprising a glycosylphosphatidylinositol (GPI) anchor. Any suitable GPI-anchored yeast cell surface anchor protein may be utilized, such as members of the agglutinin system (e.g., a-agglutinin and α-agglutinin, such as Agα1p, and Aga1p) or the flocculin system (e.g., flocculation protein 1 (Flo1), FS (Flo1 short, amino acids 1 to 1099 of Flo1) and FL (Flo1 long, positions 1 to 1447 of Flo1)). Other GPI-anchored surface anchor proteins may be utilized, including, but not limited to Suppression of Exponential Defect 1 (Sed1), stationary phase induced 1 (Spi1), cell wall protein 1 (Cwp1p), Cwp2p, Temperature shock-inducible protein 1 (Tip1), and TIP1-related protein 1 (Tir1)/Serine-rich protein 1 (Srp1). In some instances, the yeast cell surface anchor protein does not comprise a GPI anchor. In some instances, the yeast cell surface anchor protein binds or interacts with a protein anchored to the yeast cell wall. In some embodiments, the yeast cell surface anchor protein is the a-agglutinin subunit Aga2p. In some embodiments, the yeast cell surface anchor protein is a protein with internal repeats (Pir) protein, such as Pir1, Pir2, Pir3, Pir4, or Pir5.

The methods for screening an antigen disclosed herein, in some embodiments, comprise: (a) contacting an immune receptor with a plurality of engineered yeast comprising a nucleic acid molecule comprising a sequence encoding for a polypeptide; and (b) providing a plurality of partitions, wherein a partition of said plurality of partitions comprises (i) an engineered yeast cell bound to said immune receptor; and (ii) a plurality of nucleic acid barcode molecules comprising a common barcode sequence; (c) generating a barcoded nucleic acid molecule comprising (i) a sequence corresponding to the polypeptide and (ii) a sequence corresponding to the common barcode sequence. The immune receptor may be a T cell receptor (TCR). The TCR may be present in a cell, e.g., a T cell. In some embodiments, the methods disclosed herein comprise (a) contacting a cell (e.g., a T cell) comprising an immune receptor with the pMHC engineered yeast cell to yield a cell bound to the engineered yeast; and (b) generating a partition comprising the cell bound to the engineered yeast. In these embodiments, the identity of the immune receptor bound by the pMHC complex of the yeast cell may also be determined. For example, in addition to generating a barcoded molecule derived from the yeast and corresponding to the polypeptide, a barcoded molecule comprising a sequence corresponding to V(D)J sequence of an immune receptor (e.g., TCR pair) can also be generated and analyzed as described elsewhere herein. The presence of the common barcode sequence in the partition allows the identification of peptide-TCR interacting pairs (e.g., through detection means, such as nucleic acid sequencing, hybridization approaches, PCR, digital PCR, real-time PCR, etc.).

In some instances, the plurality of nucleic acid barcode molecules comprise a capture sequence and the engineered yeast comprise a sequence configured to hybridize with the capture sequence. For example, in some instances, the method comprises (a) hybridizing a capture sequence of a nucleic acid barcode molecule with a complementary (or partially complementary) sequence in a nucleic acid molecule derived from the engineered yeast and (b) performing a nucleic acid extension reaction to generate a barcoded nucleic acid molecule comprising a sequence corresponding to the polypeptide and a barcode sequence. In other instances, the method comprises (a) hybridizing a capture sequence of a nucleic acid barcode molecule with a complementary (or partially complementary) sequence in a nucleic acid molecule derived from the engineered yeast and (b) performing a ligation reaction to generate a barcoded nucleic acid molecule comprising a sequence corresponding to the polypeptide and a barcode sequence. The sequence corresponding to the polypeptide may be a sequence encoding for the polypeptide and/or other known sequence associated with the polypeptide (e.g., a barcode sequence). The plurality of nucleic acid barcode molecules may be attached to a solid support (e.g., a bead). In some instances, the plurality of nucleic acid barcode molecules is releasably attached to the bead as described elsewhere herein (e.g., through a labile bond) and are released from said bead (e.g., upon application of a stimulus). In some embodiments, the bead is a gel bead (e.g., a degradable gel bead), such as the gel beads described elsewhere herein.

A labelling agent may comprise an antigen presenting particle. In some cases, an antigen presenting particle may comprise an antigen on or adjacent to its surface. The antigen presenting particle may bind to one or more molecules on the surface of a cell in a sample, e.g., through the antigen on the antigen presenting particle. In some cases, an antigen presenting particle may be used as a labelling agent for an immune cell, e.g., a T cell or a B cell. Such antigen presenting particle may bind to a T cell receptor and/or B cell receptor. In some cases, the antigen presenting particle comprises an antigen that is recognized (e.g., bound) by an immune cell. The antigen presenting particle may be a cell, e.g., a cancer cell or other antigen presenting cell. The antigen presenting particle may be a pathogen, e.g., a bacterium, a fungus, a microbe or a virus. The antigen presenting particle may be a macromolecule, e.g., a polymer such as a dextramer or a nanotube. In certain cases, the antigen presenting particle (e.g., a cell or a virus) may comprise an antigen expression vector that expresses the antigen on the surface of the particle. The antigen expression vector may comprise a barcode for identifying the nucleic acid or amino acid sequence of the antigen.

In some embodiments, MHC-peptide complexes are presented via an antigen presenting cell (APC). An antigen presenting cell (APC) can be a natural APC or an artificial APC. Natural APCs include, for example, natural dendritic cells which can be obtained from a subject, such as a human subject. In some embodiments, immature dendritic cells are activated and matured and pulsed with a peptide of interest. Artificial APCs include artificial cell or bead based systems. In some embodiments, cell lines are used to present MHC-peptide complexes. One approach is the use of the K562 cell line or *Drosophila* spp. cell line. K562 cells or *Drosophila* spp. cells can be modified to transiently or stably express a MHC-peptide complex. For example, in some embodiments, human K562 (chronic myelogenous leukemia (CIVIL)) cells are engineered to be an artificial APC (aAPC). Expression of HLA class I and/or class II molecules can be induced in K562 cells by treatment with chemicals and/or cytokines and K562 can be genetically engineered (e.g., using a lentiviral-based expression system) to aid in the expression HLA class I and/or II molecules and immune receptor (e.g., TCR) recognition. See, e.g., Butler M. and Hirano N.; Human cell-based artificial antigen-presenting cells for cancer immunotherapy; Immunol Rev. 2014 January; 257(1): 191-209. Another approach is the use of lipid vesicles and exosomes coated with MHC-peptide complexes. In some cases, an aAPC can be a magnetic bead coated with MHC-peptide complexes. While magnetic beads are provided as an example herein, particles comprising any of a variety of materials (e.g., polymers, e.g., polystyrene) can be coated with MHC molecules or MHC-peptide complexes for antigen presentation. In some embodiments, an aAPC is a nanosize-aAPCs (e.g., 50 nm biocompatible iron-dextran paramagnetic nanoparticles or 30 nm avidin-coated quantum dot nanocrystals). Artificial APCs may also comprise additional molecules to aid in TCR binding (e.g., costimulatory agonists). The peptides of a MHC-peptide complex (e.g., MHC-peptide complexes displayed on an aAPC) can be associated with a barcode sequence (e.g., coupled to the aAPC) or other nucleic acid sequence identifier (e.g., mRNA sequence) which allows the identity of the peptide (e.g., amino acid sequence) and/or the identity of the peptide binding partner (e.g., TCR) to be determined at a later time, for example in binding assays. For example, in some embodiments, a library of nanoparticles comprising a plurality of nanoparticles, each coupled to a barcode oligonucleotide and comprising an WIC-peptide complex is generated to form an aAPC antigen library. A T-cell population can then be screened with the aAPC antigen library to generate one or more T-cells bound to an aAPC nanoparticle form the library of aAPC nanoparticles. Unbound aAPC nanoparticles can be washed away, and T-cells coupled to aAPC nanoparticles can be partitioned and processed as described herein to determine the identity of both the peptide and the TCR coupled to the peptide.

An exemplary method for using an antigen presenting particle (e.g., an APC) to analyze a cell may comprise one or more of the following operations. A sample comprising immune cells (e.g., blood or a fraction thereof) is mixed with a population of antigen presenting particles, and incubated to allow for the immune cells and antigen presenting particles to interact. The immune cells and antigen presenting particles bound to the immune cells are optionally purified, e.g., using an antibody that selectively binds to the immune cells. The bound immune cells and antigen presenting particles are partitioned into partitions (e.g., a droplet emulsion) with beads (e.g., gel beads). Each of the beads comprises capture oligonucleotide comprising a primer for mRNA molecules, a barcode and a UMI. At least one of the partitions contains an immune cell, an antigen presenting particle, and a bead. The immune cell and the antigen presenting particle (e.g., an APC) in the partition are lysed. The mRNA molecules from the immune cell and the antigen presenting particle are released. Reverse transcription is performed with the mRNA molecules and the capture oligonucleotide from the bead. Thus, the resulting cDNA are tagged with the barcode and UMI from the capture oligonucleotide. The resulting cDNA are then sequenced, e.g., to a high depth per cell on a sequencer (e.g., an Illumina sequencer). With the sequence reads, V(D)J regions of the immune cell are assembled and characteristics of the antigen presenting particle are also determined. When the antigen presenting particles are cells, the sequencing reads may be used to identify an antigen targeted by an immune cell with the corresponding V(D)J sequences. When the antigen presenting particles are, e.g., cancer cells, mutations and/or single-nucleotide polymorphisms (SNPs) may be determined with the sequence reads to identify a sub-populations of tumor cells that are targeted by an immune cell with the corresponding V(D)J sequences. When the antigen presenting particles are viruses, viral genome may be assembled to identify the sub-clone of viruses that are targeted by the immune cells with the corresponding V(D)J sequences. The method may yield pairs of V(D)J sequences and antigen-identifying sequences (e.g., mRNA of tumor cells or the genome of viruses) that are useful in developing personalized immunotherapies or vaccines against specific viral strains.

Similarly, any two cells (or virus, or other antigen displaying particle) in contact or otherwise coupled to each other may be assayed to determine a cell-cell interaction or other cell-cell relationship. For example, a first cell in contact with a second cell, or otherwise coupled to the second cell, may be partitioned into a partition with a plurality of capture oligonucleotides, as described elsewhere herein. The first and second cell may be partitioned together into a partition and subjected to lysing or enzymatic reactions as described elsewhere herein. Coupling between cells or cell-cell interactions may occur via cell-surface expression of a receptor or other molecule, in which the first cell may display a receptor which has affinity to a receptor or molecule which is displayed on the second cell. Cell surface display may be performed as described elsewhere herein. In some examples, the first cell may be an endothelial cell expressing a selectin and the second cell may be a leukocyte expressing a glycoprotein. In some examples, the first cell may be a yeast cell expressing a receptor and the second cell may be another yeast cell expressing a ligand. In some examples, a virus may express a viral capsid protein and a cell may express a protein with affinity to the viral capsid. Prior to partitioning, the first cell (or population of first cells) may be incubated with the second cell (or a population of second cells) to allow the cell to couple with the second cell. In some instances, the first cell or the second cell may be a synthetic or artificial cell (e.g. a nano- or micro-particle). In some instances, the first cell and/or second cell comprise a labelling agent or other nucleic acid molecule comprising a sequence corresponding to an analyte in the first and/or second cell. Using the partitioning and barcoding schemes described herein, the identity of any cell-cell or other interacting pair can be readily determined from the barcode sequence using, e.g., nucleic acid sequencing, hybridization approaches, PCR, digital PCR, real-time, PCR, mass spec, NMR, etc.).

In some cases, a MHC-peptide complex is displayed on a surface which is not a cell surface. Non-limiting examples of such technologies include mRNA display, ribosome, or dextramer display. In some embodiments, a MHC-peptide complex is produced by mRNA display. In mRNA display, a translated MHC-peptide complex is associated with its coding mRNA via a linkage, e.g., puromycin linkage. MHC-peptide complexes associated with coding mRNA can be used in binding assays, for example, with a T-cell having TCRs. The peptide sequence of an interacting pair can be determined from the mRNA linked to the MHC-peptide complex and the identity of the TCR can be obtained by sequencing the TCR gene or derivatives thereof. TCR genes can be sequenced according to embodiments described herein. In some embodiments, a MHC-peptide complex is produced by ribosome display. In ribosome display, a translated MHC-peptide complex is associated with its coding mRNA and a ribosome. MHC-peptide complexes associated with coding mRNA and a ribosome can be used in binding assays, for example, with a T-cell having TCRs. The peptide sequence of an interacting pair can be determined from the mRNA linked to the MHC-peptide complex and the identity of the TCR can be obtained by sequencing the TCR gene or derivatives thereof.

MHC-peptide libraries can be produced using any of the various aspects described herein (e.g., yeast displayed, ribosome displayed, mRNA displayed, dextramer displayed etc.). The library can include a plurality of peptides having different amino acid sequences. Each peptide, when presented to a T cell in the form of a MHC-peptide complex, can have a binding affinity for a particular T cell receptor. A library of MHC-peptide complexes generated according to embodiments described herein can be screened in binding or interaction assays to identify T-cell receptors capable of binding one or more MHC-peptide complexes, or in the alternative, MHC-peptide complexes capable of binding one or more T-cell receptors. MHC-peptide libraries described herein may comprise using identifiers or barcodes such as nucleic acid barcodes in order to assign a specific interaction of an immune cell with an MHC-peptide complex to a peptide sequence, a partition, a cell, etc. MHC-peptide libraries described herein may be used to characterize and/or analyze a plurality (e.g., a population or multiple populations) of immune cells and to diagnose, detect and/or stage a disease or condition in a subject (e.g., a human). Immune cells that may be used in combination with the herein described MHC-peptide libraries may be obtained from a biological sample (e.g., blood or plasma), e.g., those obtained from a subject (e.g., a human).

The MHC genes are very polymorphic in the population, and there is a large set of alleles of any given MHC gene that will have different binding specificities for peptides and TCRs. In some instances, the identity and peptide binding ability of specific MHC allele (such as common alleles of HLA-A/B/C or HLA-E/F/G) can be determined suing the methods disclosed herein. For example, disclosed herein are compositions comprising a peptide MHC complex (e.g., a MHC monomer or MHC multimer, such as a tetramer or dextramer) comprising a first barcode sequence associated with the peptide and a second barcode sequence associated with the specific MHC allele bound to the peptide. In some instances, the methods and compositions described herein comprise the use of a library of MHC multimers covering a set of MHC alleles of interest. For example, a first set of partitions is provided, e.g., a first set of wells, such that each partition of at least a subset of the first set of partitions comprises (i) a common MHC allele, wherein the MHC alleles are different in each partition of the subset of partitions; and (ii) a plurality of first nucleic acid barcode molecules comprising a common barcode sequence, wherein the barcode sequences are different in each partition of the subset of partitions. The first nucleic acid barcode molecules may then be attached to the MHC molecules (e.g., MHC monomers, MHC multimers comprising a carrier, etc.) using any suitable method, such as those previously described herein. The MHC molecules comprising the first barcode may then be collected from the first plurality of partitions and pooled (and optionally purified). A second set of partitions may then be provided, e.g., a second set of wells, such that each partition of at least a subset of the second set of partitions comprises (i) a plurality of MHC molecules (e.g., comprising a mixture of MHC alleles) comprising the first barcode; (ii) a plurality of common polypeptides, wherein the polypeptides are different in each partition of the subset of the second set of partitions; and (iii) a plurality of second nucleic acid barcode molecules comprising a common barcode sequence, wherein the barcode sequences are different in each partition of the subset of the second set of partitions. The second nucleic acid barcode molecules may then be attached to the MHC molecules comprising the first barcode sequence using any suitable method, such as those previously described herein. For example, in some instances, the first barcode molecule attached to the MHC molecules comprises a barcode sequence and a linker sequence, wherein the linker sequence is common to each of the first nucleic acid barcode molecules in the entire first set of partitions. In other words, the MHC molecule may comprise a unique first barcode sequence, but a common linker sequence. In the second set of partitions, the second nucleic acid molecules may comprise a sequence at least partially complementary to the linker sequence such the second barcode molecules hybridize to first nucleic acid barcode molecule coupled to the MHC molecule. As such, the first and second barcode molecules can be ligated together and/or subjected to a nucleic acid extension reaction to generate an MHC coupled to a nucleic acid molecule comprising the first barcode sequence (indicative of the MHC allele) and a second barcode sequences (indicative of the polypeptide in the pMHC complex). In this manner, a diverse library of WIC alleles and corresponding peptides can be generated in a high throughput manner to simultaneously for MHC alleles and pMHC-TCR binding pairs screen (e.g., using the methods for immune cell screening described elsewhere herein).

Characterization, Analysis, and Detection of Gene or Transcription Disruption Agents Disclosed herein, in some embodiments, are compositions, methods, and systems useful in the analysis of multiple analytes in a single cell or cell population. Examples of analytes include, without limitation, DNA (e.g., genomic DNA), epigenetic information (e.g., accessible chromatin or DNA methylation), RNA (e.g., mRNA or CRISPR guide RNAs), synthetic oligonucleotides (e.g., DNA transgenes), and proteins (e.g., intracellular proteins, cell surface proteins, extracellular matrix proteins, or nuclear membrane proteins). Examples of intracellular protein analytes include, but are not limited to, transcription factors, histone proteins, kinases, phosphatases, cytoskeletal proteins (e.g., actin, tubulin), polymerases, nucleases, and ribosomal proteins. An analyte may be a cell or one or more constituents of a cell. In some embodiments, a gene or transcription disruption or perturbation agent (e.g., CRISPR RNA, TALEN, zinc finger nuclease, antisense oligonucleotide, siRNA, shRNA, miRNA, etc.) is one of the analytes characterized by the compositions, methods, and systems disclosed herein.

In some cases, the methods may be used to screen cells carrying mutations, e.g., mutations generated by gene editing such as CRISPR technology. For example, a bead comprising a first capture oligonucleotide with a primer for CRISPR RNA (e.g., crRNA or guide RNA) or its complementary DNA and a second capture oligonucleotide with a primer endogenous nucleic acid in the cell, e.g., total mRNA or a specific mRNA. The bead may be made into a partition with a cell transfected with CRISPR RNA or a plasmid expressing CRISPR RNA. In some cases, the expressed CRISPR RNA or the plasmid may have a barcode (CRISPR barcode) or a capture sequence. The primers on the bead may be used to amplify and sequence the CRISPR RNA (e.g., using a barcoded adapter oligonucleotide comprising a sequence complementary to the CRISPR capture sequence, see FIGS. 12A-D) and endogenous mRNA (e.g., using a barcoded adapter oligonucleotide comprising an oligo(dT) sequence), thus determining the mutations generated by in the cell (see FIG. 12D). In some cases, the methods may be used to perform single cell RNA sequencing, e.g., as described in Dixit, et al., Perturb-Seq: Dissecting Molecular Circuits with Scalable Single-Cell RNA Profiling of Pooled Genetic Screens. Cell; Dec. 15, 2016; 167(7):1853-1866.e17, which is incorporated herein by reference in its entirety.

In some embodiments, the analyte is a gene or transcription perturbation agent. In some embodiments, the analyte is a transcription activator-like effector nuclease (TALEN). TALENS are specific restriction endonucleases that can be engineered to bind and cut specific DNA sequences. They are produced by fusing a DNA-binding domain with an endonuclease domain. TALEN analytes can be characterized analyzed through detection of a TALEN encoding nucleic acid (e.g., an mRNA transcript or plasmid DNA sequence encoding the TALEN mRNA). In some embodiments, a TALEN analyte is characterized by a capture oligonucleotide (e.g., releasably attached to a gel bed) specific for the TALEN nucleic acid sequence. In some embodiments, a TALEN analyte is characterized by a capture oligonucleotide (e.g., releasably attached to a gel bead) capable of coupling to an adapter sequence introduced into the TALEN nucleic acid sequence.

In some embodiments, the analyte is a zinc finger nucleases (ZFN). ZFNs are endonucleases formed by fusing a zinc finger DNA-binding domain to an endonuclease domain. ZFN nuclease analytes can be characterized via analysis of their nucleic acid sequences as described above for TALENS. In some embodiments, the analyte is an antisense oligonucleotide (ASO), siRNA, shRNA, miRNA, miRNA mimic or other transcription perturbation agent. ASOs and other transcription perturbation agent can be characterized via analysis of their nucleic acid sequences as described above for TALENS.

The gene and transcription perturbation agents described herein (e.g., crRNA, sgRNA, TALEN, ZFN, ASO, siRNA, shRNA, miRNA, etc.) are characterized along with one or more other analytes as described herein (e.g., mRNA transcriptome).

Characterization, Analysis, and Detection of Analytes Using a Cell Bead

Disclosed herein, in some embodiments, are compositions, methods, and systems useful in the analysis of multiple analytes in a single cell or cell population. In some aspects, the methods of the present disclosure may comprise the generation of a cell bead for capturing, processing, and analyzing (e.g., barcoding, sequencing) multiple types of analytes (e.g., components) from a cell. Analytes which can be captured within a cell bead for processing and/or analysis include any combination of one or more of proteins, metabolites, and nucleic acids. Analytes can be comprised within a cell bead matrix, attached to a cell bead, and/or attached to a particle (e.g., magnetic particle) within a cell bead (FIG. 17B). Systems and methods for generating cell beads comprising analytes from a cell are described in further detail elsewhere herein.

Cell beads may be used to identify and measure one or more targeted analytes from a cell together with one or more additional analytes (e.g., nucleic acids). One or more antibodies can be used to identify a targeted analyte, for example, by contacting a cell bead comprising an analyte. Antibodies may be coupled to one or more barcode molecules comprising one or more barcode sequences. A targeted analyte can be an internal protein and the antibody contacting the cell bead may have a binding specificity to the internal protein. An antibody may have binding affinity for an internal protein based on the presence or absence of one or more posttranslational modifications, such as phosphorylation, glycosylation, ubiquitination, methylation, or acetylation. For example, an antibody may have binding affinity for a protein when phosphorylated at one or more specific sites (i.e., may be a phosphospecific antibody). In another example, a targeted analyte can be a metabolite and the antibody contacting the cell bead may have a binding specificity to the metabolite. Multiple antibodies may be used to target multiple analytes (e.g., a protein and a metabolite). In some instances, a metabolite may be an alcohol, amino acid, nucleotide, antioxidant, organic acid, polyol, or vitamin. A metabolite may be a cofactor. The targeted analyte can be any constituent of a cell, such as any small molecule, large molecule, or macromolecule (e.g., macromolecular constituent). In yet another example, the targeted analyte can be from a class, set, or subset of analytes (e.g., proteins, metabolites, small molecules, etc.) sharing a structural similarity or homology (e.g., moiety, functional group, etc.), and the antibody contacting the cell bead may have a binding specificity to the class, set, or subset of analytes via the structural similarity. In such cases, a barcode sequence may uniquely identify the class, set, or subset of analytes. Upon binding to the antibody, the targeted analyte may be classified by the first barcode sequence as a member of the class, set, or subset of analytes.

The systems and methods described herein may allow for the production of one or more droplets containing a single cell bead and a single barcode bead. The systems and methods may also allow for the production of one or more droplets containing a single cell bead and more than barcode one bead, one or more droplets containing more than one cell bead and a single barcode bead, or one or more droplets containing more than one cell bead and more than one barcode bead.

The disclosure also provides compositions, systems and methods for generating cell beads in cell beads. Such methods, compositions and systems can be useful for positioning cells encapsulated in cell beads at the center or substantially at the center of the cells beads. In some cases, centering of a cell can prevent the contents of the cell beads (e.g., cells, components of cells, biomolecules derived from cells, nucleic acids from cells) from diffusing or leaking out of the cell bead. Loss of these materials can lead to partial or complete loss of the sequencing information for the contents of a given cell bead. For example, leakage of nucleic acids from cells at the edges of cell beads can lead to noisy profiles derived from sequencing and/or potential false positive calls. By centering cells within cell beads, a greater depth of cell bead material encapsulates cells, providing a larger diffusion distance and, thus, greater diffusion barrier for diffusion of encapsulated materials. Moreover, a cell bead in cell bead approach, itself, adds additional material that surrounds the cell, also resulting in a greater diffusion barrier. In general, cell beads in cell beads can be generated by a similar process used to generate single gel beads, as described elsewhere herein. First order cell beads can be generated as described herein, and then subjected to the same process for cell bead generation again to generate cell beads in cell beads.

FIG. 55A shows a droplet 5510 containing a cell bead 5520 that encapsulates a cell 5530 and a single gel bead 5540 comprising a barcode sequence. FIG. 55B shows a larger cell bead 5550 comprising the elements of droplet 5510 in FIG. 55, where the larger cell bead 5550 has been generated from precursors present in a droplet and subsequently polymerized or gelled.

An example method and microfluidic device architecture for generating cell beads in cell beads are schematically depicted in FIG. 56. As shown in FIG. 56, cell beads 5601, which contain cells 5602 may be generated in any suitable manner, including in a manner described herein, are provided in an aqueous phase. The cell beads 5601 are then provided 5603 to a microfluidic device 5604. The device comprises microfluidic channels arranged in a double-cross configuration. The cell beads 5601 are provided to the microfluidic device where they flow in a first channel 5605 of the microfluidic device 5604 to a first channel intersection with second and third channels 5606 and 5607. The second and third channels 5606 and 5607 provide polymeric or gel precursors that come together with the stream of cell beads 5601 from the first microfluidic channel 5605.

The stream comprising the cell beads 5601 and polymeric or gel precursors then flows through a fourth microfluidic channel 5608 to a second channel intersection with fifth and sixth channels 5609 and 5610. The fifth and sixth channels provide a phase immiscible with the aqueous phase of cell beads 5601 and polymeric or gel precursors flowing in channel 5608. The stream comprising the cell beads 5601 and polymeric or gel precursors from the fourth channel 5608 flows into the immiscible stream such that droplets 5611 comprising cell beads and polymeric or gel precursors are generated and flow away from the second intersection in a seventh channel 5612. The droplets 5611 can then be subject to conditions suitable for polymerizing or gelling the precursors in the droplets 5611 and subject to solvent exchange as is described elsewhere herein and the resulting cell beads in cell beads recovered.

A photograph showing generation of droplets comprising cell beads and polymeric or gel precursors using a microfluidic device, similar to that shown schematically in FIG. 56A, is shown in FIG. 56B. As shown an aqueous phase comprising cell beads 5601 provided from channel 5605 is provided to a first channel junction, into which aqueous phase polymeric or gel precursors flow from channel 5606. The resulting aqueous mixture, comprising both cell beads 5601 and polymeric or gel precursors, flows through channel 5608 into a second channel junction, into which oil provided by channel 5609 flows. The interaction between oil and aqueous phases generates droplets 5611 that comprise a cell bead 5601 and polymeric or gel precursors that flow away from the second channel junction in channel 5612.

Figure 57:
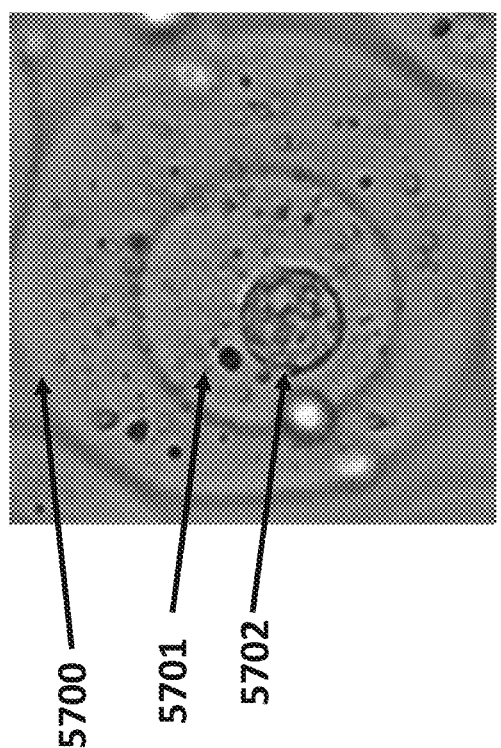
FIG. 57 is a photograph showing example generation of a cell bead in cell bead.

FIG. 57 shows a photograph of a cell bead in cell bead generated from droplets generated in FIG. 57. The cell bead in cell bead comprises a larger cell bead 5700 that encapsulates a smaller cell bead 5701. The smaller cell bead 5701 encapsulates a cell 5702. As shown in FIG. 57, the cell 5702 is substantially centered within the larger cell bead 5700.

Additionally, cells may be centered in droplets without the generation of a cell bead comprising a cell bead. For example, droplets comprising polymeric or gel precursors and cells may be subjected to shearing prior to cell bead generation. Shearing may be achieved, for example, via orbital shaking or in a microfluidic channel. In such cases, the kinetics of polymerization or gelation of the precursors can be controlled such that polymerization or gelation is sufficiently slow or delayed. Slower or delayed polymerization or gelling can permit internal circulation of droplet contents that can center a cell within a droplet, such that it can then be fixed in place at the center of a cell bead upon precursor polymerization or gelling.

Furthermore, cells may also be centered in droplets by forming core-shell beads, with cells suspended in the solution that forms the core. Cells may be formed by viscosity-mismatched flowing streams such that cells are suspended in a core fluid having a different viscosity than a shell fluid. The shell fluid may be liquid and/or formed from a cross-linked matrix such as a cross-linked polymer. Examples of such core-shell beads are described in Rossow et al., *J. Am. Chem. Soc.* 2012, 134, 4983-4989, which is incorporated herein by reference.

Core-shell beads having cells suspended in the cores may also be formed through the generation of aqueous-in-aqueous droplets made from aqueous two-phase systems. For example, the cells are suspended in a core solution (e.g., a polymer core solution, a polyethylene glycol (PEG) core solution) that is then surrounded by a cross-linked shell (e.g., cross-linked dextran shell). This bead may be generated from aqueous-in-aqueous droplets with one aqueous phase comprising cross-link precursors and another aqueous phase comprising cells. Additional details regarding the formation of core-shell beads from aqueous two-phase systems are provided in Mytnyk et al., *RSC Adv.*, 2017, 7, 11331-11337, which is incorporated herein by reference.

Cell beads comprising a nucleic acid molecule attached thereto can be generated using any suitable method(s) described herein. For a description of cell beads and cell bead generation strategies, see U.S. Pat. Pub. US 2018/0216162 and PCT Application PCT/US18/54458, filed Oct. 4, 2018, both of which are hereby incorporated by reference in their entirety. For example, in some embodiments, a biological particle (e.g., a cell or cell nucleus) is partitioned into a partition (e.g., a droplet in an emulsion) with polymeric or gel precursors and one or more nucleic acid molecules comprising, e.g., one or more functional sequences, such as the functional sequences described elsewhere herein. The partition is subjected to conditions sufficient to polymerize or cross-link the polymeric or gel precursors to generate the cell bead, wherein the cell bead encapsulates the biological particle and the one or more nucleic acid molecules.

In some cases, cell beads can be synthesized in one-step procedures, e.g., polymerization and concurrent cross-linking reactions of multifunctional monomers. In other cases, cell beads can be synthesized in multi-steps procedures, e.g., polymerization of monomers first, followed by crosslinking reactions by using, e.g., orthogonal, reactive groups that can respond to different conditions to allow stepwise approaches.

Cell beads can be synthesized by techniques that can create a crosslinked polymer. In some cases, copolymerization/cross-linking free radical polymerizations can be used to produce hydrogels by reacting hydrophilic monomers with multifunctional crosslinking molecules. This can be done by, for example, linking polymer chains via a chemical reaction(s), using ionizing radiation to generate main-chain free radicals which can recombine as crosslinking junctions, or physical interactions such as entanglements, electrostatics, and crystallite formation. Types of polymerization can include bulk, solution, and suspension polymerization.

Suspension polymerization or dispersion polymerization can be employed in water-in-oil or emulsion processes, sometimes called "inversion suspension." In some cases, the monomers and initiators can be dispersed in the oil or hydrocarbon phase as a homogenous mixture. In some cases, two types of polymer molecules can be first produced, each having a reactive, crosslinking moiety for cross-linking purposes. Then these two types of polymer molecules can be enclosed in an emulsion such that the two reactive, cross-linking moieties can react and form crosslinks between the two types of polymers, thereby completing the synthesis of the hydrogel.

In some cases, cell beads can be synthesized from monomers, polymerization initiators, and crosslinking reagents. After the polymerization reactions are complete, the hydrogels formed can be separated from remaining starting materials and unwanted by-products, etc. The length of the polymer formed can be controlled depending on the desired properties of the hydrogels.

Types of polymerizations employed to synthesize hydrogels can include, but are not limited to, free radical polymerization, controlled radical polymerization, crosslinking polymerization, networks formation of water-soluble polymers, and radiation crosslinking polymerization, etc. Polymerization can be initiated by initiators or free-radical generating compounds, such as, for example, benzoyl peroxide, 2,2-azo-isobutyronitrile (AIBN), and ammonium peroxodisulphate, or by using UV-, gamma- or electron beam-radiation.

For example, as shown in FIG. 137, cells and polymer or gel precursors are mixed with an immiscible fluid (e.g., an oil), thereby generating a plurality of aqueous droplets, including droplet 13701 comprising a biological particle, in this instance a cell 13702. Droplet 13701 may also comprise a nucleic acid molecule comprising a functional sequence 13705, as described elsewhere herein. Droplet 13701 is subjected to conditions sufficient for polymerization or gelation of the polymer or gel precursors to generate a cell bead 13703 comprising cell 13702 and nucleic acid molecule 13705. Gelation may comprise any of the gelation mechanisms and polymers described herein. In some instances, cell bead 13703 is subjected to treatment conditions sufficient to lyse cell 13702, releasing components of the cell into the cell bead. In other embodiments, cell 13702 is lysed in droplet 13701 prior to polymerization or gelation of the polymer or gel precursors to generate cell bead 13703 comprising nucleic acid molecule 13705. In still other embodiments, cell 13702 is permeabilized before, during, or after polymerization or gelation of the polymer or gel precursors. Cell beads are collected to generate a plurality of cell beads 13704. Cell beads may be stored for further processing. In some cases, nucleic acid molecule 13705 may be attached to the cell beads subsequent to polymerization or gelation of the polymer or gel precursor. For instance, polymer or gel precursors may comprise one or more functional groups that facilitate the attachment of nucleic acid molecule 13705 subsequent to polymerization or gelation of the polymer or gel precursors. In other embodiments, the polymer or gel precursors and/or nucleic acid molecule 13705 comprise functional groups, which facilitate the incorporation of nucleic acid molecule 13705 into the cell bead during polymerization or gelation of the polymer or gel precursors.

In some embodiments, the functionalized nucleic acid molecule(s) 13705 are entrapped within the cell bead polymeric and/or crosslinked matrix (also referred to herein as a "cell bead matrix"). In other embodiments, the nucleic acid molecule(s) 13705 are functionalized with chemical groups (e.g., acrydite, amine, thiol, etc.) such that the nucleic acid molecule(s) 13705 are incorporated into or otherwise attached to the cell bead matrix. For example, in a cell bead matrix comprising polyacrylamide, the nucleic acid molecule 13705 can comprise an acrydite moiety such that, upon polymerization of acrylamide monomers, the functionalized nucleic acid molecule(s) 13705 are incorporated into the cell bead matrix. In some embodiments, both the nucleic acid molecule 13705 and/or the cell bead matrix comprise one or more functional groups configured to facilitate attachment of the nucleic acid molecule 13705 to the cell bead matrix. For example, in some embodiments, generation of a cell bead comprising a nucleic acid molecule 13705 comprises: (a) providing a plurality of polymer or gel precursors (e.g., in a partition), wherein the polymer or gel precursors comprise a plurality of first crosslink precursors; (b) providing a plurality of functionalized nucleic acid molecules (e.g., comprising a poly-T sequence) comprising a second crosslink precursor; and (c) crosslinking the polymer or gel precursors and the nucleic acid molecules via a reaction between a first section of the first crosslink precursors and a second section of the second crosslink precursors, thereby forming the cell bead comprising the nucleic acid molecule(s).

In some instances, the functionalized nucleic acid molecules are irreversibly incorporated into the cell bead matrix. In other instances, the functionalized nucleic acid molecules are reversibly incorporated into the cell bead matrix. For example, a functionalized nucleic acid molecule can be functionalized with a labile moiety as described elsewhere herein (e.g., a disulfide bond) such that the functionalized nucleic acid molecule, or a portion thereof, is configured to be released from the cell bead matrix and/or cell bead.

In some embodiments, the cell bead matrix includes one or more of the following; disulfide crosslinked polyacrylamide, agarose, alginate, polyvinyl alcohol, PEG-diacrylate, PEG-acrylate/thiol, PEG-azide/alkyne, other acrylates, chitosan, hyaluronic acid, collagen, fibrin, gelatin, elastin, a polyolefin, an olefin copolymers, an acrylics, a vinyl polymer, a polyesters, a polycarbonate, a polyamide, a polyimide, a formaldehyde resin, a polyurethane, an ether polymer, a cellulosic, a thermoplastic elastomer, a thermoplastic polyurethane, or any polymeric precursor (e.g., monomer) thereof. In some embodiments, the cell bead matrix comprises polyacrylamide (e.g., disulfide crosslinked polyacrylamide).

In some embodiments, generation of the cell bead matrix comprises (a) providing a first polymer or gel precursor, wherein the first polymer or gel precursor comprises a plurality of first crosslink precursors, for example a moiety comprising an azide group; (b) providing a second polymer or gel precursor, wherein the second polymer or gel precursor comprises a plurality of second crosslink precursors, for example a moiety comprising an alkyne group; and (c) crosslinking the first polymer and the second polymer via a reaction (e.g., a click-chemistry reaction) between a first section of the first crosslink precursors and a second section of the second crosslink precursors, thereby forming the cell bead.

For example, as shown in FIG. 138, emulsion systems 13800, 13802, and 13804 represent different stages through which polymer molecules or gel precursors are crosslinked to form a cell bead matrix or hydrogel. Emulsion system 13800 can comprise a discrete droplet 13808 (comprising an aqueous phase) immersed in an oil phase 13810. Within the discrete droplet 13808, two polymer molecules 13812 and 13814 and a biological particle (e.g., a single biological particle, such as a single cell—not shown) can be partitioned together. In some instances, a functionalized nucleic acid molecule (not shown) is also partitioned with the polymer molecules or gel precursors and the biological particle. In some embodiments, the nucleic acid molecule further comprises a functional group (e.g., a click chemistry moiety such as 13818 or 13820) to facilitate attachment to the cell bead matrix. Polymer molecule 13812 can comprise a first crosslink precursor comprising a first click chemistry moiety 13818 and optionally a labile bond 13816 (e.g., a chemically, thermally, enzymatically, or photo-labile bond). Polymer molecule 13814 can comprise a second click chemistry moiety 13820. In the oil phase 13811, there can be other reagents, such as reagent 13822 (shown as a copper (II) reagent), which may be utilized to facilitate the click chemistry reaction between the first click chemistry moiety 13818 and the second click chemistry moiety 13820, either by itself or by a derivative thereof. Because the reagent 13822 remains outside of the discrete droplet 13808, generally no click chemistry reaction happens within the discrete droplet 13808 in the absence of the reagent 13822.

In emulsion system 13802, some of the reagent 13822 can penetrate the discrete droplet 13808, via, e.g., physical or chemical processes. In some instances, reagent 13822 becomes or is otherwise processed to become reagent 13824 (shown as a copper (I) reagent) in the discrete droplet 13808. In some instances, conversion into reagent 13824 requires additional reagents (not shown, e.g., a reducing agent such as sodium ascorbate). In these embodiments, reagent 13824 can be the reagent required to initiate the click chemistry reaction between the first click chemistry moiety 13818 and the second click chemistry moiety 13820. Once in the proximity of both the first click chemistry moiety 13818 and the second click chemistry moiety 13820, the reagent 13824 can initiate a click chemistry reaction, such as a Cu(I)—Catalyzed Azide-Alkyne Cycloaddition (CuAAC), see emulsion system 13804. In embodiments where the functionalized nucleic acid molecules comprise a click-chemistry moiety, the reagent can also catalyze the attachment of nucleic acid molecules to the cell bead matrix.

As shown in the emulsion system 13804 of FIG. 138, in the presence of the reagent 13824, a crosslink 13826 is formed linking the two polymer molecules 13812 and 13814 together, via the newly formed moiety 13828 because of the click chemistry reaction between the first click chemistry moiety 13818 and the second click chemistry moiety 13820. A hydrogel comprising the crosslinked polymer molecules 13812 and 13814 can thus be formed, thereby generating the cell bead. Reagents 13822 and/or 13824 can be removed from the newly formed hydrogel if desired. In some instances, the cell bead matrix comprises a labile bond 13816 (e.g., a disulfide bond) configured to release the crosslinks 13826 and/or degrade the hydrogel upon application of a stimulus (e.g., a chemical, thermal, or photostimulus). In some instances, the nucleic acid molecules are attached to the hydrogel via a labile bond 13816 configured to release the nucleic acid molecules from the cell bead matrix.

In some embodiments, the nucleic acid molecule(s) described herein are attached, entrapped, or otherwise incorporated into the cell bead matrix during cell bead generation (see, e.g., FIG. 137 and FIG. 138). In other embodiments, the nucleic acid molecule(s) described herein are attached, entrapped, or otherwise incorporated into the cell bead matrix subsequent to cell bead generation. For example, in some instances, a cell bead can be generated as described elsewhere herein and a nucleic acid molecule can be attached to the cell bead matrix by a chemical reaction, e.g., between a functional group of the nucleic acid molecule(s) and a functional group in the cell bead matrix.

FIGS. 139A-B illustrates an example of generating cell beads comprising functionalized molecule(s) attached to a polymer matrix. For instance, as shown in FIG. 139A, a partition 13900 comprising gel or polymer precursors 13901 attached to a nucleic acid molecule(s) 13902 (e.g., a nucleic acid molecule comprising a poly-T sequence configured to hybridize to a mRNA molecule) can be subjected to conditions sufficient to polymerize, gel, or crosslink the precursors 13901, thereby generating a cell bead 13910 comprising nucleic acid molecule(s) 13902 attached to the polymer matrix 13903. In some instances, a partition 13920 comprising a first polymer or gel precursor 13901 attached to nucleic acid molecule(s) 13902 and a second polymer or gel precursor 13904 can be subjected to conditions sufficient to polymerize, gel, or crosslink precursors 13901 and 13904, thereby generating a cell bead 13930 comprising nucleic acid molecule(s) 13902 attached to a polymer 13905 of polymer or gel precursors 13901 and 13904. In some instances, polymer or gel precursor 13901 is a first type of polymer, polymer or gel precursor 13904 is a second type of polymer, and polymer 13905 is a copolymer of precursors 13901 and 13904. In other instances, polymer or gel precursor 13901 is a first type of polymer comprising a nucleic acid molecule(s) 13902 and polymer or gel precursor 13904 is the same type of polymer as 13901 but lacks nucleic acid molecule 13902.

In other embodiments, as shown in FIG. 139B, a partition 13940 is provided comprising gel or polymer precursors 13901 comprising a first crosslink precursor 13906 (e.g., a first click chemistry moiety) and a nucleic acid molecule(s) 13902 (e.g., a nucleic acid molecule comprising functional sequences) comprising a second crosslink precursor 13907 (e.g., a second click chemistry moiety), wherein the first crosslink precursor 13906 and the second crosslink precursor 13907 are configured to form a crosslink 13909 thereby linking the nucleic acid molecule(s) 13902 with the polymer or gel precursor 13901 or with a polymerized gelled, or otherwise crosslinked matrix of 13901 (e.g., 13911).

In some instances, a partition 13960 is provided comprising (i) a first polymer or gel precursor 13901 comprising a first crosslink precursor 13906 (e.g., a first click chemistry moiety), (ii) a second polymer or gel precursor 13904, and (iii) a nucleic acid molecule 13902 comprising a second crosslink precursor 13907 (e.g., a second click chemistry moiety), wherein the first crosslink precursor 13906 and the second crosslink precursor 13907 are configured to form a crosslink 13909 thereby linking the nucleic acid molecule 13902 with the polymer or gel precursor 13901 or with a polymerized, gelled, or otherwise crosslinked matrix of 13901 and 13912 (e.g., 13913). In some instances, a partition 13960 comprising the first polymer or gel precursor 13901 attached to nucleic acid molecule 13902 and the second polymer or gel precursor 13912 are subjected to conditions sufficient to polymerize, gel, or crosslink precursors 13901 and 13912, thereby generating a cell bead 13970 comprising nucleic acid molecule(s) 13902 attached to a polymer or gel 13913 of polymer or gel precursors 13901 and 13912. In some instances, polymer or gel precursor 13901 is a first type of polymer, polymer or gel precursor 13912 is a second type of polymer, and polymer 13913 is a copolymer of precursors 13901 and 13912. In other instances, polymer or gel precursor 13901 is a first type of polymer comprising a nucleic acid molecule 13902 and polymer or gel precursor 13912 is the same type of polymer as 13901 but lacks the nucleic acid molecule 13902.

In some instances, one or more agents are utilized to catalyze, initiate, or otherwise facilitate the formation of crosslink 13909. In some instances, the partition 13940 is subjected to conditions sufficient to form a crosslink 13909 between crosslink precursors 13906 and 13909 prior to polymerization, gelling, or crosslinking of polymer precursors (e.g., 13901 and/or 13912) to form cell bead 13950 or 13970. In other instances, the partition (e.g., 13940 or 13960) is subjected to conditions sufficient to form a crosslink 13909 between crosslink precursors 13906 and 13909 concurrently with the polymerization, gelling, or crosslinking of the polymer or gel precursors (e.g., 13901 and/or 13912). In some embodiments, the partition (e.g., 13940 or 13960) is subjected to conditions sufficient to polymerize, gel, or otherwise crosslink the polymer or gel precursors (e.g., 13901 and/or 13912) prior to forming a crosslink 13909 between crosslink precursors 13906 and 13909. In some instances, the nucleic acid molecule comprises a labile bond 13908 configured to release the crosslink 13909 and the nucleic acid molecule 13902 upon application of a stimulus (e.g., a chemical, thermal, or photo-stimulus).

In some instances, a nucleic acid molecule 13902 is attached to the first polymer or gel precursor (e.g., 13901), the second polymer or gel precursors (e.g., 13904 or 13912), or both the first 13901 and the second polymer or gel precursors (e.g., 13904 or 13912). Furthermore, in some embodiments, additional polymers or polymer or gel precursors can be added (e.g., to partition 13900, 13920, 13940, or 13960) to generate a co-polymer or mixed polymer cell bead matrix. Additionally, the concentration of polymers (e.g., 13901, 13904, and/or 13912) in the partition (e.g., 13900, 13920, 13940, or 13960) can be controlled to generate a cell bead comprising a desired concentration of nucleic acid molecules 13902.

Functionalized nucleic acid molecules attached to cell beads may comprise any suitable functionalized sequence, such as those described elsewhere herein. For example, functionalized nucleic acid molecules may comprise a sequence configured to hybridize to a nucleic acid molecule (e.g., a poly-T sequence, a random N-mer sequence, a sequence complementary to a cellular nucleic acid sequence), a primer sequence, a template switching oligonucleotide (TSO) sequence, a barcode sequence, a unique molecular index (UMI) sequence, a sequencing primer sequence (or a partial sequencing primer sequence, such as a partial R1 and/or R2 sequence), and/or one or more adaptor sequences, such as a sequence configured to attach to the flow cell of a sequencer (e.g., P5, P7), etc. In some embodiments, the nucleic acid molecules attached to a cell bead are single-stranded nucleic acid molecules. In some embodiments, the nucleic acid molecules attached to a cell bead are double-stranded nucleic acid molecules. In some embodiments, the nucleic acid molecules attached to a cell bead are partially double-stranded nucleic acid molecules.

In some cases, the polymers (e.g., cell bead) disclosed herein can comprise poly(acrylic acid), poly(vinyl alcohol), poly(vinylpyrrolidone), poly(ethylene glycol), polyacrylamide, some polysaccharides, or any derivatives thereof. These polymers can be non-toxic and they can be used in various pharmaceutical and biomedical applications. Thus, in some instances, they may not require their removal from the reaction system, thereby eliminating the need for a purification step after the formation of hydrogels.

Polymers (e.g., cell bead) can comprise polymer molecules of a particular length or range of lengths. Polymer molecules can have a length of at least 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, 100, 110, 120, 130, 140, 150, 160, 170, 180, 190, 200, 250, 300, 350, 400, 450, 500, 1,000, 2,000, 5,000, 10,000, 20,000, 50,000, 100,000, 200,000, 500,000, 1,000,000, 2,000,000, 5,000,000, 10,000,000, 20,000,000, 100,000,000, 200,000,000, 500,000,000 or 1,000,000,000 backbone atoms or molecules (e.g., carbons). Polymer molecules can have a length of at most 2, 3, 4, 5, 6, 7, 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100, 110, 120, 130, 140, 150, 160, 170, 180, 190, 200, 250, 300, 350, 400, 450, 500, 1,000, 2,000, 5,000, 10,000, 20,000, 50,000, 100,000, 200,000, 500,000, 1,000,000, 2,000,000, 5,000,000, 10,000,000, 20,000,000, 100,000,000, 200,000,000, 500,000,000 or 1,000,000,000 backbone atoms or molecules (e.g., carbons). Polymer molecules can have a length of at least 2, 3, 4, 5, 6, 7, 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100, 110, 120, 130, 140, 150, 160, 170, 180, 190, 200, 250, 300, 350, 400, 450, 500, 1,000, 2,000, 5,000, 10,000, 20,000, 50,000, 100,000, 200,000, 500,000, 1,000,000, 2,000,000, 5,000,000, 10,000,000, 20,000,000, 100,000,000, 200,000,000, 500,000,000 or 1,000,000,000 monomer units (e.g., vinyl molecules or acrylamide molecules). Polymer molecules can have a length of at most 2, 3, 4, 5, 6, 7, 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100, 110, 120, 130, 140, 150, 160, 170, 180, 190, 200, 250, 300, 350, 400, 450, 500, 1,000, 2,000, 5,000, 10,000, 20,000, 50,000, 100,000, 200,000, 500,000, 1,000,000, 2,000,000, 5,000,000, 10,000,000, 20,000,000, 100,000,000, 200,000,000, 500,000,000 or 1,000,000,000 monomer units (e.g., vinyl molecules or acrylamide molecules).

In some cases, generating a cell bead may comprise crosslinking cellular macromolecules. For example, a plurality of macromolecules in a cell may be crosslinked, thereby forming a cell bead. Macromolecules may be proteins, nucleic acids, lipids, or any combination thereof. In some cases, macromolecules in a cell comprise proteins, such that cellular proteins are crosslinked for cell bead generation. Crosslinking macromolecules may comprise use of a bifunctional crosslinker. A bifunctional crosslinker may comprise, for example, a succinimide, aldehyde, maleimide, dicarboxylic, or diazide moiety. Crosslinking macromolecules may comprise use of an alkylating agent. An alkylating agent may be, for example, melphalan, chlorambucil, a nitrogen mustard, a nitrosurea, busulfan, psoralen, or derivatives thereof. Crosslinking macromolecules may comprise use of an intercalating agent.

Figure 46A:
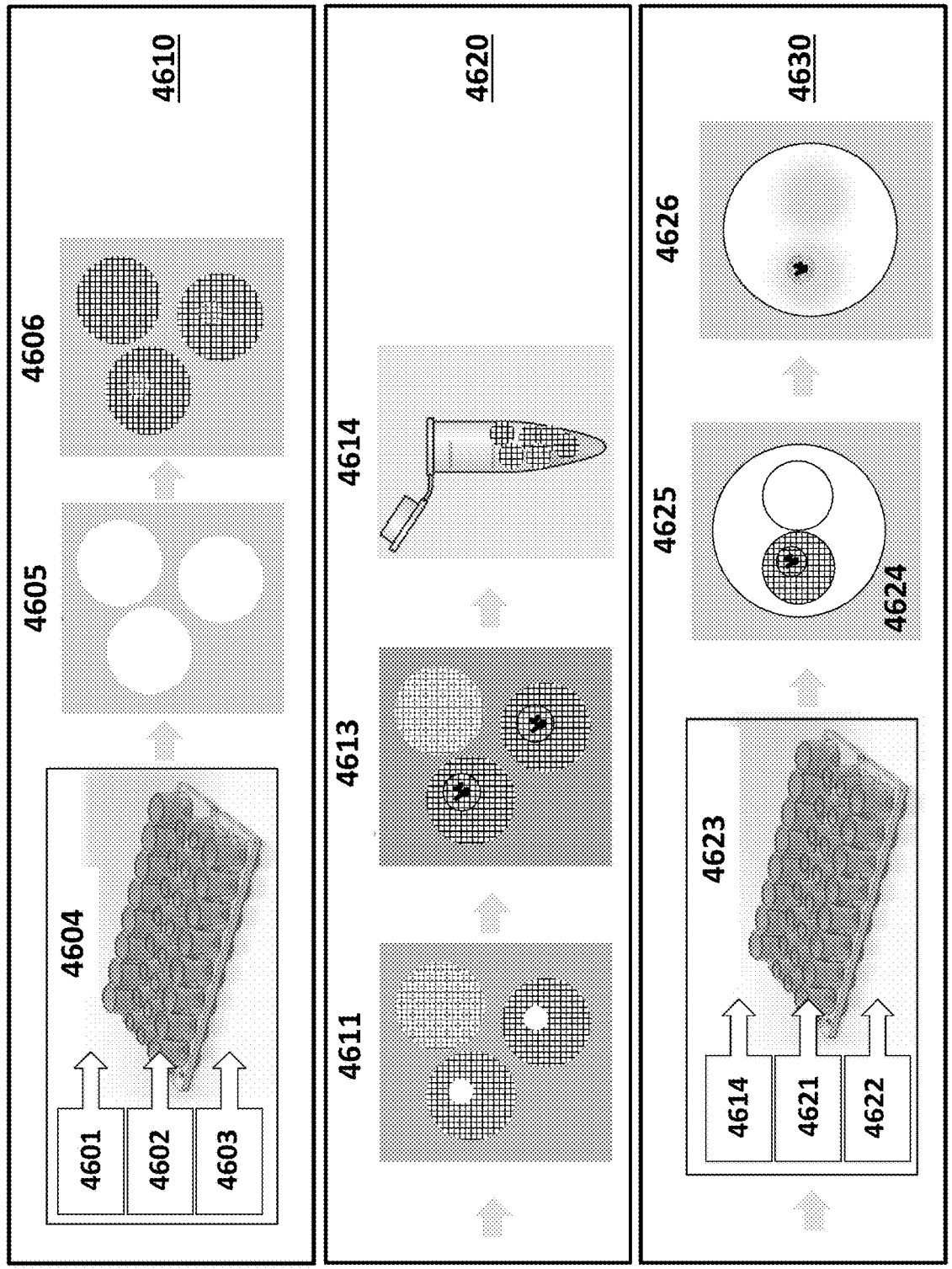
Figure 46C:
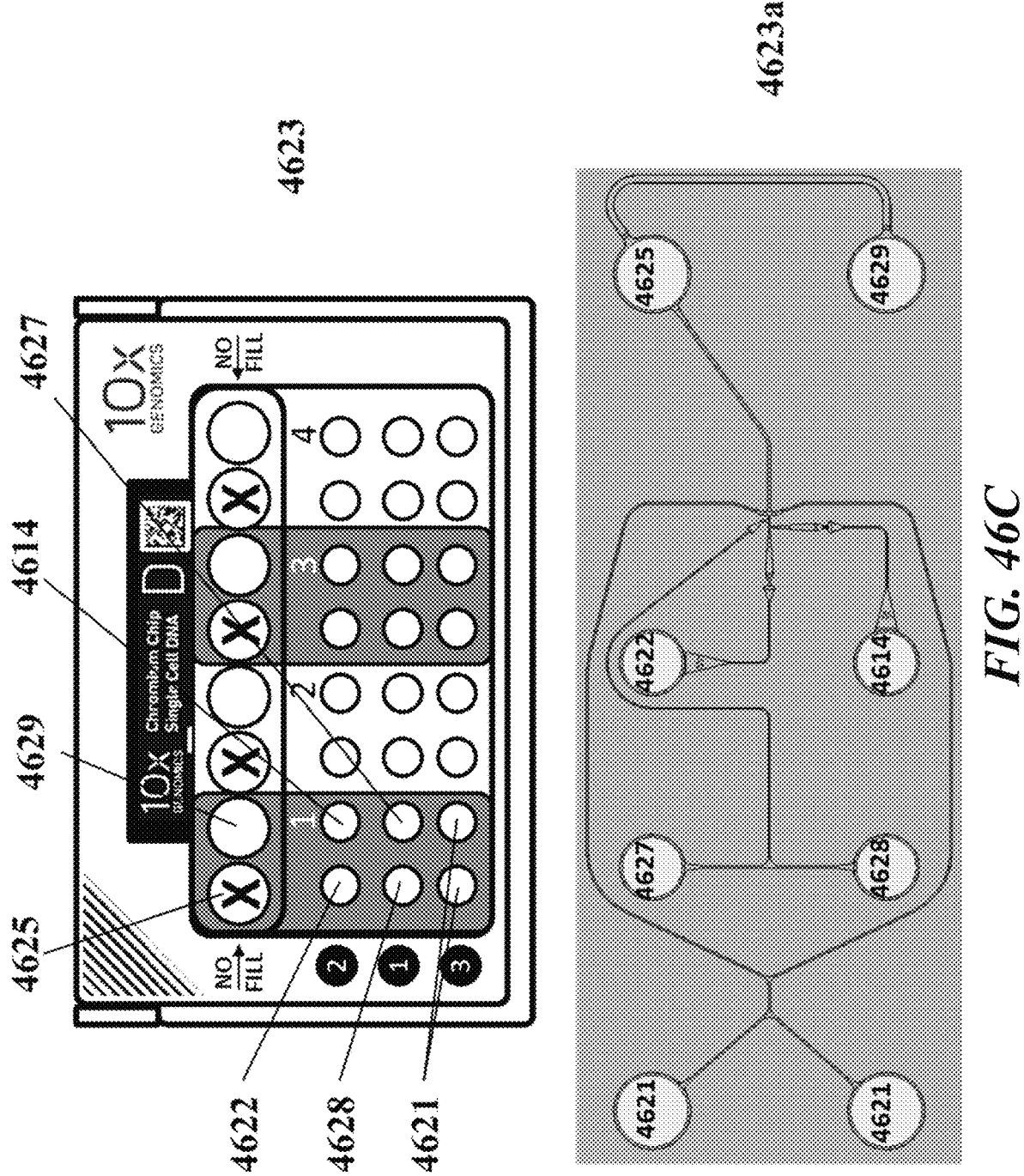

Cell beads (optionally comprising nucleic acid molecules comprising functional sequences, such as a poly-T sequence) may be partitioned together with nucleic acid barcode molecules (optionally attached to a bead) and the nucleic acid molecules of or derived from the biological particle of the cell bead (e.g., mRNA, cDNA, gDNA, etc.) may be barcoded as described elsewhere herein. An overview of an exemplary method for generating partitions comprising cell beads and nucleic acid barcode molecules is schematically depicted in FIGS. 46A-C. The method described in FIG. 46A comprises three phases 4610, 4620, and 4630 with each respective phase comprising: (1) generation of cell beads (4610); (2) cell bead solvent exchange and optional processing (4620); and (3) co-partitioning of cell beads and barcodes for subsequent tagging (e.g., barcoding) of one or more constituents of (or derived from) the cell bead (4630).

With continued reference to FIG. 46A, phase 4610 comprises providing an oil 4601, polymeric or gel precursors 4602, and biological particles 4603 (e.g., a cell, a fixed cell, a cross-linked cell, a nucleus, a permeabilized nuclei, etc.) to a microfluidic chip (e.g., 4604) for droplet generation. Functionalized nucleic acid molecules, such as those described elsewhere herein, may be further provided to microfluidic chip 4604 for co-partitioning. In some instances, the functionalized nucleic acid molecules are provided with or otherwise attached to the polymeric or gel precursors 4602. In other cases, the functionalized nucleic acid molecules are provided with the biological particles 4603. In some instances, the microfluidic chip 4604 comprises a plurality of microfluidic channels (see e.g., FIGS. 1-7) connected to a plurality of reservoirs comprising the oil 4601, polymeric or gel precursors 4602, and biological particles (e.g., cells) 4603. Microfluidic chip 4604 may also comprise one or more additional channels and/or reservoirs comprising one or more additional reagents (such as the functional nucleic acid molecules described herein). Polymeric or gel precursors 4602 and biological particles 4603 (and in some cases, functional nucleic acid molecules) are flowed (e.g., via the action of an applied force, such as negative pressure via a vacuum or positive pressure via a pump) from their reservoirs through the plurality of microfluidic channels to a first channel junction and combine to form an aqueous stream. This aqueous stream is then flowed to a second channel junction, in which oil 4601 is provided. The aqueous stream provided from the first channel junction is immiscible with the oil 4601 resulting in the generation of a suspension of aqueous droplets 4605 in the oil, which then flow to a reservoir for collection. Flow can be controlled within the microfluidic chip 4604 via any suitable method, including the use of one or more flow regulators in a channel or various channels, dimensioning of microfluidic channels, etc., as described elsewhere herein. As shown in FIG. 46A, the product comprises droplets 4605 comprising a biological particle 4603, the polymeric or gel precursors 4602, and in some cases, nucleic acid molecules comprising functional sequences. In some cases, at least some of the droplets of droplets 4605 comprise a single biological particle (e.g., a single cell or single nucleus).

In some embodiments, the droplets 4605 are subjected to conditions sufficient to lyse the biological particles (e.g., cells or nuclei) comprised therein, releasing cellular macromolecular constituents into the droplets 4605. The macromolecular constituents (e.g., nucleic acids, proteins, etc.) may additionally be subjected to one or more reactions for processing as described elsewhere herein. In other embodiments, the droplets 4605 are subjected to conditions sufficient to permeabilize the cells (or nuclei) thereby facilitating access to one or more macromolecular constituents of the cell (or nucleus) for further processing. In still other cases, the biological particles present in the droplets 4605 are not lysed or permeabilized.

Continuing with FIG. 46A, the droplets 4605 comprising biological particles are then subjected to conditions suitable to polymerize or gel the polymeric or gel precursors 4602 in the droplets 4605, to generate cell beads 4606. As the resulting cell beads 4606 are suspended in oil, in some embodiments, phase 4620 is initiated which comprises a solvent exchange configured to resuspend the cell beads 4606 in an aqueous phase 4611.

In some embodiments, the resuspended aqueous cell beads 4611 are optionally processed to, e.g., prepare the cell beads for analysis of one or more cellular components. For example, cell beads 4611 can be subjected conditions suitable to lyse or permeabilize biological particles (e.g., cells or nuclei) in the cell beads 4613, thereby releasing or otherwise allowing access to one or more cellular constituents (e.g., nucleic acids, such as mRNA and gDNA, proteins, etc.). Separately or contemporaneously from cell lysis, cell beads (e.g., 4611 or 4613) may be subjected to conditions sufficient to denature nucleic acids derived from the cells (e.g., gDNA) associated with the cell beads (e.g., using NaOH). The polymeric matrix of the cell beads (e.g., 4611 or 4613) effectively hinders or prohibits diffusion of larger molecules, such as nucleic acids and/or proteins, from the cell beads, but are sufficiently porous to facilitate diffusion of denaturation or other agents into the cell bead matrix to contact nucleic acids and other cellular components within the cell beads. In some cases, the cell beads (4611 or 4613) can be subjected to conditions suitable for performing one or more reactions on nucleic acids or other analytes derived from the cells associated with the cell beads (4611 or 4613). For example, in embodiments where cell beads comprise functional nucleic acid molecules comprising a poly-T sequence, cellular mRNA may be hybridized to the nucleic acid molecules and, optionally, a reverse transcription reaction can be performed to convert the mRNA molecules into cDNA molecules. In other embodiments, reactants such as antibodies (e.g., one or more antibodies optionally comprising an antibody barcode sequence as described elsewhere herein), transposases (e.g., such as adapter-loaded transposase molecules for performing, e.g., ATAC-seq as described elsewhere herein), or nucleases (such as DNase or MNase as described elsewhere herein) may be washed into and/or out of the resuspended cell beads (4611 or 4613). In embodiments where functional nucleic acid molecules are attached or otherwise incorporated into the cell beads subsequent to cell bead generation, functional nucleic acid molecules can be provided and one or more reactions performed on the cell bead (4611 or 4613) to attach or otherwise incorporate the functional nucleic acid molecules into the cell beads (e.g., through functional groups on the functional nucleic acid molecule(s), cell bead matrix, or both). After optional processing, the cell beads comprising can be collected 4614 and stored prior to initiation of phase 4630.

Continuing with FIG. 46C, after phase 4620, cell beads 4614 can be analyzed by, e.g., partitioning cell beads and nucleic acid barcode molecules into partitions (e.g., droplets, microwells) for analysis of cellular components (e.g., nucleic acid molecules). For example, in phase 4630, partitions (e.g., droplets) comprising cell beads 4614 and beads (e.g., a gel bead) comprising nucleic acid barcode molecules 4622 ("barcode beads") are generated such that at least some droplets comprise a cell bead and a barcode bead (e.g., a single cell bead and a single barcode bead). For example, in some embodiments, an oil 4621, the cell beads 4614, and barcode beads 4622 each comprising a barcode sequence (e.g., each bead comprising a unique barcode sequence) are provided to a microfluidic chip 4623. An exemplary microfluidic chip architecture is shown in e.g., FIGS. 1-7, but any suitable microfluidic chip or microwell array can also be utilized with the compositions, methods, and systems disclosed herein. The microfluidic chip 4623 comprises a plurality of reservoirs comprising the oil 4621, cell beads 4614, barcode beads 4622 (e.g., gel beads), and the high molecular weight functionalized polymer. The chip can also include additional reservoirs that may be used to supply additional reagents (e.g., reagents for nucleic acid amplification, reagents that can degrade or dissolve cell beads and/or gel beads, reagents that degrade linkages between barcode beads/cell beads/polymers, reagents for cell lysis, etc.). Cell beads 4614 and barcode beads 4622 are flowed (e.g., via the action of an applied force, such as negative pressure via a vacuum or positive pressure via a pump) from their reservoirs to, e.g., a first channel junction and form an aqueous mixture. Materials from reservoirs 4627 and 4628 can also be provided to the aqueous mixture at the first channel junction.

Alternatively, cell beads and barcode beads (e.g., gel beads) can be mixed before introduction into the microfluidic chip. In this case, a single reservoir of the microfluidic chip (e.g., 4623) comprises a mixture of cell beads and barcode beads. The ratio of cell beads to barcode beads in the mixture can be varied to alter the number of droplets generated that comprise a single cell bead and a single barcode bead. The mixture of cell beads and barcode beads may be flowed (e.g., via the action of an applied force, such as negative pressure via a vacuum or positive pressure via a pump) from the reservoir to a first channel junction, in some cases together with materials from reservoirs 4627 and/or 4628.

In some embodiments, the aqueous mixture comprising cell beads 4614, barcode beads 4621, and in some cases additional reagents is then flowed to a second channel junction, to which oil 4621 is provided. The aqueous mixture provided from the first channel junction is immiscible with the oil 4621 resulting in the generation of a suspension of aqueous droplets 4625 in the oil which then flow to a reservoir for collection. The microfluidic chip can also include a reservoir 4629 that can accept excess oil from the stream emerging from the second channel. Flow can be controlled within the microfluidic chip 4623 via any suitable strategy, including the use of one or more flow regulators in a channel or that connect channels, use of various channels, dimensioning of channels, etc. As shown in both FIG. 46A and FIG. 46C, the droplets 4625 comprise a cell bead 4614 and a barcode bead 4622 (e.g., a gel bead), in addition to any other reagents provided by reservoirs 4627 and 4628. In some cases, at least some droplets of droplets 4625 comprise a single cell bead and a single barcode bead (e.g., a single gel bead).

Where reagents that degrade or dissolve the cell beads 4614, barcoded beads 4622 (e.g., gel beads) and/or linkages between barcodes and barcoded beads 4622 are present in droplets, these reagents can release the nucleic acids trapped in the cell beads 4646, release the barcodes from the barcode beads 4622, and/or release functionalized nucleic acid molecule(s) from the cell bead matrix (including, e.g., cell-bead bound nucleic acid molecules hybridized to mRNA and/or cDNA molecules attached to the cell bead). The nucleic acid barcode molecules can interact with the released cellular components (e.g., cellular nucleic acids) to generate barcoded nucleic acid molecules for nucleic acid sequencing as described elsewhere herein. In embodiments where the barcode bead (e.g., gel bead) is degraded or nucleic acid barcode molecules are releasably attached to the barcode bead (e.g., gel bead), the barcoded cellular components (e.g., barcoded cDNA or gDNA fragments) are not attached to the bead. Where a given droplet comprises a cell bead (e.g., a single cell bead) and a barcoded bead (e.g., a single barcoded bead) comprising nucleic acid barcode molecules comprising a common barcode sequence, the barcoded cellular components (or derivatives thereof) can be associated with the biological particle (e.g., a cell or other biological sample, such as a bacterium or virus) of the given cell bead via the common barcode sequence.

Figure 101:
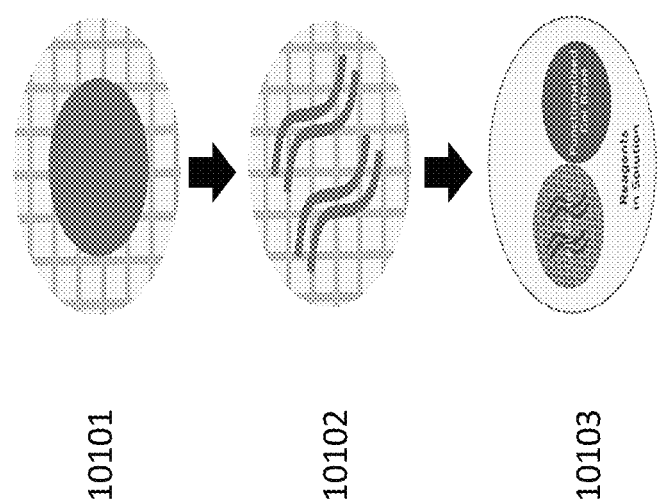
FIG. 101 illustrates a schematic depiction of the generation of a partition comprising a barcode bead and a cell bead.

Partitions comprising a barcode bead (e.g., a gel bead) associated with barcode molecules and a bead encapsulating cellular constituents (e.g., a cell bead) such as cellular nucleic acids can be useful in constituent analysis as is described in U.S. patent application Ser. No. 15/887,947, U.S. Pat. Pub. 20180216162, which is herein incorporated by reference in its entirety for all purposes. Example generation of a partition comprising a barcode bead and a cell bead is schematically depicted in FIG. 101. The cell bead is generated in 10101 by encapsulating a cell in a matrix to form the cell bead. The cell is then lysed such that the nucleic acids, and other constituents of the cell, are released into the cell. The matrix traps these materials such that they are not exposed to exogenous materials outside of the matrix. The cell bead is then subjected to conditions suitable to digest proteins and denature nucleic acids (e.g., via an alkaline reagent). The cell beads are then washed and isolated for further processing.

The cell bead is provided, along with a barcode bead (e.g., a gel bead) comprising at least 1,000, at least 10,000, at least 100,000, at least 1,000,000 or at least 10,000,000 barcode molecules, to a partition (e.g., a droplet such as an aqueous droplet, a well) where each of the barcode molecules comprise a barcode sequence that can identify the cell inside the cell bead. Example methods and devices for combining cell beads and gel beads into partitions, including droplets and wells, are described in U.S. patent application Ser. No. 15/887,947, U.S. Patent Publication No. 2018/0216162. Once partitioned, the cell bead and barcode bead can be degraded, to release barcode molecules of the barcode bead and the trapped constituents of the cell (including nucleic acids) in the cell bead to the interior of the partition. The free barcode molecules can interact with cellular nucleic acids (including genomic nucleic acids (e.g., genomic DNA), messenger RNA, etc.) to add barcode sequences to the cellular nucleic acids. In some cases, barcoding occurs inside the partition, in other cases outside the partition. Example methods of barcoding nucleic acids are described in U.S. Patent Publication No. 2014/0378345, U.S. Patent Publication No. 2015/0376609, U.S. Patent Publication No. 2016/0257984 and U.S. patent application Ser. No. 15/825, 740, U.S. Patent Publication No. 2018/0105808, each of which is herein incorporated by reference in its entirety for all purposes.

The barcoded molecules can be released or removed from the partition, if not already free, and subjected to additional reactions to add other sequences (functional sequences for sequencing such as flow-cell adaptor sequences, sequencing primer binding sites, etc.) to the constructs. The barcoded nucleic acids or downstream constructs can then be subjected to sequencing for analysis. Multiple cells (e.g., a population of cells) can be processed across multiple partitions, with each partition comprising a different barcode sequence that identifies a given cell in said partition.

Encapsulating cells into cell beads and trapping cellular components can prevent exogenous materials from mixing with cell components. For example, cell beads can minimize or eliminate contamination of cellular nucleic acids with exogenous nucleic acids. Such contamination can complicate or render inaccurate analysis of cellular nucleic acids. Minimized and eliminated contamination of exogenous nucleic acids from analysis of cellular nucleic acids can be especially useful in downstream applications that rely on analysis of lower quantity nucleic acids such as the analysis of copy number variation (CNV) in genomic nucleic acids and also rare cellular clones in a population of cells. In some cases, analysis of CNV is used to detect rare cellular clones. In other embodiments, analysis of SNPs or SNVs is used to detect single nucleotide changes in a sample versus a reference sample or as compared to another sample.

In the context of CNV analysis, cell bead based analysis of nucleic acids can reveal genome heterogeneity, provide understanding of clonal evolution and determine pathogenesis and cancer progression. Moreover, methods described herein can enable single cell CNV calling at scales of 100s, 1000s, 10000s, 100000s, 10000000s or more cells. Calls can be made down to 1000s, 100s, 10s, 1 or less kilobases. Software can aid in analyses. Additionally, example methods for determining CNV from barcoded sequencing reads/constructs are provided in U.S. Patent Publication No. 2015/0376700, which is herein incorporated by reference in its entirety for all purposes.

Figure 102:
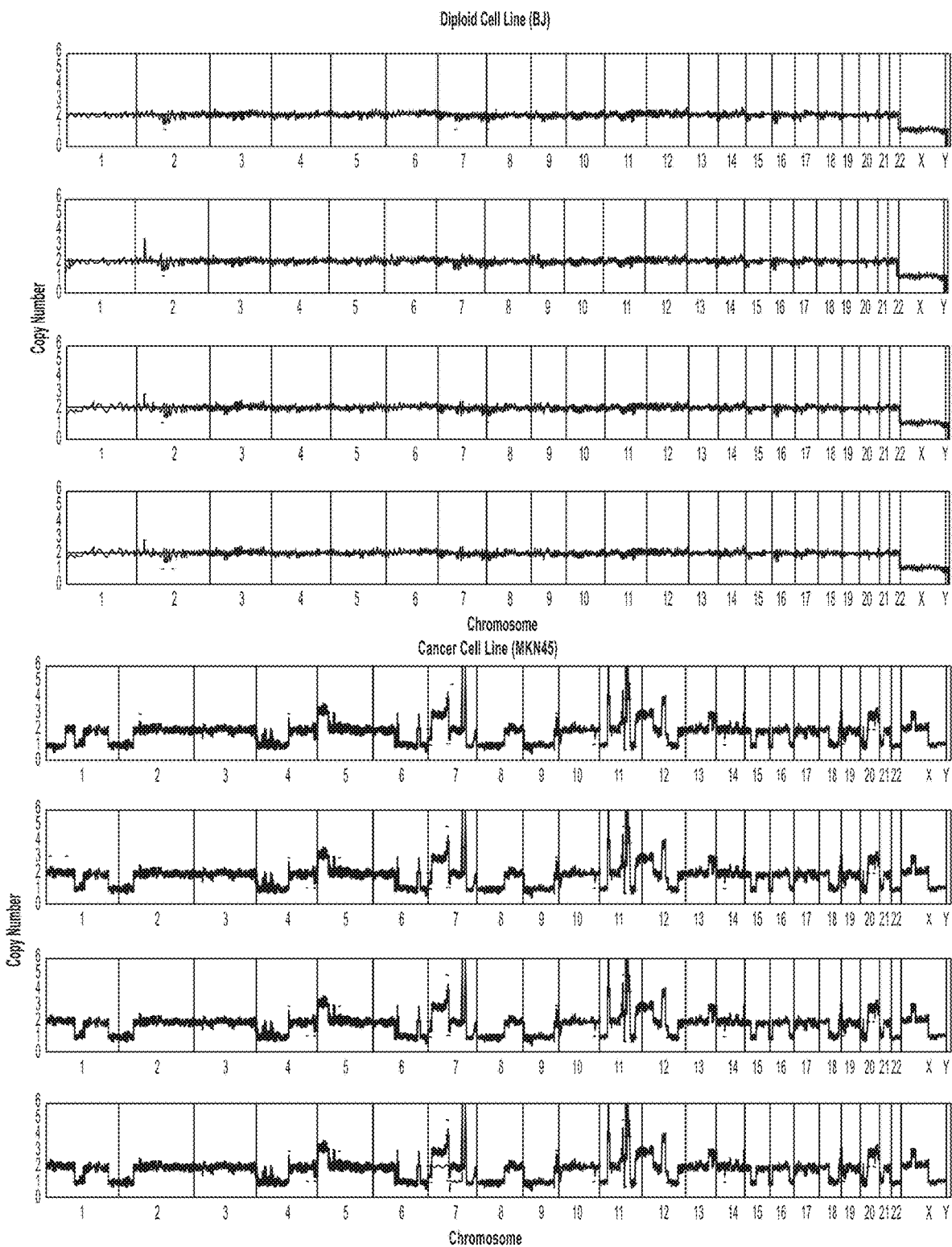
FIG. 102 shows exemplary CNV analyses using a cell bead/barcode bead approach for human fibroblasts (BJ) and human liver gastric adenocarcinoma (MKN45) cell lines.

In one example, CNV analyses using cell bead/barcode bead analysis as described herein was completed for human fibroblasts (BJ cell line) and human liver gastric adenocarcinoma (MKN45) cell lines drawn from thousands of cells. Data from the analyses are graphically shown in FIG. 102. As shown in FIG. 102, analysis resulted in an even profiling of cells.

Figure 103A:
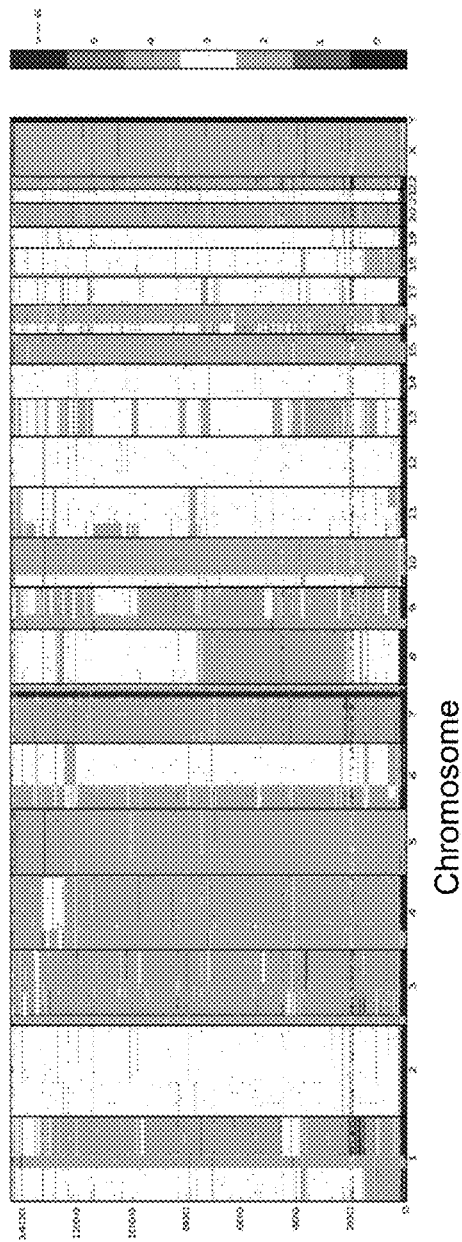
FIGS. 103A-B show additional CNV analyses using a cell bead/barcode bead approach.

In another example, CNV analyses using cell bead/barcode bead analysis as described herein was completed for COLO829 human skin melanoma cells in a population of cells. CNV data from the analyses, using 1 Mb bins, are graphically shown in FIG. 103A plotted for representative single cell profiles.

Figure 103B:
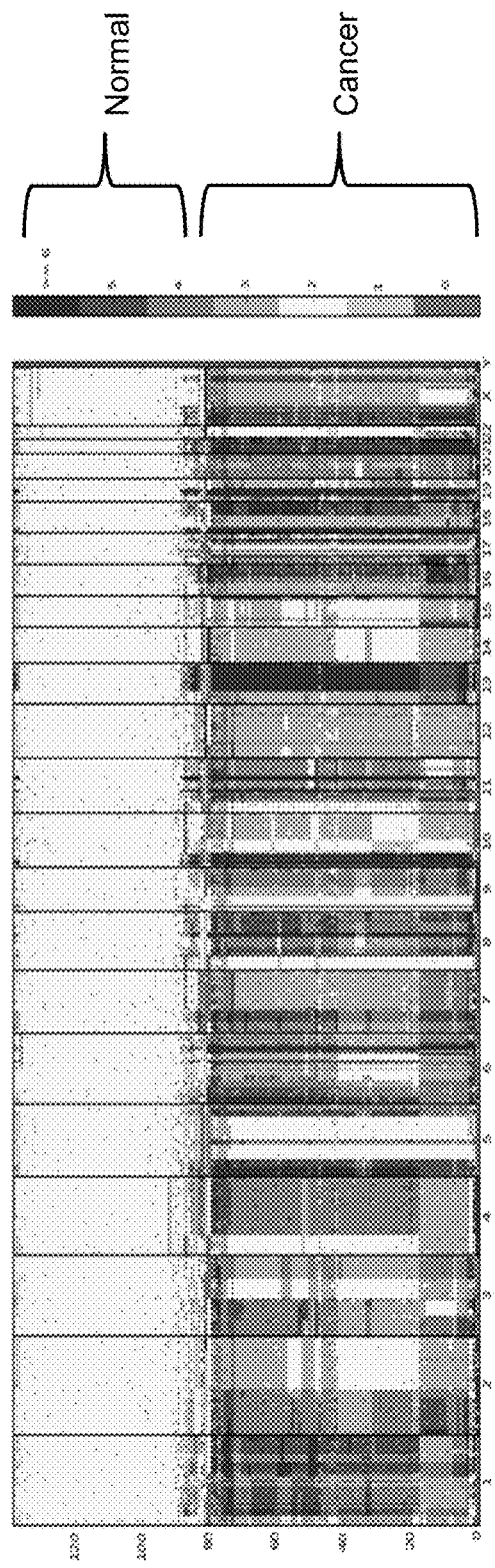

In another example, CNV analyses using cell bead/barcode bead analysis as described herein was completed for breast tumor cells (45%) in a population of cells. CNV data from the analyses, using 1 Mb bins, are graphically shown in FIG. 103B. As shown in FIG. 103B, normal cells and tumor cells are distinguished.

Figure 104A:
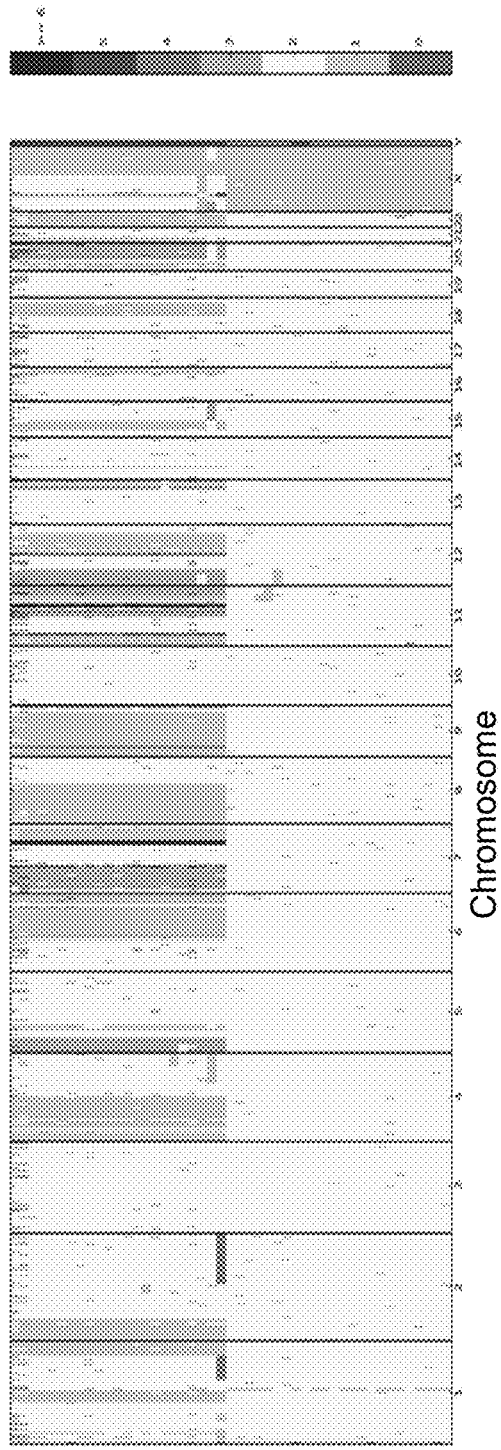
FIGS. 104A-B shows rare cell detection using a cell bead/barcode bead approach.

In another example, mixtures of cells were prepared and analyzed using cell bead/barcode bead analysis as described herein. In one mixture, 23 MKN-45 cells were added to 639 cells (MKN-45 cells represented approximately 5% of cells in the mixture) and the mixture of cells analyzed. The relatively rare MKN-45 cells were detected, using 1 Mb bins, in the population after sequencing of barcoded constructs as shown graphically in FIG. 104A.

Figure 104B:
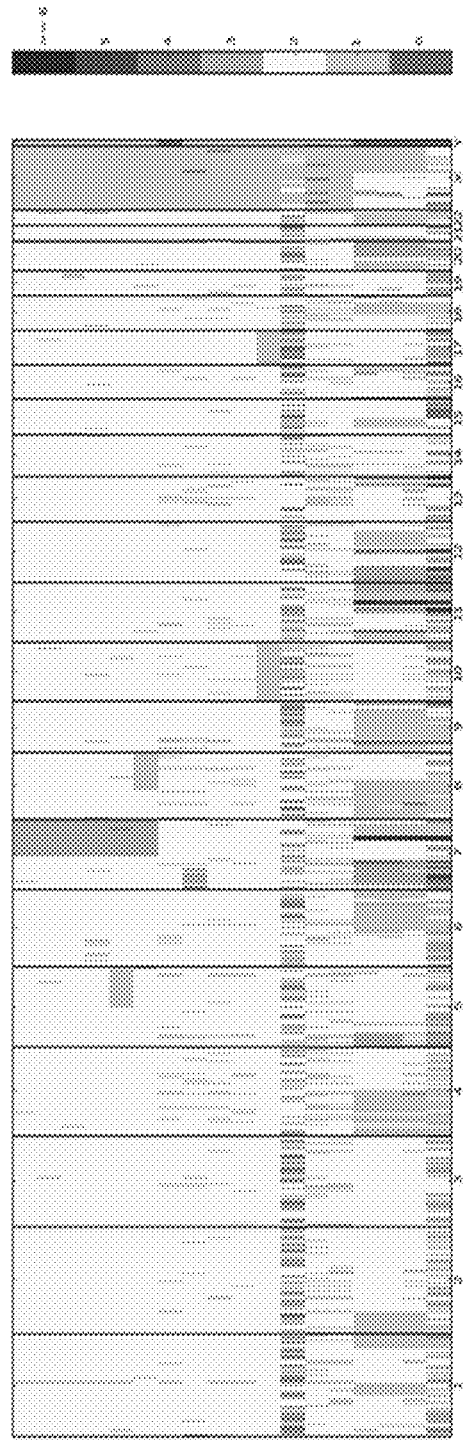

In another example, mixtures of cells were prepared and analyzed using cell bead/barcode bead analysis as described herein. In one mixture, 3 MKN-45 cells were added to 566 cells (MKN-45 cells represented approximately 1% of cells in the mixture) and the mixture of cells analyzed. The relatively rare MKN-45 cells were detected, using 1 Mb bins, in the population after sequencing of barcoded constructs as shown graphically in FIG. 104B. The aforementioned CNV and rare cell analyses of a single cell can be combined with the analysis of multiple other analytes as disclosed herein (e.g., mRNA, cell surface features, intracellular proteins, perturbation agent (e.g., sgRNA), etc.).

In some aspects, the methods of the present disclosure may comprise the generation of a cell bead for capturing, processing, and analyzing (e.g., barcoding, sequencing) multiple types of analytes (e.g., components) from a cell. Analytes which can be captured within a cell bead for processing and/or analysis include any combination of one or more of proteins, metabolites, and nucleic acids. Analytes can be comprised within a cell bead matrix, attached to a cell bead, and/or attached to a particle (e.g., magnetic particle) within a cell bead.

Cell beads may be used to identify and measure one or more targeted analytes from a cell together with one or more additional analytes (e.g., nucleic acids). One or more antibodies can be used to identify a targeted analyte, for example, by contacting a cell bead comprising an analyte. Antibodies may be coupled to one or more barcode molecules comprising one or more barcode sequences. A targeted analyte can be an internal protein and the antibody contacting the cell bead may have a binding specificity to the internal protein. In another example, a targeted analyte can be a metabolite and the antibody contacting the cell bead may have a binding specificity to the metabolite. Multiple antibodies may be used to target multiple analytes (e.g., a protein and a metabolite). In some instances, a metabolite may be an alcohol, amino acid, nucleotide, antioxidant, organic acid, polyol, or vitamin. A metabolite may be a cofactor. The targeted analyte can be any constituent of a cell, such as any small molecule, large molecule, or macromolecule (e.g., macromolecular constituent). In yet another example, the targeted analyte can be from a class, set, or subset of analytes (e.g., proteins, metabolites, small molecules, etc.) sharing a structural similarity or homology (e.g., moiety, functional group, etc.), and the antibody contacting the cell bead may have a binding specificity to the class, set, or subset of analytes via the structural similarity. In such cases, a barcode sequence may uniquely identify the class, set, or subset of analytes. Upon binding to the antibody, the targeted analyte may be classified by the first barcode sequence as a member of the class, set, or subset of analytes.

Methods of the present disclosure may comprise processing and analyzing macromolecular constituents from single cells. In some aspects, the present disclosure provides the use of cell beads for capturing, processing, and/or analyzing constituents from a cell. Multiple types of components may be analyzed from the same single cell. Components from a cell that can be identified using the methods disclosed herein can include, without limitation, nucleic acids (e.g., DNA, RNA), proteins (e.g., intracellular proteins, cell surface proteins), metabolites, and molecules introduced into a cell using various methods. Examples of intracellular protein components include, but are not limited to, transcription factors, histone proteins, kinases, phosphatases, cytoskeletal proteins (e.g., actin, tubulin), polymerases, nucleases, and ribosomal proteins. Molecules introduced into a cell may be, for example, an exogenous or synthetic nucleic acid (e.g., transgene), an RNA virus, a plasmid, a gene or transcription perturbation agent (e.g., CRISPR crRNA or sgRNA, TALEN, zinc finger nuclease, antisense oligonucleotide, siRNA, shRNA, miRNA, etc.), or any other molecule which is exogenous to a cell and introduced by natural and/or artificial means. A molecule (e.g., the labelling agents disclosed herein) may be introduced into a cell using transfection methods (e.g., electroporation, lipid-based transfection, etc.) or may be introduced into a permeabilized cell. In some embodiments, molecules introduced into a cell are detected using a sequence specific to the molecule (e.g., a sequence specific for a DNA transgene or plasmid, a coding or non-coding sequence from an mRNA molecule expressed from a plasmid or transgene, etc.) or using a universal sequence or adapter such as those described herein introduced into the molecule to aid in the capture and detection of the molecule.

One or more reactions may be performed on one or more components from a cell (e.g., in a cell bead). For example, mRNA may undergo reverse transcription to generate cDNA for expression analysis, gDNA may undergo bisulfite treatment and/or enzymatic deamination for methylation analysis, gDNA may undergo methyltransferase treatment for chromatin accessibility analysis, etc. Each type of component may be analyzed as disclosed herein, for example, by generation of barcoded molecules and sequencing. Each component may be identified with the same single cell by the use of one or more barcode sequences. Cell beads may be partitioned together with beads (e.g., gel beads) comprising barcodes, thereby enabling the tagging (e.g., barcoding) of one or more components (e.g., nucleic acid molecules, proteins, metabolites) from a cell bead. In some cases, multiple types of components (e.g., DNA, RNA, protein, metabolites, etc.) may be analyzed from the same single cell. In some cases, cell beads may be used to capture and process 1, 2, 3, 4, 5, or more types of components from a cell. In an example, cell beads may be used to capture and process RNA and DNA from a single cell, thereby enabling the analysis of both transcriptional information (e.g., gene expression, RNA velocity) and genomic information (e.g., mutations, methylation status, chromatin accessibility) from the same cell. In another example, cell beads may be used to capture and process protein and RNA from a single cell, thereby enabling the analysis of both transcriptional information (e.g., gene expression, RNA velocity) and proteomic information (e.g., protein abundance, post-translational modifications) from the same single cell.

Multiple types of components from a cell may be captured in a cell bead for processing and analysis. For example, a droplet comprising a cell and polymer precursors may be formed. The droplet may comprise a particle (e.g., a magnetic particle). The droplet may comprise oligonucleotides, which may comprise a poly-T sequence. Oligonucleotides may be attached to polymer precursors and/or to a particle via an acrydite linker. The cell may be lysed, releasing different types of macromolecular constituents from the cell into the droplet. In some cases, both RNA and DNA are released from the cell. Additional constituents may be released, including proteins, metabolites, and molecules introduced into a cell. RNA may include mRNA, which can hybridize to an oligonucleotide comprising a poly-T sequence. One or more reactions may be performed on components within a droplet. In some cases, reverse transcription may be performed within a droplet using the oligonucleotide (i.e., the oligonucleotide can act as a primer). Complementary DNA (cDNA) may be generated from mRNA from the cell, thereby attaching the cDNA to the polymer precursors and/or the particle. In some cases, DNA (e.g., genomic DNA) may be modified by one or more reactions. DNA may be subjected to oxygenase treatment. DNA may be subjected to bisulfite treatment and/or enzymatic deamination. DNA may be subjected to methyltransferase treatment. In some cases, DNA may be subjected to oxygenase treatment followed by enzymatic deamination, thereby preparing the DNA for methylation analysis via deamination of unmethylated cytosine nucleotides. In some cases, DNA may be subjected to methyltransferase treatment, thereby preparing the DNA for chromatin accessibility analysis by adding a methyl group to accessible cytosine residues on the DNA. In some instances, accessible chromatin is characterized using a cell bead and the methodologies disclosed herein (e.g., ATAC-seq, DNase-seq, MNase-seq)

A droplet may be subjected to conditions sufficient to polymerize, cross-link, and/or gel polymer precursors, thereby generating a cell bead. One or more macromolecular constituents from a cell or derivatives thereof (e.g., mRNA, cDNA, genomic DNA, protein, metabolites, molecules introduced into a cell) may be comprised in and/or attached to a cell bead. In some cases, mRNA from a cell is attached to the cell bead and/or a particle. In some cases, cDNA is attached to the cell bead and/or a particle. Following cell bead formation, cell beads can be transferred to an aqueous solution, where one or more reactions may be performed. In some cases, reverse transcription can be performed after cell bead formation, thereby generating cDNA from RNA (e.g., mRNA). Reverse transcription may use oligonucleotides attached to cell beads and/or particles, thereby generating cDNA which is attached to a cell bead and/or a particle. Additional reactions may be performed to process one or more constituents (e.g., DNA, RNA, protein, etc.). In some cases, DNA (e.g., genomic DNA) may be modified by one or more reactions. DNA may be subjected to oxygenase treatment. DNA may be subjected to bisulfite treatment and/or enzymatic deamination. DNA may be subjected to methyltransferase treatment. In some cases, DNA may be subjected to oxygenase treatment followed by enzymatic deamination, thereby preparing the DNA for methylation analysis via deamination of unmethylated cytosine nucleotides. In some cases, DNA may be subjected to methytransferase treatment, thereby preparing the DNA for chromatin accessibility analysis by adding a methyl group to accessible cytosine residues on the DNA. In some cases, binding groups (e.g., antibodies) may be washed into and/or out of a cell bead for identification of proteins and/or metabolites from a cell. Binding groups may be coupled to one or more barcode molecules. Methods and systems for identifying proteins and metabolites using binding groups coupled to barcode molecules are described in more detail elsewhere herein.

A cell bead may be partitioned together with a gel bead comprising one or more barcode molecules. The cell bead and the gel bead may be degraded or dissolved, releasing the barcode molecules from the gel bead and the multiple types of macromolecular constituents and/or derivatives thereof from the cell bead. Barcode molecules may be used to tag (e.g., barcode) the constituents or derivatives thereof (e.g., RNA, cDNA, genomic DNA, modified DNA, protein, antibody-protein complexes, antibody-metabolite complexes, molecules introduced into a cell). Barcode molecules may be useful in identifying each constituent as being derived from the same single cell. Barcoded constituents may be sequenced, thereby generating sequencing reads. Sequencing reads may be used to obtain multiple types of information about a single cell, including, for example, genetic, epigenetic, proteomic, metabolomic, and/or transcriptomic information.

Figure 47:
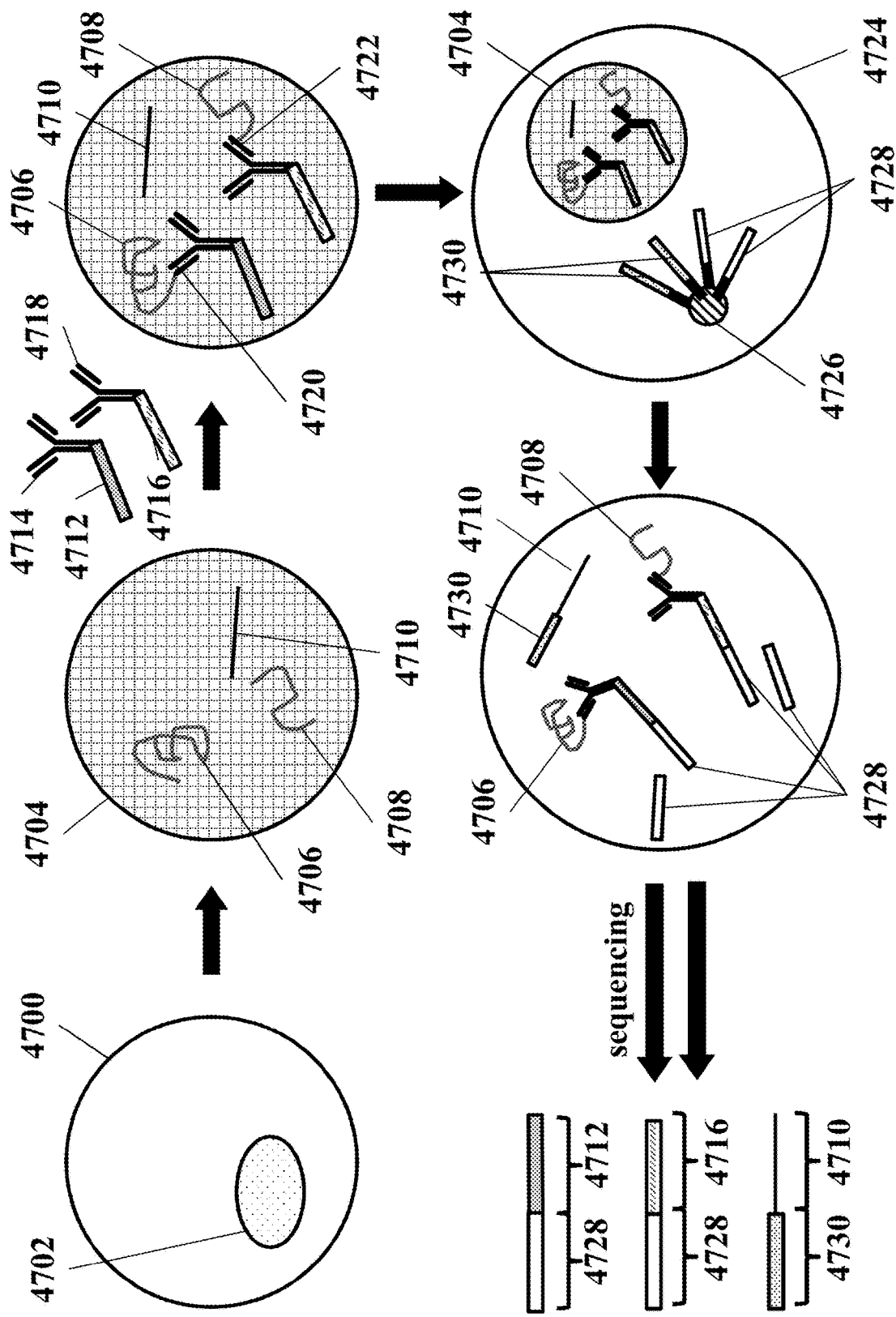
FIG. 47 illustrates a method for identifying and measuring multiple types of analytes from a cell using a cell bead.

FIG. 47 illustrates a method for identifying and measuring multiple types of analytes from a cell using a cell bead. A cell 4702 may be partitioned in a partition 4700 and processed to generate a cell bead 4704, as described herein. A cell bead may comprise a cell. A cell bead may comprise components released from a cell upon lysis of the cell. A cell bead may comprise multiple types of components including, for example, proteins, metabolites, RNA, DNA, molecules introduced into a cell, etc. Components may be attached to a cell bead. FIG. 47 shows a cell bead 4704 with proteins 4706 and 4708 and a nucleic acid 4710. Proteins can be cross-linked to each other and/or to other components within a cell bead. Alternatively, proteins may not be cross-linked.

Proteins 4706 and 4708 can be captured within the cell bead matrix. Proteins 4706 and 4708 can be attached to the cell bead. Nucleic acid 4710 can be DNA (e.g., gDNA, cDNA) or RNA (e.g., mRNA). Nucleic acid 4710 can be attached to the cell bead and/or a particle within the cell bead. For example, nucleic acid 4710 may be mRNA attached to the cell bead via an acrydite moiety.

Cell bead 4704 may be processed in bulk. For example, mRNA may be processed to generate cDNA using reverse transcription. Other analytes in a cell bead may be processed as described herein. A plurality of antibodies may be washed into the bead. Antibodies may be coupled to one or more barcode molecules comprising one or more barcode sequences. For example, antibodies 4714 and 4718 may be coupled to barcode molecules 4712 and 4716, each comprising a unique barcode sequence. Antibodies may bind to one or more analytes in accordance with the respective binding specificity. Antibody 4714 may have affinity for protein 4706 and antibody 4718 may have affinity for protein 4708. Washed into the cell bead 4704, antibody 4714 may bind to protein 4706, thereby forming a protein-antibody complex 4720 and tagging protein 4706 with the barcode sequence 4712. Antibody 4718 may bind to protein 4708, thereby forming a protein-antibody complex 4722 and tagging protein 4708 with the barcode sequence 4716. Following washing of antibodies, a cell bead may comprise one or more bound antibodies coupled to a barcode molecule, together with one or more analytes (e.g., RNA, DNA, etc.). A cell bead may comprise 1, 2, 3, 4, 5, or more types of analytes. A cell bead may comprise RNA (e.g, mRNA), DNA (e.g., gDNA, cDNA), protein, metabolites, and or additional molecules introduced into a cell (e.g., CRISPR RNA, . . . ). For example, cell bead 4704 may comprise antibody complexes 4720 and 4722, together with nucleic acid 4710.

The cell bead 4704 may be co-partitioned with a bead (e.g., gel bead) 4726 in a partition 4724. The partition 4724 may be a droplet. The bead 4726 may be coupled to a plurality of barcode molecules. Bead 4726 may comprise multiple types of barcode molecules comprising multiple types of barcode sequences. Bead 4726 may comprise barcode molecules comprising sequences for tagging (e.g., barcoding) different types of analytes (e.g., mRNA, cDNA, gDNA, protein, etc.). Beads comprising barcode molecules for barcoding multiple types of analytes are described in further detail elsewhere herein. For example, bead 4726 may comprise barcode molecules 4728 for barcoding barcode molecules 4712 and 4716 coupled to antibodies 4714 and 4718, and also may comprise barcode molecules 4730 for barcoding nucleic acid 4710. Barcode molecules 4730 and 4728 may comprise the same barcode sequences, or may comprise different barcode sequences. Barcode molecules 4730 and 4728 may comprise different priming regions (e.g., poly-T sequence, random sequence, capture sequence, riboG sequence, etc.). A bead may comprise up to 1, 2, 3, 4, 5, or more barcode molecules for barcoding 1, 2, 3, 4, 5, or more types of analytes from a single cell. Barcode molecules may be released from bead 4726 and used to generate barcoded analytes, as described elsewhere herein. In some cases, an analyte may be tagged by a composite barcode sequence, the composite barcode sequencing comprising barcode sequence 4728 and another barcode sequence (e.g., barcode sequence 4712 or 4716) tagged by an antibody. Barcoded molecules may be released from the partition and sequenced to generate sequencing reads. Barcode sequences can be used to identify analytes as having originated from the same single cell. Alternatively or in addition, barcode sequences can be used to measure one or more analytes (e.g., proteins, metabolites) in a cell. For example, barcode sequences 4728 and 4730 can identify proteins 4706 and 4708 and nucleic acid 4710 as having been derived from the same cell, while barcode sequences 4712 and 4716 can identify proteins 4706 and 4708 based on the known binding affinity of the conjugated antibody. While described in terms of analyzing proteins released from a cell, antibodies coupled to barcode molecules may also be used to identify and analyze, for example, cell surface proteins and/or metabolites from a cell.

Figure 48:
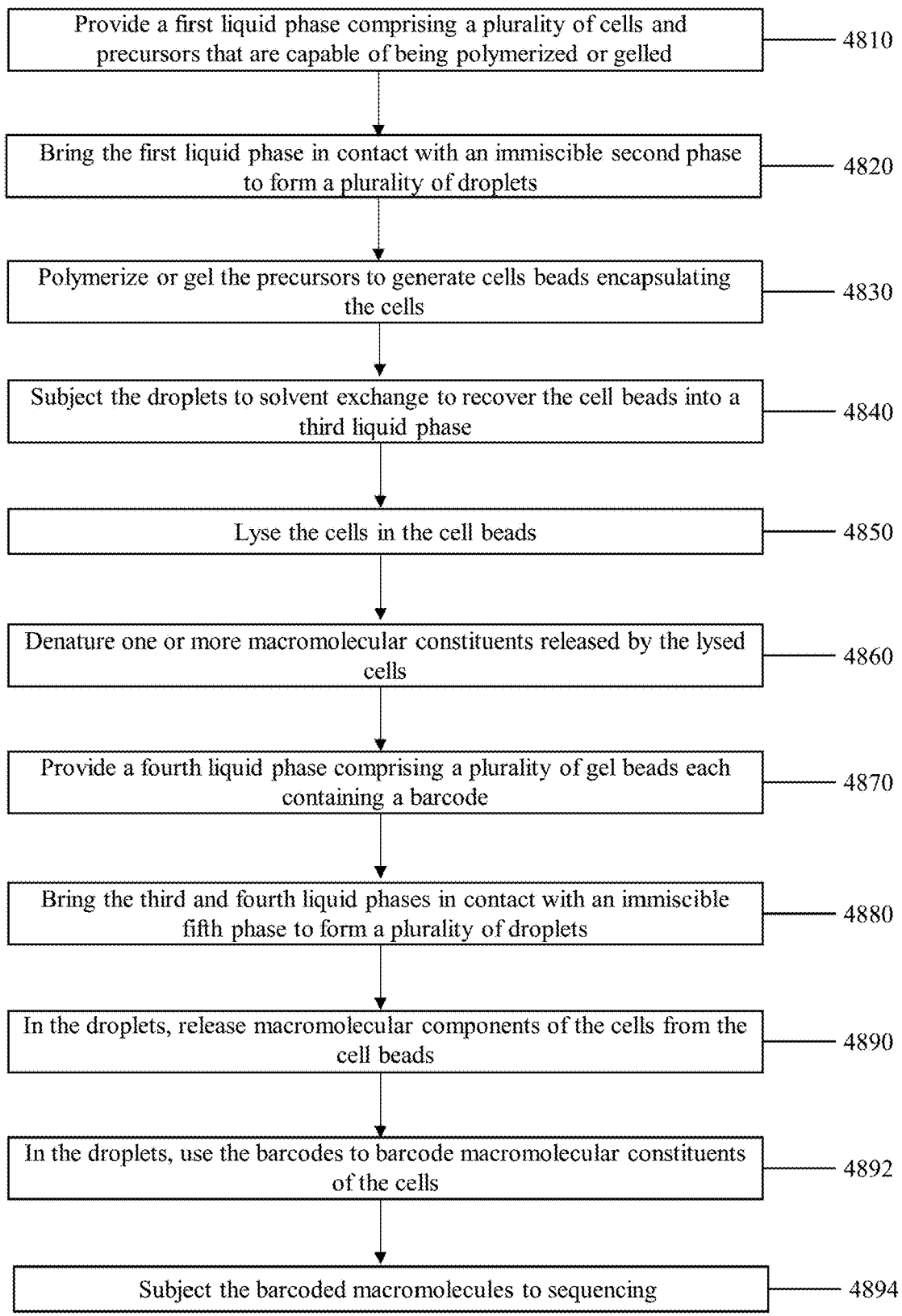
FIG. 48 shows a flowchart for a method of processing and sequencing components from a cell using cell beads.

FIG. 48 shows a flowchart that depicts an example method 4800 of producing droplets containing a cell bead (e.g., a cell bead comprising multiple different types of components of a cell) and a gel bead comprising barcode sequences and generating sequence reads from macromolecular components of a cell of which cell or components have been encapsulated by a polymer or gel. In some cases, the method 4800 may comprise the following operations.

In operation 4810, a first liquid phase comprising a plurality of cells is provided. The first liquid phase may be aqueous. The first liquid phase may comprise a cellular growth medium. The first liquid phase may comprise a minimal growth medium. The first liquid phase may further comprise precursors that are capable of being polymerized or gelled. Moreover, in some cases, precursors are pre-formed polymer chains that can be crosslinked (e.g., via gelation) to form larger structures such as beads. In some cases, precursors may be monomeric species that are polymerized to form larger structures such as beads.

The first liquid phase may comprise reagents necessary for performing one or more reactions on one or more macromolecular constituents from a cell. The first liquid phase may further comprise one or more of reagents for reverse transcription (e.g., oligonucleotide primers or reverse transcriptase), reagents for nucleic acid amplification (e.g., primers (e.g. random primers, primers specific for given DNA loci), polymerases, nucleotides (e.g. unmodified nucleotides, modified nucleotides, or non-canonical nucleotides), co-factors (e.g., ionic co-factors)) or reagents for nucleic acid modification, including ligation, digestion, methylation, random mutagenesis, bisulfite conversion, enzymatic deamination, uracil hydrolysis, nucleic acid repair, nucleic acid insertion or cleavage (e.g. via CRISPR/Cas9-mediated or transposon-mediated insertion or cleavage), capping and decapping. Reagents comprised in the first liquid phase may be attached to precursors capable of being gelled or polymerized (e.g., via an acrydite moiety). The first liquid phase may comprise one or more particles (e.g., magnetic particles). Reagents comprised in the first liquid phase may be attached to the one or more particles (e.g., via an acrydite moiety).

In operation 4820, the first liquid phase can be brought into contact with an immiscible second liquid phase to form a plurality of droplets. The second liquid phase may comprise an oil and may also comprise a surfactant. The second liquid phase may comprise a fluorinated hydrocarbon. In some cases, a given droplet may include a single cell and precursors that are capable of being polymerized or gelled. In some cases, at least 25%, at least 30%, at least 35%, at least 40%, at least 45%, at least 50%, at least 55%, at least 60%, at least 65%, at least 70%, at least 75%, at least 80%, at least 90%, at least 95%, at least 99%, at least 99.5%, at least 99.9%, at least 99.95%, or at least 99.99% of the droplets may contain a single cell.

In operation 4830, the droplets can be subjected to conditions sufficient to polymerize or gel the precursors. Following polymerization or gelling, a polymer or gel may be formed around the cells or cell components (e.g., DNA, RNA, protein, and/or metabolites), such that they are encapsulated in cell beads. The polymer or gel may be diffusively permeable to chemical or biochemical reagents. The polymer or gel may be diffusively impermeable to macromolecular constituents of the cells or cell components. In this manner, the polymer or gel may act to allow the cell beads to be subjected to chemical or biochemical operations while spatially confining the contents of the cells beads to a region defined by the polymer or gel. Additionally, cell components may be attached to the cell beads.

In some cases, one or more magnetic (e.g., paramagnetic) particles may be encapsulated within a cell bead such, as for example, by also including such particles within a droplet along with polymeric precursors. In some cases, reagents (e.g., oligonucleotides) may be attached to one or more magnetic particles encapsulated within a bead.

Cell beads may be or include a cell, cell derivative, cellular material and/or material derived from the cell in, within, or encased in a matrix, such as a polymeric matrix. A cell encapsulated by a bead may be a live cell.

In operation 4840, cell beads generated from precursors in droplets suspended in the second liquid phase may be resuspended into an aqueous environment by a solvent exchange process. Such processing can promote the processing of cell beads with additional aqueous phase materials. The solvent exchange process may comprise the operations of collecting cell beads in droplets (for instance, in an Eppendorf tube or other collection vessel), removing excess oil (for instance, by pipetting), adding a ligation buffer (such as a 3× ligation buffer), vortexing, adding a buffer (such as a 1× 1H,1H,2H,2H-perfluoro-1-octanol (PFO) buffer), vortexing, centrifugation, and separation. The separation operation may comprise magnetic separation via attraction of encapsulated magnetic particles. The magnetic separation may be accomplished by using a magnetic separating apparatus to pull cell beads containing magnetic particles away from unwanted remaining oil and solvents. For instance, the magnetic separation apparatus may be used to pull cell beads containing magnetic particles away from the ligation buffer and PFO to allow removal of the ligation buffer and PFO (for instance by pipetting). The cell beads containing magnetic particles may then be suspended in a ligation buffer and vortexed. The cell beads containing paramagnetic particles may again be separated magnetically and the ligation buffer may be removed. This cycle of re-suspension, vortexing, and magnetic separation may be repeated until the cell beads are free or substantially free of oil phase and suspended in aqueous medium. For instance, the cycle may be repeated 1, 2, 3, 4, 5, 6, 7, 8, 9, 10, or more than 10 times. The cell beads may then be processed in aqueous phases and with additional materials.

Once the cell beads are in an aqueous medium, the cell beads may be further treated. For instance, the cell beads in aqueous solution may be filtered (for instance, using a 70 µm filter) to remove clumps and/or large cell beads from the solution. In some cases, additional reagents may be added to and/or removed from the aqueous medium to further process the cell beads. Further processing can include, without limitation, reverse transcription, nucleic acid amplification, nucleic acid modification, bisulfite treatment, or enzymatic deamination of macromolecular constituents within the cell beads.

In operation 4850, the cell beads can be subjected to conditions sufficient to lyse the cells encapsulated in the cell beads. In some cases, lysis is completed via a lysis agent present in a droplet. In some cases, lysis is completed in bulk, for example with the aid of a lysis agent that contacts a plurality of cell beads in one pot. In some cases, the lysis of the cells occurs subsequent to subjecting the cells to conditions sufficient to encapsulate the cells in the polymer or gel. The lysis may release macromolecular constituents of the lysed cells. The lysis may be achieved by exposing the cell beads to sodium hydroxide (NaOH), potassium hydroxide (KOH), or any other alkaline agent. The lysis may be achieved by exposing the cell beads to a detergent, such as sodium dodecyl sulfate (SDS), 4-(1,1,3,3-Tetramethylbutyl) phenyl-polyethylene glycol (Triton X-100) or any non-ionic surfactant, or a saponin. The lysis may be achieved by exposing the cell beads to an enzyme, such as a proteinase or a lytic enzyme (such as a lysozyme, cellulose, or zymolase). The lysis may be achieved by exposing the cell beads to freeze thawing. The lysis may be achieved by exposing the cell beads to electromagnetic radiation, such as ultraviolet (UV) light. The lysis may be achieved by exposing the cell beads to heat. The lysis may be achieved by exposing the cell beads to any other lysis agent. A cell bead may retain species released from lysed cells within the cell bead, such as, for example, via its polymeric or gel structure.

In operation 4860, the cell beads can be subjected to conditions sufficient to denature one or more macromolecular constituents released by the lysed cells. In some cases, denaturation occurs in bulk where more than one cell bead is subjected to denaturation conditions in a single pot. In some cases, denaturation is achieved via a denaturation agent present in a droplet. The denaturing may be achieved by exposing the cell beads to sodium hydroxide (NaOH). The denaturing may be achieved by exposing the cell beads to any other denaturing agent. In some cases, operation 4860 is completed contemporaneously with operation 4850. In some examples, a denaturing agent can both denature macromolecular constituents and lyse the cells within the cell beads.

In operation 4870, a fourth liquid phase comprising a plurality of gel beads can be provided. The fourth liquid phase may be aqueous. The fourth liquid phase may comprise a cellular growth medium. The fourth liquid phase may comprise a minimal growth medium. The gel beads each contain barcode molecules to barcode one or more macromolecular constituents of the plurality of cell beads. In some cases, the third liquid phase and the fourth liquid phase are the same phase. In some cases, the third liquid phase and the fourth liquid phase are mixed to provide a mixed phase.

In operation 4880, the third liquid phase and the fourth liquid phase can be brought together with a fifth liquid phase that is immiscible with the third and fourth liquid phases. The fifth liquid phase may interact with the third and fourth liquid phases in such a manner as to partition cells beads encapsulating cellular material and the plurality of gel beads into a plurality of droplets. The fifth liquid phase may comprise an oil and may also comprise a surfactant. The fifth liquid phase may comprise a fluorinated hydrocarbon. In some cases, a given droplet may include a single cell bead and a single gel bead. In some cases, at least 25%, at least 30%, at least 35%, at least 40%, at least 45%, at least 50%, at least 55%, at least 60%, at least 65%, at least 70%, at least 75%, at least 80%, at least 90%, at least 95%, at least 99%, at least 99.5%, at least 99.9%, at least 99.95%, or at least 99.99% of the droplets may contain a single cell bead and a single gel bead. Moreover, while the cell beads and gel beads are partitioned into droplets in this example, other types of partitions can be implemented in operation 4880, including those described elsewhere herein, such as a well.

In operation 4890, the cell beads are subjected to conditions sufficient to release the macromolecular constituents from cell beads. The release of the macromolecular constituents may be achieved by exposing cell beads to a reducing agent (e.g., dithiothreitol (DTT)), which may be present in a droplet. The release of the macromolecular constituents may be achieved by exposing the cell beads to any substance capable of releasing the macromolecular constituents. In some cases, operation 4890 also includes releasing barcodes from the gel beads, which may be achieved with the same stimulus, such as, for example, that used to release macromolecular constituents from cell beads. In some cases, the stimuli are different. Released barcodes can then participate in barcoding as in operation 4892.

In operation 4892, the barcode molecules are used to barcode one or more macromolecular constituents of a given cell bead in a given droplet. In some cases, the macromolecular constituents of the cell bead are subjected to conditions sufficient for nucleic acid amplification for barcoding. In such cases, the barcode molecules may function as a primer during such amplification. In other cases, ligation can be used for barcoding. In some cases, the barcode molecules are used to identify one or more macromolecular constituents of the cell bead. In some cases, the barcode molecules are subjected to nucleic acid sequencing to identify one or more macromolecular components. In some cases, the sequencing is untargeted sequencing. In some cases, the sequencing is targeted sequencing.

In operation 4894, barcoded macromolecules (or derivatives thereof) are subjected to sequencing to generate reads. The sequencing may be performed within a droplet. The sequencing may be performed outside of a droplet. For instance, the sequencing may be performed by releasing the barcoded macromolecules from a droplet and sequencing the barcoded macromolecules using a sequencer, such as an Illumina sequencer or any other sequencer described herein. In some cases, a given barcoded sequencing read can be used to identify the cell (which may have been encapsulated in a cell bead) from which the barcoded sequencing read was generated. Such capability can link particular sequences to particular cells. Additional details and examples regarding nucleic acid sequencing methods are described elsewhere herein.

In some cases, prior to sequencing, the barcoded macromolecules may be further processed. For example, the barcoded macromolecules are subjected to nucleic acid amplification (e.g., PCR) prior to sequencing. In some cases, additional sequences are ligated to barcoded macromolecules. Such further processing may be performed in a droplet or external to the droplet, such as by releasing the barcoded macromolecules from the droplets.

Figure 49:
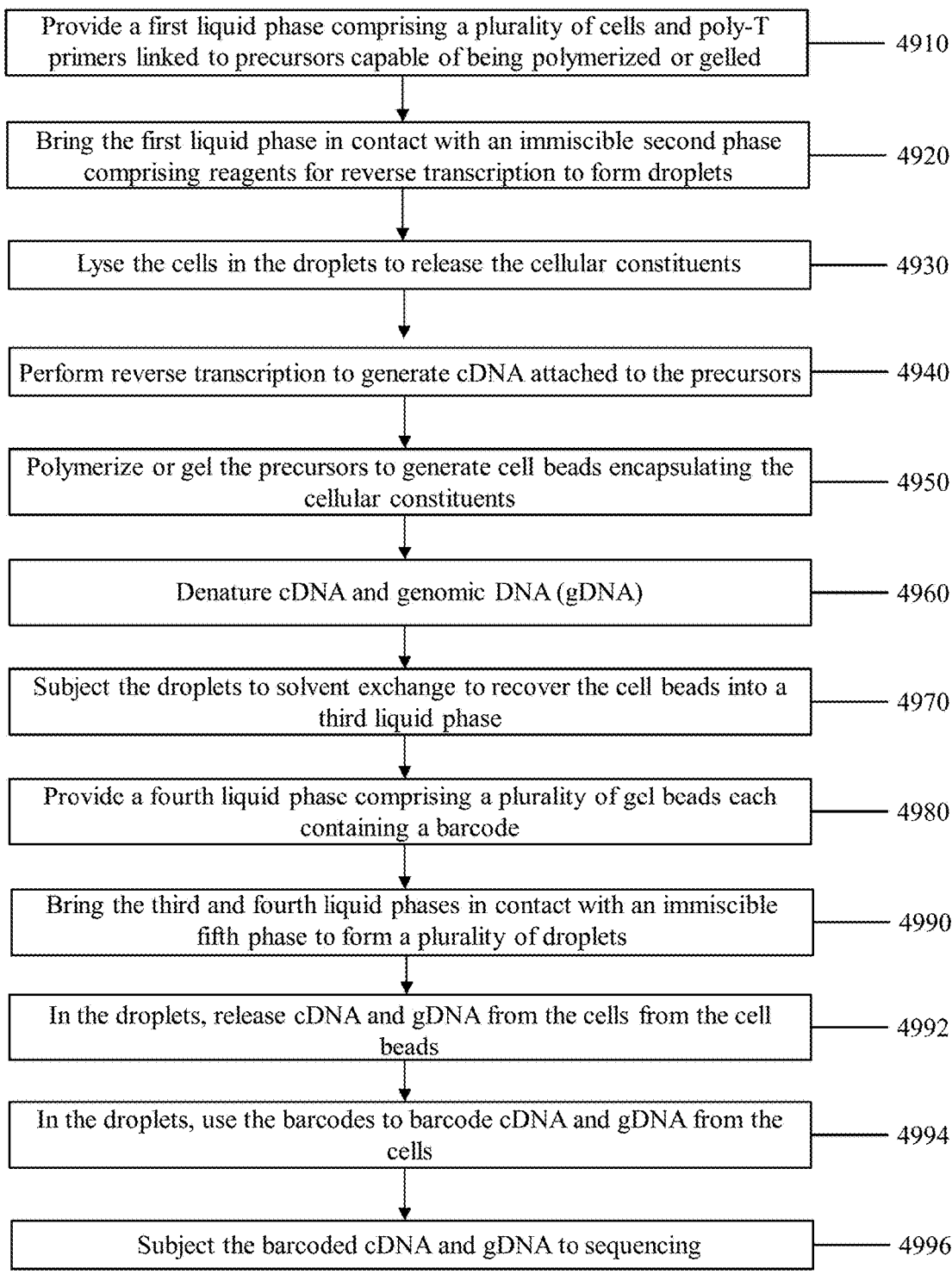
FIG. 49 shows a flowchart for a method of processing and sequencing ribonucleic acid and deoxyribonucleic acid from a cell using cell beads.

FIG. 49 shows a flowchart that depicts an example method 4900 of producing droplets containing a cell bead (e.g., a cell bead comprising multiple different components of a cell) and a gel bead comprising barcode sequences and generating sequence reads to identify and characterize at least two different types of macromolecular components (e.g., RNA and gDNA) from a cell. In some cases, the method 4900 may comprise the following operations.

In operation 4910, a first liquid phase comprising a plurality of cells is provided. The first liquid phase may be aqueous. The first liquid phase may comprise a cellular growth medium. The first liquid phase may comprise a minimal growth medium. The first liquid phase may further comprise precursors that are capable of being polymerized or gelled. Moreover, in some cases, precursors are preformed polymer chains that can be crosslinked (e.g., via gelation) to form larger structures such as beads. In some cases, precursors may be monomeric species that are polymerized to form larger structures such as beads.

The first liquid phase may further comprise reagents necessary for performing one or more reactions on one or more macromolecular constituents from a cell. The first liquid phase may further comprise one or more of reagents for reverse transcription (e.g., oligonucleotide primers or reverse transcriptase), reagents for nucleic acid amplification (e.g., primers (e.g. random primers, primers specific for given DNA loci, poly-T primers), polymerases, nucleotides (e.g. unmodified nucleotides, modified nucleotides, or non-canonical nucleotides), co-factors (e.g., ionic co-factors)) or reagents for nucleic acid modification, including ligation, digestion, methylation, random mutagenesis, bisulfite conversion, uracil hydrolysis, nucleic acid repair, nucleic acid insertion or cleavage (e.g. via CRISPR/Cas9-mediated or transposon-mediated insertion or cleavage), capping and decapping. Reagents comprised in the first liquid phase may be attached to precursors capable of being gelled or polymerized. The first liquid phase may comprise one or more particles (e.g., magnetic particles). Reagents comprised in the first liquid phase may be attached to the particle. In some cases, oligonucleotides (e.g., poly-T primers) are linked to the precursors.

In operation 4920, the first liquid phase can be brought into contact with an immiscible second liquid phase to form a plurality of droplets. The second liquid phase may comprise an oil and may also comprise a surfactant. The second liquid phase may comprise a fluorinated hydrocarbon. In some cases, a given droplet may include a single cell and precursors that are capable of being polymerized or gelled. In some cases, at least 25%, at least 30%, at least 35%, at least 40%, at least 45%, at least 50%, at least 55%, at least 60%, at least 65%, at least 70%, at least 75%, at least 80%, at least 90%, at least 95%, at least 99%, at least 99.5%, at least 99.9%, at least 99.95%, or at least 99.99% of the droplets may contain a single cell.

In operation 4930, the droplets can be subjected to conditions sufficient to lyse the cells within the droplets. In some cases, lysis is completed via a lysis agent present in a droplet. In some cases, the lysis of the cells occurs prior to subjecting the cells to conditions sufficient to encapsulate the cells in the polymer or gel. In some cases, the lysis of the cells occurs simultaneous with subjecting the cells to conditions sufficient to encapsulate the cells in the polymer or gel. The lysis may release macromolecular constituents of the lysed cells. Released macromolecular constituents can include, for example, messenger RNA (mRNA) and genomic DNA (gDNA). The lysis may be achieved by exposing the cells to sodium hydroxide (NaOH), potassium hydroxide (KOH), or any other alkaline agent. The lysis may be achieved by exposing the cell beads to a detergent, such as sodium dodecyl sulfate (SDS), 4-(1,1,3,3-Tetramethylbutyl)phenyl-polyethylene glycol (Triton X-100) or any non-ionic surfactant, or a saponin. The lysis may be achieved by exposing the cells to an enzyme, such as a proteinase or a lytic enzyme (such as a lysozyme, cellulose, or zymolase). The lysis may be achieved by exposing the cells to freeze thawing. The lysis may be achieved by exposing the cells to electromagnetic radiation, such as ultraviolet (UV) light. The lysis may be achieved by exposing the cells to heat. The lysis may be achieved by exposing the cells to any other lysis agent. A droplet may contain species released from lysed cells. Alternatively or in addition, a cell within a partition may be permeabilized. Permeabilization may allow for transfer of certain reagents, species, constituents, etc. into and/or out of a cell with or without complete cellular lysis.

In operation 4940, the droplets can be subjected to conditions sufficient to perform reverse transcription on nucleic acid (e.g., RNA) from the cells. In some cases, reverse transcription is performed on mRNA released from the cells into the droplet following lysis. Reverse transcription may be performed using poly-T primers. Poly-T primers may be attached to precursors (e.g., monomers) capable of being polymerized or gelled. In some cases, reverse transcription results in the generation of complementary DNA (cDNA) from RNA. cDNA may be attached to the precursors capable of being polymerized or gelled.

In operation 4950, the droplets can be subjected to conditions sufficient to polymerize or gel the precursors. Following polymerization or gelling, a polymer or gel may be formed around the cell components, such that they are encapsulated in cell beads. The polymer or gel may be diffusively permeable to chemical or biochemical reagents. The polymer or gel may be diffusively impermeable to macromolecular constituents of the cells or cell components. In this manner, the polymer or gel may act to allow the cell beads to be subjected to chemical or biochemical operations while spatially confining the contents of the cells beads to a region defined by the polymer or gel. Macromolecular constituents (e.g., RNA) or derivatives thereof (e.g., cDNA) may be attached to the cell beads subsequent to polymerization or gelling.

In some cases, one or more magnetic (e.g., paramagnetic) particles may be encapsulated within a cell bead such as, for example, by also including such particles within a droplet along with polymeric precursors. Reagents (e.g., oligonucleotides) may be attached to magnetic particles.

In operation 4960, the cell beads can be subjected to conditions sufficient to denature one or more macromolecular constituents released by the lysed cells (e.g., cDNA and gDNA from a cell). In some cases, denaturation occurs in bulk where more than one cell bead is subjected to denaturation conditions in a single pot. In some cases, denaturation is achieved via a denaturation agent present in a droplet. The denaturing may be achieved by exposing the cell beads to sodium hydroxide (NaOH). The denaturing may be achieved by exposing the cell beads to any other denaturing agent. In some cases, operation 4960 is completed contemporaneously with operation 4950. In some examples, a denaturing agent can both denature macromolecular constituents and lyse the cells within the cell beads.

In operation 4970, cell beads generated from precursors in droplets suspended in the second liquid phase may be resuspended into an aqueous environment by a solvent exchange process. Such processing can promote the processing of cell beads with additional aqueous phase materials. The solvent exchange process may comprise the operations of collecting cell beads in droplets (for instance, in an Eppendorf tube or other collection vessel), removing excess oil (for instance, by pipetting), adding a ligation buffer (such as a 3× ligation buffer), vortexing, adding a buffer (such as a 1× 1H,1H,2H,2H-perfluoro-1-octanol (PFO) buffer), vortexing, centrifugation, and separation. The separation operation may comprise magnetic separation via attraction of encapsulated magnetic particles. The magnetic separation may be accomplished by using a magnetic separating apparatus to pull cell beads containing magnetic particles away from unwanted remaining oil and solvents. For instance, the magnetic separation apparatus may be used to pull cell beads containing magnetic particles away from the ligation buffer and PFO to allow removal of the ligation buffer and PFO (for instance by pipetting). The cell beads containing magnetic particles may then be suspended in a ligation buffer and vortexed. The cell beads containing paramagnetic particles may again be separated magnetically and the ligation buffer may be removed. This cycle of re-suspension, vortexing, and magnetic separation may be repeated until the cell beads are free or substantially free of oil phase and suspended in aqueous medium. For instance, the cycle may be repeated 1, 2, 3, 4, 5, 6, 7, 8, 9, 10, or more than 10 times. The cell beads may then be processed in aqueous phases and with additional materials.

Once the cell beads are in an aqueous medium, the cell beads may be further treated. For instance, the cell beads in aqueous solution may be filtered (for instance, using a 70 µm filter) to remove clumps and/or large cell beads from the solution. In some cases, additional reagents may be added to and/or removed from the aqueous medium to further process the cell beads. Further processing can include, without limitation, reverse transcription, nucleic acid amplification, nucleic acid modification, bisulfite treatment, or enzymatic deamination of macromolecular constituents within the cell beads.

In operation 4980, a fourth liquid phase comprising a plurality of gel beads can be provided. The fourth liquid phase may be aqueous. The fourth liquid phase may comprise a cellular growth medium. The fourth liquid phase may comprise a minimal growth medium. The gel beads each contain barcode molecules to barcode one or more macromolecular constituents of the plurality of cell beads. In some cases, the third liquid phase and the fourth liquid phase are the same phase. In some cases, the third liquid phase and the fourth liquid phase are mixed to provide a mixed phase.

In operation 4990, the third liquid phase and the fourth liquid phase can be brought together with a fifth liquid phase that is immiscible with the third and fourth liquid phases. The fifth liquid phase may interact with the third and fourth liquid phases in such a manner as to partition cells beads encapsulating cellular material and the plurality of gel beads into a plurality of droplets. The firth liquid phase may comprise an oil and may also comprise a surfactant. The fifth liquid phase may comprise a fluorinated hydrocarbon. In some cases, a given droplet may include a single cell bead and a single gel bead. In some cases, at least 25%, at least 30%, at least 35%, at least 40%, at least 45%, at least 50%, at least 55%, at least 60%, at least 65%, at least 70%, at least 75%, at least 80%, at least 90%, at least 95%, at least 99%, at least 99.5%, at least 99.9%, at least 99.95%, or at least 99.99% of the droplets may contain a single cell bead and a single gel bead. Moreover, while the cell beads and gel beads are partitioned into droplets in this example, other types of partitions can be implemented in operation 4990, including those described elsewhere herein, such as a well.

In operation 4992, the cell beads are subjected to conditions sufficient to release the macromolecular constituents (e.g., cDNA and gDNA) from cell beads. The release of the macromolecular constituents may be achieved by exposing cell beads to a reducing agent (e.g., dithiothreitol (DTT)), which may be present in a droplet. The release of the macromolecular constituents may be achieved by exposing the cell beads to any substance capable of releasing the macromolecular constituents. In some cases, operation 4992 also includes releasing barcodes from the gel beads, which may be achieved with the same stimulus, such as, for example, that used to release macromolecular constituents from cell beads. In some cases, the stimuli are different. Released barcodes can then participate in barcoding as in operation 4994.

In operation 4994, the barcode molecules are used to barcode one or more macromolecular constituents or derivatives thereof (e.g., both cDNA and gDNA) from a given cell bead in a given droplet. In some cases, the macromolecular constituents of the cell bead are subjected to conditions sufficient for nucleic acid amplification for barcoding. In such cases, the barcodes may function as a primer during such amplification. In other cases, ligation can be used for barcoding. One method may be used to barcode one analyte (e.g., cDNA), while another method may be used to barcode another analyte (e.g., gDNA). For example, nucleic acid amplification may be used for barcoding cDNA, while ligation may be used for barcoding gDNA. Alternatively, the same method may be used to barcode both cDNA and gDNA. Different types of barcode molecules (e.g., containing different functional sequences) may be used to barcode different types of components. In some cases, the barcode molecules are used to identify one or more macromolecular constituents of the cell bead (e.g., both RNA and DNA). In some cases, the barcode molecules are subjected to nucleic acid sequencing to identify one or more macromolecular components. In some cases, the sequencing is untargeted sequencing. In some cases, the sequencing is targeted sequencing.

In operation 4996, barcoded macromolecules (or derivatives thereof) are subjected to sequencing to generate reads. The sequencing may be performed within a droplet. The sequencing may be performed outside of a droplet. For instance, the sequencing may be performed by releasing the barcoded macromolecules from a droplet and sequencing the barcoded macromolecules using a sequencer, such as an Illumina sequencer or any other sequencer described herein. In some cases, a given barcoded sequencing read can be used to identify the cell (which may have been encapsulated in a cell bead) from which the barcoded sequencing read was generated. Such capability can link particular sequences to particular cells. Additional details and examples regarding nucleic acid sequencing methods are described elsewhere herein.

In some cases, prior to sequencing, the barcoded macromolecules may be further processed. For example, the barcoded macromolecules are subjected to nucleic acid amplification (e.g., PCR) prior to sequencing. In some cases, additional sequences are ligated to barcoded macromolecules. Such further processing may be performed in a droplet or external to the droplet, such as by releasing the barcoded macromolecules from the droplets.

Figure 50:
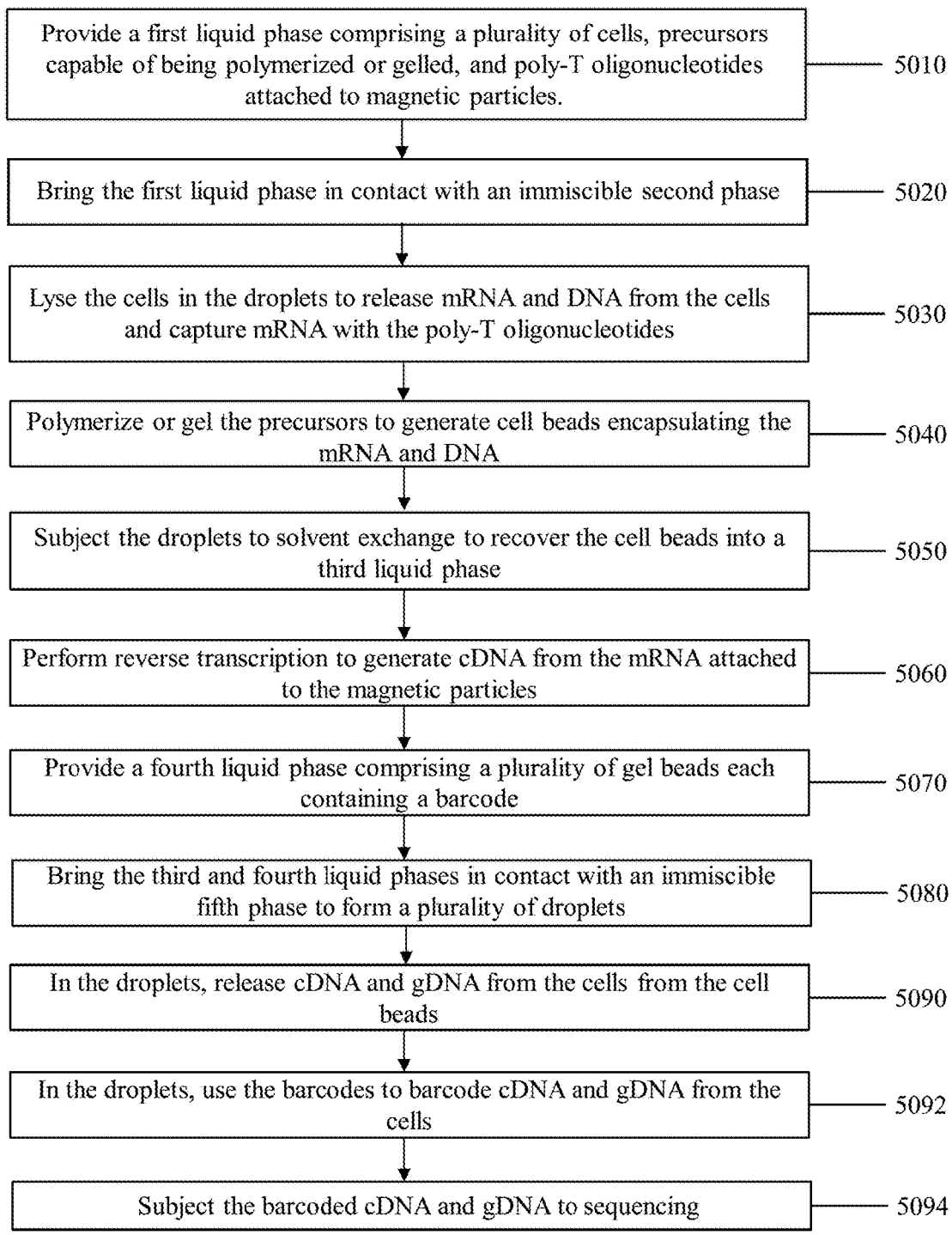
FIG. 50 shows a flowchart for another method of processing and sequencing ribonucleic acid and deoxyribonucleic acid from a cell using cell beads.

FIG. 50 shows a flowchart that depicts an example method 5000 of producing droplets containing a cell bead (e.g., comprising components of a cell) and a gel bead comprising barcode sequences and generating sequence reads from at least two different types of macromolecular components (e.g., RNA and gDNA) from a cell. In some cases, the method 5000 may comprise the following operations.

In operation 5010, a first liquid phase comprising a plurality of cells is provided. The first liquid phase may be aqueous. The first liquid phase may comprise a cellular growth medium. The first liquid phase may comprise a minimal growth medium. The first liquid phase may further comprise precursors that are capable of being polymerized or gelled. Moreover, in some cases, precursors are pre-formed polymer chains that can be crosslinked (e.g., via gelation) to form larger structures such as beads. In some cases, precursors may be monomeric species that are polymerized to form larger structures such as beads.

The first liquid phase may further comprise reagents necessary for performing one or more reactions on one or more macromolecular constituents from a cell. The first liquid phase may further comprise one or more of reagents for reverse transcription (e.g., oligonucleotide primers or reverse transcriptase), reagents for nucleic acid amplification (e.g., primers (e.g. random primers, primers specific for given DNA loci, poly-T primers), polymerases, nucleotides (e.g. unmodified nucleotides, modified nucleotides, or non-canonical nucleotides), co-factors (e.g., ionic co-factors)) or reagents for nucleic acid modification, including ligation, digestion, methylation, random mutagenesis, bisulfite conversion, uracil hydrolysis, nucleic acid repair, nucleic acid insertion or cleavage (e.g. via CRISPR/Cas9-mediated or transposon-mediated insertion or cleavage), capping and decapping. Reagents comprised in the first liquid phase may be attached to precursors capable of being gelled or polymerized. The first liquid phase may comprise one or more particles (e.g., magnetic particles). Reagents comprised in the first liquid phase may be attached to the particle. In some cases, oligonucleotides (e.g., poly-T primers) are linked to the magnetic particle.

In operation 5020, the first liquid phase can be brought into contact with an immiscible second liquid phase to form a plurality of droplets. The second liquid phase may comprise an oil and may also comprise a surfactant. The second liquid phase may comprise a fluorinated hydrocarbon. In some cases, a given droplet may include a single cell and precursors that are capable of being polymerized or gelled. In some cases, at least 25%, at least 30%, at least 35%, at least 40%, at least 45%, at least 50%, at least 55%, at least 60%, at least 65%, at least 70%, at least 75%, at least 80%, at least 90%, at least 95%, at least 99%, at least 99.5%, at least 99.9%, at least 99.95%, or at least 99.99% of the droplets may contain a single cell.

In operation 5030, the droplets can be subjected to conditions sufficient to lyse the cells within the droplets. In some cases, lysis is completed via a lysis agent present in a droplet. In some cases, the lysis of the cells occurs prior to subjecting the cells to conditions sufficient to encapsulate the cells in the polymer or gel. In some cases, the lysis of the cells occurs simultaneous with subjecting the cells to conditions sufficient to encapsulate the cells in the polymer or gel. The lysis may release macromolecular constituents of the lysed cells. Released macromolecular constituents can include, for example, messenger RNA (mRNA) and genomic DNA (gDNA). The lysis may be achieved by exposing the cells to sodium hydroxide (NaOH), potassium hydroxide (KOH), or any other alkaline agent. The lysis may be achieved by exposing the cell beads to a detergent, such as sodium dodecyl sulfate (SDS), 4-(1,1,3,3-Tetramethylbutyl)phenyl-polyethylene glycol (Triton X-100) or any non-ionic surfactant, or a saponin. The lysis may be achieved by exposing the cells to an enzyme, such as a proteinase or a lytic enzyme (such as a lysozyme, cellulose, or zymolase). The lysis may be achieved by exposing the cells to freeze thawing. The lysis may be achieved by exposing the cells to electromagnetic radiation, such as ultraviolet (UV) light. The lysis may be achieved by exposing the cells to heat. The lysis may be achieved by exposing the cells to any other lysis agent. A droplet may contain species released from lysed cells. In some cases, lysis results in attachment (e.g., hybridization) of mRNA to poly-T oligonucleotides attached to magnetic particles. Conditions suitable for lysis of a cell may also result in the denaturation of macromolecular constituents (e.g., nucleic acids) from the cell. Alternatively or in addition, a cell within a partition may be permeabilized. Permeabilization may allow for transfer of certain reagents, species, constituents, etc. into and out of a cell with or without complete cellular lysis.

In operation 5040, the droplets can be subjected to conditions sufficient to polymerize or gel the precursors. The conditions sufficient to polymerize or gel the precursors may comprise exposure to heating, cooling, electromagnetic radiation, or light. The conditions sufficient to polymerize or gel the precursors may comprise any conditions sufficient to polymerize or gel the precursors. Following polymerization or gelling, a polymer or gel may be formed around the cell components, such that they are encapsulated in cell beads. The polymer or gel may be diffusively permeable to chemical or biochemical reagents. The polymer or gel may be diffusively impermeable to macromolecular constituents of the cells or cell components. In this manner, the polymer or gel may act to allow the cell beads to be subjected to chemical or biochemical operations while spatially confining the contents of the cells beads to a region defined by the polymer or gel. Macromolecular constituents or derivatives thereof (e.g., cDNA) may be attached to the cell beads subsequent to polymerization or gelling.

In some cases, one or more magnetic (e.g., paramagnetic) particles may be encapsulated within a cell bead such as, for example, by also including such particles within a droplet along with polymeric precursors. Reagents (e.g., oligonucleotides) may be attached to magnetic particles.

In operation 5050, cell beads generated from precursors in droplets suspended in the second liquid phase may be resuspended into an aqueous environment by a solvent exchange process. Such processing can promote the processing of cell beads with additional aqueous phase materials. The solvent exchange process may comprise the operations of collecting cell beads in droplets (for instance, in an Eppendorf tube or other collection vessel), removing excess oil (for instance, by pipetting), adding a ligation buffer (such as a 3× ligation buffer), vortexing, adding a buffer (such as a 1× 1H,1H,2H,2H-perfluoro-1-octanol (PFO) buffer), vortexing, centrifugation, and separation. The separation operation may comprise magnetic separation via attraction of encapsulated magnetic particles. The magnetic separation may be accomplished by using a magnetic separating apparatus to pull cell beads containing magnetic particles away from unwanted remaining oil and solvents. For instance, the magnetic separation apparatus may be used to pull cell beads containing magnetic particles away from the ligation buffer and PFO to allow removal of the ligation buffer and PFO (for instance by pipetting). The cell beads containing magnetic particles may then be suspended in a ligation buffer and vortexed. The cell beads containing paramagnetic particles may again be separated magnetically and the ligation buffer may be removed. This cycle of re-suspension, vortexing, and magnetic separation may be repeated until the cell beads are free or substantially free of oil phase and suspended in aqueous medium. For instance, the cycle may be repeated 1, 2, 3, 4, 5, 6, 7, 8, 9, 10, or more than 10 times. The cell beads may then be processed in aqueous phases and with additional materials.

Once the cell beads are in an aqueous medium, the cell beads may be further treated. For instance, the cell beads in aqueous solution may be filtered (for instance, using a 70 µm filter) to remove clumps and/or large cell beads from the solution. In some cases, additional reagents may be added to and/or removed from the aqueous medium to further process the cell beads. Further processing can include, without limitation, reverse transcription, nucleic acid amplification, nucleic acid modification, bisulfite treatment, or enzymatic deamination of macromolecular constituents within the cell beads.

In operation 5060, the droplets can be subjected to conditions sufficient to perform reverse transcription on nucleic acid (e.g., RNA) from the cells. In some cases, reverse transcription is performed on mRNA released from the cells following lysis. Reverse transcription can be performed in an aqueous medium following solvent exchange. Reverse transcription may be performed using poly-T oligonucleotides attached to magnetic particles. Reverse transcription may generate complementary DNA (cDNA) from RNA. In some cases, resultant cDNA is attached to the magnetic particles.

In operation 5070, a fourth liquid phase comprising a plurality of gel beads can be provided. The fourth liquid phase may be aqueous. The fourth liquid phase may comprise a cellular growth medium. The fourth liquid phase may comprise a minimal growth medium. The gel beads each contain barcode molecules to barcode one or more macromolecular constituents of the plurality of cell beads. In some cases, the third liquid phase and the fourth liquid phase are the same phase. In some cases, the third liquid phase and the fourth liquid phase are mixed to provide a mixed phase.

In operation 5080, the third liquid phase and the fourth liquid phase can be brought together with a fifth liquid phase that is immiscible with the third and fourth liquid phases. The fifth liquid phase may interact with the third and fourth liquid phases in such a manner as to partition cells beads encapsulating cellular material and the plurality of gel beads into a plurality of droplets. The firth liquid phase may comprise an oil and may also comprise a surfactant. The fifth liquid phase may comprise a fluorinated hydrocarbon. In some cases, a given droplet may include a single cell bead and a single gel bead. In some cases, at least 25%, at least 30%, at least 35%, at least 40%, at least 45%, at least 50%, at least 55%, at least 60%, at least 65%, at least 70%, at least 75%, at least 80%, at least 90%, at least 95%, at least 99%, at least 99.5%, at least 99.9%, at least 99.95%, or at least 99.99% of the droplets may contain a single cell bead and a single gel bead. Moreover, while the cell beads and gel beads are partitioned into droplets in this example, other types of partitions can be implemented in operation 5080, including those described elsewhere herein, such as a well.

In operation 5090, the cell beads are subjected to conditions sufficient to release the macromolecular constituents (e.g., cDNA and gDNA) from cell beads. The release of the macromolecular constituents may be achieved by exposing cell beads to a reducing agent (e.g., dithiothreitol (DTT)), which may be present in a droplet. The release of the macromolecular constituents may be achieved by exposing the cell beads to any substance capable of releasing the macromolecular constituents. In some cases, operation 5090 also includes releasing barcodes from the gel beads, which may be achieved with the same stimulus, such as, for example, that used to release macromolecular constituents from cell beads. In some cases, the stimuli are different. Released barcodes can then participate in barcoding as in operation 5092.

In operation 5092, the barcode molecules are used to barcode one or more macromolecular constituents or derivatives thereof (e.g., both cDNA and gDNA) of a given cell bead in a given droplet. In some cases, the macromolecular constituents of the cell bead are subjected to conditions sufficient for nucleic acid amplification for barcoding. In such cases, the barcode molecules may function as a primer during such amplification. In other cases, ligation can be used for barcoding. One method may be used to barcode one analyte (e.g., cDNA), while another method may be used to barcode another analyte (e.g., gDNA). For example, nucleic acid amplification may be used for barcoding cDNA, while ligation may be used for barcoding gDNA. Alternatively, the same method may be used to barcode both cDNA and gDNA. Different types of barcode molecules (e.g., containing different functional sequences) may be used to barcode different types of components. In some cases, the barcode molecules are used to identify one or more macromolecular constituents of the cell bead (e.g., RNA and DNA). In some cases, the barcode molecules are subjected to nucleic acid sequencing to identify one or more macromolecular components. In some cases, the sequencing is untargeted sequencing. In some cases, the sequencing is targeted sequencing.

In operation 5094, barcoded macromolecules (or derivatives thereof) are subjected to sequencing to generate reads. The sequencing may be performed within a droplet. The sequencing may be performed outside of a droplet. For instance, the sequencing may be performed by releasing the barcoded macromolecules from a droplet and sequencing the barcoded macromolecules using a sequencer, such as an Illumina sequencer or any other sequencer described herein. In some cases, a given barcoded sequencing read can be used to identify the cell (which may have been encapsulated in a cell bead) from which the barcoded sequencing read was generated. Such capability can link particular sequences to particular cells. In particular, obtaining sequences from multiple types of macromolecular constituents (e.g., RNA and DNA) can link multiple types of genetic information to a particular cell. Additional details and examples regarding nucleic acid sequencing methods are described elsewhere herein.

In an aspect, the present disclosure provides methods and systems for the generation of cell beads, which may be useful in processing different components from single cells. Cell beads may be generated by methods as described herein, for example by polymerization of molecular precursors (e.g., polymer precursors) in a partition comprising a cell or constituents from a cell. Cell beads can comprise two or more different types of components from a cell, including, for example, DNA, RNA, proteins, metabolites, and/or molecules introduced into a cell. Components may be comprised in and/or attached to cell beads. Cell beads can be generated by encapsulating a cell in a polymer or gel matrix and lysing the cell in the gel or polymer matrix, lysing the cell while it is being encapsulated in the polymer or gel matrix, or lysing the cell so that its constituents are encapsulated in the polymer or gel matrix.

A partition used in generating a cell bead may comprise species (e.g., reagents) for conducting one or more reactions. Species may include, for example, reagents for a nucleic acid amplification reaction (e.g., primers, polymerases, nucleotides, co-factors (e.g., ionic co-factors), buffers) including those described herein, reagents for enzymatic reactions (e.g., enzymes, co-factors, substrates, buffers), reagents for nucleic acid modification reactions (e.g., polymerization, ligation, digestion, deamination, methylation) and/or reagents for template preparation. One or more reagents within a partition may be attached to precursors. Reagents may be covalently attached to precursors. Reagents may be reversibly or irreversible attached to precursors. Regents may be attached to precursors via an acrydite moiety. In some cases, oligonucleotides may be attached to the precursors. Oligonucleotides attached to precursors may be useful in, for example, capturing RNA and/or performing reverse transcription. Oligonucleotides may comprise a poly-T sequence (e.g., may be a poly-T primer). A poly-T sequence may be capable of hybridizing to a poly-A sequence, for example, from mRNA of a cell.

A partition used in generating a cell bead may comprise one or more particles (e.g., magnetic particles). One or more reagents within a partition may be attached to a particle. Reagents may be covalently attached to a particle. Reagents may be reversibly or irreversible attached to a particle. Regents may be attached to a particle via an acrydite moiety. In some cases, oligonucleotides may be attached to a particle (see, for example, FIGS. 17A-B). Oligonucleotides attached to a particle may be useful in, for example, capturing RNA and/or performing reverse transcription. Oligonucleotides may comprise a poly-T sequence (e.g., may be a poly-T primer). A poly-T sequence may be capable of hybridizing to a poly-A sequence, for example, from mRNA of a cell.

A cell within a partition may be lysed as described herein, thereby releasing constituents from the cell into the partition. Constituents may include multiple types of cellular components, including proteins, metabolites, and/or nucleic acid molecules (e.g., DNA, RNA (e.g. messenger RNA), etc.). Alternatively or in addition, a cell within a partition may by permeabilized. Permeabilization may allow for transfer of certain reagents, species, constituents, etc. into and/or out of a cell with or without complete cellular lysis. Reagents within a partition, including reagents attached to precursors, particles, etc., may be used to perform a reaction on constituents from a cell. A reaction may be any kind of reaction, such as amplification, reverse transcription, deamination, methylation, etc. In some cases, oligonucleotides (e.g., primers) are used to perform a reverse transcription reaction on messenger RNA from a cell, thereby generating complementary DNA (cDNA). Reverse transcription may comprise the addition of additional nucleotides, e.g., polyC, to the cDNA. In some cases, template switching may be performed to further extend the cDNA. Template switching may append one or more additional sequences to the cDNA. Additional sequences may, in some cases, be used to facilitate barcoding, as described herein. cDNA may be attached to precursors and/or particles. In some cases, oligonucleotides are used to capture messenger RNA from a cell, (e.g., via hybridization) prior to generation of a cell bead. One or more additional reactions may be performed in a droplet on one or more additional components (e.g., RNA, DNA, protein, etc.).

Figure 51:
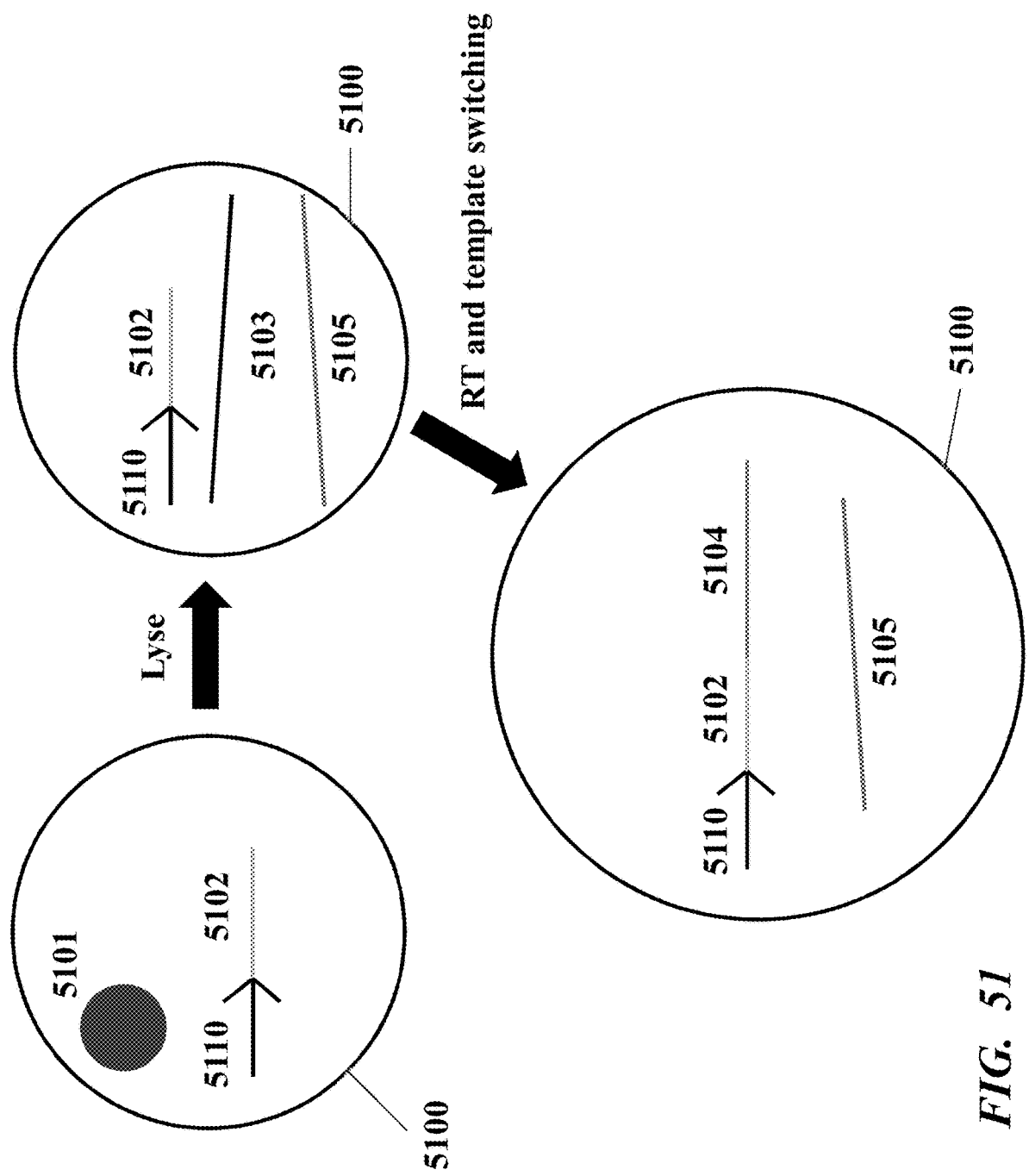
FIG. 51 illustrates an example process for generating droplets comprising constituents from a cell.

FIG. 51 illustrates an example of generating cDNA from cellular mRNA and attaching the cDNA to a polymeric precursor. A droplet 5100 may comprise a cell 5101, an oligonucleotide comprising a poly-T sequence 5102 attached to a polymeric precursor 5110, and a template switching oligonucleotide (not shown in FIG. 51). Cell 5101 may be lysed, generating multiple types of cellular constituents including messenger RNA 5103 and genomic DNA 5105. Primer 5102 and the template switching oligonucleotide may be used to perform reverse transcription (RT) and template switching, thereby generating complementary DNA 5104 attached to polymeric precursor 5110.

Figure 52:
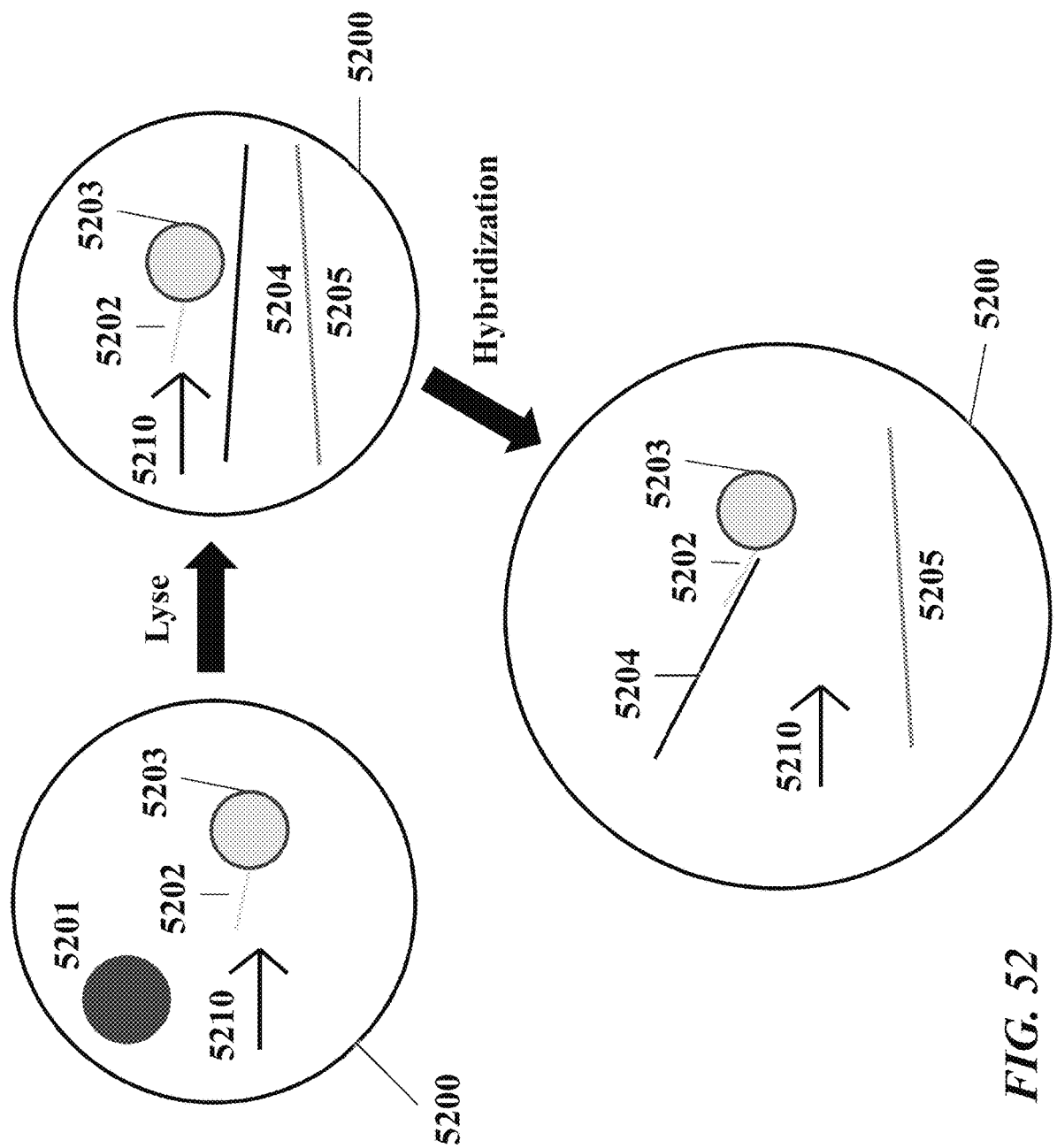
FIG. 52 illustrates another example process for generating droplets comprising constituents from a cell.

FIG. 52 illustrates an example of capturing cellular mRNA using an oligonucleotide attached to a magnetic particle. A droplet 5200 may comprise a cell 5201, an oligonucleotide comprising a poly-T sequence 5202 attached to a magnetic particle 5203, and polymeric precursors 5210. Cell 5201 may be lysed, generating multiple types of cellular constituents including mRNA 5204 and genomic DNA 5205. mRNA may hybridize to the oligonucleotide 5202 via its poly-T sequence, thereby capturing the mRNA.

A droplet comprising multiple types of constituents from a cell and precursors may be subjected to conditions sufficient to generate a cell bead. For example, a droplet comprising polymer precursors may be subjected to conditions to polymerize the precursors, as described herein. Precursors attached to species (e.g., primers, nucleic acid molecules, etc.) may be polymerized or gelled such that the species are attached to the polymer or gel matrix (i.e., attached to a cell bead). Species may be covalently attached to a cell bead. Species may be reversible or irreversibly attached to a cell bead. Species may be attached to the surface of a gel bead. Species may be attached to the inside of a cell bead. In some cases, mRNA is attached to a cell bead. For example, polymer precursors attached to mRNA from a cell may be polymerized or gelled to generate a cell bead such that the mRNA is attached to the cell bead. In some cases, cDNA is attached to a cell bead. For example, polymer precursors attached to cDNA derived from a cell may be polymerized to generate a cell bead such that the cDNA is attached to the cell bead. FIG. 53 illustrates an example of generating cell beads comprising reagents attached to a polymer matrix. A droplet 5310 comprising polymer precursors 5301 attached to nucleic acid molecules 5302 (e.g., mRNA, cDNA, etc.) may be subjected to conditions sufficient to polymerize the polymer precursors, thereby generating a cell bead 5311. Cell bead 5311 may comprise nucleic acid molecules 5302 attached to the polymer matrix 5303 formed by polymerization of polymer precursors 5301.

Following cell bead formation, cell beads may be transferred to an aqueous solution and subjected to additional processing as described herein. For example, cell beads may be subjected, in bulk, to reverse transcription to generate cDNA from captured mRNA. FIG. 54 illustrates an example of performing reverse transcription on a cell bead to generate cDNA attached to a magnetic particle. Cell bead 5410 is in an aqueous solution and comprises a polymer matrix 5404 and an oligonucleotide comprising a poly-T sequence 5402 attached to a magnetic particle 5401. mRNA 5403 from a lysed cell is hybridized to oligonucleotide 5402. The cell bead is subjected to conditions sufficient to perform reverse transcription on mRNA 5403, generating cDNA 5404. cDNA 5404 is attached to magnetic particle 5401. A similar process may be performed using, for example, mRNA attached to a cell bead to generate cDNA attached to the cell bead.

Attaching macromolecular constituents (e.g., nucleic acid molecules, protein, etc.) to a cell bead or a particle within a cell bead may be useful in preparing the species for further processing. For example, nucleic acid molecules attached to a cell bead or particle may be processed while remaining attached to the cell bead or particle. Following processing, a nucleic acid may be released (e.g., released into a partition) from a cell bead and/or particle for analysis. In some cases, it may be useful to attach one type of cellular component or derivative thereof (e.g., mRNA, cDNA) to a cell bead or a particle within a cell bead, while encapsulating but not attaching another type of cellular component (e.g., genomic DNA). This may be useful in, for example, facilitating separate processing of multiple types of components.

Cell beads may be partitioned as described herein. Prior to partitioning, one or more reactions may be performed on macromolecular constituents comprised in and/or attached to cell beads. Additional reactions may serve to process macromolecular constituents (e.g., nucleic acids, proteins, etc.) for further analysis. Examples of reactions which may be performed include one or more of nucleic acid amplification, reverse transcription, bisulfite treatment, enzymatic deamination (e.g., using a cytosine deaminase enzyme), oxygenase treatment, methyltransferase treatment, and RNase treatment. Multiple reactions may be performed on multiples types of macromolecular constituents for downstream analysis. For example, reverse transcription may be performed to generate cDNA from mRNA, and bisulfite treatment may be performed to prepare DNA for methylation analysis. Alternatively or in addition, binding groups (e.g., antibodies) linked to barcode molecules may be washed into and/or out of the cell beads, as described herein. Any combination of various reactions may be performed on one or more constituents from each of multiple types of constituents. Performing reactions on constituents comprised in a cell bead may be useful in preparing the constituents for further analysis, such as the partitioning, barcoding, and/or sequencing methods described herein.

In some cases, prior to sequencing, the barcoded macromolecules may be further processed. For example, the barcoded macromolecules are subjected to nucleic acid amplification (e.g., PCR) prior to sequencing. In some cases, additional sequences are ligated to barcoded macromolecules. Such further processing may be performed in a droplet or external to the droplet, such as by releasing the barcoded macromolecules from the droplets.

The partitioning and analysis methods described herein may be useful in identification and/or analysis of multiple different types of macromolecular constituents from a single cell. Each type of constituent from a cell may be identified with the same single cell via the use of barcodes as described herein. The types of analyses that can be performed on single cells as described include, without limitation, cell surface protein analysis, internal protein analysis, transcription profiling, genetic sequencing, epigenetic analysis, and chromatin accessibility analysis. In some cases, these analyses can be useful in obtaining a transcription profile (e.g., transcriptome) and a genetic profile (e.g., genome, methylome, etc.) from the same single cell. In some cases, these analyses can be useful in obtaining a cell surface protein profile, a transcription profile (e.g., transcriptome) and a genetic profile (e.g., genome, methylome, etc.) from the same single cell. In some cases, these analyses can be useful in obtaining an internal protein and/or metabolite profile, a transcription profile (e.g., transcriptome), and/or a genetic profile (e.g., genome, methylome, etc.) from the same single cell.

In some aspects, the disclosure provides for barcoding of multiple types of components (e.g., analytes) from a cell. Barcoding multiple types of components can, in some cases, comprise the use of multiple different barcode molecules. Multiple barcode molecules may each comprise one or more sequences which enable barcoding of a given type of component from a cell. For example, one barcode molecule may comprise a sequence which enables barcoding mRNA or a derivative thereof (e.g., cDNA), while another barcode molecule may comprise a sequence which enables barcoding of gDNA. In some cases, a single sequence may enable barcoding of multiple types of components (e.g., both cDNA and gDNA). In some cases, one barcode molecule may comprise a sequence which enables barcoding mRNA, a second barcode molecule may comprise a sequence which enables barcoding of gDNA, and a third barcode molecule may comprise a sequence which enables barcoding of molecules introduced into a cell (e.g., CRISPR crRNA or sgRNA, TALEN, zinc finger nuclease, antisense oligonucleotide, siRNA, shRNA, miRNA, etc.). Any number of a given barcode molecule may be used. Barcode molecules may be attached to beads (e.g., gel beads) for use in barcoding components from a cell.

Barcode molecules may comprise various sequences for use in barcoding one or more components (e.g., nucleic acids) from a cell. Sequences which may be used to facilitate barcoding (e.g., act as primer sequences) can include, for example, an mRNA specific sequence (e.g., poly-T sequence), a targeted priming sequence, a random priming sequence (e.g., a random hexamer), a polyG (e.g., riboG) sequence, and/or an adaptor sequence. Barcode molecules comprising one or more different sequences may be attached to a single bead, thereby enabling barcoding of multiple types of components, or derivatives thereof, from a single cell.

Figure 10G:
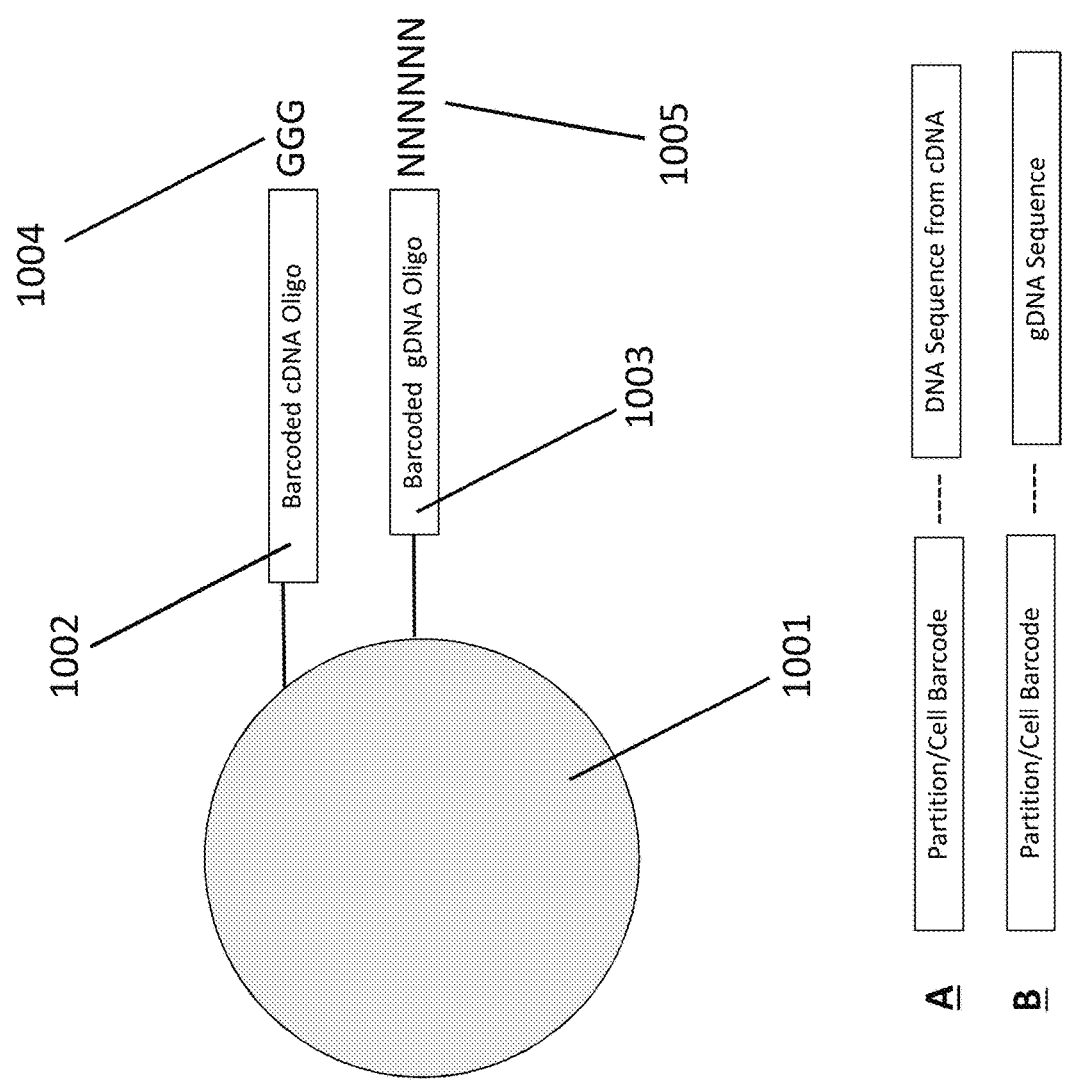

In an example, schematically depicted in FIG. 10G, a partition (e.g., a droplet, a well or any other type of partition described herein) comprises a bead 1001, which is coupled (e.g., reversibly coupled) to barcoded oligonucleotides 1002 and 1003. The bead 1001 and barcoded oligonucleotides 1002 and 1003 are schematically depicted in FIG. 10G. Barcoded oligonucleotide 1002 comprises a first nucleic acid barcode sequence and a polyG (e.g., riboG) priming sequence 1004 that can hybridize with a polyC sequence present on a cDNA molecule generated from an mRNA transcript. Barcoded oligonucleotide 1002 may also comprise a UMI sequence that can uniquely identify a given transcript. Barcoded oligonucleotide 1003 comprises a second nucleic acid barcode sequence and a random N-mer priming sequence 1005 that is capable of randomly hybridizing with gDNA. In this configuration, barcoded oligonucleotides 1002 and 1003 comprise the same nucleic acid barcode sequence, which permits association of downstream sequencing reads with the partition. In some cases, though, the first nucleic acid barcode sequence and the second nucleic acid barcode sequence are different.

The partition also comprises a cell bead (not shown) and can also comprise an agent (e.g., a reducing agent) that can degrade the gel bead and/or break a covalent linkage between the barcoded oligonucleotides 1002 and 1003 and bead 1001, releasing them into the partition. The partition can also comprise an agent (e.g., a reducing agent) that can degrade the cell bead, releasing components (e.g., cDNA and gDNA) into the partition. The released barcoded oligonucleotide 1002 can hybridize with cDNA released from the cell bead and the released barcoded oligonucleotide 1003 can hybridize with gDNA released from the cell. Barcoded constructs A and B can then be generated for each of the mRNA and barcoded oligonucleotide 1023 as described elsewhere herein, such as via the action of a polymerase (and/or reverse transcriptase) and/or primer extension. Barcoded construct A can comprises a sequence corresponding to the original barcode sequence from the bead and a sequence corresponding to a transcript from the cell (e.g., from cDNA from the cell bead). Barcoded construct B can comprise a sequence corresponding to the original barcode sequence from the bead and a sequence corresponding to genomic DNA from the cell. The barcoded constructs can then be released/removed from the partition and, in some cases, further processed to add any additional sequences. The resulting constructs are then sequenced, sequencing data processed, and the results used to characterize the mRNA and the gDNA from the cell. Analysis can be completed, for example, as described elsewhere herein. The information received from the characterization can then be used in a subsequent analysis of another cell bead or cell in a partition. Moreover, barcoded oligonucleotides 1002 and 1003 can be designed to prime any particular type of nucleic acid, including those that are not derived from a cell. Moreover, the priming sequences shown in FIG. 10G are for example purposes only and are not meant to be limiting.

While the examples described involve the analysis of two different types of components (e.g., constituents), these examples are not meant to be limiting. Any suitable number of components may be evaluated. Accordingly, in various aspects, there may be at least about 2, at least about 3, at least about 4, at least about 5, at least about 6, at least about 7, at least about 8, at least about 9, at least about 10, at least about 11, at least about 12, at least about 13, at least about 14, at least about 15, at least about 20, at least about 25, at least about 30, at least about 40, at least about 50, at least about 100 or more different components present in a partition, that can be subject to barcoded sequencing analysis. Higher number, multi-assay analysis can be completed by including primer species (one or more of which may be barcoded) that are capable of generating barcoded constructs and capable of specifically hybridizing with a particular component or oligonucleotide coupled to a labelling agent that is itself coupled to a particular analyte in the partition and subjecting the partition to suitable conditions for barcoding.

Characterization, Analysis, and Detection of DNA Methylation

Disclosed herein, in some embodiments, are compositions, methods, and systems useful in the analysis of multiple analytes in a single cell or cell population. In some aspects, the present disclosure provides methods for processing and analyzing DNA (e.g., genomic DNA) from a cell, together with one or more additional analytes from a cell. DNA may be obtained by, for example, release from a cell in a partition (e.g., a droplet) as described herein. Alternatively, a cell may be permeabilized, enabling access to DNA without complete cellular lysis. Prior to or subsequent to partitioning, DNA from a cell may be subjected to conditions sufficient to undergo one or more reactions using reagents present in the partition. In some cases, DNA may be subjected to one or more nucleic acid modification reactions. Reactions may be used to process DNA from a cell, thereby enabling one or more types of information about the DNA to be obtained. Examples of reactions include, but are not limited to, bisulfite treatment, oxygenase treatment, enzymatic deamination, and methyltransferase treatment. Modified DNA or derivatives thereof may be subjected to barcoding and sequencing as described herein, thereby generating sequencing reads. Sequencing reads can be analyzed, wherein barcode sequences can serve to identify the DNA as being derived from a single cell. Reads from a DNA sequence can provide one or more types of information, depending on the nature of the DNA modification. In some cases, sequences obtained from DNA which underwent bisulfite treatment and/or enzymatic deamination can be used to obtain methylation information, for example, by using sequencing reads corresponding to unmethylated and methylated cytosine residues to identify regions of methylation in the DNA. In some cases, sequences obtained from DNA which underwent methyltransferase treatment can be used to obtain chromatin accessibility information, for example, by using sequencing reads corresponding to methylated cytosine residues to identify regions of chromatin inaccessibility. In some embodiments, DNA is subjected to bisulfite treatment prior to DNA sequencing to determine methylated DNA residues. In other embodiments, DNA is processed to detect hydroxymethylation (5hmC). For example, in some embodiments, genomic DNA is glycosylated to protect 5hmC residues and then subjected to enzymatic oxidation and bisulfite treatment. DNA sequencing libraries can then be generated and sequenced as described herein to reveal hydroxymethylated bases. See, e.g., Yu M., et al., Base-Resolution Analysis of 5-Hydroxymethylcytosine in the Mammalian Genome, Cell. 2012 Jun. 8; 149(6): 1368-80. In some embodiments, the determination of methylated and/or hydroxymethylated DNA residues is performed in combination with one or more additional analytes (e.g., mRNA) as described herein. In other embodiments, the determination of methylated and/or hydroxymethylated DNA residues is performed with the aid of a cell bead and the cell bead processing methods for, e.g., gDNA, mRNA, and protein described herein. In some cases, sequences obtained serve to identify the DNA, together with any and all additional analytes processed and analyzed simultaneously, with a single cell (e.g., via the use of a molecular barcode sequence). In this way, multiple types of information can be obtained from a single cell (e.g., proteomic profile, transcription profile, methylation profile, chromatin accessibility profile, etc.). Additional analytes which can be processed together with DNA from a cell include RNA, proteins, metabolites, and molecules introduced to a cell (e.g., CRISPR crRNA or sgRNA, TALEN, zinc finger nuclease, antisense oligonucleotide, siRNA, shRNA, etc.). Additional analytes can be processed and analyzed as described elsewhere herein.

Characterization, Analysis, and Detection of Chromatin Accessibility

ATAC-seq

Disclosed herein, in some embodiments, are compositions, methods, and systems useful in the analysis of multiple analytes in a single cell or cell population. In some embodiments, an analyte is accessible chromatin. Disclosed herein, in some embodiments, are systems and methods for assaying chromatin accessibility in transposase-accessible chromatin in a single cell, such as via an Assay for Transposase Accessible Chromatin using sequencing (ATAC-seq). ATAC-seq may be performed in combination and/or in conjunction with other assay(s) directed to other analyte(s) in the single cell, such as those described elsewhere herein. For example, ATAC-seq may be performed in combination and/or in conjunction with assay(s) for internal proteins, surface proteins, mRNA, perturbation agents, any other type of analyte described herein in the single cell, or any combination thereof. A multi-assay may assay any number of types of analytes. For example, the multi-assay may assay at least about 2, 3, 4, 5, 6, 7, 8, or more types of analytes. Alternatively or in addition to, the multi-assay may assay at most about 8, 7, 6, 5, 4, 3, 2, or 1 type of analyte. In an example, a multi-assay may perform analysis on chromatins and proteins (e.g., internal, surface, etc.). In another example, a multi-assay may perform analysis on chromatins and perturbation agents. In another example, a multi-assay may perform analysis on chromatins and mRNA. In another example, a multi-assay may perform analysis on chromatins, mRNA, and perturbation agents. In another example, a multi-assay may perform analysis on chromatins, proteins, and perturbation agents. In another example, a multi-assay may perform analysis on chromatins, proteins, and mRNA. In another example, a multi-assay may perform analysis on chromatins, proteins, mRNA, and perturbation agents. Alternatively or in addition to, transposase accessible chromatin may be assayed in isolation (of other assays and/or other analytes).

Nucleic acid fragments may be barcoded in partitions (e.g., droplets, wells, etc.) using various methods. In some instances, nucleic acid fragments from single cells may be barcoded in partitions using forked adaptors comprising transposon end sequences. A plurality of transposase molecules, a plurality of cells of interest (or a plurality of nuclei harvested from cells of interest, such as by nonionic detergents (e.g., NP-40 (IGEPAL CA-630) or Triton X-100)), and a plurality of barcode nucleic acid molecules (e.g., oligonucleotides) can be partitioned such that at least some partitions comprise a plurality of transposase molecules, a single cell (or nucleus), and a plurality of barcode oligonucleotides. A barcode oligonucleotide may comprise a sequencing primer sequence, a barcode sequence, and a transposon end sequence. The single cell (or nucleus) may comprise one or more template nucleic acid molecules. In some cases, the plurality of barcode oligonucleotides may be attached to a gel bead and partitioned such that at least some partitions comprise transposase molecules, a single cell (or nucleus), and a single gel bead.

Figure 63:
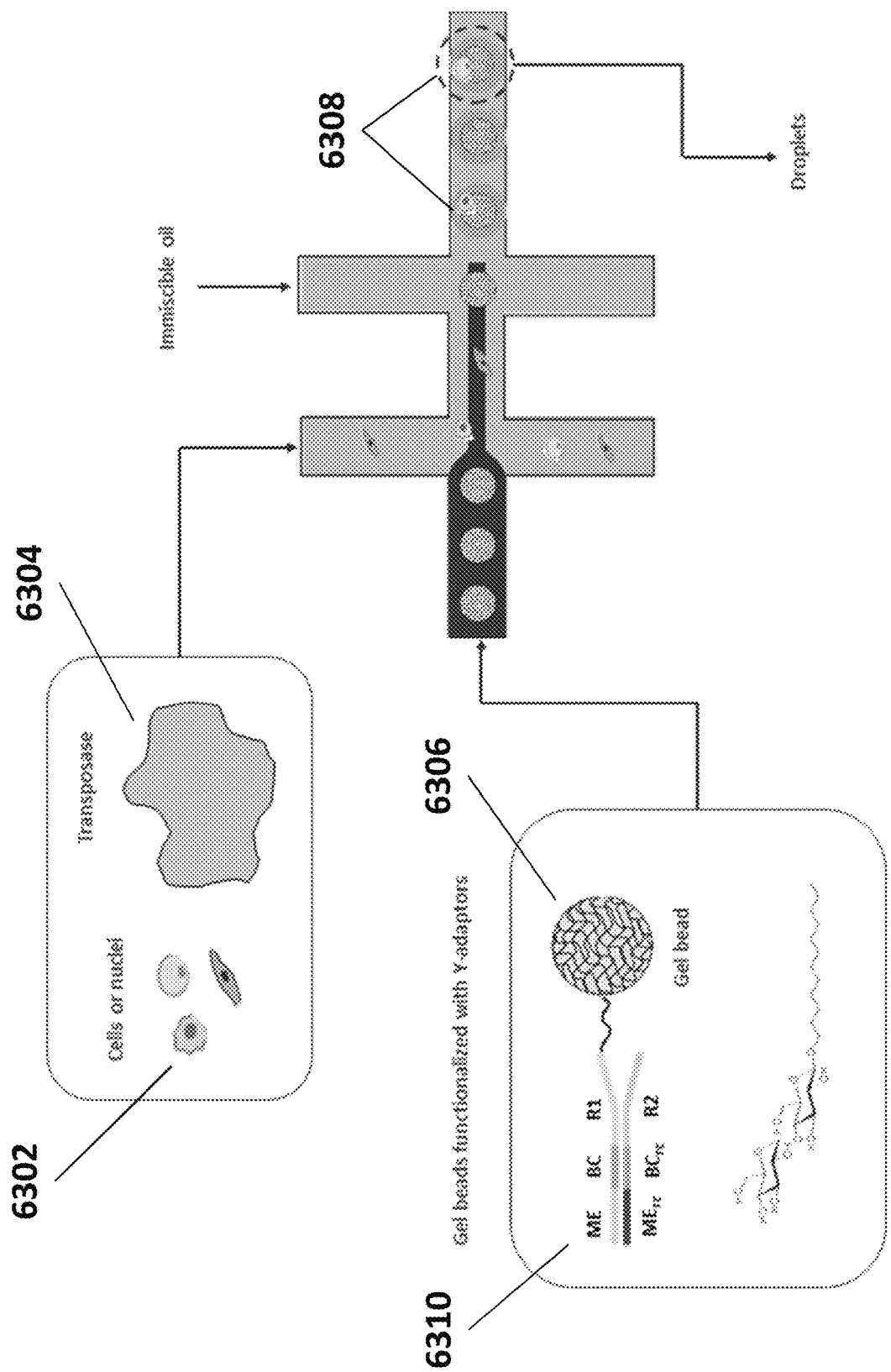
FIG. 63 illustrates a method to generate droplets wherein at least some of the droplets formed will comprise transposase molecules, a single cell, and a single gel bead comprising a forked adaptor.

FIG. 63 illustrates a method to generate droplets wherein at least some of the droplets formed will comprise transposase molecules, a single cell, and a single gel bead comprising a forked adaptor. The gel bead may comprise a plurality of forked adaptor oligonucleotides, each forked adaptor oligonucleotide comprising a sequencing primer sequence, a barcode sequence, and a transposon end sequence. The partitions may be generated as described elsewhere herein, such that at least some of the droplets 6308 formed will comprise transposase molecules 6304, cell lysis reagents, a single cell 6302, and a single gel bead 6306 comprising a plurality of barcoded forked adapter oligonucleotides 6310. In the aqueous droplet, the cell may be lysed in a manner that releases template nucleic acid molecules from the nucleus into the aqueous droplet, but that substantially maintains native chromatin organization. The droplets may then be processed as outlined in FIGS. 64A-64B.

Figure 65A:
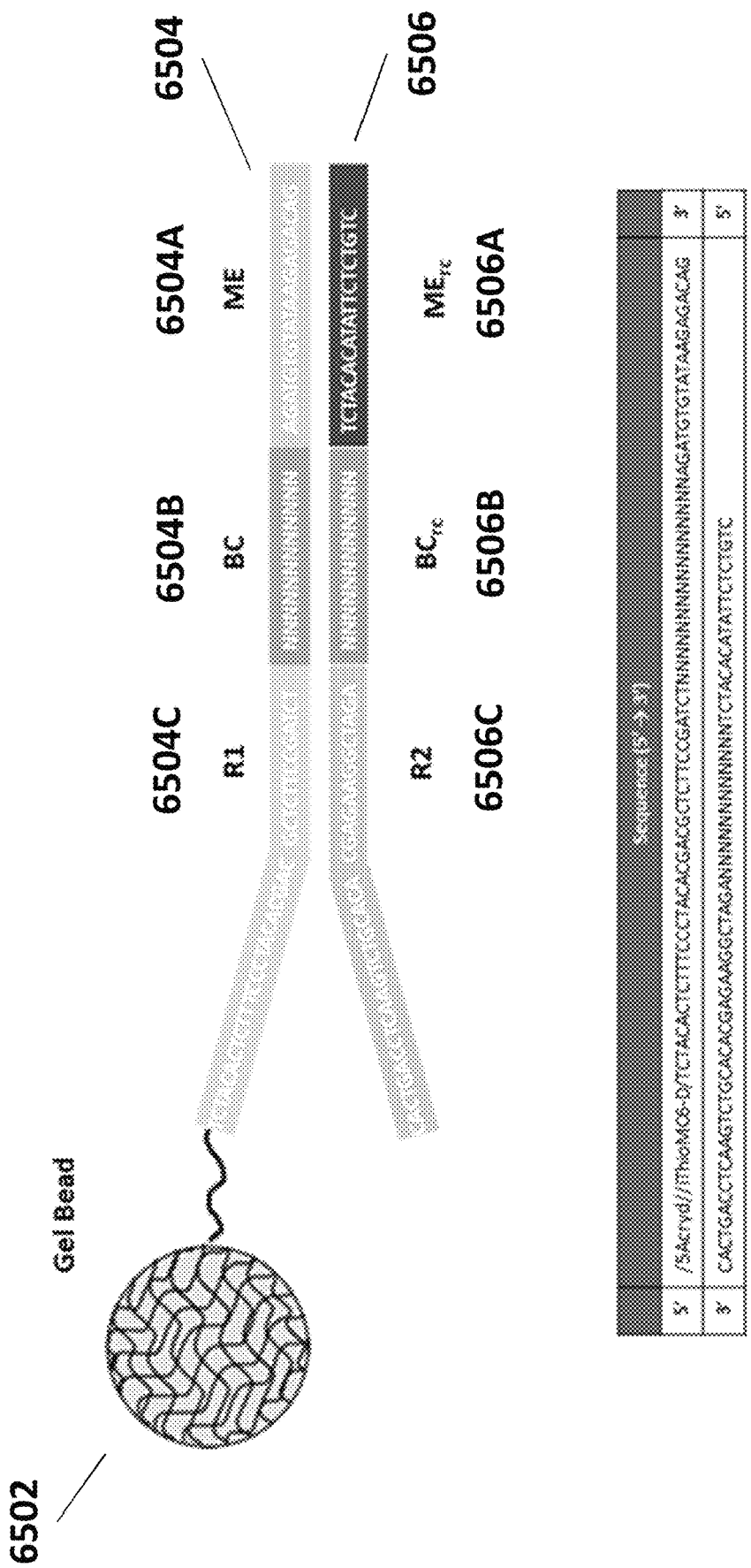
FIGS. 65A-65B illustrate examples of forked adaptors.
Figure 65B:
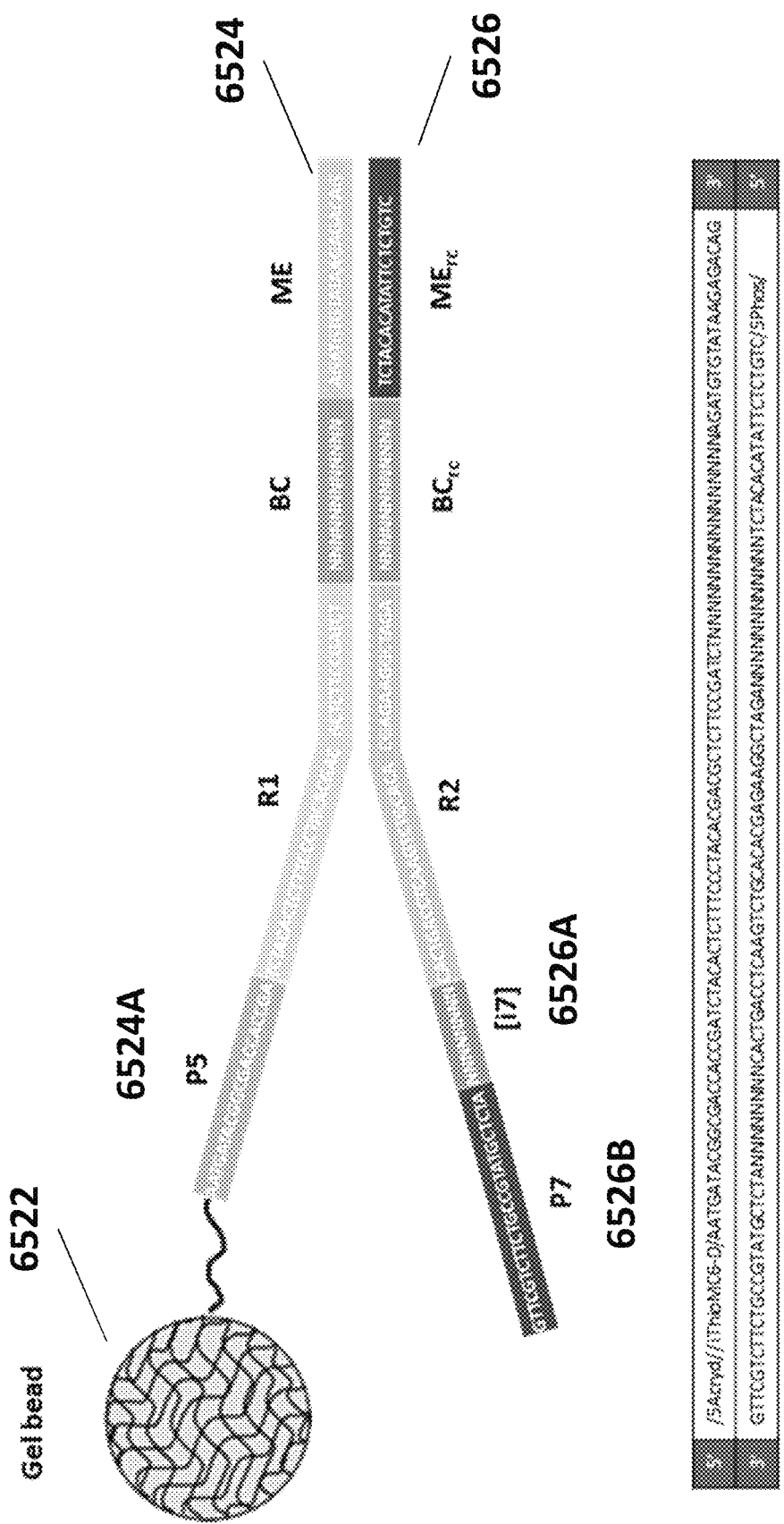

Although the forked adaptors can be prepared in a variety of different configurations, an example of a forked adaptor is illustrated in FIG. 65A. FIG. 65A illustrates a partially complementary double-stranded oligonucleotide comprising a first oligonucleotide strand 6504 releasably attached to a gel bead 6502 and a second partially complementary oligonucleotide strand 6506. The first strand 6504 may comprise a transposon end sequence ("mosaic end" or "ME") 6504A, a barcode sequence ("BC") 6504B, and a sequencing primer sequence ("R1") 6504C. The partially complementary second strand 6506 may comprise: (i) a region 6506A fully complementary to the transposon end sequence 6504A; (ii) a region 6506B fully complementary to the barcode sequence 6504B; and (iii) a primer sequence ("R2") 6506C partially complementary to the first strand primer sequence 6504C. In alternative embodiments, such as illustrated in FIG. 65B, the double-stranded forked adaptor of FIG. 65A may further comprise: (a) a first oligonucleotide strand 6524 further comprising a P5 sequence 6524A releasably attached to the gel bead 6522; and (b) a second partially complementary oligonucleotide strand 6526 further comprising an index sequence ("i7") 6526A and a P7 sequence 6526B.

Figure 64A:
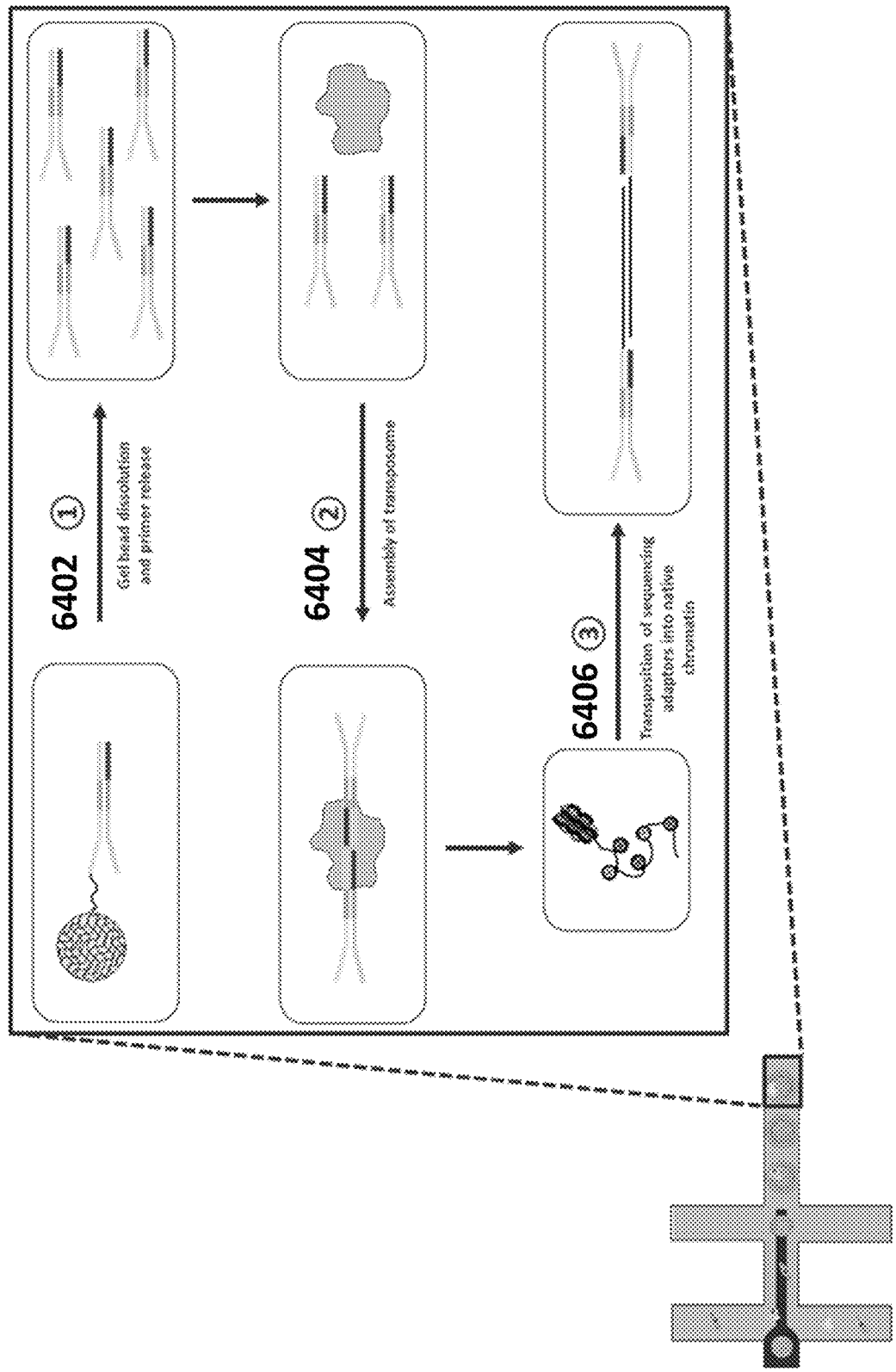
FIGS. 64A-64B illustrate a method to generate forked adaptor flanked double-stranded template nucleic acid fragments.
Figure 64B:
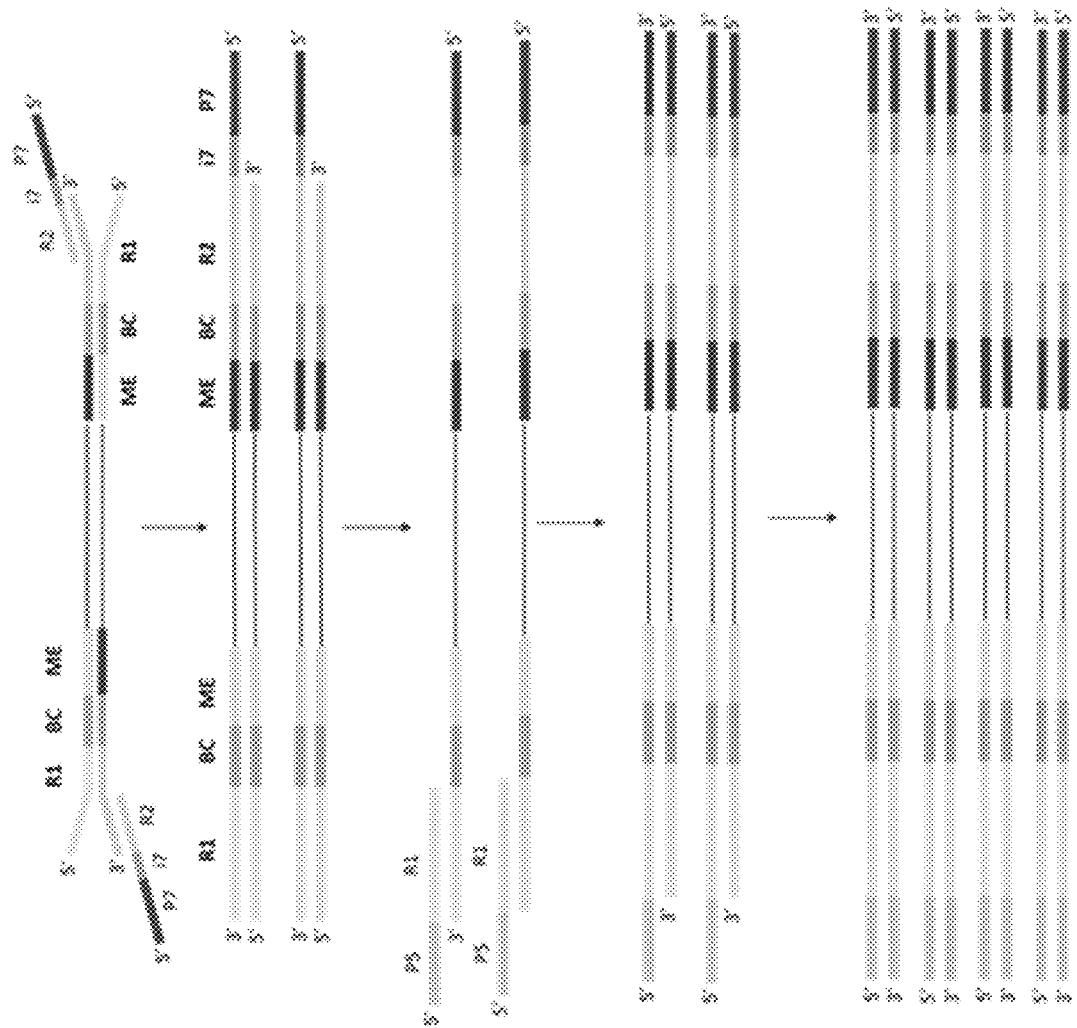

FIGS. 64A-64B illustrate a method to generate forked adaptor flanked double-stranded template nucleic acid fragments. FIG. 64A illustrates a method for the in-partition transposition of sequencing adaptors into native chromatin while FIG. 64B illustrates a method for the in-bulk production of a next-generation sequencing compatible library from the fragments generated in FIG. 64A. In operation 6402, the droplet (e.g., illustrated in FIG. 63) may be subjected to conditions such that the forked adaptors are released from the gel bead into the droplet (e.g., by gel bead depolymerization using a reducing agent, such as DTT). After the forked adaptors are released from the gel bead, in operation 6404, the droplet may then be subjected to conditions such that a transposase-nucleic acid complex is formed comprising a transposase molecule and two forked adaptors. The droplets may then be subjected to conditions such that the transposase-nucleic acid complexes integrate the transposon end sequences into the template nucleic acid molecules and fragment the template nucleic acid molecules into double-stranded template nucleic acid fragments flanked by the forked adaptors.

In alternative embodiments, cells (or nuclei) may be permeabilized/permeable and the transposase-nucleic acid complexes may enter the nucleus to fragment the template nucleic acid molecules. Cells may then be lysed to release the fragmented double-stranded template nucleic acid fragments. Because the transposase-nucleic acid complex can only act on a nucleosome-free template, the fragmented double-stranded template nucleic acid fragments may be representative of genome-wide areas of accessible chromatin in a single cell.

The fragmented double-stranded template nucleic acid fragments may then be collected from the droplets and processed in bulk to fill any gaps created from the transposition reaction and to generate a library suitable for next generation high throughput sequencing. For example, the fragments, or derivatives thereof, may be subjected to one or more reactions (e.g., nucleic acid amplification) to add functional sequences to facilitate Illumina sequencing, such as in FIG. 64B. The fully constructed library may then be sequenced according to any suitable sequencing protocol.

In some instances, nucleic acid fragments from single cells may be barcoded in partitions using forked adaptors and transposase-nucleic acid complexes. A plurality of transposase-nucleic acid complexes, a plurality of cells of interest (or a plurality of nuclei harvested from cells of interest), and a plurality of barcode oligonucleotides can be partitioned such that at least some partitions comprise a plurality of transposase-nucleic acid complexes, a single cell (or nucleus), and a plurality of barcode oligonucleotides. A barcode oligonucleotide may comprise a sequencing primer sequence and a barcode sequence. In some cases, the plurality of barcode oligonucleotides may be attached to a gel bead and partitioned such that at least some partitions comprise transposase-nucleic acid complexes, a single cell (or nucleus), and a single gel bead. In alternative embodiments, a plurality of transposase molecules and a plurality of transposon end sequence oligonucleotides may be partitioned along with a single cell (or nucleus) and the barcode oligonucleotides and transposase-nucleic acid complexes may be generated in the partition.

A variety of transposase-nucleic acid complex designs may be used for transposon loading. A method of the present disclosure may allow for loading of adapter nucleic acid sequences onto transposases. One or more methods provided herein may allow for loading of a first adapter nucleic acid sequence and a second adapter nucleic acid sequence onto a transposase. In some embodiments, the first adapter nucleic acid sequence may comprise a sequencing primer sequence. In some embodiments, the second adapter nucleic acid sequence may comprise a different sequencing primer sequence. In some embodiments, the first adapter sequence may comprise a target-specific or capture sequence. In some embodiments, the second adapter sequence may comprise a target-specific or capture sequence. In such an embodiment, the first or second adapter sequence may comprise a sequence that may hybridize with a target nucleic acid molecule (e.g., DNA, RNA). Additional adapter sequences (e.g., an adapter comprising a sequencing primer sequence) may be hybridized to the first and/or second adapter sequences. One or more methods provided herein may produce a nucleic acid fragment comprising only the first adapter nucleic acid sequence at one end of the nucleic acid fragment and only the second adapter nucleic acid sequence at the other end of the nucleic acid fragment. One or more methods provided herein may produce a nucleic acid fragment comprising the first adapter nucleic acid sequence at one end of the nucleic acid fragment and the second adapter nucleic acid sequence at the other end of the nucleic acid fragment. One or more methods provided herein may prevent potential nucleic acid fragment loss or exchange during sample processing. Any or all of these methods may be performed within a partition. A product or a plurality of products from a reaction of the methods described herein may be further processed. For example, the product or the plurality of products may be barcoded within or outside a partition. The product or the plurality of products may then be prepared for sequencing.

In an aspect, the present disclosure provides a method for processing a nucleic acid molecule, comprising (a) loading a transposase molecule with a pair of nucleic acid adapters, where each of the pair of nucleic acid adapters comprises a first single-stranded portion comprising a first nucleic acid sequence and a second single-stranded portion comprising a second nucleic acid sequence, where the first nucleic acid sequence is different from the second nucleic acid sequence; (b) bringing the transposase molecules in contact with the nucleic acid molecule under conditions sufficient to generate a nucleic acid fragment, where the nucleic acid fragment (i) comprises at each of the first end and the second end, both the first nucleic acid sequence and the second nucleic acid sequence and (ii) is at least partially double-stranded; and (c) subjecting the nucleic acid fragment under conditions sufficient to generate a processed nucleic acid fragment, where the processed nucleic acid fragment comprises (i) the first nucleic acid sequence at the first end and the second nucleic acid sequence at the second end, or (ii) the second nucleic acid sequence at the first end and the first nucleic acid sequence at the second end.

In some embodiments, each of the pair of nucleic acid adapter comprises a double-stranded portion. In some embodiments, the double-stranded portion comprises between about 4 and about 50 basepairs in length. For example, the double-stranded portion may comprise about 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 nucleotides (or basepairs) in length. In some embodiments, the nucleic acid insert may comprise at least about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 nucleotides (or basepairs) in length. In some embodiments, the double-stranded portion is 19 basepairs in length. In some embodiments, the double-stranded portion corresponds to a mosaic end (ME) sequence. In some cases, the first single-stranded portion and the second double-stranded portion are adjacent to a same end of the double-stranded portion. In some cases, the first single-stranded portion and the second single-stranded portion are not attached. In some cases, the first single-stranded portion and the second single-stranded portion are cleavably attached as a loop sequence, or a portion thereof. In such embodiments, the first single-stranded portion and the second single-stranded portion may be cleavably attached by a linker. In one embodiment, the first single-stranded portion and the second single-stranded portion may be cleavably attached by a linker comprising a uracil. In another embodiment, the first single-stranded portion and the second single-stranded portion may be cleavably attached by a linker comprising a restriction enzyme recognition site. In another embodiment, the first single-stranded portion and the second single-stranded portion may be cleavably attached by a chemical linker (e.g., polyethylene glycol (PEG)). In another embodiment, the first single-stranded portion and the second single-stranded portion may be cleavable by application of a stimulus, where the stimulus comprises a photo-stimulus, thermal stimulus, biological stimulus, or chemical stimulus. In some embodiments, (c) comprises a uracil. In some embodiments, (c) comprises PEG. In some embodiments, (c) comprises a restriction enzyme recognition site. In such embodiments, one or more suitable restriction enzymes may be used. Non-limiting examples of restriction enzymes include: MspI, NarI, BfaI, NdeI, HinP1I, ClaI, MseI, CviQI, TaqαI, AcII, RsaI, PmeI, AluI, EcoRV, BstUI, PmeI, DpnI, StuI, HaeIII, HpyCH4V, SfoI, rare-cutter enzymes, e.g., NotI, XmaIII, SstII, SalI, NruI, NheI, Nb.BbvCI, BbvCI, AscI, AsiSI, FseI, PacI, PmeI, SbfI, SgrAI, SwaI, BspQI, SapI, SfiI, CspCI, AbsI, CciNI, FspAI, MauBI, MreI, MssI, PalAI, RgaI, RigI, SdaI, SfaAI, SgfI, SgrDI, SgsI, SmiI, SrfI, Sse2321, Sse83871, LguI, PciSI, AarI, AjuI, AloI, BarI, PpiI, PsrI, and any variants thereof.

In some cases, a suitable stimulus may be used to cleave a nucleic acid molecule (e.g., the first single-stranded portion or the second single-stranded portion of the nucleic acid adapter), as described elsewhere herein. In some cases, the nucleic acid molecule (e.g., the first single-stranded portion or the second single-stranded portion of the nucleic acid adapter) may comprise a site that is cleavable upon application of a biological stimulus (e.g., restriction enzyme). In such cases, the first single-stranded portion or the second single-stranded portion may comprise a restriction recognition site and may be cleaved upon addition of one or more restriction enzymes. In some embodiments, the nucleic acid molecule may comprise a linker that is cleavable upon application of a thermal or chemical stimulus. In one non-limiting example, an amino group on a nucleotide (e.g., a dC or dT nucleotide or base pair) may be cleaved. In another non-limiting example, the nucleic acid molecule may comprise a thiol linkage that may be cleaved upon addition of a reducing agent.

In some embodiments, the loop sequence can comprise a nucleic acid sequence of any suitable length. In some embodiments, the loop sequence may comprise a continuous nucleic acid sequence. In some embodiments, a loop sequence may comprise a nucleic acid sequence having a double-stranded (e.g., paired) and single-stranded (e.g., hairpin) configuration (see, FIGS. 10A and 10B). In some embodiments, the loop sequence may comprise a continuous nucleic acid sequence of about 10 nucleotides to about 3,500 nucleotides (or basepairs) in length. In another embodiment, the loop sequence can comprise a nucleic acid sequence of about 50 nucleotides to about 500 nucleotides (or basepairs) in length. In another embodiment, the loop sequence can comprise a nucleic acid sequence of about 10 nucleotides to about 100 nucleotides (or basepairs) in length. In some embodiments, the loop sequence can comprise single-stranded DNA. In some embodiments, the loop sequence can comprise double-stranded DNA. In some embodiments, the loop sequence can comprise single-stranded RNA. In some embodiments, the loop sequence can comprise a RNA/DNA hybrid. In some embodiments, the loop sequence may comprise a linker such as, but not limited to, a chemical linker (e.g., polyethylene glycol). In some embodiments, the linker can include a cleavage moiety (e.g., uracil, restriction enzyme recognition site or PEG) to facilitate cleavage of the loop sequence, or a portion thereof, from the nucleic acid adapter. In some embodiments, the loop sequence may comprise a nucleic acid sequence having a greater double-stranded configuration (e.g., 60% base paired) as compared to single-stranded configuration (e.g., 5%) (See, FIGS. 11A-C).

In some embodiments, (c) comprises filling a gap in the nucleic acid fragment. In some cases, the gap is a 9-base pair (bp) gap. In some embodiments, filling the gap in the nucleic acid fragment comprises contacting the gap with one or more nucleotides (e.g., dNTPs) and a polymerase. In some embodiments, the contacting further includes a ligase.

In some embodiments, one or both (b) and (c) are performed in a partition. In some cases, the partition comprises a droplet. In some cases, the partition comprises a well.

In some embodiments, (b) comprises bringing the transposase molecule in contact with a nucleus of a cell comprising the nucleic acid molecule. In some cases, the cell is permeabilized. In some cases, the nucleus is permeabilized.

In some embodiments, the method further comprises (d) reacting a barcode molecule with the processed nucleic acid fragment, where the barcode molecule comprises a sequence complementary to the first nucleic acid sequence or the second nucleic acid sequence, to generate a barcoded nucleic acid fragment.

In some embodiments, (d) is performed in a partition. In some cases, (d) further comprises filling a gap in the barcoded nucleic acid fragment. In some embodiments, filling the gap in the barcoded nucleic acid fragment comprises contacting the gap with one or more nucleotides (e.g., dNTPs) and a polymerase. In some embodiments, the contacting further includes a ligase.

In some embodiments, the barcode molecule is attached to a bead. In some cases, the barcode molecule is releasably attached to the bead. In some cases, the barcode molecule comprises a common barcode sequence that is common to a plurality of barcode molecules attached to the bead. In some cases, the barcode molecule comprises a functional sequence. In some cases, the barcode molecule comprises a unique molecular identifier that is unique within a plurality of barcode molecules attached to the bead.

In some embodiments, the method further comprises sequencing the barcoded nucleic acid fragment or a derivative thereof.

In another aspect, the present disclosure provides a method for processing a nucleic acid molecule, comprising (a) loading a transposase molecule with a pair of first nucleic acid adapters, where each of the pair of first nucleic acid adapters comprises a single-stranded portion comprising a first nucleic acid sequence (b) bringing the transposase molecules in contact with the nucleic acid molecule under conditions sufficient to generate a nucleic acid fragment, where the nucleic acid fragment (i) comprises, at each of the first end and the second end, the first nucleic acid sequence and (ii) is at least partially double-stranded; and (c) denaturing the nucleic acid fragment to generate a first single-stranded fragment and a second single-stranded fragment, where each of the first single-stranded fragment and the second single-stranded fragment comprises the first nucleic acid sequence; and (d) bringing the first single-stranded fragment and the second single-stranded fragment in contact with a plurality of second nucleic acid adaptors to generate processed nucleic acid fragments, where the plurality of second nucleic acid adaptors each comprises a second nucleic acid sequence, and where each of the processed nucleic acid fragments comprises the first nucleic acid sequence at the first end and the second nucleic acid sequence at the second end, or the first nucleic acid sequence at the second end and the second nucleic acid sequence at the first end.

In some embodiments, (d) comprises ligating the first single-stranded fragment to a second nucleic acid adapter of the plurality of second nucleic acid adapters and ligating the second single-stranded fragment to another second nucleic acid adapter of the plurality of second nucleic acid adapters.

In some embodiments, (d) is performed at a temperature that prevents reannealing of the first single-stranded fragment and the second single-stranded fragment.

A nucleic acid molecule may be deoxyribonucleic acid (DNA) or ribonucleic acid (RNA), including variants or derivatives thereof (e.g., single-stranded DNA). In some cases, the nucleic acid molecule may comprise genomic DNA. In some cases, the nucleic acid molecule may be RNA. The RNA may be coding or non-coding. The RNA may be messenger RNA (mRNA), ribosomal RNA (rRNA) or transfer RNA (tRNA), for example. The RNA may be a transcript. The RNA may be small RNA that are less than 200 nucleic acid bases in length, or large RNA that are greater than 200 nucleic acid bases in length. Small RNAs may include 5.8S ribosomal RNA (rRNA), 5S rRNA, transfer RNA (tRNA), microRNA (miRNA), small interfering RNA (siRNA), short hairpin RNA (shRNA), small nucleolar RNA (snoRNAs), Piwi-interacting RNA (piRNA), tRNA-derived small RNA (tsRNA) and small rDNA-derived RNA (srRNA). The RNA may be double-stranded RNA or single-stranded RNA. The RNA may be circular RNA. Other variants and derivatives of nucleic acid molecules may also be processed and analyzed.

In some cases, the transposase may be loaded with a pair of nucleic acid adapters where each of the pair of nucleic acid adapters comprises a first single-stranded portion comprising a first nucleic acid sequence and a second single-stranded portion comprising a second nucleic acid sequence. The first and second nucleic acid sequences may be a first type of sequencing primer sequence and a second type of sequencing primer sequence, respectively. The pair of nucleic acid adapters may further comprise a loading sequence that allow for loading of the nucleic acid adapters onto the transposase. In some cases, the loading sequence may comprise an inverted repeat sequence. In some cases, in one or more nucleic acid adapters, both the first single-stranded portion comprising the first nucleic acid sequence and the second single-stranded portion comprising the second nucleic acid sequence may each comprise a mosaic end sequence. In some cases, the mosaic end sequence of the first single-stranded portion may hybridize with the mosaic end sequence of the second single-stranded portion, forming a "Y-like" nucleic acid adapter. In some embodiments, the transposase may be loaded with two identical species of Y-like nucleic acid adapters, generating a Y-adapter transposase (see, FIGS. 9A and 9B).

The Y-adapter transposase may then be brought in contact with the nucleic acid molecule under conditions sufficient to generate a nucleic acid fragment, where the nucleic acid fragment (i) comprises at each of the first end and the second end, both the first nucleic acid sequence and the second nucleic acid sequence and (ii) is at least partially double-stranded. In some cases, the conditions sufficient to generate a nucleic acid fragment may comprise a transposition or tagmentation reaction. The nucleic acid fragment from the transposition reaction may be partially double-stranded, and each strand may comprise the first nucleic acid sequence on one end and the second nucleic acid sequence at the other end. The nucleic acid fragment may also comprise a gap region (e.g., approximately 9 base-pairs in length). The nucleic acid fragment may then be subjected to a nucleic acid reaction, e.g., a gap-fill and ligation reaction to generate a gap-filled nucleic acid fragment. The gap-filled nucleic acid fragment may then be subjected under conditions sufficient to generate a processed nucleic acid fragment, where the processed nucleic acid fragment comprises (i) the first nucleic acid sequence at the first end and the second nucleic acid sequence at the second end, or (ii) the second nucleic acid sequence at the first end and the first nucleic acid sequence at the second end.

Gap filling may occur through a variety of mechanisms. In one example, the gap region may be extended using an enzyme (e.g., a polymerase) to add one or more nucleotides to the gap region. Ligation may then occur, for example, using another enzyme (e.g., ligase). Examples of suitable ligases include, but are not limited to, T4 RNA ligase, T4 DNA ligase, T7 DNA ligase, *E. coli* DNA ligase, Thermostable 5' App DNA/RNA ligase (New England Biolabs, Catalog No. M0319S), or CircLigase™ ssDNA Ligase (Epicentre, Catalog No. CL4111K). In some embodiments, the ligase can comprise a single-stranded DNA ligase.

Figures 106A, 106B:
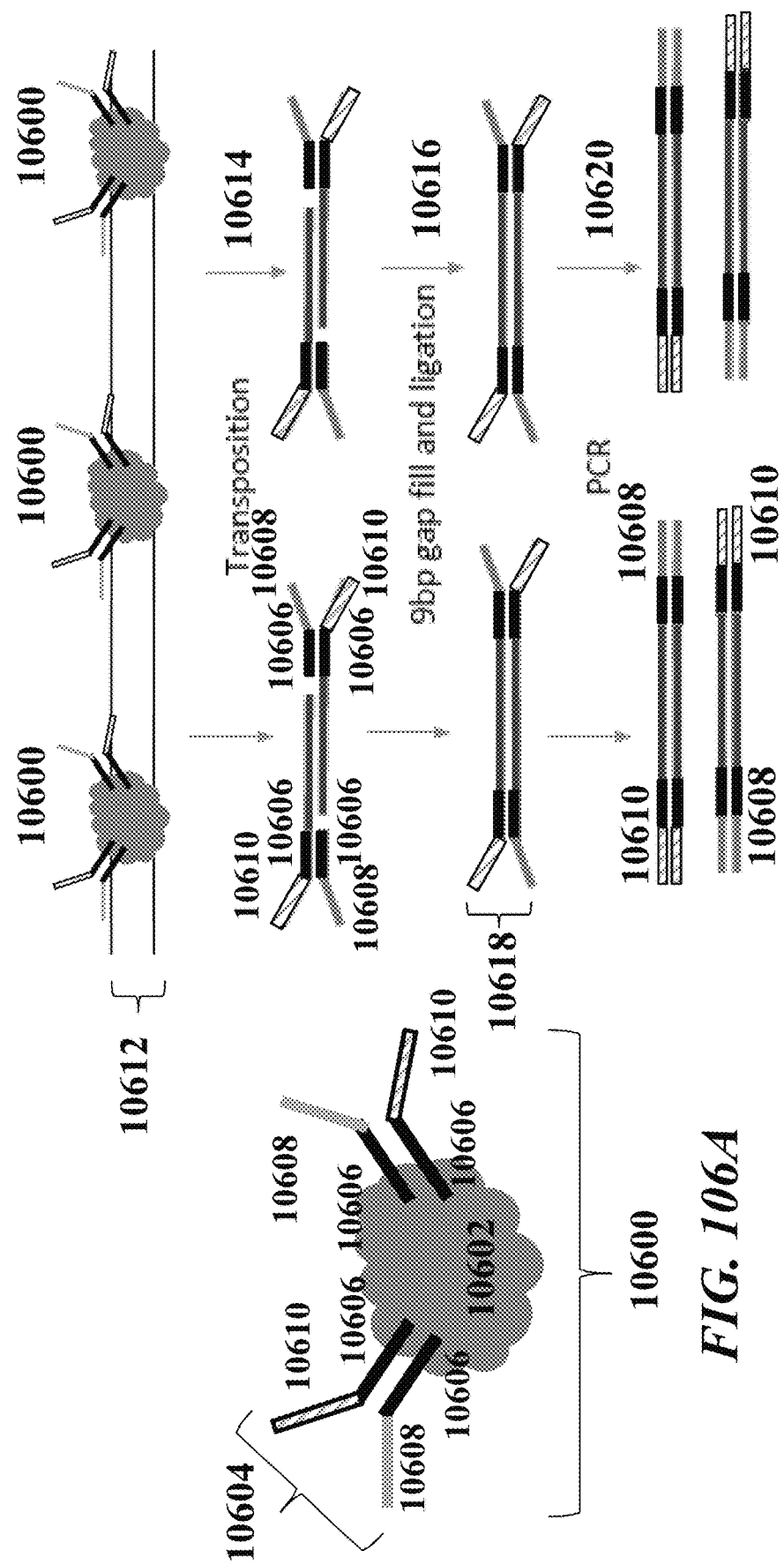
FIG. 106A shows schematically an example of loading nucleic acid molecules on a transposase.
FIG. 106B shows schematically an example method of processing nucleic acid molecules.

FIG. 106 illustrates schematically an example of a method for nucleic acid processing. In Panel 106A, a transposase 10602 is loaded with a pair of Y-like nucleic acid adapters 10604 to generate a Y-adapter transposase 10600. The Y-like nucleic acid adapters may comprise a first and a second nucleic acid strand. The first nucleic acid strand may comprise a first nucleic acid sequence, such as a mosaic end sequence 10606, which allows for loading of the nucleic acid on the transposase, and a second nucleic acid sequence 10608, which may comprise a first sequencing primer sequence. The second nucleic acid strand may comprise (i) a third nucleic acid sequence, which may be also a mosaic end sequence 10606 that is complementary to the mosaic end sequence 10606 of the first nucleic acid strand and (ii) a fourth nucleic acid sequence 10610, which may comprise a second sequencing primer sequence. In Panel 106B, the Y-adapter transposase 10600 may be brought in contact with a nucleic acid molecule 10612. In process 10614, the Y-adapter transposase 10600 may interact with the nucleic acid molecule 10612, e.g., in a transposition reaction, to generate a nucleic acid fragment comprising the mosaic end sequences 10606 of the first and the second nucleic acid strands, and, at each end, the first sequencing primer sequence 10608 and the second sequencing primer sequence 10610. In process 10616, the nucleic acid fragment may be subjected to a nucleic acid reaction that allows for gap-fill and ligation to generate a gap-filled nucleic acid fragment 10618. The gap-filled nucleic acid fragment can comprise a double-stranded gap-filled nucleic acid fragment. In process 10620, the gap-filled nucleic acid fragment 10618 may then be further processed. In some cases, further processing comprises an amplification reaction (e.g., PCR). The further processing may generate a processed nucleic acid fragment comprising the second nucleic acid sequence 10608 (e.g., comprising the first sequencing primer sequence) on one end and the fourth nucleic acid sequence 10610, e.g., comprising the second sequencing primer sequence at the opposite end.

In some cases, the transposase may be loaded with a pair of nucleic acid adapters, where each of the pair of nucleic acid adapters comprises a first single-stranded portion comprising a first nucleic acid sequence and a second single-stranded portion comprising a second nucleic acid sequence, and where the first nucleic acid sequence is connected to the second nucleic acid sequence. The first nucleic acid and the second nucleic acid sequences may be a first type of sequencing primer sequence and a second type of sequencing primer sequence, respectively. The pair of nucleic acid adapters may further comprise a loading sequence that allow for loading of the nucleic acid adapters onto the transposase. In some cases, the loading sequence may comprise an inverted repeat sequence (e.g., "mosaic end sequence"). In some cases, in one or more nucleic acid adapters, both the first single-stranded portion comprising the first nucleic acid sequence and the second single-stranded portion comprising the second nucleic acid sequence may each comprise a mosaic end sequence. In some cases, the mosaic end sequence of the first single-stranded portion may hybridize with the mosaic end sequence of the second single-stranded portion, and the first nucleic acid sequence is connected to the second nucleic acid sequence, forming a hairpin nucleic acid adapter. In some cases, the first single-stranded portion and the second single-stranded portion of the hairpin nucleic acid adapter may be cleavably attached as a loop sequence. In some embodiments, the loop sequence may comprise a uracil that may be excised using an enzyme, as described elsewhere herein. In some embodiments, the loop sequence may be cleavable by application of a stimulus, as described elsewhere herein. In some embodiments, the transposase may be loaded with two identical species of hairpin nucleic acid adapters, generating a hairpin-adapter transposase (see, e.g., panels 107A-107C in FIG. 107).

The hairpin-adapter transposase may then be brought in contact with the nucleic acid molecule under conditions sufficient to generate a nucleic acid fragment, where the nucleic acid fragment (i) comprises at each of the first end and the second end, both the first nucleic acid sequence and the second nucleic acid sequence and (ii) is at least partially double-stranded. In some cases, the conditions sufficient to generate a nucleic acid fragment may comprise a transposition reaction. The nucleic acid fragment from the transposition reaction may be partially double-stranded, and each strand may comprise the first nucleic acid sequence on one end and the second nucleic acid sequence at the other end. The nucleic acid fragment may also comprise a gap region (e.g., approximately 9 base-pairs in length). The nucleic acid fragment may then be subjected to a nucleic acid reaction, e.g., gap-fill and ligation reaction to generate a gap-filled nucleic acid fragment. At any convenient point in the process (e.g., after gap-fill and ligation), the first nucleic acid sequence and the second nucleic acid sequence may be disconnected, e.g., via cleavage. Subsequent to the disconnection process, the nucleic acid fragment may comprise a nucleic acid molecule that is partially hybridized (i.e., double-stranded). The gap-filled, cleaved nucleic acid fragment may then be subjected under conditions sufficient to generate a processed nucleic acid fragment, where the processed nucleic acid fragment comprises (i) the first nucleic acid sequence at the first end and the second nucleic acid sequence at the second end, or (ii) the second nucleic acid sequence at the first end and the first nucleic acid sequence at the second end Gap filling may occur through a variety of mechanisms. In one example, the gap region may be extended using an enzyme (e.g., a polymerase) to add one or more nucleotides to the gap region. Ligation may then occur, for example, using another enzyme (e.g., ligase).

Cleavage of the nucleic acid fragment may occur through a variety of strategies. In one non-limiting example, a uracil base may be included in the loop sequence of the hairpin adapter, e.g., between the first nucleic acid sequence and the second nucleic acid sequence. Cleavage may then be initiated, for example, using a polyamine (e.g., DMED) or an enzyme, e.g., uracil-n-glycosylase. In another non-limiting example, a restriction sequence may be included in the hairpin adapter, e.g., between the first nucleic acid sequence and the second nucleic acid sequence. Cleavage may then occur using a restriction enzyme. In other non-limiting examples, the first nucleic acid sequence and the second nucleic acid sequence may be linked by a labile linkage, such that exposure to a stimulus (e.g., photo, thermal, chemical, or biological) may result in cleavage of the hairpin nucleic acid adapter.

Figures 107A, 107B, 107C:
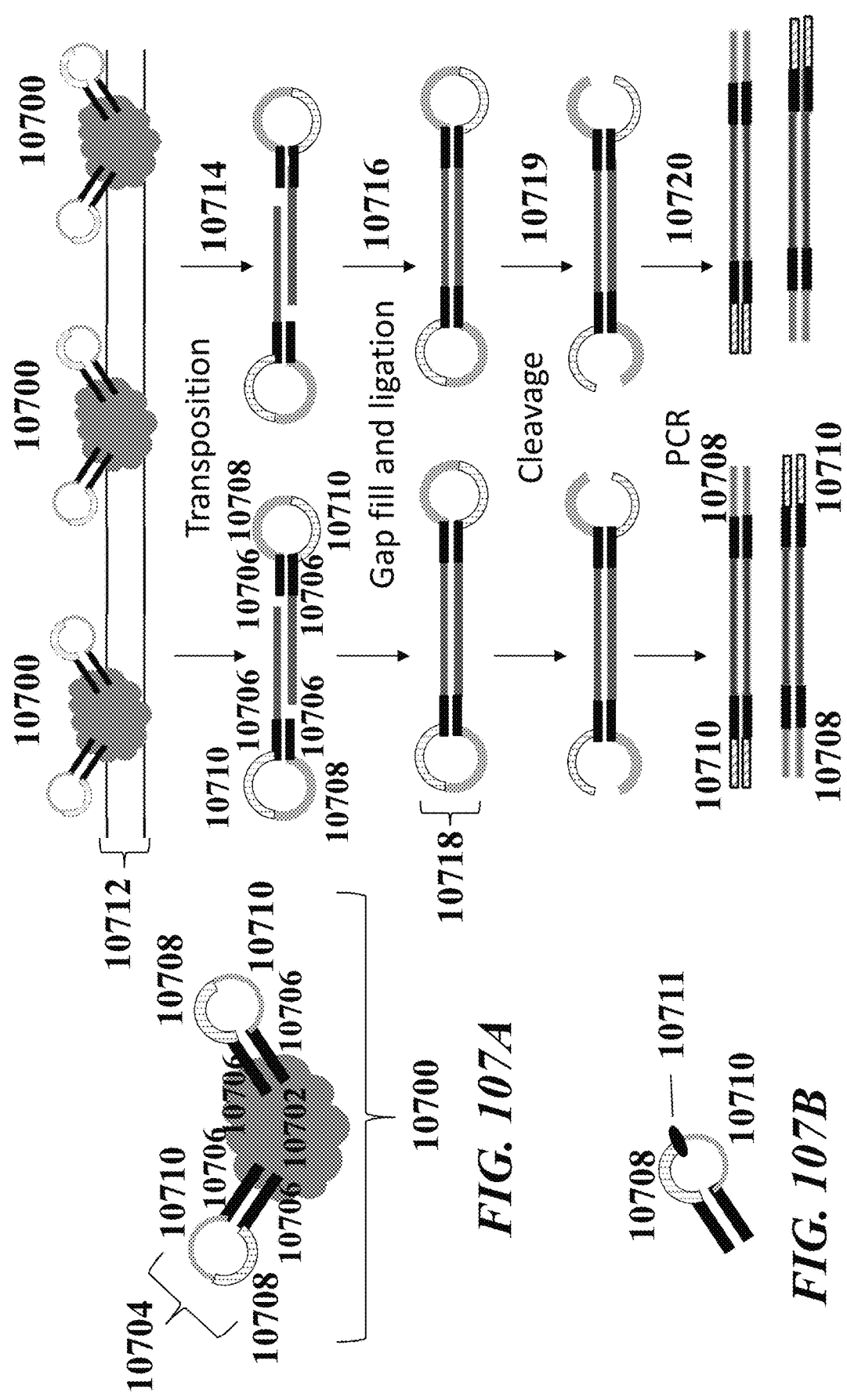
FIG. 107A shows schematically another example of loading nucleic acid molecules on a transposase.
FIG. 107B shows schematically a linker molecule on a nucleic acid adapter.
FIG. 107C shows schematically another example method of processing nucleic acid molecules.

FIG. 107 illustrates schematically an example of a method for nucleic acid processing. In Panel 107A, a transposase 10702 is loaded with a pair of hairpin nucleic acid adapters 10704 to generate a hairpin transposase 10700. The hairpin nucleic acid adapters may comprise a first and a second nucleic acid strand. The first nucleic acid strand may comprise a first nucleic acid sequence, such as a mosaic end sequence 10706, which allows for loading of the nucleic acid on the transposase, and a second nucleic acid sequence 10708, such as a first sequencing primer sequence. The second nucleic acid strand may comprise (i) a third nucleic acid sequence, which may be also a mosaic end sequence 10706 that is complementary to the mosaic end sequence 10706 of the first nucleic acid strand and (ii) a fourth nucleic acid sequence 10710, which may comprise a second sequencing primer sequence. The second nucleic acid sequence and the fourth nucleic acid sequence, which may comprise the first and second sequencing primer sequences, respectively, may be connected via a linker 10711, as shown in Panel 107B. In Panel 107C, the hairpin transposase 10700 may be brought in contact with a nucleic acid molecule 10712. In process 10714, the hairpin transposase 10700 may interact with the nucleic acid molecule 10712, e.g., in a transposition reaction, to generate a nucleic acid fragment comprising the mosaic end sequences 10706 of the first and the second nucleic acid strands, and, at each end, the second nucleic acid sequence 10708 (e.g., comprising the first sequencing primer sequence) and the fourth nucleic acid sequence 10710, (e.g., comprising the second sequencing primer sequence). In process 10716, the nucleic acid fragment may be subjected to a nucleic acid reaction that allows for gap-fill and ligation to generate a gap-filled nucleic acid fragment 10718. In some cases, process 10719 may occur following gap-fill and may comprise cleavage of the linker 10711 between the second 10708 and fourth 10710 nucleic acid sequences. In other embodiments, process 10719 may occur at any convenient operation in the process. In process 10720, further processing may occur. In some cases, further processing comprises an amplification reaction (e.g., PCR). The further processing may generate a processed nucleic acid fragment comprising the second nucleic acid sequence 10708 (e.g., comprising the first sequencing primer sequence) on one end and the fourth nucleic acid sequence, 10710 (e.g., comprising the second sequencing primer sequence) at the opposite end.

In some cases, the transposase may be loaded with a pair of nucleic acid adapters, where each of the pair of nucleic acid adapters comprises a first single-stranded portion comprising a first nucleic acid sequence and a second single-stranded portion comprising a second nucleic acid sequence, and where the pair of nucleic acid adapters are connected.

The first and second nucleic acid sequences may be a first type of sequencing primer sequence and a second type of sequencing primer sequence, respectively. The pair of nucleic acid adapters may further comprise a loading sequence that allow for loading of the nucleic acid adapters onto the transposase. In some cases, the loading sequence may comprise an inverted repeat sequence (e.g., "mosaic end sequence"). In some cases, in one or more nucleic acid adapters, both the first single-stranded portion comprising the first nucleic acid sequence and the second single-stranded portion comprising the second nucleic acid sequence may each comprise a mosaic end sequence. In some cases, the mosaic end sequence of the first single-stranded portion may hybridize with the mosaic end sequence of the second single-stranded portion, and i) the first nucleic acid sequence of one of the nucleic acid adapters is connected to the second nucleic acid sequence of the other nucleic acid adapter, forming a hairpin nucleic acid adapter and ii) the second nucleic acid sequence of one of the nucleic acid adapters is connected to the first nucleic acid sequence of the other nucleic acid adapter. In some embodiments, the transposase may be loaded with the connected pair of nucleic acid adapters, generating a continuous-adapter transposase (see, e.g., panels 108A-B in FIG. 108).

The continuous-adapter transposase may then be brought in contact with the nucleic acid molecule under conditions sufficient to generate a nucleic acid fragment, where the nucleic acid fragment (i) comprises at each of the first end and the second end, both the first nucleic acid sequence and the second nucleic acid sequence and (ii) is at least partially double-stranded. In some cases, the conditions sufficient to generate a nucleic acid fragment may comprise a transposition reaction. The nucleic acid fragment may also comprise a gap region (e.g., approximately 9 base-pairs in length). The nucleic acid fragment may then be subjected to a nucleic acid reaction, e.g., gap-fill and ligation reaction to generate a gap-filled nucleic acid fragment. At any convenient point in the process, the pair of nucleic acid adapters may be disconnected, e.g., via cleavage. The nucleic acid fragment may be subjected under conditions sufficient to generate a processed nucleic acid fragment, where the processed nucleic acid fragment comprises the first nucleic acid sequence at the first end and the second nucleic acid sequence at the second end, or (ii) the second nucleic acid sequence at the first end and the first nucleic acid sequence at the second end. In some embodiments, the continuous-adapter transposase can comprise a nucleic acid sequence (e.g., a nucleic acid insert) flanked by a mosaic end sequence. The nucleic acid insert can comprise any suitable length. In some embodiments, the nucleic acid insert can be prepared such that it is suitable for incorporation into the genome of an animal, such as a mammal, e.g., via a transposition reaction. In some embodiments, the nucleic acid insert can comprise about 10 nucleotides to about 3,500 nucleotides (or basepairs) in length. For example, the nucleic acid insert may comprise about 10, 20, 30, 40, 50, 60, 70, 80, 90, 100, 200, 300, 400, 500, 600, 700, 800, 900, 1000, 1500, 2000, 2500, 3000, 3500, 4000, 4500, or 5000 nucleotides (or basepairs) in length. In some embodiments, the nucleic acid insert may comprise at least about 10, 20, 30, 40, 50, 60, 70, 80, 90, 100, 200, 300, 400, 500, 600, 700, 800, 900, 1000, 1500, 2000, 2500, 3000, 3500, 4000, 4500, or 5000 nucleotides (or basepairs) in length. In some embodiments, the nucleic acid insert may comprise at most 5000, 4500, 4000, 3500, 3000, 2500, 2000, 1500, 1000, 900, 800, 700, 600, 500, 400, 300, 200, 100, 90, 80, 70, 60, 50, 40, 30, 20, or 10 nucleotides (or basepairs) in length. In another embodiment, the nucleic acid insert can comprise about 50 nucleotides to about 500 nucleotides (or basepairs) in length. In another embodiment, the nucleic acid insert can comprise about 10 nucleotides to about 1 kilobase in length. In some embodiments, the nucleic acid insert can comprise single-stranded DNA. In some embodiments, the nucleic acid insert can comprise double-stranded DNA. In some embodiments, the nucleic acid insert can comprise single-stranded RNA. In some embodiments, the nucleic acid insert can comprise a RNA/DNA hybrid. In some embodiments, the nucleic acid insert may comprise a single-stranded nucleic acid sequence and a double-stranded nucleic acid sequence. In some embodiments, the nucleic acid insert can further comprise a linker, such as but not limited to a chemical linker. In some cases, the linker may comprise a linear polymer material, such as a linear polyacrylamide, poly-ethylene glycol (PEG), (PEG)-diacrylate, PEG-acrylate, PEG-thiol, PEG-azide, PEG-alkyne, other acrylates or other linear polymeric material, as described elsewhere herein. In some cases, the linker may be cleavable upon application of a stimulus.

Gap filling may occur through a variety of mechanisms. In one example, the gap region may be extended using an enzyme (e.g., a polymerase) to add one or more nucleotides to the gap region. Ligation may then occur, for example, using another enzyme (e.g., ligase). In some embodiments, the gap filling may comprise a polymerizing enzyme (e.g., a reverse transcriptase or polymerase) and a ligase. In some aspects, the gap filling does not include a polymerizing enzyme having strand displacement activity. In some aspects, the gap filling does not include a polymerizing enzyme having exonuclease activity. In some aspects, the gap filling does not include a polymerizing enzyme having strand displacement and exonuclease activity.

Cleavage of the nucleic acid fragment may occur through a variety of strategies. In one non-limiting example, a uracil base may be included in the hairpin adapter, e.g., between the first nucleic acid sequence and the second nucleic acid sequence. Cleavage may then be initiated, for example, using a polyamine (e.g., DMED) or an enzyme, e.g., uracil-n-glycosylase. In another non-limiting example, a restriction sequence may be included in the hairpin adapter, e.g., between the first nucleic acid sequence and the second nucleic acid sequence. Cleavage may then occur using a restriction enzyme. In other non-limiting examples, the first nucleic acid sequence and the second nucleic acid sequence may be linked by a labile linkage, such that exposure to a stimulus (e.g., photo, thermal, chemical, or biological) may result in cleavage of the hairpin nucleic acid adapter.

Figures 108A, 108B:
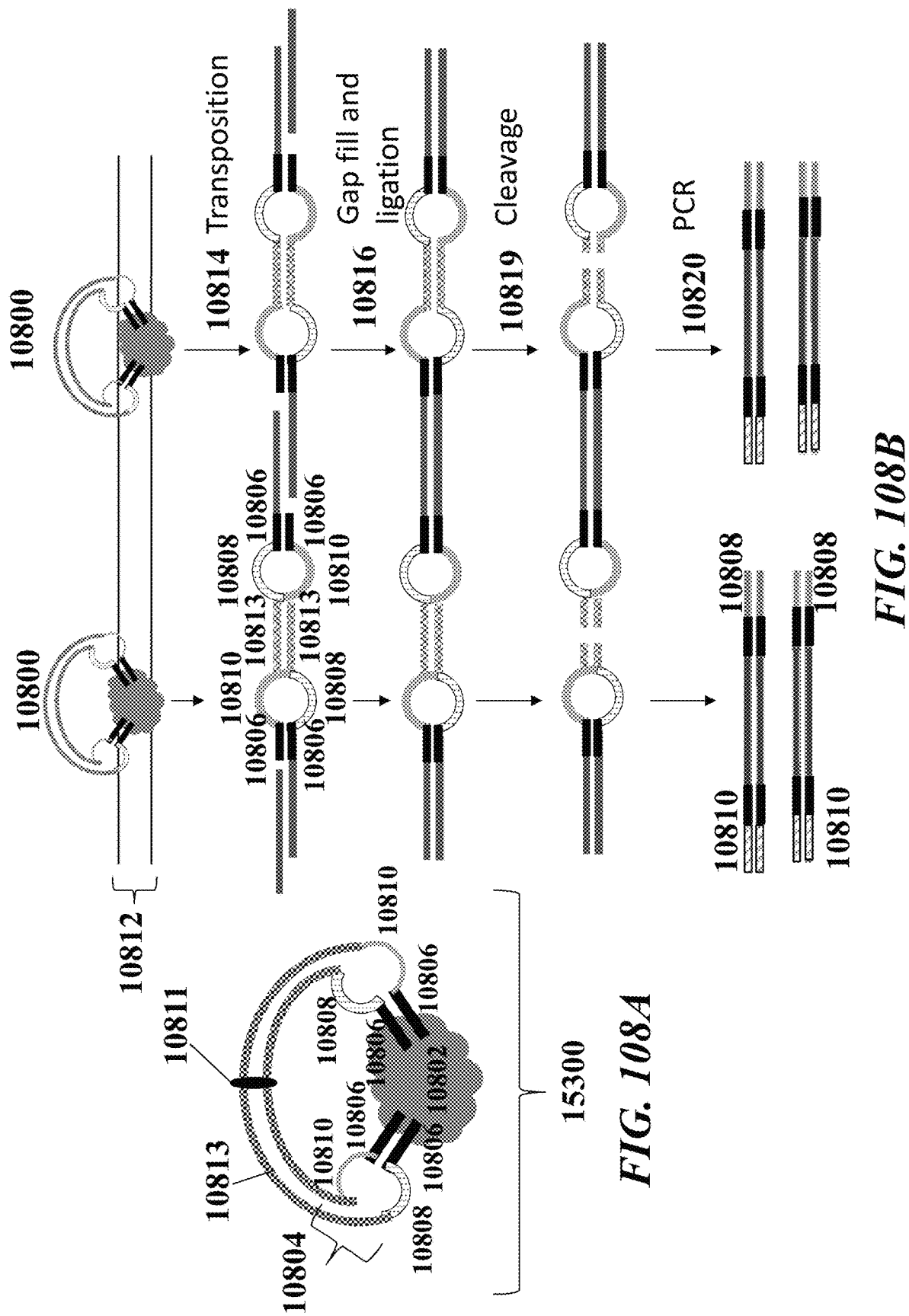
FIG. 108A shows schematically another example of loading nucleic acid molecules on a transposase.
FIG. 108B shows schematically another example method of processing nucleic acid molecules.

FIG. 108 illustrates schematically an example of a method for nucleic acid processing. In Panel 108A, a transposase 10802 is loaded with a connected pair of nucleic acid adapters 10804 to generate a continuous-adapter transposase 10800. The continuous-adapter transposase 10800 may comprise a first nucleic acid strand comprising a first nucleic acid sequence, such as a mosaic end sequence 10806, which allows for loading of the nucleic acid on the transposase, and a second nucleic acid sequence 10808, such as a first sequencing primer sequence. The second nucleic acid strand may comprise (i) a third nucleic acid sequence, which may be also a mosaic end sequence 10806 that is complementary to the mosaic end sequence 10806 of the first nucleic acid strand and (ii) a fourth nucleic acid sequence 10810, which may comprise a second sequencing primer sequence. The second nucleic acid sequence and the fourth nucleic acid sequence of the first nucleic acid adapter, which may comprise the first and second sequencing primer sequences, respectively, may be connected to the fourth nucleic acid sequence and second nucleic acid sequence of the second nucleic acid adapter via a nucleic acid sequence 10813 and a cleavable linker 10811. In Panel 108B, the continuous-adapter transposase 10800 may be brought in contact with a nucleic acid molecule 10812. In process 10814, the continuous-adapter transposase 10800 may interact with the nucleic acid molecule 10812, e.g., in a transposition reaction, to generate a nucleic acid fragment comprising the mosaic end sequences 10806 of the first and the second nucleic acid strands and the second nucleic acid sequence 10808 (e.g., comprising the first sequencing primer sequence) and the fourth nucleic acid sequence 10810, (e.g., comprising the second sequencing primer sequence). The second nucleic acid sequence 10808 and the fourth nucleic acid sequence 10810 may be adjacent to the fourth nucleic acid sequence 10810 and the second nucleic acid 10808, respectively. In process 10816, the nucleic acid fragment may be subjected to a nucleic acid reaction that allows for gap-fill and ligation to generate a gap-filled nucleic acid fragment. In some cases, process 10819 may occur following gap-fill and may comprise cleavage of the linker 108108 between the pair of nucleic acid adapters 10804. In other embodiments, process 10819 may occur at any convenient operation in the process. In process 10820, further processing may occur. In some cases, further processing comprises an amplification reaction (e.g., PCR). The further processing may generate a processed nucleic acid fragment comprising the second nucleic acid sequence 10808 (e.g., comprising the first sequencing primer sequence) on one end and the fourth nucleic acid sequence, 10810 (e.g., comprising the second sequencing primer sequence) at the opposite end.

In some cases, the transposase may be loaded with a pair of first nucleic acid adapters, where each of the pair of first nucleic acid adapters comprises a single-stranded portion comprising a first nucleic acid sequence. The first nucleic acid sequences may comprise a first type of sequencing primer sequence. The pair of first nucleic acid adapters may further comprise a loading sequence that allow for loading of the nucleic acid adapters onto the transposase. In some cases, the loading sequence may comprise an inverted repeat sequence (e.g., "mosaic end sequence"). In some cases, the mosaic end sequence is double-stranded. In some cases, the pair of first nucleic acid adapters loaded onto the transposase may be identical, forming a single-adapter transposase.

The single-adapter transposase may then be brought in contact with the nucleic acid molecule under conditions sufficient to generate a nucleic acid fragment, where the nucleic acid fragment (i) comprises at each of the first end and the second end, the first nucleic acid and (ii) is at least partially double-stranded. In some cases, the conditions sufficient to generate a nucleic acid fragment may comprise a transposition reaction. The nucleic acid fragment may also comprise a gap region (e.g., approximately 9 base-pairs in length). The nucleic acid fragment may then be subjected to a nucleic acid reaction, e.g., gap-fill and ligation reaction to generate a gap-filled nucleic acid fragment. The nucleic acid fragment may be subjected under conditions sufficient to denature the nucleic acid fragment to generate a first single-stranded fragment and a second single-stranded fragment, where each of the first single-stranded fragment and the second single-stranded fragment comprises the first nucleic acid sequence. The first single-stranded fragment and the second single-stranded fragment may then be brought in contact with a plurality of second nucleic acid adapters to generate processed nucleic acid fragments, where the plurality of second nucleic acid adapters each comprises a second nucleic acid sequence (e.g., a second sequencing primer sequence), and where the processed nucleic acid fragments comprises the first nucleic acid sequence at the first end (e.g., the first sequencing primer sequence) and the second nucleic acid sequence (e.g., the second sequencing primer sequence) at the second end, or (ii) the second nucleic acid sequence at the first end and the first nucleic acid sequence at the second end. In some embodiments, processing of the nucleic acid fragments comprises ligation of the second nucleic acid adapters to the single-stranded nucleic acid fragments.

Ligation of the nucleic acid adapters may occur through a variety of mechanisms. In some cases, the nucleic acid adapter may comprise a reactive moiety. Similarly, the first single-stranded fragment and the second single-stranded fragment may each comprise a second reactive moiety. A reactive moiety may be selected from the non-limiting group consisting of azides, alkynes, nitrones (e.g., 1,3-nitrones), strained alkenes (e.g., trans-cycloalkenes such as cyclooctenes or oxanorbornadiene), tetrazines, tetrazoles, iodides, thioates (e.g., phosphorothioate), acids, amines, and phosphates. For example, the first reactive moiety may comprise an azide moiety, and the second reactive moiety may comprise an alkyne moiety. The first and second reactive moieties may react to form a linking moiety. A reaction between the first and second reactive moieties may be, for example, a cycloaddition reaction such as a strain-promoted azide-alkyne cycloaddition, a copper-catalyzed azide-alkyne cycloaddition, a strain-promoted alkyne-nitrone cycloaddition, a Diels-Alder reaction, a [3+2] cycloaddition, a [4+2] cycloaddition, or a [4+1] cycloaddition; a thiol-ene reaction; a nucleophilic substation reaction; or another reaction. In some cases, reaction between the first and second reactive moieties may yield a triazole moiety or an isoxazoline moiety. A reaction between the first and second reactive moieties may involve subjecting the reactive moieties to suitable conditions such as a suitable temperature, pH, or pressure and providing one or more reagents or catalysts for the reaction. For example, a reaction between the first and second reactive moieties may be catalyzed by a copper catalyst, a ruthenium catalyst, or a strained species such as a difluorooctyne, dibenzylcyclooctyne, or biarylazacyclooctynone.

In some embodiments, reaction between a first reactive moiety of the nucleic acid adapter and a second reactive moiety of the first single-stranded fragment may link the nucleic acid adapter and the first single-stranded fragment to form an adapter-linked nucleic acid molecule. In some embodiments, reaction between a first reactive moiety of the nucleic acid adapter and a second reactive moiety of the second single-stranded fragment may link the nucleic acid adapter and the second single-stranded fragment to form an adapter-linked nucleic acid molecule. Upon linking, the nucleic acid adapter and the first single-stranded fragment or the second single-stranded nucleic acid fragment may be considered ligated. In some embodiments, the nucleic acid adapter may be linked to an at least partially double-stranded nucleic acid fragment. Accordingly, reaction of the first and second reactive moieties may comprise a chemical ligation reaction such as a copper-catalyzed 5' azide to 3' alkyne "click" chemistry reaction to form a triazole linkage between the nucleic acid adapter and the first single-stranded fragment or the second single-stranded fragment. In other non-limiting examples, an iodide moiety may be chemically ligated to a phosphorothioate moiety to form a phosphorothioate bond, an acid may be ligated to an amine to form an amide bond, and/or a phosphate and amine may be ligated to form a phosphoroamidate bond.

In some embodiments, the nucleic acid adapter may be ligated to the first single-stranded fragment or the second single-stranded fragment. The first or the second single-stranded fragment and the nucleic acid adapter may be subjected to an enzymatic ligation reaction, using a ligase, e.g., SplintR ligases, T4 ligases, Mu polymerase, PBCV1 enzymes, and/or any combinations, derivatives, and variants thereof. In some embodiments, ribonucleotides are ligated between the adapter and the first or the second single-stranded fragments. In some embodiments, deoxyribonucleotides are ligated between the adapter and the first or the second single-stranded fragments. In some embodiments, the nucleic acid adapter may be ligated to a double-stranded fragment. In some embodiments, the nucleic acid adapter may be double-stranded.

Figures 109A, 109B:
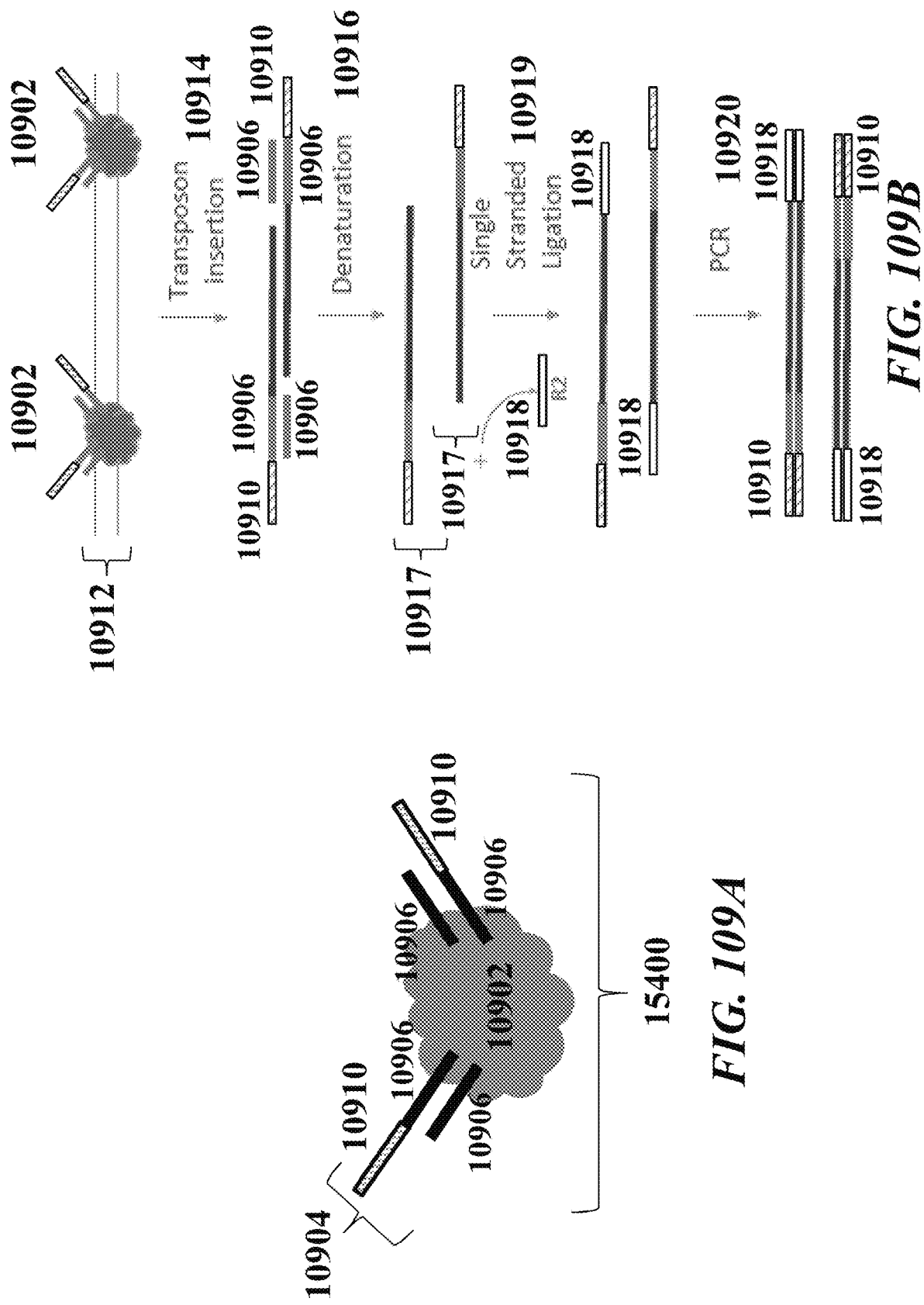
FIGS. 109A and 109B illustrate an example workflow of a method for barcoding nucleic acids in cells.

FIG. 109 illustrates schematically an example of a method for nucleic acid processing. In Panel 109A, a transposase 10902 is loaded with a pair of nucleic acid adapters 10904 to generate a single-adapter transposase 10900. The nucleic acid adapters 10904 may comprise a first and a second nucleic acid strand. The first nucleic acid strand may comprise a first nucleic acid sequence, such as a mosaic end sequence 10906, which allows for loading of the nucleic acid on the transposase, and a second nucleic acid sequence 10910, which may comprise a first sequencing primer sequence. The second nucleic acid strand may comprise a mosaic end sequence 10906 that is complementary to the mosaic end sequence 10906 of the first nucleic acid strand. In Panel 109B, the single-adapter transposase 10900 may be brought in contact with a nucleic acid molecule 109109. In process 10914, the single-adapter transposase 10900 may interact with the nucleic acid molecule 109109, e.g., in a transposition reaction, to generate a nucleic acid fragment comprising the mosaic end sequences 10906 of the first and the second nucleic acid strands, and, at each end, the first sequencing primer sequence 10910. In process 10916, the nucleic acid fragment may be subjected to a nucleic acid reaction that allows for denaturation of the nucleic acid fragment into single-stranded nucleic acid fragments 10917. In process 10919, a second nucleic acid sequence 10918 (e.g., comprising a second sequencing primer site) may be added (e.g., ligated) to the single-stranded nucleic acid fragments 10917. In some cases, process 10919 comprises the use of enzyme (e.g., a DNA ligase). In other embodiments, click-chemistry or other ligation strategies may be employed. In process 10920, further processing (e.g., PCR) may occur to generate nucleic acid fragments that comprise the first nucleic acid sequence 10910 (e.g., the first sequencing primer sequence) at the first end and the sequence of the second nucleic acid sequence 10918 (e.g., the second sequencing primer sequence) at the second end 10920, or the first nucleic acid sequence 10910 at the second end and the second nucleic acid sequence 10918 at the first end 10920.

In some cases, the processed nucleic acid fragments may be subjected under conditions sufficient to generate barcoded nucleic acid fragments. In some cases, the barcode molecule may be single-stranded. In other cases, the barcode molecules may be double-stranded or partially double-stranded. In some cases, the barcoding may be performed in a partition. In some embodiments, one or more operations in the methods provided herein may be performed in a partition. In other embodiments, one or more operations in the methods provided herein may be performed outside a partition (e.g., in bulk).

Figure 66:
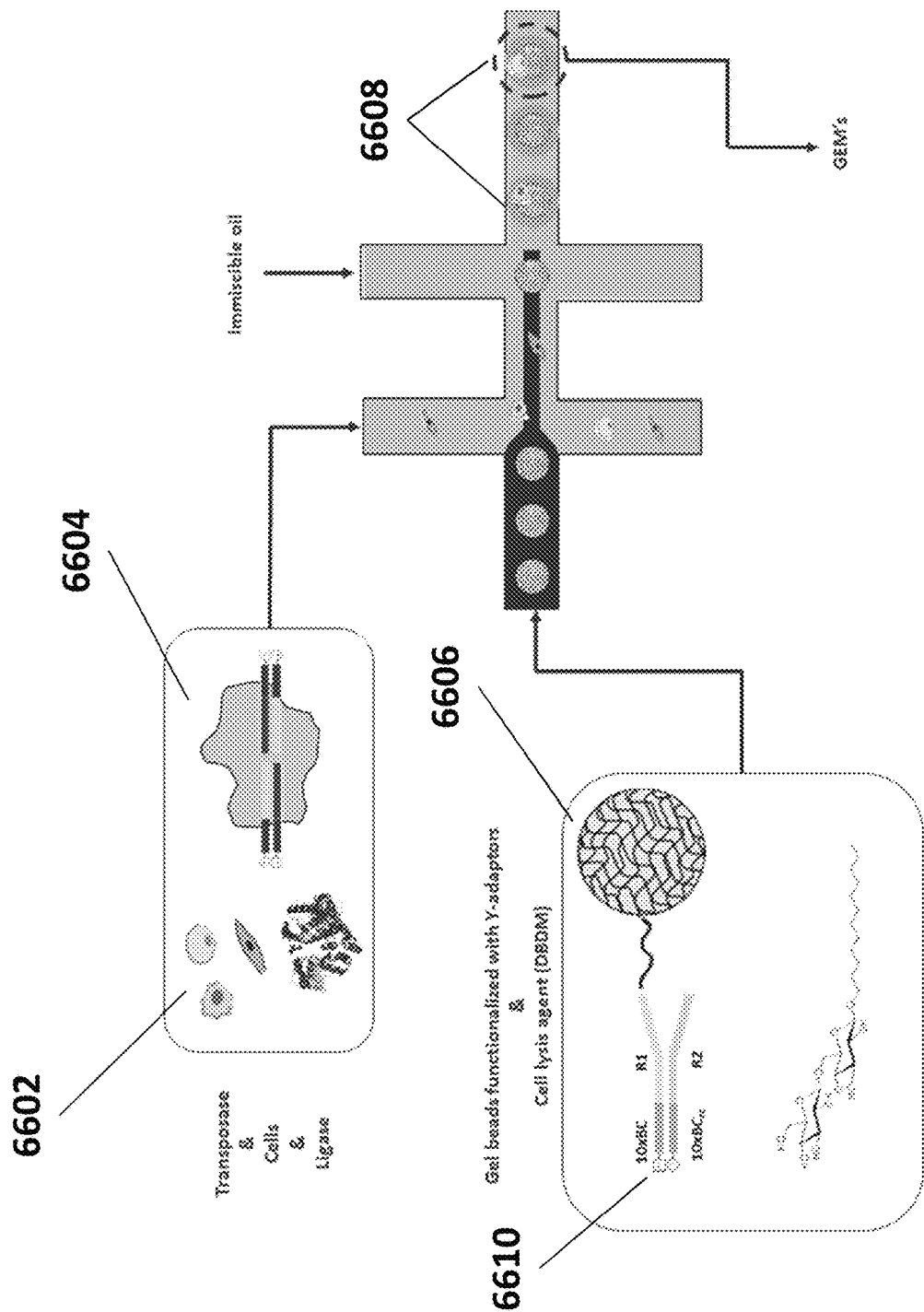
FIG. 66 illustrates a method to generate droplets wherein at least some of the droplets formed will comprise transposase-nucleic acid complexes, a single cell, and a single gel bead comprising a forked adaptor.

FIG. 66 illustrates a method to generate droplets wherein at least some of the droplets formed will comprise transposase-nucleic acid complexes, a single cell, and a single gel bead comprising a forked adaptor. The gel bead may comprise a plurality of forked adaptor oligonucleotides, each forked adaptor oligonucleotide comprising a sequencing primer sequence and a barcode sequence. The partitions may be generated as described elsewhere herein, such that at least some of the droplets 6608 comprise transposase-nucleic acid complexes 6604, cell lysis reagents, T4 DNA ligase, a single cell 6602, and a single gel bead 6606 comprising a plurality of barcoded forked adaptor oligonucleotides 6610. An individual transposase-nucleic acid complex 6604 comprises a transposase and a pair of double-stranded oligonucleotides each comprising a transposon end sequence (e.g., an ME sequence). In some cases, the double-stranded transposon-end sequence containing oligonucleotides may further comprise a spacer sequence. In the aqueous droplet, the cell may be lysed in a manner that releases template nucleic acid molecules from the nucleus into the aqueous droplet, but that substantially maintains native chromatin organization. The droplets may then be processed as outlined in FIGS. 67A-67B.

Figure 68A:
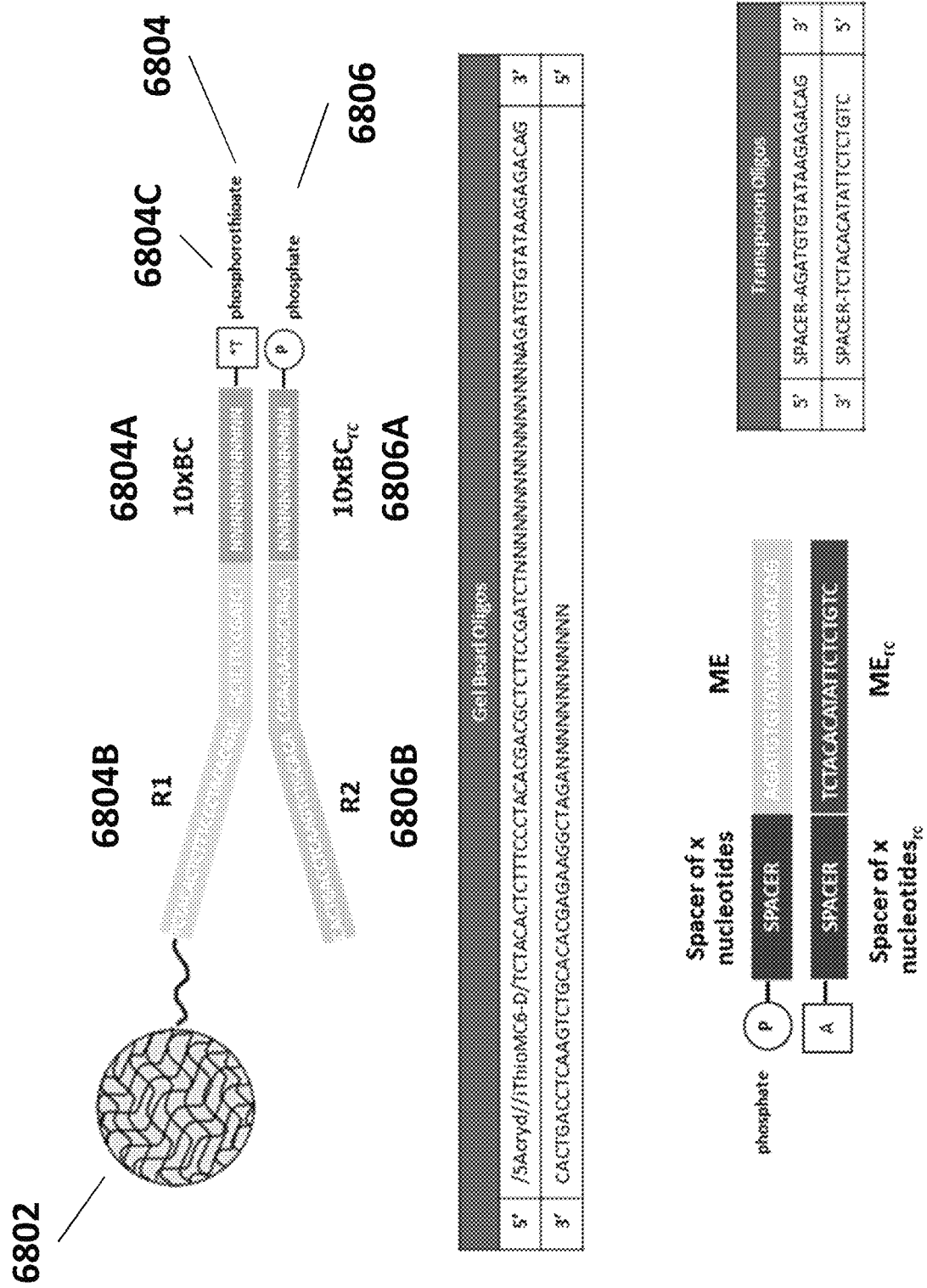

Although the forked adaptors can be prepared in a variety of different configurations, an example of a forked adaptor is illustrated in FIG. 68A. FIG. 68A illustrates a partially complementary double-stranded oligonucleotide comprising a first oligonucleotide strand 6804 releasably attached to a gel bead 6802 and a second partially complementary oligonucleotide strand 6806. The first strand 6804 may comprise a barcode sequence ("BC") 6804A and a primer sequence ("R1") 6804B. The partially complementary second strand 6806 may comprise a region 6806A fully complementary to the barcode sequence 6804A and a primer sequence ("R2") 6806B partially complementary to the first strand primer sequence 6804B. In some cases, the first strand 6804 may further comprise a phosphorothioate linkage 6804C in the terminal nucleotide at the 3' end. In some cases, the first strand may comprise phosphorothioate linkages in the last 3-5 nucleotides at the 3' end. In still other cases, the first strand may comprise phosphorothioate linkages throughout the first strand. In alternative embodiments, such as illustrated in FIG. 68B, the double-stranded forked adaptor described in FIG. 68A may further comprise a first oligonucleotide strand 6824 further comprising a P5 adapter sequence 6824A releasably attached to the gel bead 6822; and (b) a second partially complementary oligonucleotide strand 6826 further comprising an index primer ("i7") 6826A and an adaptor sequence ("P7") 6826B different than the first strand.

Figure 67A:
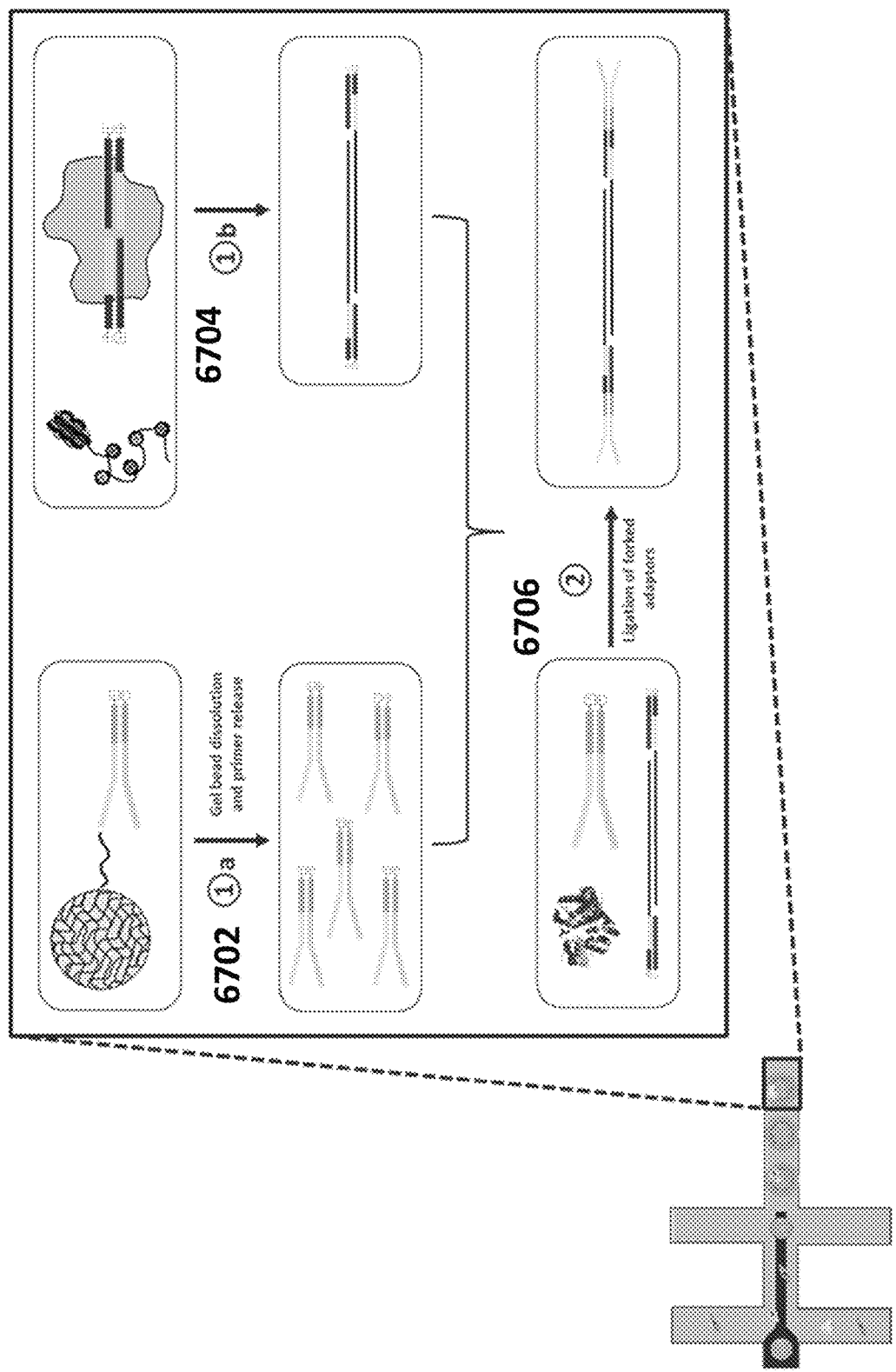
FIGS. 67A-67B illustrate an alternative method to generate forked adaptor flanked double-stranded template nucleic acid fragments.
Figure 67B:
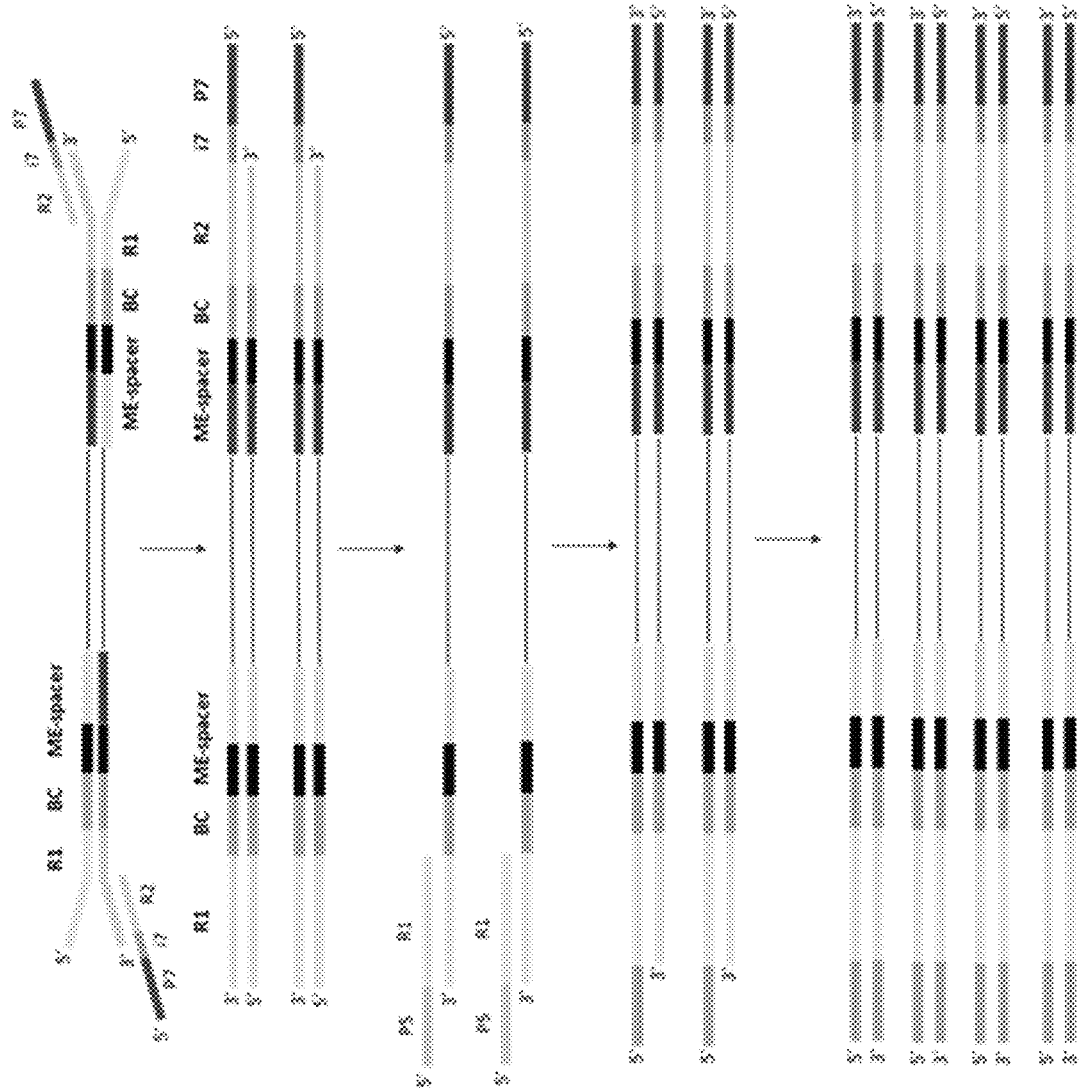

FIGS. 67A-67B illustrate another method to generate forked adaptor flanked double-stranded template nucleic acid fragments. FIG. 67A illustrates a method for the in-partition ligation of forked adaptors onto fragments of native chromatin generated by an in-partition transposition reaction while FIG. 67B illustrates a method for the in-bulk production of a next-generation sequencing compatible library from the fragments generated in FIG. 67A. In operation 6702, a droplet (e.g., illustrated in FIG. 66) may be subjected to conditions such that the forked adaptors are released from the gel bead into the droplet (e.g., by gel bead depolymerization using a reducing agent, such as DTT). In operation 6704, the droplet may be subjected to conditions such that the transposase-nucleic acid complexes integrate the transposon end sequences into the template nucleic acid molecules and fragment the template nucleic acid molecules into double-stranded template nucleic acid fragments flanked by transposon end sequences. In operation 6706, the forked adaptors may then be ligated onto the ends of the double-stranded stranded template nucleic acid fragments.

In alternative embodiments, cells (or nuclei) may be permeabilized/permeable and the transposase-nucleic acid complexes may enter the nucleus to fragment the template nucleic acid. Cells may then be lysed to release the fragmented double-stranded template nucleic acid fragments. Because the transposase-nucleic acid complex can only act on a nucleosome-free template, the fragmented double-stranded template nucleic acid fragments are representative of genome-wide areas of accessible chromatin in a single cell.

The fragmented double-stranded template nucleic acid fragments may then be collected from the droplets and processed in bulk to fill any gaps created from the transposition reaction and to generate a library suitable for next generation high throughput sequencing. For example, the fragments, or derivatives thereof, may be subjected to one or more reactions (e.g., nucleic acid amplification) to add functional sequences to facilitate Illumina sequencing, such as in FIG. 67B. The fully constructed library may then be sequenced according to any suitable sequencing protocol. In some embodiments, custom sequencing primers directed against the spacer-ME sequence are utilized to avoid sequencing the barcode-spacer-ME region of the library.

In some instances, nucleic acid fragments from single cells may be barcoded in partitions using adaptors comprising a T7 promoter sequence. A plurality of transposase molecules, a plurality of cells of interest (or a plurality of nuclei harvested from cells of interest), and a plurality of barcode oligonucleotides can be partitioned such that at least some partitions comprise a plurality of transposase molecules, a single cell (or nucleus), and a plurality of barcode oligonucleotides. A barcode oligonucleotide may comprise a T7 promoter sequence, a sequencing primer sequence, a barcode sequence, and a transposon end sequence. In some cases, the plurality of barcode oligonucleotides may be attached to a gel bead and partitioned such that at least some partitions comprise transposase molecules, a single cell (or nucleus), and a single gel bead.

Figure 69:
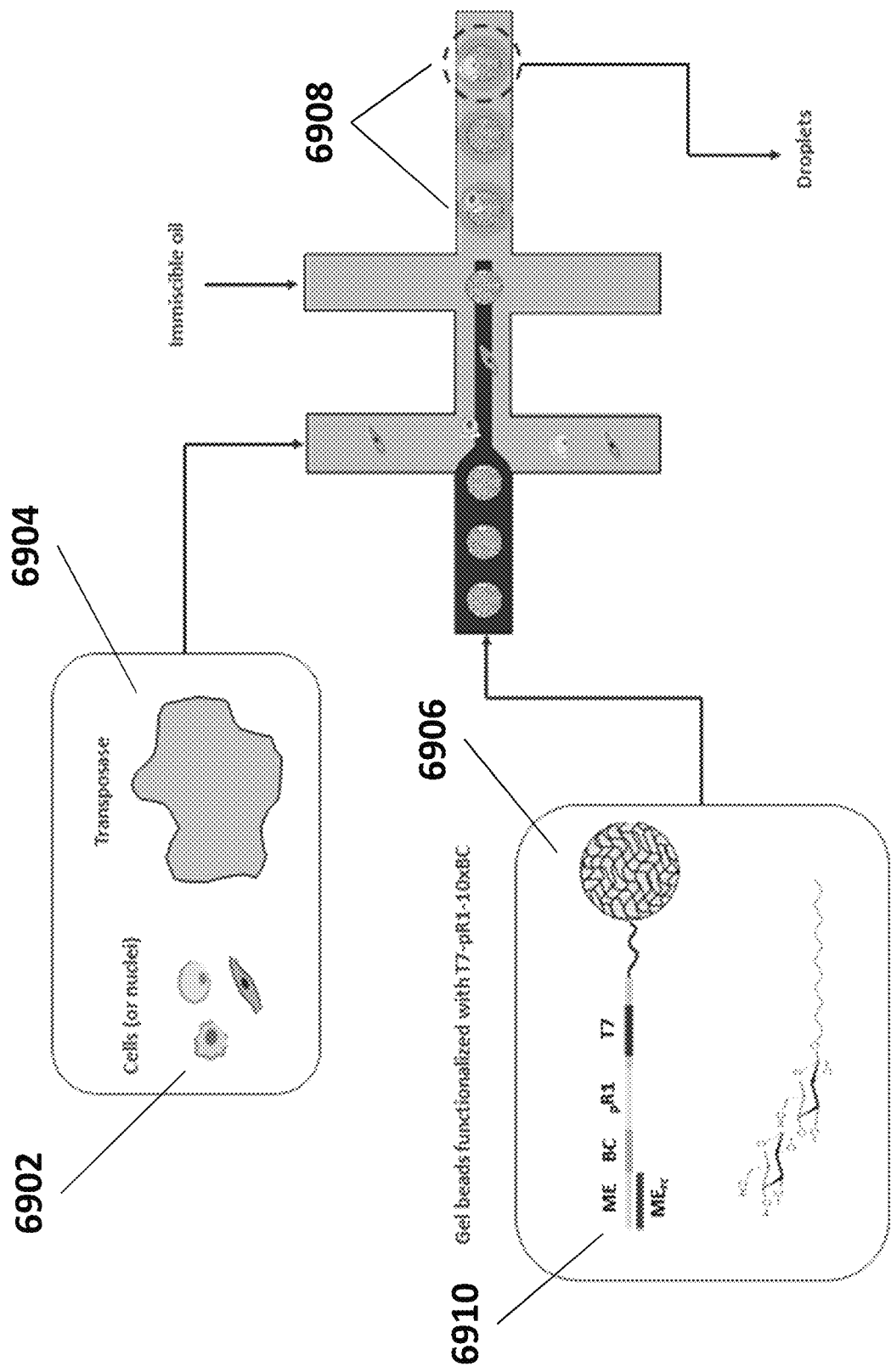
FIG. 69 illustrates a method to generate droplets wherein at least some of the droplets formed will comprise transposase molecules, a single cell, and a single gel bead comprising a T7-containing adaptor.

FIG. 69 illustrates a method to generate droplets wherein at least some of the droplets formed will comprise transposase molecules, a single cell, and a single gel bead comprising a T7-containing adaptor. The gel bead may comprise a plurality of adaptor oligonucleotides, each adaptor oligonucleotide comprising a T7 promoter sequence, a sequencing primer sequence, a barcode sequence, and a transposon end sequence. The partitions may be generated as described elsewhere herein such that at least some droplets 6908 comprise transposase molecules 6904, cell lysis reagents, a single cell 6902, and a single gel bead 6906 comprising partially double-stranded T7 promoter oligonucleotide adaptors 6910. In the aqueous droplet, the cell may be lysed in a manner that releases template nucleic acid molecules from the nucleus into the aqueous droplet, but that substantially maintains native chromatin organization. The droplets may then be processed as outlined in FIG. 70.

Figure 71:
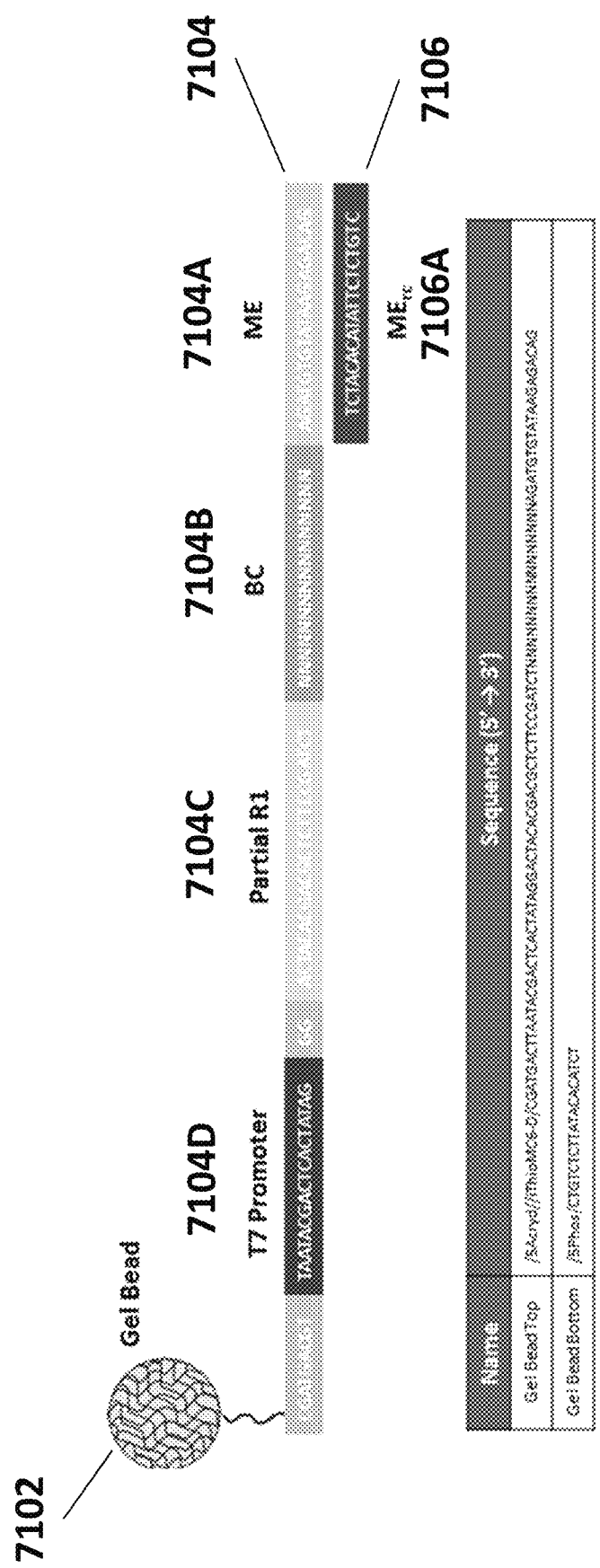
FIG. 71 illustrates an example of a T7-containing barcoded adaptor. Figure discloses SEQ ID NOS 82, 78, 83, and 78, respectively, in order of appearance.

Although the partially double-stranded adaptors can be prepared in a variety of different configurations, an example partially double-stranded adaptor is illustrated in FIG. 71. FIG. 71 illustrates a partially double-stranded oligonucleotide comprising a first oligonucleotide strand 7104 releasably attached to a gel bead 7102 and a second, shorter complementary oligonucleotide strand 7106. The first strand 7104 may comprise a transposon end ("mosaic end" or "ME") sequence 7104A, a barcode sequence ("BC") 7104B, a partial sequencing primer sequence ("pR1" or "Partial R1") 7104C, and a T7 promoter sequence 7104D while the second oligonucleotide strand 7106 may comprise a sequence 7106A fully complementary to the transposon end sequence 7104A.

Figure 70:
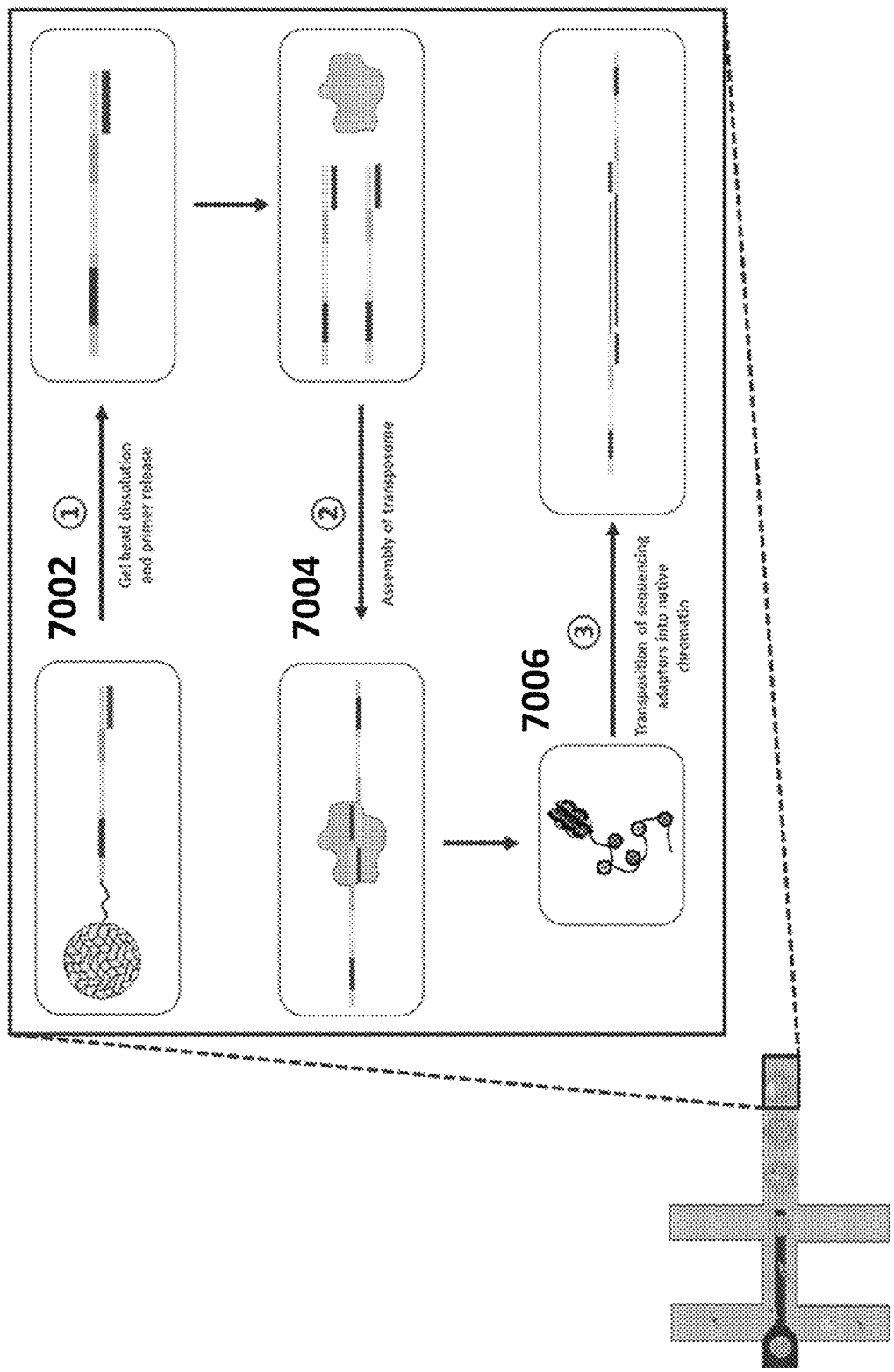
FIG. 70 illustrates a method to generate T7-containing adaptor flanked double-stranded template nucleic acid fragments.

FIG. 70 illustrates a method to generate T7-containing adaptor flanked double-stranded template nucleic acid fragments. In operation 7002, a droplet (e.g., illustrated in FIG. 69) may be subjected to conditions such that the partially double-stranded adaptors are released from the gel bead into the aqueous droplet (e.g., by gel bead depolymerization using a reducing agent, such as DTT). After the partially double-stranded adaptors are released from the gel bead, in operation 7004, the droplet may then be subjected to conditions such that a transposase-nucleic acid complex is formed comprising a transposase molecule and two partially double-stranded oligonucleotides adaptors. In process 7006, the droplets may then be subjected to conditions such that the transposase-nucleic acid complexes integrate the adaptors into the template nucleic acid and generate double-stranded template nucleic acid fragments flanked by the partially double-stranded adaptors.

In alternative embodiments, cells (or nuclei) may be permeabilized/permeable and the transposase-nucleic acid complexes enter the nucleus to fragment the template nucleic acid. Cells may then be lysed to release the fragmented double-stranded template nucleic acid fragments. Because the transposase-nucleic acid complex can only act on a nucleosome-free template, the fragmented double-stranded template nucleic acid fragments are representative of genome-wide areas of accessible chromatin in a single cell.

The fragmented double-stranded template nucleic acid fragments may then be collected from the droplets and processed in bulk to fill any gaps created from the transposition reaction. RNA may be generated from the double-stranded template nucleic acid fragments using an in vitro transcription reaction and T7 RNA polymerase. RNA may be collected and purified, followed by first and second strand cDNA synthesis. Double-stranded cDNA molecules may then further processed (including fragmentation and adaptor insertion by, e.g., a second transposase-mediated fragmentation) to generate a library suitable for next generation high throughput sequencing. For example, the fragments, or derivatives thereof, may be subjected to one or more reactions (e.g., nucleic acid amplification) to add functional sequences to facilitate Illumina sequencing. The fully constructed library may then be sequenced according to any suitable sequencing protocol.

In some instances, nucleic acid fragments from single cells may be barcoded in partitions using transposition of sequencing adaptors followed by random priming and extension. A plurality of transposase molecules, a plurality of cells of interest (or a plurality of nuclei harvested from cells of interest), and a plurality of barcode oligonucleotides may be partitioned such that at least some partitions comprise a plurality of transposase molecules, a single cell (or nucleus), and a plurality of barcode oligonucleotides. A barcode oligonucleotide may comprise a sequencing primer sequence, a barcode sequence, and a transposon end sequence. In some cases, the plurality of barcode oligonucleotides may be attached to a gel bead and partitioned such that at least some partitions comprise transposase molecules, a single cell (or nucleus), and a single gel bead.

Figure 72:
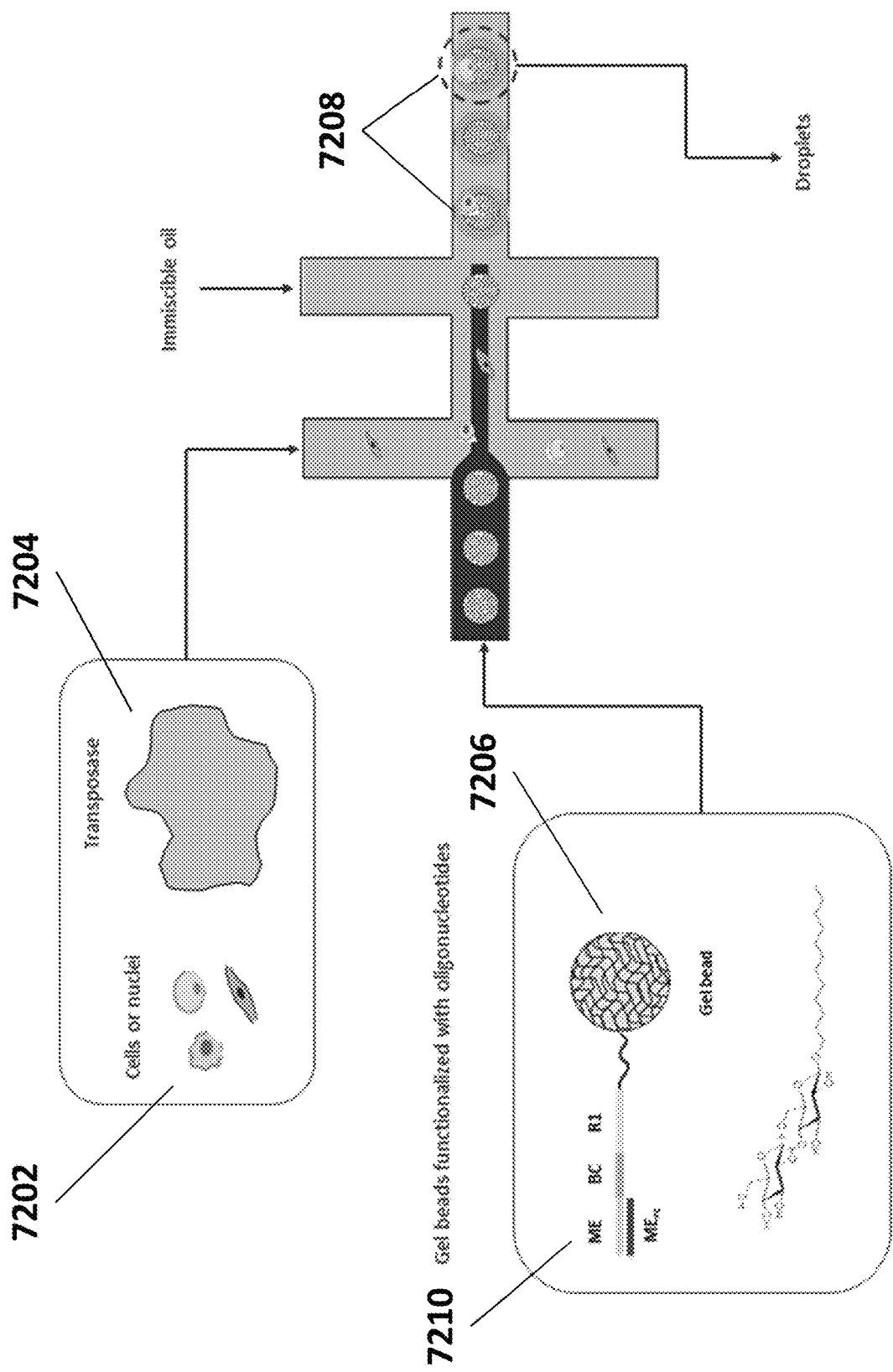
FIG. 72 illustrates a method to generate droplets wherein at least some of the droplets formed will comprise transposase molecules, a single cell, and a single gel bead comprising a barcoded adaptor.

FIG. 72 illustrates a method to generate droplets wherein at least some of the droplets formed will comprise transposase molecules, a single cell, and a single gel bead comprising a barcoded adaptor. The gel bead may comprise a plurality of adaptor oligonucleotides, each adaptor oligonucleotide comprising a sequencing primer sequence, a barcode sequence, and a transposon end sequence. The partitions may be generated as described elsewhere herein such that at least some droplets 7208 that comprise transposase molecules 7204, cell lysis reagents, a single cell 7202, and a single gel bead 7206 comprising partially double-stranded barcoded oligonucleotide adaptors 7210. In the aqueous droplet, the cell may be lysed in a manner that releases template nucleic acid molecules from the nucleus into the aqueous droplet, but that substantially maintains native chromatin organization. The droplets may then be processed as outlined in FIG. 73.

Figure 74:
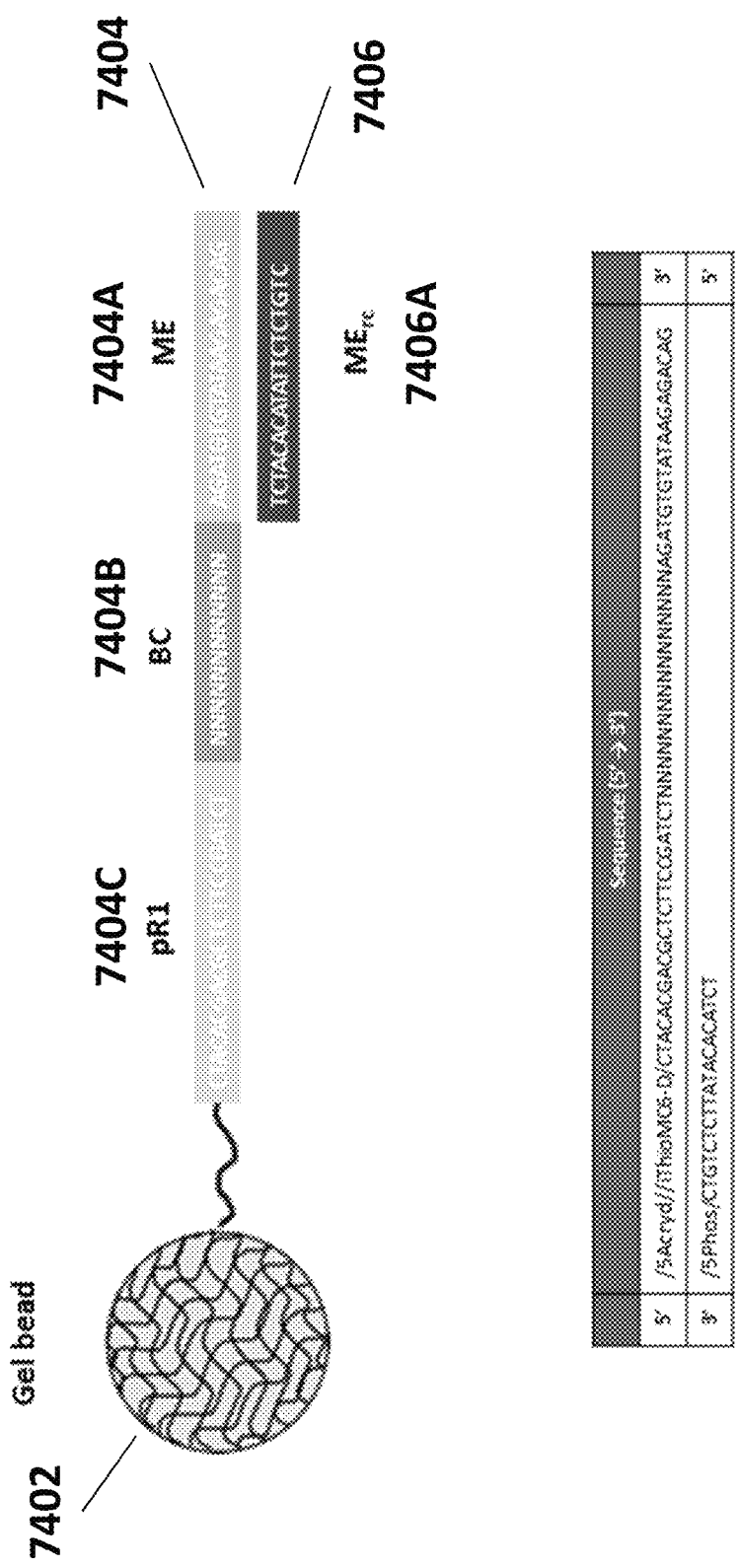
FIG. 74 illustrates an example of a partially double-stranded barcode oligonucleotide releasably attached to a gel bead. Figure discloses SEQ ID NOS 84, 78, 85, and 78, respectively, in order of appearance.

Although the partially double-stranded adaptors can be prepared in a variety of different configurations, an example of a partially double-stranded adaptor is illustrated in FIG. 74. FIG. 74 illustrates a partially double-stranded oligonucleotide comprising a first oligonucleotide strand 7404 releasably attached to a gel bead 7402 and a second, shorter complementary oligonucleotide strand 7406. The first strand 7404 may comprise a transposon end ("mosaic end" or "ME") sequence 7404A, a barcode sequence ("BC") 7404B, and a partial sequencing primer sequence ("pR1" or "Partial R1") 7404C while the second oligonucleotide strand 7406 may comprise a sequence 7406A fully complementary to the transposon end sequence 7404A.

Figure 73:
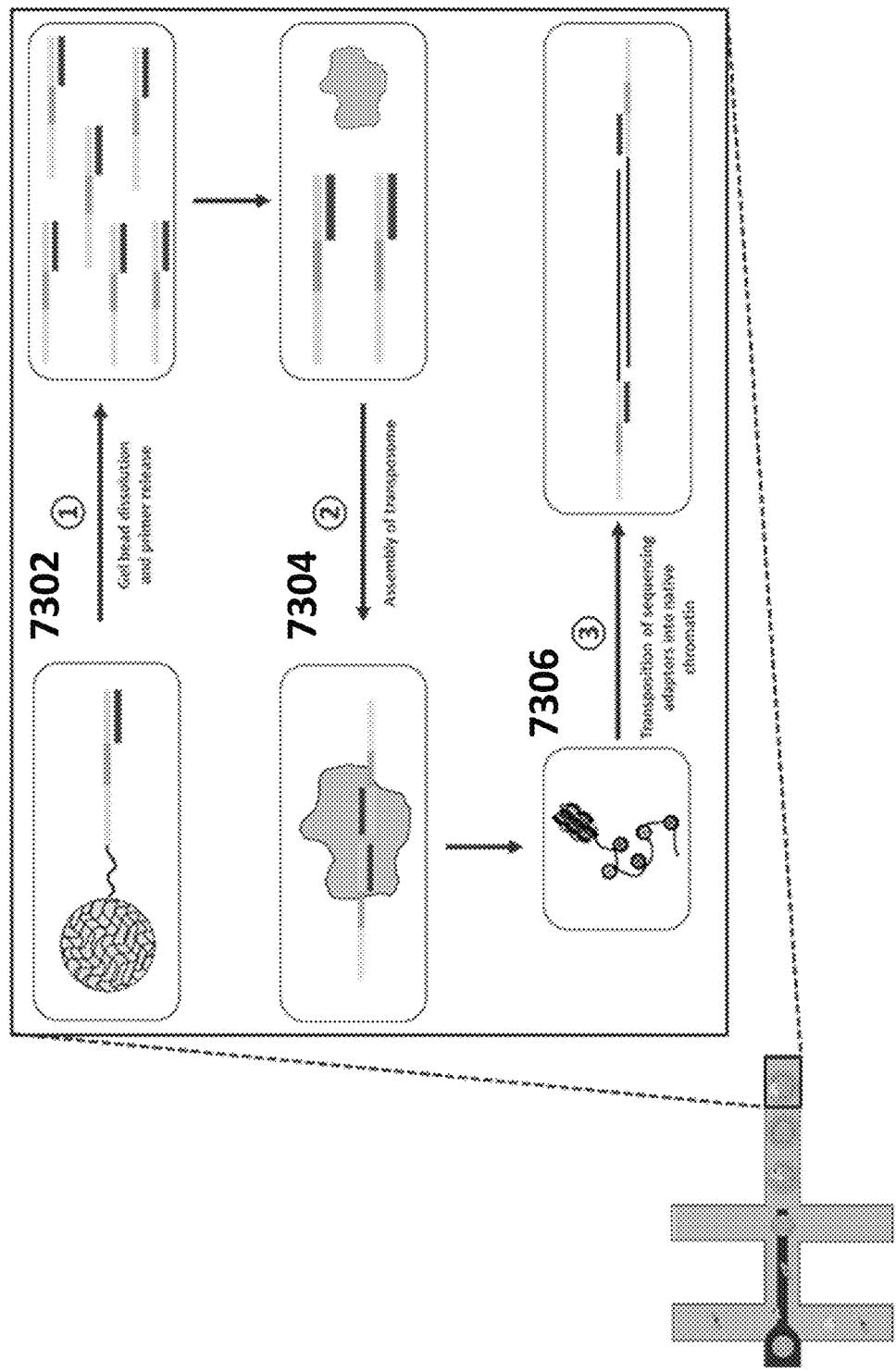
FIG. 73 illustrates an example scheme for producing barcoded, adapter-flanked nucleic acid fragments.

FIG. 73 illustrates a method for generating barcoded, adapter-flanked nucleic acid fragments. In operation 7302, a droplet (e.g., illustrated in FIG. 72) may be subjected to conditions such that the partially double-stranded adaptors are released from the gel bead into the aqueous droplet (e.g., by gel bead depolymerization using a reducing agent, such as DTT). After the partially double-stranded adaptors are released from the gel bead, in operation 7304, the droplet may then be subjected to conditions such that a transposase-nucleic acid complex is formed comprising a transposase molecule and two partially double-stranded oligonucleotides. In operation 7306, the droplet may then be subjected to conditions such that the transposase-nucleic acid complexes integrate the adaptors into the template nucleic acid and generate double-stranded template nucleic acid fragments flanked by the partially double-stranded adaptors.

In alternative embodiments, cells (or nuclei) may be permeabilized/permeable and the transposase-nucleic acid complexes enter the nucleus to fragment the template nucleic acid. Cells may then be lysed to release the fragmented double-stranded template nucleic acid fragments. Because the transposase-nucleic acid complex can only act on a nucleosome-free template, the fragmented double-stranded template nucleic acid fragments are representative of genome-wide areas of accessible chromatin in a single cell.

Figure 75:
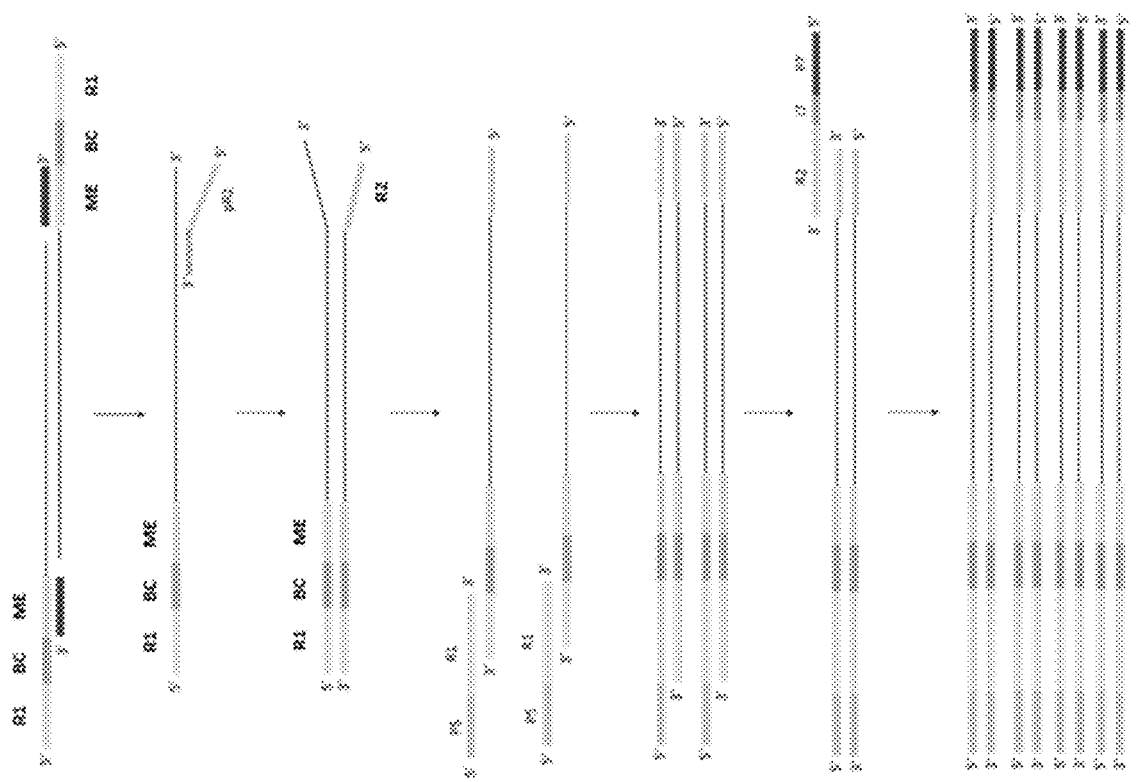
FIG. 75 illustrates a random priming extension reaction scheme.

The fragmented double-stranded template nucleic acid fragments may then be collected from the droplets and processed in bulk to generate a library suitable for next generation high throughput sequencing. In some embodiments, for example, double-stranded template nucleic acid fragments may be processed in bulk in a random priming extension reaction, such as illustrated in FIG. 75. The random extension primer may have a sequence of random nucleotides (N-mer) and, for example, can be attached to a second PCR handle (e.g., partial R2 sequence (pR2)). The random extension primers may be annealed to the double-stranded template nucleic acid fragments, or derivatives thereof, and extended. Reactions can then be cleaned-up and extension products may be subjected to one or more reactions (e.g., nucleic acid amplification) to add functional sequences to facilitate Illumina sequencing. The fully constructed library may then be sequenced according to any suitable sequencing protocol.

Figure 76:
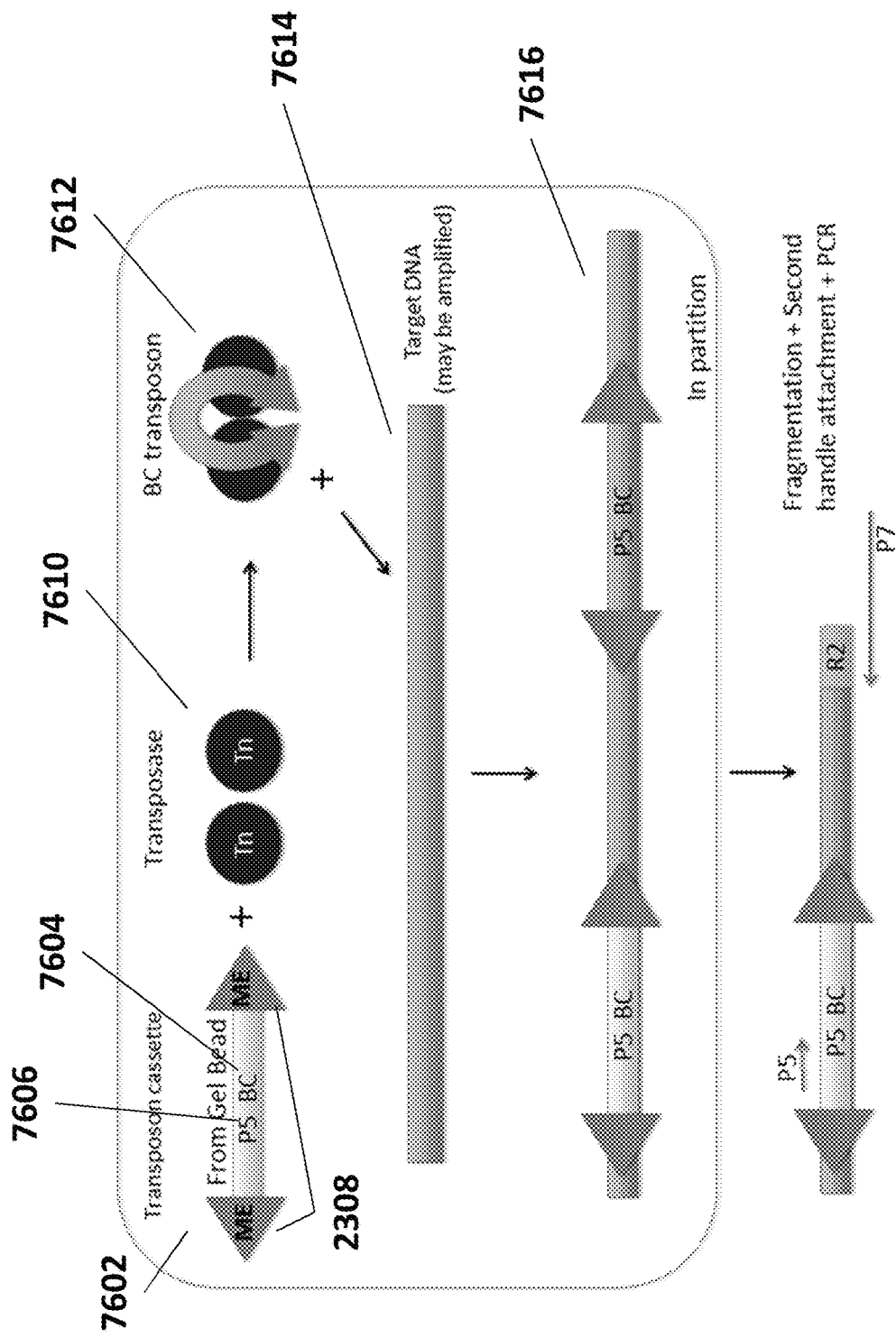
FIG. 76 illustrates a method of inserting barcodes into a template nucleic acid.

In some instances, artificial transposons may be configured to insert sequences of interest into a target DNA molecule (e.g., open chromatin) and barcode by insert. FIG. 76 illustrates a method of inserting barcodes into a template nucleic acid. An artificial transposon oligonucleotide 7602 comprising a barcode sequence 7604 and an adapter sequence 7606 is flanked by a transposon end sequence 7608 on each end of the oligonucleotide. A plurality of transposase molecules 7610, a plurality of cells of interest (or a plurality of nuclei harvested from cells of interest), and a plurality of artificial transposon oligonucleotides (e.g., 7602) may be partitioned such that at least some partitions comprise a plurality of artificial transposon oligonucleotides, a plurality of transposase molecules, and a single cell (or nucleus). In some cases, the plurality of artificial transposon oligonucleotides may be attached to a gel bead and partitioned such that at least some partitions comprise a plurality of transposase molecules, a single cell (or nucleus), and a single gel bead.

In alternative embodiments, a plurality of transposon nucleic acid complexes comprising an artificial transposon oligonucleotide (e.g., 7602) may be partitioned such that at least some partitions comprise a plurality of transposon nucleic acid complexes and a single cell (or nucleus). In some cases, the plurality of artificial transposon oligonucleotides may be attached to a gel bead and partitioned such that at least some partitions comprise a single cell (or nucleus) and a single gel bead.

In an example, droplets may be generated as described elsewhere herein such that at least some droplets comprise transposase molecules 7610, cell lysis reagents, a single cell, and a single gel bead. The gel bead may comprise a plurality of adaptor oligonucleotides, each adaptor oligonucleotide comprising an artificial transposon oligonucleotide (e.g., 7602). In the partition, the cells may then be lysed to release template nucleic acid molecules (e.g., 7614) from the nucleus into the aqueous droplet. The droplet may be subjected to conditions such that the barcoded adaptors (e.g., artificial transposon oligonucleotides 7602) are released from the gel bead into the aqueous droplet (e.g., by gel bead depolymerization using a reducing agent, such as DTT). Although the barcoded adaptors can be prepared in a variety of different configurations, an example of a barcoded adaptor is illustrated in FIG. 76 and is a double-stranded oligonucleotide releasably attached to a gel bead, wherein the barcoded adaptor 7602 comprises a pair of transposon end ("mosaic end" or "ME") sequences 7606 flanking a barcode sequence ("BC") 7604 and an adaptor sequence ("P5") 7606.

After the barcoded adaptors are released from the gel bead, the droplet may then subjected to conditions such that a transposase-nucleic acid complex 7612 is formed comprising a transposase molecule and a barcoded adaptor comprising a pair of transposon end sequences. The droplets may then be subjected to conditions such that the transposase-nucleic acid complexes integrate the barcoded adaptors into the template nucleic acid, such as to generate a barcode-transposed nucleic acid 7616. In alternative embodiments, cells (or nuclei) are permeabilized/permeable and the transposase-nucleic acid complexes enter the nucleus to perform the transposition reaction. Cells are then lysed to release the transposon-containing template nucleic acid fragments.

The barcode-transposed template nucleic acids (e.g., 7616) may then collected from the droplets and processed in bulk to fragment the barcode-transposed template nucleic acids and to generate a library suitable for next generation high throughput sequencing. For example, the fragments, or derivatives thereof, may be subjected to one or more reactions (e.g., nucleic acid amplification) to add functional sequences to facilitate Illumina sequencing. The fully constructed library may then be sequenced according to any suitable sequencing protocol.

In some instances, nucleic acid fragments from single cells may be barcoded in partitions using gel bead-functionalized transposase-nucleic acid complexes. A plurality of transposase nucleic acid complexes and a plurality of cells of interest (or a plurality of nuclei harvested from cells of interest) may be partitioned such that at least some partitions comprise a single cell (or nucleus) and a plurality of transposase nucleic acid complexes comprising a transposase molecule and a barcode oligonucleotide. The barcode oligonucleotide may comprise a sequencing primer sequence, a barcode sequence, and a transposon end sequence. In some cases, the plurality of transposase nucleic acid complexes may be attached to a gel bead and partitioned such that at least some partitions comprise a single cell (or nucleus) and a single gel bead. The partitions may be processed as outlined in FIG. 80.

For example, partitions may be generated as described elsewhere herein, such that at least some of the droplets comprise cell lysis reagents, a single cell, and a single gel bead functionalized with a transposase-nucleic acid complex. The cells may then be lysed in a manner that releases template nucleic acid molecules from the nucleus into the aqueous droplet, but that substantially maintains native chromatin organization. The droplets may then be subjected to conditions such that the transposase-nucleic acid complexes are released from the gel bead into the aqueous droplet (e.g., by gel bead depolymerization using a reducing agent, such as DTT).

Although the transposase-nucleic acid complexes can be prepared in a variety of different configurations, a transposase-nucleic acid complex is illustrated in FIG. 77A. FIG. 77A shows a complex comprising a transposase 7704, a first partially double-stranded oligonucleotide 7706, and a second partially double-stranded oligonucleotide 7708. The first partially double-stranded oligonucleotide 7706 may comprise: (a) a first strand 7710 releasably attached to a gel bead 7702, wherein the first strand comprises a transposon end sequence ("ME") 7710A, a barcode sequence ("BC") 7710B, and a first sequencing primer sequence ("R1") 7710C; and (b) a second strand 7712 complementary to the transposon end sequence of the first oligonucleotide strand. The second partially double-stranded oligonucleotide 7708 may comprise: (a) a first oligonucleotide strand 7714 comprising a transposon end sequence ("ME") 7714A and a second primer sequence ("R2") 7714B; and (b) a second strand 7716 complementary to the transposon end sequence. FIG. 77B illustrates another embodiment, in which the complex comprises a first partially double-stranded oligonucleotide identical to the above described embodiment (e.g., oligonucleotide 7706) and a second partially double-stranded oligonucleotide 7728 comprising: (a) a first oligonucleotide strand 7734 comprising a transposon end sequence ("ME") 7734A, a barcode sequence ("BC") 7734B, and the first primer sequence ("R1") 7734C; and (b) a second strand 7736 complementary to the transposon end sequence of the second oligonucleotide strand.

Figure 78:
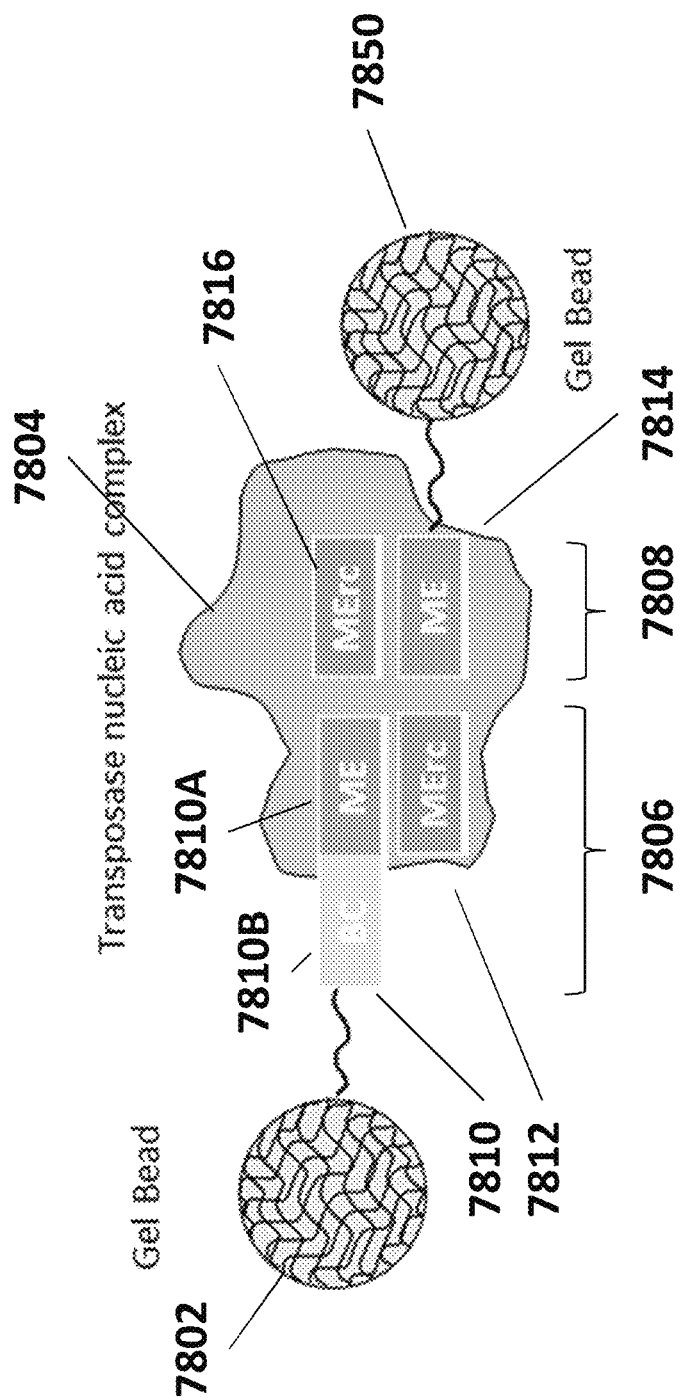
FIG. 78 illustrates examples of a transposase-nucleic acid complex showing a transposase, a first double-stranded oligonucleotide comprising a barcode sequence and a transposon end sequence releasably attached to a first gel bead and a second double-stranded oligonucleotide comprising a transposon end sequence releasably attached to a second gel bead.

Alternatively, gel-bead functionalized transposase-nucleic acid complexes may be prepared as illustrated in FIG. 78, which shows a complex comprising a transposase 7804, a first partially double-stranded oligonucleotide 7806 and a second double-stranded oligonucleotide 7808. In this embodiment, the first partially double-stranded oligonucleotide 7806 may comprise: (a) a first strand 7810 releasably attached to a first gel bead 7802, wherein the first strand comprises a transposon end sequence ("ME") 7810A and a barcode sequence ("BC") 7810B and (b) a second strand 7812 complementary to the transposon end sequence of the first oligonucleotide strand. The second double-stranded oligonucleotide 7808 may comprise: (a) a first strand 7814 releasably attached to a second gel bead 7850, wherein the first strand comprises a transposon end sequence ("ME") and (b) a second strand 7816 complementary to the first oligonucleotide strand. Alternative embodiments of FIG. 78 may comprise additional functional sequences, such as a sequencing primer sequence (e.g., R1 and/or R2) or an adapter sequence (e.g., P5 and/or P7).

Figure 79A:
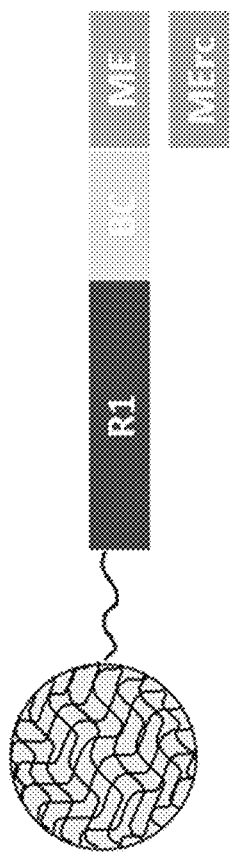
FIGS. 79A-B illustrate examples of barcode oligonucleotides.
Figure 79B:
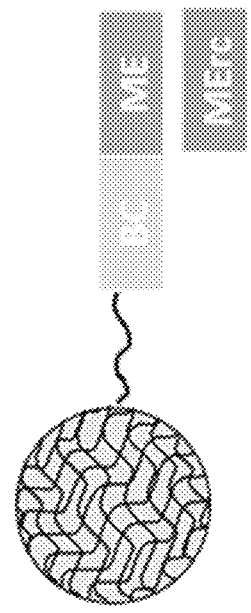

In other embodiments, droplets may be partitioned such that at least some droplets comprise cell lysis reagents, a plurality of transpose molecules, a single cell, and a single gel bead comprising a barcode oligonucleotide. The gel bead may comprise a barcode sequence ("BC") and a transposon end sequence ("ME"). The droplets may then be subjected to conditions such that transposase nucleic acid complexes comprising a transposase molecule and a barcode oligonucleotide are formed in the partition. FIGS. 79A-B illustrate examples of the barcode oligonucleotides. FIG. 79A illustrates a partially double-stranded oligonucleotide releasably attached to a gel bead, the first strand comprising a transposon end sequence, a barcode sequence, and a first primer sequence and a second strand comprising a sequence complementary to the transposon end sequence. FIG. 79B illustrates a partially double-stranded oligonucleotide releasably attached to a gel bead, the first strand comprising a transposon end sequence and a barcode sequence and the second strand comprising a sequence complementary to the transposon end sequence.

Figure 80:
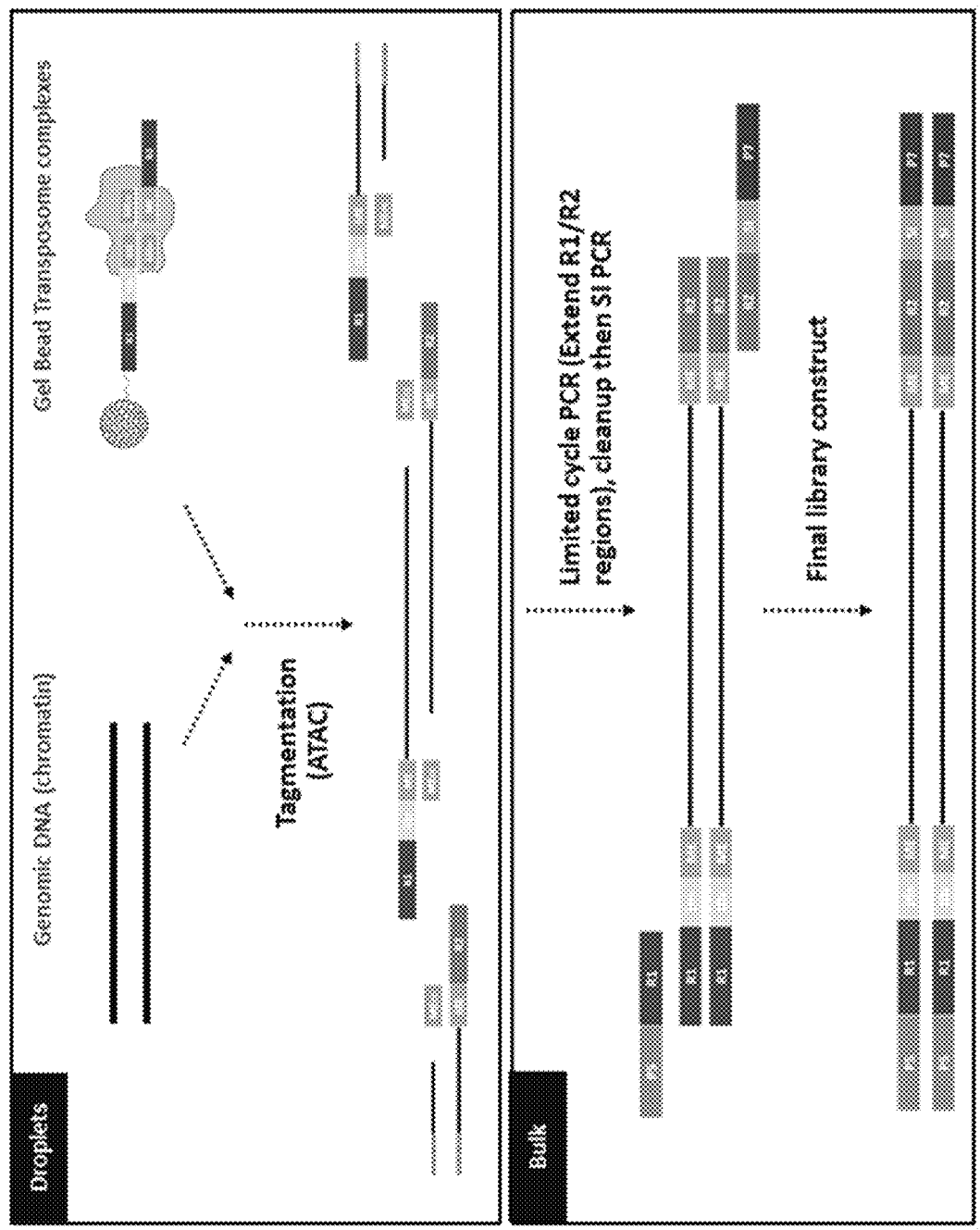
FIG. 80 illustrates a method to generate barcoded nucleic acid fragments suitable for next generation sequencing.

As illustrated in FIG. 80, after the transposase-nucleic acid complex is released from the gel bead (or is formed in the partition in embodiments containing barcode oligonucleotides described with respect to FIGS. 79A-B), the droplet may then be subjected to conditions such that the transposase-nucleic acid complexes integrate the transposon end sequences into the template nucleic acid and fragments the template nucleic acid into double-stranded template nucleic acid fragments flanked by first and second partially double-stranded oligonucleotides. In alternative embodiments, cells (or nuclei) are permeabilized/permeable and the transposase-nucleic acid complexes enter the nucleus to fragment the template nucleic acid. Cells are then lysed to release the fragmented double-stranded template nucleic acid fragments. Because the transposase-nucleic acid complex can only act on a nucleosome-free template, the fragmented double-stranded template nucleic acid fragments are representative of genome-wide areas of accessible chromatin in a single cell.

The fragmented double-stranded template nucleic acid fragments may then be collected from the droplets and processed in bulk to fill any gaps created from the transposition reaction and to generate a library suitable for next generation high throughput sequencing. For example, the fragments, or derivatives thereof, may be subjected to one or more reactions (e.g., nucleic acid amplification) to add functional sequences to facilitate Illumina sequencing, such as in FIG. 80. The fully constructed library may then be sequenced according to any suitable sequencing protocol.

Figure 81A:
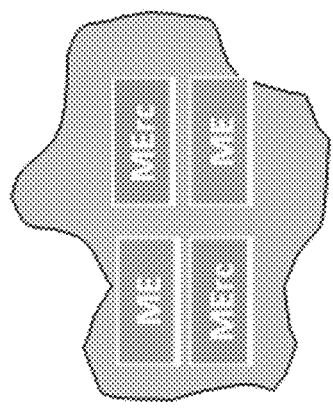
FIGS. 81A-B illustrate examples of a transposase-nucleic acid complex and an exemplary barcoded adaptor releasably attached to a gel bead.
Figure 81B:
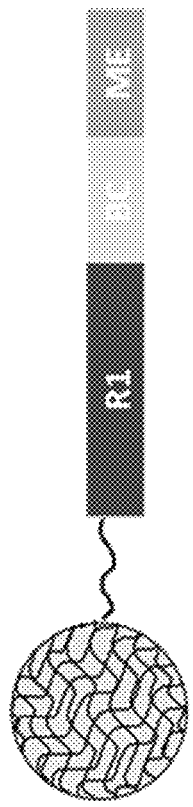

In some instances, nucleic acid fragments from single cells may be barcoded in partitions using transposase-nucleic acid complexes and barcoded adaptors. A plurality of transposase nucleic acid complexes and a plurality of cells of interest (or a plurality of nuclei harvested from cells of interest) may be partitioned such that at least some partitions comprise a single cell (or nucleus), a plurality of transposase nucleic acid complexes comprising a transposon end sequence, and a plurality of barcoded oligonucleotides. A barcoded oligonucleotide may comprise a barcode sequence and a sequencing primer sequence (see, e.g., FIGS. 81A-B). In some cases, the barcode oligonucleotide may further comprise a transposon end sequence. In some cases, the plurality of barcode oligonucleotides may be attached to a gel bead, such as illustrated in FIG. 81B, and partitioned such that at least some partitions comprise a plurality of transposase nucleic acid complexes, a single cell (or nucleus), and a single gel bead.

For example, in some embodiments, droplet emulsion partitions may be generated as described elsewhere herein such that at least some droplets comprise a transposase-nucleic acid complex, cell lysis reagents, a single cell, and a single gel bead comprising a barcoded adaptor. The transposase-nucleic acid complex may comprise a transposase and a pair of double-stranded oligonucleotides. Although the transposase-nucleic acid complexes can be prepared in a variety of different configurations, an example of a transposase-nucleic acid complex is illustrated in FIG. 81A and shows a complex comprising a transposase, a first double-stranded oligonucleotide comprising a transposon end ("mosaic end" or "ME") sequence, and a second double-stranded oligonucleotide comprising a transposon end ("mosaic end" or "ME") sequence.

In the droplet, the cells may be lysed in a manner that releases template nucleic acid molecules from the nucleus into the droplet, but that substantially maintains native chromatin organization. Droplets may then be subjected to conditions such that the barcoded adaptors are released from the gel bead into the aqueous droplet. Although the barcoded adaptors can be prepared in a variety of different configurations, an example of a barcoded adaptor is illustrated in FIG. 81B and shows a single-stranded oligonucleotide comprising a transposon end ("mosaic end" or "ME") sequence, a barcode sequence ("BC"), and a primer sequence ("R1") releasably attached to a gel bead.

After the barcoded adaptors are released from the gel bead, the droplet may then be subjected to conditions such that the transposase-nucleic acid complexes integrate the transposon end sequences into the template nucleic acid and fragment the template nucleic acid into double-stranded template nucleic acid fragments. In alternative embodiments, cells (or nuclei) are permeabilized/permeable and the transposase-nucleic acid complexes enter the nucleus to fragment the template nucleic acid. Cells are then lysed to release the fragmented double-stranded template nucleic acid fragments. Because the transposase-nucleic acid complex can only act on a nucleosome-free template, the fragmented double-stranded template nucleic acid fragments are representative of genome-wide areas of accessible chromatin in a single cell. After transposition and fragmentation, a PCR reaction may be performed to fill any gaps created from the transposition reaction and to add the barcoded adaptors to the ends of the fragmented double-stranded template nucleic acid fragments.

The fragmented double-stranded template nucleic acid fragments may then collected from the droplets and processed in bulk to fragment the barcode-transposed template nucleic acids and to generate a library suitable for next generation high throughput sequencing. For example, the fragments, or derivatives thereof, may be subjected to one or more reactions (e.g., nucleic acid amplification) to add functional sequences to facilitate Illumina sequencing. The fully constructed library may then be sequenced according to any suitable sequencing protocol.

In some instances, transposase-nucleic acid complexes may be generated and combined with a target double-stranded DNA which is fragmented and ligated to adaptor oligonucleotide sequences, in a single reaction step. Traditional tube-based implementations of Tn5-based tagmentation systems typically rely upon sample processing steps that take place in two independent reactions to generate the final transposase-fragmented nucleic acid sample. For example, in Reaction #1, oligonucleotide adaptors containing the Tn5 transposon end sequences and the Tn5 transposase enzyme are incubated to form a transposase-nucleic acid complex. Typically, magnesium (or other divalent cations) is omitted from the reaction buffer to keep the transposases catalytically inactive. In Reaction #2, the transposase-nucleic acid complex from Reaction #1 is combined with a target double-stranded DNA and an appropriate reaction buffer containing magnesium (or other divalent cations) to activate the transposase-nucleic acid complex and cause fragmentation of the target DNA and ligation of the adapter oligonucleotide sequences. While the above-described serial reaction workflow is straightforward, implementing a tagmentation reaction within a single reaction or reaction vessel ("one-pot reaction") can be complicated. Beneficially, the transposition methods described herein can be utilized in a one-pot reaction as described above. These one-pot reactions can be done either in bulk or in discrete partitions, such as a well or droplet.

Figure 82A:
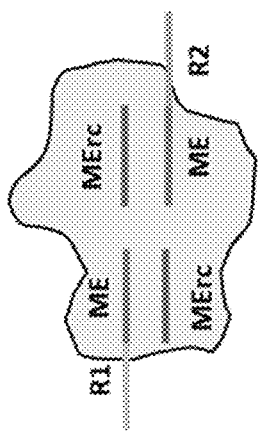
FIGS. 82A-D illustrate examples of a transposase-nucleic acid complex and an exemplary barcoded adaptor, which can be releasably attached to a gel bead.
Figure 82B:
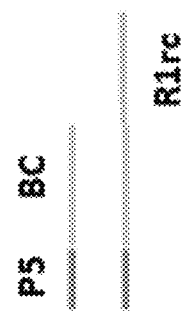
Figure 82C:
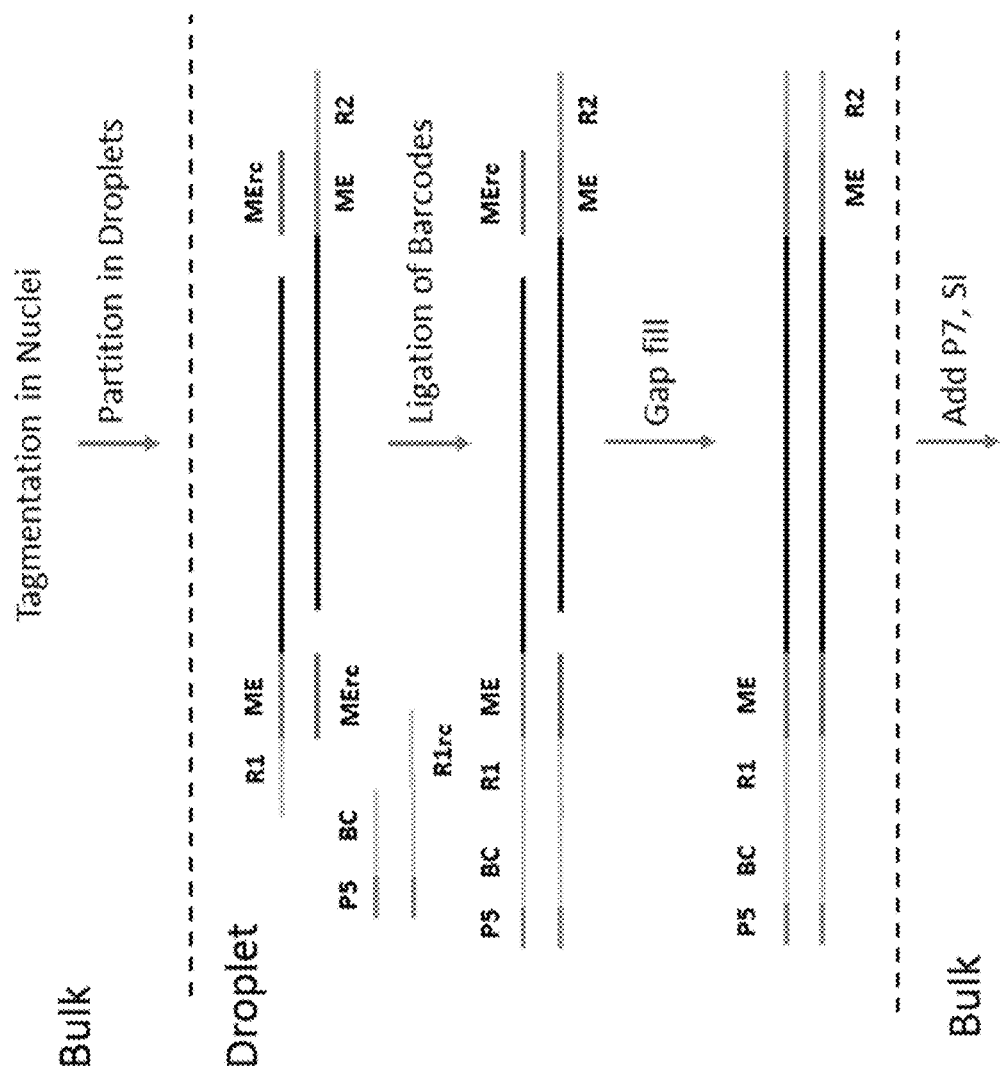

In some instances, nucleic acid fragments may be barcoded using bulk tagmentation (before partitioning) and barcoding by ligation in partitions (e.g., droplets). FIG. 82C illustrates such a method. Intact nuclei are harvested in bulk from cells in a cell population of interest in a manner that substantially maintains native chromatin organization (e.g., using IGEPAL CA-630 mediated cell lysis). Nuclei are then incubated in the presence of a transposase-nucleic acid complex comprising a transposase molecule and two partially double-stranded adaptor oligonucleotides, such as illustrated in FIG. 82A. Alternatively, cells can be permeabilized, allowing the transposase-nucleic acid complex to gain access to the nucleus. FIG. 82A illustrates a transposase-nucleic acid complex comprising a transposase molecule and two partially double-stranded adaptor oligonucleotides. The first adapter oligonucleotide may comprises a double stranded transposon end sequence (ME) and a single stranded Read1 sequencing primer sequence (R1) while the second adapter oligonucleotide may comprise a double stranded transposon end sequence (ME) and a single stranded Read2 sequencing primer sequence (R2). In some cases, the R1 and/or R2 sequencing primer in the first and/or second adapter oligonucleotide, respectively, comprises a TruSeq R1 and/or R2 sequence, or a portion thereof. The transposase-nucleic acid complexes may integrate the adaptors into the template nucleic acid and generate template nucleic acid fragments flanked by the partially double-stranded adaptors, such as illustrated in FIG. 82C. Because the transposase-nucleic acid complex can only act on a nucleosome-free template, the fragmented template nucleic acid fragments are representative of genome-wide areas of accessible chromatin. In some embodiments, the transposase molecules may be inactivated prior to further processing steps.

Nuclei (or cells) comprising the adapter-flanked template nucleic acid fragments may then be partitioned into a plurality of droplets such that at least some droplets comprise (1) a single nucleus (or cell) comprising the adapter-flanked template nucleic acid fragments; and (2) a plurality of partially double-stranded barcode oligonucleotide molecules (e.g., illustrated in FIG. 82B) comprising a doubled stranded barcode sequence (BC), a doubled stranded P5 adapter sequence (P5), and a single stranded sequence complementary to the Read1 sequence (R1rc). In some cases, the partially double-stranded barcode oligonucleotide molecules may be attached to a gel bead and partitioned such that at least some droplets comprise (1) a single nucleus (or cell) and (2) a single gel bead. In addition to the aforementioned components, in some embodiments, the plurality of droplets further comprises reagents (e.g., enzymes and buffers) that facilitate the reactions described below.

Single nucleus containing droplets may then be subjected to conditions to release the adapter-flanked template nucleic acid fragments from the nuclei (e.g., cell lysis). In certain embodiments, where barcode oligonucleotides are attached to a gel bead, droplets are subjected to conditions to cause release of the barcode oligonucleotide molecules from the gel bead (e.g., depolymerization of gel beads, for example, using a reducing agent such as DTT). After release from single nuclei, the adapter-flanked template nucleic acid fragments may be subjected to conditions to phosphorylate the 5' end of the Read1 sequence (e.g., using T4 polynucleotide kinase) for subsequent ligation steps. After phosphorylation, the barcode oligonucleotide molecules may be ligated onto the adapter-flanked template nucleic acid fragments using a suitable DNA ligase enzyme (e.g., T4 or E. coli DNA ligase) and the complementary Read1 sequences in the barcode oligonucleotides and the adapter-flanked template nucleic acid fragments.

After barcode ligation, gaps remaining from the transposition reaction may be filled to generate barcoded, adapter-flanked template nucleic acid fragments. The barcoded, adapter-flanked template nucleic acid fragments may then be released from the droplets and processed in bulk to complete library preparation for next generation high throughput sequencing (e.g., to add sample index (SI) sequences (e.g., i7) and/or further adapter sequences (e.g., P7)). In alternative embodiments, the gap filling reaction is completed in bulk after barcoded, adapter-flanked template nucleic acid fragments have been released from the droplets. The fully constructed library is then sequenced according to a suitable next-generation sequencing protocol (e.g., Illumina sequencing).

Figure 82D:
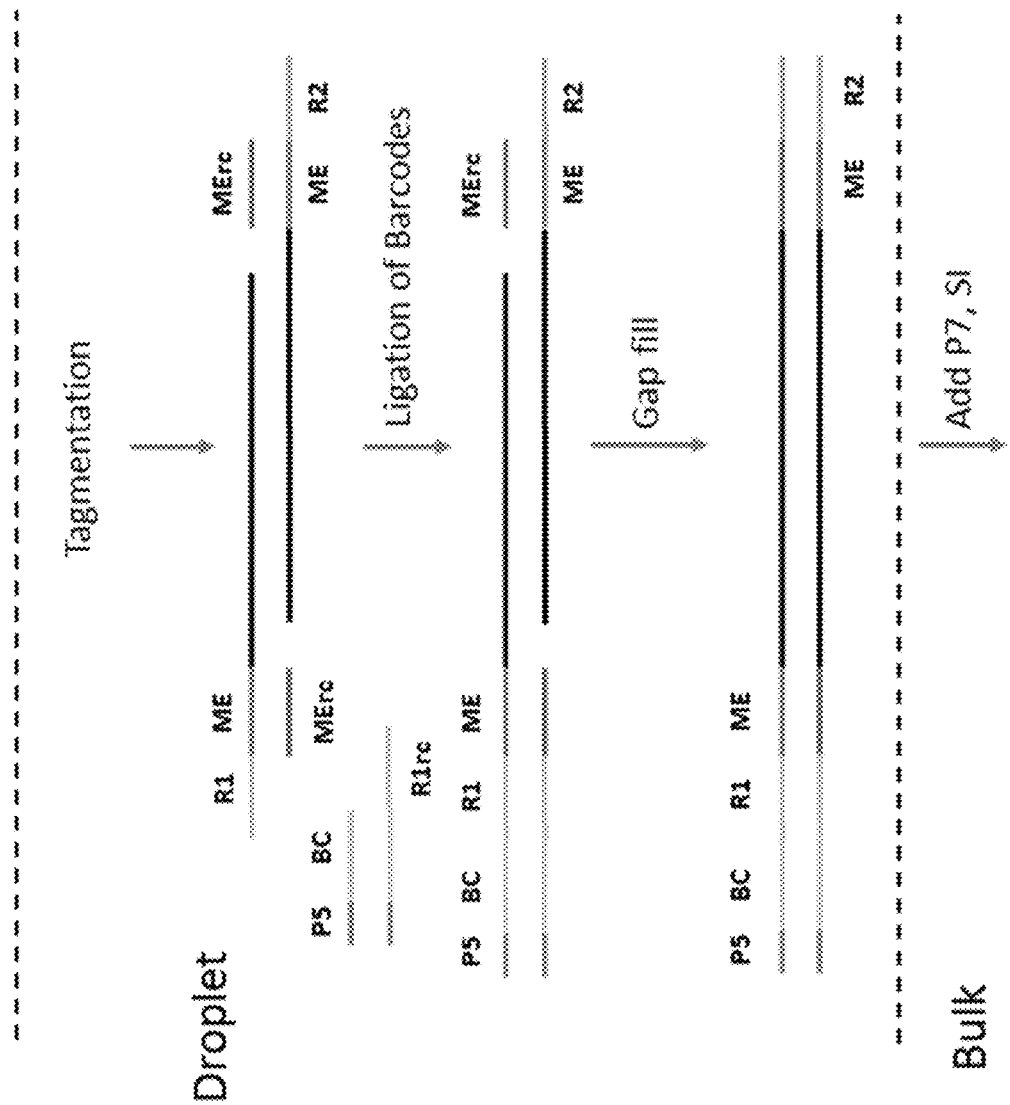

In some instances, tagmentation may be performed in partitions, such as illustrated in FIG. 82D. Cells from a cell population of interest (or nuclei from cells in a cell population of interest) are partitioned into a plurality of droplets such that at least some droplets comprise (1) a single cell (or a single nucleus) comprising a template nucleic acid; and (2) a plurality of partially double-stranded barcode oligonucleotide molecules. A barcode oligonucleotide molecule may comprise a doubled stranded barcode sequence (BC), a doubled stranded P5 adapter sequence (P5), and a single stranded sequence complementary to a Read1 sequence (R1rc) (e.g., FIG. 82B). In some embodiments, the partially double-stranded barcode oligonucleotide molecules are attached to a gel bead and partitioned such that at least some droplets comprise (1) a single cell (or a single nucleus) and (2) a single gel bead. In addition to the aforementioned components, in some embodiments, the plurality of droplets further comprises reagents (e.g., enzymes and buffers) that facilitate the reactions described below.

After partitioning into droplets, the single cells (or nuclei) are lysed to release the template genomic DNA in a manner that substantially maintains native chromatin organization. Droplets are then subjected to conditions to generate a transposase-nucleic acid complex, such as the complex illustrated in FIG. 82A. Alternatively, in some embodiments, a plurality of pre-formed transposase-nucleic acid complexes (e.g., as shown in FIG. 82A) are partitioned into the plurality of droplets. Droplets may then be subjected to conditions such that the transposase-nucleic acid complexes integrate the first and second adapter sequences into the template nucleic acid to generate double-stranded adapter-flanked template nucleic acid fragments. Because the transposase-nucleic acid complex can only act on nucleosome-free DNA, the adapter-flanked template nucleic acid fragments are representative of genome-wide areas of accessible chromatin in a single cell. Alternatively, in some embodiments, the tagmentation reaction is performed in intact nuclei, and the nuclei are lysed after transposition to release the double-stranded adapter-flanked template nucleic acid fragments. After generating the double-stranded adapter-flanked template nucleic acid fragments, the partitions may then be processed as described with respect to FIG. 82C.

In certain embodiments, where barcode oligonucleotides are attached to a gel bead, droplets are subjected to conditions to cause release of the barcode oligonucleotide molecules from the gel bead (e.g., depolymerization of gel beads, for example, using a reducing agent such as DTT). In some embodiments, the transposase molecules are inactivated (e.g., by heat inactivation) prior to further processing steps. The adapter-flanked template nucleic acid fragments may be subjected to conditions to phosphorylate the 5' end of the Read1 sequence (e.g., using T4 polynucleotide kinase) of the adapter-flanked template nucleic acid fragments. After phosphorylation, the barcode oligonucleotide molecules are ligated onto the adapter-flanked template nucleic acid fragments using a suitable DNA ligase enzyme (e.g., T4, 9° N, or E. coli DNA ligase) and the complementary Read1 sequences in the barcode oligonucleotides and the adapter-flanked template nucleic acid fragments.

After barcode ligation, gaps remaining from the transposition reaction may be filled to generate barcoded, adapter-flanked template nucleic acid fragments. The barcoded, adapter-flanked template nucleic acid fragments may then be released from the droplets and processed in bulk to complete library preparation for next generation high throughput sequencing (e.g., to add sample index (SI) sequences (e.g., i7) and/or further adapter sequences (e.g., P7)). In alternative embodiments, the gap filling reaction is completed in bulk after barcoded, adapter-flanked template nucleic acid fragments have been released from the droplets. The fully constructed library may then be sequenced according to a suitable next-generation sequencing protocol (e.g., Illumina sequencing).

In some instances, nucleic acid fragments may be barcoded using bulk tagmentation (before partitioning) and barcoding by linear amplification in partitions (e.g., droplets), as outlined in FIG. 83B. Nuclei are harvested in bulk from cells in a cell population of interest in a manner that substantially maintains native chromatin organization. Alternatively, cells are permeabilized, allowing the transposase-nucleic acid complex to gain access to the nucleus. Nuclei (or permeabilized cells) are then incubated in the presence of a transposase-nucleic acid complex (e.g., as illustrated in FIG. 83B).

Nuclei (or cells) comprising the adapter-flanked template nucleic acid fragments are then partitioned into a plurality of droplets such that at least some droplets comprise (1) a single nucleus (or cell) comprising the adapter-flanked template nucleic acid fragments; and (2) a plurality of single-stranded barcode oligonucleotide molecules comprising a transposon end sequence (ME), a Read1 sequence (R1), or a portion thereof, a barcode sequence (BC), and a P5 adapter sequence (P5). FIG. 83A illustrates an example of a single-stranded barcode oligonucleotide molecule. In some embodiments, the single-stranded barcode oligonucleotide molecules are attached to a gel bead and partitioned such that at least some droplets comprise (1) a single nucleus (or cell) comprising the adapter-flanked template nucleic acid fragments and (2) a single gel bead. In addition to the aforementioned components, in some embodiments, the plurality of droplets further comprises reagents (e.g., enzymes and buffers) that facilitate the reactions described below.

Single nucleus containing droplets are then subjected to conditions to release the adapter-flanked template nucleic acid fragments from the nuclei. After the adapter-flanked template nucleic acid fragments are released, gaps from the transposition reaction are filled with a suitable enzyme. In certain embodiments, where barcode oligonucleotides are attached to a gel bead, droplets are subjected to conditions to cause release of the barcode oligonucleotide molecules from the gel bead (e.g., depolymerization of gel beads, for example, using a reducing agent such as DTT). Gap-filled adapter-flanked template nucleic acid fragments may then be subjected to a linear amplification reaction using the single-stranded barcode oligonucleotide molecules as primers to generate barcoded, adapter-flanked template nucleic acid fragments.

The barcoded, adapter-flanked template nucleic acid fragments may then be released from the droplets and processed in bulk to complete library preparation for next generation high throughput sequencing (e.g., to add sample index (SI) sequences (e.g., i7) and/or further adapter sequences (e.g., P7)). The fully constructed library may then be sequenced according to a suitable next-generation sequencing protocol (e.g., Illumina sequencing).

Figure 84:
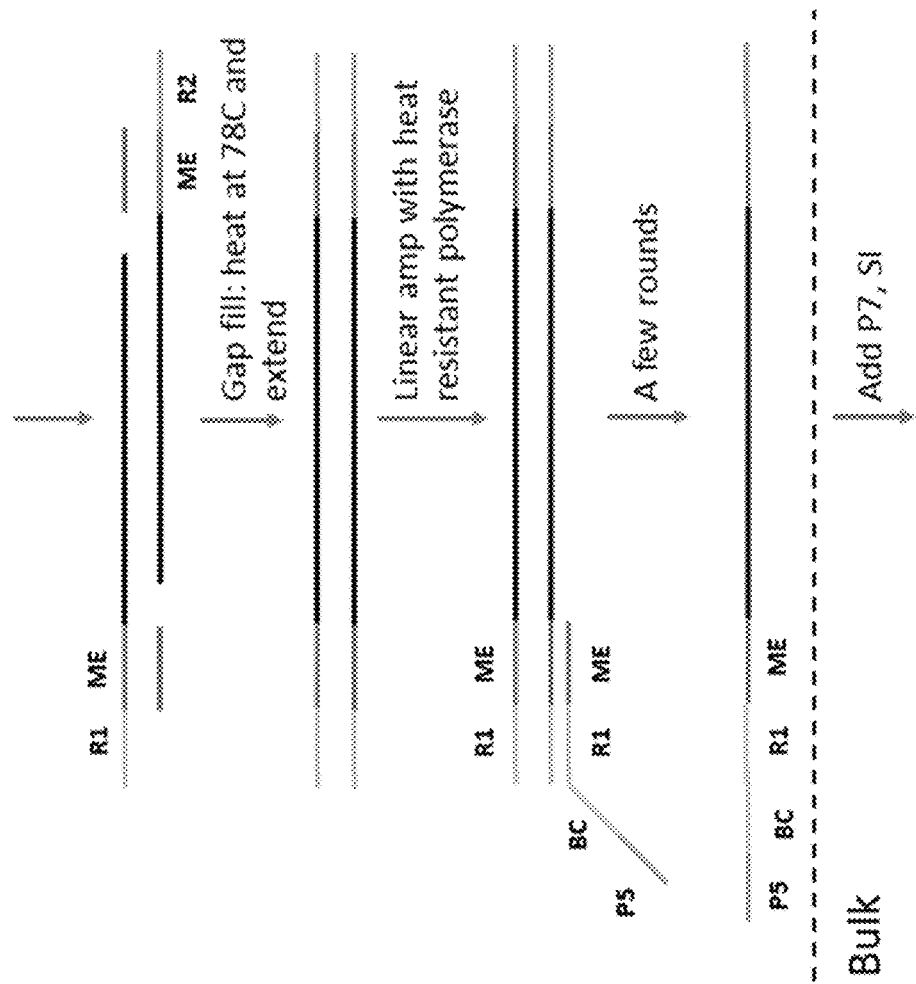
FIG. 84 illustrates an example of an in-partition transposition and barcoding scheme.

In some instances, tagmentation may be performed in partitions, such as illustrated in FIG. 84, and linear amplification performed thereafter. Cells from a cell population of interest (or intact nuclei from cells in a cell population of interest) may be partitioned into a plurality of droplets such that at least some droplets comprise (1) a single cell (or a single nucleus) comprising a template nucleic acid; and (2) a plurality of single-stranded barcode oligonucleotide molecules (e.g., as illustrated in FIG. 83A) comprising a transposon end sequence (ME), a Read1 sequence (R1), a barcode sequence (BC), and a P5 adapter sequence (P5). In some embodiments, the single-stranded barcode oligonucleotide molecules may be attached to a gel bead and partitioned such that at least some droplets comprise (1) a single cell (or a single nucleus) and (2) a single gel bead. In addition to the aforementioned components, in some embodiments, the plurality of droplets further comprises reagents (e.g., enzymes and buffers) that facilitate the reactions described below.

After partitioning into droplets, the single cells (or nuclei) may be lysed to release the template genomic DNA in a manner that substantially maintains native chromatin organization. In certain embodiments, where barcode oligonucleotides are attached to a gel bead, droplets are subjected to conditions to cause release of the barcode oligonucleotide molecules from the gel bead (e.g., depolymerization of gel beads, for example, using a reducing agent such as DTT). The droplets may then be subjected to conditions to generate a transposase-nucleic acid complex (e.g., complex illustrated in FIG. 82A). Alternatively, in some embodiments, a plurality of pre-formed transposase-nucleic acid complexes is partitioned into the plurality of droplets. Droplets may then be subjected to conditions such that the transposase-nucleic acid complexes integrate the first and second adapter sequences into the template nucleic acid to generate double-stranded adapter-flanked template nucleic acid fragments. Because the transposase-nucleic acid complex can only act on nucleosome-free DNA, the adapter-flanked template nucleic acid fragments may be representative of genome-wide areas of accessible chromatin in a single cell. Alternatively, in some embodiments, the tagmentation reaction is performed in intact nuclei, and the nuclei are lysed to release the double-stranded adapter-flanked template nucleic acid fragments.

Samples may then be processed generally as described with respect to FIG. 83B. After tagmentation, gaps from the transposition reaction may be filled with a suitable gap-filling enzyme. Gap-filled adapter-flanked template nucleic acid fragments may then be subjected to a linear amplification reaction using the single-stranded barcode oligonucleotide molecules as primers to generate barcoded, adapter-flanked template nucleic acid fragments. The barcoded, adapter-flanked template nucleic acid fragments may then be released from the droplets and processed in bulk to complete library preparation for next generation high throughput sequencing (e.g., to add sample index (SI) sequences (e.g., i7) and/or further adapter sequences (e.g., P7)). The fully constructed library may be sequenced according to a suitable next-generation sequencing protocol (e.g., Illumina sequencing).

Figures 85A, 85B:
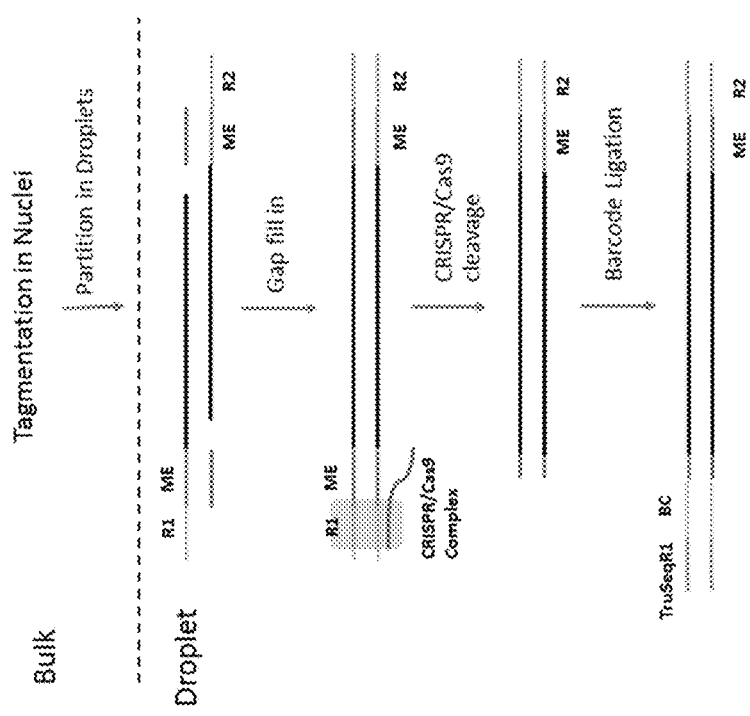
FIGS. 85A-C illustrate an example of a barcoding scheme.

In some instances, nucleic acid fragments may be generated using bulk tagmentation and CRISPR/Cas9 cleavage in partitions (e.g., droplets), as illustrated in FIG. 85B. Nuclei are harvested in bulk from cells in a cell population of interest in a manner that substantially maintains native chromatin organization. Alternatively, cells are permeabilized, allowing the transposase-nucleic acid complex to gain access to the nucleus. Nuclei are then incubated in the presence of a transposase-nucleic acid complex (e.g., complex in FIG. 82A). In some embodiments, after transposition, the transposase is inactivated or dissociated from the adapter-flanked template nucleic acid fragments.

Nuclei (or cells) comprising the adapter-flanked template nucleic acid fragments are then partitioned into a plurality of droplets such that at least some droplets comprise (1) a single nucleus comprising the adapter-flanked template nucleic acid fragments; (2) a plurality of double-stranded barcode oligonucleotide molecules (e.g., FIG. 85A) comprising a barcode sequence (BC) and a TruSeqR1 sequencing primer sequence; and (3) a plurality of CRISPR/Cas9 complexes comprising a Cas9 nuclease and a synthetic guide RNA (gRNA) that targets the Read1/ME adapter sequence in the adapter-flanked template nucleic acid fragments. In some embodiments, the double-stranded barcode oligonucleotide molecules are attached to a gel bead and partitioned such that at least some droplets comprise (1) a single nucleus; (2) a single gel bead; and (3) a plurality of CRISPR/Cas9 complexes. In addition to the aforementioned components, in some embodiments, the plurality of droplets further comprises reagents (e.g., enzymes and buffers) that facilitate the reactions described below.

Single nucleus containing droplets may then be subjected to conditions to release the adapter-flanked template nucleic acid fragments from the nuclei. After the adapter-flanked template nucleic acid fragments are released, gaps from the transposition reaction may be filled with a suitable gap-filling enzyme. Gap-filled, adapter-flanked template nucleic acid fragments may be subjected to Cas9-mediated cleavage of the R1/ME adaptor, or some portion thereof. In certain embodiments, where barcode oligonucleotides are attached to a gel bead, droplets are subjected to conditions to cause release of the barcode oligonucleotide molecules from the gel bead (e.g., depolymerization of gel beads, for example, using a reducing agent such as DTT). The barcode oligonucleotides may be ligated onto the R1 adapter-cleaved ends of the template nucleic acid fragments to generate barcoded, adapter-flanked template nucleic acid fragments.

The barcoded, adapter-flanked template nucleic acid fragments may be released from the droplets and processed in bulk to complete library preparation for next generation high throughput sequencing (e.g., subjecting the fragments, or derivatives thereof, to one or more reactions (e.g., nucleic acid amplification) to add functional sequences to facilitate Illumina sequencing). In some embodiments, a second CRISPR/Cas9 mediated cleavage event using a synthetic guide RNA (gRNA) that targets the Read2/ME adapter sequence may be performed either in the partition or in bulk after release from the partition. The fully constructed library may be sequenced according to any suitable sequencing protocol.

Figure 85C:
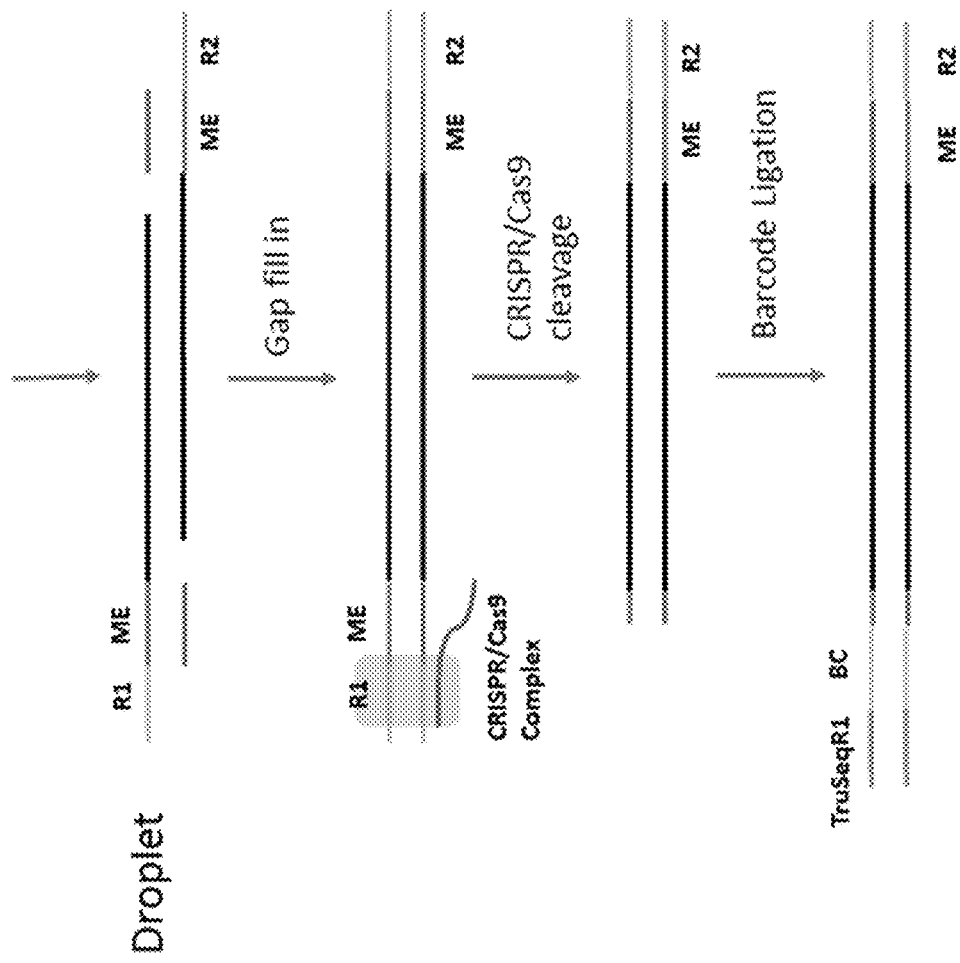

In some instances, tagmentation and CRISPR/Cas9 cleavage may be performed in partitions, such as illustrated in FIG. 85C. Cells from a cell population of interest (or intact nuclei from cells in a cell population of interest) may be partitioned into a plurality of droplets such that at least some droplets comprise (1) a single cell (or a single nucleus) comprising a template nucleic acid; (2) a plurality of double-stranded barcode oligonucleotide molecules comprising a barcode sequence (BC) and a TruSeqR1 sequencing primer sequence (e.g., FIG. 85A); and (3) a plurality of CRISPR/Cas9 complexes comprising a Cas9 nuclease and a synthetic guide RNA (gRNA) that targets the Read1/ME adapter sequence in the adapter-flanked template nucleic acid fragments. In some embodiments, the double-stranded barcode oligonucleotide molecules are attached to a gel bead and partitioned such that at least some droplets comprise (1) a single cell (or single nucleus); (2) a single gel bead; and (3) a plurality of CRISPR/Cas9 complexes. In addition to the aforementioned components, in some embodiments, the plurality of droplets further comprises reagents (e.g., enzymes and buffers) that facilitate the reactions described below.

After partitioning into droplets, the single cells (or nuclei) may be lysed to release the template genomic DNA in a manner that substantially maintains native chromatin organization. Droplets may then be subjected to conditions to generate a transposase-nucleic acid complex (e.g., FIG. 82A). Alternatively, in some embodiments, a plurality of pre-formed transposase-nucleic acid are partitioned into the plurality of droplets. The droplets may then be subjected to conditions such that the transposase-nucleic acid complexes integrate the first and second adapter sequences into the template nucleic acid to generate double-stranded adapter-flanked template nucleic acid fragments. Because the transposase-nucleic acid complex can only act on nucleosome-free DNA, the adapter-flanked template nucleic acid fragments are representative of genome-wide areas of accessible chromatin in a single cell. Alternatively, in some embodiments, the tagmentation reaction is performed in intact nuclei, and the nuclei are lysed to release the double-stranded adapter-flanked template nucleic acid fragments.

Samples may then be processed as described with respect to FIG. 85B. After tagmentation, gaps from the transposition reaction may be filled with a suitable gap-filling enzyme. Gap-filled adapter-flanked template nucleic acid fragments may be subjected to Cas9-mediated cleavage of the R1 adaptor. In certain embodiments, where barcode oligonucleotides are attached to a gel bead, droplets may be subjected to conditions to cause release of the barcode oligonucleotide molecules from the gel bead (e.g., depolymerization of gel beads, for example, using a reducing agent such as DTT). The barcode oligonucleotides may be ligated onto the R1 adapter-cleaved ends of the template nucleic acid fragments to generate barcoded, adapter-flanked template nucleic acid fragments.

The barcoded, adapter-flanked template nucleic acid fragments may be released from the droplets and processed in bulk to complete library preparation for next generation high throughput sequencing (e.g., subjecting the fragments, or derivatives thereof, to one or more reactions (e.g., nucleic acid amplification) to add functional sequences to facilitate Illumina sequencing). In some embodiments, a second CRISPR/Cas9 mediated cleavage event using a synthetic guide RNA (gRNA) that targets the Read2/ME adapter sequence may be performed either in the partition or in bulk after release from the partition. The fully constructed library may be sequenced according to any suitable sequencing protocol.

In some instances, nucleic acid fragments may be barcoded using bulk tagmentation (prior to partitioning) and CRISPR/CAS9 cleavage in partitions (e.g., droplets) using Y-adaptors, as illustrated in FIG. 86B. Nuclei are harvested in bulk from cells in a cell population of interest in a manner that substantially maintains native chromatin organization. Alternatively, cells are permeabilized, allowing the transposase-nucleic acid complex to gain access to the nucleus. Nuclei are then incubated in the presence of a transposase-nucleic acid complex (e.g., FIG. 82A). In some embodiments, after transposition, the transposase is inactivated or dissociated from the adapter-flanked template nucleic acid fragments.

Nuclei (or cell) comprising the adapter-flanked template nucleic acid fragments may be partitioned into a plurality of droplets such that at least some droplets comprise (1) a single nucleus comprising the adapter-flanked template nucleic acid fragments; (2) a plurality of Y-adaptor barcode oligonucleotide molecules (e.g., such as illustrated in FIG. 86A) comprising a barcode sequence (BC), a Read1 sequencing primer sequence (R1), and a Read2 sequencing primer sequence (R2); (3) a first plurality of CRISPR/Cas9 complexes comprising a Cas9 nuclease and a synthetic guide RNA (gRNA) that targets the Read1/ME adapter sequence in the adapter-flanked template nucleic acid fragments; and (4) a second plurality of CRISPR/Cas9 complexes comprising a Cas9 nuclease and a synthetic guide RNA (gRNA) that targets the Read2/ME adapter sequence in the adapter-flanked template nucleic acid fragments. In some embodiments, the Y-adaptor barcode oligonucleotide molecules may be attached to a gel bead (e.g., such as illustrated in FIG. 68A) and partitioned such that at least some droplets comprise (1) a single nucleus; (2) a single gel bead; (3) the first plurality of CRISPR/Cas9 complexes; and (4) the second plurality of CRISPR/Cas9 complexes. In addition to the aforementioned components, in some embodiments, the plurality of droplets may further comprise reagents (e.g., enzymes and buffers) that facilitate the reactions described below.

Single nucleus containing droplets may then be subjected to conditions to release the adapter-flanked template nucleic acid fragments from the nuclei. After the adapter-flanked template nucleic acid fragments are released, gaps from the transposition reaction may be filled with a suitable gap-filling enzyme. Gap-filled adapter-flanked template nucleic acid fragments may be subjected to Cas9-mediated cleavage of the R1 and R2 adaptors, or a portion thereof. In certain embodiments, where barcode oligonucleotides are attached to a gel bead, droplets are subjected to conditions to cause release of the barcode oligonucleotide molecules from the gel bead (e.g., depolymerization of gel beads, for example, using a reducing agent such as DTT). The Y-adaptor barcode oligonucleotides may be ligated onto the R1/R2 adapter-cleaved ends of the template nucleic acid fragments to generate barcoded, adapter-flanked template nucleic acid fragments.

The barcoded, adapter-flanked template nucleic acid fragments may then be released from the droplets and processed in bulk to complete library preparation for next generation high throughput sequencing (e.g., subjecting the fragments, or derivatives thereof, to one or more reactions (e.g., nucleic acid amplification) to add functional sequences to facilitate Illumina sequencing). The fully constructed library may be sequenced according to any suitable sequencing protocol.

Figure 86C:
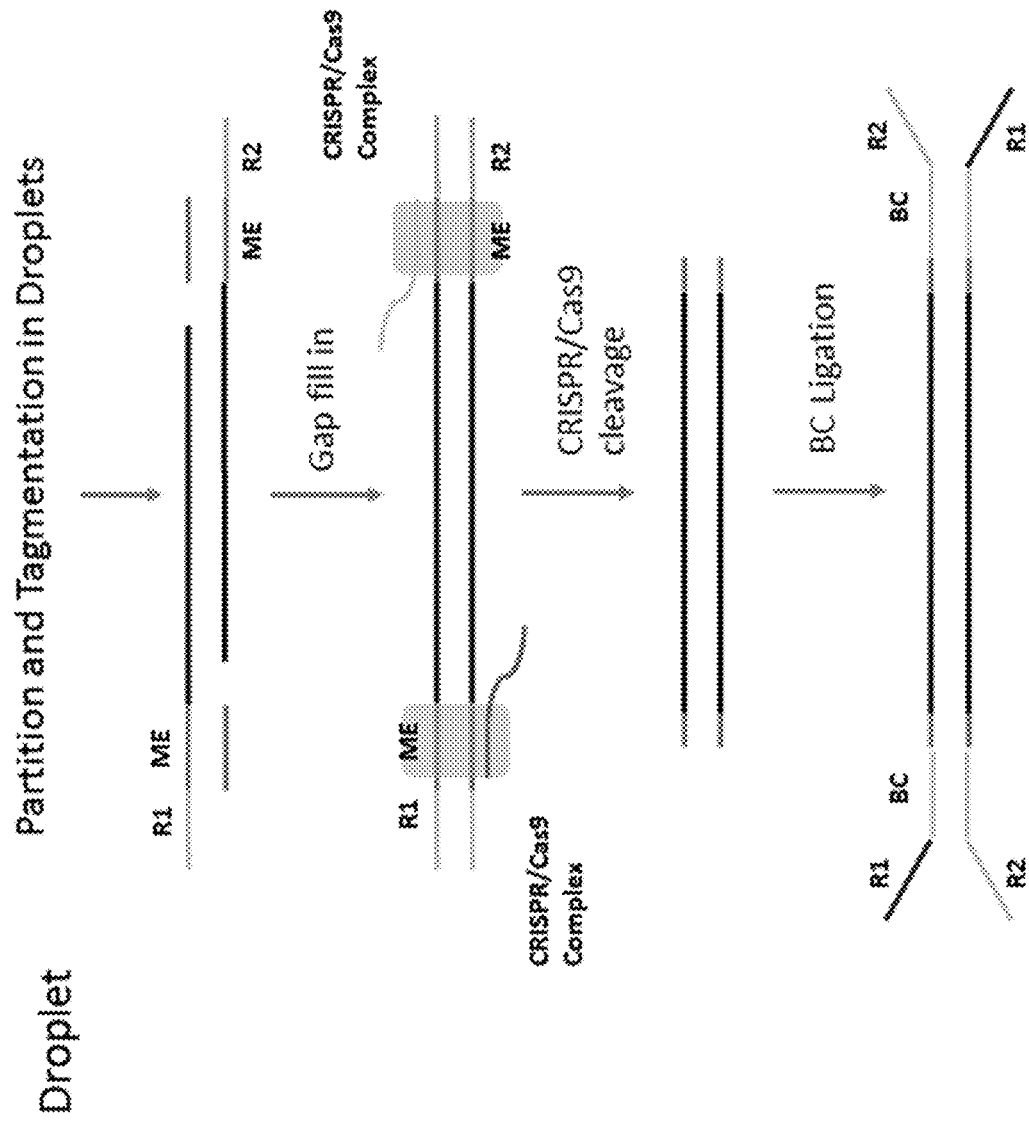

In some instances, tagmentation and CRISPR/Cas9 cleavage may be performed in partitions using Y-adapters, as illustrated in FIG. 86C. Cells from a cell population of interest (or intact nuclei from cells in a cell population of interest) may be partitioned into a plurality of droplets such that at least some droplets comprise (1) a single cell (or a single nucleus) comprising a template nucleic acid; (2) a plurality of Y-adaptor barcode oligonucleotide molecules (e.g., FIG. 86A) comprising a barcode sequence (BC), a Read1 sequencing primer sequence (R1), and a Read2 sequencing primer sequence (R2); (3) a first plurality of CRISPR/Cas9 complexes comprising a Cas9 nuclease and a synthetic guide RNA (gRNA) that targets the Read1/ME adapter sequence in the adapter-flanked template nucleic acid fragments; and (4) a second plurality of CRISPR/Cas9 complexes comprising a Cas9 nuclease and a synthetic guide RNA (gRNA) that targets the Read2/ME adapter sequence in the adapter-flanked template nucleic acid fragments. In some cases, the Y-adaptor barcode oligonucleotide molecules may be attached to a gel bead and partitioned such that at least some droplets comprise (1) a single cell (or single nucleus); (2) a single gel bead; (3) the first plurality of CRISPR/Cas9 complexes; and (4) the second plurality of CRISPR/Cas9 complexes. In addition to the aforementioned components, in some embodiments, the plurality of droplets may further comprise reagents (e.g., enzymes and buffers) that facilitate the reactions described below.

After partitioning into droplets, the single cells (or nuclei) may be lysed to release the template genomic DNA in a manner that substantially maintains native chromatin organization. The droplets may then subjected to conditions to generate a transposase-nucleic acid complex (e.g., FIG. 82A). Alternatively, in some embodiments, a plurality of pre-formed transposase-nucleic acid complexes as shown in FIG. 82A are partitioned into the plurality of droplets. Droplets may then be subjected to conditions such that the transposase-nucleic acid complexes integrate the first and second adapter sequences into the template nucleic acid to generate double-stranded adapter-flanked template nucleic acid fragments. Because the transposase-nucleic acid complex can only act on nucleosome-free DNA, the adapter-flanked template nucleic acid fragments are representative of genome-wide areas of accessible chromatin in a single cell. Alternatively, in some embodiments, the tagmentation reaction is performed in intact nuclei, and the nuclei are lysed to release the double-stranded adapter-flanked template nucleic acid fragments.

The samples may then processed as described with respect to FIG. 86B. After tagmentation, gaps from the transposition reaction may be filled with a suitable gap-filling enzyme. Gap-filled adapter-flanked template nucleic acid fragments may be subjected to Cas9-mediated cleavage of the R1 and R2 adaptors, or a portion thereof. In certain embodiments, where barcode oligonucleotides are attached to a gel bead, the droplets may be subjected to conditions to cause release of the barcode oligonucleotide molecules from the gel bead (e.g., depolymerization of gel beads, for example, using a reducing agent such as DTT). The Y-adaptor barcode oligonucleotides may be ligated onto the R1/R2 adapter-cleaved ends of the template nucleic acid fragments to generate barcoded, adapter-flanked template nucleic acid fragments.

The barcoded, adapter-flanked template nucleic acid fragments may be released from the droplets and processed in bulk to complete library preparation for next generation high throughput sequencing (e.g., subjecting the fragments, or derivatives thereof, to one or more reactions (e.g., nucleic acid amplification) to add functional sequences to facilitate Illumina sequencing). The fully constructed library may be sequenced according to any suitable sequencing protocol.

A multi-assay may barcode nucleic acid fragments and other analytes, such as internal proteins, surface proteins, mRNA, perturbation agents, any other type of analyte described herein in the single cell, or any combination thereof. For example, such analytes (from the same cell) may be barcoded in a partition.

Cells from a cell population of interest (or intact nuclei from cells in a cell population of interest) may be partitioned into a plurality of droplets such that at least some droplets comprise (1) a single cell (or a single nucleus) comprising template analyte molecules (e.g., internal proteins, surface proteins, mRNA, DNA, perturbation agents, etc.); (2) a plurality of first barcoded oligonucleotide molecules comprising a barcode sequence; (3) a plurality of transposase molecules, and (4) a plurality of second barcoded oligonucleotide molecules comprising a barcode sequence and a capture probe. In addition to the aforementioned components, in some embodiments, the droplets may further comprise reagents (e.g., enzymes and buffers) that facilitate various reactions. For example, for multi-assays designed to probe mRNA, the partition may comprise a plurality of reverse transcriptase molecules. In some embodiments, the barcode sequence from the first barcoded oligonucleotide and the barcode sequence from the second barcoded oligonucleotide is the same. In some embodiments, the barcode sequence from the first barcoded oligonucleotide and the barcode sequence from the second barcoded oligonucleotide are different.

In some embodiments, the plurality of first barcoded oligonucleotides and the plurality of second barcoded oligonucleotides may be attached to a gel bead and partitioned such that at least some droplets comprise (1) a single cell (or single nucleus); (2) a single gel bead comprising the first and second plurality of barcoded oligonucleotides; (3) a plurality of transposase molecules; and (4) other reagents (e.g., enzymes or buffers). In other embodiments, the plurality of first barcoded oligonucleotides are attached to a first gel bead while the plurality of second barcoded oligonucleotides are attached to a second gel bead and partitioned such that at least some droplets comprise (1) a single cell (or single nucleus); (2) a single first gel bead; (2) a single second gel bead; (3) a plurality of transposase molecules; and (4) other reagents.

In certain embodiments, the plurality of first barcoded oligonucleotides are attached to a gel bead while the plurality of second barcoded oligonucleotides are attached to a plurality of magnetic beads, wherein the plurality of magnetic beads are embedded within the gel bead or in the cell bead as described herein. Continuing these embodiments, the abovementioned components may be partitioned such that at least some droplets comprise: (1) a single cell (or single nucleus); (2) a single gel bead comprising (i) a plurality of first barcoded oligonucleotides attached to the single gel bead; and (ii) a plurality of magnetic particles embedded within the single gel bead or cell bead, wherein the magnetic particles comprise the second barcode oligonucleotide attached thereto; (3) a plurality of transposase molecules; and (4) other reagents. FIGS. 17A-B illustrates an example of a bead with embedded magnetic beads. Similarly, in other embodiments, the second barcode oligonucleotides are attached to the gel bead while the first oligonucleotides are attached to a plurality of magnetic particles embedded within the gel bead or cell bead.

The first barcoded oligonucleotide and related nucleic acid processing steps can take on the structure of any of the aforementioned methods or systems related to barcoding nucleic acid fragments described herein and may include additional components as described herein. For instance, in some embodiments, the first barcoded oligonucleotide may comprises a barcode sequence and a transposon end sequence (e.g., a ME sequence) and is, for example, (1) a forked adapter such as those described with respect to FIGS. 65A-B; (2) a T7-containing oligonucleotide such as those described with respect to FIG. 71; or (3) a barcoded oligonucleotide such as those described with respect to (i) FIG. 81B; (ii) FIGS. 83A-B; and (iii) FIG. 84. In other embodiments, the first barcoded oligonucleotide comprises a barcode sequence and is, for example, (1) a forked adapter such as those described with respect to FIGS. 68A-B or FIGS. 86A-C; or (2) a barcoded oligonucleotide such as those described with respect to FIGS. 82A-C or FIGS. 85A-C.

The second barcoded oligonucleotide may comprise a barcode sequence and a capture probe. The capture probe may comprise a capture sequence configured to capture DNA or RNA, such as, for example, an oligo(dT) sequence, a random primer sequence (e.g., a random hexamer), or a gene-specific sequence. The capture probe may be configured to capture antibodies with a capture sequence. Alternatively, the capture probe may comprise an antibody configured to capture proteins. The capture probe may be a targeted probe. The capture probe may comprise an adaptor. The capture probe may be a general or random probe. The capture probe may be configured to capture any type of analyte described herein (e.g., metabolites, perturbation agents, etc.).

In some instances, after partitioning into droplets, the single cells (or nuclei) may be lysed to release template genomic DNA and template RNA (e.g., cytoplasmic mRNA or nuclear mRNA) in a manner that substantially maintains native chromatin organization of the genomic DNA. In certain embodiments, where barcode oligonucleotides are attached to a gel bead, the droplets may be subjected to conditions to cause release of barcode oligonucleotide molecules from the gel bead (e.g., depolymerization of gel beads, for example, using a reducing agent such as DTT). The droplets may then be subjected to conditions to generate a transposase-nucleic acid complex as described elsewhere herein. Alternatively, in some embodiments, a plurality of pre-formed transposase-nucleic acid complexes may be partitioned into the plurality of droplets. The droplets may be subjected to conditions such that the transposase-nucleic acid complexes generate double-stranded template genomic DNA fragments.

The transposition reaction can take on the structure of any of the methods described elsewhere herein to generate double-stranded template genomic DNA fragments flanked by a wide variety of functional sequences and suitable for a number of downstream processing steps. For example, in some embodiments, the transposition reaction can directly integrate the barcode sequence into the template genomic DNA fragments, while, in other embodiments, the barcode sequence can be added to template genomic DNA fragments subsequent to the transposition reaction (such as by ligation). Because the transposase-nucleic acid complex can only act on nucleosome-free DNA, the template genomic DNA fragments are representative of genome-wide areas of accessible chromatin in a single cell. Alternatively, in some embodiments, the transposition reaction can be performed in intact nuclei, and the nuclei can be lysed to release the adapter-flanked template genomic DNA fragments. Alternatively, in some embodiments, the transposition reaction may be performed in bulk in intact nuclei and a single nucleus comprising template genomic DNA fragments may be partitioned and processed as described elsewhere herein. In some embodiments, gaps from the transposition reaction may be filled in-partition (e.g., within the droplet) with a suitable gap-filling enzyme. In other embodiments, a gap-filling reaction may be performed in bulk after the double-stranded, barcoded adapter-flanked DNA fragments have been released from the partition.

The droplets may then be subjected to conditions to generate barcoded analytes (e.g., mRNA, proteins, perturbation agents, metabolites, etc.). In an example, where the multi-assay is directed to capturing RNA, the capture probe in the second barcode oligonucleotide may be a capture sequence. Single-stranded, barcoded cDNA molecules may be generated from the template RNA using the capture sequence from the second barcode oligonucleotide to prime the reverse transcription reaction (e.g., an oligo (dT) sequence). In some embodiments, second strand cDNA is generated (e.g., through a template switching oligonucleotide or through random priming) to generate double-stranded, barcoded cDNA molecules. In some embodiments, the template switching oligonucleotide also comprises a barcode sequence such that both the 5' and 3' end of the cDNA comprise a barcode sequence. The barcode sequence on the 5' and 3' end can be the same barcode sequence or the 5' end can have a different barcode sequence than the 3' end. In other embodiments, the plurality of second barcode oligonucleotide molecules is omitted and replaced with plurality of second oligonucleotide molecules comprising a capture sequence and no barcode sequence. Continuing with these embodiments, first strand cDNA molecules are generated using the capture sequence while second strand cDNA is generated through use of a barcoded template switching oligonucleotide to barcode the 5' end of the template RNA. In some embodiments, an in-droplet amplification reaction, such as linear amplification, is performed on the adapter-flanked DNA fragments, the barcoded cDNA molecules, or both the adapter-flanked DNA fragments and the barcoded cDNA molecules. In some embodiments, a barcode oligonucleotide is directly ligated onto the template RNA.

Figure 87A:
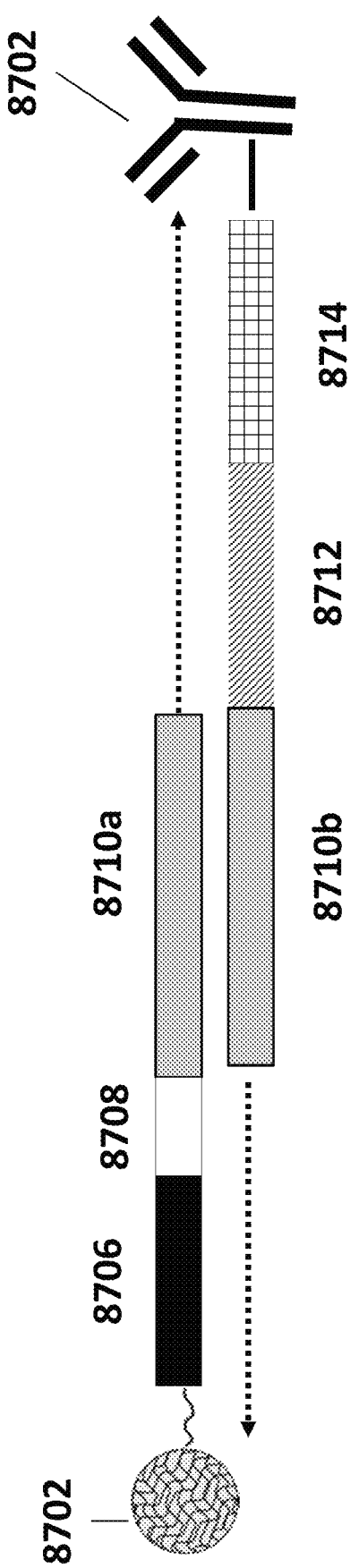
FIGS. 87A-87B illustrates examples of a barcoded antibody.
Figure 87B:
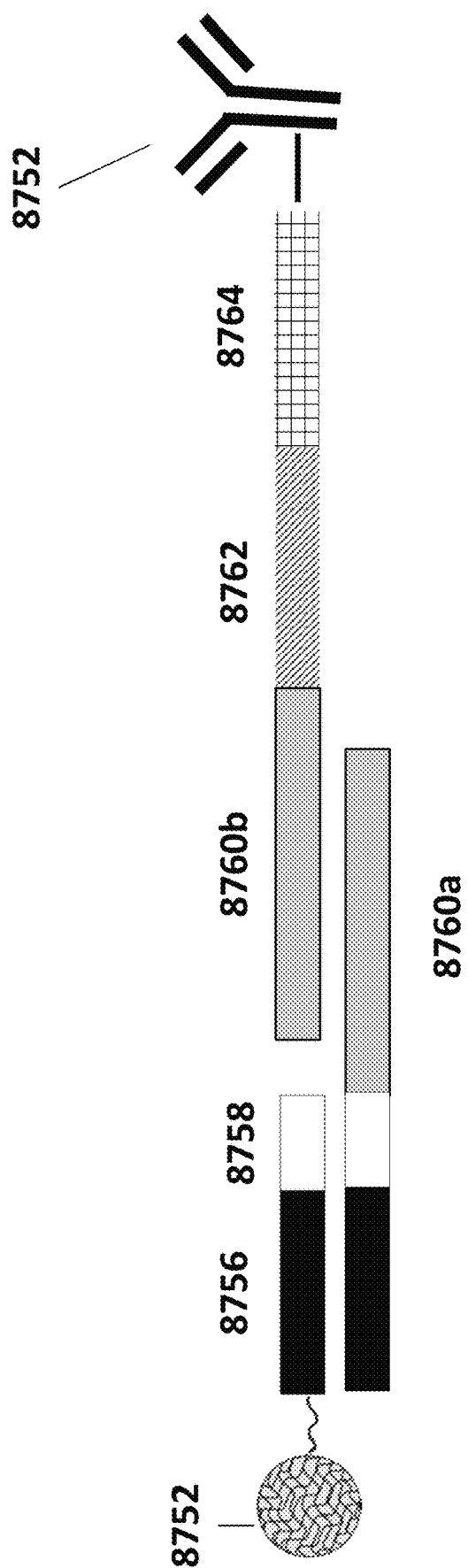
Figure 88A:
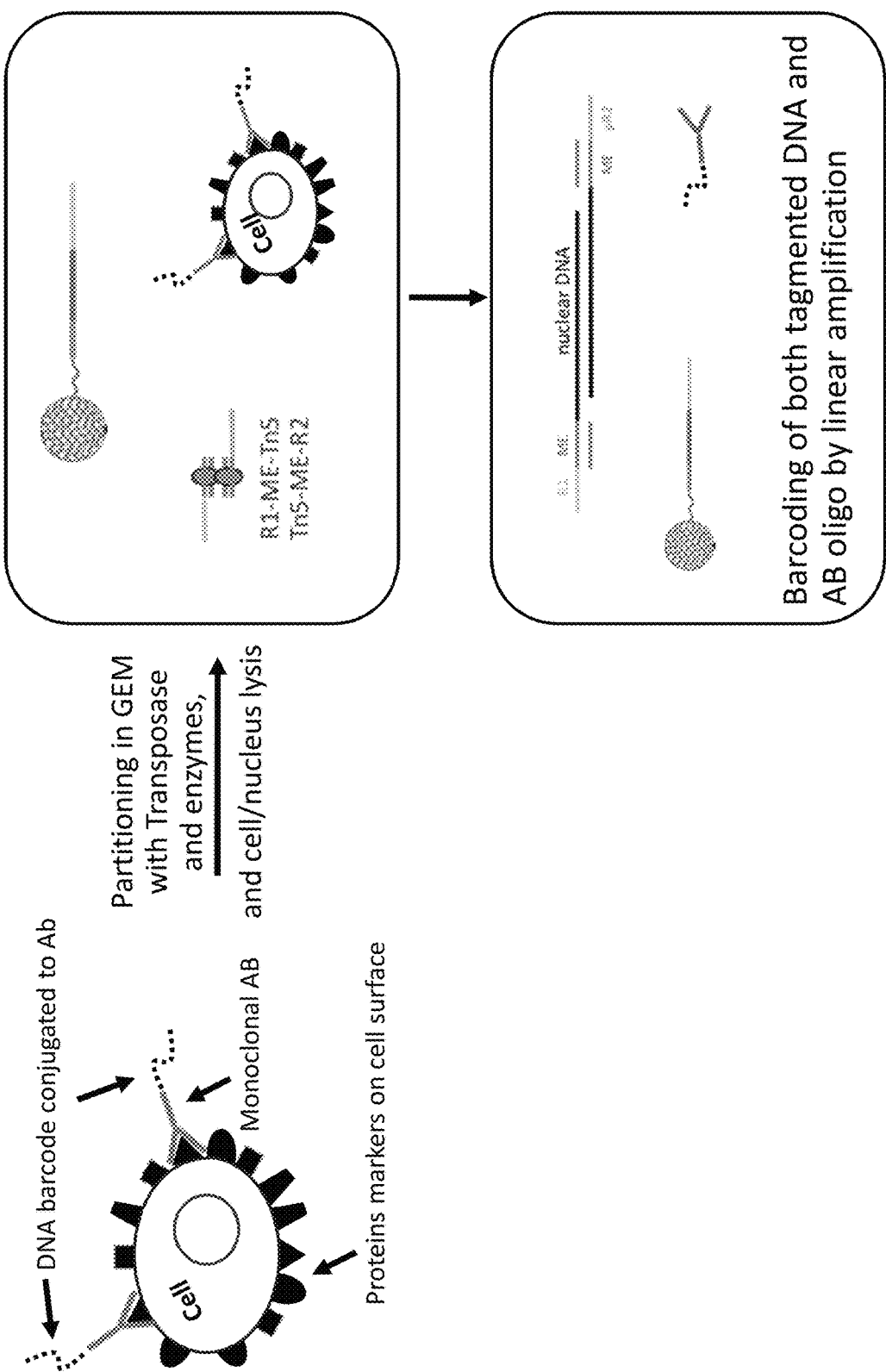
FIGS. 88A-88B illustrate methods for assaying proteins and nucleic acid fragments by conjugating antibodies to a cell surface.
Figure 88B:
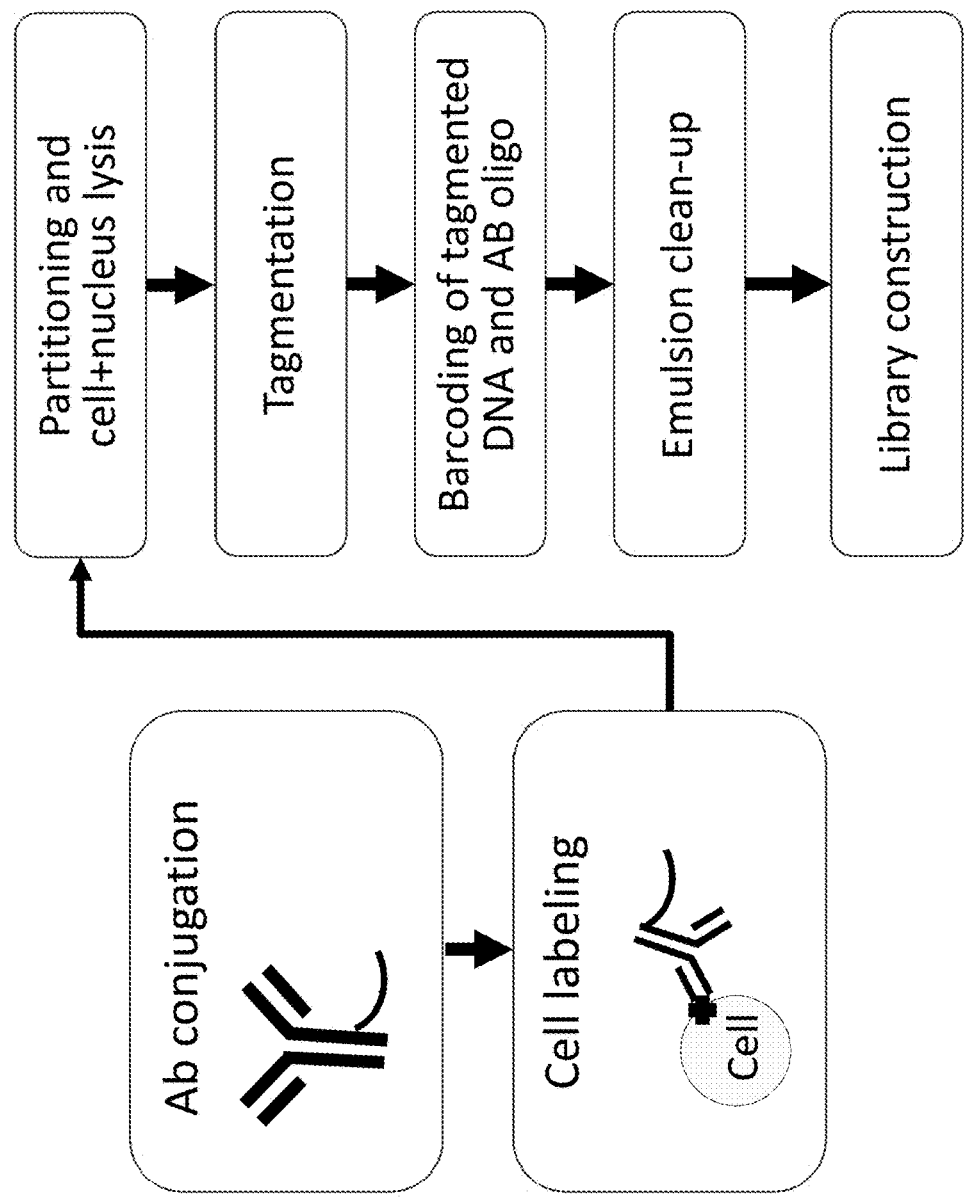

In another example, where the multi-assay is directed to capturing proteins, the capture probe in the second barcode oligonucleotide may comprise an antibody. FIGS. 87A-87B show examples of a barcoded antibody. FIG. 87A illustrates an example for use in amplification. A first oligonucleotide molecule may comprise a functional sequence 8706 (e.g., sequencer specific flow cell attachment sequence, sequencing primer sequence, etc.) releasably attached to a gel bead 8702, a barcode sequence 8708, and a first adaptor sequence 8710a. The first oligonucleotide molecule may correspond to second barcoded oligonucleotide. A second oligonucleotide molecule may comprise a second adaptor sequence 8710b complementary to and attached to the first adaptor sequence, a unique molecular identifier 8712, and a primer sequence ("R2", such as, e.g., Nextera R2, TruSeq R2, etc.) attached to an antibody 8702. The unique molecular identifier may identify the specific antibody 8702. The specific antibody 8702 may or may not have binding specificity to a type of protein. In some embodiments, as illustrated in FIGS. 88A-88B, prior to partitioning, a plurality of second oligonucleotide molecules can be introduced to the cells of interest such that the respective antibodies (e.g., 8702) of the second oligonucleotide molecules bind to proteins of interest on or in the cell (e.g., for surface proteins or internal proteins, respectively), labelling the cell with the unique molecular identifiers of the antibodies. The labelled cell may be partitioned with a gel bead comprising the first oligonucleotide molecule, such that the first adaptor sequence from the gel bead captures the second adaptor sequence from the conjugated cell to form the partially double-stranded oligonucleotide (of FIG. 87). In FIG. 87B, in another example for use in ligation reactions, a first oligonucleotide molecule may comprise a double stranded functional sequence 8756 releasably attached to a gel bead 8752, a double stranded barcode sequence 8758, and a first single stranded adaptor sequence 8760a. A second oligonucleotide molecule may comprise a second single stranded adaptor sequence 8760b complementary to the first single stranded adaptor sequence 8760a, a unique molecular identifier 8762, and a primer sequence 8764 (e.g., "R2").

FIGS. 88A-88B illustrate methods for assaying proteins and nucleic acid fragments by conjugating antibodies to a cell surface. A plurality of barcode-conjugated antibodies (e.g., second oligonucleotide molecule in FIG. 87) is introduced to a cell (or nucleus) comprising a plurality of protein markers on the cell (or nucleus) surface. The barcode-conjugated antibodies, where there is a match, bind to the protein markers on the cell surface, thereby labelling the cells with the barcodes conjugated to the antibodies. The mixture may be washed to wash out the unbound antibodies from the labelled cell. The labelled cell is partitioned, as described elsewhere herein, such as with a gel bead comprising a first barcoded oligonucleotide (for barcoding nucleic acid fragments of transposase accessible chromatin) and a second barcoded oligonucleotide (for barcoding the barcode-conjugated antibodies bound to the proteins). In some cases, the labelled cell may be partitioned with a first gel bead comprising the first barcoded oligonucleotide and a second gel bead comprising the second barcoded oligonucleotide. In the partition, the cell (or nucleus) may be lysed to release the analytes of interest in a manner that substantially maintains native chromatin organization of the genomic DNA. In alternative embodiments, as described elsewhere herein, barcode-conjugated antibodies may be washed into cell beads, wherein the cells in the cell beads have been lysed, to bind to internal proteins.

In certain embodiments, where barcode oligonucleotides are attached to a gel bead, the droplets may be subjected to conditions to cause release of barcode oligonucleotide molecules from the gel bead (e.g., depolymerization of gel beads, for example, using a reducing agent such as DTT). In certain embodiments, the droplets may then be subjected to conditions to generate a transposase-nucleic acid complex as described elsewhere herein. Alternatively, in some embodiments, a plurality of pre-formed transposase-nucleic acid complexes may be partitioned into the plurality of droplets. The droplets may be subjected to conditions such that the transposase-nucleic acid complexes generate double-stranded template genomic DNA fragments. The template genomic DNA fragments and the antibodies (binding to the proteins) may be barcoded, such as by linear amplification.

Figure 89A:
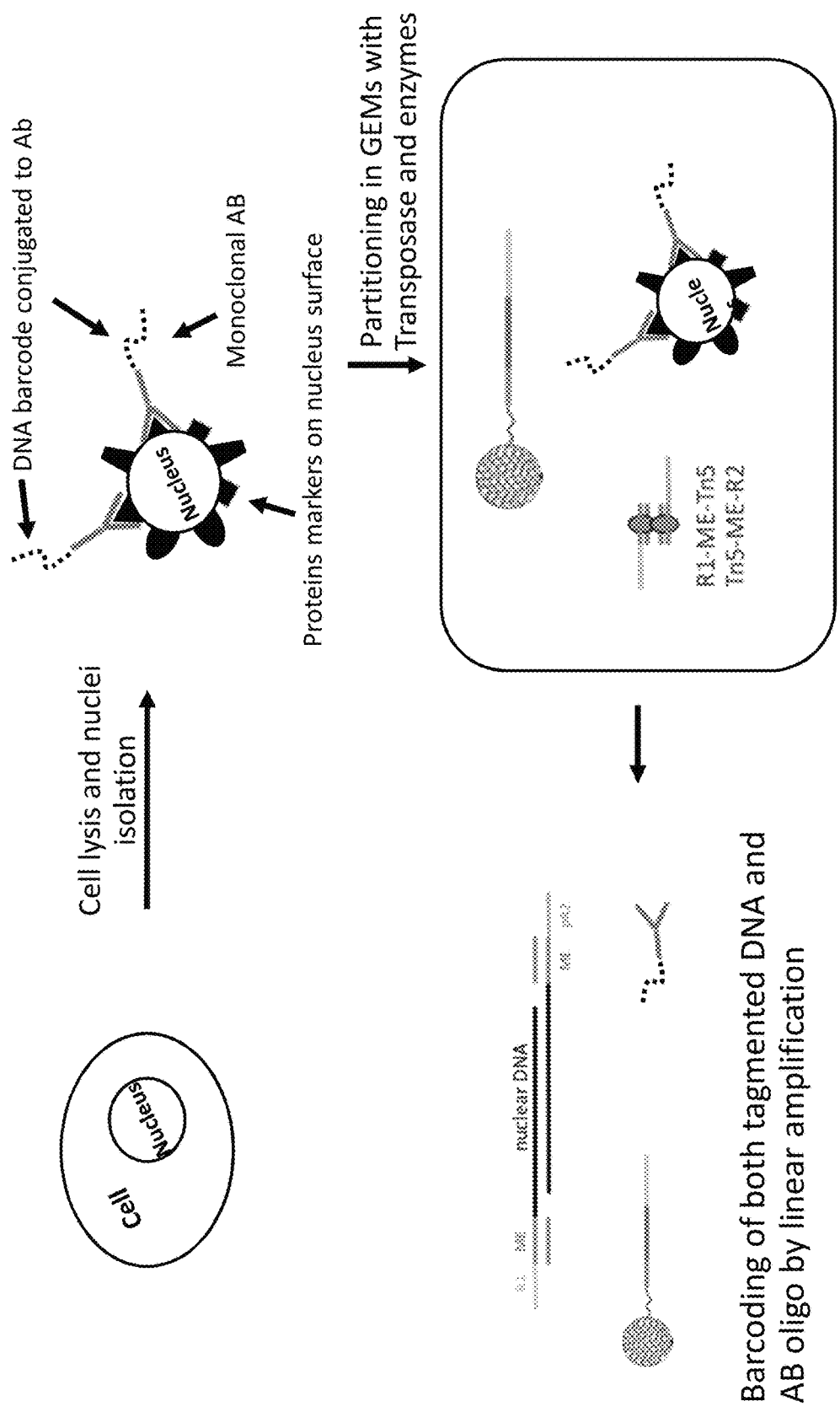
FIGS. 89A-89B illustrate methods for assaying proteins and nucleic acid fragments by conjugating antibodies to a nucleus surface.
Figure 89B:
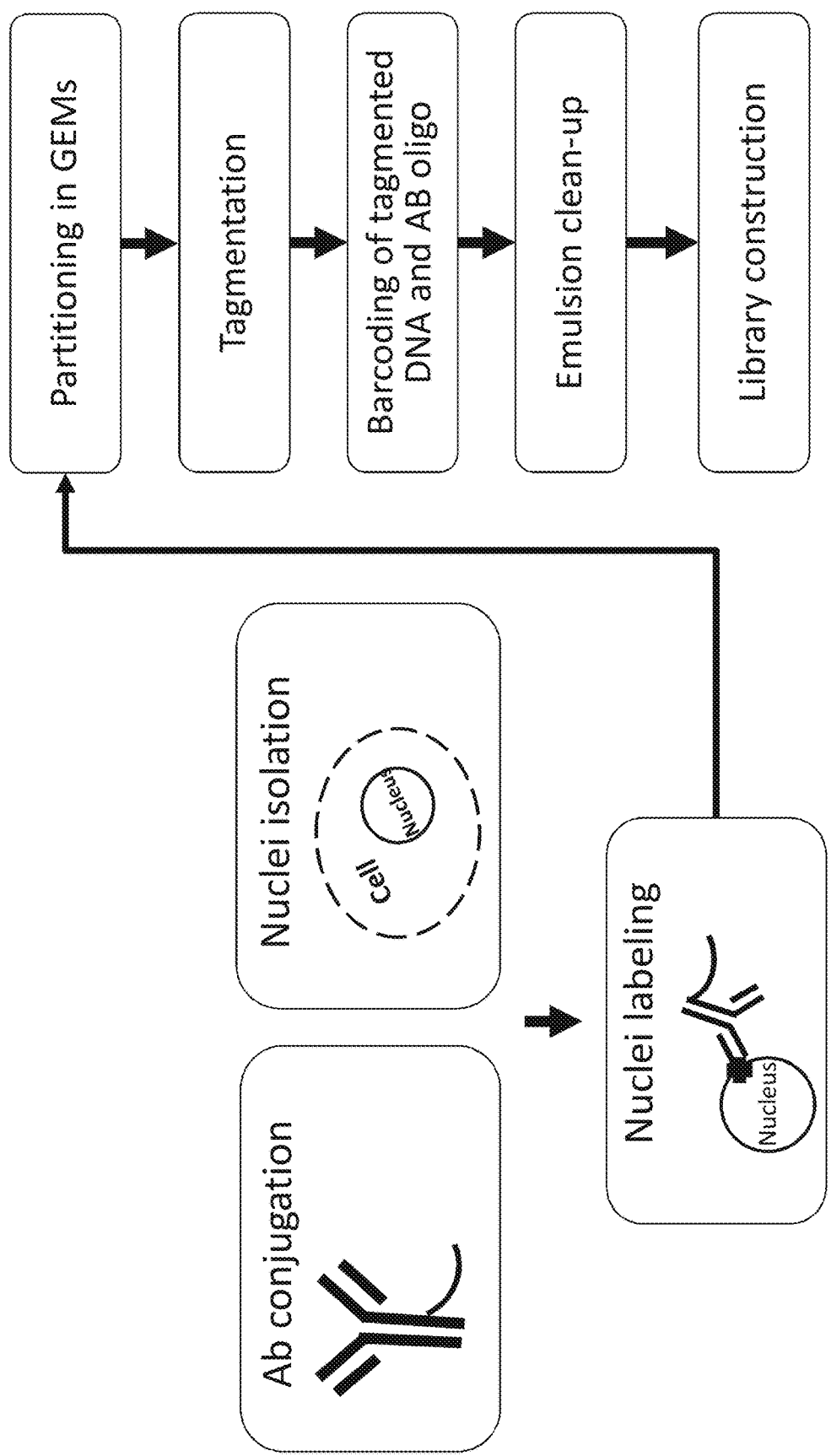

In FIGS. 89A-89B illustrate a method for assaying proteins and nucleic acid fragments by conjugating antibodies to a nucleus surface. The cells are lysed and nuclei isolated. A plurality of barcode-conjugated antibodies (e.g., second oligonucleotide molecule in FIG. 87A) is introduced to the nuclei comprising a plurality of protein markers on the nuclei surface. The barcode-conjugated antibodies, where there is a match, bind to the protein markers on the nucleus surface, thereby labelling the nuclei with the barcodes conjugated to the antibodies. The mixture may be washed to wash out the unbound antibodies from the labelled nuclei. The labelled nuclei is partitioned, as described elsewhere herein, such as with a gel bead comprising a first barcoded oligonucleotide (for barcoding nucleic acid fragments of transposase accessible chromatin) and a second barcoded oligonucleotide (for barcoding the barcode-conjugated antibodies bound to the proteins). In some cases, the labelled cell may be partitioned with a first gel bead comprising the first barcoded oligonucleotide and a second gel bead comprising the second barcoded oligonucleotide. In the partition, the nucleus may be lysed to release the analytes of interest in a manner that substantially maintains native chromatin organization of the genomic DNA. In certain embodiments, where barcode oligonucleotides are attached to a gel bead, the droplets may be subjected to conditions to cause release of barcode oligonucleotide molecules from the gel bead (e.g., depolymerization of gel beads, for example, using a reducing agent such as DTT). In certain embodiments, the droplets may then be subjected to conditions to generate a transposase-nucleic acid complex as described elsewhere herein. Alternatively, in some embodiments, a plurality of pre-formed transposase-nucleic acid complexes may be partitioned into the plurality of droplets. The droplets may be subjected to conditions such that the transposase-nucleic acid complexes generate double-stranded template genomic DNA fragments. The template genomic DNA fragments and the antibodies (binding to the proteins) may be barcoded, such as by linear amplification.

The barcoded, adapter-flanked DNA fragments and the barcoded analyte molecules (e.g., cDNA, antibodies, etc.) may then be released from the droplets and processed in bulk to complete library preparation for next generation high throughput sequencing (e.g., subjecting the fragments, or derivatives thereof, to one or more reactions (e.g., nucleic acid amplification) to add functional sequences to facilitate Illumina sequencing). In some embodiments, a first portion of the released emulsion comprising the adapter-flanked DNA fragments and the barcoded analyte molecules is taken and processed in bulk to complete library preparation for the barcoded, adapter-flanked DNA fragments while a second portion of the released emulsion is taken and processed in bulk to complete library preparation for the barcoded analyte molecules. In other embodiments, a first portion of the droplets comprising the barcoded, adapter-flanked DNA fragments and the barcoded analyte molecules is taken and processed in bulk to complete library preparation for the barcoded, adapter-flanked DNA fragments while a second portion of the droplets comprising the barcoded, adapter-flanked DNA fragments and the barcoded analyte molecules is taken and processed in bulk to complete library preparation for the barcoded analyte molecules. In embodiments that utilize a magnetic bead, the barcoded template molecules attached thereto can be magnetically separated and further processed to complete library preparation. The fully constructed library or libraries are then sequenced according to a suitable next-generation sequencing protocol (e.g., Illumina sequencing).

The systems and methods described herein may be used in combination with cell beads, as described elsewhere herein. For example, the abovementioned components may be partitioned such that at least some droplets comprise: (1) a cell bead comprising a single cell (or other biological particle, such as a nucleus); (2) either a single gel bead comprising a plurality of first barcoded oligonucleotides and a plurality of second barcoded oligonucleotides attached to the single gel bead, or two gel beads, first gel bead comprising the plurality of first barcoded oligonucleotides and the second gel bead comprising the plurality of second barcoded oligonucleotides; (3) a plurality of transposase molecules; and (4) other reagents. The other reagents may comprise an agent, such as a reducing agent, to degrade the cell bead to release the components into the partition. For example, prior to partitioning, the barcode-conjugated antibodies may be introduced into the cell bead to label the protein markers in the cell bead, and the cell bead may be degraded in the partition to release the labels. The cell in the cell bead may or may not be lysed. In some instances, a cell may be labelled with the barcode-conjugated antibodies and the labelled cell may be generated into the cell bead, which may be degraded in the partition.

The systems and methods described herein may be used to perform multi-assay on any number of types of analytes. For example, for assaying three types of analytes, including accessible chromatin, mRNA, and proteins, the method may comprise partitioning three types of barcoded oligonucleotides, one for each type. The three types of barcoded oligonucleotides may be releasably attached to a single gel bead and partitioned with the cell (or nucleus). Alternatively, the three types of barcoded oligonucleotides may each be releasably attached to three different gel beads and partitioned with the cell (or nucleus). Beneficially, systems and methods may allow epigenetic analysis and protein analysis of the same cells, for example, by using single cell ATAC to identify cell types and states, and using protein markers to infer signaling pathways. The protein markers may be analyzed to add a spatial dimension to single cell ATAC-seq data, such as to differentiate epigenetic analysis of cells enriched in the cortex versus the hippocampus. In some instances, protein markers may be limited to membrane receptors, such as for fresh and cryp-preserved cells. In some instances, proteins markers may be extended to intracellular proteins. The system and methods may be applied to multi-plex proteins.

DNase and MNase

In another aspect, the present disclosure provides a method of assaying two or more analytes comprising processing a nucleic acid molecule with an enzyme. The method may comprise providing a partition (e.g., a droplet or a well) comprising (i) two or more analytes, (ii) a bead (e.g., a gel bead), and (iii) one or more deoxyribonuclease (DNase) molecules or functional variants thereof. The partition may be an individual partition of a plurality of partitions (e.g., a droplet of an emulsion). The two or more analytes may be selected from the group consisting of, for example, nucleic acid molecules (e.g., deoxyribonucleic acid (DNA) molecules or ribonucleic acid (RNA) molecules), proteins, and perturbation agents (e.g., CRISPR crRNA or sgRNA, TALEN, zinc finger nuclease, antisense oligonucleotide, siRNA, shRNA, miRNA, etc. as described herein). One or more of the analytes may be included within or on a biological particle (e.g., a cell) or a collection of biological particles. One or more of the analytes may be a nucleic acid molecule comprising chromatin. Chromatin may comprise at least two nucleosomes that flank a nucleic acid sequence when the chromatin is in an open configuration. The bead may comprise two or more nucleic acid barcode molecules comprising two or more barcode sequences (e.g., as described herein). The barcode sequence and/or a functional sequence of a nucleic acid barcode molecule may correspond to a particular analyte of the two or more analytes. The one or more DNase molecules or functional variants thereof may be used to process a nucleic acid molecule (e.g., chromatin) to yield a barcoded analyte (e.g., a barcoded nucleic acid molecule) comprising (i) a nucleic acid sequence (e.g., a nucleic acid sequence from a segment between at least two nucleosomes of a chromatin in an open configuration), and (ii) a barcode sequence of the nucleic acid barcode molecule of the bead. Before, during, or after processing the nucleic acid molecule (e.g., chromatin), the one or more additional analytes (e.g., nucleic acid molecules, proteins, or perturbation agents) may be processed to generate a second barcoded analyte comprising (i) the second analyte, or a fragment or derivative thereof, and (ii) a second barcode sequence of a second nucleic acid barcode molecule of the bead. The barcoded analytes may then undergo further processing and analysis.

An analyte for use in the presently disclosed method may be, for example, a nucleic acid molecule, a protein, or a perturbation agent. A protein may be, for example, an internal (e.g., intracellular) or a surface protein (e.g., a transmembrane or extracellular protein). A protein may be, for example, an extracellular matrix protein. A protein may be an antibody. A perturbation agent may be, for example, a CRISPR, Talens, zinc finger, or antisense oligo (e.g., as described herein). A nucleic acid molecule may be, for example, a DNA or an RNA. An RNA may be, for example, a messenger RNA (mRNA), ribosomal RNA (rRNA), transfer RNA (tRNA), transcript, microRNA (miRNA), small interfering RNA (siRNA), small nucleolar RNA (snoRNAs), Piwi-interacting RNA (piRNA), tRNA-derived small RNA (tsRNA), or small rDNA-derived RNA (srRNA). A DNA may comprise genomic DNA. In some cases, a nucleic acid molecule may comprise a chromatin. Additional examples and details of analytes are described herein.

An analyte may comprise chromatin, which chromatin typically comprises one or more nucleosomes. In some cases, chromatin may comprise at least 2, 3, 4, 5, 6, 7, 8, 9, 10, 20, 30, 40, 50, 100, 200, 300, 400, 500, 1,000, or more nucleosomes. A chromatin may support a nucleic acid molecule. For example, two or more nucleosomes of a chromatin may flank a nucleic acid sequence. A chromatin may comprise one or more nucleic acid molecules wrapped around one or more nucleosomes (e.g., regularly spaced protein complexes). Each nucleosome may comprise, for example, a histone octamer core wrapped around by a nucleosome-associated nucleic acid molecule of length ~147 base pairs (bp). Nucleosomes of a given chromatin may be separated by a nucleic acid sequence or a linker DNA. The two nucleosomes may be separated by a segment of nucleic acid molecule having a nucleic acid sequence.

Chromatin may be packaged tightly or loosely based on the nucleosome occupancy of the chromatin. For example, chromatin with greater nucleosome occupancy may comprise a tightly packaged chromatin. Chromatin with a nucleosome depleted region (NDR) or with lower nucleosome occupancy may comprise a loosely packaged chromatin. Nucleosome occupancy may be correlated with chromatin accessibility. For example, a tightly packaged chromatin may have lower chromatin accessibility with the chromatin in a "closed" configuration, while a loosely packaged chromatin may have higher chromatin accessibility with the chromatin in an "open" chromatin configuration. A chromatin in an open configuration may be accessible to various moieties such as DNA-binding factors, DNA endonucleases, transposons, etc.

The accessibility of a chromatin may be assessed by subjecting a native chromatin from a biological particle to an enzymatic treatment. For example, deoxyribonuclease I (DNase I) may preferentially cleave DNA in an "open" or "accessible" chromatin, releasing a segment of a nucleic acid molecule between two nucleosomes. DNase I hypersensitive sites (DHSs) may be generally correlated with an open chromatin configuration. DHSs may be indicative of regulatory DNA, such as promoters, enhancers, insulators, silencers, and locus control regions. Another deoxyribonuclease, Micrococcal nuclease (MNase), may fragment a segment between two nucleosomes, releasing a nucleosome-associated nucleic acid molecule. A nucleosome-associated nucleic acid molecule may be associated with a "closed" chromatin configuration.

Enzymatic treatment of a chromatin with a DNase molecule or functional variant thereof may catalyze a hydrolytic cleavage of a phosphodiester linkage in a nucleic acid backbone. A DNase molecule may catalyze the cleavage of a nucleic acid molecule in a substantially sequence-independent manner (e.g., DNase I) or in a substantially sequence-dependent manner (e.g. cleavage preference of MNase at AT sites). A DNase molecule may cleave a single-stranded and/or a double-stranded nucleic acid molecule. A DNase molecule may be an endo- and/or exonuclease enzyme. The concentration of an enzyme used in enzymatic treatment of a chromatin may affect the rate and/or extent of the reaction between the enzyme and chromatin. Similarly, the duration of treatment may affect the extent of the reaction between the enzyme and chromatin. Optimal reaction parameters may be determined by using, e.g., a titration assay. In some cases, DNA in a chromatin may be completely digested during enzymatic treatment. For example, DNA in a chromatin may be completely digested when subjected to a DNase molecule (e.g., an MNase molecule) to ensure fragmentation of DNA segments between nucleosomes. In some examples, DNA may be only partially digested when subjected to a DNase molecule (e.g., a DNase I molecule).

Subsequent to digestion of a nucleic acid molecule (e.g., a chromatin) with a DNase molecule, the DNase molecule or functional variant thereof may be deactivated. For example, heat may be applied to the partition comprising the DNase molecule and the digested nucleic acid molecule. The amount of heat applied to the partition and the duration of the application may depend upon the identity of the DNase molecule and the properties of the partition (e.g., size, density, composition, surface tension, components, etc.). Deactivation of the DNase molecule may prevent the DNase molecule from digesting other DNA molecules that may exist within or be generated within the partition.

A partially or completely digested DNA molecule (e.g., a chromatin or component thereof digested by a DNase molecule) may come in contact with a nucleic acid barcode molecule of a bead (e.g., a gel bead). As described elsewhere herein, a nucleic acid barcode molecule may be releasably attached or coupled to the bead. For example, a nucleic acid barcode molecule may be attached the bead by bonds that may be broken by a stimulus (e.g., chemical stimulus), thereby releasing the nucleic acid barcode molecule. In another example, a nucleic acid barcode molecule may not be releasably attached or coupled to the bead. For example, a nucleic acid barcode molecule may be attached to the bead by bonds that are resistant to a stimulus (e.g., chemical stimulus).

A bead may comprise two or more nucleic acid barcode molecules. A bead may comprise a plurality of nucleic acid barcode molecules of a first type (e.g., first nucleic acid barcode molecules) and a plurality of nucleic acid barcode molecules of a second type (e.g., second nucleic acid barcode molecules). The first and second nucleic acid barcode molecules may be present in equal or different numbers on the bead. For example, greater than 50%, such as 51%, 52%, 55%, 60%, 65%, 70%, 75%, 80%, 85%, 90%, 95%, or greater than 95%, of the nucleic acid barcode molecules of a bead may be first nucleic acid barcode molecules and the remainder may be second nucleic acid barcode molecules. Alternatively, less than 50%, such as 49%, 48%, 45%, 40%, 35%, 30%, 25%, 20%, 15%, 10%, 5%, or less than 5%, of the nucleic acid barcode molecules of a bead may be second nucleic acid barcode molecules. For a bead comprising three or more nucleic acid barcode molecule types (e.g., first, second, and third nucleic acid barcode molecules), the first, second, and third nucleic acid barcode molecules may be present in equal or different numbers. For example, the first and second nucleic acid barcode molecules may be present in equal numbers and the third nucleic acid barcode molecules may be present in greater or lesser number than the first and second nucleic acid barcode molecules. The concentration of a given nucleic acid barcode molecule type on the bead may be adjusted to match the needs of a specific application.

A nucleic acid barcode molecule attached to a bead may comprise one or more different features (e.g., as described herein). For example, a nucleic acid barcode molecule may comprise a linking sequence, a barcode sequence, a unique molecular identifier, a functional sequence, and/or one or more additional sequences such as additional functional sequences. One or more sequences may comprise a random N-mer. First and second nucleic acid barcode molecules attached to the same bead may comprise the same or different sequences. For example, a first nucleic acid barcode molecule attached to a bead may comprise a first linking sequence, a first barcode sequence, and a first functional sequence and a second nucleic acid barcode molecule attached to the same bead may comprise a second linking sequence, a second barcode sequence, and a second functional sequence. The first linking sequence may be the same as or different from the second linking sequence. The first barcode sequence may be the same as or different from the second barcode sequence. Similarly, the first functional sequence may be the same as or different from the second functional sequence. In some cases, the first and second functional sequences may be different so that each nucleic acid barcode molecule may interact with a different analyte (e.g., a different type of analyte). For example, the first functional sequence may comprise a DNA capture sequence capable of attaching to a DNA molecule, while the second functional sequence may comprise a poly(T)-tail capable of attached to a poly(A)-tail of an mRNA molecule. A functional sequence of a nucleic acid barcode molecule (e.g., an additional functional sequence) may be useful in a downstream assay such as a sequencing assay. Accordingly, the functional sequence may be selected based on the assay used. A functional sequence may include, for example, a primer binding site such as a sequencing primer site (e.g., R1 or R2) or a flow cell binding sequence (e.g., P5, P7). A primer binding site may comprise one or more sequences for a primer to hybridize to during an amplification reaction, an extension reaction, or a sequencing reaction.

A nucleic acid barcode molecule may attach to a nucleic acid sequence or a segment thereof of a nucleic acid molecule (e.g., a nucleic acid molecule digested by a DNase treatment) to generate a barcoded nucleic acid molecule. In some cases, a nucleic acid barcode molecule may be attached to a nucleic acid sequence or a segment thereof with the aid of a reagent such as a polymerization or ligation reagent. For example, a nucleic acid barcode molecule may be attached to the nucleic acid sequence or a segment thereof via a polymerization reaction. A polymerization reaction may comprise annealing a sequence (e.g., a functional sequence such as a DNA capture sequence or a poly(T)-tail) nucleic acid barcode molecule to the nucleic acid sequence or a segment thereof, extending the nucleic acid barcode molecule, and amplifying the nucleic acid sequence to generate the barcoded nucleic acid molecule. Non-limiting examples of reagents useful in attaching a nucleic acid barcode molecule to a nucleic acid sequence or segment thereof may include polymerases (e.g., DNA and RNA polymerases), nucleoside triphosphates, and buffers with co-factors (e.g. $Mg^{2+}$). Reagents may be co-partitioned with analytes (e.g., analytes included within or on biological particles) and/or beads. A nucleic acid barcode molecule may be attached to a nucleic acid sequence or a segment thereof at either one or both ends of a nucleic acid sequence or segment thereof to yield a barcoded nucleic acid molecule.

A bead in a partition may comprise one or more DNase molecules or functional variants thereof. For example, a DNase molecule may be attached (e.g., releasably attached) to a bead and/or a nucleic acid barcode molecule attached thereto.

One or more analytes (e.g., nucleic acid molecules) may be contained within or otherwise associated with a biological particle such as a cell (e.g., as described herein). For example, a protein may be included within a cell (e.g., an intracellular protein), attached to a surface of a cell (e.g., an extracellular or surface protein), or contained within or spanning a membrane of a cell (e.g., a transmembrane protein). A cell may comprise one or more nucleic acid molecules. For example, a cell may comprise one or more RNA molecules, DNA molecules, and/or chromatins. A single cell may comprise, for example, at least 1, 2, 3, 4, 5, 6, 7, 8, 9, 10, 20, 30, 40, 50, 100, 200, 300, 400, 500, 1000, 10,000, 100,000 or more nucleic acid molecules. A biological particle may be provided within a partition (e.g., a droplet or well) intact. For example, a bead, a biological particle, and a DNase molecule or functional variant thereof may be co-partitioned (e.g., as described herein) within an aqueous droplet. In some cases, a cell may be co-partitioned with a lysis or permeabilization reagent. The cell may then be lysed or permeabilized within a partition to provide access to an analyte therein. In some cases, a biological particle such a cell may be encapsulated within a gel matrix before and/or subsequent to partitioning within a partition.

A DNase molecule or functional variant thereof may be co-partitioned with a single bead and a single biological particle in an individual partition. The bead may comprise two or more nucleic acid barcode molecules each comprising a barcode sequence releasably attached thereto. The biological particle may include a nucleic acid molecule associated with nucleosomes in a chromatin. An additional analyte such as a protein or another nucleic acid molecule may be included within or associated with the biological particle. The occupancy of the nucleosomes in the chromatin may be inversely correlated with the accessibility of the chromatin to the DNase molecule. A chromatin with a lower nucleosome occupancy may be highly accessible and may be considered to be in an "open" configuration. A nucleic acid molecule associated with an open chromatin configuration may include DNase hypersensitive sites (DHS) where a DNase molecule may fragment the nucleic acid molecule, releasing a segment between the nucleosomes. The released segment of the nucleic acid molecule may then be barcoded with a nucleic acid barcode molecule of the bead to yield a barcoded nucleic acid molecule.

A partition for use according to the methods disclosed herein may be any useful container or vessel, such as a well, droplet, microwell, tube, nanoarray, or other container. A partition may be flowable within a fluid stream, such as a microcapsule having an inner fluid core surrounded by an outer barrier. A partition may be a droplet of aqueous fluid within a non-aqueous phase, such as an oil phase. A partition may be generated as described elsewhere herein. Briefly, a first liquid phase (e.g., an aqueous phase) comprising one or more DNase molecules or functional variants thereof, a plurality of biological particles (e.g., cells), and a plurality of beads may be provided and brought in contact with a second liquid phase (e.g., a non-aqueous phase, such as an oil) that is immiscible with the at least the first liquid phase to partition the DNase molecules or functional variants thereof, the plurality of biological particles, and the plurality of beads into a plurality of droplets. Individual droplets may comprise a one or more DNase molecules or functional variants thereof, a single biological particle, and a single bead. One or more additional analytes (e.g., proteins, perturbation agents, or nucleic acid molecules) or reagents (e.g., polymerases, nucleotides, lysis agents, or other reagents described herein) may also be co-partitioned with the DNase molecules or functional variants thereof, biological particles, and beads.

Processing of one or more analytes may take place within a partition (e.g., a droplet or well). For example, an analyte may be barcoded within a partition. Other processes including lysis or permeabilization of a cell, degradation or dissolution of a bead, release of a nucleic acid barcode molecule or another component from a bead, reverse transcription, hybridization or ligation of one or more nucleic acid sequences, extension of a nucleic acid sequence, denaturation of a double-stranded nucleic acid molecule or protein, and/or amplification of a nucleic acid sequence may take place within a partition.

A partition may include two or more analytes for processing according to the presently disclosed method. For example, a partition may comprise 2, 3, 4, or more analytes. The analytes may be of the same or a different type. One or more analytes may be provided within or associated with a biological particle (e.g., cell) within the partition. In some cases, a partition may include a first analyte that is a DNA molecule (e.g., a chromatin) that may be processed using a DNase molecule or a functional variant thereof and a second analyte that is a different DNA molecule. The different DNA molecule may also be processed using the same or another DNase molecule or functional variant thereof. In some cases, a partition may include a first analyte that is a DNA molecule (e.g., a chromatin) that may be processed using a DNase molecule or a functional variant thereof and a second analyte that is an RNA molecule (e.g., an mRNA molecule). In some cases, a partition may include a first analyte that is a DNA molecule (e.g., a chromatin) that may be processed using a DNase molecule or a functional variant thereof and a second analyte that is a protein (e.g., an intracellular, extracellular, surface, or transmembrane protein coupled to a labelling agent, e.g., a barcoded antibody, as described herein). In some cases, a partition may include a first analyte that is a DNA molecule (e.g., a chromatin) that may be processed using a DNase molecule or a functional variant thereof and a second analyte that is a perturbation agent (e.g., as described herein).

In one example of the presently disclosed method, a single cell, a single bead, one or more DNase molecules, and various reagents are provided within a partition (e.g., a droplet). The bead may comprise a first nucleic acid barcode molecule comprising a first linking sequence, a first barcode sequence, and a first functional sequence and a second nucleic acid barcode molecule comprising a second linking sequence, a second barcode sequence, and a second functional sequence. The first and second linking sequences may be the same, as may the first and second barcode sequences. The first and second functional sequences may be different. The first functional sequence may comprise a DNA capture sequence, while the second functional sequence may comprise a poly(T)-tail. The first and second nucleic acid barcode molecules may be releasably attached to the bead (e.g., as described herein). The cell may comprise a first analyte that is a DNA molecule comprising a chromatin and a second analyte that is an mRNA molecule. The cell may be lysed within the droplet using a lysing agent to provide access to the nucleic acid molecules contained therein. The bead may then be degraded or dissolved upon application of a stimulus (e.g., as described herein) to release the nucleic acid barcode molecules attached thereto. A DNase molecule may then completely or partially digest the first analyte, thereby releasing a nucleic acid sequence or segment thereof. The released nucleic acid sequence or segment thereof may then be ligated to the first functional sequence of the first nucleic acid barcode molecule to generate a barcoded nucleic acid molecule. The DNase molecule may then be deactivated (e.g., by applying heat to the partition). Before, during, or after the barcoding of the nucleic acid sequence or segment thereof derived from the first analyte, the second analyte may ligate to the second functional sequence of the second nucleic acid barcode molecule to generate a second barcoded nucleic acid molecule that comprises an mRNA molecule. The mRNA molecule may be reverse transcribed using a reverse transcriptase (e.g., as described elsewhere herein) to generate a complementary DNA (cDNA) molecule. The cDNA molecule may comprise the second barcode sequence or a complement thereof. Deactivation of the DNase molecule prior to generation of the cDNA molecule ensures that the cDNA molecule will not be digested by the DNase molecule. The barcoded nucleic acid sequence or segment thereof corresponding to the first analyte (e.g., chromatin) and the barcoded cDNA molecule corresponding to the second analyte (e.g., mRNA molecule) may then be further processed. In some cases, the barcoded species may be released from the partition prior to further processing (e.g., by disrupting the partition, as described elsewhere herein). For example, the barcoded species may be released prior to undergoing an amplification reaction such as a polymerase chain reaction (e.g., as described herein). Barcoded species or amplified products corresponding to the barcoded species may undergo sequencing (e.g., using a high throughput sequencer, as described elsewhere herein) to identify the sequences of the nucleic acid molecules associated therewith. Barcoded species or amplified products corresponding to the barcoded species may also be quantified using a quantitative assay, such as a fluorometric assay.

In some cases, the first and second barcode sequences of the first and second nucleic acid barcode molecules of the preceding example may be the same, such that analytes processed within the same partition are barcoded with the same barcode. Multiple analytes may be processed within a plurality of different partitions and each partition may comprise a bead comprising first and second nucleic acid barcode molecules comprising the same barcode sequence, where each partition comprises a different barcode sequence. In this manner, barcoded analytes or derivatives thereof may be pooled for further analysis while preserving information about the cell and/or partition from which each analyte derives.

Sequencing reads corresponding to barcoded species, derivatives thereof, and/or amplified products corresponding thereto (e.g., from an analyte comprising a chromatin) from sequencers may be mapped to a reference genome sequence to determine DHSs and/or to determine DNA footprints. DHSs may be determined by assessing coverage of the sequencing reads across the reference genome. For example, DHSs may include sequences represented by a greater coverage of the sequencing reads. Sequences represented by a lesser coverage of the sequencing reads may be DNase-resistant sites. DNA footprints may be determined within DHSs as sites with atypical cleavage patterns, such as lack of cleavage. For example, a DNA footprint may include a sequence within DHSs that may be represented by a lesser coverage of the sequencing reads, instead of a greater coverage. In some cases, the lesser coverage of the sequencing reads may be due to protein-bound regions, such as transcription factors bound to DNA, protecting DNA from DNase cleavage.

In some cases, the presently disclosed methods may make use of cell beads (e.g., as described elsewhere herein). In the example described above in which a partition comprises a first analyte comprising a chromatin and a second analyte that is an mRNA molecule, the cell contained within the partition may be lysed to provide access to analytes included therein. The mRNA may then be attached to a polymer or gel matrix. The polymer or gel matrix may comprise oligonucleotides (e.g., nucleic acid barcode molecules) attached to the matrix via an acrydite linker. The mRNA molecule may then be attached to the matrix by hybridization to a sequence of an oligonucleotide attached to the matrix. The mRNA may undergo barcoding, reverse transcription, and or template switching while attached to the polymer matrix. For example, reverse transcription performed using an mRNA attached to a matrix may generate cDNA which is attached to a cell bead. In some cases, the partition may comprise a magnetic particle that is used to capture, e.g., an mRNA molecule, as described herein.

Characterization, Analysis, and Detection of Chromosome Conformation and Epigenetic Profiling In some aspects, the present disclosure provides methods and systems for determining chromatin interaction information from one or more single cells. Chromatin interaction information may be determined together with one or more additional types of information from a cell including, for example, expression information, genomic information, additional epigenetic information (e.g., methylation information), metabolomic information, proteomic information, etc. Chromatin interaction information may be obtained by identifying the regions of a nucleic acid (e.g., DNA) which are in close special proximity within a cell as a result of chromatin interactions. In some cases, chromatin confirmation capture sequencing is used to obtain chromatin interaction information.

Figure 90:
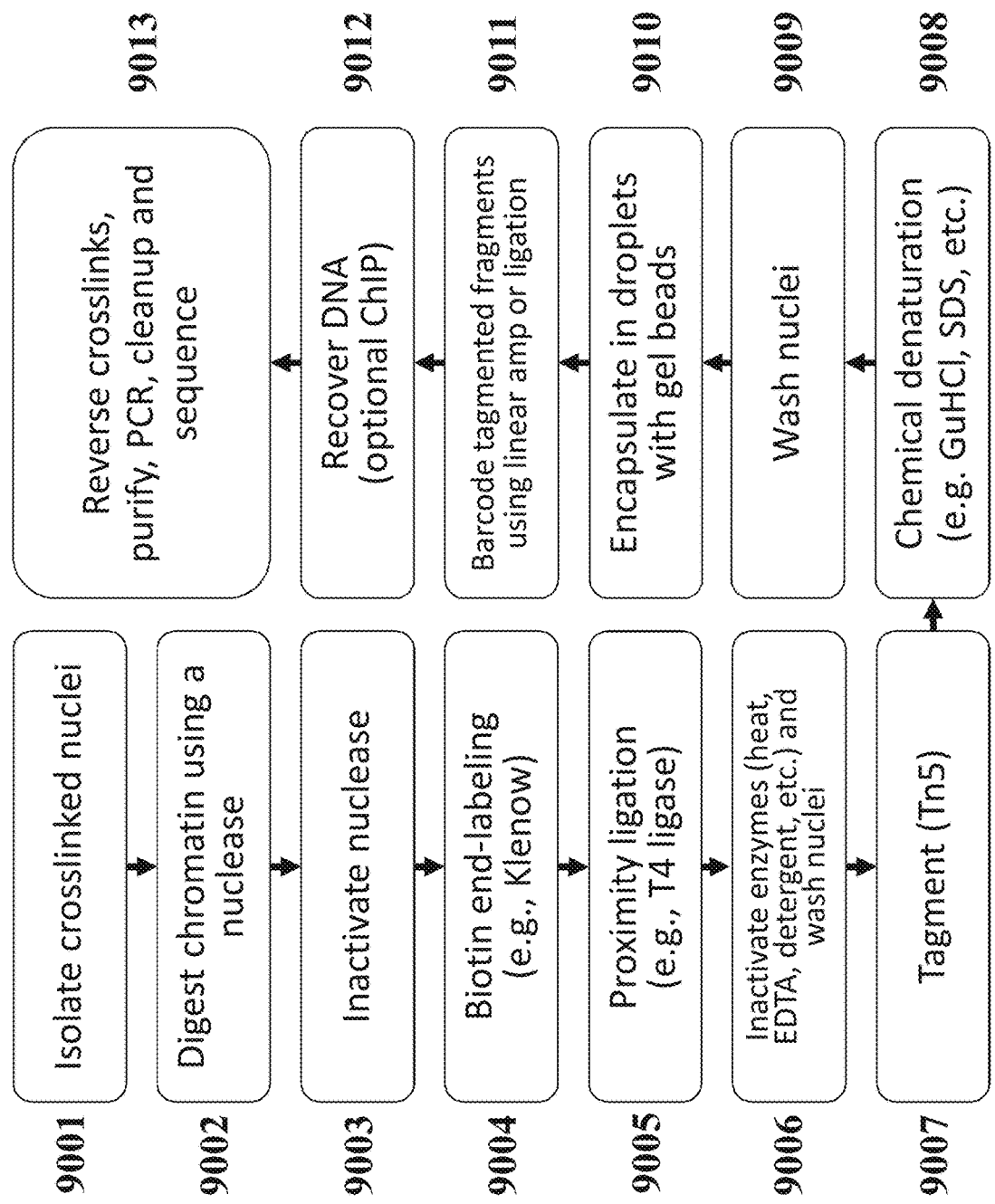
FIG. 90 illustrates an example method for identifying chromatin interaction information from a single cell.
Figure 91:
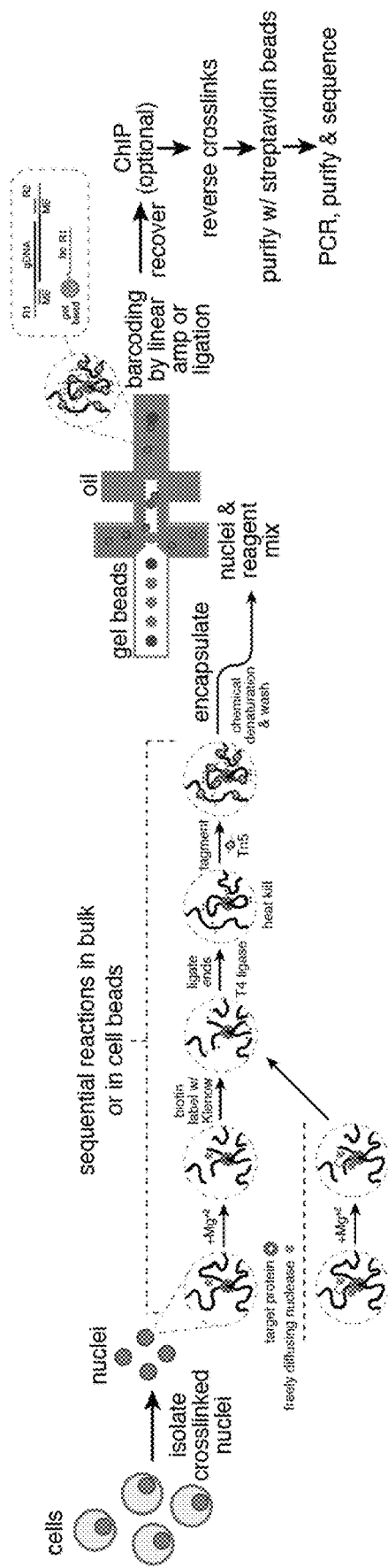
FIG. 91 shows a diagram illustrating the example method of FIG. 90.

FIG. 90 illustrates an example method for identifying chromatin interaction information from a single cell. In operation 9001, one or more nuclei can be isolated from cells and cross-linked with a chemical cross-linker, for example, formaldehyde. Cross-linking may serve to immobilize regions of DNA and/or proteins. Alternatively or in addition, nuclei may be comprised in a cell bead. As described herein, cells or nuclei may be partitioned into droplets comprising polymer precursors, which may be polymerized to generate a cell bead comprising a single cell or nucleus. Cell beads may comprise one or more additional analytes (e.g., components) from a cell (e.g., mRNA, cDNA, etc.). In operation 9002, nuclei can be subjected to nuclease treatment. A nuclease may be a restriction endonuclease, an MNase, or a DNase. A nuclease may be attached to an antibody, which may serve to direct the nuclease to a specific region of a genome by virtue of the specificity of the antibody. Nuclease treatment may fragment DNA within the nuclei. Fragmentation may be specific for a given region of DNA. In some cases, regions of DNA which are bound to one or more proteins may be protected from fragmentation. In operation 9003, a nuclease can be inactivated. A nuclease may be inactivated by the addition of one or more chemical reagents. In operation 9004, the ends of the fragmented DNA can be labeled with a nucleotide comprising a biotin molecule. Fragmented DNA may be labeled using a polymerase. In some cases, fragmented DNA is labeled using a Klenow fragment. In operation 9005, one or more regions of the fragmented DNA which are in proximity to one another can be ligated together. Regions of DNA may be ligated using a ligase. A ligase may be a T4 ligase. In operation 9006, one or more enzymes (e.g., polymerase, ligase, etc.) can be inactivated and removed from the nuclei. Enzymes may be inactivated by the addition of one or more of heat, detergents, or other chemical agents. Enzymes may be removed by washing the nuclei. In operation 9007, the nuclei can be subjected to tagmentation. Tagmentation may be used to add one or more additional sequences (e.g., barcode sequences, flow cell sequences, etc.) into a DNA fragment. Tagmentation may comprise use of a transposase. A transposase may be a Tn5 transposase. In operation 9008, nuclei can be subjected to conditions sufficient to denature the DNA. Denaturation is described elsewhere herein, and may include the use of chemical agents such as SDS, guanidine hydrochloride (GuHCl), etc. In operation 9009, nuclei can be washed to remove chemical denaturation agents. In operation 9010, nuclei can be partitioned into droplets together with gel beads, as described elsewhere herein. Gel beads may comprise barcode molecules for barcoding DNA (e.g., genomic DNA). Gel beads may comprise one or more additional barcode molecules for barcoding different types of analytes (e.g., RNA, cDNA, antibody barcode molecules, etc.). In operation 9011, barcode molecules may be used to barcode tagmented DNA (i.e., DNA fragments subjected to tagmenetation). Barcoding may comprise amplification (e.g., linear amplification, polymerase chain reaction). Barcoding may not comprise amplification. Barcoding may comprise ligation. In operation 9012, nuclei can be released from the partitions. In some cases, chromatin immunoprecipitation (ChIP) may be performed on the nuclei. In operation 9013, the crosslinks can be reversed, DNA isolated, and subjected to sequencing to generate sequencing reads. Isolated DNA labeled with a biotin molecule can be purified using, for example, streptavidin-coupled beads. Sequencing may determine chromatin interaction information from each single cell, identified by the presence of a unique barcode sequence. Sequencing may also identify additional genetic information from the cell. FIG. 91 shows a diagram illustrating the example method of FIG. 90.

Figure 92:
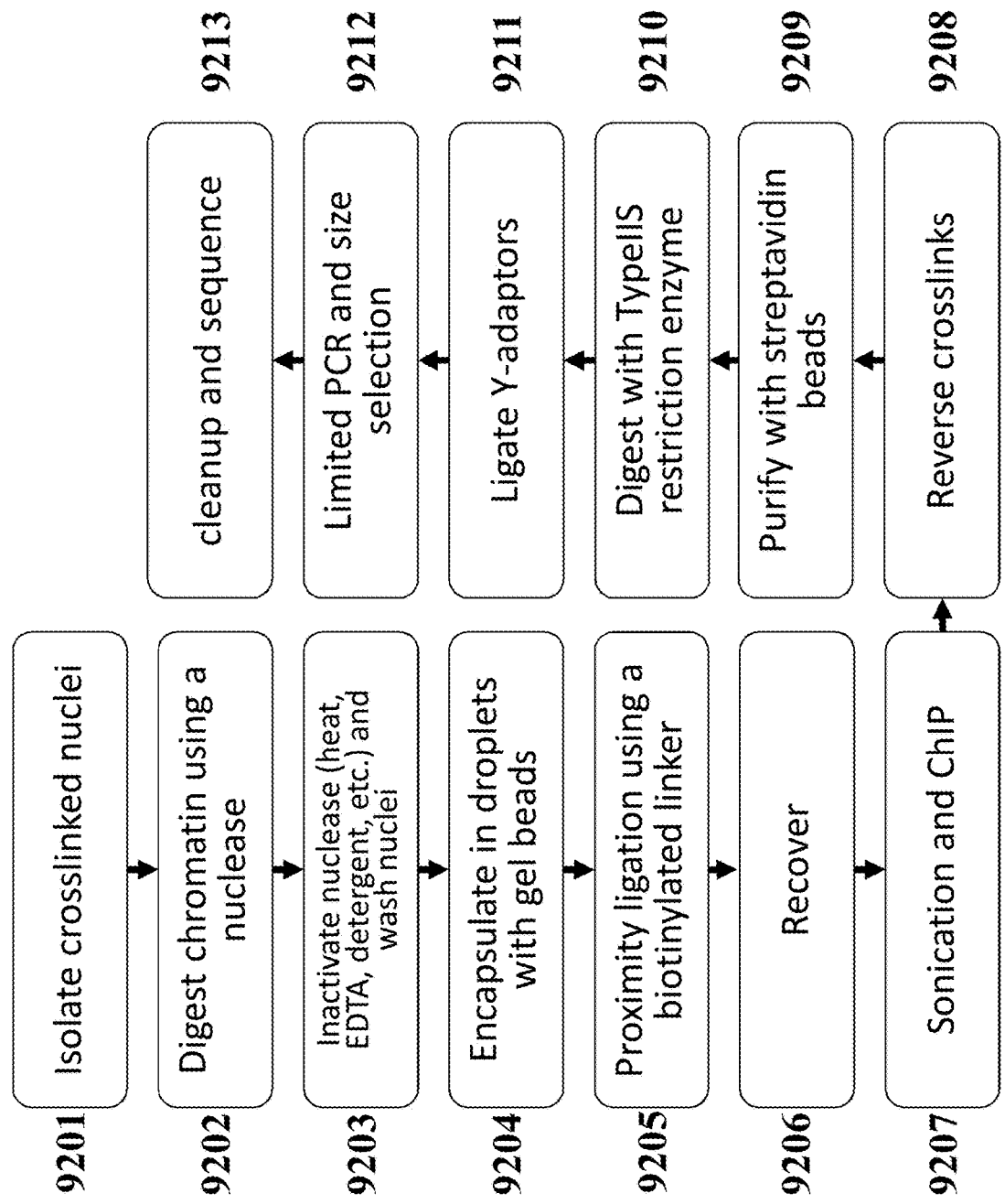
FIG. 92 illustrates another example method for identifying chromatin interaction information from a single cell.
Figure 93:
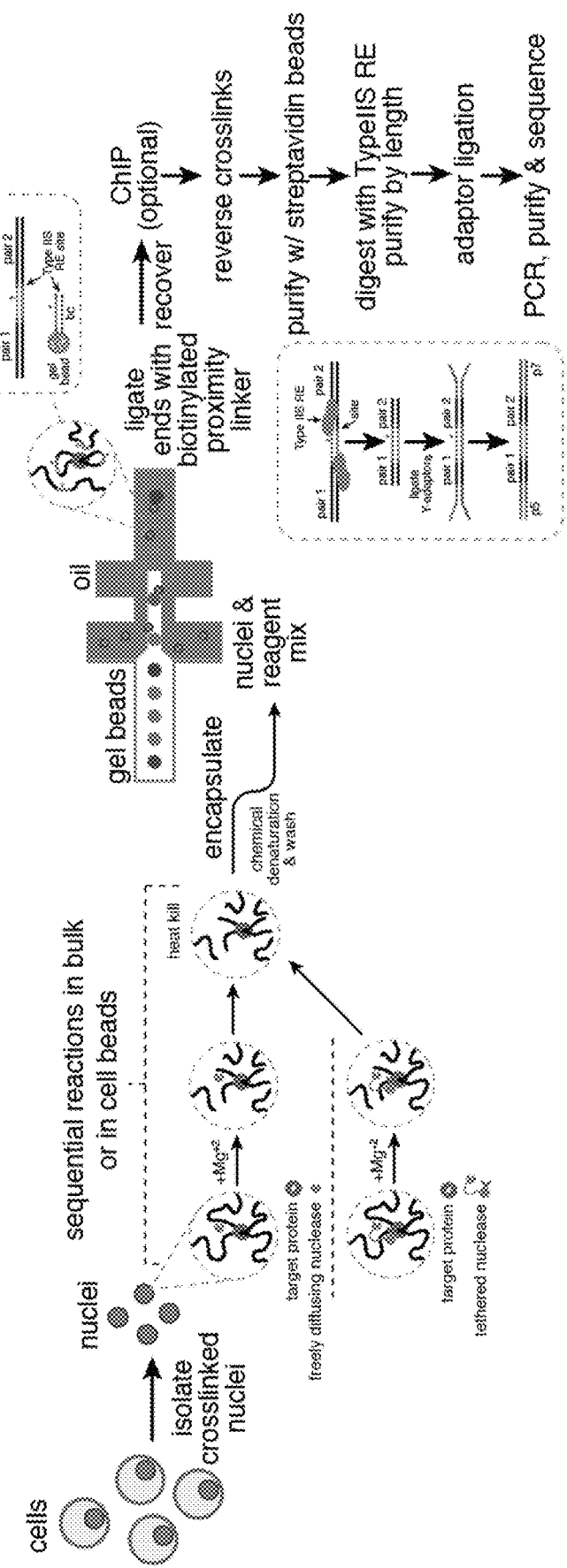
FIG. 93 shows a diagram illustrating the example method of FIG. 92.

FIG. 92 illustrates another example method for identifying chromatin interaction information from a single cell. In operation 9201, one or more nuclei can be isolated from cells and cross-linked with a chemical cross-linker, for example, formaldehyde. Cross-linking may serve to immobilize regions of DNA and/or proteins. Alternatively or in addition, nuclei may be comprised in a cell bead. As described herein, cells or nuclei may be partitioned into droplets comprising polymer precursors, which may be polymerized to generate a cell bead comprising a single cell or nucleus. Cell beads may comprise one or more additional analytes (e.g., components) from a cell (e.g., mRNA, cDNA, etc.). In operation 9202, nuclei can be subjected to nuclease treatment. A nuclease may be a restriction endonuclease, an MNase, or a DNase. A nuclease may be attached to an antibody, which may serve to direct the nuclease to a specific region of a genome by virtue of the specificity of the antibody. Nuclease treatment may fragment DNA within the nuclei. Fragmentation may be specific for a given region of DNA. In some cases, regions of DNA which are bound to one or more proteins may be protected from fragmentation. In operation 9203, a nuclease can be inactivated. A nuclease may be inactivated by the addition of one or more chemical reagents. In operation 9204, nuclei can be partitioned into droplets together with gel beads, as described elsewhere herein. Gel beads may comprise barcode molecules for barcoding DNA (e.g., genomic DNA). Gel beads may comprise one or more additional barcode molecules for barcoding different types of analytes (e.g., RNA, cDNA, antibody barcode molecules, etc.). Gel beads may comprise a biotinylated proximity linker. In operation 9205, a biotinylated proximity linker can be ligated onto the ends of digested DNA in a droplet. A proximity linker can serve to link together regions of DNA which are in proximity. A proximity linker may comprise one or more restriction enzyme sequences. A restriction enzyme site may be a Type IIS restriction enzyme sequence. In operation 9206, nuclei can be released from the partitions and recovered. In operation 9207, nuclei can be subjected to sonication and ChIP may be performed. In operation 9208, the crosslinks can be reversed. In operation 9209, DNA labeled with a biotin molecule (e.g., from a biotinylated proximity linker) can be purified using, for example, streptavidin-coupled beads. In operation 9210, DNA can be digested with a restriction enzyme. A restriction enzyme may be a Type IIs restriction enzyme. In operation 9211, one or more adaptor molecules can be ligated to the digested DNA. An adaptor molecule can be a Y-adaptor. An adaptor molecule can comprise one or more barcode sequences. In operation 9212, DNA can be subjected to PCR and purified, for example, using size selection. In operation 9213, DNA can be sequenced to obtain sequencing reads from the DNA. Sequencing reads can also be obtained from one or more additional barcoded analytes from a cell or nucleus. Sequencing may determine chromatin interaction information from each single cell, identified by the presence of a unique barcode sequence. Sequencing may also identify additional genetic information from the cell. FIG. 93 shows a diagram illustrating the example method of FIG. 92.

Figure 94:
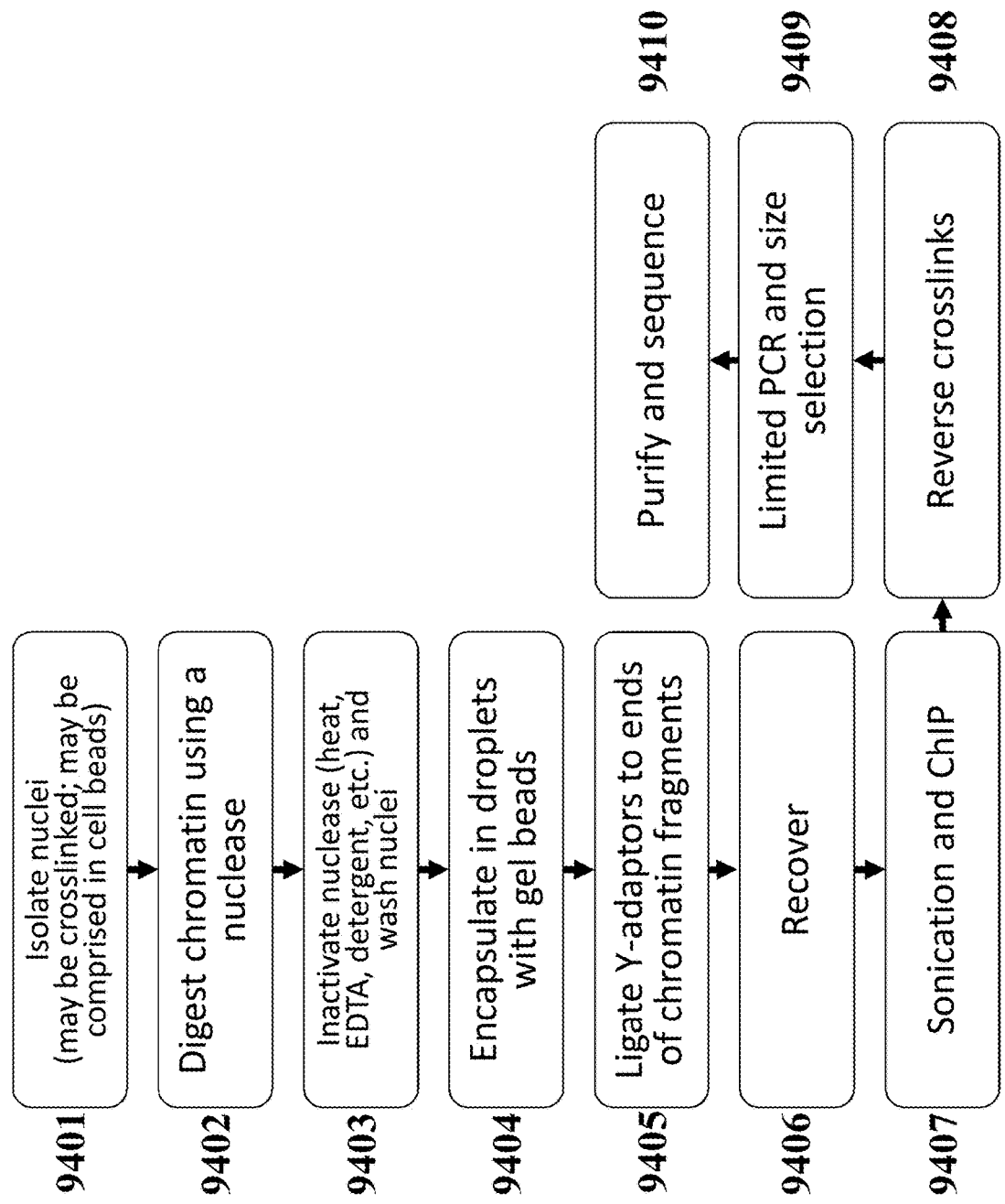
FIG. 94 illustrates an example method for analyzing nucleic acid-protein interactions from a single cell.
Figure 95:
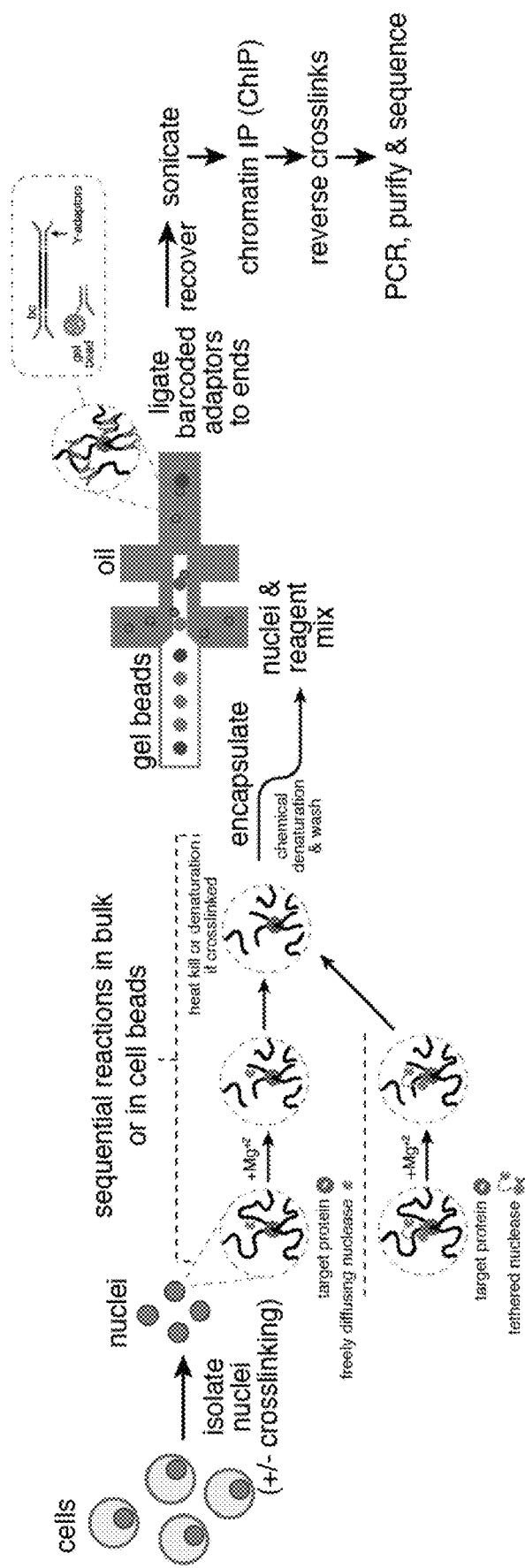
FIG. 95 shows a diagram illustrating the example method of FIG. 94.

In some aspects, the present disclosure provides methods and systems for analyzing interactions between nucleic acid (e.g., DNA) and protein from one or more single cells. Nucleic acid-protein interactions may be analyzed together with one or more additional types of information from a cell including, for example, expression information, genomic information, additional epigenetic information (e.g., methylation information), metabolomics information, proteomic information, etc. Nucleic acid-protein interactions may be obtained by isolating and/or purifying regions of nucleic acid bound to one or more proteins of interest. Purification may comprise immunoprecipitation. In some cases, chromatin immunoprecipitation can be used in the analyses of nucleic acid-protein interactions. FIG. 94 illustrates an example method for analyzing nucleic acid-protein interactions from a single cell. In operation 9401, one or more nuclei can be isolated from cells. In some cases, nuclei may be cross-linked with a chemical cross-linker, for example, formaldehyde. Cross-linking may serve to immobilize regions of DNA and/or proteins. Alternatively or in addition, nuclei may be comprised in a cell bead. As described herein, cells or nuclei may be partitioned into droplets comprising polymer precursors, which may be polymerized to generate a cell bead comprising a single cell or nucleus. Cell beads may comprise one or more additional analytes (e.g., components) from a cell (e.g., mRNA, cDNA, etc.). In operation 9402, nuclei can be subjected to nuclease treatment. A nuclease may be a restriction endonuclease, an MNase, or a DNase. A nuclease may be attached to an antibody, which may serve to direct the nuclease to a specific region of a genome by virtue of the specificity of the antibody. Nuclease treatment may fragment DNA within the nuclei. Fragmentation may be specific for a given region of DNA. In some cases, regions of DNA which are bound to one or more proteins may be protected from fragmentation. In operation 9403, a nuclease can be inactivated. A nuclease may be inactivated by the addition of one or more chemical reagents. Nuclei may be washed to remove one or more enzymes (e.g., nuclease enzymes). In operation 9404, nuclei can be partitioned into droplets together with gel beads, as described elsewhere herein. Gel beads may comprise barcode molecules for barcoding DNA (e.g., genomic DNA). Gel beads may comprise one or more additional barcode molecules for barcoding different types of analytes (e.g., RNA, cDNA, antibody barcode molecules, etc.). Gel beads may comprise an adaptor molecule. An adaptor may be a Y-adaptor. An adaptor molecule can comprise one or more barcode sequences. In operation 9405, one or more adaptor molecules can be ligated to the DNA fragments in the droplet. An adaptor molecule can be a Y-adaptor. An adaptor molecule can comprise one or more barcode sequences. In operation 9406, nuclei can be released from the partitions and recovered. In operation 9407, nuclei can be subjected to sonication and ChIP may be performed. ChIP may comprise using one or more antibodies to bind to one or more proteins from a cell. The one or more antibodies may comprise an antibody barcode sequence. An antibody may be used to pull down regions of DNA bound to a protein for which an antibody has affinity. In operation 9408, the crosslinks can be reversed. In operation 9409, DNA (e.g., DNA pulled down by an antibody) can be subjected to PCR and purified, for example, using size selection. In operation 9410, DNA can be sequenced to obtain sequencing reads from the DNA. Sequencing reads can also be obtained from one or more additional barcoded analytes from a cell or nucleus. Sequencing may determine chromatin interaction information from each single cell, identified by the presence of a unique barcode sequence. Sequencing may also identify additional genetic information from the cell. FIG. 95 shows a diagram illustrating the example method of FIG. 94.

Figure 96:
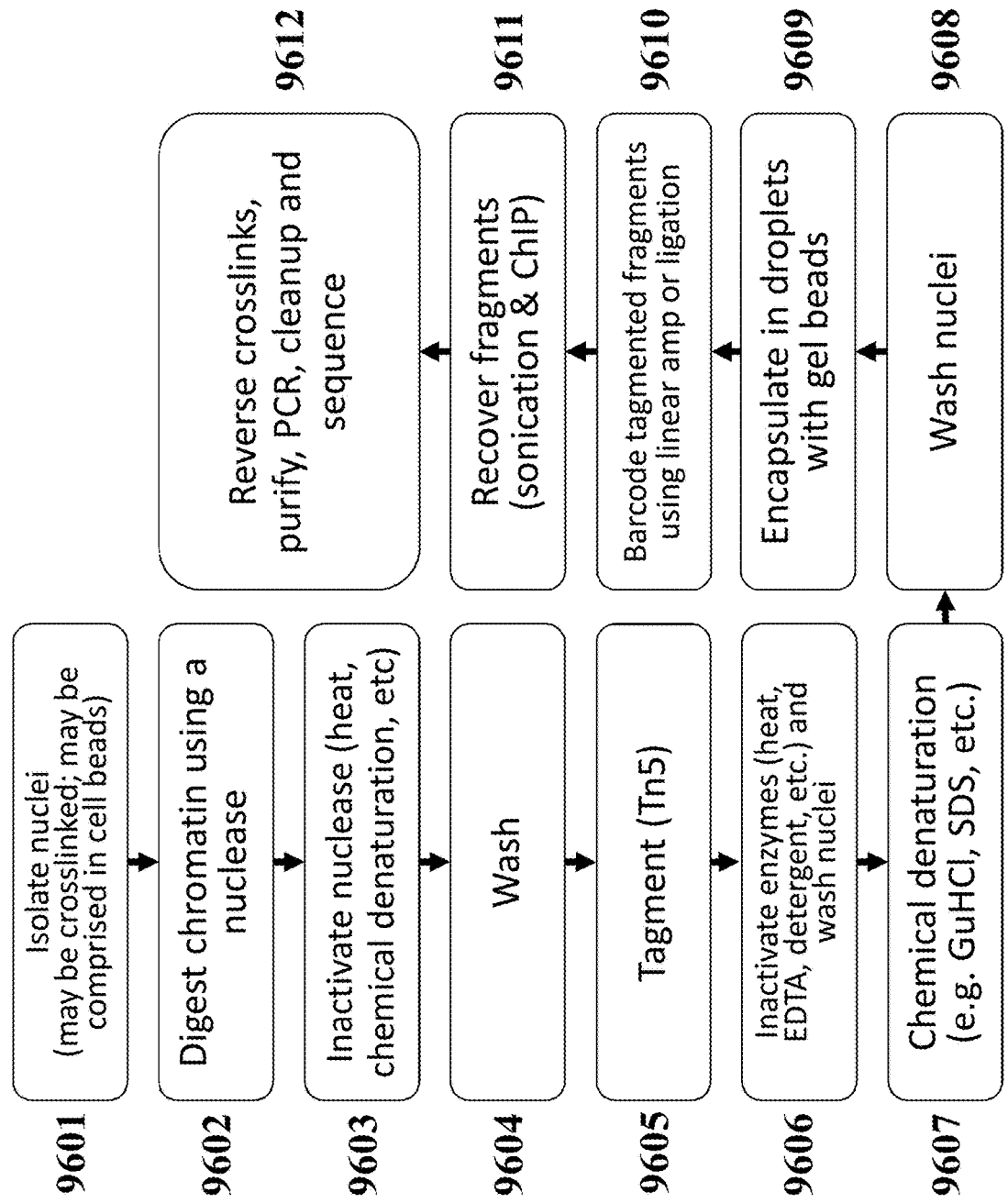
FIG. 96 illustrates another example method for analyzing nucleic acid-protein interactions from a single cell.
Figure 97:
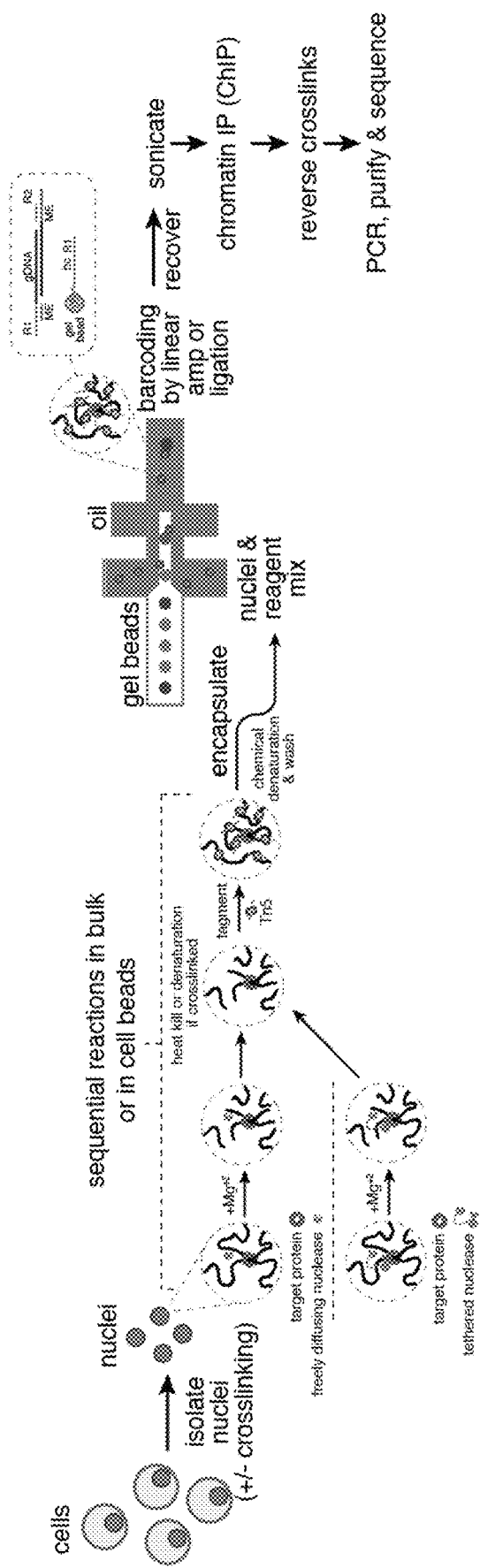
FIG. 97 shows a diagram illustrating the example method of FIG. 96.

FIG. 96 illustrates another example method for analyzing nucleic acid-protein interactions from a single cell. In operation 9601, one or more nuclei can be isolated from cells. In some cases, nuclei may be cross-linked with a chemical cross-linker, for example, formaldehyde. Cross-linking may serve to immobilize regions of DNA and/or proteins. Alternatively or in addition, nuclei may be comprised in a cell bead. As described herein, cells or nuclei may be partitioned into droplets comprising polymer precursors, which may be polymerized to generate a cell bead comprising a single cell or nucleus. Cell beads may comprise one or more additional analytes (e.g., components) from a cell (e.g., mRNA, cDNA, etc.). In operation 9602, nuclei can be subjected to nuclease treatment. A nuclease may be a restriction endonuclease, an MNase, or a DNase. A nuclease may be attached to an antibody, which may serve to direct the nuclease to a specific region of a genome by virtue of the specificity of the antibody. Nuclease treatment may fragment DNA within the nuclei. Fragmentation may be specific for a given region of DNA. In some cases, regions of DNA which are bound to one or more proteins may be protected from fragmentation. In operation 9603, a nuclease can be inactivated. A nuclease may be inactivated by the addition of one or more chemical reagents. In operation 9604, Nuclei can be washed to remove one or more enzymes (e.g., nuclease enzymes). In operation 9605, the nuclei can be subjected to tagmentation. Tagmentation may be used to add one or more additional sequences (e.g., barcode sequences, flow cell sequences, etc.) into a DNA fragment. Tagmentation may comprise use of a transposase. A transposase may be a Tn5 transposase. In operation 9606, one or more enzymes (e.g., polymerase, ligase, transposase, etc.) can be inactivated and removed from the nuclei. Enzymes may be inactivated by the addition of one or more of heat, detergents, or other chemical agents. Enzymes may be removed by washing the nuclei. In operation 9607, nuclei can be subjected to conditions sufficient to denature the DNA. Denaturation is described elsewhere herein, and may include the use of chemical agents such as SDS, guanidine hydrochloride (GuHCl), etc. In operation 9608, nuclei can be washed to remove chemical denaturation agents. In operation 9609, nuclei can be partitioned into droplets together with gel beads, as described elsewhere herein. Gel beads may comprise barcode molecules for barcoding DNA (e.g., genomic DNA). Gel beads may comprise one or more additional barcode molecules for barcoding different types of analytes (e.g., RNA, cDNA, antibody barcode molecules, etc.). In operation 9610, barcode molecules may be used to barcode tagmented DNA (i.e., DNA fragments subjected to tagmenetation). Barcoding may comprise amplification (e.g., linear amplification, polymerase chain reaction). Barcoding may not comprise amplification. Barcoding may comprise ligation. In operation 9611, nuclei can be released from the partitions. In some cases, the DNA (e.g., DNA fragments) from the nuclei may be subjected to sonication. Chromatin immunoprecipitation (ChIP) may be performed on the DNA from the nuclei. In operation 9612, the crosslinks can be reversed. In operation 9613, the crosslinks can be reversed, DNA isolated, and subjected to sequencing to generate sequencing reads. Sequencing may determine chromatin interaction information from each single cell, identified by the presence of a unique barcode sequence. FIG. 97 shows a diagram illustrating the example method of FIG. 96.

Figure 98:
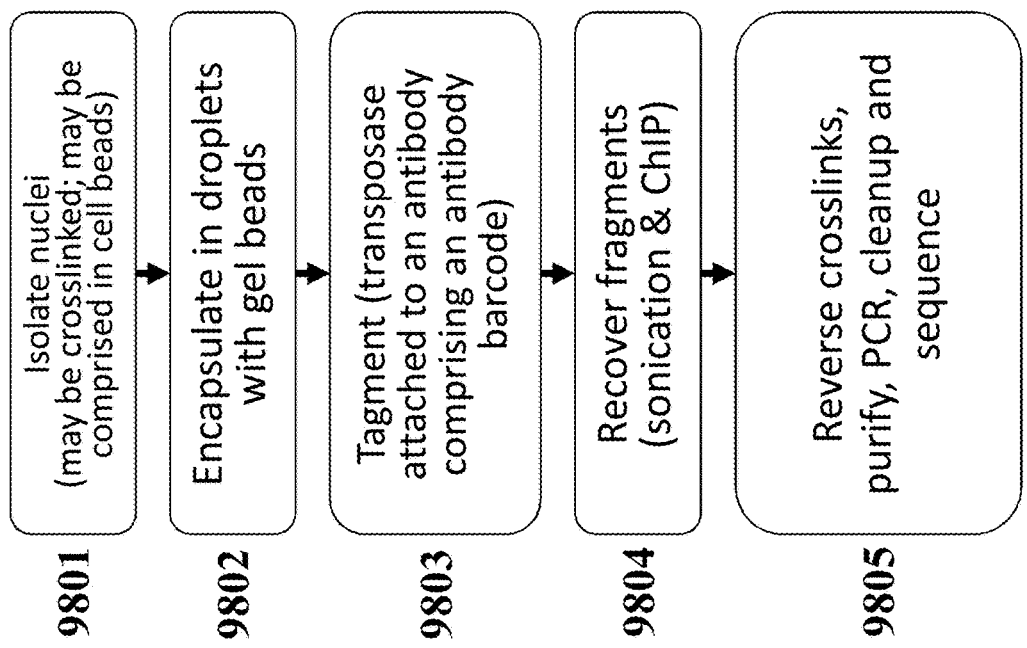
FIG. 98 illustrates another example method for analyzing nucleic acid-protein interactions from a single cell.
Figure 99:
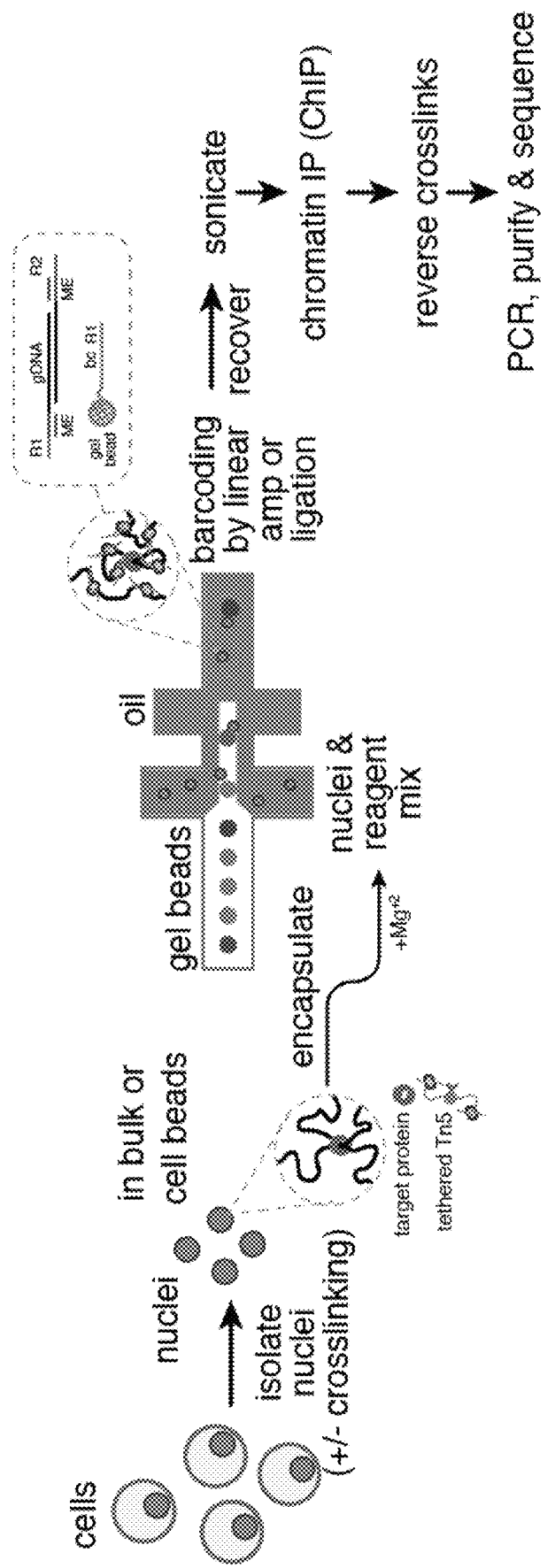
FIGS. 99-100 show diagrams illustrating the example method of FIG. 98.
Figure 100:
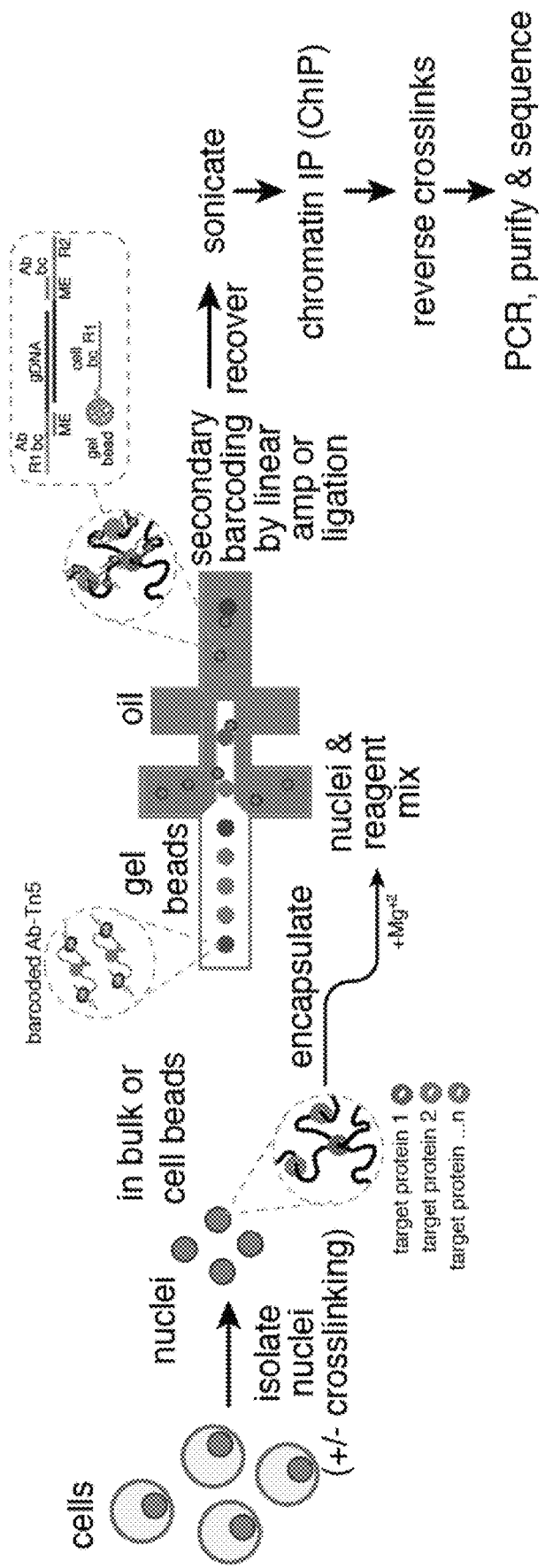

FIG. 98 illustrates another example method for analyzing nucleic acid-protein interactions from a single cell. In operation 9801, one or more nuclei can be isolated from cells. In some cases, nuclei may be cross-linked with a chemical cross-linker, for example, formaldehyde. Cross-linking may serve to immobilize regions of DNA and/or proteins. Alternatively or in addition, nuclei may be comprised in a cell bead. As described herein, cells or nuclei may be partitioned into droplets comprising polymer precursors, which may be polymerized to generate a cell bead comprising a single cell or nucleus. Cell beads may comprise one or more additional analytes (e.g., components) from a cell (e.g., mRNA, cDNA, etc.). In operation 9802, nuclei can be partitioned into droplets together with gel beads, as described elsewhere herein. Nuclei can be partitioned together with a transposase. A transposase can be a Tn5 transposase. A transposase can be attached to one or more antibodies. Antibodies attached to a transposase may comprise one or more antibody barcode sequences. Antibodies attached to a transposase may serve to direct a transposase to a specific region of a genome. This may be useful in directing tagmentation of a specific region of DNA, based on the antibody specificity. For example, an antibody may direct a transposase to a region of DNA bound to a DNA binding protein, thereby directing tagmentation in the region surrounding the DNA binding protein. Gel beads may comprise barcode molecules for barcoding DNA (e.g., genomic DNA). Gel beads may comprise one or more additional barcode molecules for barcoding different types of analytes (e.g., RNA, cDNA, antibody barcode molecules, etc.). In operation 903, the nuclei can be subjected to tagmentation. Tagmentation may be performed in a droplet. Alternatively or in addition, tagmentation may be performed outside of a droplet (e.g., in bulk). Tagmentation may be used to add one or more additional sequences (e.g., barcode sequences, flow cell sequences, etc.) into a DNA fragment. Tagmentation may comprise use of a transposase. A transposase may be a Tn5 transposase. In operation 9804, nuclei can be released from the partitions. Nuclei can be subjected to sonication and ChIP may be performed. ChIP may comprise using one or more antibodies to bind to one or more proteins from a cell. The one or more antibodies may comprise an antibody barcode sequence. The one or more antibodies may be attached to a transposase. In some cases, the one or more antibodies used to perform ChIP may be those attached to the transposase used to perform tagmentation in operation 9805. An antibody may be used to pull down regions of DNA bound to a protein for which an antibody has affinity. In operation 9806, the crosslinks can be reversed, DNA isolated, and subjected to sequencing to generate sequencing reads. Isolated DNA labeled with a biotin molecule can be purified using, for example, streptavidin-coupled beads. Sequencing may determine chromatin interaction information from each single cell, identified by the presence of a unique barcode sequence. Sequencing may also determine the identity of the protein bound to a given region of DNA by the identification of one or more antibody barcode sequences. FIGS. 99-100 show diagrams illustrating the example method of FIG. 98.

Characterization, Analysis, and Detection of a Lineage Tracing Construct

Disclosed herein are methods compositions and systems for analyzing analytes (e.g. cell surface features, proteins, nucleic acids, and cell lineage tracing constructs) of small population of cells, and in some cases, of individual cells. Also provided herein are methods, compositions and systems for large-scale, simultaneous capture of transcriptome and lineage information from individual cells or a small population of cells for the characterization of cell types and their cell lineage relationships. The methods described herein may compartmentalize the analysis of individual cells or small populations of cells, including e.g., cell surface features, proteins, nucleic acids, and cell lineage tracing constructs in individual cells or small groups of cells, and then allow that analysis to be attributed back to the individual cell or small group of cells from which the cell surface features, proteins, nucleic acids, and cell lineage tracing constructs were derived. This can be accomplished regardless of whether the cell population represents a 50/50 mix of cell types, a 90/10 mix of cell types, or virtually any ratio of cell types, as well as a complete heterogeneous mix of different cell types, or any mixture between these. Differing cell types may include cells from different tissue types of an individual or the same tissue type from different individuals, or biological organisms such as microorganisms from differing genera, species, strains, variants, or any combination of any or all of the foregoing. For example, differing cell types may include normal and tumor tissue from an individual, various cell types obtained from a human subject such as a variety of immune cells (e.g., B cells, T cells, and the like), multiple different bacterial species, strains and/or variants from environmental, forensic, microbiome or other samples, or any of a variety of other mixtures of cell types.

In one aspect, the methods and systems described herein may be used to analyze multiple analytes from individual cells or a small population of cells. In one aspect, the methods and systems described herein may be used to analyze multiple analytes (e.g. RNA and the cell lineage tracing construct) to capture both the transcriptome and lineage information from individual cells or a small population of cells.

The method for analyzing an analyte in a cell may comprise: (a) providing a plurality of partitions, wherein a given partition of said plurality of partitions comprises a plurality of analytes and a plurality of barcode molecules coupled to a bead, wherein (i) a first barcode molecule of said plurality of barcode molecules comprises a first nucleic acid barcode sequence capable of coupling to a first analyte of said plurality of analytes, wherein said first analyte is a cell lineage tracing construct, and wherein (ii) a second barcode molecule of said plurality of barcoded molecules comprises a second nucleic acid barcode sequence capable of coupling to a second analyte of said plurality of analytes, wherein said second analyte is a nucleic acid of said cell; (b) in said given partition, (i) coupling said first barcode molecule to said first analyte or a derivative thereof, and synthesizing a first nucleic acid molecule comprising at least a portion of said first nucleic acid barcode sequence or a complement thereof and a sequence of said first analyte or a complement thereof; and (ii) coupling said second barcode molecule to said second analyte or a derivative thereof, and synthesizing a second nucleic acid molecule comprising at least a portion of said second nucleic acid barcode sequence or complement thereof and a sequence of said second analyte or complement thereof; (c) processing (i) said first nucleic acid molecule or a derivative thereof and (ii) said second nucleic acid molecule or a derivative thereof, to identify said at least said portion of said first nucleic acid barcode sequence and said at least said portion of said second nucleic acid barcode sequence; and (d) using said at least said portion of said first nucleic acid barcode sequence and said at least said portion of said second nucleic acid barcode sequence to identify said first analyte and said second analyte as originating from said cell. The method may further comprise removing said first nucleic acid molecule and said second nucleic acid molecule, or a derivative of said first nucleic acid molecule and/or said second nucleic acid molecule, from said given partition. The method may further comprise performing one or more reactions subsequent to removing said first nucleic acid molecule and said second nucleic acid molecule from said given partition. In an aspect, after (a) of the method, said first barcode molecule and/or said second barcode molecule is released from said bead. The method may further comprise subjecting said first nucleic acid molecule and said second nucleic acid molecule, or a derivative of said first nucleic acid molecule and/or said second nucleic acid molecule, to sequencing to characterize said first analyte or said second analyte. The first barcode molecule or said second barcode molecule may comprise a unique molecular identification (UMI) sequence.

The first barcode molecule may comprise a first priming sequence capable of hybridizing to said first analyte, or a derivative thereof. The second barcode molecule may comprise a second priming sequence capable of hybridizing to said second analyte, or a derivative thereof. The first barcode molecule may comprise a first priming sequence capable of hybridizing to said first analyte, or a derivative thereof, and said second barcode molecule may comprise a second priming sequence capable of hybridizing to said second analyte, or a derivative thereof. The first analyte may comprise an adapter sequence complementary to said first priming sequence. The first priming sequence may be complementary to a sequence in said cell lineage tracing construct. The second priming sequence may comprise a poly-deoxy-thymine (poly(dT)) sequence. The nucleic acid of said cell may be messenger ribonucleic acid (mRNA). The first nucleic acid barcode sequence and said second nucleic acid barcode sequence may be identical.

The bead may be a gel bead. The plurality of barcode molecules may be reversibly coupled to said gel bead (e.g. through chemical cross-links, disulfide bonds, etc). The given partition may further comprise an agent (e.g. reducing agent) capable of releasing said first barcode molecule or said second barcode from said bead. In some cases, after (a), said first barcode molecule and said second barcode molecule are released from said bead. In some cases, before or during (b), said first barcode molecule or said second barcode molecule is released from said bead. The given partition may be a droplet among a plurality of droplets. The given partition may be a well among a plurality of wells. The plurality of partitions may further comprise a template switching oligonucleotide (TSO). In some cases, in (b), synthesizing said first nucleic acid molecule or synthesizing said second nucleic acid molecule, or a derivative of said first nucleic acid molecule or said second nucleic acid molecule, includes the use of said template switching oligonucleotide. The TSO may comprise a primer sequence and wherein said first nucleic acid molecule or said second nucleic acid molecule, or a derivative of said first nucleic acid molecule or said second nucleic acid molecule, comprise said TSO primer sequence. The plurality of partitions may comprise a plurality of cells, wherein at least a subset of said plurality of cells comprise one or more cell lineage tracing construct, and wherein said given partition of said plurality of partitions comprises a cell comprising said one or more cell lineage tracing construct. The given partition of said plurality of partitions may comprise a single cell.

The cell lineage tracing construct may comprise an editable nucleic acid array, wherein said editable nucleic acid array is edited by a gene editing system (e.g. CRISPR/Cas, TALENs, ZFNs, meganucleases, etc). The gene editing system may be CRISPR/Cas. The editable nucleic acid array may comprise a genomic array of CRISPR target sites. The genomic array of CRISPR target sites comprises between 5 to 12 said CRISPR target sites. The genomic array of CRISPR target sites may comprise at least 5 said CRISPR target sites. The genomic array of CRISPR target sites may comprise at least 6 said CRISPR target sites. The genomic array of CRISPR target sites may comprise at least 7 said CRISPR target sites. The genomic array of CRISPR target sites may comprise at least 8 said CRISPR target sites. The genomic array of CRISPR target sites may comprise at least 9 said CRISPR target sites. The genomic array of CRISPR target sites may comprise at least 10 said CRISPR target sites. The genomic array of CRISPR target sites may comprise at least 11 said CRISPR target sites. The genomic array of CRISPR target sites may comprise at least 12 said CRISPR target sites. The genomic array of CRISPR target sites may comprise at most 5 said CRISPR target sites. The genomic array of CRISPR target sites may comprise at most 6 said CRISPR target sites. The genomic array of CRISPR target sites may comprise at most 7 said CRISPR target sites. The genomic array of CRISPR target sites may comprise at most 8 said CRISPR target sites. The genomic array of CRISPR target sites may comprise at most 9 said CRISPR target sites. The genomic array of CRISPR target sites may comprise at most 10 said CRISPR target sites. The genomic array of CRISPR target sites may comprise at most 11 said CRISPR target sites. The genomic array of CRISPR target sites may comprise at most 12 said CRISPR target sites. The genomic array of CRISPR target sites may comprise 5 said CRISPR target sites. The genomic array of CRISPR target sites may comprise 6 said CRISPR target sites. The genomic array of CRISPR target sites may comprise 7 said CRISPR target sites. The genomic array of CRISPR target sites may comprise 8 said CRISPR target sites. The genomic array of CRISPR target sites may comprise 9 said CRISPR target sites. The genomic array of CRISPR target sites may comprise 10 said CRISPR target sites. The genomic array of CRISPR target sites may comprise 11 said CRISPR target sites. The genomic array of CRISPR target sites may comprise 12 said CRISPR target sites.

In some aspects, (a) said given partition may further comprise a third barcode molecule of said plurality of barcode molecules comprising a third nucleic acid barcode sequence, wherein said third barcode molecule is capable of coupling to a third analyte of said plurality of analytes; and wherein (b) further comprises coupling said third barcode molecule to said third analyte and synthesizing a third nucleic acid molecule comprising at least a portion of said third nucleic acid barcode sequence or complement thereof and a sequence of said third analyte or complement thereof. The third molecule may comprise a third priming sequence capable of hybridizing to said third analyte, or a derivative thereof. The third analyte may be genomic deoxyribonucleic acid (gDNA) of said cell. The first nucleic acid barcode sequence, said second nucleic barcode sequence, and said third nucleic barcode sequence may be at least 80% identical.

In some aspects, (a) said given partition may further comprise a fourth barcode molecule of said plurality of barcode molecules comprising a fourth nucleic acid barcode sequence, wherein said fourth barcode molecule is capable of coupling to a fourth analyte of said plurality of analytes; and wherein (b) further comprises coupling said fourth barcode molecule to said fourth analyte and synthesizing a fourth nucleic acid molecule comprising at least a portion of said fourth nucleic acid barcode sequence or complement thereof and a sequence of said fourth analyte or complement thereof. The fourth analyte may be a labelling agent capable of coupling to a protein of said cell (e.g. via a fourth nucleic acid molecule of said labelling agent). The labelling agent may comprise a protein, an antibody, an antibody fragment, a major histocompatibility complex (WIC) molecule, or a small molecule. The first nucleic acid barcode sequence, said second nucleic acid barcode sequence, said third nucleic barcode sequence, and said fourth nucleic acid barcode sequence may be at least identical.

In some cases, the first analyte (i.e. a cell lineage tracing construct) and the second analyte (i.e. mRNA) are analyzed. In some cases, the first analyte (i.e. a cell lineage tracing construct) the second analyte (i.e. mRNA), and the third analyte (i.e. gDNA) are analyzed. In some cases, the first analyte (i.e. a cell lineage tracing construct) the second analyte (i.e. mRNA), the third analyte (i.e. gDNA), and the fourth analyte (i.e. labelling agent) are analyzed. In some cases, the first analyte (i.e. a cell lineage tracing construct) the second analyte (i.e. mRNA), and the fourth analyte (i.e. labelling agent) are analyzed. In some cases, the first analyte (i.e. a cell lineage tracing construct) and the third analyte (i.e. gDNA) are analyzed. In some cases, the first analyte (i.e. a cell lineage tracing construct) and the fourth analyte (i.e. labelling agent) are analyzed. In some cases, the first analyte (i.e. a cell lineage tracing construct), the third analyte (i.e. gDNA), and the fourth analyte (i.e. labelling agent) are analyzed.

Provided herein are methods and compositions for sequencing a cell lineage tracing construct and RNA (e.g., mRNA) molecules from a cell in parallel and/or simultaneously. In some cases, the methods and compositions may be used for determining the cell lineage and transcriptome from a single cell in parallel.

In one aspect, the present invention provides methods for cell lineage or cell lineage tracing analysis comprising providing partitions containing biological particles (e.g., a cell, a cell nucleus, or a cell bead), wherein the biological particles comprise lineage tracing nucleic acid molecules. In one embodiment, the method includes the operation of providing biological particles that comprise a lineage tracing nucleic acid molecule which is configured to permit identification of the lineage tracing nucleic acid molecule with a progenitor cell. For instance, the lineage tracing nucleic acid molecule in a biological particle comprises a lineage tracing barcode molecule. In one embodiment, the lineage tracing barcode molecule comprises a lineage tracing target region and a lineage tracing barcode sequence. In another embodiment, the biological particles further comprise other analytes as described herein.

In an additional embodiment, the method further includes the operation of contacting the biological particles with a plurality of nucleic acid barcode molecules. The method may comprise providing a reaction mixture comprising the biological particles and the plurality of nucleic acid barcode molecules. The plurality of nucleic acid barcode molecules may be attached to a solid support. In one embodiment, the solid support is a bead. In certain embodiments, the plurality of nucleic acid barcode molecules is releasably attached to said bead.

In other embodiments, the plurality of nucleic acid barcode molecules comprise (i) a first type of barcode molecule for lineage tracing analysis and (ii) a second type of barcode molecule for processing of analytes of a different type (i.e., non-lineage tracing molecules). In another embodiment, one or more of the plurality of nucleic acid barcode molecules comprise a plurality of lineage tracing barcode molecules. A lineage tracing barcode molecule of the plurality of lineage tracing barcode molecules can comprise (i) a lineage tracing capture region that is configured to attach or couple to a lineage tracing target region of a lineage tracing nucleic acid molecule from a biological particle and (ii) a common barcode sequence. In another embodiment, one or more of the plurality of nucleic acid barcode molecules further comprise a plurality of analyte barcode molecules. The analyte barcode molecules are configured to process an analyte that is of a different type than the lineage tracing nucleic acid molecule of the biological particle. In one embodiment, an analyte barcode molecule of a plurality of analyte barcode molecules comprises (i) an analyte capture region that is configured to attach or couple to a nucleic acid molecule that corresponds to the analyte of a different type and (ii) the same common barcode sequence that is present in the plurality of lineage tracing barcode molecules. In some embodiments, the common barcode sequence of the lineage tracing barcode molecule and the analyte barcode molecule (i) comprise identical barcode sequence segments, or (ii) are identical.

In one embodiment, the lineage tracing capture region does not comprise a poly(dT) sequence, lacks a poly(dT) sequence, or is not a poly(dT) sequence. In another embodiment, the analyte capture region does not comprise a poly(dT) sequence, lacks a poly(dT) sequence, or is not a poly(dT) sequence.

In some instances, the method may include the operation of coupling (attaching or capturing) nucleic acid molecules from a biological particle to barcode molecules to generate barcoded molecules. In one embodiment, the method comprises coupling a lineage tracing nucleic acid molecule to a lineage tracing barcode molecule. In one embodiment, the coupling is via contact of a lineage tracing capture region with (or capture by a lineage tracing capture region of) a lineage tracing target region of a lineage tracing nucleic acid molecule. In one other embodiment, the step of coupling (attaching or capturing) further comprises coupling an analyte barcode molecule to a nucleic acid molecule corresponding to an analyte from the biological partition. In one embodiment, the analyte is a different type of analyte than the lineage tracing nucleic acid molecule. In other embodiments, the coupling is via contact of an analyte capture region with (or capture by an analyte capture region of) a nucleic acid molecule that corresponds to the different analyte.

In certain embodiments, the nucleic acid molecule that corresponds to the different analyte is coupled to a labelling agent, wherein the labelling agent is configured to couple to the different analyte. In other embodiments, the nucleic acid molecule coupled to the labelling agent comprises an analyte target region, where the analyte target region comprises a target sequence configured to couple or attach to the analyte capture region via a sequence that is complementary to the target sequence. In one embodiment, the labelling agent includes antibodies and other labelling agents, as further described herein.

In some embodiments, the method may include the operation of generating (or synthesizing) a first nucleic acid molecule comprising said common barcode sequence and a sequence corresponding to the lineage tracing nucleic acid molecule, and (2) a second nucleic acid molecule comprising said common barcode sequence and a sequence corresponding to said nucleic acid molecule corresponding to the analyte.

In other embodiments, one or more of the operations of providing biological particles comprising a lineage tracing nucleic acid molecules, contacting the biological particles with a plurality of nucleic acid barcode molecules, coupling (attaching or capturing) nucleic acid molecules from a biological particle to barcode molecules, and generating (or synthesizing) barcoded molecules are performed in a partition. In another embodiment, the partition is an aqueous droplet in an emulsion or a well as further described elsewhere herein.

In certain embodiments, the operation of contacting the biological particles with a plurality of nucleic acid barcode molecules, coupling (attaching or capturing) nucleic acid molecules from a biological particle to barcode molecules, or generating (or synthesizing) barcoded molecules comprises releasing the plurality of nucleic acid barcode molecules from the solid support. In other embodiments, the solid support is a bead that is degradable upon application of a stimulus as described herein.

In some embodiments, the method comprises the operation of sequencing (i) said first nucleic acid molecule or a derivative thereof and (ii) said second nucleic acid molecule or a derivative thereof, to identify (a) said common barcode sequence, (b) said sequence corresponding to said lineage tracing nucleic acid molecule, and (c) said sequence of said nucleic acid molecule corresponding to said analyte. In one embodiment, the common barcode sequence identifies the lineage tracing nucleic acid molecule and the different analyte as having originated from the biological particle.

In other embodiments, the analyte that is a different type of analyte than the lineage tracing nucleic acid molecule is selected from the group consisting of a ribonucleic acid (RNA), a metabolite, and a protein. In another embodiment, the RNA molecule is selected from the group consisting of (i) a messenger RNA molecule, (ii) a clustered regularly interspaced short palindromic (CRISPR) RNA molecule (crRNA), and (iii) a single guide RNA (sgRNA) molecule.

In some embodiments, the analyte capture region for the different analyte comprises a poly(dT) sequence and the lineage tracing capture region does not comprise a poly(dT) sequence, lacks a poly(dT) sequence, or is not a poly(dT) sequence. In other embodiments, the lineage tracing capture region comprises a poly(dT) sequence and the analyte capture region for the different analyte does not comprise a poly(dT) sequence, lacks a poly(dT) sequence, or is not a poly(dT) sequence.

In one embodiment, the analyte capture region or the lineage tracing capture region comprises a template switching sequence as described herein. In a further embodiment, the method includes the operation of generating (or synthesizing) a barcoded nucleic acid molecule with the use of assay primers, an extension reaction (e.g., reverse transcription enzyme/polymerase), and template switching as further described herein.

In another embodiment, the analyte that is a different type of analyte than the lineage tracing nucleic acid molecule is genomic deoxyribonucleic acid (gDNA) molecule. In other embodiments, the gDNA molecule is fragmented. For instance, the gDNA molecule may be enzymatically fragmented. In one embodiment, the gDNA molecule comprises a nucleic acid fragment generated from chromatin with the aid of a transposase molecule or with the aid of a deoxyribonuclease enzyme, as further described herein. In other embodiments, the gDNA molecule has been subjected to cytosine deamination or the gDNA comprises deaminated cytosines including, without limitation, chemically or enzymatically deaminated cytosines. In one embodiment, the gDNA molecule comprises oxidized 5-hydroxymethylcytosine bases or the gDNA molecule has been subjected to oxidation of 5-hydroxymethylcytosine bases.

A microcapsule (e.g., a bead) entrapping one or more magnetic particles may be used in the methods. The magnetic particles may not diffuse out of the microcapsule until the microcapsule is dissolved. The magnetic particles entrapped within the microcapsule may comprise an oligonucleotide comprising a cell lineage tracing construct primer. The cell lineage tracing construct primer may bind to a cell lineage tracing construct from a cell. In some cases, the cell lineage tracing construct primer is a primer that is complementary to an adapter sequence in the cell lineage tracing construct from the cell.

The magnetic particles entrapped within the microcapsule may comprise an oligonucleotide comprising an RNA primer. The RNA primer may bind to RNA molecules from a cell. In some cases, the RNA primer is an mRNA primer that binds to the mRNA molecules from the cell. For example, the mRNA primer may comprise a poly-T sequence that binds to the poly-A sequence of the mRNA molecules from the cell.

The magnetic particles may be made from materials such as iron oxide (e.g., superparamagnetic iron oxide), ferromagnetic, ferrimagnetic, or paramagnetic materials. Ferromagnetic materials may be strongly susceptible to magnetic fields and capable of retaining magnetic properties when the field can be removed. Ferromagnetic materials include, but are not limited to, iron, cobalt, nickel, alloys thereof, and combinations thereof. Other ferromagnetic rare earth metals or alloys thereof can also be used to make the magnetic particles.

The oligonucleotides on both the microcapsule and the magnetic particle may comprise the same barcode sequence. The barcode sequence may allow matching the information (e.g., sequence reads) of the cell lineage tracing construct, and RNA, and from the same cell.

In some cases, the barcode sequence may comprise a unique identifier of the cell. For example, the unique identifier may distinguish a cell from other cells in a sample. Thus, the unique identifier may allow parallel analysis of cell lineage tracing construct, and RNA molecules in a plurality of cells, e.g., at least 10, 50, 100, 200, 300, 400, 500, 600, 800, or 1000 cells. For example, the unique identifier may allow parallel analysis of cell lineage tracing construct and RNA molecules in a plurality of cells, e.g., at least 200, or 500 cells.

In some cases, the microcapsule may also contain one or more reagents for analyzing cells. For example, the microcapsule may contain a lysis agent. When the microcapsule is dissolved, the lysis agent may be released and lyse the cell in the same partition with the microcapsule.

In some cases, the microcapsule may be a gel bead. An example method for making a gel bead with one or more magnetic particles may comprise one or more of the following operations: 1) Magnetic particles are added to the aqueous phase of the material for making the gel beads, e.g., the gel beads monomer mixture; 2) The gel beads are made using a microfluidic approach, e.g., by forming droplets that polymerize to form the gel beads. When the droplets polymerize, the magnetic particles are entrapped within; 3) The same barcode sequence is added to the gel bead and the magnetic particles entrapped within, e.g., using dual ligation strategy.

Once a partition is generated to include a cell, a microcapsule, and a magnetic particle entrapped in the microcapsule, the partition may be incubated with one or more reagents (e.g., a lysis agent) to lyse the cell and dissolve the microcapsule. The incubation may be performed on a microfluidic chip device, e.g., with a delay line device as described in Frenz et al., Reliable microfluidic on-chip incubation of droplets in delay-lines. Lab Chip. 2009 May 21; 9(10):1344-8, which is incorporated herein by reference in its entirety. After the incubation, the partition may be collected and placed in a container e.g., a strip tube or plate.

The incubation may be performed for a period that allows sufficient time for the cell to lyse and the magnetic particles to be released from the microcapsule. The incubation time may also allow sufficient binding of the RNA primers on the magnetic particles with the RNA molecules from the cell. In some cases, the incubation time may be from 1 minute to 100 minutes, from 5 minutes to 50 minutes, from 10 minutes to 30 minutes, or from 10 minutes to 20 minutes.

One or more RNA molecules bound to the RNA primers on the magnetic particles may be separated from other components in the partition. The separation may be performed by concentrating the magnetic particles. The magnetic particles may be concentrated by a magnetic field. The separation may be performed on a microfluidic device, e.g., a device as described in Gao et al., Wash-free magnetic immunoassay of the PSA cancer marker using SERS and droplet microfluidics, Lab Chip, 2016, 16, 1022-1029; Brouzes et al., Rapid and continuous magnetic separation in droplet microfluidic devices. Lab Chip. 2015 Feb. 7; 15(3): 908-19; or Lombardi et al., Droplet microfluidics with magnetic beads: a new tool to investigate drug-protein interactions. Anal Bioanal Chem. 2011 January; 399(1):347-52, which are incorporated herein by reference in their entireties. In some cases, the one or more RNA molecules may be separated from cell lineage tracing construct. The separated RNA molecules and cell lineage tracing construct from a single cell may be analyzed using approaches described herein, e.g., sequencing, to determine a characteristic of the cell.

Also provided herein are methods and compositions for sequencing a cell lineage tracing construct, DNA (e.g., genomic DNA) molecules and RNA (e.g., mRNA) molecules from a cell in parallel and/or simultaneously. In some cases, the methods and compositions may be used for cell lineage tracing and sequencing the genome and transcriptome from a single cell in parallel.

A microcapsule (e.g., a bead) entrapping one or more magnetic particles may be used in the methods. The magnetic particles may not diffuse out of the microcapsule until the microcapsule is dissolved. The magnetic particles entrapped within the microcapsule may comprise an oligonucleotide comprising a cell lineage tracing construct primer. The cell lineage tracing construct primer may bind to a cell lineage tracing construct from a cell. In some cases, the cell lineage tracing construct primer is a primer that is complementary to an adapter sequence in the cell lineage tracing construct from the cell.

The magnetic particles entrapped within the microcapsule may comprise an oligonucleotide comprising an RNA primer. The RNA primer may bind to RNA molecules from a cell. In some cases, the RNA primer is an mRNA primer that binds to the mRNA molecules from the cell. For example, the mRNA primer may comprise a poly-T sequence that binds to the poly-A sequence of the mRNA molecules from the cell.

The microcapsule may comprise an oligonucleotide comprising a DNA primer. For example, the DNA primer may be a genomic DNA primer. The DNA primer may bind to DNA molecules from a cell. The DNA primer may be used to amplify and/or sequence DNA molecules from a cell. DNA primers may be entrapped and/or bound to the microcapsule and released when the microcapsule is dissolved.

The magnetic particles may be made from materials such as iron oxide (e.g., superparamagnetic iron oxide), ferromagnetic, ferrimagnetic, or paramagnetic materials. Ferromagnetic materials may be strongly susceptible to magnetic fields and capable of retaining magnetic properties when the field can be removed. Ferromagnetic materials include, but are not limited to, iron, cobalt, nickel, alloys thereof, and combinations thereof. Other ferromagnetic rare earth metals or alloys thereof can also be used to make the magnetic particles.

The oligonucleotides on both the microcapsule and the magnetic particle may comprise the same, or at least 80% identical barcode sequences. The barcode sequence may allow matching the information (e.g., sequence reads) of the cell lineage tracing construct, RNA and DNA, from the same cell.

In some cases, the barcode sequence may comprise a unique identifier of the cell. For example, the unique identifier may distinguish a cell from other cells in a sample. Thus, the unique identifier may allow parallel analysis of cell lineage, RNA molecules, and DNA molecules, in a plurality of cells, e.g., at least 10, 50, 100, 200, 300, 400, 500, 600, 800, or 1000 cells. For example, the unique identifier may allow parallel analysis of cell lineage, RNA molecules, and DNA molecules in a plurality of cells, e.g., at least 200, or 500 cells.

In some cases, the methods may be used for lineage tracing, for example by tracing modifications made by gene editing methods (such as CRISPR technology, TALEN, ZFN, meganucleases, etc) in a cell lineage tracing construct.

Methods disclosed herein comprise editing of a cell lineage tracing construct using a site-specific, targetable, and/or engineered nuclease or nuclease system. Such nucleases may create double-stranded break (DSBs) at desired locations in the construct. In other examples, a nuclease may create a single strand break. In some cases, two nucleases are used, each of which generates a single strand break.

The one or more double or single strand break may be repaired by natural processes of homologous recombination (HR) and non-homologous end-joining (NHEJ) using the cell's endogenous machinery. Additionally or alternatively, endogenous or heterologous recombination machinery may be used to repair the induced break or breaks.

Engineered nucleases such as zinc finger nucleases (ZFNs), Transcription Activator-Like Effector Nucleases (TALENs), engineered homing endonucleases, and RNA or DNA guided endonucleases, such as CRISPR/Cas such as Cas9 or CPF1, and/or Argonaute systems, are particularly appropriate to carry out some of the methods of the present disclosure. Additionally or alternatively, RNA targeting systems may be used, such as CRISPR/Cas systems including c2c2 nucleases.

Methods disclosed herein may comprise editing of a cell lineage tracing construct using CRISPR systems, such as a Type I, Type II, Type III, Type IV, Type V, or Type VI CRISPR system. CRISPR/Cas systems may be multi-protein systems or single effector protein systems. Multi-protein, or Class 1, CRISPR systems include Type I, Type III, and Type IV systems. Alternatively, Class 2 systems include a single effector molecule and include Type II, Type V, and Type VI.

CRISPR systems may comprise a single or multiple guiding RNAs. Guide RNAs to different CRISPR target sites in the construct may be introduced into the cell at different time points. The gRNA may comprise a crRNA. The gRNA may comprise a chimeric RNA with crRNA and tracrRNA sequences. The gRNA may comprise a separate crRNA and tracrRNA. Target nucleic acid sequences in the cell lineage tracing construct may comprise a protospacer adjacent motif (PAM) or a protospacer flanking site (PFS). The PAM or PFS may be 3' or 5' of the target or protospacer site.

A gRNA may comprise a spacer sequence. Spacer sequences may be complementary to target sequences or protospacer sequences. Spacer sequences may be 10, 11, 12, 13, 14, 15, 16, 17, 18, 19, 20, 21, 22, 23, 24, 25, 26, 27, 28, 29, 30, 31, 32, 33, 34, 35, or 36 nucleotides in length. In some examples, the spacer sequence may be less than 10 or more than 36 nucleotides in length.

A gRNA may comprise a repeat sequence. In some cases, the repeat sequence is part of a double stranded portion of the gRNA. A repeat sequence may be 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 nucleotides in length. In some examples, the spacer sequence may be less than 10 or more than 50 nucleotides in length.

A gRNA may comprise one or more synthetic nucleotides, non-naturally occurring nucleotides, nucleotides with a modification, deoxyribonucleotide, or any combination thereof. Additionally or alternatively, a gRNA may comprise a hairpin, linker region, single stranded region, double stranded region, or any combination thereof. Additionally or alternatively, a gRNA may comprise a signaling or reporter molecule.

A CRISPR nuclease may be endogenously or recombinantly expressed within a cell. A CRISPR nuclease may be encoded on a chromosome, extrachromosomally, or on a plasmid, synthetic chromosome, or artificial chromosome. A CRISPR nuclease may be provided or delivered to the cell as a polypeptide or mRNA encoding the polypeptide. In such examples, polypeptide or mRNA may be delivered through standard mechanisms known in the art, such as through the use of cell permeable peptides, nanoparticles, or viral particles.

gRNAs may be encoded by genetic or episomal DNA within a cell. In some examples, gRNAs may be provided or delivered to a cell expressing a CRISPR nuclease. gRNAs may be provided or delivered concomitantly with a CRISPR nuclease or sequentially. Guide RNAs may be chemically synthesized, in vitro transcribed or otherwise generated using standard RNA generation techniques known in the art.

Non-limiting examples of suitable nucleases, including nucleic acid-guided nucleases, for use in the present disclosure include C2c1, C2c2, C2c3, Cas1, Cas1B, Cas2, Cas3, Cas4, Cas5, Cas6, Cas7, Cas8, Cas9 (also known as Csn1 and Csx12), Cas10, Cpf1, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx100, Csx16, CsaX, Csx3, Csx1, Csx15, Csf1, Csf2, Csf3, Csf4, homologues thereof, orthologues thereof, or modified versions thereof.

In some methods disclosed herein, Argonaute (Ago) systems may be used to edit a cell lineage tracing construct. Ago protein may be derived from a prokaryote, eukaryote, or archaea. The cell lineage tracing construct may be RNA or DNA. A DNA target may be single stranded or double stranded. In some examples, the target nucleic acid does not require a specific target flanking sequence, such as a sequence equivalent to a protospacer adjacent motif or protospacer flanking sequence.

Ago proteins may be targeted to target nucleic acid sequences by a guiding nucleic acid. In many examples, the guiding nucleic acid is a guide DNA (gDNA). The gDNA may have a 5' phosphorylated end. The gDNA may be single stranded or double stranded. Single stranded gDNA may be 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 nucleotides in length. In some examples, the gDNA may be less than 10 nucleotides in length. In some examples, the gDNA may be more than 50 nucleotides in length.

Argonaute protein may be endogenously or recombinantly expressed within a cell. Argonaute may be encoded on a chromosome, extrachromosomally, or on a plasmid, synthetic chromosome, or artificial chromosome. Additionally or alternatively, an Argonaute protein may be provided or delivered to the cell as a polypeptide or mRNA encoding the polypeptide. In such examples, polypeptide or mRNA may be delivered through standard mechanisms known in the art, such as through the use of cell permeable peptides, nanoparticles, or viral particles.

Guide DNAs may be provided by genetic or episomal DNA within a cell. In some examples, gDNA are reverse transcribed from RNA or mRNA within a cell. In some examples, gDNAs may be provided or delivered to a cell expressing an Ago protein. Guide DNAs may be provided or delivered concomitantly with an Ago protein or sequentially. Guide DNAs may be chemically synthesized, assembled, or otherwise generated using standard DNA generation techniques known in the art. Guide DNAs may be cleaved, released, or otherwise derived from genomic DNA, episomal DNA molecules, isolated nucleic acid molecules, or any other source of nucleic acid molecules.

A guide nucleic acid may complex with a compatible nucleic acid-guided nuclease and may hybridize with a target sequence in the cell lineage tracing construct, thereby directing the nuclease to the target sequence. A subject nucleic acid-guided nuclease capable of complexing with a guide nucleic acid may be referred to as a nucleic acid-guided nuclease that is compatible with the guide nucleic acid. Likewise, a guide nucleic acid capable of complexing with a nucleic acid-guided nuclease may be referred to as a guide nucleic acid that is compatible with the nucleic acid-guided nucleases.

A guide nucleic acid may be DNA. A guide nucleic acid may be RNA. A guide nucleic acid may comprise both DNA and RNA. A guide nucleic acid may comprise modified of non-naturally occurring nucleotides. In cases where the guide nucleic acid comprises RNA, the RNA guide nucleic acid may be encoded by a DNA sequence on a polynucleotide molecule such as a plasmid, linear construct, or editing cassette as disclosed herein.

A guide nucleic acid may comprise a guide sequence. A guide sequence is a polynucleotide sequence having sufficient complementarity with a target polynucleotide sequence to hybridize with the target sequence and direct sequence-specific binding of a complexed nucleic acid-guided nuclease to the target sequence. The degree of complementarity between a guide sequence and its corresponding target sequence, when optimally aligned using a suitable alignment algorithm, is about or more than about 50%, 60%, 75%, 80%, 85%, 90%, 95%, 97.5%, 99%, or more. Optimal alignment may be determined with the use of any suitable algorithm for aligning sequences. In some aspects, a guide sequence is about or more than about 5, 10, 11, 12, 13, 14, 15, 16, 17, 18, 19, 20, 21, 22, 23, 24, 25, 26, 27, 28, 29, 30, 35, 40, 45, 50, 75, or more nucleotides in length. In some aspects, a guide sequence is less than about 75, 50, 45, 40, 35, 30, 25, 20 nucleotides in length. Preferably the guide sequence is 10-30 nucleotides long. The guide sequence may be 10-25 nucleotides in length. The guide sequence may be 10-20 nucleotides in length. The guide sequence may be 15-30 nucleotides in length. The guide sequence may be 20-30 nucleotides in length. The guide sequence may be 15-25 nucleotides in length. The guide sequence may be 15-20 nucleotides in length. The guide sequence may be 20-25 nucleotides in length. The guide sequence may be 22-25 nucleotides in length. The guide sequence may be 15 nucleotides in length. The guide sequence may be 16 nucleotides in length. The guide sequence may be 17 nucleotides in length. The guide sequence may be 18 nucleotides in length. The guide sequence may be 19 nucleotides in length. The guide sequence may be 20 nucleotides in length. The guide sequence may be 21 nucleotides in length. The guide sequence may be 22 nucleotides in length. The guide sequence may be 23 nucleotides in length. The guide sequence may be 24 nucleotides in length. The guide sequence may be 25 nucleotides in length.

A guide nucleic acid may comprise a scaffold sequence. In general, a "scaffold sequence" includes any sequence that has sufficient sequence to promote formation of a targetable nuclease complex, wherein the targetable nuclease complex comprises a nucleic acid-guided nuclease and a guide nucleic acid comprising a scaffold sequence and a guide sequence. Sufficient sequence within the scaffold sequence to promote formation of a targetable nuclease complex may include a degree of complementarity along the length of two sequence regions within the scaffold sequence, such as one or two sequence regions involved in forming a secondary structure. In some cases, the one or two sequence regions are comprised or encoded on the same polynucleotide. In some cases, the one or two sequence regions are comprised or encoded on separate polynucleotides. Optimal alignment may be determined by any suitable alignment algorithm, and may further account for secondary structures, such as self-complementarity within either the one or two sequence regions. In some aspects, the degree of complementarity between the one or two sequence regions along the length of the shorter of the two when optimally aligned is about or more than about 25%, 30%, 40%, 50%, 60%, 70%, 80%, 90%, 95%, 97.5%, 99%, or higher. In some aspects, at least one of the two sequence regions is about or more than about 5, 6, 7, 8, 9, 10, 11, 12, 13, 14, 15, 16, 17, 18, 19, 20, 21, 22, 23, 24, 25, 30, 40, 50, or more nucleotides in length. In some aspects, at least one of the two sequence regions is about 10-30 nucleotides in length. At least one of the two sequence regions may be 10-25 nucleotides in length. At least one of the two sequence regions may be 10-20 nucleotides in length. At least one of the two sequence regions may be 15-30 nucleotides in length. At least one of the two sequence regions may be 20-30 nucleotides in length. At least one of the two sequence regions may be 15-25 nucleotides in length. At least one of the two sequence regions may be 15-20 nucleotides in length. At least one of the two sequence regions may be 20-25 nucleotides in length. At least one of the two sequence regions may be 22-25 nucleotides in length. At least one of the two sequence regions may be 15 nucleotides in length. At least one of the two sequence regions may be 16 nucleotides in length. At least one of the two sequence regions may be 17 nucleotides in length. At least one of the two sequence regions may be 18 nucleotides in length. At least one of the two sequence regions may be 19 nucleotides in length. At least one of the two sequence regions may be 20 nucleotides in length. At least one of the two sequence regions may be 21 nucleotides in length. At least one of the two sequence regions may be 22 nucleotides in length. At least one of the two sequence regions may be 23 nucleotides in length. At least one of the two sequence regions may be 24 nucleotides in length. At least one of the two sequence regions may be 25 nucleotides in length.

A solid support (e.g., a bead) may comprise different types of anchor oligonucleotides for analyzing both intrinsic and extrinsic information of a cell. For example, a solid support may comprise one or more of the following: 1) an anchor oligonucleotide comprising a primer that binds to one or more endogenous nucleic acids in the cell; 2) an anchor oligonucleotide comprising a primer that binds to one or more exogenous nucleic acids in the cell, e.g., nucleic acids from a microorganism (e.g., a virus, a bacterium) that infects the cell, nucleic acids introduced into the cell (e.g., such as plasmids or nucleic acid derived therefrom), synthetic nucleic acids for gene editing (e.g., cell lineage tracing construct); 3) an anchor oligonucleotide comprising a primer that binds to a barcode (e.g., a barcode of a nucleic acid, of a protein, or of a cell); and 4) an anchor oligonucleotide comprising a sequence (e.g., a primer) that binds to a protein, e.g., an exogenous protein expressed in the cell, an protein from a microorganism (e.g., a virus, a bacterium) that infects the cell, or an binding partner for a protein of the cell (e.g., an antigen for an immune cell receptor).

Tandem DNA and RNA Barcoding

In an aspect, the present disclosure provides a method for processing nucleic acid molecules deriving from a given cell, cell bead, or cell nucleus. The method may comprise contacting a cell, cell bead, or cell nucleus with a transposase-nucleic acid complex comprising a transposase molecule and one or more transposon end oligonucleotide molecules.

In some embodiments, the cell, cell bead or cell nucleus is contacted with a transposase-nucleic acid complex in bulk solution, such that the cell, cell bead or cell nucleus undergoes "tagmentation" via a tagmentation reaction. Contacting the cell, cell bead, or cell nucleus with the transposase-nucleic acid complex may generate one or more template nucleic acid fragments (e.g., "tagmented fragments"). The one or more template nucleic acid fragments may correspond to one or more target nucleic acid molecules (e.g., DNA molecules) within the cell, cell bead, or cell nucleus. In parallel, the cell, cell bead, or cell nucleus may be contacted with a primer molecule (e.g., a poly-T primer) configured to interact with one or more additional target nucleic acid molecules (e.g., RNA molecules, such as messenger RNA (mRNA) molecules). In some embodiments, the cell, cell bead, or cell nucleus may be contacted with a primer molecule in bulk solution. Alternatively, the cell, cell bead, or cell nucleus may be contacted with a primer molecule within a partition. Interaction between these moieties may yield one or more additional template nucleic acid fragments (e.g., RNA fragments). For example, the primer molecule may have at least partial sequence complementarity to the one or more additional target nucleic acid molecules (e.g., mRNA molecules). The primer molecule may hybridize to a sequence of an additional target nucleic acid molecule of the one or more additional target nucleic acid molecules. The cell, cell bead, or cell nucleus may be partitioned (e.g., co-partitioned with one or more reagents) into a partition (e.g., of a plurality of partitions). The partition may be, for example, a droplet or a well. The partition may comprise one or more reagents, including, for example, one or more particles (e.g., beads) comprising one or more nucleic acid barcode molecules. The cell, cell bead, or cell nucleus may be lysed, permeabilized, fixed, cross-linked or otherwise manipulated to provide access to the one or more template nucleic acid fragments and the one or more additional template nucleic acid fragments therein. The one or more template nucleic acid fragments and the one or more additional template nucleic acid fragments therein may undergo one or more processing steps within the partition. For example, the one or more template nucleic acid fragments and/or the one or more additional template nucleic acid fragments may undergo a barcoding process, a ligation process, a reverse transcription process, a template switching process, a linear amplification process, and/or a gap filling process. The resultant one or more processed template nucleic acid fragments (e.g., tagmented fragments) and/or the one or more processed additional template nucleic acid fragments (e.g., RNA fragments) may each include a barcode sequence. The one or more processed template nucleic acid fragments and/or the one or more processed additional template nucleic acid fragments may be released from the partition (e.g., pooled with contents of other partitions of a plurality of partitions) and may undergo one or more additional processing steps in bulk. For example, the one or more processed template nucleic acid fragments and/or the one or more processed additional template nucleic acid fragments may undergo a gap filling process, a dA tailing process, a terminal-transferase process, a ligation process, a nucleic acid amplification process, or any combination thereof. For example, the one or more processed template nucleic acid fragments and/or the one or more processed additional template nucleic acid fragments may be subjected to conditions sufficient to undergo one or more polymerase chain reactions (PCR, such as sequence independent PCR) to generate amplification products corresponding to the one or more processed template nucleic acid fragments (e.g., tagmented fragments) and/or the one or more processed additional template nucleic acid fragments (e.g., RNA fragments). Sequences of such amplification products can be detected using, for example, a nucleic acid sequencing assay and used to identify sequences of the one or more target nucleic acid molecules (e.g., DNA molecules) and the one or more additional target nucleic acid molecules (e.g., RNA molecules) of the cell, cell bead, or cell nucleus from which they derive.

A biological sample (e.g., a nucleic acid sample) may comprise one or more cells, cell beads, and/or cell nuclei. A biological sample may also comprise tissue, which tissue may comprise one or more cells, cell beads, and/or cell nuclei. In some cases, a biological sample may comprise a plurality of cells comprising a plurality of cell nuclei. In some cases, a biological sample may comprise a plurality of cell nuclei, which plurality of cell nuclei are not included within cells (e.g., other components of the cell have degraded, dissociated, dissolved, or otherwise been removed). A biological sample may comprise a plurality of cell-free nucleic acid molecules (e.g., nucleic acid molecules that are not included within cells). For example, a biological sample may comprise a plurality of cell-free fetal DNA (cffDNA) or circulating tumor DNA (ctDNA) or other cell-free nucleic acid molecules (e.g., deriving from degraded cells). Such a biological sample may be processed to separate such cell-free nucleic acid molecules from cells, cell beads, and/or cell nuclei, which cells, cell beads, and/or cell nuclei may be subjected to further processing (e.g., as described herein).

Nucleic acid molecules included within a biological sample may include, for example, DNA molecules and RNA molecules. For example, a biological sample may comprise genomic DNA comprising chromatin (e.g., within a cell, cell bead, or cell nucleus). A biological sample may comprise a plurality of RNA molecules, such as a plurality of pre-mRNA or mRNA molecules. mRNA molecules and other RNA molecules may comprise a polyA sequence. At least a subset of a plurality of RNA molecules included in a cell or cell bead may be present in a cell nucleus.

A nucleic acid molecule may undergo one or more processing steps within a cell, cell bead, or cell nucleus. For example, chromatin within a cell, cell bead, or cell nucleus may be contacted with a transposase. A transposase may be included within a transposase-nucleic acid complex, which transposase-nucleic acid complex may comprise a transposase molecule and one or more transposon end oligonucleotide molecules. A transposase may be a Tn transposase, such as a Tn3, Tn5, Tn7, Tn10, Tn552, Tn903 transposase. Alternatively, a transposase may be a MuA transposase, a Vibhar transposase (e.g. from *Vibrio harveyi*), Ac-Ds, Ascot-1, Bs1, Cin4, Copia, En/Spm, F element, hobo, Hsmar1, Hsmar2, IN (HIV), IS1, IS2, IS3, IS4, IS5, IS6, IS10, IS21, IS30, IS50, IS51, IS150, IS256, IS407, IS427, IS630, IS903, IS911, IS982, IS1031, ISL2, L1, Mariner, P element, Tam3, Tc1, Tc3, Te1, THE-1, Tn/O, TnA, Tn3, Tn5, Tn7, Tn10, Tn552, Tn903, Tol1, Tol2, TnlO, Ty1, any prokaryotic transposase, or any transposase related to and/or derived from those listed above. In certain cases, a transposase may be a Tn5 transposase or a mutated, hyperactive Tn5 transposase. In certain instances, a transposase related to and/or derived from a parent transposase can comprise a peptide fragment with at least about 50%, about 55%, about 60%, about 65%, about 70%, about 75%, about 80%, about 85%, about 90%, about 91%, about 92%, about 93%, about 94%, about 95%, about 96%, about 97%, about 98%, or about 99% amino acid sequence homology to a corresponding peptide fragment of the parent transposase. The peptide fragment can be at least about 10, about 15, about 20, about 25, about 30, about 35, about 40, about 45, about 50, about 60, about 70, about 80, about 90, about 100, about 150, about 200, about 250, about 300, about 400, or about 500 amino acids in length. For example, a transposase derived from Tn5 can comprise a peptide fragment that is 50 amino acids in length and about 80% homologous to a corresponding fragment in a parent Tn5 transposase. Action of a transposase (e.g., insertion) may be facilitated and/or triggered by addition of one or more cations, such as one or more divalent cations (e.g., $Ca^{2+}$, $Mg^{2+}$, or $Mn^{2+}$).

A transposase-nucleic acid complex may comprise one or more nucleic acid molecules. For example, a transposase-nucleic acid complex may comprise one or more transposon end oligonucleotide molecules. A transposon end oligonucleotide molecule may comprise one or more primer sequences and/or one or more transposon end sequences. A transposon end sequence may be, for example, a Tn5 or modified Tn5 transposon end sequence or a Mu transposon end sequence. A transposon end sequence may have a sequence of, for example,

```
                                              (SEQ ID NO: 1)
                  AGATGTGTATAAGAGACA.
```

A primer sequence of a transposon end oligonucleotide molecule may be a sequencing primer, such as an R1 or R2 sequencing primer, or a portion thereof. A sequencing primer may be, for example, a TrueSeq or Nextera sequencing primer. An R1 sequencing primer region may have a sequence of

```
                                              (SEQ ID NO: 2)
        TCTACACTCTTTCCCTACACGACGCTCTTCCGATCT,
``` or some portion thereof. An R1 sequencing primer region may have a sequence of

```
                                              (SEQ ID NO: 3)
            TCGTCGGCAGCGTCAGATGTGTATAAGAGACAG,
``` or some portion thereof. A transposon end oligonucleotide molecule may comprise a partial R1 sequence. A partial R1 sequence may be

```
                                              (SEQ ID NO: 4)
                     ACTACACGACGCTCTTCCGATCT.
```

A transposon end oligonucleotide molecule may comprise an R2 sequencing priming region. An R2 sequencing primer region may have a sequence of

```
                                              (SEQ ID NO: 5)
            GTGACTGGAGTTCAGACGTGTGCTCTTCCGATCT,
``` or some portion thereof. An R2 sequencing primer region may have a sequence of

```
                                              (SEQ ID NO: 6)
            GTCTCGTGGGCTCGGAGATGTGTATAAGAGACAG,
``` or some portion thereof. A transposon end oligonucleotide molecule may comprise a T7 promoter sequence. A T7 promoter sequence may be

```
                                              (SEQ ID NO: 7)
                        TAATACGACTCACTATAG.
```

A transposon end oligonucleotide molecule may comprise a region at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% identical to any one of SEQ ID NO: 1-7. A transposon end oligonucleotide molecule may comprise a P5 sequence and/or a P7 sequence. A transposon end oligonucleotide molecule may comprise a sample index sequence, such as a barcode sequence or unique molecular identifier sequence. One or more transposon end oligonucleotide molecules of a transposase-nucleic acid complex may be attached to a solid support (e.g., a solid or semi-solid particle such as a bead (e.g., gel bead)). A transposon end oligonucleotide molecule may be releasably coupled to a solid support (e.g., a bead). Examples of transposon end oligonucleotide molecules may be found in, for example, PCT Patent Publications Nos. WO2018/218226 and WO2014/189957, both of which are herein incorporated by reference in their entireties.

FIG. 121 includes an example of a transposase-nucleic acid complex for use in the methods provided herein. Transposase-nucleic acid complex 12100 comprises partially double-stranded oligonucleotide 12101 and partially double-stranded oligonucleotide 12105. Partially double-stranded oligonucleotide 12101 comprises transposon end sequence 12103, first primer sequence 12102, and a sequence 12104 that is complementary to transposon end sequence 12103. Partially double-stranded oligonucleotide 12105 comprises transposon end sequence 12106, first primer sequence 12107, and a sequence 12108 that is complementary to transposon end sequence 12106. Primer sequences 12102 and 12107 may be the same or different. In some cases, primer sequence 12102 may be designated "R1" and primer sequence 12107 may be designated "R2". Transposon end sequences 12103 and 12106 may be the same or different. These sequences may alternately be referred to as "mosaic end" or "ME" sequences, while their complementary sequences 12104 and 12108 may be referred to as "mosaic end reverse complement" or "MErc" sequences.

FIG. 122 includes another example of a transposase-nucleic acid complex for use in the methods provided herein. Transposase-nucleic acid complex 12200 comprises forked adapters 12201 and 12206, which forked adapters are partially double-stranded oligonucleotides. Partially double-stranded oligonucleotide 12201 comprises transposon end sequence 12203, first primer sequence 12202, second primer sequence 12205, and a sequence 12204 that is complementary to transposon end sequence 12203. Partially double-stranded oligonucleotide 12206 comprises transposon end sequence 12207, first primer sequence 12208, second primer sequence 12210, and a sequence 12209 that is complementary to transposon end sequence 12207. Primer sequences 12202, 12205, 12208, and 12210 may be the same or different. In some cases, primer sequences 12202 and 12208 may be designated "R1" and primer sequences 12205 and 12210 may be designated "R2". Alternatively, primer sequences 12202 and 12210 may be designated "R1" and primer sequences 12205 and 12208 may be designated "R2". Alternatively, primer sequences 12202 and 12208 may be designated "R2" and primer sequences 12205 and 12210 may be designated "R1". Alternatively, primer sequences 12202 and 12210 may be designated "R2" and primer sequences 12205 and 12208 may be designated "R1". Transposon end sequences 12203 and 12207 may be the same or different. These sequences may alternately be referred to as "mosaic end" or "ME" sequences, while their complementary sequences 12204 and 12209 may be referred to as "mosaic end reverse complement" or "MErc" sequences.

FIG. 123 shows transposase-nucleic acid complex 12300 comprises hairpin molecules 12301 and 12306. Hairpin molecule 12301 comprises transposon end sequence 12303, first hairpin sequence 12302, second hairpin sequence 12305, and a sequence 12304 that is complementary to transposon end sequence 12303. Hairpin molecule 12306 comprises transposon end sequence 12307, third hairpin sequence 12308, fourth hairpin sequence 12310, and a sequence 12309 that is complementary to transposon end sequence 12307. Hairpin sequences 12302, 12305, 12308, and 12310 may be the same or different. For example, hairpin sequence 12305 may be the same or different as hairpin sequence 12310, and/or hairpin sequence 12302 may be the same or different as hairpin sequence 12308. Hairpin sequences 12302 and 12308 may be spacer sequences or adapter sequences. Hairpin sequences 12305 and 12310 may be a promoter sequence such as T7 recognition or promoter sequences and/or UMI sequences. Transposon end sequences 12303 and 12307 may be the same or different. These sequences may alternately be referred to as "mosaic end" or "ME" sequences, while their complementary sequences 12304 and 12309 may be referred to as "mosaic end reverse complement" or "MErc" sequences. In some cases, sequence 12304 is a transposon end sequence and 12303 is a sequence complementary to sequence 12304. In some cases, sequence 12309 is a transposon end sequence and 12307 is a sequence complementary to sequence 12309.

Contacting a cell, cell bead, or cell nucleus comprising one or more target nucleic acid molecules (e.g., DNA molecules) with a transposase-nucleic acid complex may generate one or more template nucleic acid fragments (e.g., "tagmented fragments"). The one or more template nucleic acid fragments may each comprise a sequence of the one or more target nucleic acid molecules (e.g., a target sequence). The transposase-nucleic acid complex may be configured to target a specific region of the one or more target nucleic acid molecules to provide one or more template nucleic acid fragments comprising specific target sequences. The one or more template nucleic acid fragments may comprise target sequences corresponding to accessible chromatin. Generation of tagmented fragments may take place within a bulk solution. In other cases, generation of tagmented fragments may take place within a partition (e.g., a droplet or well). A template nucleic acid fragment (e.g., tagmented fragment) may comprise one or more gaps (e.g., between a transposon end sequence or complement thereof and a target sequence on one or both strands of a double-stranded fragment). Gaps may be filled via a gap filling process using, e.g., a polymerase (e.g., DNA polymerase), ligase, or reverse transcriptase. In some cases, a mixture of enzymes may be used to repair a partially double-stranded nucleic acid molecule and fill one or more gaps. Gap filling may not include strand displacement. Gaps may be filled within or outside of a partition.

Alternatively or in addition, one or more additional nucleic acid molecules may be contacted with one or more capture nucleic acid molecules within a cell, cell bead, or cell nucleus to provide one or more additional template nucleic acid fragments. For example, an RNA molecule (e.g., an mRNA) molecule may be contacted with a primer molecule within a cell, cell bead, or cell nucleus. A primer molecule may comprise a primer sequence, which primer sequence may be a targeted primer sequence or a non-specific primer sequence (e.g., random N-mer). A targeted primer sequence may be, for example, a polyT sequence, which polyT sequence may interact with a polyA sequence of an RNA molecule. A primer nucleic acid molecule may also comprise one or more additional sequences, such as one or more sample index sequences, spacer or linker sequences, or one or more additional primer sequences. Generation of additional template nucleic acid fragments (e.g., RNA fragments) may take place within a bulk solution. In other cases, generation of additional template nucleic acid fragments may take place within a partition (e.g., a droplet or well).

Processing of nucleic acid molecules within a cell, cell bead, or cell nucleus (e.g., generation of template nucleic acid fragments using a transposase-nucleic acid complex and/or generation of additional template nucleic acid fragments using a capture nucleic acid molecule) may occur in a bulk solution comprising a plurality of cells, cell beads, and/or cell nuclei. In some cases, template nucleic acid fragments (e.g., tagmented fragments) may be generated in bulk solution and additional template nucleic acid fragments (e.g., RNA fragments) may be generated in a partition.

A plurality of cells, cell beads, and/or cell nuclei (e.g., a plurality of cells, cell beads, and/or cell nuclei that have undergone processing such as a tagmentation process) may be partitioned amongst a plurality of partitions. Partitions may be, for example, droplets or wells. Droplets (e.g., aqueous droplets) may be generated according to the methods provided herein. Partitioning may be performed according to the method provided herein. For example, partitioning a biological particle (e.g., cell, cell bead, or cell nucleus) and one or more reagents may comprise flowing a first phase comprising an aqueous fluid, the biological particle, and the one or more reagents and a second phase comprising a fluid that is immiscible with the aqueous fluid toward a junction. Upon interaction of the first and second phases, a discrete droplet of the first phase comprising the biological particle and the one or more reagents may be formed. The plurality of cells, cell beads, and/or cell nuclei may be partitioned amongst a plurality of partitions such that at least a subset of the plurality of partitions may comprise at most one cell, cell bead, or cell nucleus. Cells, cell beads, and/or cell nuclei may be co-partitioned with one or more reagents such that a partition of at least a subset of the plurality of partitions comprises a single cell, cell bead, or cell nucleus and one or more reagents. The one or more reagents may include, for example, enzymes (e.g., polymerases, reverse transcriptases, ligases, etc.), nucleic acid barcode molecules (e.g., nucleic acid barcode molecules comprising one or more barcode sequences, such as nucleic acid barcode molecules coupled to one or more beads), template switching oligonucleotides, deoxynucleotide triphosphates, buffers, lysis agents, primers, barcodes, detergents, reducing agents, chelating agents, oxidizing agents, nanoparticles, beads, antibodies, or any other useful reagents. Enzymes may include, for example, temperature-sensitive enzymes, pH-sensitive enzymes, light-sensitive enzymes, reverse transcriptases, proteases, ligases, polymerases, restriction enzymes, nucleases, protease inhibitors, exonucleases, and nuclease inhibitors.

A reagent of the one or more reagents may be useful for lysing or permeabilizing a cell, cell bead, or cell nucleus, or otherwise providing access to nucleic acid molecules and/or template nucleic acid fragments therein. A cell may be lysed using a lysis agent such as a bioactive agent. A bioactive agent useful for lysing a cell may be, for example, an enzyme (e.g., as described herein). An enzyme used to lyse a cell may or may not be capable of carrying out additional actions such as degrading one or more RNA molecules. Alternatively, an ionic, zwitterionic, or non-ionic surfactant may be used to lyse a cell. Examples of surfactants include, but are not limited to, TritonX-100, Tween 20, sarcosyl, or sodium dodecyl sulfate. Cell lysis may also be achieved using a cellular disruption method such as an electroporation or a thermal, acoustic, or mechanical disruption method. Alternatively, a cell may be permeabilized to provide access to a plurality of nucleic acid molecules included therein. Permeabilization may involve partially or completely dissolving or disrupting a cell membrane or a portion thereof. Permeabilization may be achieved by, for example, contacting a cell membrane with an organic solvent or a detergent such as Triton X-100 or NP-40. By lysing or permeabilizing a cell, cell bead, or cell nucleus within a partition (e.g., droplet) to provide access to the plurality of nucleic acid molecules and/or template nucleic acid fragments therein, molecules originating from the same cell, cell bead, or cell nucleus may be isolated within the same partition.

A partition of a plurality of partitions (e.g., a partition comprising a cell, cell bead, and/or cell nucleus) may comprise one or more beads (e.g., gel beads). A bead may be a gel bead. A bead may comprise a plurality of nucleic acid barcode molecules (e.g., nucleic acid molecules each comprising one or more barcode sequences, as described herein). A bead may comprise at least 10,000 nucleic acid barcode molecules attached thereto. For example, the bead may comprise at least 100,000, 1,000,000, or 10,000,000 nucleic acid barcode molecules attached thereto. The plurality of nucleic acid barcode molecules may be releasably attached to the bead. The plurality of nucleic acid barcode molecules may be releasable from the bead upon application of a stimulus. Such a stimulus may be selected from the group consisting of a thermal stimulus, a photo stimulus, and a chemical stimulus. For example, the stimulus may be a reducing agent such as dithiothreitol Application of a stimulus may result in one or more of (i) cleavage of a linkage between nucleic acid barcode molecules of the plurality of nucleic acid barcode molecules and the bead, and (ii) degradation or dissolution of the bead to release nucleic acid barcode molecules of the plurality of nucleic acid barcode molecules from the bead.

A plurality of nucleic acid barcode molecules attached (e.g., releasably attached) to a bead (e.g., gel bead) may be suitable for barcoding template nucleic acid fragments or additional template nucleic acid fragments deriving from DNA and/or RNA molecules of the plurality of cells, cell beads, and/or cell nuclei. For example, a nucleic acid barcode molecule of a plurality of nucleic acid barcode molecule may comprise a barcode sequence, unique molecular identifier (UMI) sequence, primer sequence, universal primer sequence, sequencing adapter or primer, flow cell adapter sequence, or any other useful feature. In an example, a nucleic acid barcode molecule of a plurality of nucleic acid barcode molecules attached to a bead may comprise a flow cell adapter sequence (e.g., a P5 or P7 sequence), a barcode sequence, a capture sequence, and a sequencing primer sequence or portion thereof (e.g., an R1 or R2 sequence or portion thereof), or a complement of any of these sequences. These sequences may be arranged in any useful order and may be linked or may include one or more spacer sequences disposed between them. For instance, the flow cell adapter sequence may be disposed near (e.g., proximal to) an end of the nucleic acid barcode molecule that is closest to the bead, while the sequencing primer or portion thereof may be disposed at an end of the nucleic acid barcode molecule that is furthest from (e.g., distal to) the bead (e.g., most available to template nucleic acid fragments for interaction). In another example, a nucleic acid barcode molecule of a plurality of nucleic acid barcode molecules attached to a bead may comprise a flow cell adapter sequence (e.g., a P5 or P7 sequence), a barcode sequence, a sequencing primer sequence or portion thereof (e.g., an R1 or R2 sequence or portion thereof), and a UMI sequence, or a complement of any of these sequences. The nucleic acid barcode molecule may further comprise a capture sequence, which capture sequence may be a targeted capture sequence (e.g., a polyC sequence). These sequences may be arranged in any useful order and may be linked or may include one or more spacer sequences disposed between them. For instance, the flow cell adapter sequence may be disposed near (e.g., proximal to) an end of the nucleic acid barcode molecule that is closest to the bead, while the capture sequence may be disposed at an end of the nucleic acid barcode molecule that is furthest from the bead (e.g., most available to template nucleic acid fragments for interaction).

All of the nucleic acid barcode molecules attached (e.g., releasably attached) to a bead (e.g., gel bead) of a plurality of beads may be the same. For example, all of the nucleic acid barcode molecules attached to the bead may have the same nucleic acid sequence. In such an instance, all of the nucleic acid barcode molecules attached to the bead may comprise the same flow cell adapter sequence, sequencing primer or portion thereof, and barcode sequence. The barcode sequence of a plurality of nucleic acid barcode molecules attached to a bead of a plurality of beads may be different from other barcode sequences of other nucleic acid barcode molecules attached to other beads of the plurality of beads. For example, a plurality of beads may comprise a plurality of barcode sequences, such that, for at least a subset of the plurality of beads, each bead comprises a different barcode sequence of the plurality of barcode sequences. This differentiation may permit template nucleic acid fragments (e.g., included within cells, cell beads, and/or cell nuclei) co-partitioned with a plurality of beads between a plurality of partitions to be differentially barcoded within their respective partitions, such that the template nucleic acid fragments or molecules derived therefrom may be identified with the partition (and thus the cell, cell bead, and/or cell nucleus) to which they correspond (e.g., using a nucleic acid sequencing assay, as described herein). A barcode sequence may comprise between 4-20 nucleotides. A barcode sequence may comprise one or more segments, which segments may range in size from 2-20 nucleotides, such as from 4-20 nucleotides. Such segments may be combined to form barcode sequences using a combinatorial assembly method, such as a split-pool method. Details of such methods can be found, for example, in PCT/US2018/061391, filed Nov. 15, 2018, which is herein incorporated by reference in its entirety.

In some cases, nucleic acid barcode molecules attached to a bead may not be the same. For example, the plurality of nucleic acid barcode molecules attached to a bead may each comprise a UMI sequence, which UMI sequence varies across the plurality of nucleic acid barcode molecules. All other sequences of the plurality of nucleic acid barcode molecules attached to the bead may be the same.

In some cases, a bead may comprise multiple different nucleic acid barcode molecules attached thereto. For example, a bead may comprise a first plurality of nucleic acid barcode molecules and a second plurality of nucleic acid barcode molecules, which first plurality of nucleic acid barcode molecules is different than the second plurality of nucleic acid barcode molecules. The first plurality of nucleic acid barcode molecules and the second plurality of nucleic acid barcode molecules coupled to a bead may comprise one or more shared sequences. For example, each nucleic acid barcode molecule of the first plurality of nucleic acid barcode molecules and each nucleic acid barcode molecule of the second plurality of nucleic acid barcode molecules may comprise the same barcode sequence (e.g., as described herein). Such a barcode sequence may be prepared using a combinatorial assembly process (e.g., as described herein). Similarly, each nucleic acid barcode molecule of the first plurality of nucleic acid barcode molecules coupled to a bead may comprise the same flow cell adapter sequence and/or sequencing primer or portion thereof as each nucleic acid barcode molecule of the second plurality of nucleic acid barcode molecules coupled to the bead. In an example, each nucleic acid barcode molecule of the first plurality of nucleic acid barcode molecules coupled to a bead comprises a sequencing primer, and each nucleic acid barcode molecule of the second plurality of nucleic acid barcode molecules coupled to the bead comprises a portion of the same sequencing primer. Sequences shared between different sets of nucleic acid barcode molecules coupled to the same bead may be included in the same or different order and may be separated by the same or different sequences. Alternatively or in addition, the first plurality of nucleic acid barcode molecules and the second plurality of nucleic acid barcode molecules coupled to a bead may include one or more different sequences. For example, each nucleic acid barcode molecule of a first plurality of nucleic acid barcode molecules coupled to a bead of a plurality of beads may comprise a flow cell adapter sequence, a barcode sequence, UMI sequence, capture sequence, and a sequencing primer or portion thereof, while each nucleic acid barcode molecule of a second plurality of nucleic acid barcode molecules coupled to the bead may comprise a flow cell adapter sequence (e.g., the same flow cell adapter sequence), a barcode sequence (e.g., the same barcode sequence), UMI sequence, capture sequence, and a sequencing primer or portion thereof (e.g., the same sequencing primer or portion thereof). Nucleic acid barcode molecules of the first plurality of nucleic acid barcode molecules may not include a UMI sequence or capture sequence. A bead comprising multiple different populations of nucleic acid barcode molecules, such as a first plurality of nucleic acid molecules and a second plurality of nucleic acid molecules (e.g., as described above), may be referred to as a "multi-functional bead."

A cell, cell bead, or cell nucleus comprising template nucleic acid fragments (e.g., template nucleic acid fragments and additional template nucleic acid fragments deriving from DNA or RNA molecules included within the cell, cell bead, or cell nucleus) may be co-partitioned with one or more beads (e.g., as described herein). For example, a cell, cell bead, or cell nucleus may be co-partitioned with a first bead configured to interact with a first set of template nucleic acid fragments (e.g., template nucleic acid fragments deriving from DNA molecules, such as tagmented fragments) and a second bead configured to interact with a second set of template nucleic acid fragments (e.g., additional template nucleic acid fragments deriving from RNA molecules). The first bead may comprise a flow cell adapter sequence, a barcode sequence, and a sequencing primer or portion thereof, which sequencing primer or portion thereof may be configured to interact with (e.g., anneal or hybridize to) a complementary sequence included in template nucleic acid fragments deriving from DNA molecules of the cell, cell bead, or cell nucleus, or derivatives thereof. The second bead may comprise the flow cell adapter sequence, the barcode sequence, the sequencing primer or a portion thereof, a UMI sequence, and a capture sequence, which capture sequence may be configured to interact with (e.g., anneal or hybridize to) a sequence of template nucleic acid fragments deriving from RNA molecules of the cell, cell bead, or cell nucleus, or derivatives thereof. In some cases, the capture sequence may be configured to interact with a sequence of a cDNA molecule generated upon reverse transcription of an RNA fragment. The first and second beads may be linked together (e.g., covalently or non-covalently).

Alternatively, a cell, cell bead, or cell nucleus comprising template nucleic acid fragments (e.g., template nucleic acid fragments or additional template nucleic acid fragments deriving from DNA or RNA molecules included within the cell, cell bead, or cell nucleus) may be co-partitioned with a single bead. For example, a cell, cell bead, or cell nucleus may be co-partitioned with a bead comprising (i) a first plurality of nucleic acid barcode molecules configured to interact with a first set of template nucleic acid fragments (e.g., template nucleic acid fragments deriving from DNA molecules, such as tagmented fragments), or derivatives thereof, and (ii) a second plurality of nucleic acid barcode molecules configured to interact with a second set of template nucleic acid fragments (e.g., additional template nucleic acid fragments deriving from RNA molecules), or derivatives thereof (such as cDNA generated from an RNA fragment). A nucleic acid barcode molecule of the first plurality of nucleic acid barcode molecules may comprise a flow cell adapter sequence, a barcode sequence, and a sequencing primer or portion thereof, which sequencing primer or portion thereof may be configured to interact with (e.g., anneal or hybridize to) a complementary sequence included in template nucleic acid fragments deriving from DNA molecules of the cell, cell bead, or cell nucleus, or derivatives thereof. A nucleic acid barcode molecule of the second plurality of nucleic acid barcode molecules may comprise the flow cell adapter sequence, the barcode sequence, the sequencing primer or a portion thereof, a UMI sequence, and a capture sequence, which capture sequence may be configured to interact with (e.g., anneal or hybridize to) a sequence of template nucleic acid fragments deriving from RNA molecules of the cell, cell bead, or cell nucleus, or derivatives thereof, such as cDNA generated from an RNA fragment. The first plurality of nucleic acid barcode molecules may comprise approximately the same number of nucleic acid barcode molecules as the second plurality of nucleic acid barcode molecules. Alternatively, the first plurality of nucleic acid barcode molecules may comprise a greater number of nucleic acid barcode molecules than the second plurality of nucleic acid barcode molecules, or vice versa. The distribution of nucleic acid barcode molecules on a bead may be controlled by, for example, sequence control, concentration control, and or blocking methods during assembly of the nucleic acid barcode molecules on the bead. Details of such processes are provided in, for example, PCT/US2018/061391, filed Nov. 15, 2018, which is incorporated by reference in its entirety.

FIGS. 136A and 136B show examples of beads for use according to the method provided herein. FIG. 136A shows a first bead 13601 and a second bead 13611 that may be co-partitioned with a cell, cell bead, or cell nucleus into a partition of a plurality of partitions (e.g., droplets or wells). First bead 13601 may comprise nucleic acid molecule 13602. Nucleic acid molecule 13602 may comprise sequences 13603, 13604, and 13605. Sequence 13603 may be, for example, a flow cell adapter sequence (e.g., a P5 or P7 sequence). Sequence 13604 may be, for example, a barcode sequence. Sequence 13605 may be, for example, a sequencing primer or portion thereof (e.g., an R1 or R2 primer sequence, or portion thereof). Nucleic acid molecule 13602 may also include additional sequences, such as a UMI sequence. First bead 13601 may comprise a plurality of nucleic acid molecules 13602. Second bead 13611 may comprise nucleic acid molecule 13612. Nucleic acid molecule 13612 may comprise sequences 13613, 13614, and 13615. Sequence 13613 may be, for example, a flow cell adapter sequence (e.g., a P5 or P7 sequence). Sequence 13614 may be, for example, a barcode sequence. Sequence 13615 may be, for example, a sequencing primer or portion thereof (e.g., an R1 or R2 primer sequence, or portion thereof). Nucleic acid molecule 13612 may also include additional sequences, such as a UMI sequence and a capture sequence. Second bead 13601 may comprise a plurality of nucleic acid molecules 13612.

FIG. 136B shows a bead 13621 (e.g., a multifunctional bead having two or more species of nucleic acid barcode molecules attached or coupled thereto) that may be co-partitioned with a cell, cell bead, or cell nucleus into a partition of a plurality of partitions (e.g., droplets or wells). Bead 13621 may comprise nucleic acid molecule 13622 and nucleic acid molecule 13626. Nucleic acid molecule 13622 may comprise sequences 13623, 13624, and 13625. Sequence 13623 may be, for example, a flow cell adapter sequence (e.g., a P5 or P7 sequence). Sequence 136136 may be, for example, a barcode sequence. Sequence 13625 may be, for example, a sequencing primer or portion thereof (e.g., an R1 or R2 primer sequence, or portion thereof). Nucleic acid molecule 13626 may comprise sequences 13627, 13628, and 13629. Sequence 13627 may be, for example, a flow cell adapter sequence (e.g., a P5 or P7 sequence). Sequence 13628 may be, for example, a barcode sequence. Sequence 13629 may be, for example, a sequencing primer or portion thereof (e.g., an R1 or R2 primer sequence, or portion thereof). Nucleic acid molecule 13626 may also include additional sequences, such as a UMI sequence and a capture sequence. Bead 13621 may comprise a plurality of nucleic acid molecules 13622 and a plurality of nucleic acid molecules 13626.

Within a partition (e.g., as described herein), an RNA fragment (e.g., a molecule comprising a sequence of an RNA molecule of a cell, cell bead, or cell nucleus that is hybridized to a primer molecule) may be processed to provide a barcoded molecule. The RNA fragment may be reverse transcribed to generate a complementary cDNA strand, which cDNA strand may be barcoded. In some cases, template switching can be used to increase the length of a cDNA (e.g., via incorporation of one or more sequences, such as one or more barcode or unique molecular identifier sequences). In one example of template switching, cDNA can be generated from reverse transcription of a template (e.g., an mRNA molecule) where a reverse transcriptase with terminal transferase activity can add additional nucleotides, e.g., polyC, to the cDNA that are not encoded by the template, such, as at an end of the cDNA. Template switch oligonucleotides (e.g., switch oligos) can include sequences complementary to the additional nucleotides, e.g. polyG (such as poly-riboG). The additional nucleotides (e.g., polyC) on the cDNA can hybridize to the sequences complementary to the additional nucleotides (e.g., polyG) on the template switch oligonucleotide, whereby the template switch oligonucleotide can be used by the reverse transcriptase as template to further extend the cDNA. Template switch oligonucleotides may comprise deoxyribonucleic acids, ribonucleic acids, modified nucleic acids including locked nucleic acids (INA), or any combination thereof. A template switch oligonucleotide may comprise one or more sequences including, for example, one or more sequences selected from the group consisting of a sequencing primer, a barcode sequence, a unique molecular identifier sequence, and a homopolymer sequence (e.g., a polyG sequence), or a complement of any of the preceding sequence.

In some cases, the length of a template switch oligonucleotide may be 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250 nucleotides or longer.

In some cases, an adapter and/or barcode sequence may be added to an RNA molecule via a method other than template switching. For example, one or more sequences may be ligated to an end of an RNA molecule. Similarly, one or more sequences may be ligated to an end of a cDNA molecule generated via reverse transcription of an RNA molecule.

In an example, a cell, cell bead, or cell nucleus comprising chromatin and one or more RNA molecules is provided. The chromatin in the cell, cell bead, or cell nucleus may be processed to provide a first template nucleic acid fragment derived from the chromatin (e.g., a tagmented fragment, as described herein). The chromatin may be processed in bulk solution. An RNA molecule may be processed to provide a second template nucleic acid fragment derived from the RNA molecule (e.g., as described herein). The RNA molecule may be processed within a partition. The configuration of the first template nucleic acid fragment may be at least partially dependent on the structure of the transposase-nucleic acid complex used to generate the first template nucleic acid fragment. For example, a transposase-nucleic acid complex such as that shown in FIG. 121 may be used to prepare the first template nucleic acid fragment. The first template nucleic acid fragment may be at least partially double-stranded. The first template nucleic acid fragment may comprise a double-stranded region comprising sequences of chromatin of the cell, cell bead, or cell nucleus. A first end of a first strand of the double-stranded region may be linked to a first transposon end sequence (e.g., mosaic end sequence), which first transposon end sequence may be linked to a first sequencing primer or portion thereof. A first end of the second strand of the double-stranded region, which end is opposite the first end of the first strand, may be linked to a second transposon end sequence (e.g., mosaic end sequence), which second transposon end sequence may be linked to a second sequencing primer or portion thereof. The second transposon end sequence may be the same as or different from the first transposon end sequence. The first sequencing primer or portion thereof may be the same as or different from the second sequencing primer or portion thereof. In some cases, the first sequencing primer or portion thereof may be an R1 sequence or portion thereof, and the second sequencing primer or portion thereof may be an R2 sequence or portion thereof. The first transposon end sequence may be hybridized to a first complementary sequence (e.g., mosaic end reverse complement sequence), which first complementary sequence may not be linked to a second end of the second strand of the double-stranded region of the first template nucleic acid fragment. Similarly, the second transposon end sequence may be hybridized to a second complementary sequence (e.g., mosaic end reverse complement sequence), which second complementary sequence may not be linked to a second end of the first strand of the double-stranded region of the first template nucleic acid fragment. In other words, the first template nucleic acid fragment may comprise one or more gaps. In some cases, the one or more gaps may be approximately 9 bp in length each. The second template nucleic acid fragment (e.g., an additional template nucleic acid fragment) may comprise a sequence of an RNA molecule of the cell, cell bead, or cell nucleus and a sequence hybridized to a primer molecule (e.g., a capture nucleic acid molecule). For example, the second template nucleic acid fragment may comprise a sequence of an RNA molecule of the cell, cell bead, or cell nucleus and a polyA sequence hybridized to a polyT sequence of a primer molecule. The primer molecule may also comprise an additional primer sequence.

The cell, cell bead, or cell nucleus comprising the first template nucleic acid fragment (e.g., tagmented fragment) may be co-partitioned with one or more reagents into a partition of a plurality of partitions (e.g., as described herein). The partition may be, for example, a droplet or well. The partition may comprise one or more beads (e.g., as described herein). A bead of the one or more beads may comprise a first plurality of nucleic acid barcode molecules. A nucleic acid barcode molecule of the first plurality of nucleic acid barcode molecules may comprise a flow cell adapter sequence (e.g., P5 sequence), a barcode sequence, and a sequencing primer or portion thereof (e.g., R1 sequence or portion thereof, or a complement thereof). The sequencing primer or portion thereof may be complementary to a sequence of the first template nucleic acid fragment. A bead of the one or more beads may also comprise a second plurality of nucleic acid barcode molecules. A nucleic acid barcode molecule of the second plurality of nucleic acid barcode molecules may comprise a flow cell adapter sequence (e.g., P5 sequence), a barcode sequence, and a sequencing primer or portion thereof (e.g., R1 sequence or portion thereof, or a complement thereof). In some cases, the first plurality of nucleic acid barcode molecules and the second plurality of nucleic acid barcode molecules may be the same.

Within the partition, the RNA molecule may be processed to provide the second template nucleic acid fragment (e.g., as described herein).

Within the partition, the cell, cell bead, or cell nucleus may be lysed or permeabilized to provide access to the first and/or second template nucleic acid fragments therein (e.g., as described herein). The second template nucleic acid fragment may be generated after the cell, cell bead, or cell nucleus is lysed or permeabilized.

The first and second template nucleic acid fragments may undergo processing within the partition. Within the partition, the gaps in the first template nucleic acid molecule may be filled via a gap filling extension process (e.g., using a DNA polymerase or reverse transcriptase). The resultant double-stranded nucleic acid molecule may be denatured to provide a single strand comprising a chromatin sequence flanked by transposon end sequences and/or sequences complementary to transposon end sequences. Each transposon end sequence and/or sequence complementary to transposon end sequence may be linked to a sequencing primer or portion thereof, or a complement thereof (e.g., an R1 or R2 sequence or a portion thereof, or a complement thereof). A nucleic acid barcode molecule of the first plurality of nucleic acid barcode molecules may hybridize to a sequencing primer or portion thereof, or a complement thereof, of the single strand. A primer extension reaction may then be used to generate a complement of the single strand (e.g., using a DNA polymerase or reverse transcriptase). Such a process may amount to a linear amplification process. This process incorporates the barcode sequence of the nucleic acid barcode molecule of the first plurality of nucleic acid barcode molecules, or a complement thereof. The resultant double-stranded molecule may be denatured to provide a single strand comprising the flow cell adapter sequence, or complement thereof, of the nucleic acid barcode molecule of the first plurality of nucleic acid barcode molecules; barcode sequence, or complement thereof, of the nucleic acid barcode molecule of the first plurality of nucleic acid barcode molecules; sequencing primer or portion thereof, or complement thereof, of the nucleic acid barcode molecule of the first plurality of nucleic acid barcode molecules; transposon end sequences, and/or complements thereof; second sequencing primer or portion thereof, or complement thereof.

Within the partition, the second template nucleic acid fragment derived from the RNA molecule of the cell, cell bead, or cell nucleus may be reverse transcribed (e.g., using a reverse transcriptase) to provide a cDNA strand. The reverse transcription process may append a sequence to an end of a strand of the resultant double-stranded nucleic acid molecule comprising the RNA strand and the cDNA strand, such as a polyC sequence. A template switching oligonucleotide may comprise a sequence (e.g., a polyG sequence) that may hybridize to at least a portion of the double-stranded nucleic acid molecule (e.g., to the appended polyC sequence) and be used to further extend the strand of the double-stranded nucleic acid molecule to provide an extended double-stranded nucleic acid molecule. Such a sequence may comprise ribobases. The template switching oligonucleotide may comprise a UMI sequence, or complement thereof, and a sequencing primer or portion thereof, or complement thereof. The extended double-stranded nucleic acid molecule comprising the template switching oligonucleotide and a complement thereof, and the prior double-stranded nucleic acid molecule may be denatured to provide a single strand comprising a sequencing primer or portion thereof, or complement thereof, of the nucleic acid barcode molecule of the second plurality of nucleic acid barcode molecules; the UMI sequence, or complement thereof the poly(C) or poly(G) sequence; the sequence corresponding to the RNA molecule of the cell, cell bead, or cell nucleus, or complement thereof; and sequences of the capture nucleic acid molecule, or complements thereof. A nucleic acid barcode molecule of the second plurality of nucleic acid barcode molecules may hybridize to a sequencing primer or portion thereof, or a complement thereof, of the single strand. A primer extension reaction may then be used to generate a complement of the single strand (e.g., using a DNA polymerase). Such a process may amount to a linear amplification process. This process incorporates the barcode sequence of the nucleic acid barcode molecule of the second plurality of nucleic acid barcode molecules, or a complement thereof. The resultant double-stranded molecule may be denatured to provide a single strand comprising a flow cell adapter sequence, or complement thereof, of the nucleic acid barcode molecule of the second plurality of nucleic acid barcode molecules; a barcode sequence, or complement thereof, of the nucleic acid barcode molecule of the second plurality of nucleic acid barcode molecules; a sequencing primer or portion thereof, or complement thereof, of the nucleic acid barcode molecule of the second plurality of nucleic acid barcode molecules; the UMI sequence, or complement thereof; the poly(C) or poly(G) sequence; the sequence corresponding to the RNA molecule of the cell, cell bead, or cell nucleus, or complement thereof; and sequences of the capture nucleic acid molecule, or complements thereof.

The linear amplification products corresponding to the chromatin and the RNA molecule of the cell, cell bead, or cell nucleus included within the partition of the plurality of partitions may be recovered from the partition. For example, the contents of the plurality of partitions may be pooled to provide the linear amplification products in a bulk solution. The linear amplification product corresponding to the chromatin may then be subjected to conditions sufficient to undergo one or more nucleic acid amplification reactions (e.g., PCR) to generate one or more amplification products corresponding to the chromatin. A nucleic acid amplification process may incorporate one or more additional sequences, such as one or more additional flow cell adapter sequences. The linear amplification product corresponding to the RNA molecule may be subjected to fragmentation, end repair, and dA tailing processes. An additional primer sequence (e.g., a sequencing primer or portion thereof, such as an R2 sequence) may then be ligated to the resultant molecule. A nucleic acid amplification reaction (e.g., PCR) may then be performed to generate one or more amplification products corresponding to the RNA molecule. A nucleic acid amplification process may incorporate one or more additional sequences, such as one or more additional flow cell adapter sequences (see, for example, FIG. 124).

In the RNA workflow, in-partition template switching may attach a sequencing primer (e.g., a TruSeq R1 sequence) to the 3' or 5' end of the RNA transcript. The bead (e.g., gel bead) carrying the sequencing primer, or portion thereof (e.g., partial TruSeq R1 sequence) may be also used for priming in the chromatin workflow. This allows for differential amplification of ATAC and RNA libraries after removing materials from partitions (e.g., breaking emulsions) and sample splitting. Another advantage of this method is that the same enzyme (e.g. DNA polymerase or reverse transcriptase) may be used to barcode nucleic acid fragments derived from both DNA (e.g., chromatin) and RNA.

FIG. 124 shows an example schematic corresponding to the preceding example. Panel 12400 shows a workflow corresponding to processing of chromatin from a cell, cell bead, or cell nucleus, and panel 12450 shows a workflow corresponding to processing of an mRNA molecule from the cell, cell bead, or cell nucleus. In the figure, two distinct gel beads are shown. However, the same gel bead may be used in each workflow.

As shown in panel 12400, in bulk solution, chromatin included within a cell, cell bead, or cell nucleus is processed (e.g., as described herein) to provide a template nucleic acid fragment (e.g., tagmented fragment) 12404 comprising insert sequence 12408 and a complement thereof, transposon end sequences 12406 and complements thereof, sequencing primer or portion thereof 12402 (e.g., an R1 sequence), sequencing primer or portion thereof 12410 (e.g., an R2 sequence), and gaps 12407. Template nucleic acid fragment 12404 may then be partitioned within a partition (e.g., a droplet or well, as described herein). Within the partition, the cell, cell bead, or cell nucleus comprising template nucleic acid fragment 12404 may be lysed, permeabilized, or otherwise processed to provide access to template nucleic acid fragment 12404 (and one or more RNA molecules) therein. Gaps 12407 may be filled 12412 via a gap filling extension process (e.g., using a DNA polymerase). The partition may include a gel bead 12416a coupled to a nucleic acid barcode molecule 12418a. Nucleic acid barcode molecule 12418a may comprise a flow cell adapter sequence 12420a (e.g., a P5 sequence), a barcode sequence 12422a, and a sequencing primer or portion thereof or complement thereof 12402'. Sequence 12402' may hybridize to sequence 12402 of template nucleic acid fragment 12404, or its complement, and undergo primer extension 12414 to yield a strand comprising sequences 12420a, 12422a, 12402', 12410, and insert sequence 12408 or a complement thereof. The contents of the partition may then be recovered in bulk solution (e.g., a droplet may be broken) to provide the strand in bulk solution. This strand may undergo amplification (e.g., PCR) 12424 to provide a double-stranded amplification product 12426 that includes sequences of the nucleic acid barcode molecule 12418a, the original chromatin molecule, and, optionally, an additional sequence 12428 that may be a flow cell adapter sequence (e.g., a P7 sequence).

In parallel to the chromatin workflow of panel 12400, an RNA molecule deriving from the same cell, cell bead, or cell nucleus may be processed. As shown in panel 12450, RNA molecule 12458 comprising RNA sequence 12460 and polyA sequence 12462 may be contacted 12464 with primer molecule 12452 comprising polyT sequence 12454 and additional primer sequence 12456. RNA molecule 12458 may then be reverse transcribed 12466 off of polyT sequence 12454 using a reverse transcriptase with terminal transferase activity, which reverse transcriptase may append sequence 12468 to the resultant cDNA molecule comprising cDNA sequence 12470. Sequence 12468 may be a polyC sequence. A template switch oligonucleotide 12472 comprising sequencing primer or portion thereof or complement thereof 12474, unique molecule identifier sequence or complement thereof 12476, and capture sequence (e.g., polyG sequence) 12478 may then hybridize 12480 to the RNA-cDNA molecule and template switching may take place. The partition may include a gel bead 12416b coupled to a nucleic acid barcode molecule 12418b. Nucleic acid barcode molecule 12418b may comprise a flow cell adapter sequence 12420b (e.g., a P5 sequence), a barcode sequence 12422b, and a sequencing primer or portion thereof or complement thereof 12474'. Gel bead 12416b may be the same as gel bead 12416a such that partition comprises a single gel bead. In such a case, nucleic acid barcode molecule 12418b and nucleic acid barcode molecule 12418a may have the same sequences. Sequence 12474' may hybridize to sequence 12474 of the RNA-cDNA molecule, or its complement, and undergo primer extension 12482 to yield a strand comprising sequences 12420b, 12422b, 12474', 12476 or a complement thereof, 12468 or a complement thereof, and insert sequence 12470 or a complement thereof. The contents of the partition may then be recovered in bulk solution (e.g., a droplet may be broken) to provide the strand in bulk solution. This strand may undergo amplification (e.g., PCR) 12484 to provide a double-stranded amplification product 12486 that includes sequences of the nucleic acid barcode molecule 12418b, the original RNA molecule or cDNA corresponding thereto, and, optionally, an additional sequence 12488 that may comprise a sequencing primer or portion thereof (e.g., an R2 sequence) 12490, a sample index sequence 12492, and a flow cell adapter sequence (e.g., a P7 sequence) 12494.

FIG. 125 shows another example schematic corresponding to the preceding example. Panel 12500 shows a workflow corresponding to processing of chromatin from a cell, cell bead, or cell nucleus, and panel 12550 shows a workflow corresponding to processing of an mRNA molecule from the cell, cell bead, or cell nucleus. In the figure, two distinct gel beads are shown. However, the same gel bead may be used in each workflow.

As shown in panel 12500, in bulk solution, chromatin included within a cell, cell bead, or cell nucleus is processed (e.g., as described herein) to provide a template nucleic acid fragment (e.g., tagmented fragment) 12504 comprising insert sequence 12508 and a complement thereof, transposon end sequences 12506 and complements thereof, sequencing primer or portion thereof 12502 (e.g., an R1 sequence), sequencing primer or portion thereof 12510 (e.g., an R2 sequence), and gaps 12507. Template nucleic acid fragment 12504 may then be partitioned within a partition (e.g., a droplet or well, as described herein). Within the partition, the cell, cell bead, or cell nucleus comprising template nucleic acid fragment 12504 may be lysed, permeabilized, or otherwise processed to provide access to template nucleic acid fragment 12504 (and one or more RNA molecules) therein. Gaps 12507 may be filled 12512 via a gap filling extension process (e.g., using a DNA polymerase). The partition may include a gel bead 12516a coupled to a nucleic acid barcode molecule 12518a. Nucleic acid barcode molecule 12518a may comprise a flow cell adapter sequence 12520a (e.g., a P5 sequence), a barcode sequence 12522a, and a sequencing primer or portion thereof or complement thereof 12502'. Sequence 12502' may hybridize to sequence 12502 of template nucleic acid fragment 12504, or its complement, and undergo primer extension 12514 to yield a strand comprising sequences 12520a, 12522a, 12502', 12510, and insert sequence 12508 or a complement thereof. The contents of the partition may then be recovered in bulk solution (e.g., a droplet may be broken) to provide the strand in bulk solution. This strand may undergo amplification (e.g., PCR) 12524 to provide a double-stranded amplification product 12526 that includes sequences of the nucleic acid barcode molecule 12518a, the original chromatin molecule, and, optionally, an additional sequence 12528 that may be a flow cell adapter sequence (e.g., a P7 sequence).

In parallel to the chromatin workflow of panel 12500, an RNA molecule deriving from the same cell, cell bead, or cell nucleus may be processed. As shown in panel 12550, RNA molecule 12558 comprising RNA sequence 12560 and polyA sequence 12562 may be contacted with primer molecule 12552 comprising polyT sequence 12554, UMI sequence 12555, and sequencing primer or portion thereof (e.g., R1 sequence) 12556. RNA molecule 12558 may be reverse transcribed 12564 off of polyT sequence 12554 using a reverse transcriptase with terminal transferase activity, which reverse transcriptase may append sequence 12566 (e.g., a polyC sequence) to the resultant cDNA molecule comprising cDNA sequence 12568. A template switch oligonucleotide 12570 comprising additional primer sequence 12572 and a homopolymer sequence 12574 (e.g., a polyG) sequence that is complementary to sequence 12566 may then hybridize 12576 to the RNA-cDNA molecule and template switching may take place. The partition may include a gel bead 12516b coupled to a nucleic acid barcode molecule 12518b. Nucleic acid barcode molecule 12518b may comprise a flow cell adapter sequence 12520b (e.g., a P5 sequence), a barcode sequence 12522b, and a sequencing primer or portion thereof or complement thereof 12556'. Gel bead 12516b may be the same as gel bead 12516a such that partition comprises a single gel bead. In such a case, nucleic acid barcode molecule 12518b and nucleic acid barcode molecule 12518a may have the same sequences. Sequence 12556' may hybridize to sequence 12556 of the RNA-cDNA molecule, or its complement, and undergo primer extension 12578 to yield a strand comprising sequences 12520b, 12522b, 12556', 12555 or a complement thereof, 12566 or a complement thereof, and insert sequence 12568 or a complement thereof. The contents of the partition may then be recovered in bulk solution (e.g., a droplet may be broken) to provide the strand in bulk solution. This strand may undergo amplification (e.g., PCR) 12580 to provide a double-stranded amplification product 12582 that includes sequences of the nucleic acid barcode molecule 12518b, the original RNA molecule or cDNA corresponding thereto, and, optionally, an additional sequence 12584 that may comprise a sequencing primer or portion thereof (e.g., an R2 sequence) 12590, a sample index sequence 12588, and a flow cell adapter sequence (e.g., a P7 sequence) 12586.

In another example, a cell, cell bead, or cell nucleus comprising chromatin and one or more RNA molecules is provided. The chromatin in the cell, cell bead, or cell nucleus may be processed to provide a first template nucleic acid fragment derived from the chromatin (e.g., a tagmented fragment, as described herein). The chromatin may be processed in bulk solution. An RNA molecule may be processed to provide a second template nucleic acid fragment derived from the RNA molecule (e.g., as described herein). The RNA molecule may be processed within a partition. The configuration of the first template nucleic acid fragment may be at least partially dependent on the structure of the transposase-nucleic acid complex used to generate the first template nucleic acid fragment. For example, a transposase-nucleic acid complex such as that shown in FIG. 121 may be used to prepare the first template nucleic acid fragment. The first template nucleic acid fragment may be at least partially double-stranded. The first template nucleic acid fragment may comprise a double-stranded region comprising sequences of chromatin of the cell, cell bead, or cell nucleus. A first end of a first strand of the double-stranded region may be linked to a first transposon end sequence (e.g., mosaic end sequence), which first transposon end sequence may be linked to a first sequencing primer or portion thereof. A first end of the second strand of the double-stranded region, which end is opposite the first end of the first strand, may be linked to a second transposon end sequence (e.g., mosaic end sequence), which second transposon end sequence may be linked to a second sequencing primer or portion thereof. The second transposon end sequence may be the same as or different from the first transposon end sequence. The first sequencing primer or portion thereof may be the same as or different from the second sequencing primer or portion thereof. In some cases, the first sequencing primer or portion thereof may be an R1 sequence or portion thereof, and the second sequencing primer or portion thereof may be an R2 sequence or portion thereof. The first transposon end sequence may be hybridized to a first complementary sequence (e.g., mosaic end reverse complement sequence), which first complementary sequence may not be linked to a second end of the second strand of the double-stranded region of the first template nucleic acid fragment. Similarly, the second transposon end sequence may be hybridized to a second complementary sequence (e.g., mosaic end reverse complement sequence), which second complementary sequence may not be linked to a second end of the first strand of the double-stranded region of the first template nucleic acid fragment. In other words, the first template nucleic acid fragment may comprise one or more gaps. In some cases, the one or more gaps may be approximately 9 bp in length each. The second template nucleic acid fragment (e.g., an additional template nucleic acid fragment) may comprise a sequence of an RNA molecule of the cell, cell bead, or cell nucleus and a sequence hybridized to a primer molecule (e.g., a capture nucleic acid molecule). For example, the second template nucleic acid fragment may comprise a sequence of an RNA molecule of the cell, cell bead, or cell nucleus and a polyA sequence hybridized to a polyT sequence of a primer molecule. The primer molecule may also comprise an additional primer sequence.

The cell, cell bead, or cell nucleus comprising the first template nucleic acid fragment (e.g., tagmented fragment) may be co-partitioned with one or more reagents into a partition of a plurality of partitions (e.g., as described herein). The partition may be, for example, a droplet or well. The partition may comprise one or more beads (e.g., as described herein). A bead of the one or more beads may comprise a first plurality of nucleic acid barcode molecules. A nucleic acid barcode molecule of the first plurality of nucleic acid barcode molecules may comprise a flow cell adapter sequence (e.g., P5 sequence), a barcode sequence, and a sequencing primer or portion thereof (e.g., R1 sequence or portion thereof, or a complement thereof). The sequencing primer or portion thereof may be complementary to a sequence of the first template nucleic acid fragment. The flow cell adapter sequence and/or barcode sequence may be hybridized to their complementary sequences. A bead of the one or more beads may also comprise a second plurality of nucleic acid barcode molecules. A nucleic acid barcode molecule of the second plurality of nucleic acid barcode molecules may comprise a flow cell adapter sequence (e.g., P5 sequence), a barcode sequence, a sequencing primer or portion thereof (e.g., R1 sequence or portion thereof, or a complement thereof), a UMI sequence, and a capture sequence (e.g., a polyG sequence, a polydT sequence or target specific sequence). In some cases, the first plurality of nucleic acid barcode molecules and the second plurality of nucleic acid barcode molecules may be coupled to the same bead, and the partition may comprise a single bead.

Within the partition, the RNA molecule may be processed to provide the second template nucleic acid fragment (e.g., as described herein).

Within the partition, the cell, cell bead, or cell nucleus may be lysed or permeabilized to provide access to the first and/or second template nucleic acid fragments therein (e.g., as described herein). The second template nucleic acid fragment may be generated after the cell, cell bead, or cell nucleus is lysed or permeabilized.

The first and second template nucleic acid fragments may undergo processing within the partition. Within the partition, a sequencing primer or portion thereof of the first template nucleic acid fragment corresponding to the chromatin of the cell, cell bead, or cell nucleus may hybridize to a sequencing primer or portion thereof of the nucleic acid barcode molecule of the first plurality of nucleic acid barcode molecules. The sequencing primer or portion thereof of the nucleic acid barcode molecule may then be ligated (e.g., using a ligase) to a transposon end sequence of the first template nucleic acid fragment, or a complement thereof to provide a partially double-stranded nucleic acid molecule corresponding to the chromatin of the cell, cell bead, or cell nucleus.

Within the partition, the second template nucleic acid fragment derived from the RNA molecule of the cell, cell bead, or cell nucleus may be reverse transcribed (e.g., using a reverse transcriptase) to provide a cDNA strand. The reverse transcription process may append a sequence to an end of a strand of the resultant double-stranded nucleic acid molecule comprising the RNA strand and the cDNA strand, such as a polyC sequence. The capture sequence of the nucleic acid barcode molecule of the second plurality of nucleic acid barcode molecules may hybridize to the appended sequence (e.g., polyC sequence) of the double-stranded nucleic acid molecule and a template switching process may take place to provide an extended double-stranded nucleic acid molecule. Such a sequence may comprise ribobases. The sequence of the nucleic acid barcode molecule of the second plurality of nucleic acid barcode molecules may be considered a template switching oligonucleotide. Accordingly, barcoding and template switching may take place contemporaneously to provide a barcoded RNA-cDNA molecule. The cDNA strand of the barcoded RNA-cDNA molecule may comprise the polyC sequence, a sequence complementary to the sequence of the template switch oligonucleotide or a portion thereof (e.g., sequences complementary to the sequencing primer, barcode sequence, and UMI sequence of the template switch oligonucleotide), the cDNA sequence, the polyT sequence, and the additional primer sequence of the primer molecule. The RNA strand of the barcoded RNA-cDNA molecule may comprise the sequence of the template switch oligonucleotide, the mRNA sequence, and a sequence complementary to the additional primer sequence of the primer molecule.

The partially double-stranded molecule corresponding to the chromatin of the cell, cell bead, or cell nucleus and the barcoded RNA-cDNA molecule corresponding to the RNA molecule of the cell, cell bead, or cell nucleus included within the partition of the plurality of partitions may be recovered from the partition. For example, the contents of the plurality of partitions may be pooled to provide these products in a bulk solution.

Outside of the partition, the gaps in the partially double-stranded nucleic acid molecule corresponding to the chromatin may be filled using via a gap filling extension process (e.g., using a DNA polymerase or reverse transcriptase). In some embodiments, the gap filling extension process does not include strand displacement. The resultant gap-filled double-stranded nucleic acid molecule may be denatured to provide a single strand, which single strand may be subjected to conditions sufficient to perform one or more nucleic acid amplification reactions (e.g., PCR) to generate amplification products corresponding to the chromatin of the cell, cell bead, or cell nucleus. A nucleic acid amplification process may incorporate one or more additional sequences, such as one or more additional flow cell adapter sequences.

Outside of the partition, the barcoded RNA-cDNA molecule corresponding to the RNA molecule may be subjected to fragmentation, end repair, a dA tailing process, tagmentation, or any combination thereof. An additional primer sequence (e.g., a sequencing primer or portion thereof, such as an R2 sequence) may be ligated to the resultant molecule. Alternatively or in addition, a nucleic acid amplification reaction (e.g., PCR) may be performed to generate one or more amplification products corresponding to the RNA molecule or the cDNA molecule generated therefrom. A nucleic acid amplification process may incorporate one or more additional sequences, such as one or more additional flow cell adapter sequences.

FIG. 126 shows an example schematic corresponding to the preceding example. Panel 12600 shows a workflow corresponding to processing of chromatin from a cell, cell bead, or cell nucleus, and panel 12650 shows a workflow corresponding to processing of an mRNA molecule from the cell, cell bead, or cell nucleus.

As shown in panel 12600, in bulk solution, chromatin included within a cell, cell bead, or cell nucleus is processed (e.g., as described herein) to provide a template nucleic acid fragment (e.g., tagmented fragment) 12604 comprising insert sequence 12608 and a complement thereof, transposon end sequences 12606 and complements thereof, sequencing primer or portion thereof 12602 (e.g., an R1 sequence), sequencing primer or portion thereof 12610 (e.g., an R2 sequence), and gaps 12607. Template nucleic acid fragment 12604 may then be partitioned within a partition (e.g., a droplet or well, as described herein). Within the partition, the cell, cell bead, or cell nucleus comprising template nucleic acid fragment 12604 may be lysed, permeabilized, or otherwise processed to provide access to template nucleic acid fragment 12604 (and one or more RNA molecules) therein. The partition may include a gel bead 12616 coupled to a nucleic acid barcode molecule 12618a. Nucleic acid barcode molecule 12618a may comprise a flow cell adapter sequence 12620a (e.g., a P5 sequence), a barcode sequence 12622a, and a sequencing primer or portion thereof or complement thereof 12602'. Sequences 12620a and 12622a may be hybridized to complementary sequences 12620' and 12622', respectively. Sequence 12602' may hybridize to sequence 12602 of template nucleic acid fragment 12604, or its complement, and sequence 12622' may be ligated 12612 to sequence 12602 of template nucleic acid fragment 12604. The contents of the partition may then be recovered in bulk solution (e.g., a droplet may be broken) to provide the partially double-stranded nucleic acid molecule comprising nucleic acid barcode molecule 12618a attached to template nucleic acid fragment 12604 in bulk solution. In bulk solution, gaps 12607 may be filled 12624 via a gap filling extension process (e.g., using a DNA polymerase) to provide a double-stranded nucleic acid molecule. This molecule may undergo amplification (e.g., PCR) 12626 to provide a double-stranded amplification product 12628 that includes sequences of the nucleic acid barcode molecule 12618a, the original chromatin molecule, and, optionally, an additional sequence 12630 that may be a flow cell adapter sequence (e.g., a P7 sequence).

In parallel to the chromatin workflow of panel 12600, an RNA molecule deriving from the same cell, cell bead, or cell nucleus may be processed. As shown in panel 12650, RNA molecule 12658 comprising RNA sequence 12660 and polyA sequence 12662 may be contacted 12664 with primer molecule 12652 comprising polyT sequence 12654 and additional primer sequence 12656. RNA molecule 12658 may then be reverse transcribed 12676 off of polyT sequence 12654 using a reverse transcriptase with terminal transferase activity, which reverse transcriptase may append sequence 12670 to the resultant cDNA molecule comprising cDNA sequence 12668. Sequence 12670 may be a polyC sequence. Gel bead 12616 (e.g., the same gel bead described in panel 12600) may be included within the partition and may be coupled to nucleic acid barcode molecule 12618b. Nucleic acid barcode molecule 12618b may comprise a flow cell adapter sequence 12620b (e.g., a P5 sequence), a barcode sequence 12622b, UMI sequence 12672, and a sequence 12674 complementary to sequence 12670 (e.g., a polyG sequence). Nucleic acid barcode molecule 12618b may be used to perform template switching 12678, which process may also result in the generation of a barcoded RNA-cDNA molecule. The contents of the partition may then be recovered in bulk solution (e.g., a droplet may be broken) to provide the barcoded RNA-cDNA molecule in bulk solution. The barcoded RNA-cDNA molecule may undergo amplification (e.g., PCR) 12680 to provide a double-stranded amplification product 12684 that includes sequences of the nucleic acid barcode molecule 12618b, the original RNA molecule or cDNA corresponding thereto, a flow cell adapter sequence 12686, and an additional sequence 12688 that may comprise a sequencing primer or portion thereof (e.g., an R2 sequence) 12690, a sample index sequence 12692, and a flow cell adapter sequence (e.g., a P7 sequence) 12694. The barcoded RNA-cDNA molecule may also or alternatively undergo fragmentation, end repair, dA tailing, ligation of one or more adapter sequences, and/or nucleic acid amplification.

FIG. 127 shows another example schematic corresponding to the preceding example. Panel 12700 shows a workflow corresponding to processing of chromatin from a cell, cell bead, or cell nucleus, and panel 12750 shows a workflow corresponding to processing of an mRNA molecule from the cell, cell bead, or cell nucleus.

As shown in panel 12700, in bulk solution, chromatin included within a cell, cell bead, or cell nucleus is processed (e.g., as described herein) to provide a template nucleic acid fragment (e.g., tagmented fragment) 12704 comprising insert sequence 12708 and a complement thereof, transposon end sequences 12706 and complements thereof, sequencing primer or portion thereof 12702 (e.g., an R1 sequence), sequencing primer or portion thereof 12710 (e.g., an R2 sequence), and gaps 12707. Template nucleic acid fragment 12704 may then be partitioned within a partition (e.g., a droplet or well, as described herein). Within the partition, the cell, cell bead, or cell nucleus comprising template nucleic acid fragment 12704 may be lysed, permeabilized, or otherwise processed to provide access to template nucleic acid fragment 12704 (and one or more RNA molecules) therein. The partition may include a gel bead 12716 coupled to a nucleic acid barcode molecule 12718a. Nucleic acid barcode molecule 12718a may comprise a flow cell adapter sequence 12720a (e.g., a P5 sequence), a barcode sequence 12722a, and a sequencing primer or portion thereof or complement thereof 12702'. Sequences 12720a and 12722a may be hybridized to complementary sequences 12720' and 12722', respectively. Sequence 12702' may hybridize to sequence 12702 of template nucleic acid fragment 12704, or its complement, and sequence 12722' may be ligated 12712 to sequence 12702 of template nucleic acid fragment 12704. The contents of the partition may then be recovered in bulk solution (e.g., a droplet may be broken) to provide the partially double-stranded nucleic acid molecule comprising nucleic acid barcode molecule 12718a attached to template nucleic acid fragment 12704 in bulk solution. In bulk solution, gaps 12707 may be filled 12724 via a gap filling extension process (e.g., using a DNA polymerase) to provide a double-stranded nucleic acid molecule. This molecule may undergo amplification (e.g., PCR) 12726 to provide a double-stranded amplification product 12728 that includes sequences of the nucleic acid barcode molecule 12718a, the original chromatin molecule, and, optionally, an additional sequence 12730 that may be a flow cell adapter sequence (e.g., a P7 sequence).

In parallel to the chromatin workflow of panel 12700, an RNA molecule deriving from the same cell, cell bead, or cell nucleus may be processed. As shown in panel 12750, RNA molecule 12758 comprising RNA sequence 12760 and polyA sequence 12762 may and gel bead 12716 may be provided within a partition. Gel bead 12716 (e.g., the same gel bead described in panel 12700) may be included within the partition and may be coupled to nucleic acid barcode molecule 12718b. Nucleic acid barcode molecule 12718b may comprise a flow cell adapter sequence 12768 (e.g., a P5 sequence), a barcode sequence 12722b (e.g., the same barcode sequence as barcode sequence 12722a), UMI sequence 12766, and a polyT sequence 12764 complementary to polyA sequence 12762. PolyT sequence 12764 may hybridize to polyA sequence 12762 of RNA molecule 12758. RNA molecule 12758 may be reverse transcribed 12770 off of polyT sequence 12764 to provide an RNA-cDNA molecule comprising cDNA sequence 12772. The reverse transcription process may use a reverse transcriptase with terminal transferase activity, which reverse transcriptase may append sequence 12774 to the resultant cDNA molecule comprising cDNA sequence 12772. Sequence 12774 may be a polyC sequence. A template switch oligonucleotide 12778 comprising a primer sequence 12780 and a sequence complementary to sequence 12774 (e.g., a polyG sequence) may hybridize to the RNA-cDNA molecule. The contents of the partition may then be recovered in bulk solution (e.g., a droplet may be broken) to provide the RNA-cDNA molecule in bulk solution. The RNA-cDNA molecule may undergo amplification (e.g., PCR) 12784. Additional amplification (e.g., PCR) 12786 may to performed to provide a double-stranded amplification product 12788 that includes sequences of the nucleic acid barcode molecule 12718*b*, the original RNA molecule or cDNA corresponding thereto, a flow cell adapter sequence 12798 (e.g., a P7 sequence), and an additional sequence 12790 that may comprise a sequencing primer or portion thereof (e.g., an R2 sequence) 12796, a sample index sequence 12794, and a flow cell adapter sequence (e.g., a P5 sequence) 12792. The barcoded RNA-cDNA molecule may also or alternatively undergo fragmentation, end repair, dA tailing, ligation of one or more adapter sequences, and/or nucleic acid amplification.

In another example, a cell, cell bead, or cell nucleus comprising chromatin and one or more RNA molecules is provided. The chromatin in the cell, cell bead, or cell nucleus may be processed to provide a first template nucleic acid fragment derived from the chromatin (e.g., a tagmented fragment, as described herein). The chromatin may be processed in bulk solution. An RNA molecule may be processed to provide a second template nucleic acid fragment derived from the RNA molecule (e.g., an additional nucleic acid fragment, as described herein). The RNA molecule may be processed within a partition. The second template nucleic acid fragment derived from the RNA molecule may be processed according to the preceding examples. The configuration of the first template nucleic acid fragment may be at least partially dependent on the structure of the transposase-nucleic acid complex used to generate the first template nucleic acid fragment. For example, a transposase-nucleic acid complex such as that shown in FIG. 121 may be used to prepare the first template nucleic acid fragment. Relative to the preceding examples, the polarities of the transposase-nucleic acid may be reversed such that sequencing primers (e.g., R1 and R2 sequencing primers) are not directly linked to the chromatin (see, e.g., FIG. 129). The first template nucleic acid fragment may be at least partially double-stranded. The first template nucleic acid fragment may comprise a double-stranded region comprising sequences of chromatin of the cell, cell bead, or cell nucleus. A first end of a first strand of the double-stranded region may be linked to a first transposon end sequence (e.g., mosaic end sequence). A first end of the second strand of the double-stranded region, which end is opposite the first end of the first strand, may be linked to a second transposon end sequence (e.g., mosaic end sequence). The second transposon end sequence may be the same as or different from the first transposon end sequence. The first transposon end sequence may be hybridized to a first complementary sequence (e.g., mosaic end reverse complement sequence), which first complementary sequence may not be linked to a second end of the second strand of the double-stranded region of the first template nucleic acid fragment. The first complementary sequence may be linked to a first sequencing primer or portion thereof. Similarly, the second transposon end sequence may be hybridized to a second complementary sequence (e.g., mosaic end reverse complement sequence), which second complementary sequence may not be linked to a second end of the first strand of the double-stranded region of the first template nucleic acid fragment. The second complementary sequence may be linked to a second sequencing primer or portion thereof. In other words, the first template nucleic acid fragment may comprise one or more gaps. In some cases, the one or more gaps may be approximately 9 bp in length each. The first sequencing primer or portion thereof may be the same as or different from the second sequencing primer or portion thereof. In some cases, the first sequencing primer or portion thereof may be an R1 sequence or portion thereof, and the second sequencing primer or portion thereof may be an R2 sequence or portion thereof.

The cell, cell bead, or cell nucleus comprising the first template nucleic acid fragment (e.g., tagmented fragment) may be co-partitioned with one or more reagents into a partition of a plurality of partitions (e.g., as described herein). The partition may be, for example, a droplet or well. The partition may comprise one or more beads (e.g., as described herein). A bead of the one or more beads may comprise a first plurality of nucleic acid barcode molecules. A nucleic acid barcode molecule of the first plurality of nucleic acid barcode molecules may comprise a flow cell adapter sequence (e.g., P5 sequence), a barcode sequence, and a sequencing primer or portion thereof (e.g., R1 sequence or portion thereof, or a complement thereof). The sequencing primer or portion thereof may be complementary to a sequence of the first template nucleic acid fragment. The flow cell adapter sequence and/or barcode sequence may be hybridized to their complementary sequences. The same bead or another bead may comprise a second plurality of nucleic acid barcode molecules. A nucleic acid barcode molecule of the second plurality of nucleic acid barcode molecules may comprise a sequencing primer or portion thereof (e.g., an R1 sequence or portion thereof, or complement thereof), a barcode sequence, a unique molecular identifier sequence, and a capture sequence.

Within the partition, the RNA molecule may be processed to provide the second template nucleic acid fragment (e.g., as described herein). For example, the RNA molecule (e.g., mRNA molecule) may be contacted with a primer molecule comprising a first primer sequence (e.g., a polyT sequence) and an additional primer sequence).

Within the partition, the cell, cell bead, or cell nucleus may be lysed or permeabilized to provide access to the first and/or second template nucleic acid fragments therein (e.g., as described herein). The second template nucleic acid fragment may be generated after the cell, cell bead, or cell nucleus is lysed or permeabilized.

The first and second template nucleic acid fragments may undergo processing within the partition. Within the partition, a sequencing primer or portion thereof of the first template nucleic acid fragment corresponding to the chromatin of the cell, cell bead, or cell nucleus may hybridize to a sequencing primer or portion thereof of the nucleic acid barcode molecule of the first plurality of nucleic acid barcode molecules. The sequencing primer or portion thereof of the nucleic acid barcode molecule may then be ligated (e.g., using a ligase) to a transposon end sequence of the first template nucleic acid fragment, or a complement thereof to provide a partially double-stranded nucleic acid molecule corresponding to the chromatin of the cell, cell bead, or cell nucleus. The second template nucleic acid fragment corresponding to the RNA molecule may be reverse transcribed using a reverse transcriptase with terminal transferase activity, which reverse transcriptase may append a sequence (e.g., a polyC sequence) to the cDNA strand of the resultant RNA-cDNA molecule. The RNA-cDNA molecule may then be contacted with a nucleic acid barcode molecule of the second plurality of nucleic acid barcode molecules that may be a template switch oligonucleotide. The nucleic acid barcode molecule may comprise a sequencing primer or portion thereof (e.g., an R1 sequence or portion thereof, or complement thereof), a barcode sequence, a unique molecular identifier sequence, and a capture sequence. The capture sequence may be a sequence that is complementary to the sequence appended to the cDNA strand (e.g., a polyG sequence). Template switching and barcoding may then take place to provide a barcoded RNA-cDNA molecule.

The partially double-stranded molecule corresponding to the chromatin of the cell, cell bead, or cell nucleus and the barcoded RNA-cDNA molecule corresponding to the RNA molecule (e.g., prepared as described above) of the cell, cell bead, or cell nucleus included within the partition of the plurality of partitions may be recovered from the partition. For example, the contents of the plurality of partitions may be pooled to provide the linear amplification products in a bulk solution.

Outside of the partition, the gaps in the partially double-stranded nucleic acid molecule corresponding to the chromatin may be filled using via a gap filling extension process (e.g., using a DNA polymerase). The resultant gap-filled double-stranded nucleic acid molecule may be denatured to provide a single strand, which single strand may be subjected to conditions sufficient to perform one or more nucleic acid amplification reactions (e.g., PCR) to generate amplification products corresponding to the chromatin of the cell, cell bead, or cell nucleus. A nucleic acid amplification process may incorporate one or more additional sequences, such as one or more additional flow cell adapter sequences. The barcoded RNA-cDNA molecule corresponding to the RNA molecule may also be processed and amplified according to the preceding examples.

FIG. 128 shows an example schematic corresponding to the preceding example. Panel 12800 shows a workflow corresponding to processing of chromatin from a cell, cell bead, or cell nucleus, and panel 12850 shows a workflow corresponding to processing of an mRNA molecule from the cell, cell bead, or cell nucleus.

As shown in panel 12800, in bulk solution, chromatin included within a cell, cell bead, or cell nucleus is processed (e.g., as described herein) to provide a template nucleic acid fragment (e.g., tagmented fragment) 12804 comprising insert sequence 12808 and a complement thereof, transposon end sequences 12806 and complements thereof, sequencing primer or portion thereof 12802 (e.g., an R1 sequence), sequencing primer or portion thereof 12810 (e.g., an R2 sequence), and gaps 12807. Template nucleic acid fragment 12804 may then be partitioned within a partition (e.g., a droplet or well, as described herein). Within the partition, the cell, cell bead, or cell nucleus comprising template nucleic acid fragment 12804 may be lysed, permeabilized, or otherwise processed to provide access to template nucleic acid fragment 12804 (and one or more RNA molecules) therein. The partition may include a gel bead 12816 coupled to a nucleic acid barcode molecule 12818a. Nucleic acid barcode molecule 12818a may comprise a flow cell adapter sequence 12820a (e.g., a P5 sequence), a barcode sequence 12822a, and a sequencing primer or portion thereof or complement thereof 12802'. Sequence 12802' may hybridize to sequence 12802 of template nucleic acid fragment 12804, or its complement. Sequence 12802' may then be ligated 12812 to a transposon end sequence 12806 of template nucleic acid fragment 12804. The contents of the partition may then be recovered in bulk solution (e.g., a droplet may be broken) to provide the partially double-stranded nucleic acid molecule comprising nucleic acid barcode molecule 12818a attached to template nucleic acid fragment 12804 in bulk solution. In bulk solution, gaps 12807 may be filled 12814 via a gap filling extension process (e.g., using a DNA polymerase) and the molecule extended from sequence 12802 to provide a double-stranded nucleic acid molecule. This molecule may undergo amplification (e.g., PCR) 12824 to provide a double-stranded amplification product 12826 that includes sequences of the nucleic acid barcode molecule 12818a, the original chromatin molecule, and, optionally, an additional sequence 12828 that may be a flow cell adapter sequence (e.g., a P7 sequence).

In parallel to the chromatin workflow of panel 12800, an RNA molecule deriving from the same cell, cell bead, or cell nucleus may be processed. As shown in panel 12850, RNA molecule 12858 comprising RNA sequence 12860 and polyA sequence 12862 may be contacted 12864 with primer molecule 12852 comprising polyT sequence 12854 and additional primer sequence 12856. RNA molecule 12858 may then be reverse transcribed 12876 off of polyT sequence 12854 using a reverse transcriptase with terminal transferase activity, which reverse transcriptase may append sequence 12870 to the resultant cDNA molecule comprising cDNA sequence 12868. Sequence 12870 may be a polyC sequence. Gel bead 12816 (e.g., the same gel bead described in panel 12800) may be included within the partition and may be coupled to nucleic acid barcode molecule 12818b. Nucleic acid barcode molecule 12818b may comprise a flow cell adapter sequence 12820b (e.g., a P5 sequence), a barcode sequence 12822b, UMI sequence 12872, and a sequence 12874 complementary to sequence 12870 (e.g., a polyG sequence). Nucleic acid barcode molecule 12818b may be used to perform template switching 12878, which process may also result in the generation of a barcoded RNA-cDNA molecule. The contents of the partition may then be recovered in bulk solution (e.g., a droplet may be broken) to provide the barcoded RNA-cDNA molecule in bulk solution. The barcoded RNA-cDNA molecule may undergo amplification (e.g., PCR) 12880 to provide a double-stranded amplification product 12884 that includes sequences of the nucleic acid barcode molecule 12818b, the original RNA molecule or cDNA corresponding thereto, a flow cell adapter sequence 12886, and an additional sequence 12888 that may comprise a sequencing primer or portion thereof (e.g., an R2 sequence) 12890, a sample index sequence 12892, and a flow cell adapter sequence (e.g., a P7 sequence) 12894. The barcoded RNA-cDNA molecule may also or alternatively undergo fragmentation, end repair, dA tailing, ligation of one or more adapter sequences, and/or nucleic acid amplification.

FIG. 129 shows another example schematic corresponding to the preceding example. Panel 12900 shows a workflow corresponding to processing of chromatin from a cell, cell bead, or cell nucleus, and panel 12950 shows a workflow corresponding to processing of an mRNA molecule from the cell, cell bead, or cell nucleus.

As shown in panel 12900, in bulk solution, chromatin included within a cell, cell bead, or cell nucleus is processed (e.g., as described herein) to provide a template nucleic acid fragment (e.g., tagmented fragment) 12904 comprising insert sequence 12908 and a complement thereof, transposon end sequences 12906 and complements thereof, sequencing primer or portion thereof 12902 (e.g., an R1 sequence), sequencing primer or portion thereof 12910 (e.g., an R2 sequence), and gaps 12907. Template nucleic acid fragment 12904 may then be partitioned within a partition (e.g., a droplet or well, as described herein). Within the partition, the cell, cell bead, or cell nucleus comprising template nucleic acid fragment 12904 may be lysed, permeabilized, or otherwise processed to provide access to template nucleic acid fragment 12904 (and one or more RNA molecules) therein. The partition may include a gel bead 129129 coupled to a nucleic acid barcode molecule 12918a. Nucleic acid barcode molecule 12918a may comprise a flow cell adapter sequence 12920a (e.g., a P5 sequence), a barcode sequence 12922a, and a sequencing primer or portion thereof or complement thereof 12902'. Sequence 12902' may hybridize to sequence 12902 of template nucleic acid fragment 12904, or its complement. Sequence 12902' may then be ligated 12912 to a transposon end sequence 12906 of template nucleic acid fragment 12904. The contents of the partition may then be recovered in bulk solution (e.g., a droplet may be broken) to provide the partially double-stranded nucleic acid molecule comprising nucleic acid barcode molecule 12918a attached to template nucleic acid fragment 12904 in bulk solution. In bulk solution, gaps 12907 may be filled 12914 via a gap filling extension process (e.g., using a DNA polymerase) and the molecule extended from sequence 12902 to provide a double-stranded nucleic acid molecule. This molecule may undergo amplification (e.g., PCR) 12924 to provide a double-stranded amplification product 12926 that includes sequences of the nucleic acid barcode molecule 12918a, the original chromatin molecule, and, optionally, an additional sequence 12928 that may be a flow cell adapter sequence (e.g., a P7 sequence).

In parallel to the chromatin workflow of panel 12900, an RNA molecule deriving from the same cell, cell bead, or cell nucleus may be processed. As shown in panel 12950, RNA molecule 12958 comprising RNA sequence 12960 and polyA sequence 12962 may and gel bead 12916 may be provided within a partition. Gel bead 12916 (e.g., the same gel bead described in panel 12900) may be included within the partition and may be coupled to nucleic acid barcode molecule 12918b. Nucleic acid barcode molecule 12918b may comprise a flow cell adapter sequence 12968 (e.g., a P5 sequence), a barcode sequence 12922b (e.g., the same barcode sequence as barcode sequence 12922a), UMI sequence 12966, and a polyT sequence 12964 complementary to polyA sequence 12962. PolyT sequence 12964 may hybridize to polyA sequence 12962 of RNA molecule 12958. RNA molecule 12958 may be reverse transcribed 12970 off of polyT sequence 12964 to provide an RNA-cDNA molecule comprising cDNA sequence 12972. The reverse transcription process may use a reverse transcriptase with terminal transferase activity, which reverse transcriptase may append sequence 12974 to the resultant cDNA molecule comprising cDNA sequence 12972. Sequence 12974 may be a polyC sequence. A template switch oligonucleotide 12978 comprising a primer sequence 12980 and a sequence complementary to sequence 12974 (e.g., a polyG sequence) may hybridize to the RNA-cDNA molecule. The contents of the partition may then be recovered in bulk solution (e.g., a droplet may be broken) to provide the RNA-cDNA molecule in bulk solution. The RNA-cDNA molecule may undergo amplification (e.g., PCR) 12984. Additional amplification (e.g., PCR) 12986 may to performed to provide a double-stranded amplification product 12988 that includes sequences of the nucleic acid barcode molecule 12918b, the original RNA molecule or cDNA corresponding thereto, a flow cell adapter sequence 12998 (e.g., a P7 sequence), and an additional sequence 12990 that may comprise a sequencing primer or portion thereof (e.g., an R2 sequence) 12996, a sample index sequence 12994, and a flow cell adapter sequence (e.g., a P5 sequence) 12992. The barcoded RNA-cDNA molecule may also or alternatively undergo fragmentation, end repair, dA tailing, ligation of one or more adapter sequences, and/or nucleic acid amplification.

In another example, a cell, cell bead, or cell nucleus comprising chromatin and one or more RNA molecules is provided. The chromatin in the cell, cell bead, or cell nucleus may be processed to provide a first template nucleic acid fragment derived from the chromatin (e.g., a tagmented fragment, as described herein). The chromatin may be processed in bulk solution. An RNA molecule may be processed to provide a second template nucleic acid fragment derived from an RNA molecule (e.g., as described herein). The RNA molecule may be processed within a partition. The configuration of the first template nucleic acid fragment may be at least partially dependent on the structure of the transposase-nucleic acid complex used to generate the first template nucleic acid fragment. For example, a transposase-nucleic acid complex such as that shown in FIG. 121 may be used to prepare the first template nucleic acid fragment. The first template nucleic acid fragment may be at least partially double-stranded. The first template nucleic acid fragment may comprise a double-stranded region comprising sequences of chromatin of the cell, cell bead, or cell nucleus. A first end of a first strand of the double-stranded region may be linked to a first transposon end sequence (e.g., mosaic end sequence), which first transposon end sequence may be linked to a first sequencing primer or portion thereof. A first end of the second strand of the double-stranded region, which end is opposite the first end of the first strand, may be linked to a second transposon end sequence (e.g., mosaic end sequence), which second transposon end sequence may be linked to a second sequencing primer or portion thereof. The second transposon end sequence may be the same as or different from the first transposon end sequence. The first sequencing primer or portion thereof may be the same as or different from the second sequencing primer or portion thereof. In some cases, the first sequencing primer or portion thereof may be an R1 sequence or portion thereof, and the second sequencing primer or portion thereof may be an R2 sequence or portion thereof. The first transposon end sequence may be hybridized to a first complementary sequence (e.g., mosaic end reverse complement sequence), which first complementary sequence may not be linked to a second end of the second strand of the double-stranded region of the first template nucleic acid fragment. Similarly, the second transposon end sequence may be hybridized to a second complementary sequence (e.g., mosaic end reverse complement sequence), which second complementary sequence may not be linked to a second end of the first strand of the double-stranded region of the first template nucleic acid fragment. In other words, the first template nucleic acid fragment may comprise one or more gaps. In some cases, the one or more gaps may be approximately 9 bp in length each. The second template nucleic acid fragment (e.g., an additional template nucleic acid fragment) may comprise a sequence of an RNA molecule of the cell, cell bead, or cell nucleus and a sequence hybridized to a primer molecule (e.g., a capture nucleic acid molecule). For example, the second template nucleic acid fragment may comprise a sequence of an RNA molecule of the cell, cell bead, or cell nucleus and a polyA sequence hybridized to a polyT sequence of a primer molecule. The primer molecule may also comprise an additional primer sequence.

The cell, cell bead, or cell nucleus comprising the first template nucleic acid fragment (e.g., tagmented fragment) may be co-partitioned with one or more reagents into a partition of a plurality of partitions (e.g., as described herein). The partition may be, for example, a droplet or well. The partition may comprise one or more beads (e.g., as described herein). A bead of the one or more beads may comprise a first plurality of nucleic acid barcode molecules. A nucleic acid barcode molecule of the first plurality of nucleic acid barcode molecules may comprise a flow cell adapter sequence (e.g., P5 sequence), a barcode sequence, and an overhang sequence. The partition may also comprise a splint sequence comprising a sequence complementary to the overhang sequence and a sequencing primer or portion thereof that may be complementary to a sequence of the first template nucleic acid fragment. A bead of the one or more beads may also comprise a second plurality of nucleic acid barcode molecules. A nucleic acid barcode molecule of the second plurality of nucleic acid barcode molecules may comprise a flow cell adapter sequence (e.g., P5 sequence), a barcode sequence, a sequencing primer or portion thereof (e.g., R1 sequence or portion thereof, or a complement thereof), a UMI sequence, and a capture sequence (e.g., a polyG sequence or a polydT sequence). In some cases, the first plurality of nucleic acid barcode molecules and the second plurality of nucleic acid barcode molecules may be coupled to the same bead, and the partition may comprise a single bead.

Within the partition, the RNA molecule may be processed to provide the second template nucleic acid fragment (e.g., as described herein).

Within the partition, the cell, cell bead, or cell nucleus may be lysed or permeabilized to provide access to the first and/or second template nucleic acid fragments therein (e.g., as described herein). The second template nucleic acid fragment may be generated after the cell, cell bead, or cell nucleus is lysed or permeabilized.

The first and second template nucleic acid fragments may undergo processing within the partition. Within the partition, a sequencing primer or portion thereof of the first template nucleic acid fragment corresponding to the chromatin of the cell, cell bead, or cell nucleus may hybridize to a complementary sequence of the sequencing primer or portion thereof in the splint sequence. The splint sequence may also hybridize to the overhang sequence of the nucleic acid barcode molecule of the first plurality of nucleic acid barcode molecules. The overhang sequence of the nucleic acid barcode molecule may then be ligated (e.g., using a ligase) to a sequencing primer or portion thereof of the first template nucleic acid fragment. The resultant partially double-stranded nucleic acid molecule may comprise the barcode sequence as well as one or more gaps.

Within the partition, the second template nucleic acid fragment derived from the RNA molecule of the cell, cell bead, or cell nucleus may be reverse transcribed (e.g., using a reverse transcriptase) to provide a cDNA strand. The reverse transcription process may append a sequence to an end of a strand of the resultant double-stranded nucleic acid molecule comprising the RNA strand and the cDNA strand, such as a polyC sequence. The capture sequence of the nucleic acid barcode molecule of the second plurality of nucleic acid barcode molecules may hybridize to the appended sequence (e.g., polyC sequence) of the double-stranded nucleic acid molecule and a template switching process may take place to provide a second double-stranded nucleic acid molecule. The sequence of the nucleic acid barcode molecule of the second plurality of nucleic acid barcode molecules may be considered a template switching oligonucleotide. The template switch process may result in a barcoded RNA-cDNA molecule. The barcoded RNA-cDNA molecule may comprise the sequencing primer or portion thereof, or complement thereof, of the nucleic acid barcode molecule of the second plurality of nucleic acid barcode molecules; the barcode sequence, or complement thereof, of the nucleic acid barcode molecule of the second plurality of nucleic acid barcode molecules; the UMI sequence, or complement thereof, of the nucleic acid barcode molecule of the second plurality of nucleic acid barcode molecules; the capture sequence, or complement thereof, of the nucleic acid barcode molecule of the second plurality of nucleic acid barcode molecules; the poly(C) or poly(G) sequence; the sequence corresponding to the RNA molecule of the cell, cell bead, or cell nucleus, or complement thereof; and sequences of the capture nucleic acid molecule, or complements thereof.

The partially double-stranded nucleic acid molecule corresponding to the chromatin of the cell, cell bead, or cell nucleus and the barcoded RNA-cDNA molecule corresponding to the RNA molecule of the cell, cell bead, or cell nucleus included within the partition of the plurality of partitions may be recovered from the partition. For example, the contents of the plurality of partitions may be pooled to provide the partially double-stranded nucleic acid molecule and the barcoded RNA-cDNA molecule in a bulk solution.

Outside of the partition, the gaps in the partially double-stranded nucleic acid molecule corresponding to the chromatin may be filled using via a gap filling extension process (e.g., using a DNA polymerase or reverse transcriptase). In some embodiments, the DNA polymerase may lack strand displacement activity. The resultant gap-filled double-stranded nucleic acid molecule may be denatured to provide a single strand, which single strand may be subjected to conditions sufficient to perform one or more nucleic acid amplification reactions (e.g., PCR) to generate amplification products corresponding to the chromatin of the cell, cell bead, or cell nucleus. A nucleic acid amplification process may incorporate one or more additional sequences, such as one or more additional flow cell adapter sequences.

Outside of the partition, the barcoded RNA-cDNA molecule corresponding to the RNA molecule may be subjected to fragmentation, end repair, a dA tailing process, tagmentation, or any combination thereof. An additional primer sequence (e.g., a sequencing primer or portion thereof, such as an R2 sequence) may then be ligated to the resultant molecule. A nucleic acid amplification reaction (e.g., PCR) may then be performed to generate one or more amplification products corresponding to the RNA molecule. A nucleic acid amplification process may incorporate one or more additional sequences, such as one or more additional flow cell adapter sequences.

FIG. 130 shows an example schematic corresponding to the preceding example. Panel 13000 shows a workflow corresponding to processing of chromatin from a cell, cell bead, or cell nucleus, and panel 13050 shows a workflow corresponding to processing of an mRNA molecule from the cell, cell bead, or cell nucleus.

As shown in panel 13000, in bulk solution, chromatin included within a cell, cell bead, or cell nucleus is processed (e.g., as described herein) to provide a template nucleic acid fragment (e.g., tagmented fragment) 13004 comprising insert sequence 13008 and a complement thereof, transposon end sequences 13006 and complements thereof, sequencing primer or portion thereof 13002 (e.g., an R1 sequence), sequencing primer or portion thereof 13010 (e.g., an R2 sequence), and gaps 13007. Template nucleic acid fragment 13004 may then be partitioned within a partition (e.g., a droplet or well, as described herein). Within the partition, the cell, cell bead, or cell nucleus comprising template nucleic acid fragment 13004 may be lysed, permeabilized, or otherwise processed to provide access to template nucleic acid fragment 13004 (and one or more RNA molecules) therein. The partition may comprise splint sequence 13012, which splint sequence may comprise a first sequence 13002' that is complementary to sequencing primer or portion thereof 13002 and a second sequence 13024. Sequence 13024 may comprise a blocking group (e.g., a 3' blocking group), which blocking group may prevent extension by reverse transcription. The partition may also include a gel bead 13016 coupled to a nucleic acid barcode molecule 13018a. Nucleic acid barcode molecule 13018a may comprise a flow cell adapter sequence 13020a (e.g., a P5 sequence), a barcode sequence 13022a, and an overhang sequence 13024' that is complementary to sequence 13024 of the splint sequence. Sequence 13024 may hybridize to sequence 13024' to provide a partially double-stranded nucleic acid molecule comprising the sequences of nucleic acid barcode molecule 13018a and the template nucleic acid fragment 13004. Sequence 13024' of nucleic acid barcode molecule 13018a may be ligated (e.g., using a ligase) 13026 to sequence 13002 of template nucleic acid fragment 13004. The contents of the partition may then be recovered in bulk solution (e.g., a droplet may be broken) to provide the partially double-stranded nucleic acid molecule comprising nucleic acid barcode molecule 13018a attached to template nucleic acid fragment 13004 in bulk solution. In bulk solution, gaps 13007 may be filled 13028 via a gap filling extension process (e.g., using a DNA polymerase) to provide a double-stranded nucleic acid molecule. This molecule may undergo amplification (e.g., PCR) 13030 to provide a double-stranded amplification product 13032 that includes sequences of the nucleic acid barcode molecule 13018a, the original chromatin molecule, and, optionally, an additional sequence 13034 that may be a flow cell adapter sequence (e.g., a P7 sequence).

In parallel to the chromatin workflow of panel 13000, an RNA molecule deriving from the same cell, cell bead, or cell nucleus may be processed. As shown in panel 13050, RNA molecule 13058 comprising RNA sequence 13060 and polyA sequence 13062 may be contacted 13064 with primer molecule 13052 comprising polyT sequence 13054 and additional primer sequence 13056. RNA molecule 13058 may then be reverse transcribed 13076 off of polyT sequence 13054 using a reverse transcriptase with terminal transferase activity, which reverse transcriptase may append sequence 13070 to the resultant cDNA molecule comprising cDNA sequence 13068. Sequence 13070 may be a polyC sequence. Gel bead 13016 (e.g., the same gel bead described in panel 13000) may be included within the partition and may be coupled to nucleic acid barcode molecule 13018b. Nucleic acid barcode molecule 13018b may comprise a flow cell adapter sequence 13020b (e.g., a P5 sequence), a barcode sequence 13022b, UMI sequence 13072, and a sequence 13074 complementary to sequence 13070 (e.g., a polyG sequence). Nucleic acid barcode molecule 13018b may be used to perform template switching 13078, which process may also result in the generation of a barcoded RNA-cDNA molecule. The contents of the partition may then be recovered in bulk solution (e.g., a droplet may be broken) to provide the barcoded RNA-cDNA molecule in bulk solution. The barcoded RNA-cDNA molecule may undergo amplification (e.g., PCR) 13080 to provide a double-stranded amplification product 13084 that includes sequences of the nucleic acid barcode molecule 13018b, the original RNA molecule or cDNA corresponding thereto, a flow cell adapter sequence 13086, and an additional sequence 13088 that may comprise a sequencing primer or portion thereof (e.g., an R2 sequence) 13090, a sample index sequence 13092, and a flow cell adapter sequence (e.g., a P7 sequence) 13094. The barcoded RNA-cDNA molecule may also or alternatively undergo fragmentation, end repair, dA tailing, ligation of one or more adapter sequences, and/or nucleic acid amplification.

FIG. 131 shows an example schematic corresponding to the preceding example. Panel 13100 shows a workflow corresponding to processing of chromatin from a cell, cell bead, or cell nucleus, and panel 13150 shows a workflow corresponding to processing of an mRNA molecule from the cell, cell bead, or cell nucleus.

As shown in panel 13100, in bulk solution, chromatin included within a cell, cell bead, or cell nucleus is processed (e.g., as described herein) to provide a template nucleic acid fragment (e.g., tagmented fragment) 13104 comprising insert sequence 13108 and a complement thereof, transposon end sequences 13106 and complements thereof, sequencing primer or portion thereof 13102 (e.g., an R1 sequence), sequencing primer or portion thereof 13110 (e.g., an R2 sequence), and gaps 13107. Template nucleic acid fragment 13104 may then be partitioned within a partition (e.g., a droplet or well, as described herein). Within the partition, the cell, cell bead, or cell nucleus comprising template nucleic acid fragment 13104 may be lysed, permeabilized, or otherwise processed to provide access to template nucleic acid fragment 13104 (and one or more RNA molecules) therein. The partition may comprise splint sequence 13112, which splint sequence may comprise a first sequence 13102' that is complementary to sequencing primer or portion thereof 13102 and a second sequence 13124. Sequence 13124 may comprise a blocking group (e.g., a 3' blocking group), which blocking group may prevent extension by reverse transcription. The partition may also include a gel bead 13116 coupled to a nucleic acid barcode molecule 13118a. Nucleic acid barcode molecule 13118a may comprise a flow cell adapter sequence 13120a (e.g., a P5 sequence), a barcode sequence 13122a, and an overhang sequence 13124' that is complementary to sequence 13124 of the splint sequence. Sequence 13124 may hybridize to sequence 13124' to provide a partially double-stranded nucleic acid molecule comprising the sequences of nucleic acid barcode molecule 13118a and the template nucleic acid fragment 13104. Sequence 13124' of nucleic acid barcode molecule 13118a may be ligated (e.g., using a ligase) 13126 to sequence 13102 of template nucleic acid fragment 13104. The contents of the partition may then be recovered in bulk solution (e.g., a droplet may be broken) to provide the partially double-stranded nucleic acid molecule comprising nucleic acid barcode molecule 13118a attached to template nucleic acid fragment 13104 in bulk solution. In bulk solution, gaps 13107 may be filled 13128 via a gap filling extension process (e.g., using a DNA polymerase) to provide a double-stranded nucleic acid molecule. This molecule may undergo amplification (e.g., PCR) 13130 to provide a double-stranded amplification product 13132 that includes sequences of the nucleic acid barcode molecule 13118a, the original chromatin molecule, and, optionally, an additional sequence 13134 that may be a flow cell adapter sequence (e.g., a P7 sequence).

In parallel to the chromatin workflow of panel 13100, an RNA molecule deriving from the same cell, cell bead, or cell nucleus may be processed. As shown in panel 13150, RNA molecule 13158 comprising RNA sequence 13160 and polyA sequence 13162 may and gel bead 13116 may be provided within a partition. Gel bead 13116 (e.g., the same gel bead described in panel 13100) may be included within the partition and may be coupled to nucleic acid barcode molecule 13118b. Nucleic acid barcode molecule 13118b may comprise a flow cell adapter sequence 13168 (e.g., a P5 sequence), a barcode sequence 13122b (e.g., the same barcode sequence as barcode sequence 13122a), UMI sequence 13166, and a polyT sequence 13164 complementary to polyA sequence 13162. PolyT sequence 13164 may hybridize to polyA sequence 13162 of RNA molecule 13158. RNA molecule 13158 may be reverse transcribed 13170 off of polyT sequence 13164 to provide an RNA-cDNA molecule comprising cDNA sequence 13172. The reverse transcription process may use a reverse transcriptase with terminal transferase activity, which reverse transcriptase may append sequence 13174 to the resultant cDNA molecule comprising cDNA sequence 13172. Sequence 13174 may be a polyC sequence. A template switch oligonucleotide 13178 comprising a primer sequence 13180 and a sequence complementary to sequence 13174 (e.g., a polyG sequence) may hybridize to the RNA-cDNA molecule. The contents of the partition may then be recovered in bulk solution (e.g., a droplet may be broken) to provide the RNA-cDNA molecule in bulk solution. The RNA-cDNA molecule may undergo amplification (e.g., PCR) 13184. Additional amplification (e.g., PCR) 13186 may to performed to provide a double-stranded amplification product 13188 that includes sequences of the nucleic acid barcode molecule 13118b, the original RNA molecule or cDNA corresponding thereto, a flow cell adapter sequence 13198 (e.g., a P7 sequence), and an additional sequence 13190 that may comprise a sequencing primer or portion thereof (e.g., an R2 sequence) 13196, a sample index sequence 13194, and a flow cell adapter sequence (e.g., a P5 sequence) 13192. The barcoded RNA-cDNA molecule may also or alternatively undergo fragmentation, end repair, dA tailing, ligation of one or more adapter sequences, and/or nucleic acid amplification.

In another aspect, the present disclosure provides a method for processing a biological sample (e.g., a nucleic acid sample), which method may comprise performing sequential transcription and reverse transcription processes within a partition. The method may comprise providing a partition (e.g., droplet or well) of a plurality of partitions comprising a nucleic acid molecule (e.g., DNA molecule) derived from a nucleic acid sample. The nucleic acid molecule may be transcribed (e.g., using a transcriptase) to provide an RNA molecule. The RNA molecule may then be reverse transcribed (e.g., using a reverse transcriptase) within the partition to generate a complementary DNA (cDNA) molecule. The cDNA molecule may undergo further processing within the partition to provide a derivative of the cDNA molecule. The cDNA molecule or derivative thereof may be recovered from the partition (e.g., by pooling the contents of the plurality of partitions). The partition may be a well among a plurality of wells. Alternatively, the partition may be a droplet among a plurality of droplets.

A nucleic acid molecule (e.g., DNA molecule) processed according to the method provided herein may derive from a cell, cell bead, or cell nucleus. In some cases, the nucleic acid molecule may be included within the cell, cell bead, or cell nucleus. The nucleic acid molecule may be chromatin. The cell, cell bead, or cell nucleus comprising the nucleic acid molecule may be included within the partition. For example, the cell, cell bead, or cell nucleus may be co-partitioned with one or more reagents (e.g., as described herein) into a partition (e.g., droplet or well). The cell, cell bead, or cell nucleus may be lysed or permeabilized (e.g., within a partition) to provide access to the nucleic acid molecule therein (e.g., as described herein).

A nucleic acid molecule processed according to the method provided herein may be a DNA molecule, such as chromatin. In some cases, the method may further comprise processing an open chromatin structure of the nucleic acid sample with a transposase (e.g., included within a transposase-nucleic acid complex) to provide the nucleic acid molecule. For example, a nucleic acid molecule (e.g., within a cell, cell bead, or cell nucleus) may be contacted with a transposase-nucleic acid complex (e.g., as described herein). A transposase used in such a process may be, for example, a Tn5 transposase. A transposase-nucleic acid complex may have a structure such as that of FIG. 121 or FIG. 122. Alternatively, a transposase-nucleic acid complex may comprise one or more transposon end oligonucleotide molecules, which transposon end oligonucleotide molecules comprise hairpin molecules. An example of such a transposase-nucleic acid complex is shown in FIG. 123.

A nucleic acid molecule processed using a transposase-nucleic acid complex comprising one or more hairpin molecules may be a tagmented fragment comprising a double-stranded region comprising sequences corresponding to the nucleic acid molecule (e.g., chromatin) of the cell, cell bead, or cell nucleus from which it originates or is derived, as well as one or more hairpin molecules appended to either end of the double-stranded region. For example, the double-stranded region may comprise a first hairpin molecule at one end and a second hairpin molecule at a second end. Generally, only one end of a hairpin molecule may be attached to the double-stranded region, such that the tagmented fragment comprises a gap at either end. For example, a hairpin molecule may be attached to a 3' end of the double-stranded region. The hairpin molecule may comprise a promoter sequence, such as a T7 promoter sequence, and/or a UMI sequence.

Within the partition, the nucleic acid molecule (e.g., tagmented fragment) may undergo a gap filling process with a reverse transcriptase. In some embodiments, the reverse transcriptase enzyme is a mutant reverse transcriptase enzyme such as, but not limited to, Moloney Murine Leukemia Virus (MMLV) reverse transcriptase. In one aspect, the reverse transcriptase is a mutant MMLV reverse transcriptase such as, but not limited to, enzyme "42B" (see, US Patent Publication No. 20180312822). Enzyme 42B was demonstrated to reduce inhibition of reverse transcription of mRNAs from a single cell due to one or more unknown components present in cell lysate of the single cell when prepared in reaction volumes of less than 1 nL. Enzyme 42B as compared to a commercially available mutant MMLV RT enzyme (CA-MMLV) showed improved reverse transcriptase activity. Such a process may generate a double-stranded nucleic acid molecule comprising the double-stranded region corresponding to the nucleic acid molecule (e.g., chromatin) of the cell, cell bead, or cell nucleus from which it is derived, the sequences of the hairpin molecules at either end of the double-stranded region, and sequences complementary to the sequences of the hairpin molecules. The double-stranded nucleic acid molecule may then undergo transcription with a T7 polymerase, which process begins at an end of a T7 promoter sequences of a hairpin molecules. Both strands may be transcribed in this manner to provide two nucleic acid strands each comprising the T7 promoter sequence, and a complement thereof; one or more transposon end sequences, and one or more complements thereof; and a sequence of the original nucleic acid molecule of the cell, cell bead, or cell nucleus. The strands may also comprise one or more spacer, UMI, or other sequences (e.g., from the hairpin molecules). A strand may then undergo a self-priming process in which the transposon end sequence and complement thereof of a hairpin molecule hybridize to one another to regenerate a hairpin molecule at an end of the strand. The hairpin molecule may serve as the priming site for reverse transcription. A reverse transcriptase process may then be performed (e.g., using a reverse transcriptase). Before, during, or after this process, a sequence may be appended to the end of the molecule, which sequence may be a polyC sequence. A template switching oligonucleotide comprising a sequence complementary to the appended sequence (e.g., a polyG sequence) may hybridize to the appended sequence. The template switching oligonucleotide may comprise a UMI sequence (e.g., a second UMI sequence that may index transcripts that undergo template switching), a barcode sequence, and/or a priming sequence such as a sequencing primer sequence or portion thereof (e.g., an R1 or R2 sequence, or portion thereof). The template switching oligonucleotide may be attached to a bead (e.g., a gel bead) included within the partition. For example, the template switching oligonucleotide may be a nucleic acid barcode molecule of a plurality of nucleic acid barcode molecules attached to the bead (e.g., as described herein). The resultant partially double-stranded nucleic acid molecule may comprise a hairpin moiety; sequences corresponding to the original nucleic acid molecule of the cell, cell bead, or cell nucleus; and the sequences of the template switching oligonucleotide, including a barcode sequence (see, e.g., FIG. 312).

The partially double-stranded nucleic acid molecule may be released from the partition (e.g., droplet or well). Releasing materials from the partition may comprise breaking or disrupting a droplet. The contents of multiple partitions of the plurality of partitions may be pooled together to provide a bulk solution for further processing. Nucleic acid molecules (e.g., partially double-stranded nucleic acid molecule) of the partitions of the plurality of partitions may each be differentially barcoded such that the nucleic acid molecule of each such partition comprises a different barcode sequence.

Outside of the partition, the partially double-stranded nucleic acid molecule may be partially denatured to provide a single-stranded molecule (e.g., a single-stranded cDNA molecule). An RNase treatment may be used to remove the hairpin molecule as well as the shorter strand (e.g., the RNA sequence) of the partially double-stranded nucleic acid molecule. The single-stranded molecule remaining may include the template switching oligonucleotide comprising the barcode sequence and, optionally, UMI sequence. A primer molecule comprising a priming sequence complementary to the priming sequence of the template switching oligonucleotide may be provided and may hybridize to the priming sequence of the template switching oligonucleotide. The priming sequence of the primer molecule may be a 5'-blocked priming sequence. A polymerase with dA tailing activity (e.g., a Klenow fragment having 5'-3' polymerase activity, such as an exo-Klenow fragment lacking exonuclease activity) may be used to generate a second nucleic acid strand. The resultant second strand may be dA tailed. The first strand may also be dA tailed. However, if a 5'-blocking priming sequence is used in the preceding processes, the dA tail appended to the first strand may not be available as a hybridization site for another moiety. Instead, a priming sequence comprising a sequencing primer (e.g., an R1 sequence or complement thereof) and a flow cell adapter sequence (e.g., a P5 sequence or complement thereof) may hybridize to a complementary sequence of the double-stranded nucleic acid molecule. At the opposite end of the double-stranded nucleic acid molecule, the dA moiety appended to the end of the second strand may serve as a site for hybridization of a priming sequence comprising a dT moiety at an end, a sequencing primer (e.g., an R2 sequence or complement thereof), and a flow cell adapter sequence (e.g., a P7 sequence or complement thereof). The double-stranded nucleic acid molecule may then be subjected to conditions sufficient to perform one or more nucleic acid amplification reactions (e.g., PCR) to provide amplification products corresponding to the original nucleic acid molecule of the cell, cell bead, or cell nucleus. The amplification products may comprise flow cell adapter sequences (e.g., P5 and P7 sequences) at either end to facilitate sequencing (e.g., as described herein).

The method provided herein overcomes certain challenges of performing reverse transcription within partitions. For example, reverse transcriptase may have a DNA-dependent DNA polymerase activity, and/or terminal transferase activities. The latter may result in generation of variable overhangs under certain reaction conditions. In the methods provided herein, every insertion site may be provided a T7 promoter, averting losses that may otherwise be encountered via R1-R1 and R2-R2 interactions. Moreover, both mRNA and chromatin-derived fragments may be barcoded using the same biochemistry (RT template switching). Performance of linear amplification of both strands of a nucleic acid molecule provides strand awareness and introduces a new dimension for ATAC-seq processes. Further, this method enables isothermal linear amplification of transposase derived nucleic acid fragments within partitions. Notably, this method may be combined with any of the RNA workflows described elsewhere herein.

FIG. 132 shows a workflow 13200 corresponding to the preceding example. Workflow 13200 may be performed in parallel with an RNA workflow, such as an RNA workflow of any of FIGS. 124-131. Multiple beads, each comprising nucleic acid barcode molecules configured for analysis of DNA or RNA molecules, may be included within a partition. Alternatively, a single bead (e.g., gel bead) comprising nucleic acid barcode molecules configured for analysis of both DNA and RNA molecules (e.g., as described herein) may be included within a partition. In some embodiments, the single bead (e.g., in a single partition) comprises a plurality of identical nucleic acid barcode molecules for both RNA and DNA analysis. In some cases, a single bead (e.g., within a single partition) comprises a first plurality of nucleic acid barcode molecules for DNA analysis and a second plurality of nucleic acid barcode molecules for RNA molecules, where the first and second plurality of nucleic acid barcode molecules comprise a common barcode sequence.

Template nucleic acid fragment (e.g., tagmented fragment) 13202 may be prepared (e.g., using a transposase-nucleic acid complex such as that shown in FIG. 11) and provided in a partition (as described herein). Template nucleic acid fragment 13202 may comprise hairpin moieties 13203 and 13204 and target sequences 13205 and 13206. Template nucleic acid fragment 13202 also comprises gaps 13207. Gaps 13207 may be filled using a reverse transcriptase (e.g., a 42B enzyme), which process may result in the generation of a double-stranded nucleic acid molecule comprising the double-stranded region corresponding to the original nucleic acid molecule (e.g., chromatin) of the cell, cell bead, or cell nucleus comprising sequences 13205 and 13206 and sequences of the hairpin molecules 13203 and 13204. The double-stranded nucleic acid molecule may comprise transposon end sequences 13208, promoter (e.g., T7 promoter) sequences 13210, and UMI sequences 13212. The double-stranded nucleic acid molecule may then undergo transcription with a T7 polymerase, which process begins at an end of a T7 promoter sequences of a hairpin molecule. Both strands may be transcribed in this manner to provide two nucleic acid strands. FIG. 132 shows one such strand comprising T7 promoter sequence 13210, and a complement thereof; one or more transposon end sequences 13208, and one or more complements thereof; UMI sequence 13212, and a complement of a UMI sequence; and an RNA sequence 13206' corresponding to sequence 13206 of the original nucleic acid molecule of the cell, cell bead, or cell nucleus. The strand may then undergo a self-priming process in which the transposon end sequence and complement thereof of hairpin molecule 13204 hybridize to one another to regenerate a hairpin molecule at an end of the strand. Regenerated hairpin molecule 13204 may serve as the priming site for reverse transcription. Reverse transcription and template switching may then be performed (e.g., using a reverse transcriptase). The reverse transcription process may append sequence 13214 (e.g., a polyC sequence) to the resultant RNA-cDNA molecule comprising cDNA sequence 13226 and sequences 13212' and 13208' that are complementary to sequences 13212 and 13208, respectively. The template switching process may comprise the use of a template switch oligonucleotide coupled to gel bead 13216 included within the partition. Gel bead 13216 may be coupled to nucleic acid barcode molecule 13218 that is the template switch oligonucleotide that comprises sequencing primer or portion thereof 13220, barcode sequence 13222, UMI sequence 13224, and a sequence 13214' that is complementary to sequence 13214 (e.g., a polyG sequence). The resultant RNA-cDNA molecule may comprise a first strand comprising nucleic acid barcode molecule 13218 and RNA sequence 13206' and a second strand comprising cDNA sequence 13226, appended sequence 13214, and sequences 13220', 13222', and 13224' that are complementary to sequences 13220, 13222, and 13224, respectively.

The RNA-cDNA molecule may be released from the partition (e.g., droplet or well). Releasing materials from the partition may comprise breaking or disrupting a droplet. The contents of multiple partitions of the plurality of partitions may be pooled together to provide a bulk solution for further processing. Outside of the partition, the RNA-cDNA molecule may be treated with RNase to remove the hairpin molecule as well as the shorter strand (e.g., the RNA sequence) of the partially double-stranded nucleic acid molecule. The single-stranded molecule remaining may include sequences 13220', 13222', 13224', 13214, 13212', 13208', and 13226. Primer molecule 13228 may then hybridize to sequence 13220'. Primer molecule 13228 may be a 5'-blocked priming sequence. A polymerase with dA tailing activity (e.g., a Klenow fragment having 5'→3' polymerase activity, such as an exo-Klenow fragment lacking exonuclease activity) may be used to generate a second nucleic acid strand comprising sequence 13226' that is complementary to cDNA sequence 13226. The resultant second strand may be dA tailed. The first strand may also be dA tailed at an end of sequence 13220'. However, if a 5'-blocking priming sequence is used in the preceding processes, the dA tail appended to the first strand may not be available as a hybridization site for another moiety. A priming sequence 13230 comprising a dT moiety, a sequencing primer (e.g., an R2 sequence or complement thereof) 13232 and a flow cell adapter sequence (e.g., a P7 sequence or complement thereof) 13234 may hybridize to the dA moiety of the double-stranded nucleic acid molecule. A priming sequence 13236 comprising a sequencing primer (e.g., an R1 sequence or complement thereof) 13238 and a flow cell adapter sequence (e.g., a P5 sequence or complement thereof) 13240 may hybridize to sequence 13228 of the double-stranded nucleic acid molecule. The double-stranded nucleic acid molecule may then be amplified to provide amplified product 13242, which amplification product may be subjected to further processing such as nucleic acid sequencing.

FIG. 133 provides an overview of a workflow 13300 for processing a nucleic acid molecule (e.g., a nucleic acid molecule included within a cell, cell bead, or cell nucleus). The nucleic acid molecule (e.g., DNA molecule, such as chromatin) is tagmented (e.g., as described herein) to generate a tagmented fragment. The tagmented fragment then undergoes transcription, reverse transcription, and barcoding within a partition (e.g., as described herein). The resultant products are released from the partition and subjected to one of two processes, the first of which provides an ATAC library and the second of which provides a gene expression library. The first process may involve RNase treatment to remove RNA and provide cDNA, dA tailing and ligation of a sequencing primer, and PCR. The second process may involve cDNA amplification; fragmentation, dA tailing, and ligation of a sequencing primer; and PCR.

The present disclosure also provides a method of processing a nucleic acid molecule of a cell, cell bead, or cell nucleus using a reverse transcriptase fill-in process coupled with a barcoding process. The nucleic acid molecule (e.g., DNA molecule) may derive from a cell, cell bead, or cell nucleus. In some cases, the nucleic acid molecule may be included within the cell, cell bead, or cell nucleus. The nucleic acid molecule may be chromatin. The cell, cell bead, or cell nucleus comprising the nucleic acid molecule may be included within the partition. For example, the cell, cell bead, or cell nucleus may be co-partitioned with one or more reagents (e.g., as described herein) into a partition (e.g., droplet or well). The cell, cell bead, or cell nucleus may be lysed or permeabilized (e.g., within a partition) to provide access to the nucleic acid molecule therein (e.g., as described herein).

A nucleic acid molecule processed according to the method provided herein may be a DNA molecule, such as chromatin. In some cases, the method may further comprise processing an open chromatin structure of the nucleic acid sample with a transposase (e.g., included within a transposase-nucleic acid complex) to provide the nucleic acid molecule. For example, a nucleic acid molecule (e.g., within a cell, cell bead, or cell nucleus) may be contacted with a transposase-nucleic acid complex (e.g., as described herein).

A transposase used in such a process may be, for example, a Tn5 tranposase. A transposase-nucleic acid complex may have a structure such as that of FIG. 121, 122, or 123. Subsequent to generation of a tagmented fragment (e.g., as described herein), the transposase of the transposase-nucleic acid complex may leave or be removed (e.g., displaced, for example, by an enzyme). Alternatively, the transposase may remain in place. The tagmented fragment may comprise sequences corresponding to the original nucleic acid molecule of the cell, cell bead, or cell nucleus; transposon end sequences and sequences complementary thereto; and one or more sequencing primers or portions thereof. A splint sequence comprising a sequence complementary to a sequencing primer or portion thereof the tagmented fragment may hybridize to the sequencing primer or portion thereof. The splint sequence may be ligated to a transposon end sequence or complement thereof of the tagmented fragment (e.g., using a ligase). Prior to or after hybridization and/or ligation of the splint sequence, the tagmented fragment may be partitioned into a partition of a plurality of partitions (e.g., droplets of wells). The tagmented fragment may be co-partitioned with one or more reagents. The tagmented fragment may be included within a cell, cell bead, or cell nucleus, which cell, cell bead, or cell nucleus may be lysed or permeabilized to provide access to the tagmented fragment therein (e.g., as described herein). A sequence of the splint sequence may then hybridize to a nucleic acid barcode molecule (e.g., a nucleic acid barcode molecule coupled to a bead, as described herein). The bead may comprise a plurality of nucleic acid barcode molecules, where a nucleic acid barcode molecule of the plurality of nucleic acid barcode molecules may comprise, for example, a flow cell adapter sequence, a barcode sequence, and a UMI sequence. The nucleic acid barcode molecule may also comprise an overhang sequence having sequence complementarity to a sequence of the splint sequence. The overhang sequence may hybridize to the sequence of the splint sequence. A transposase reserved in the tagmented fragment may block gap filling during these processes. The splint sequence may then be extended within the partition (e.g., using a reverse transcriptase).

Subsequent to the barcoding/template switching and extension (e.g., reverse transcription) processes, the contents of the partition of the plurality of partitions may be released from the partition (e.g., as described herein). Prior or subsequent to release of the contents of the partition, the nucleic acid barcode molecule may be ligated to the sequencing primer of the processed tagmented fragment. Outside of the partition, the nucleic acid barcode molecule may hybridize to the sequencing primer or portion thereof of the template nucleic acid fragment. If a transposase is reserved in the tagmented fragment, the transposase may leave the processed tagmented fragment (e.g., via a strand displacing polymerase) and the remaining gaps may be filled to provide a double-stranded nucleic acid molecule. Alternatively, gaps may be filled as described elsewhere herein. The double-stranded nucleic acid molecule may then be subjected to a nucleic acid amplification process (e.g., PCR, as described herein). Amplification may comprise incorporation of one or more additional sequences, such as one or more flow cell adapter sequences (e.g., P7 sequences).

FIG. 134 shows an example schematic corresponding to the preceding example. Panel 13400 shows a workflow corresponding to processing of chromatin from a cell, cell bead, or cell nucleus, and panel 13450 shows a workflow corresponding to processing of an mRNA molecule from the cell, cell bead, or cell nucleus. Multiple beads, each comprising nucleic acid barcode molecules configured for analysis of DNA or RNA molecules, may be included within a partition. Alternatively, a single bead (e.g., gel bead) comprising nucleic acid barcode molecules configured for analysis of both DNA and RNA molecules (e.g., as described herein) may be included within a given partition.

As shown in panel 13400, in bulk solution, chromatin included within a cell, cell bead, or cell nucleus is processed (e.g., as described herein) to provide a template nucleic acid fragment (e.g., tagmented fragment) 13404 comprising insert sequence 13408 and a complement thereof, transposon end sequences 13406 and complements thereof, sequencing primer or portion thereof 13402 (e.g., an R1 sequence), sequencing primer or portion thereof 13410 (e.g., an R2 sequence), and gaps 13407. The cell, cell bead, or cell nucleus comprising template nucleic acid fragment 13404 may be lysed, permeabilized, or otherwise processed to provide access to template nucleic acid fragment 13404 (and one or more RNA molecules) therein. Template nucleic acid fragment 13404 may be contacted with splint sequence 13412, which splint sequence may comprise a first sequence 13402' that is complementary to sequencing primer or portion thereof 13402 and a second sequence 13424. Sequence 13424 may comprise a blocking group (e.g., a 3' blocking group), which blocking group may prevent extension by reverse transcription. Sequence 13402' may hybridize 13414 to sequence 13402 of template nucleic acid fragment 13404 to provide a partially double-stranded nucleic acid molecule comprising splint sequence 13412 and template nucleic acid fragment 13404. Sequence 13402' may be ligated 13426 to the complement of transposon end sequence 13406 of template nucleic acid fragment 13404 (e.g., using a ligase). Template nucleic acid fragment 13404 attached to splint sequence 13412 may then be partitioned within a partition (e.g., droplet or well) within a plurality of partitions (e.g., as described herein). The partition may also include a gel bead 13416 coupled to a nucleic acid barcode molecule 13418a. Nucleic acid barcode molecule 13418a may comprise a flow cell adapter sequence 13420a (e.g., a P5 sequence), a barcode sequence 13422a, and an overhang sequence 13424' that is complementary to sequence 13424 of the splint sequence 13412. Sequence 13424 may hybridize 13428 to sequence 13424'. Splint sequence 13412 may then be extended 13430 (e.g., using a reverse transcriptase) to provide sequences 13420a' and 13422a' that are complementary to sequences 13420a and 13422a of nucleic acid barcode molecule 13418a. The contents of the partition may then be recovered in bulk solution (e.g., a droplet may be broken) to provide the partially double-stranded nucleic acid molecule comprising nucleic acid barcode molecule 13418a attached to splint sequence 13412 and template nucleic acid fragment 13404 in bulk solution. Sequence 13424' of nucleic acid barcode molecule 13418a may be ligated (e.g., using a ligase) 13432 to sequence 13402 of template nucleic acid fragment 13404. In bulk solution, gaps 13407 may be filled 13434 via a gap filling extension process (e.g., using a DNA polymerase) to provide a double-stranded nucleic acid molecule. This molecule may also undergo amplification (e.g., PCR) to provide a double-stranded amplification product 13436 that includes sequences of the nucleic acid barcode molecule 13418a, the original chromatin molecule, and, optionally, an additional sequence 13438 that may be a flow cell adapter sequence (e.g., a P7 sequence).

In parallel to the chromatin workflow of panel 13400, an RNA molecule deriving from the same cell, cell bead, or cell nucleus may be processed. As shown in panel 13450, RNA molecule 13458 comprising RNA sequence 13460 and polyA sequence 13462 may be contacted 13464 with primer molecule 13452 comprising polyT sequence 13454 and additional primer sequence 13456. RNA molecule 13458 may then be reverse transcribed 13476 off of polyT sequence 13454 using a reverse transcriptase with terminal transferase activity, which reverse transcriptase may append sequence 13470 to the resultant cDNA molecule comprising cDNA sequence 13468. Sequence 13470 may be a polyC sequence. Gel bead 13416 (e.g., the same gel bead described in panel 13400) may be included within the partition and may be coupled to nucleic acid barcode molecule 13418*b*. Nucleic acid barcode molecule 13418*b* may comprise a flow cell adapter sequence 13420*b* (e.g., a P5 sequence), a barcode sequence 13422*b*, UMI sequence 13472, and a sequence 13474 complementary to sequence 13470 (e.g., a polyG sequence). Nucleic acid barcode molecule 13418*b* may be used to perform template switching 13478, which process may also result in the generation of a barcoded RNA-cDNA molecule. The contents of the partition may then be recovered in bulk solution (e.g., a droplet may be broken) to provide the barcoded RNA-cDNA molecule in bulk solution. The barcoded RNA-cDNA molecule may undergo amplification (e.g., PCR) 13480 to provide a double-stranded amplification product 13484 that includes sequences of the nucleic acid barcode molecule 13418*b*, the original RNA molecule or cDNA corresponding thereto, a flow cell adapter sequence 13486, and an additional sequence 13488 that may comprise a sequencing primer or portion thereof (e.g., an R2 sequence) 13490, a sample index sequence 13492, and a flow cell adapter sequence (e.g., a P7 sequence) 13494. The barcoded RNA-cDNA molecule may also or alternatively undergo fragmentation, end repair, dA tailing, ligation of one or more adapter sequences, and/or nucleic acid amplification.

FIG. 135 shows another example schematic corresponding to the preceding example. Panel 13500 shows a workflow corresponding to processing of chromatin from a cell, cell bead, or cell nucleus, and panel 13550 shows a workflow corresponding to processing of an mRNA molecule from the cell, cell bead, or cell nucleus. Multiple beads, each comprising nucleic acid barcode molecules configured for analysis of DNA or RNA molecules, may be included within a partition. Alternatively, a single bead (e.g., gel bead) comprising nucleic acid barcode molecules configured for analysis of both DNA and RNA molecules (e.g., as described herein) may be included within a given partition.

As shown in panel 13500, in bulk solution, chromatin included within a cell, cell bead, or cell nucleus is processed (e.g., as described herein) to provide a template nucleic acid fragment (e.g., tagmented fragment) 13504 comprising insert sequence 13508 and a complement thereof, transposon end sequences 13506 and complements thereof, sequencing primer or portion thereof 13502 (e.g., an R1 sequence), sequencing primer or portion thereof 13510 (e.g., an R2 sequence), and gaps 13507. The cell, cell bead, or cell nucleus comprising template nucleic acid fragment 13504 may be lysed, permeabilized, or otherwise processed to provide access to template nucleic acid fragment 13504 (and one or more RNA molecules) therein. Template nucleic acid fragment 13504 may be contacted with splint sequence 13512, which splint sequence may comprise a first sequence 13502' that is complementary to sequencing primer or portion thereof 13502 and a second sequence 13524. Sequence 13524 may comprise a blocking group (e.g., a 3' blocking group), which blocking group may prevent extension by reverse transcription. Sequence 13502' may hybridize 13514 to sequence 13502 of template nucleic acid fragment 13504 to provide a partially double-stranded nucleic acid molecule comprising splint sequence 13512 and template nucleic acid fragment 13504. Sequence 13502' may be ligated 13526 to the complement of transposon end sequence 13506 of template nucleic acid fragment 13504 (e.g., using a ligase). Template nucleic acid fragment 13504 attached to splint sequence 13512 may then be partitioned within a partition (e.g., droplet or well) within a plurality of partitions (e.g., as described herein). The partition may also include a gel bead 13516 coupled to a nucleic acid barcode molecule 13518*a*. Nucleic acid barcode molecule 13518*a* may comprise a flow cell adapter sequence 13520*a* (e.g., a P5 sequence), a barcode sequence 13522*a*, and an overhang sequence 13524' that is complementary to sequence 13524 of the splint sequence 13512. Sequence 13524 may hybridize 13528 to sequence 13524'. Splint sequence 13512 may then be extended 13530 (e.g., using a reverse transcriptase) to provide sequences 13520*a*' and 13522*a*' that are complementary to sequences 13520*a* and 13522*a* of nucleic acid barcode molecule 13518*a*. The contents of the partition may then be recovered in bulk solution (e.g., a droplet may be broken) to provide the partially double-stranded nucleic acid molecule comprising nucleic acid barcode molecule 13518*a* attached to splint sequence 13512 and template nucleic acid fragment 13504 in bulk solution. Sequence 13524' of nucleic acid barcode molecule 13518*a* may be ligated (e.g., using a ligase) 13532 to sequence 13502 of template nucleic acid fragment 13504. In bulk solution, gaps 13507 may be filled 13534 via a gap filling extension process (e.g., using a DNA polymerase) to provide a double-stranded nucleic acid molecule. This molecule may also undergo amplification (e.g., PCR) to provide a double-stranded amplification product 13536 that includes sequences of the nucleic acid barcode molecule 13518*a*, the original chromatin molecule, and, optionally, an additional sequence 13538 that may be a flow cell adapter sequence (e.g., a P7 sequence).

In parallel to the chromatin workflow of panel 13500, an RNA molecule deriving from the same cell, cell bead, or cell nucleus may be processed. As shown in panel 13550, RNA molecule 13558 comprising RNA sequence 13560 and polyA sequence 13562 may and gel bead 13516 may be provided within a partition. Gel bead 13516 (e.g., the same gel bead described in panel 13500) may be included within the partition and may be coupled to nucleic acid barcode molecule 13518*b*. Nucleic acid barcode molecule 13518*b* may comprise a flow cell adapter sequence 13568 (e.g., a P5 sequence), a barcode sequence 13522*b* (e.g., the same barcode sequence as barcode sequence 13522*a*), UMI sequence 13566, and a polyT sequence 13564 complementary to polyA sequence 13562. PolyT sequence 13564 may hybridize to polyA sequence 13562 of RNA molecule 13558. RNA molecule 13558 may be reverse transcribed 13570 off of polyT sequence 13564 to provide an RNA-cDNA molecule comprising cDNA sequence 13572. The reverse transcription process may use a reverse transcriptase with terminal transferase activity, which reverse transcriptase may append sequence 13574 to the resultant cDNA molecule comprising cDNA sequence 13572. Sequence 13574 may be a polyC sequence. A template switch oligonucleotide 13578 comprising a primer sequence 13580 and a sequence complementary to sequence 13574 (e.g., a polyG sequence) may hybridize to the RNA-cDNA molecule. The contents of the partition may then be recovered in bulk solution (e.g., a droplet may be broken) to provide the RNA-cDNA molecule in bulk solution. The RNA-cDNA molecule may undergo amplification (e.g., PCR) 13584. Additional amplification (e.g., PCR) 13586 may to performed to provide a double-stranded amplification product 13588 that includes sequences of the nucleic acid barcode molecule 13518b, the original RNA molecule or cDNA corresponding thereto, a flow cell adapter sequence 13598 (e.g., a P7 sequence), and an additional sequence 13590 that may comprise a sequencing primer or portion thereof (e.g., an R2 sequence) 13596, a sample index sequence 13594, and a flow cell adapter sequence (e.g., a P5 sequence) 13592. The barcoded RNA-cDNA molecule may also or alternatively undergo fragmentation, end repair, dA tailing, ligation of one or more adapter sequences, and/or nucleic acid amplification.

Characterization, Analysis, and Detection of Other Analytes

Additional useful applications of the above described single cell sequencing and characterization processes are in the field of neuroscience research and diagnosis. In particular, neural cells can include long interspersed nuclear elements (LINEs), or 'jumping' genes that can move around the genome, which cause each neuron to differ from its neighbor cells. Research has shown that the number of LINEs in human brain exceeds that of other tissues, e.g., heart and liver tissue, with between 80 and 300 unique insertions (See, e.g., Coufal, N. G. et al. Nature 460, 1127-1131 (2009)). These differences have been postulated as being related to a person's susceptibility to neurological disorders (see, e.g., Muotri, A. R. et al. Nature 468, 443-446 (2010)), or provide the brain with a diversity with which to respond to challenges. As such, the methods described herein may be used in the sequencing and characterization of individual neural cells.

Also provided herein are compositions and methods for screening a chemical compound library. The methods may comprise providing a partition comprising at least one chemical compound and an identifier of the partition. The identifier may be an oligonucleotide comprising a nucleic acid barcode sequence as described in the application. The identifier oligonucleotide may be amplified and subject to sequence. The sequence read of the identifier oligonucleotide or a fragment thereof may be used to identify the partition and the at least one chemical compound in the partition. The methods may be used for screening a chemical compound library in a reaction of small volumes, e.g., on the scale of nanoliters. Multiple reactions may be performed in different partitions with the same substrate and/or reagent. The reaction may be multiplexed to decrease the effort and time needed to process the same number of compounds in reactions of larger scale, e.g., on the scale of microliters. The methods and compositions may allow high throughput screening of a chemical compound library with low noise and/or false-positive results. In some cases, a method for screening a chemical compound library may comprise one or more of the following operations: (1) providing a plurality of partitions, wherein a given partition of the plurality of partitions (i) has or is suspected of having at least one chemical compound and (ii) comprises an identifier oligonucleotide comprising a nucleic acid barcode sequence that permits identification of the given partition; (2) subjecting the plurality of partitions to screening under conditions sufficient to select a subset of the plurality of partitions from a remainder of the plurality of partitions, which subset comprises the given partition having or suspected of having the at least one chemical compound; (3) subjecting the subset of the plurality of partitions, including the given partition, to conditions sufficient to generate a nucleic acid molecule comprising at least a portion of the nucleic acid barcode sequence or a complement thereof; and (4) sequencing the nucleic acid molecule to generate sequence reads, which sequence reads permit identification of the at least one chemical compound.

The methods may comprise building combinatorial chemical and identifier oligonucleotide libraries on a solid support, e.g., a monodispersed polymeric bead. The oligonucleotide barcoding may be intrinsically linked to a chemical synthesis path unique for that monodispersed polymer bead. Upon partitioning this polymeric bead, the population of compounds may be released from the substrate to interact with the target molecule unencumbered by the identifier oligonucleotides. Partitions may then be sorted based on positive/negative interactions as indicated by a traditional reporter assay. Positives partitions may then be homogenized and pooled. The identifier oligonucleotides in the positive partitions may be amplified for sequencing. The methods may allow for large quantities of single compounds to be packaged into nanoliter partitions individually and for the subsequent deconvolution of partitions with positive interactions that may be pooled and processed in a multiplexed format.

In some cases, the methods comprise synthesizing a controlled number of chemical compounds on a solid support (e.g., a bead) while simultaneously synthesizing a controlled number of identifier oligonucleotides unique to the compounds on the solid support. The combinatorial libraries of the chemical compounds and identifier oligonucleotides may be made through sequential additions of chemical compound subunits that concord with simultaneous or subsequent sequential additions of identifier oligonucleotides on the solid matrix. The methods may be multiplexed in a single vessel for additions of chemical compounds and identifier oligonucleotides in a massively parallel way. The quantity of the chemical compounds to be screened may be normalized.

The number of chemical compounds and/or identifier oligonucleotides synthesized on a solid support may be controlled by adjusting the number of attachment points. An attachment point may be a location on a solid support where a chemical compound or identifier oligonucleotide may be attached to. Attachment points may include multiple types of chemistries for the cleavage of chemical compounds and/or identifier oligonucleotides. This allows for selective release of chemical compounds and/or identifier oligonucleotides in a controlled fashion. The solid may have a single or multiple attachment points.

The solid support may act as a covalent linker between chemical compounds and identifier oligonucleotides. A single type of solid support or multiple types of solid support may be used in the screening. If multiple types of solid support are used, they may be covalently linked to form a single solid support. In certain cases, if multiple types of solid support are used, they may be comingled (but not covalently linked) and occupy the same physical space. A solid support may have two or more matrices intermingled. In these cases, chemical compounds and the identifier oligonucleotides may be on the same matrix or on separate matrices of the solid support. In the latter case, the chemical compounds and the identifier oligonucleotides are comingled (and not covalently linked) and occupy the same physical space. In some cases, the solid support may be permeable or non-permeable. In certain cases, the solid support may be dissolvable or non-dissolvable.

A chemical compound may be a protein (e.g., an antibody or a fragment thereof, or an antigen or a fragment thereof), a nucleic acid molecule. In some cases, a chemical compound may be a small molecule compound. A small molecule compound may be a low molecular weight (e.g., no greater than 1000 daltons) organic compound that may help regulate a biological process. A small compound may have a size on the order of 1 nm. For example, a small molecule compound may be a small molecule drug.

Screening of a chemical compound library may be performed using methods for screening small molecules for drug discovery. For example, the screening may be performed using high-throughput screening or high-content analysis in drug discovery. A high-throughput screening may be a screening that identifies active compounds, antibodies, or genes that modulate a particular biomolecular pathway. A high-content analysis may be a screening that identifies substances such as small molecules, peptides, or RNAi that alter the phenotype of a cell in certain manner. In some cases, a screening may be an immunoassay, e.g., enzyme-linked immunosorbent assay (ELISA).

Also provided herein are scaffolds for delivery of one or more reagents. In some cases, a reagent is not covalently bound to the solid scaffold. For example, the reagent may be inside the scaffold and hindered (e.g., through steric interaction with the scaffold) from diffusing out of the scaffold. The reagent may be released from the scaffold when the scaffold is dissolved. In some cases, the scaffold may be a microcapsule described herein, such as a gel bead.

The scaffold may be used in a method for characterizing a cell. The method may comprise providing a partition comprising a cell, a scaffold, and an reagent in the scaffold. To characterize the cell in the partition, the scaffold may be dissolved to release the reagent. The reagent then contacts with the cell for determining one or more characteristics of the cell. In some cases, the partition may comprise a plurality of reagents. Any reagent described in the disclosure may be used in this method.

The scaffold may be used to deliver two or more reagents. In some cases, a first reagent be non-covalently bound to the scaffold, and the second reagent may be covalently bound to the scaffold. In other cases, multiple scaffolds may be used to deliver multiple reagents. In these cases, a first reagent may be covalently bound to a first scaffold, and a second reagent may be non-covalently bound to a second scaffold. The first scaffold and the second scaffold may be encapsulated in the same partition with a cell.

The reagent that is non-covalently bound to the scaffold may be released when the scaffold is dissolved. A scaffold is dissolved when at least 0.01%, 0.1, 1%, 5%, 10%, 20%, 30%, 40%, 50%, 60%, 70%, 80%, 90%, 95%, 99%, or 100% of the volume of the scaffold is dissolved in the solution around it.

The scaffold may comprise one or more pores and the reagent non-covalently bound to the scaffold may be in the one or more pores. The diameter of the one or more pores may be up to 0.01 nm, 0.1 nm, 1 nm, 5 nm, 10 nm, 50 nm, 100 nm, 200 nm, 400 nm, 600 nm, 800 nm, 1 µm, or 10 µm.

Figure 29:
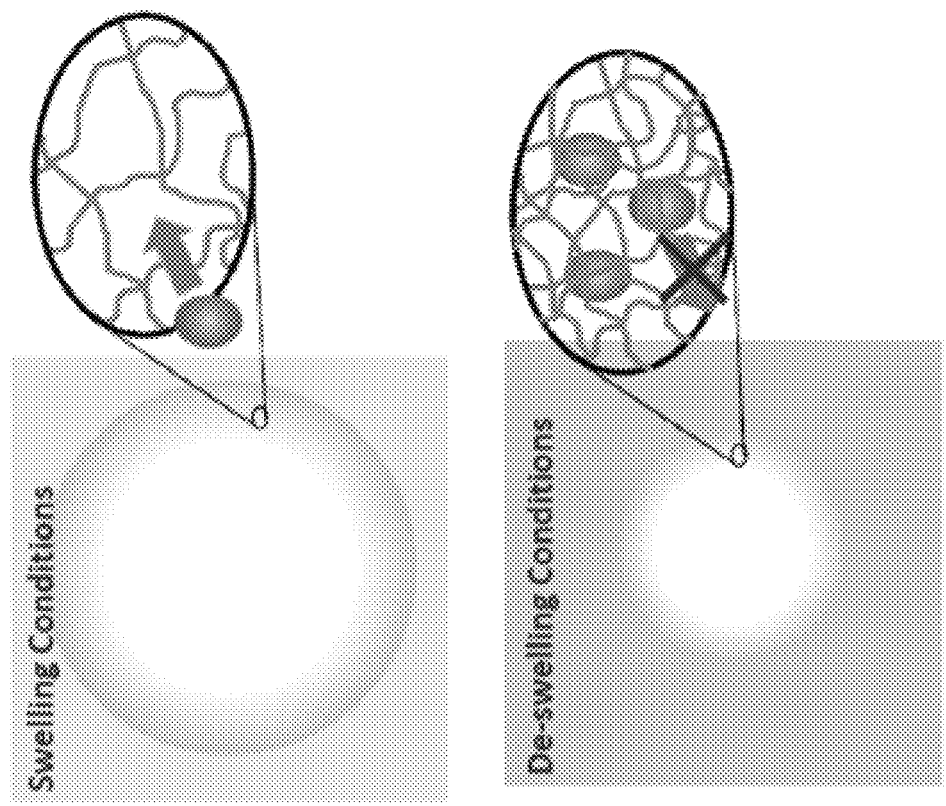
FIG. 29 demonstrates swelling conditions and de-swelling conditions in the process of making gel beads with magnetic particles.

A scaffold loaded with a non-covalently bound reagent may be made using any method of incorporating an agent in a solid substance. In some cases, the scaffold loaded with a non-covalently bound reagent may be made using the one or more of following operations: 1) Placing the scaffold (e.g., gel bead) and the reagent under a condition that causes the scaffold to swell and the pores defined by the polymer scaffold to enlarge. Such condition may include: in a thermodynamically-favorable solvent, at higher or lower temperatures (e.g., for temperature-responsive hydrogel materials), in a solvent with higher or lower ion concentration and/or in the presence or absence of an electric field for electric charge-/field-responsive hydrogel materials; 2) Allowing sufficient time for the reagent to diffuse into the interior of the scaffold; 3) Transferring the scaffold into a condition that causes the pores to shrink. The reagent molecules within the scaffold are then hindered from diffusing out of the scaffold by steric interactions with the polymer scaffold. The transfer in operation 3) may be achieved microfluidically, e.g., by moving the scaffold from one co-flowing solvent stream to another. FIG. 29 demonstrates examples of swelling conditions and de-swelling conditions in the process. The swellability and pore sizes of the scaffold may be adjusted by changing the polymer composition.

In a partition comprising a scaffold loaded with non-covalently bound reagent, the composition of the partition may be adjusted by including a scaffold of a certain volume. For example, when a partition has a fixed volume, the concentration of the reagent in the partition may be upregulated by including a reagent-loaded scaffold of a larger volume. In some cases, the adjustment may be performed without changing the initial concentration of the components in the partition. In certain cases, the adjustment may be performed without changing the total volume of the partition. Such methods are useful for delivering a reagent that interferes with the partition generation, e.g., a cell lysis agent.

Figure 30:
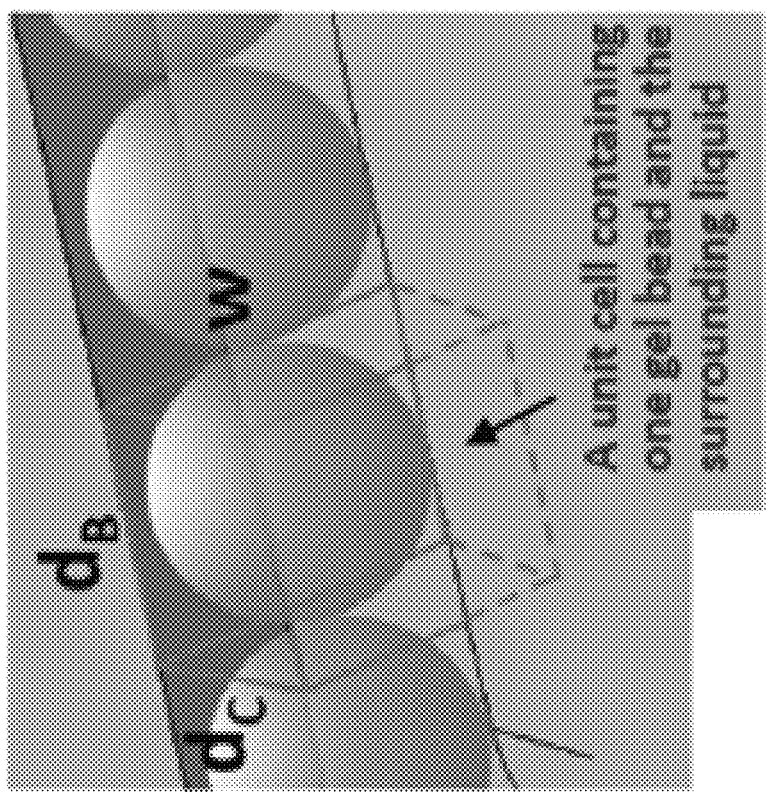
FIG. 30 shows a unit cell comprising a scaffold and liquid immediately surrounding the scaffold.

A partition with the scaffold may be generated using methods described in the disclosure. In certain cases, during the partition generation, both the scaffold and the liquid immediately surrounding the scaffold are encapsulated in a single partition as shown in FIG. 30. The volume of the scaffold and the surrounding liquid comprise a "unit cell". Unit cells may be defined by the geometry of the microchannel in which scaffolds flow and by the pressure applied. For example, higher pressures may compress the scaffold, which are deformable, thereby reducing the volume of the unit cell.

The composition of a partition may be determined by the volume of scaffold suspension (Z1) and the volume of the sample (Z2) encapsulated in that partition. The characteristic of the composition may be described by the ratio of these two volumes (Z1/Z2). The maximum Z1 possible for single-scaffold encapsulations is equal to the volume of the unit cell. Thus, to increase the concentration of a reagent delivered by the scaffold in a partition of a fixed volume without increasing the concentration of the reagent in the scaffold suspension, the dimensions of the scaffold may be increased. Thus, the encapsulated unit cell may occupy a greater volume of the partition (at higher Z1/Z2 ratio). In a microchannel for making the partitions, the dimension of the microchannel may or may not have to be increased to accommodate the larger partitions, depending on the mechanical properties of the scaffolds. When higher pressures are applied, the scaffold may compress, the volume of the unit cell may decrease, and a lower Z1/Z2 ratio may be achieved.

EXAMPLES

Example 1: Producing CD3 Protein Conjugated with Short ssDNA Molecules

The CD3 protein and the ssDNA molecule are first activated for click chemistry reaction. The CD3 protein is activated with 5-(methacrylamido)tetrazole (MTet) and the ssDNA molecule is activated with trans-cyclooctene (TCO). The ssDNA molecule comprises a biotin group. The activated CD3 protein and ssDNA molecule are mixed for conjugation by click chemistry reactions. The ssDNA molecule concentration is 5 times excess over the CD3 protein concentration to avoid multiple barcode copies conjugating on the same protein molecule. In some cases, the ssDNA concentration is 10 times excess over the CD3 protein to maximize barcode attachment. A biotin group may also be incorporated in the activated CD3-ssDNA conjugate for purification. The CD3 protein and ssDNA conjugate is purified and tested as shown in FIG. 31.

Example 2: Labelling Jurkat Cells with Human CD3 and Mouse CD3

Figure 32:
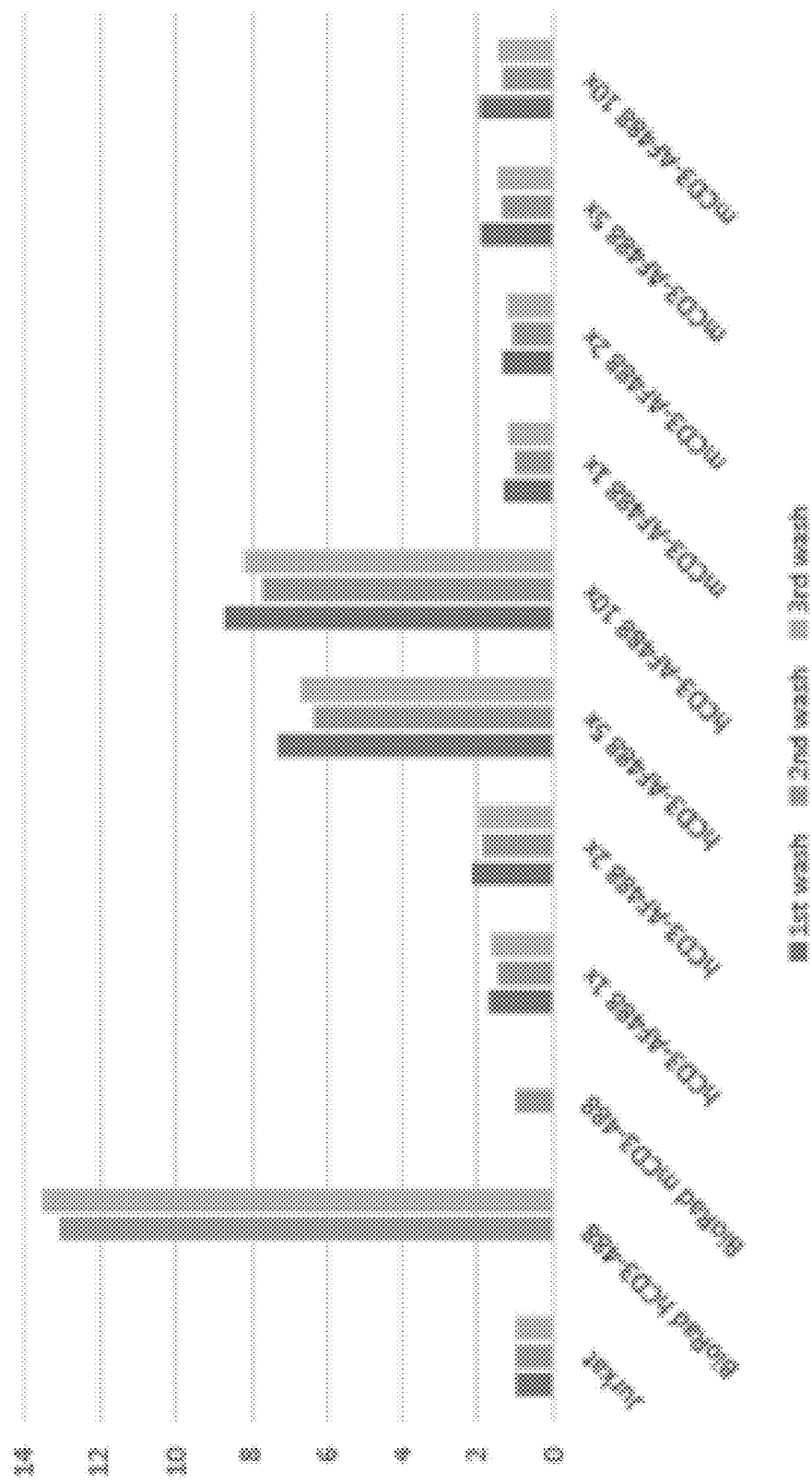
FIG. 32 shows the fluorescence signals from the cells bound by labeled antibodies.

The impact of DNA conjugation on the binding of CD3 on Jurkat cells is tested. Human CD3 (hCD3, MCA463) and mouse CD3 (mCD3, MCA500) are incubated with AF488-NHS, where the concentration of AF499-NHS is 1×, 2×, 5×, and 10× excess over the CD3 protein, in order to generate labeled CD3, where the AF999 is coupled to an amine of the CD3. The conjugated hCD3 and mCD3 are incubated with Jurkat cells. Unbound CD3 proteins are washed away. The fluorescence signals from the labeled cells are determined (FIG. 32). The fluorescent signals are normalized by comparing to commercial Jurkat cells control. The data show that Jurkat cells specifically bind to hCD3 over mCD3, indicating that the conjugation of dye/DNA does not affect the binding of CD3 proteins with Jurkat cells. Blocking reagents (e.g., FBS, 5% BSA) may be added to improve specificity.

Example 3: Conjugating a DNA Barcode to IgG of an Antibody

Figure 33A:
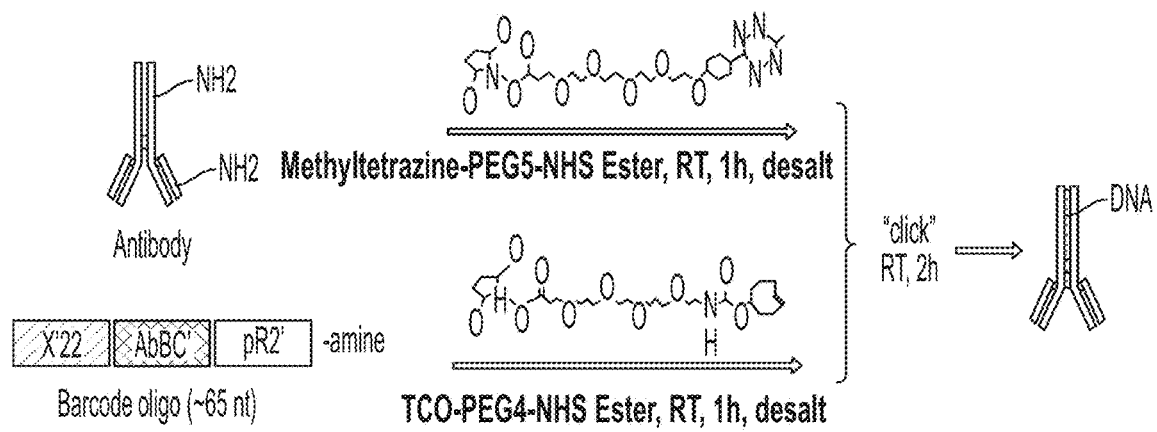
FIG. 33A shows an approach for conjugating an oligonucleotide with an antibody.
Figure 33B:
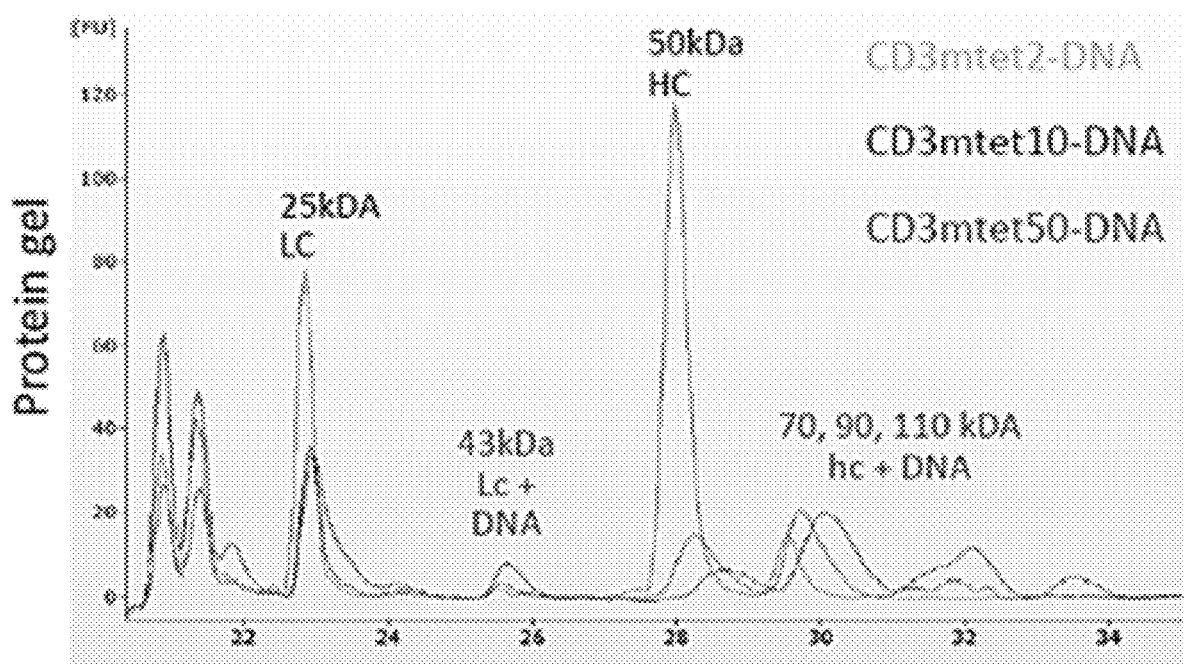
FIG. 33B shows analysis results of barcoded antibodies.

An antibody is incubated with Methyltetrazine-PEG5-NHS Ester at room temperature for 1 hour and desalted. A DNA barcode of about 65 nt long is incubated with TCO-PEG4-NHS Ester at room temperature for an hour and desalted. The resulting antibody and DNA barcode are incubated at room temperature for 2 hours for conjugation. FIG. 33A shows the conjugation strategy. The conjugated antibody-DNA complex is subject to protein gel analysis. As shown in FIG. 33B, protein gel shifts of about 20 kDa indicates successful conjugation of the DNA barcode to IgG of the antibody. Multiple viable chemistries for primary antibody barcoding are validated (e.g., mTet, dibenzocyclooctyne (DBCO), SiteClick). The conjugated antibody-DNA complex is incubated with cells for labelling.

Example 4: Conjugating Oligonucleotides to Antibodies Using Antibody-Binding Proteins Antibody-binding proteins Protein X (Protein A or Protein G) are functionalized with dibenzocyclooctyne-N-hydroxysuccinimidyl ester (DBCO-NHS). Fluorescein amidite (FAM)-labeled oligoX22-azide (3eq) is used as the oligonucleotides to be conjugated with the antibody-binding proteins. The functionalized antibody-binding proteins and the oligonucleotides are conjugated as shown in FIG. 34A. The degree of conjugation between the dibenzocyclooctyne (DBCO) and Protein G may be controlled based on Gong et al., Simple Method To Prepare Oligonucleotide-Conjugated Antibodies and Its Application in Multiplex Protein Detection in Single Cells. Bioconjugate Chem., 2016, which is incorporated herein by reference in its entirety. Degree of DBCO incorporation may be controlled by adjusting input DBCO-NHS concentration as shown in FIG. 34B.

Figure 34C:
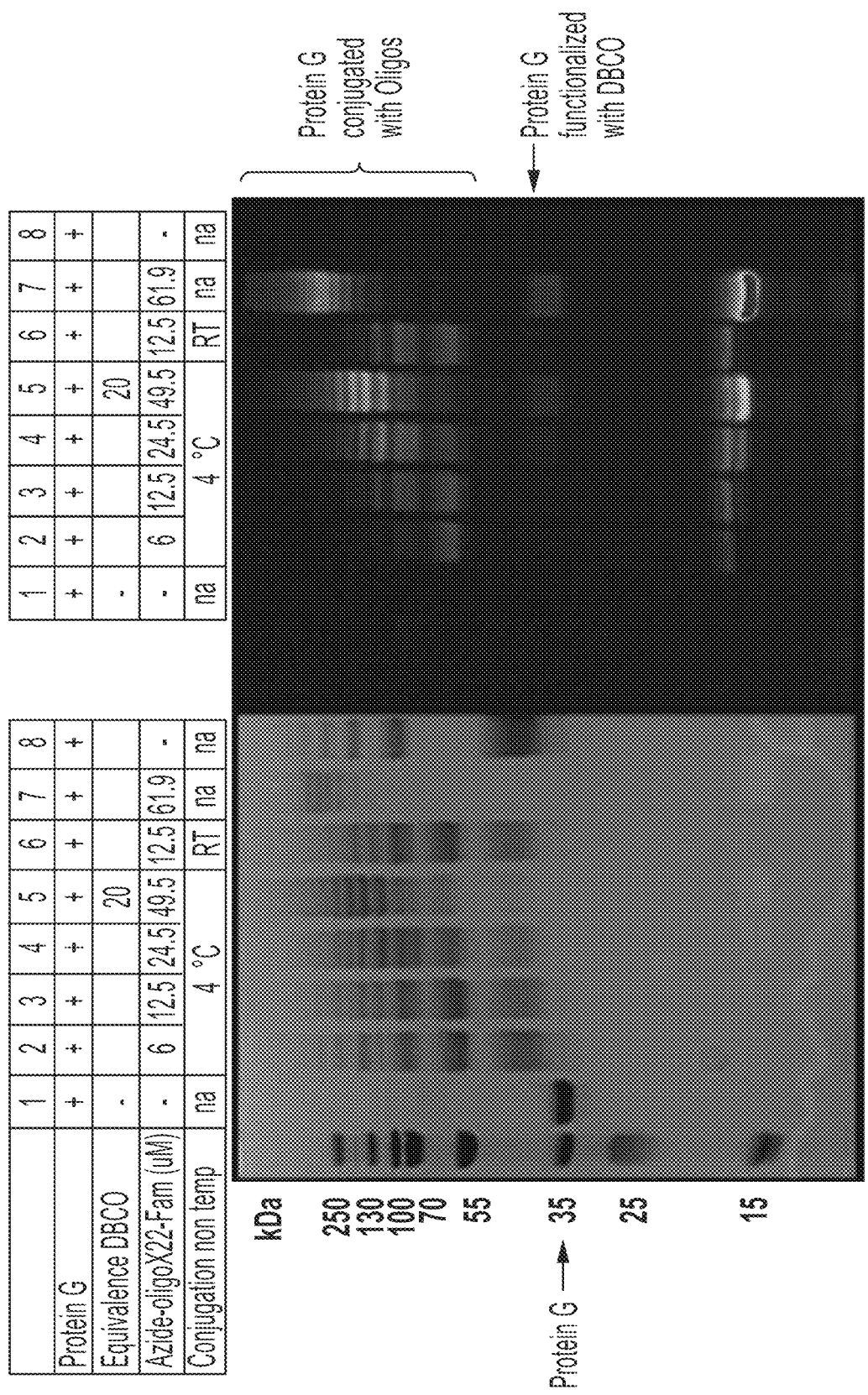
FIG. 34C shows an example relationship between the degree of conjugation and oligonucleotide equivalence.

Moreover, the degree of conjugation may be controlled through oligonucleotide equivalence as shown in FIG. 34C. A crude protein-oligonucleotide conjugation reaction was analyzed by gel electrophoresis (SDS-PAGE) to determine conjugation efficiency and the number of oligonucleotides conjugated. Increase of oligonucleotide equivalence with respect to the protein leads to a higher degree of conjugation as shown in FIG. 34C. Because the oligonucleotide contains a fluorescent molecule, the unused oligonucleotide can easily be visualized with in-gel fluorescence imaging (black panel in FIG. 34C).

Figure 34D:
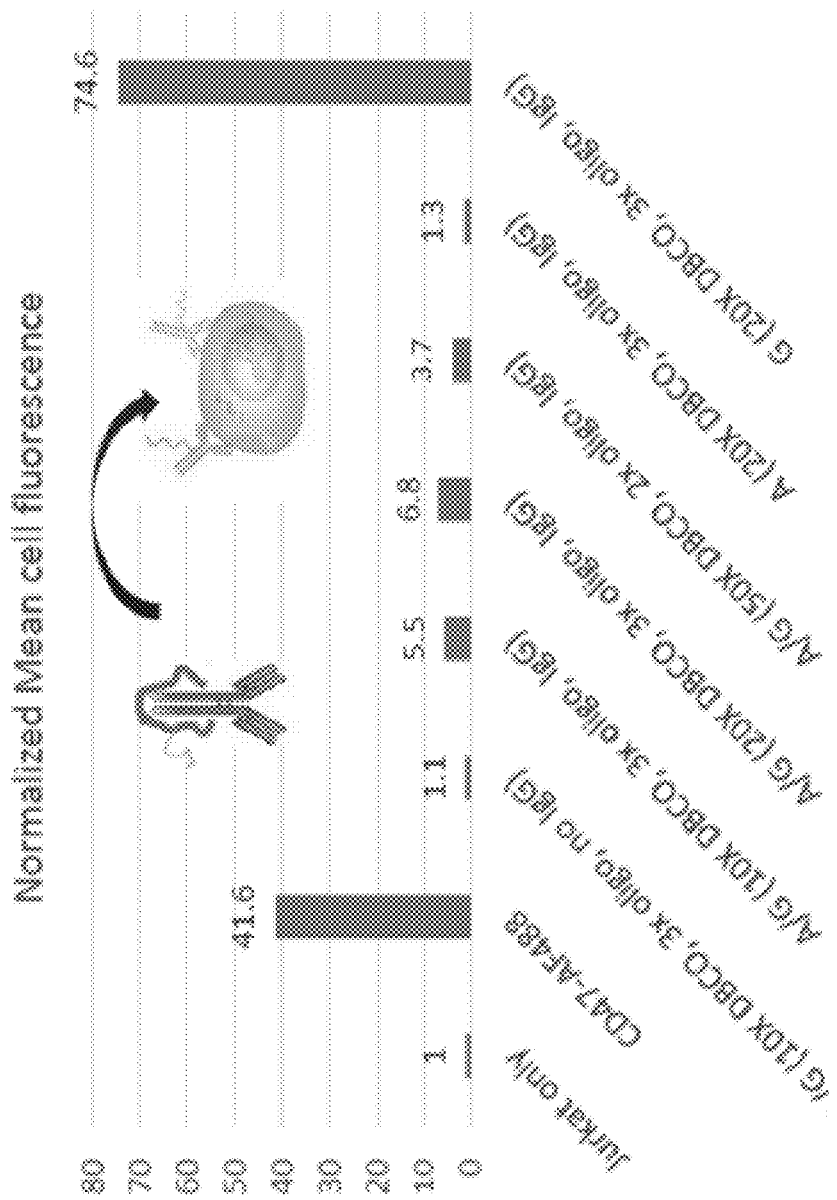
FIG. 34D shows fluorescence signals of labeled cells measured by flow cytometry.

The oligonucleotide-Protein X conjugates are incubated with CD47 antibodies to form labeled antibodies. The labeled antibodies are incubated with Jurkat cells and washed twice to make labeled cells. The labelling of cells is measured by fluorescence signals using flow cytometry (FIG. 34D).

Figure 35A:
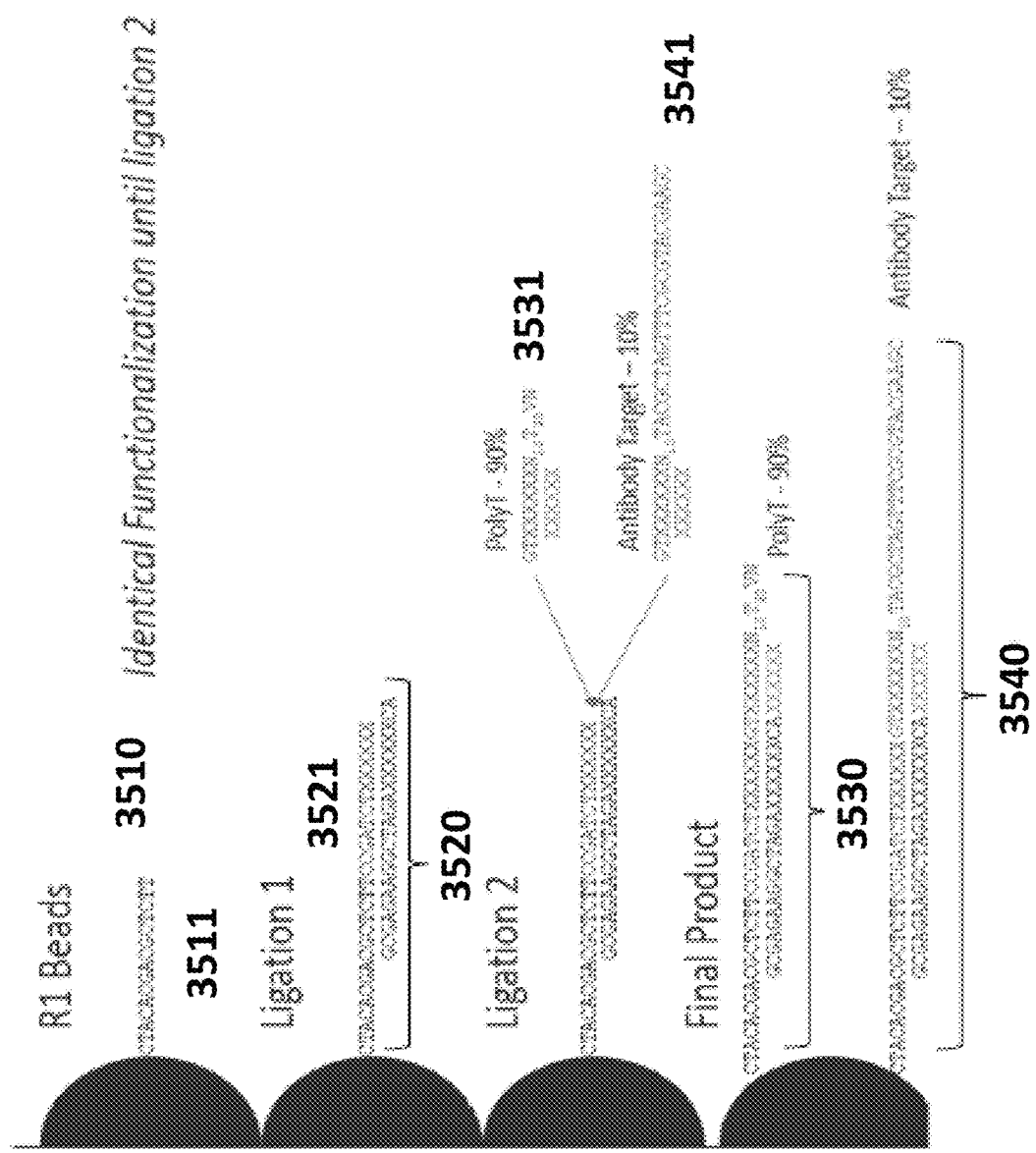
FIG. 35A shows a method for producing a bead coupled with oligonucleotides with different primer sequences. Figure discloses SEQ ID NOS 41, 58-60, 58, 59, 61, 24, 25, 62, and 25, respectively, in order of appearance.
Figures 35B, 35C:
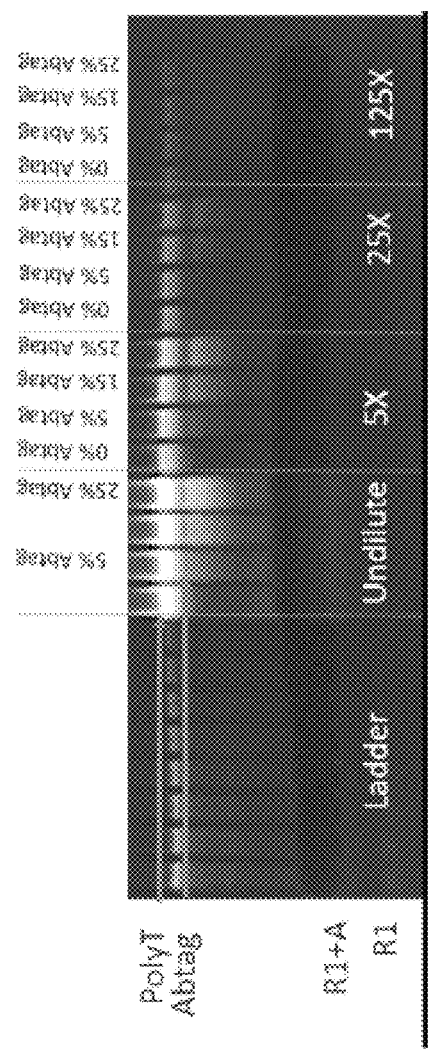
FIG. 35B shows a bead coupled with a plurality of oligonucleotides. Figure discloses SEQ ID NOS 63, 63, 63, 64, 63, 63, 63, 63, 63, 63, 63, 64, 63, and 63, respectively, in order of appearance.
FIG. 35C shows results from gel electrophoresis analysis of beads; on the beads, 0%, 5%, 15%, or 25% of coupled oligonucleotides contain antibody target primers.

Example 5: Producing a Bead Coupled with Oligonucleotides with Different Primer Sequences This example shows a method for producing a bead coupled with oligonucleotides with different primer sequences. The work flow is shown in FIG. 35A. A barcode sequence 3521 is ligated to a sequence primer R1 3511 coupled to a bead. The R1 primer 3511 and barcode sequence 3521 form the backbone 3520 of the oligonucleotides on the bead. A plurality of backbone oligonucleotides 3520 are coupled to the same bead. Different primers sequences are then ligated to the backbone oligonucleotides 3520. The primers include a poly-T primer 3531 that targets the poly-A of mRNA molecules. The primers also include a target specific primer, e.g., an antibody target primer that binds to a barcode on an antibody. After the second ligation, the bead comprises oligonucleotides with poly-T primers (3530) and oligonucleotides with antibody target primers (3540). The resulting product from the method is a bead coupled with a plurality of oligonucleotides (FIG. 35B). All of the oligonucleotides comprise the same backbone. Some of the oligonucleotide comprises poly-T primers and some comprises the antibody target primers. Beads with 0%, 5%, 15%, and 25% of coupled oligonucleotides containing antibody target primers are analyzed by gel electrophoresis (FIG. 35C)

Figure 36A:
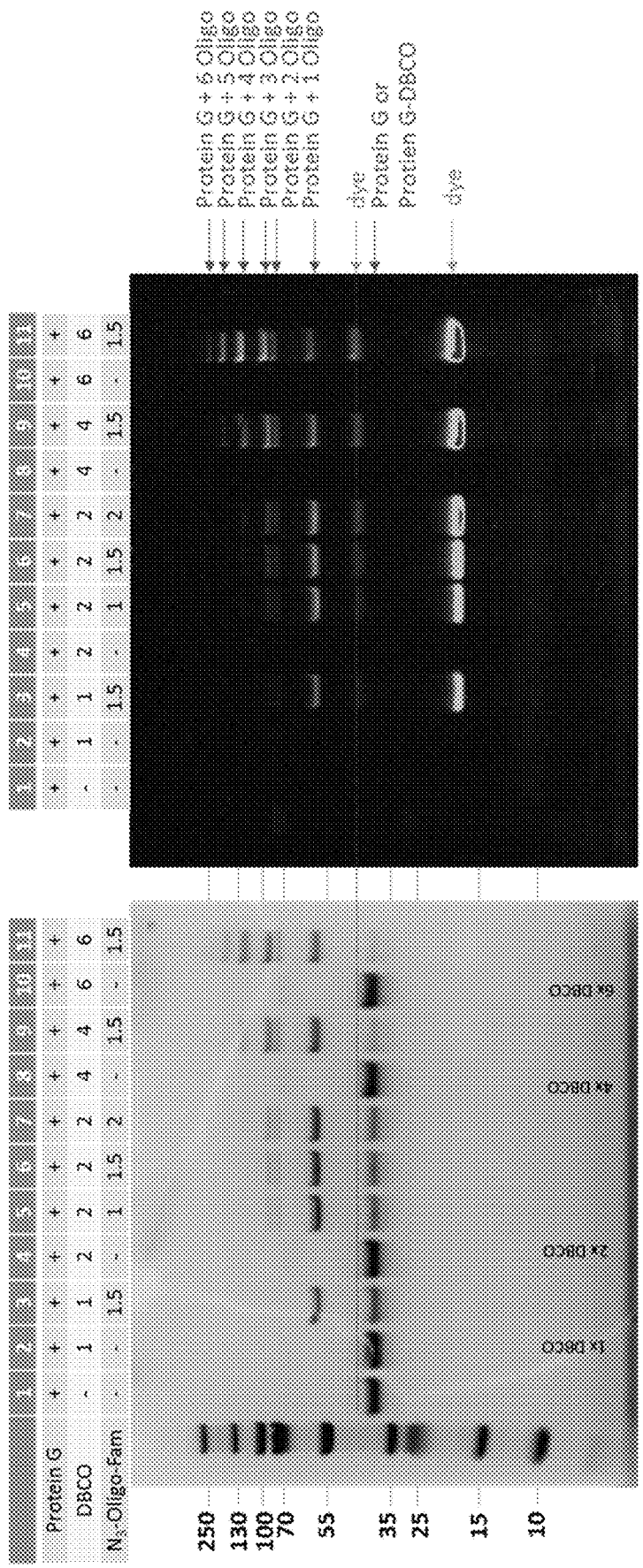

Example 6: Barcoding Antibody Labelling Agents and Cell Surface Feature Analysis In a first set of experiments, a barcoded oligonucleotide comprising an azide functional group and a FAM dye was conjugated to a Protein G labelling agent using a click chemistry reaction scheme. The barcoded oligonucleotide included a barcode sequence that may be used to identify Protein G and also a sequence that may be used as a priming site. Protein G was mixed with increasingly higher molar equivalents of DBCO-NHS (0×, 1×, 2×, 4× and 6×) in a series of mixtures. The DBCO-NHS was used to activate amine groups to become reactive to azide. Also included were varying equivalents of azide oligonucleotide to DBCO (0×, 1×, 1.5× and 2×) in the mixtures. Reactions were then allowed to proceed for 4 hours and the reaction mixtures evaluated with gel electrophoresis on a 4-12% bis-Tris gel. The results of the analysis are graphically depicted in FIGS. 36A-B. Protein G having up to 6 oligonucleotides linked were observed.

Figure 37A:
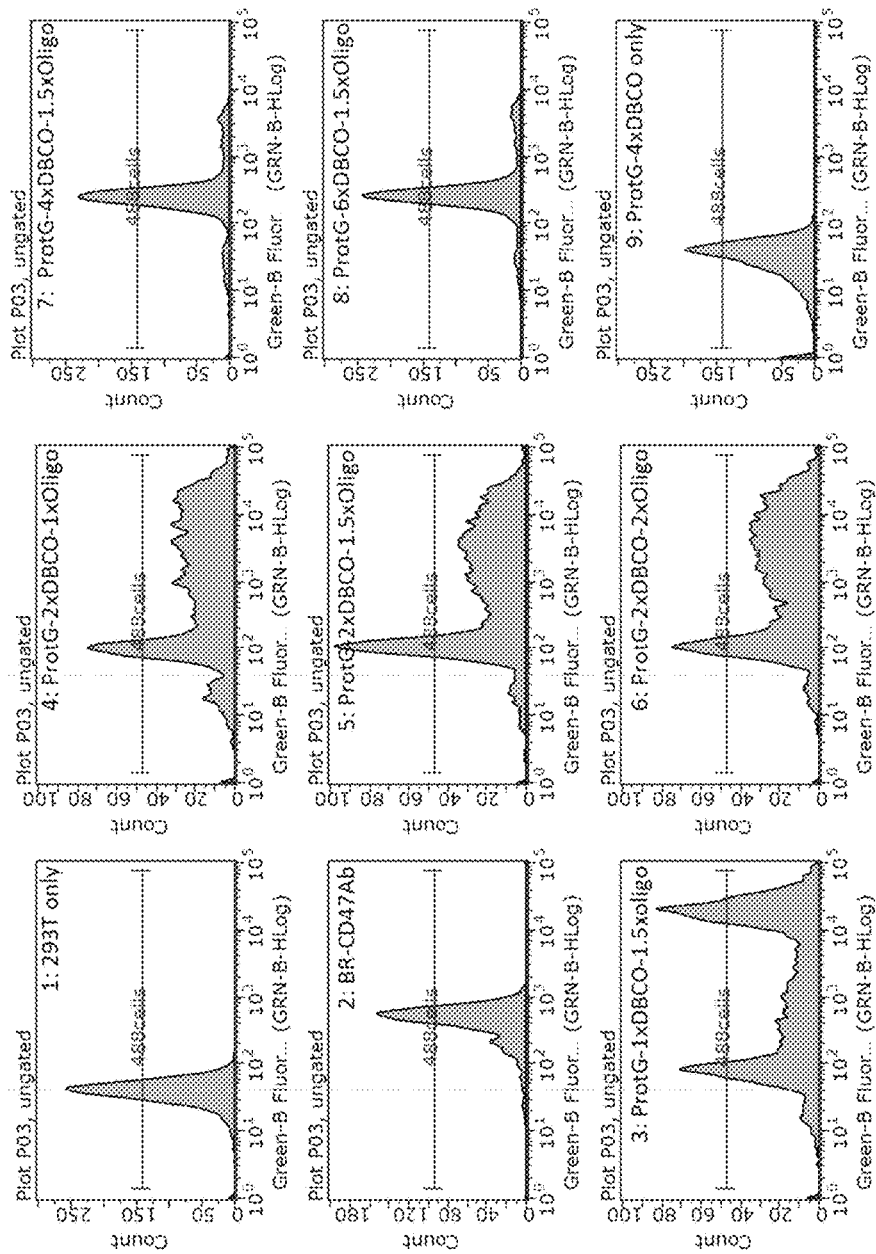
FIGS. 37A-B depict data obtained from an example experiment described in Example 6.
Figure 37B:
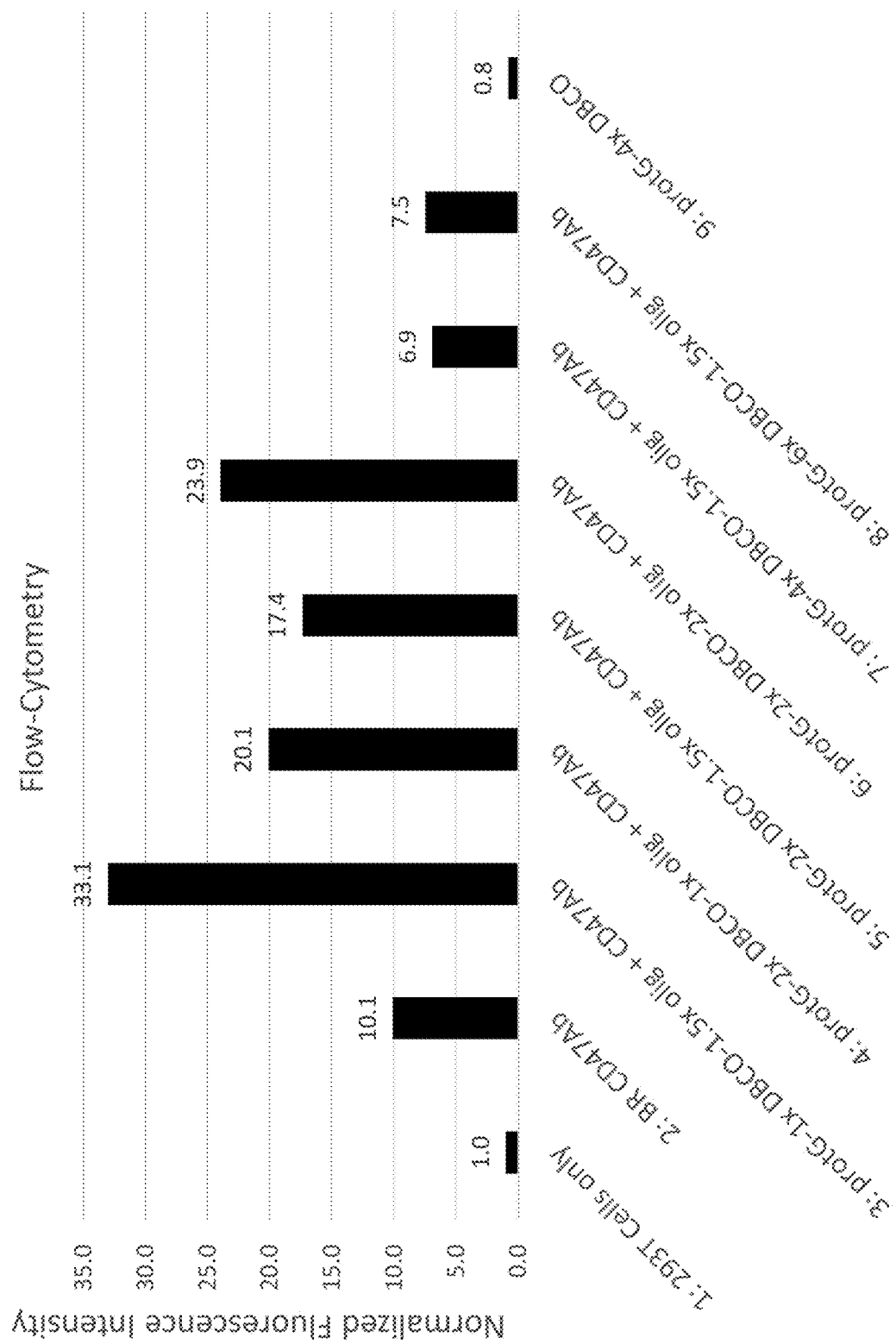

The various labeled Protein G moieties were then mixed with CD47 antibody to bind the labeled Protein G moieties to CD47 antibodies. The resulting Protein G-CD47 complexes were then incubated with 293T cells such that the complexes may bind CD47 on the surface of cells. Cells were washed to remove unbound complex and then subject to flow cytometry to observe binding of antibodies via the oligo-bound FAM dye. Results of flow cytometry are graphically depicted in FIG. 37A-B.

Figure 38B:
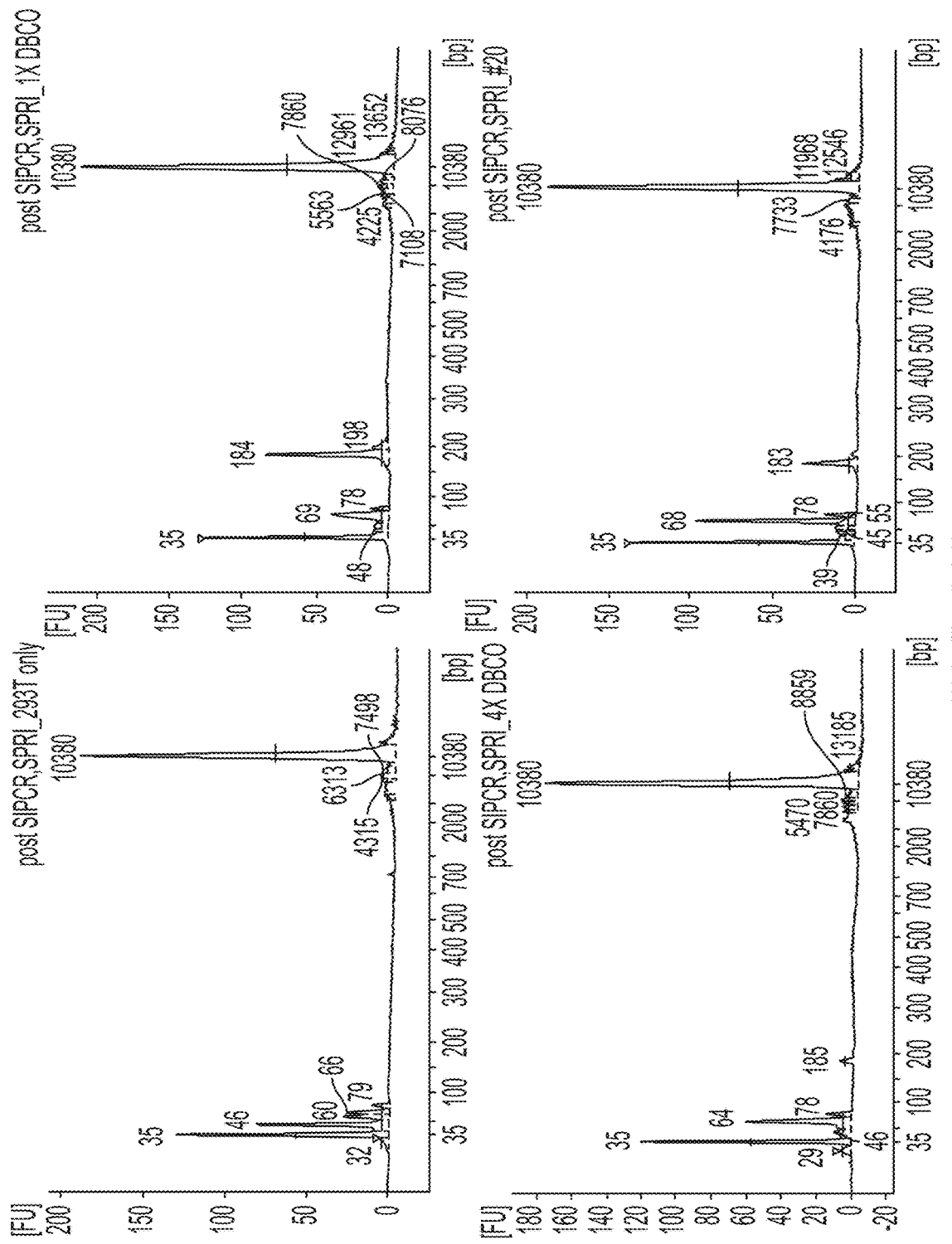

Next, labeled cells were mixed with a bead coupled to an oligonucleotide comprising a nucleic acid barcode sequence, a UMI and a poly-T sequence capable of binding the poly-A sequence of mRNA transcripts in a cell. Also included was a barcoded primer having a priming sequence capable of specifically hybridizing the barcoded oligonucleotide coupled to CD47 antibodies via the barcoded oligonucleotide's priming site. The mixture was then partitioned into a droplets in an emulsion. The emulsion was then subject to conditions suitable for priming sequences to hybridize with their respective targets (mRNA or barcoded antibody oligonucleotide) and for extension of primers via the action of a polymerase or reverse transcriptase. Extension generated barcoded constructs. Following reactions, the emulsion was broken. Barcoded transcript constructs still attached to beads were removed by removing beads and the supernatant subject to 2X SPRI separation to recover the ~110 bp antibody barcode. The recovered products were then analyzed, with results shown in FIGS. 38A-C.

Example 7: Coupling of Barcodes

In a bulk experiment, two oligonucleotides shown in FIG. 39A, 3901 and 3902, were linked together via extension reactions. Oligonucleotide 3901 represented an oligonucleotide comprising a barcode sequence that may be used to identify a partition comprising the oligonucleotide 3901 and oligonucleotide 3902 represented an oligonucleotide comprising a barcode sequence that may be used to identify a labelling agent, such as an antibody coupled to oligonucleotide 3902. Oligonucleotide 3902 also included a FAM dye and a 3' reverse complement of a template switch oligonucleotide spacer-rGrGrG region included on oligonucleotide 3901. In the experiment, 50 nM AbBC of oligonucleotide 3902 was mixed with oligonucleotide 3901 in two separate mixtures. Included in the mixture were reagents for conducting a primer extension reaction, including one of two reverse transcriptases capable of facilitating a primer extension reaction and dNTPs. Extension products were then analyzed via capillary electrophoresis.

Figure 39B:
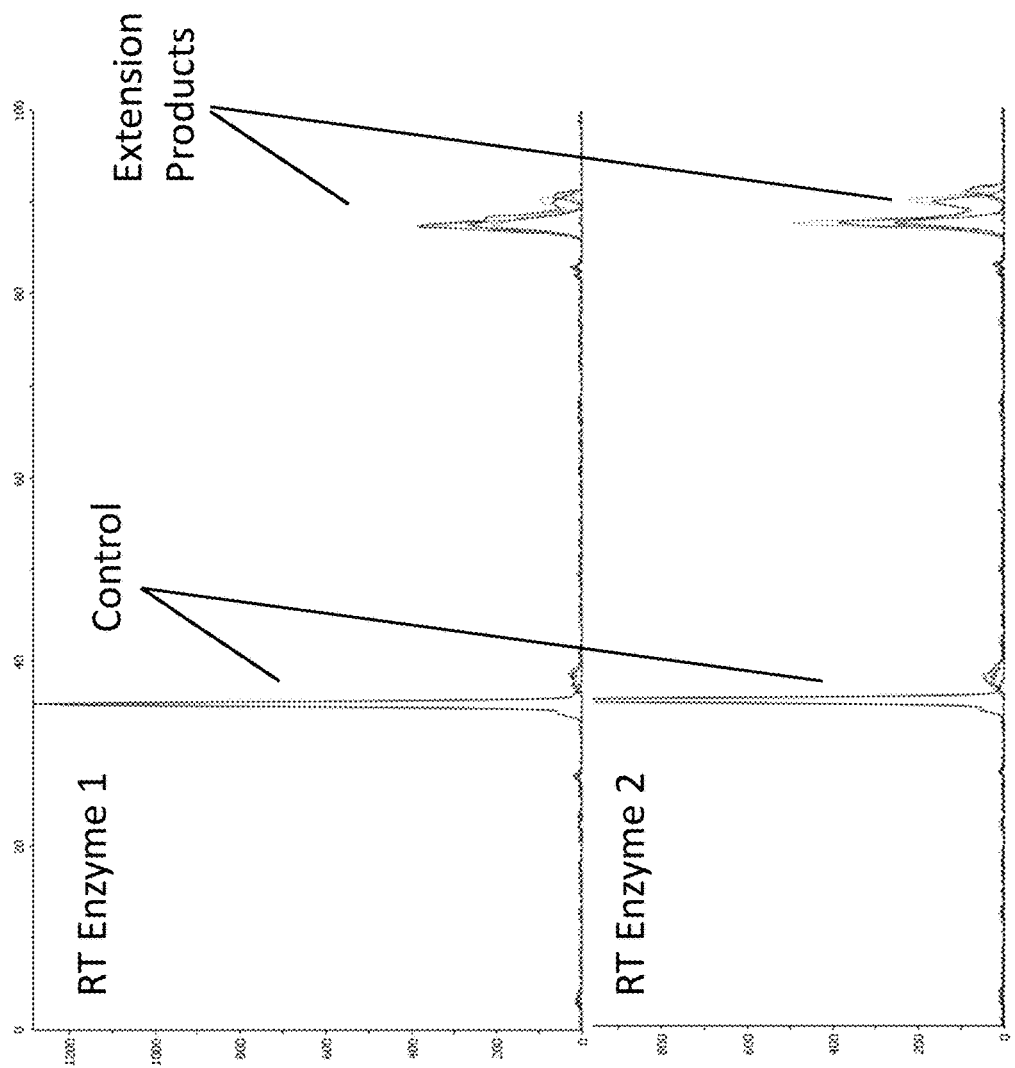
FIG. 39B graphically depicts data from an example experiment described in Example 7.

The results of the experiment are graphically shown in FIG. 39B. As shown, expected extension products having both a sequence corresponding to the barcode sequence of oligonucleotide 3901 (or a complement of the barcode sequence) and a sequence corresponding to the barcode sequence of oligonucleotide 3902 (or a complement of the barcode sequence) were detected. These results confirm that the reverse transcriptases tested may be used to generate extension products having sequences corresponding to both barcode sequences of oligonucleotides 3901 and 3902.

Example 8: Single-Cell Barcode Behavior

Figure 40:
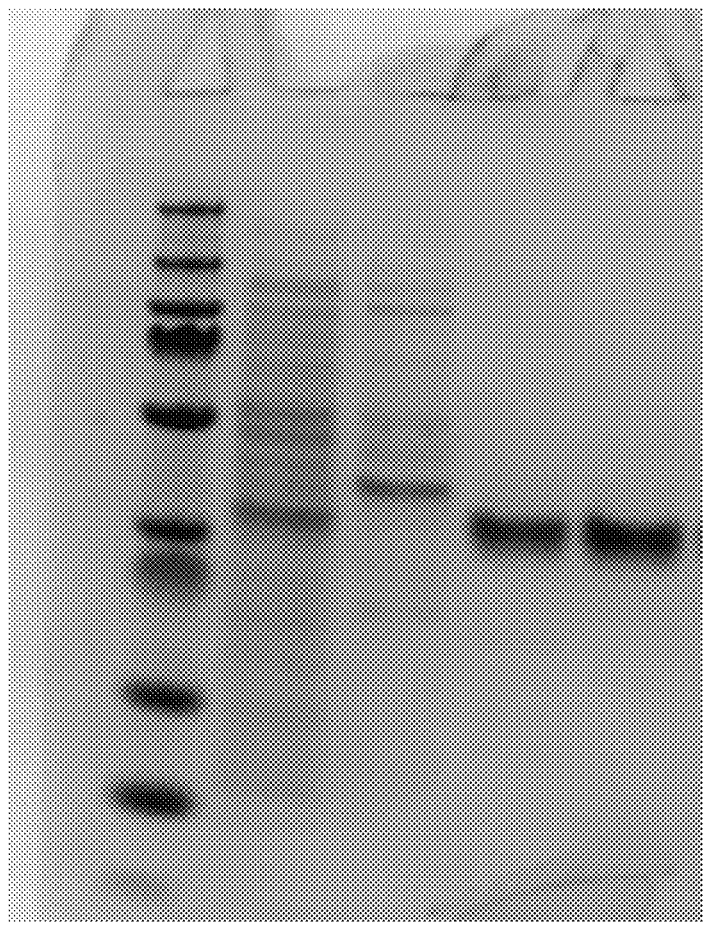
FIG. 40 depicts data obtained from an example experiment described in Example 8.

Anti-CD47 and Anti-CD99 antibodies were obtained and both types were coupled to an oligonucleotide comprising a barcode sequence that was suitable for identifying its respective antibody and also comprising a unique molecular identification (UMI) sequence and a template switch oligonucleotide reverse complement sequence (e.g., C C C). The antibody-oligonucleotide constructs were generated by linking the oligonucleotides to protein G and then binding the protein G-oligonucleotide constructs to the antibodies. The oligonucleotides were linked to protein G by modifying protein G with a single cysteine residue and linking it to oligonucleotides via the cysteine residue. Protein G also included a His×6 tag (SEQ ID NO: 8) which may be used to separate unconjugated oligonucleotides from those coupled to Protein G. Sample data from gel electrophoresis analysis of generated constructs is shown in FIG. 40. The lanes in FIG. 40 show expression of a cysteine-containing protein G antibody binding protein. The culture lane depicts a homogenized cell culture, the flow through lane depicts is all proteins that did not bind to a nickel-NTA column, and the two elution lanes are eluted purified protein G.

Jurkat cells were then incubated with antibody-oligonucleotide constructions to bind antibodies to the surface of cells via their respective cell surface feature targets. The cells were then partitioned into aqueous droplets in an emulsion, along with beads linked to oligonucleotides comprising a barcode sequence, a UMI sequence, a priming sequences capable of hybridizing with antibody-bound oligonucleotides (e.g., primer sequence include a template switch sequence, such as rGrGrG). A reducing agent, capable of disrupting disulfide linkages of beads and linkages between beads and its oligonucleotides was also included in the partitions. The reducing agent released the bead's oligonucleotides and the droplets were then subjected to conditions suitable for hybridizing the previously bead-bound oligonucleotides to cell-bound antibody oligonucleotides via an interaction of sequences of the two oligonucleotides, including via an rGrGrG/CCC interaction. While a particular sequence is shown, hybridization may be achieved via any constant sequence at the ends of the two oligonucleotides.

The two hybridized oligonucleotides were then extended in primer extension reactions to generate constructs comprising sequences corresponding to both bead oligonucleotide and antibody barcode sequences, similar to the example scheme shown in FIG. 22 (panel I). The emulsion was then broken, the extended products further processed and then subject to sequencing. Sequencing results for Jurkat+CD47 and Jurkat+CD47/CD99 runs are graphically depicted in panels I and II, respectively, of FIG. 41A and tabulated in FIG. 41B. The data shown in FIG. 41A and FIG. 41B indicate that the antibody-oligonucleotide constructions comprising barcode sequences were able to show single cell behavior, as evidenced, for example, by an approximately 2-log enrichment of antibody-oligonucleotide UMIs in bead-originating barcode constructs corresponding to cells.

Example 9: Linking T-Cell Receptor Sequence to Antigen Binding Phenotype Using Barcoded MHC-Antigen Multimers Many TCRs can bind a particular antigen (with varying affinity) and identifying individual clonotypes specific to a particular antigen is difficult. While flow cytometry and bead-based enrichment schemes allow physical sorting of antigen-binding cells, when cells are rare or samples are limited, cell losses associated with traditional methodologies can be unacceptable. Moreover, traditional approaches based on fluorescent detection have important limitations with regard to multiplexing (the ability to simultaneously assay the binding properties of multiple independent antigens/ligands in single experiment) due to the small number of spectrally distinguishable fluorescent labels that can be effectively used in combination. Furthermore, multiple antigen-binding clonotypes may be present in a heterogeneous sample, which makes identifying specific antigen-binding TCR complexes difficult, even when the cells expressing antigen-binding clonotypes are physically sorted.

The compositions, methods, and systems described herein allow functionalization of MHC-peptide multimers with an oligonucleotide (DNA or RNA) that includes a unique peptide barcode sequence specific to the MHC-peptide identity (e.g., Barcode 1 associated with peptide EGALIYWPN (SEQ ID NO: 9), Barcode 2 associated with peptide AHMRDSQQ (SEQ ID NO: 10), etc). A single peptide-MHC complex or peptide-MHC library can be exposed to a cell population (e.g., T-cells) to produce cells "tagged" with barcoded MHC multimers. These cells can then be partitioned and processed as described herein to assemble TCR sequences and quantify the number of MHC-peptide barcodes associated with each cell. Clonotypes with low levels of MHC-peptide derived UMIs have a low affinity for the MHC-peptide while clonotypes with high levels of the MHC-peptide UMIs have a high affinity for the antigen.

Barcoded, peptide-bound MHC tetramers bound to a streptavidin core were generated generally as depicted in FIG. 28A and as described below. Although Class I MHC-tetramers were utilized in the following series of experiments, there are many possible configurations of Class I and/or Class II MHC-antigen multimers that can be utilized with the compositions, methods, and systems disclosed herein, e.g., MHC pentamers (MHC assembled via a coiled-coil domain, e.g., Pro5® MHC Class I Pentamers, (ProImmune, Ltd.), MHC decorated dextran molecules (e.g., MHC Dextramer® (Immudex)), etc.

Figure 42A:
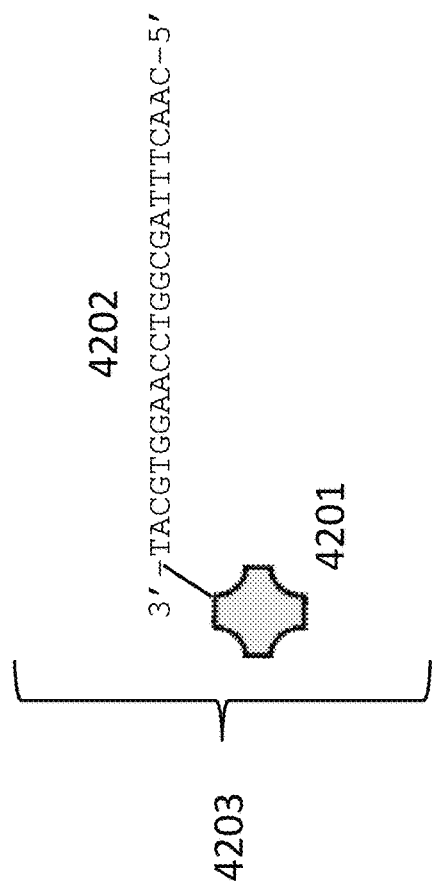
FIGS. 42A-B graphically depicts an exemplary barcoded streptavidin complex.
Figure 42B:
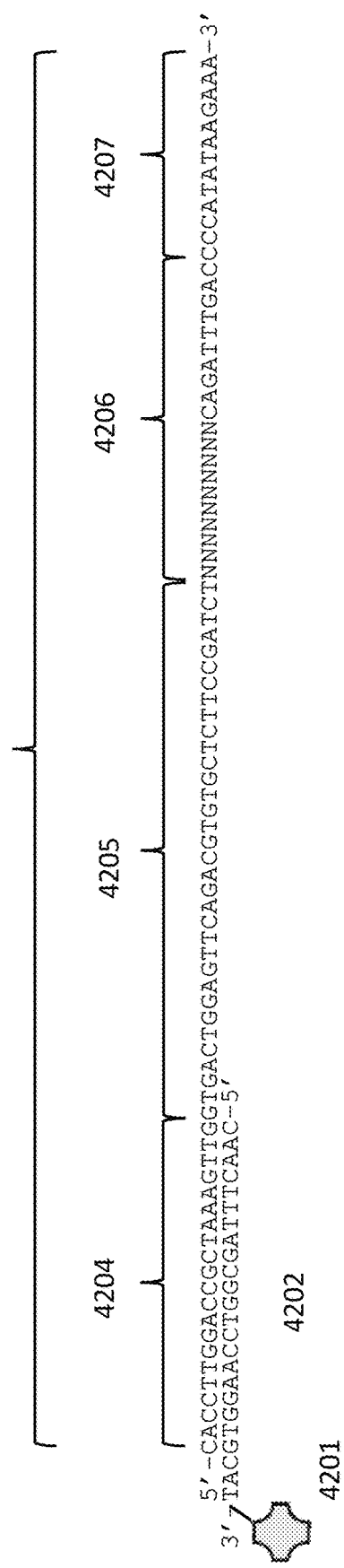
Figure 43B:
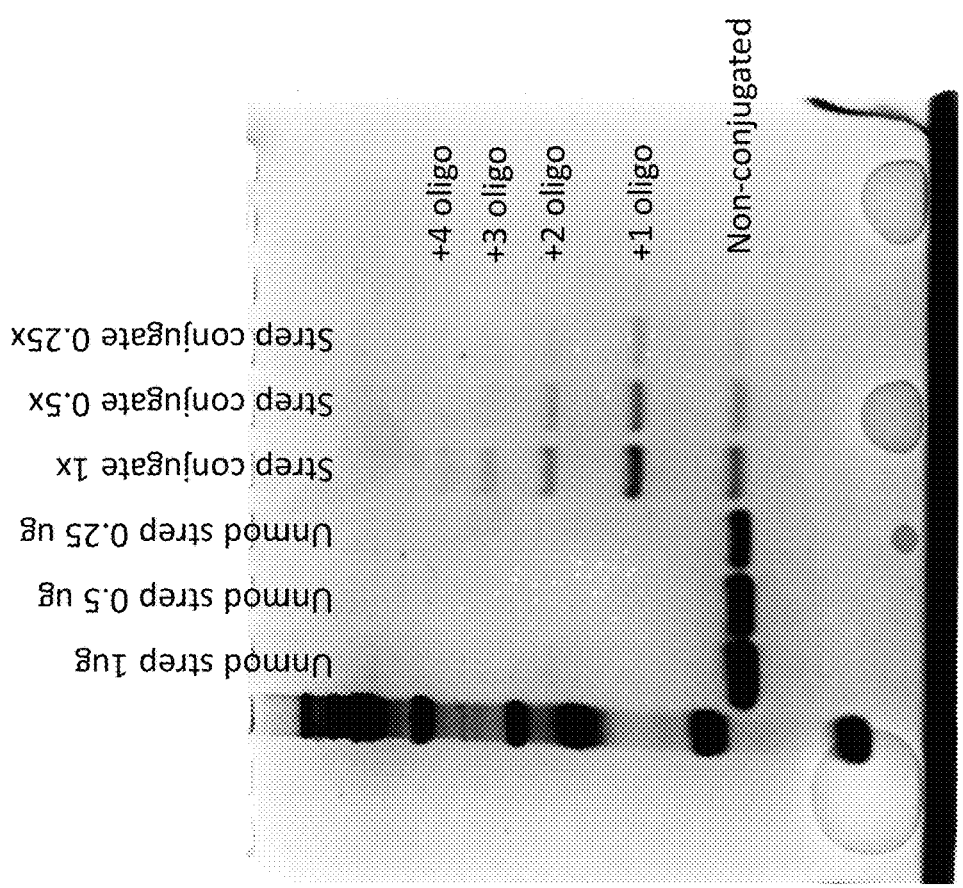
FIGS. 43A-B illustrate an exemplary analysis of barcoded streptavidin complexes.
Figure 43A:
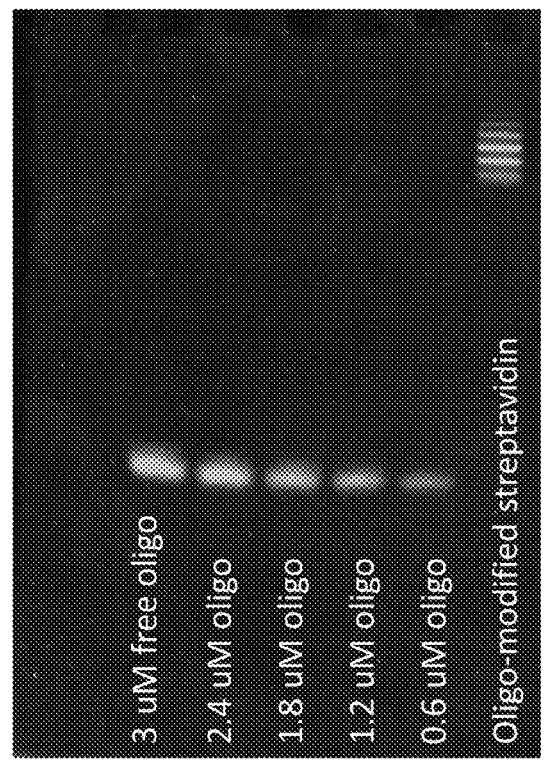

Streptavidin molecules (4201) were conjugated to a hybridization oligonucleotide (4202) using general lysine chemistry (streptavidin modified via lysine residues with NHS-DBCO; subsequently an azide-modified oligonucleotide was attached via the DBCO functional group) to produce streptavidin-conjugated oligonucleotides (4203) as depicted in FIG. 42A. Streptavidin-conjugated oligonucleotides (4203) were then analyzed on a TBE-urea denaturing agarose gel. As shown in FIG. 43A, 0.6 µM, 1.2 µM, 1.8 µM, 2.4 µM, and 3 µM of unmodified oligonucleotide were all observed to have bands of a similar size while streptavidin-conjugated oligonucleotides exhibited a clear shift in molecular weight indicating successful streptavidin conjugation. The multiple bands observed in the streptavidin-conjugated oligonucleotide lane correspond to conjugated streptavidin molecules with increasing numbers of oligonucleotides attached (e.g., 1 oligo, 2 oligos, 3 oligos, etc.). As seen in FIG. 43A, streptavidin-conjugated oligonucleotides are produced with minimal excess non-conjugated oligonucleotide.

Streptavidin-conjugated oligonucleotides (4203) were also analyzed on an SDS-PAGE protein gel. As shown in FIG. 43B, 0.25 µg, 0.5 µg, and 1.0 µg of unmodified streptavidin exhibit a similar molecular weight while streptavidin-conjugated oligonucleotides exhibit a molecular weight shift indicative of streptavidin conjugated with 0, 1, 2, 3, 4 (or more) oligonucleotides. Quantification of the conjugated oligonucleotide can be estimated by comparing the density of the conjugated oligonucleotide bands with the density of the 0.25 µg, 0.5 µg, and 1.0 µg unmodified streptavidin bands. From this comparison, the overall degree of conjugation is approximately 1 oligonucleotide per each streptavidin subunit (resulting in approximately 4 oligonucleotides for each MHC tetramer).

Following quantification of the degree of conjugation, barcode oligonucleotides (4208) are hybridized to the streptavidin-conjugated oligonucleotides (4203) via the reverse complement (4204) of the hybridization oligo sequence (4202) at a stoichiometry of between 0.25:1 to 1:1 of barcode oligonucleotides (4208) to streptavidin-conjugated oligonucleotides (4203). Here, the barcode oligonucleotides (4208) comprise a sequence that is the reverse complement (4204) of the hybridization oligo sequence (4202), a TruSeq R2 sequencing primer sequence (4205), a unique molecular identification (UMI) (series of any "N" nucleotides) and a barcode sequence (4206), and an adapter sequence (4207) that is complementary to a sequence on a gel bead. Alternatively, the barcode oligonucleotide can be directly conjugated to the streptavidin.

After hybridization, the barcoded streptavidin (4209) is added to a pool of biotinylated HLA-A-02:01 MHC monomers (see, e.g., 2806) displaying an Epstein-Barr Virus (EBV) peptide antigen (GLCTLVAML (SEQ ID NO: 11)) to produce barcoded MHC tetramers (see, e.g., 2808). The barcoded streptavidin (4209) is added until a 1:1 ratio of biotinylated EBV MHC monomers to biotin binding sites is achieved (4 biotinylated MHC monomers/streptavidin complex).

Barcoded MHC tetramers (0.4 µg or 4.0 µg) are then incubated for 30 minutes with ~200,000 (100 µL) EBV antigen-expanded T-cells (Astarte Biologics) and/or ~200,000 (100 µL) of naïve T cells. Cells were washed three times with PBS/1% FBS to remove unbound multimers. The cells were then resuspended in PBS+0.04% BSA and partitioned into droplets comprising a barcoded MHC bound T-cell and a barcoded gel bead (see, e.g., FIG. 11A-B). Barcoded MHC tetramers are then generally processed as described herein (see, e.g., FIG. 28C and accompanying text). T-cells are then lysed and released mRNA molecules are generally processed as described herein (see, e.g., FIG. 11A-B and accompanying text). The droplet emulsion was then broken and bulk PCR-amplification used to enrich for barcoded, full-length V(D)J segments from TCR cDNA. A second library was prepared to quantify the number of MHC-EBV peptide UMIs associated with each cell. The fully constructed sequencing libraries were then sequenced using an Illumina sequencer. T-cell receptor clonotypes were assembled bioinformatically and the number of UMI counts from barcoded MHC tetramers were quantified per cell and per clonotype.

Figure 44:
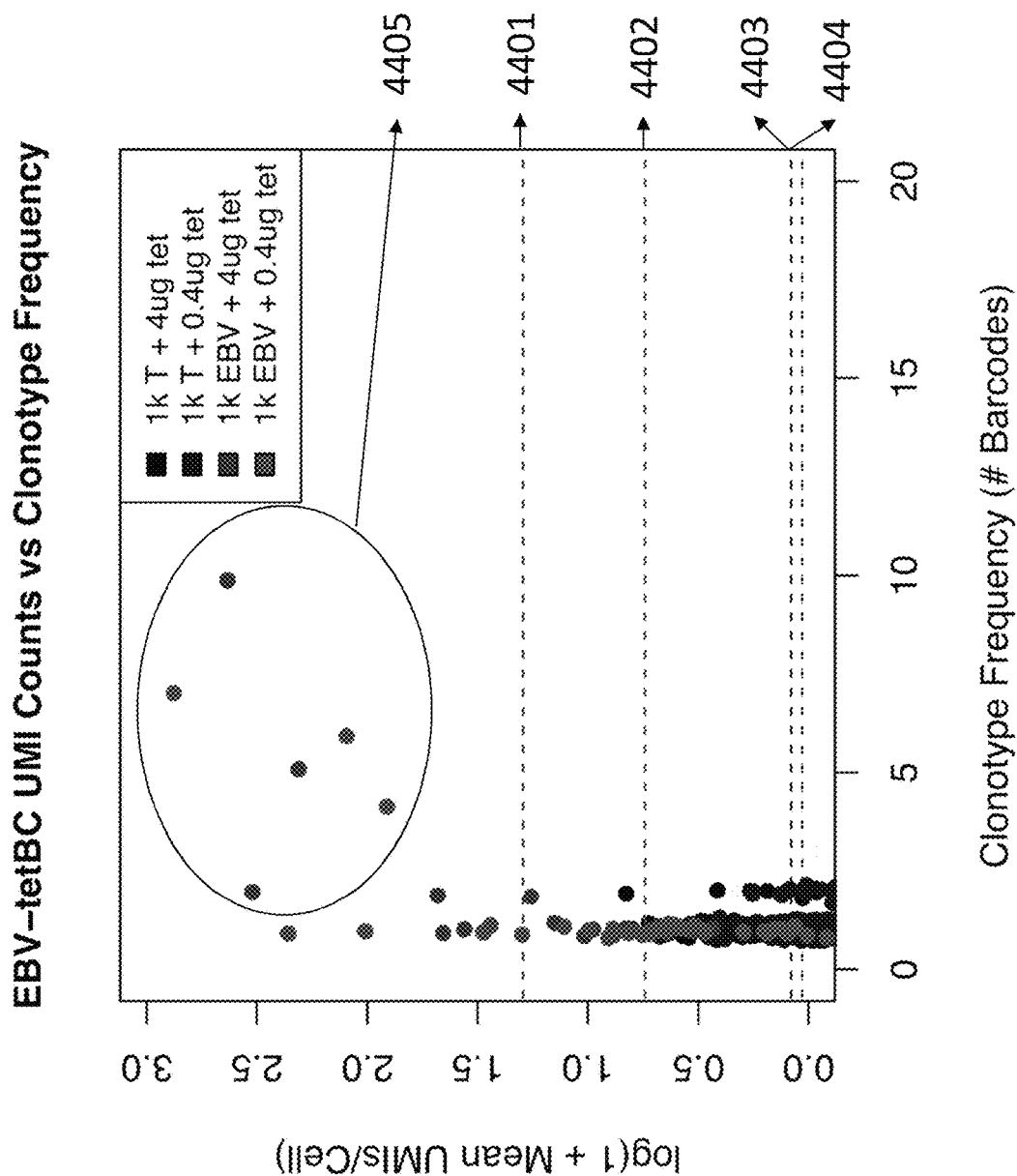
FIG. 44 shows results of data obtained from an example barcoded WIC tetramer T-cell experiment as described in Example 9.
Figure 45:
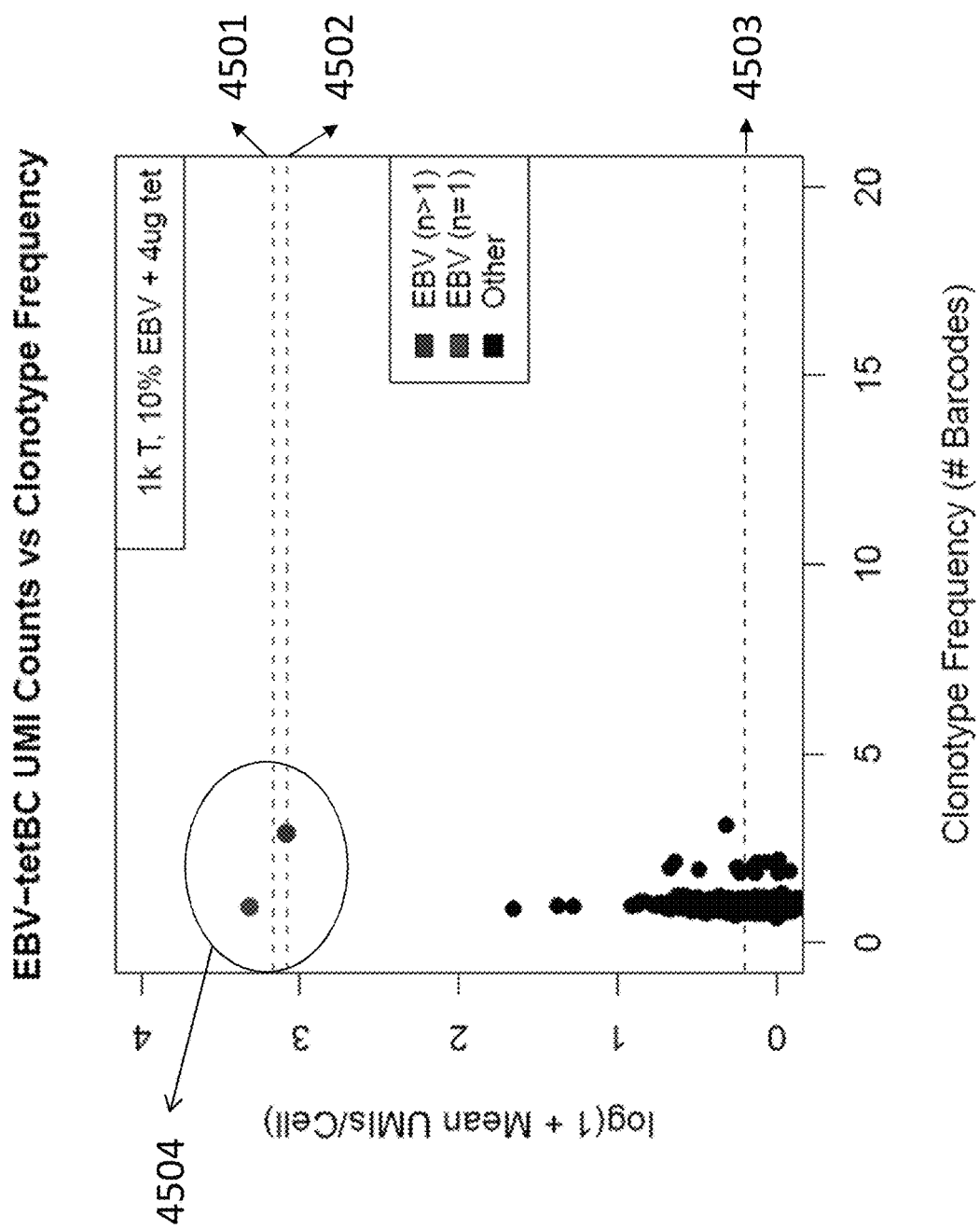
FIG. 45 shows results of data obtained from example EBV-expanded T-cell spike-in experiment as described in Example 9.

FIG. 44 shows the number of UMI counts from barcoded MHC tetramers vs. the clonotype frequency as measured by the number of barcodes. For each clonotype detected, the average number of MHC multimer-derived UMI counts per cell-barcode was computed for all cell-associated cell-barcodes corresponding to that clonotype, and the log 10 of one plus its mean UMI counts per cell value is plotted on the y-axis. The number of cell-associated cell-barcodes detected with each clonotype is plotted on the x-axis. For visualization purposes, a random amount of Gaussian noise was added to each point's x and y coordinate values to avoid overplotting. Feature 4401 shows the mean y-axis value of log 10 (1+UMI counts per cell) averaged across all clonotypes from EBV-expanded T-cells incubated with 4 µg MHC multimer ("1 k EBC+4 ug tet"); feature 4402 shows the mean y-axis value of log 10 (1+UMI counts per cell) averaged across all clonotypes from EBV-expanded T-cells incubated with 0.4 µg MHC multimer ("1 k EBC+0.4 ug tet"); feature 4403 shows the mean y-axis value of log 10 (1+UMI counts per cell) averaged across all clonotypes from naïve T-cells incubated with 4 µg MHC multimer ("1 k T+4 ug tet"); and feature 4404 shows the mean y-axis value of log 10 (1+UMI counts per cell) averaged across all clonotypes from naïve T-cells incubated with 0.4 µg MHC multimer ("1 k T+0.4 ug tet"). As seen in FIG. 44, the EBV-expanded cell types have the most UMI counts associated with the tetramer (Features 4401 and 4402) as compared to the values obtained for the naïve T cell populations (Features 4403 and 4404). Moreover, clonotypes from the EBV-expanded cells that occur at high frequency within the EBV-expanded cell population (bounded circle, feature 4405) exhibited even greater values of MHC-tetramer UMIs, indicating their enriched frequency in the EBV-expanded population is associated with preferential MHC-tetramer binding. Conversely, naïve T-cells are not expected to preferentially bind the antigen and all have low background levels of tetramer-associated UMIs. In another experiment, EBV-expanded T-cells were spiked-into a naïve T cell background prior to incubation with the barcoded MHC tetramer described above. Cells were then processed, sequenced, and analyzed as previously described. FIG. 45 shows the number of UMI counts from barcoded MHC tetramers vs. the clonotype frequency from the mixed T-cell population (following the axes and plotting conventions used in FIG. 44). Feature 4501 shows the mean y-axis value of log 10 (1+UMI counts per cell) averaged across all clonotypes from cells containing clonotypes which were previously observed to occur in at least one sample of independently processed EBV-expanded cells ("EBV (n=1)"); feature 4502 shows the mean y-axis value of log 10 (1+UMI counts per cell) averaged across all clonotypes from cells containing clonotypes which were previously observed to occur in more than one sample of independently processed EBV-expanded cells ("EBV (n>1)"); while feature 4503 shows the mean y-axis value of log 10 (1+UMI counts per cell) averaged across all clonotypes from all cells detected in the experiment ("Other"). As seen in FIG. 45, while the precise number of cells originating from the EBV spike-in is unknown (due to differences in cell recovery during washing between naïve T cells and EBV-expanded cells), two clonotypes representing a total of four cells (bounded circle, feature 4504) were detected in this mixed sample that exhibited very high tetramer-associated UMI counts (~1000× greater than background). These four cells were determined to correspond to the clonotype of the most frequently detected cell in the EBV-expanded sample and corresponded to the EBV spike-in cells. Thus, particular clonotypes of interest can be distinguished from a mixed population of cells containing a complex distribution of clonotypes.

Example 10: Single-Cell Analysis of a Tumor Sample to Identify a Rare Mutation

A tumor sample is obtained from a subject. Tumor cells are extracted and purified. Tumor cells are partitioned into droplets together with polymer precursors attached to primers comprising a poly-T sequence, template switching oligonucleotides, a lysis agent, and reagents for reverse transcription. Each droplet comprises a single tumor cell. The droplets are subjected to conditions sufficient to allow the lysis agent to lyse the cells, facilitating the release of cellular RNA (including messenger RNA) and genomic DNA (gDNA) into the droplet. Droplets are then subjected to conditions sufficient to perform reverse transcription using the primers and template switching oligonucleotides to generate complementary DNA (cDNA) from the cellular messenger RNA. Following reverse transcription, the cDNA is attached to the polymer precursors (see FIG. 51). Droplets are then exposed to conditions sufficient to polymerize the polymer precursors, thereby generating cell beads each comprising cDNA and gDNA molecules derived from a single cell, where the cDNA molecules are attached to the cell beads (see FIG. 53).

Cell beads are suspended in an aqueous solution. Cell beads are then partitioned into droplets together with gel beads comprising barcode molecules. A first subset of the barcode molecules comprises a random N-mer sequence, and a second subset of the barcode molecules comprises a polyG (e.g., riboG) sequence. Each droplet contains a single cell bead and a single gel bead. The droplets are subjected to conditions sufficient to degrade the cell beads and the gel beads, thereby releasing the barcode molecules, the cDNA, and the gDNA. The barcode molecules are used to generate barcoded nucleic acid molecules from the cDNA and gDNA, thereby identifying each with the same single cell. Following barcoding, the barcoded nucleic acid molecules are released from the droplets and subjected to sequencing to generate sequencing reads. Sequencing reads are used to obtain both transcription and genomic information from each single cell from the tumor sample. This information is used to identify both the presence of a rare mutation in the genome of a small subset of the cells from the tumor sample and also the expression levels of that rare mutation in the same subset.

Example 11: Single-Cell Analysis of a Blood Sample to Characterize a Rare Cancer Cell A blood sample is obtained from a subject. Nucleated cells are extracted and purified. Cells are partitioned into droplets together with polymer precursors and paramagnetic particles attached to oligonucleotides comprising a poly-T sequence. Each droplet comprises a cell. The droplets are subjected to conditions sufficient to allow the lysis agent to lyse the cells, facilitating the release of cellular RNA (including messenger RNA) and genomic DNA (gDNA) into the droplet. The messenger RNA hybridizes to the oligonucleotides via their poly-T sequence. Droplets are then exposed to conditions sufficient to polymerize the polymer precursors, thereby generating cell beads each comprising mRNA and gDNA molecules derived from a single cell, where the mRNA molecules are attached to the paramagnetic particles via the oligonucleotides (see FIG. 52).

Cell beads are suspended in an aqueous solution. Cell beads are then subjected to conditions sufficient to perform reverse transcription to generate complementary DNA (cDNA) from the cellular messenger RNA. Following reverse transcription, the cDNA is attached to the paramagnetic particles (see FIG. 54). Cell beads are treated with RNaseH to degrade remaining RNA. Cell beads are then partitioned into droplets together with gel beads comprising barcode molecules. Each droplet contains a single cell bead and a single gel bead. The droplets are subjected to conditions sufficient to degrade the cell beads and the gel beads, thereby releasing the barcode molecules, the cDNA, and the gDNA. The barcode molecules are used to generate barcoded nucleic acid molecules from the cDNA and gDNA, thereby identifying each with the same single cell. Following barcoding, the nucleic acid molecules are released from the droplets and subjected to sequencing to generate sequencing reads. Sequencing reads are used to obtain both transcription information and genomic from each single cell from the subject. This information is used to identify both the presence of a rare cancer cell in the blood of the subject via the presence of a genetic abnormality, and also to characterize the expression profile of the rare cancer cell.

Example 12: Epigenetic and Transcriptional Analysis of a Tumor Sample

A tumor sample is obtained from a subject. Tumor cells are extracted and purified. Cells are partitioned into droplets together with polymer precursors and paramagnetic particles attached to oligonucleotides comprising a poly-T sequence. Each droplet comprises a cell. The droplets are subjected to conditions sufficient to allow the lysis agent to lyse the cells, facilitating the release of cellular RNA (including messenger RNA) and genomic DNA (gDNA) into the droplet. The messenger RNA hybridizes to the oligonucleotides via their poly-T sequence. Droplets are then exposed to conditions sufficient to polymerize the polymer precursors, thereby generating cell beads each comprising mRNA and gDNA molecules derived from a single cell, where the mRNA molecules are attached to the paramagnetic particles via the oligonucleotides (see FIG. 52).

Cell beads are suspended in an aqueous solution. Cell beads are then subjected to conditions sufficient to perform reverse transcription to generate complementary DNA (cDNA) from the cellular messenger RNA. Following reverse transcription, the cDNA is attached to the paramagnetic particles (see FIG. 54). Cell beads are treated with RNaseH to degrade remaining RNA. Then, cell beads are subjected to oxygenase treatment to convert 5-methylcytosine nucleotides in the gDNA to 5-hydroxymethylcytosine. Following this, cell beads are treated with a cytosine deaminase enzyme to convert unmethylated cytosine nucleotides in the gDNA to uracil.

Cell beads are then partitioned into droplets together with gel beads comprising barcode molecules. Each droplet contains a single cell bead and a single gel bead. The droplets are subjected to conditions sufficient to degrade the cell beads and the gel beads, thereby releasing the barcode molecules, the cDNA, and the gDNA. The barcode molecules are used to generate barcoded nucleic acid molecules from the cDNA and gDNA, thereby identifying each with the same single cell. Following barcoding, the barcoded nucleic acid molecules are released from the droplets and subjected to sequencing to generate sequencing reads. Sequencing reads are used to obtain both transcription and epigenetic (e.g., methylation) information from each single cell from the subject. This information is used to characterize the epigenetic and transcriptional landscape of the tumor sample.

Example 13: Method of Generating Barcoded pMHC Complexes Using Oligo-Peptide Gel Beads In this example, a plurality of soluble MHC molecules 5803 and a plurality of oligo-peptide gel beads 5805 are partitioned into a plurality of partitions (e.g., droplets in an emulsion or wells in a micro/nanowell array) such that at least some partitions 5804 comprise a single gel bead 5805 and MHC molecules 5803. The oligo-peptide gel beads 5805 are configured such that each gel bead 5805 comprises, releasably attached thereto (e.g., by a labile bond), a plurality of a common peptide (e.g., 5801*a*) and a nucleic acid barcode molecule (e.g., 5802*a*) comprising a barcode sequence associated with the common peptide. Different partitions will comprise a gel bead 5805 comprising a peptide (e.g., 5801*a*) and a nucleic acid barcode (e.g., 5802*a*) different than peptides (e.g., 5801*b* or 5801*c*) and their corresponding nucleic acid barcodes (e.g., 5802*b* or 5802*c*) in other gel beads in other partitions. Thus, the schemes described herein enable the high throughput generation of diverse libraries of unique pMHC complexes, where the identity of the peptide can be readily determined by the nucleic acid barcode sequence.

Figure 58:
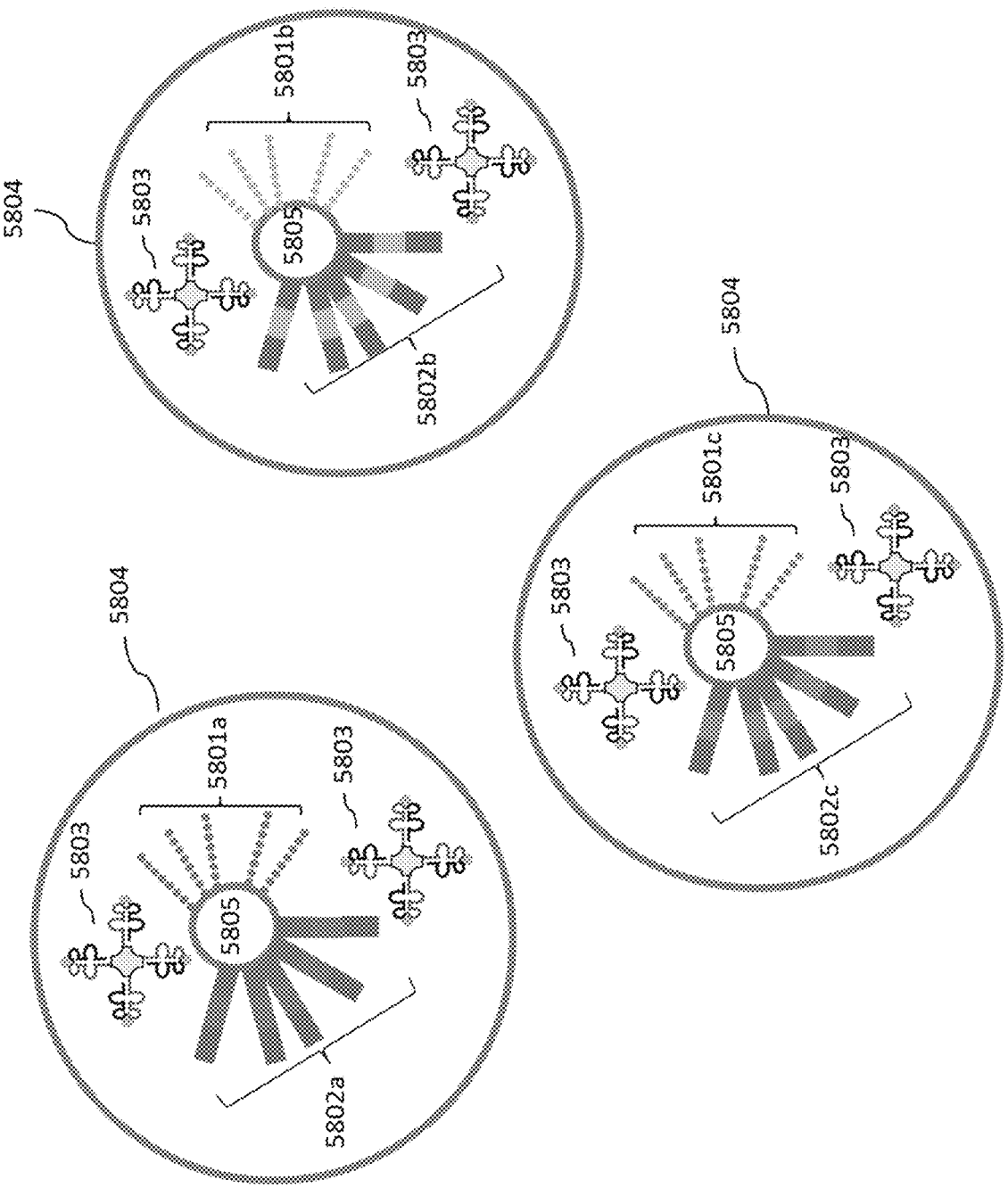
FIG. 58 illustrates the generation of MHC multimer complexes in a partition using an oligo-peptide gel bead.
Figure 59:
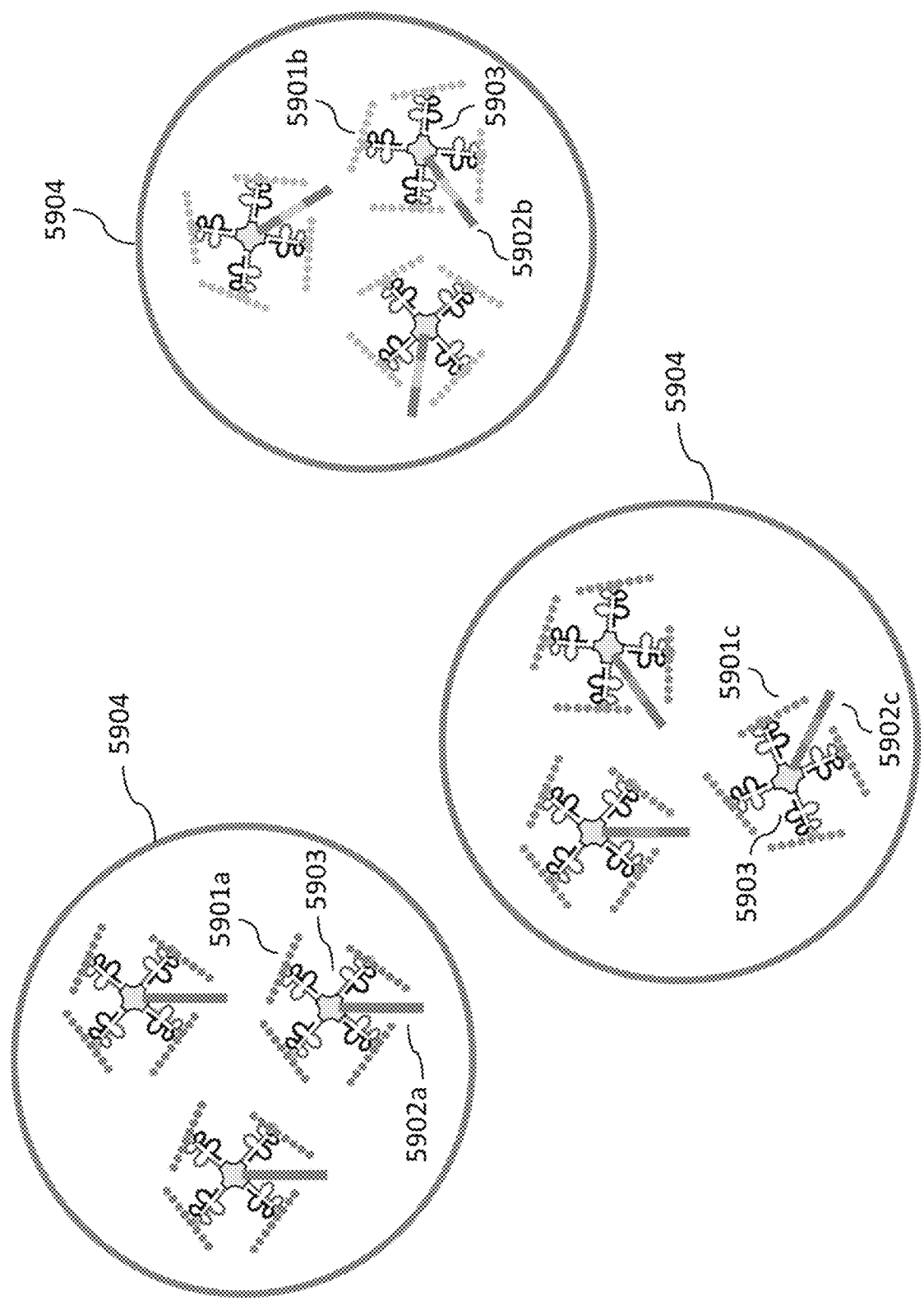
FIG. 59 illustrates the generation of barcoded MHC multimer complexes within a partition.

As shown in FIG. 58, soluble MHC molecules 5803 may be tetramers comprising four biotinylated MHC monomers bound to a tetrameric streptavidin core. Although MHC molecules 5803 shown in FIG. 58 are depicted as MHC tetramers, the schemes described herein are applicable to MHC monomers as well as other MHC multimer configurations (e.g., pentamers, dextramers, etc.). In some instances, prior to partitioning, MHC molecules 5803 comprise a conditional polypeptide ligand (such as a polypeptide comprising a photolabile amino acid or a protease cleavage domain). As such, partitions 5804 may also comprise one or more reagents sufficient to release the conditional ligand (such as a protease). Partitions may also be subjected to stimuli (such as UV light) to release the conditional ligand (e.g., by cleaving a photolabile amino acid in the conditional ligand). Likewise, partitions 5804 may also comprise one or more reagents (e.g., a reducing agent) sufficient to release the bead-bound peptides (e.g., 5801*a*) and nucleic acid barcode molecules (e.g., 5802*a*) and/or degrade gel bead 5805. Upon release of polypeptides (e.g., 5801*a*, 5801*b*, and 5801*c*) and nucleic acid barcode molecules (e.g., 5802*a*, 5802*b* and 5802*c*) and release of any optional conditional ligand, barcoded pMHC complexes 5903 are formed within partitions 5904 as shown in FIG. 59. In instances where the nucleic acid barcode molecules (e.g., 5902*a*, 5902*b* and 5902*c*) are conjugated to a carrier, e.g., streptavidin, partitions 5804 may further comprise one or more conjugation reagents and/or cofactors to facilitate conjugation. As such, the MHC carrier (e.g., streptavidin) and/or nucleic acid barcode molecules (e.g., 5802*a*, 5802*b* and 5802*c*) may comprise one or more functional groups (e.g., amines, thiols, etc.) or moieties (e.g., biotin) configured to couple nucleic acid barcode molecules (e.g., 5802*a*, 5802*b* and 5802*c*) to the WIC molecule or carrier.

Example 14: Method of Generating Labeled MHC Multimer Complexes Using In Vitro Transcription and In Vitro Translation In these examples, MHC multimer complexes are generated using in vitro transcription and in vitro translation. FIG. 60 illustrates an exemplary method for producing labeled MHC tetramers using in vitro transcription/translation. In FIG. 60, a plurality of MHC tetramers (biotinylated MHC molecules linked to a streptavidin core) and a plurality of beads (e.g., gel beads) are partitioned into a plurality of partitions (e.g., droplets in an emulsion or wells in a micro/nanowell array) such that at least some partitions 6000 comprise a single bead (not shown) and a WIC tetramer 6005 comprising MHC molecules 6004. The beads are configured such that each bead comprises a plurality of nucleic acid molecules 6002 comprising a sequence encoding for a polypeptide ("Peptide ORF"). The nucleic acid molecules may also comprise other functional sequences, such as a protomer sequence (e.g., a T7 promoter sequence) and a capture sequence (e.g., FIG. 28B, 2803) configured to hybridize to a sequence on, e.g., a barcoded bead as described elsewhere herein. Different partitions 6000 will comprise a bead comprising nucleic acid molecules 6002 encoding for a polypeptide that is different from other polypeptides encoded by nucleic acid molecules in other partitions. Thus, diverse libraries of unique pMHC complexes can be generated in a high throughput manner, where the identity of the peptide can be readily determined by the nucleic acid molecule associated with the MHC tetramer (e.g., via the sequence encoding the polypeptide and/or via a separate proxy sequence, such as a barcode sequence, associated with the peptide).

A bead comprising nucleic acid molecules 6002 is encapsulated into partition 6000 (e.g., a droplet emulsion) comprising in vitro transcription and translation reagents and MHC tetramer 6005. Nucleic acid molecules 6002 may be released from the bead (e.g., are releasably attached to the bead, such as by a labile bond), or may remain attached to the bead. Nucleic acid molecules 6002 are subjected to in vitro transcription to generate mRNA 6001. mRNA 6001 is subjected to in vitro translation to generate peptide 6003. Peptide 6003 then couples to WIC molecules 6004 and a nucleic acid molecule 6002 is coupled to the MHC tetramer though any suitable method described elsewhere herein (e.g., chemical conjugation, biotin-streptavidin interactions, etc.). The labeled MHC tetramers are then recovered from the plurality of partition, purified, and used in binding assays (e.g., T cell binding assays) as described elsewhere herein.

In some instances, MHC molecules 10508 comprise a conditional polypeptide ligand (not shown, such as a polypeptide comprising a photolabile amino acid or a protease cleavage domain) that is exchanged for the polypeptide 10505. As such, partitions 10506 may also comprise one or more reagents sufficient to release the conditional ligand (such as a protease). Partitions may also be subjected to stimuli (such as UV light) to release the conditional ligand (e.g., by cleaving a photolabile amino acid in the conditional ligand).

FIG. 105 illustrates an exemplary method for producing labeled MHC dextramers using in vitro transcription/translation. In FIG. 105, a plurality of dextramers (MHC multimer linked to a dextran backbone) and a plurality of beads (e.g., gel beads) are partitioned into a plurality of partitions (e.g., droplets in an emulsion or wells in a micro/nanowell array) such that at least some partitions 10506 comprise a single bead 10501 and a dextramer 10507 comprising MHC molecules 10508. The beads 10501 are configured such that each bead 10501 comprises a plurality of nucleic acid molecules 10503 comprising a sequence encoding for a polypeptide. The nucleic acid molecules may also comprise other functional sequences, such as a protomer sequence (e.g., a T7 promoter sequence) and a capture sequence (e.g., FIG. 28B, 2803) configured to hybridize to a sequence on, e.g., a barcoded bead as described elsewhere herein. Nucleic acid molecules also comprise a biotin moiety 10502 capable of binding to a free streptavidin moiety 10509 on dextramer 10507. Different partitions 10506 will comprise a bead 10501 comprising nucleic acid molecules 10503 encoding for a polypeptide that is different from other polypeptides encoded by nucleic acid molecules in other partitions. Thus, diverse libraries of unique pMHC complexes can be generated in a high throughput manner, where the identity of the peptide can be readily determined by the nucleic acid molecule associated with the dextramer (e.g., via the sequence encoding the polypeptide and/or via a separate proxy sequence, such as a barcode sequence, associated with the peptide).

Bead 10501 is encapsulated into partition 10506 (e.g., a droplet emulsion) comprising in vitro transcription and translation reagents and dextramer 10507. Nucleic acid molecules 10503 may be released from the bead (e.g., are releasably attached to the bead, such as by a labile bond), or may remain attached to the bead. Nucleic acid molecules 10503 are subjected to in vitro transcription to generate mRNA 10504. mRNA 10504 is subjected to in vitro translation to generate peptide 10505. Dextramer 10507 comprises MHC molecules 10508 and streptavidin molecules 10509. Peptide 10505 attaches to MHC molecules 10508, and biotin molecules 10502 attach to streptavidin molecules 10509. The dextramers are then recovered from the plurality of partition, where empty streptavidin sites may optionally be blocked with biotin molecules. Dextramers are purified and used in binding assays (e.g., T cell binding assays) as described elsewhere herein.

In some instances, MHC molecules 10508 comprise a conditional polypeptide ligand (not shown, such as a polypeptide comprising a photolabile amino acid or a protease cleavage domain) that is exchanged for the polypeptide 10505. As such, partitions 10506 may also comprise one or more reagents sufficient to release the conditional ligand (such as a protease). Partitions may also be subjected to stimuli (such as UV light) to release the conditional ligand (e.g., by cleaving a photolabile amino acid in the conditional ligand).

Figure 61:
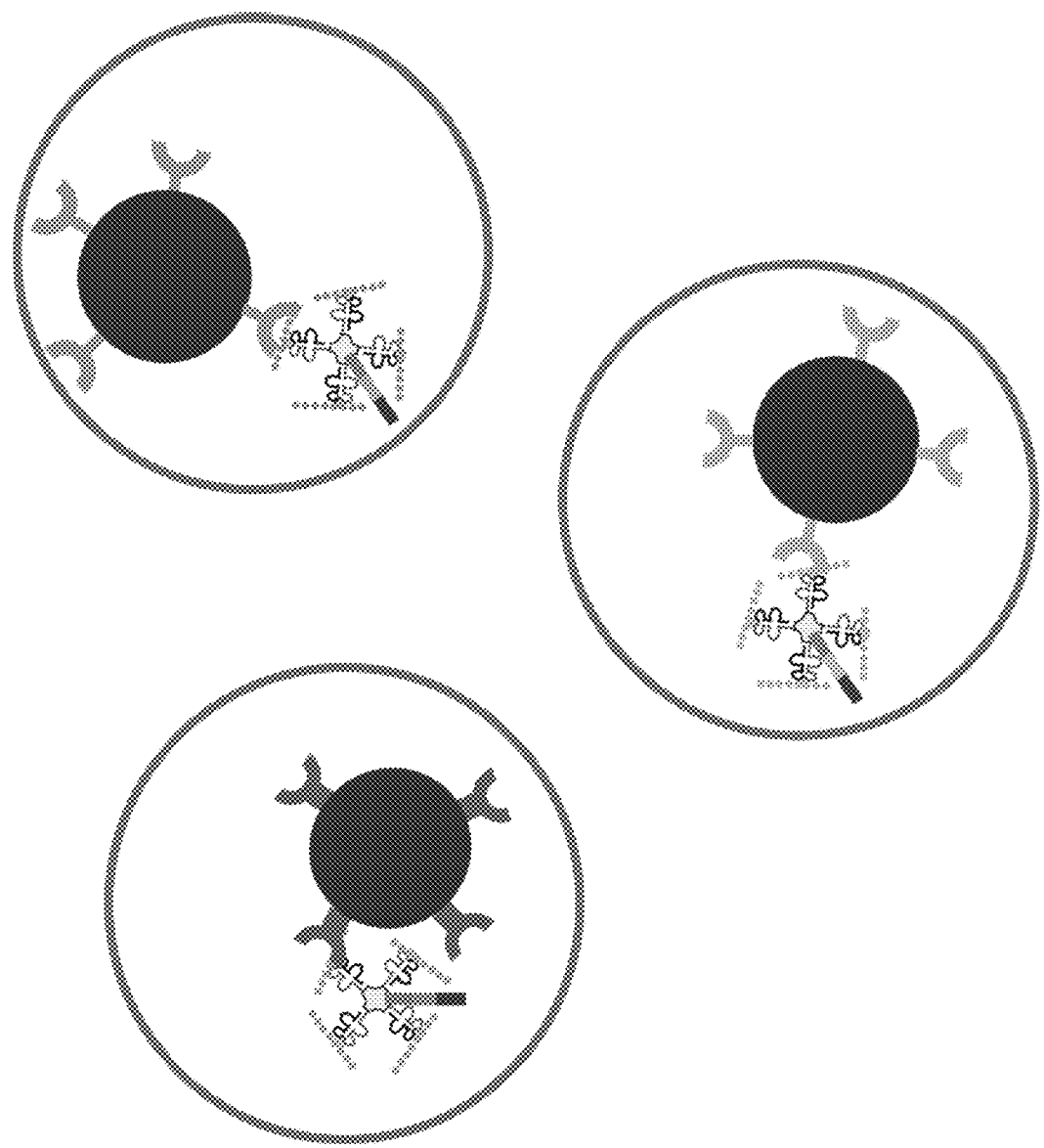
FIG. 61 illustrates the co-partitioning of interacting pairs of MHC-peptide multimers and T cells.

Example 15: Identifying Peptide Sequences and Corresponding T-cell Receptor (TCR) Sequences In this example, a library of MHC-peptide multimer complexes is mixed with a plurality of T cells. Peptides coupled to different MHC multimers have different peptide sequences. Interacting MHC-peptide multimers and T-cells are co-partitioned into a plurality of droplets as shown in FIG. 61. For each interacting pair of MHC-peptide multimer and T cell, the identity of the peptide can be determined by sequencing the corresponding barcode sequence. For each interacting pair, the T cell receptor sequence can be obtained sequencing the T cell receptor gene or a derivative thereof. The interacting TCR and peptide pair can be associated together through the presence of the common barcode sequence.

In some cases, the sequence of the T cell receptor gene is obtained by first lysing the T-cell and generating cDNA transcripts of mRNA from the cell. Generating cDNA transcripts can comprise hybridizing a polyT primer to the polyA region of mRNA molecules and reverse transcription by a reverse transcriptase. In some cases, the reverse transcriptase has terminal transferase activity and the reverse transcriptase adds additional nucleotides, e.g., polyC, to the 3' end of the cDNA transcript in a template independent manner. In some cases, a template switching oligonucleotide which includes a polyG sequence is present in the reaction and can hybridize to the cDNA transcript and facilitate template switching. The template switching oligonucleotide can comprise a cell-specific barcode sequence and template switching allows the barcode sequence to be appended to the cDNA transcript. In downstream analysis, the barcode sequence can be used to identify the T cell from which a particular cDNA transcript was derived. Using this procedure, the barcode sequence can be appended to the 5' end of the gene sequence.

Example 16: Displaying MHC Peptide Complexes on the Yeast Cell Surface

Figure 62:
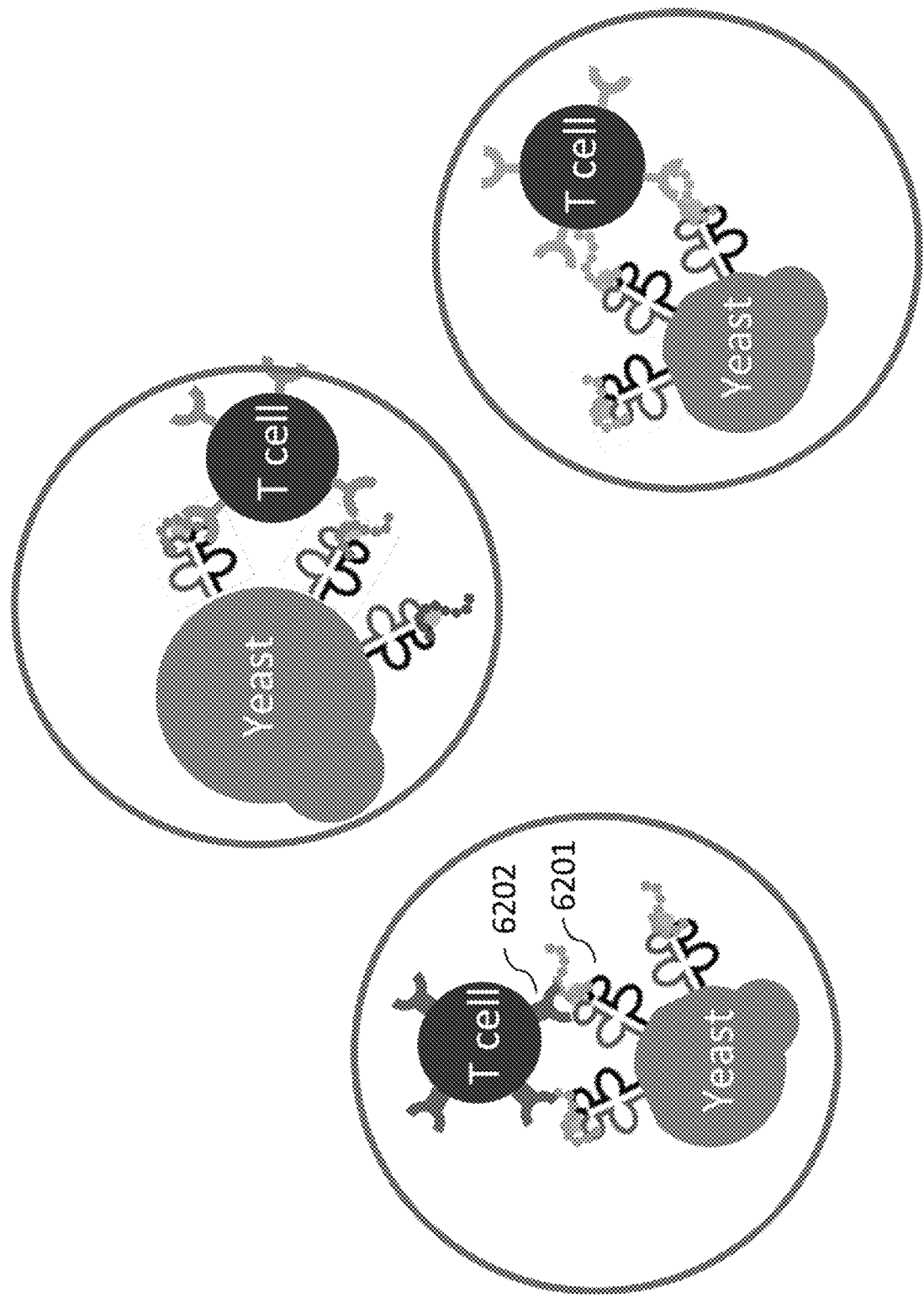
FIG. 62 illustrates the co-partitioning of interacting pairs of a MHC-peptide multimers displayed on the surface of yeast cells and T cells.

In this example, WIC-peptide complexes are displayed on the surface of yeast cells. Yeast displaying a library of WIC-peptide complexes can be mixed with a plurality of T cells. T cells having TCRs 6202 bound to MHC-peptide complexes displayed on a yeast cell surface 6201 can be co-partitioned, for example into droplets 6203, as shown in FIG. 62.

While preferred embodiments of the present invention have been shown and described herein, it will be obvious to those skilled in the art that such embodiments are provided by way of example only. It is not intended that the invention be limited by the specific examples provided within the specification. While the invention has been described with reference to the aforementioned specification, the descriptions and illustrations of the embodiments herein are not meant to be construed in a limiting sense. Numerous variations, changes, and substitutions will now occur to those skilled in the art without departing from the invention. Furthermore, it shall be understood that all aspects of the invention are not limited to the specific depictions, configurations or relative proportions set forth herein which depend upon a variety of conditions and variables. It should be understood that various alternatives to the embodiments of the invention described herein may be employed in practicing the invention. It is therefore contemplated that the invention shall also cover any such alternatives, modifications, variations or equivalents. It is intended that the following claims define the scope of the invention and that methods and structures within the scope of these claims and their equivalents be covered thereby.

What is claimed is:

1. A method comprising:
   (a) providing a reaction mixture in a partition comprising a major histocompatibility complex (MHC) molecule and a nucleic acid molecule comprising a sequence encoding a polypeptide, wherein said MHC molecule is a soluble MHC molecule; and
   (b) subjecting said reaction mixture to conditions sufficient to (i) generate said polypeptide from said nucleic acid molecule by an in vitro translation reaction, and (ii) couple said polypeptide and said nucleic acid molecule to said MHC molecule, thereby yielding a labeled MHC molecule.

2. The method of claim 1, wherein said nucleic acid molecule is a ribonucleic acid (RNA) molecule and wherein in (b)(i), said polypeptide is generated from said nucleic acid molecule by said in vitro translation reaction.

3. The method of claim 1, wherein said nucleic acid molecule is a deoxyribonucleic acid (DNA) molecule, wherein prior to (b), said DNA molecule is transcribed to yield a messenger RNA (mRNA) molecule, and wherein in (b)(i), said polypeptide is generated from said mRNA molecule by said in vitro translation reaction.

4. The method of claim 3, wherein said nucleic acid molecule further comprises a T7 promoter sequence.

5. The method of claim 3, wherein said nucleic acid molecule further comprises a capture sequence.

6. The method of claim 3, wherein said MHC molecule is coupled to a carrier.

7. The method of claim 6, wherein said carrier is a protein or polypeptide.

8. The method of claim 6, wherein said carrier comprises a polymer.

9. The method of claim 8, wherein said polymer comprises dextran.

10. The method of claim 6, wherein said nucleic acid molecule comprises biotin, wherein said carrier comprises streptavidin, and wherein said nucleic acid molecule is coupled to said carrier through a biotin-streptavidin interaction.

11. The method of claim 1, wherein in (a), said MHC molecule comprises a conditional ligand and wherein (b) comprises a peptide exchange action wherein said conditional ligand is exchanged for said polypeptide.

12. The method of claim 11, wherein said conditional ligand is a polypeptide comprising a photo-labile amino acid, and wherein said conditional ligand is released from said MHC molecule upon application of a photo-stimulus.

13. The method of claim 11, wherein said conditional ligand is covalently linked to said MHC molecule, wherein said conditional ligand is a polypeptide comprising a protease cleavage domain, and wherein said conditional ligand is released from said MHC molecule upon cleavage of said protease cleavage domain by a protease.

14. The method of claim 11, wherein said reaction mixture further comprises a molecular chaperone.

15. The method of claim 14, wherein said molecular chaperone comprises a luminal domain of transporter associated with antigen processing (TAP)-binding protein related (TAPBPR).

16. The method of claim 1, wherein in (a), said nucleic acid molecule is attached to a support.

17. The method of claim 16, wherein said support is a bead.

18. The method of claim 17, wherein said nucleic acid molecule is releasably attached to said bead.

19. The method of claim 18, further comprising releasing said nucleic acid molecule from said bead.

20. The method of claim 17, wherein said bead is a gel bead.

21. The method of claim 20, wherein said gel bead is degradable upon application of a stimulus.

22. The method of claim 21, wherein said stimulus is a chemical stimulus.

23. The method of claim 22, wherein said reaction mixture comprises said chemical stimulus.

24. The method of claim 1, wherein said partition is an aqueous droplet in an emulsion.

25. The method of claim 1, wherein said partition is a well.

26. The method of claim 1, further comprising:
(c) providing a plurality of partitions, including said partition, wherein at least a subset of said plurality of partitions each comprises (i) a plurality of soluble MHC molecules and (ii) a plurality of nucleic acid molecules comprising a sequence encoding a common polypeptide, wherein each partition of said subset of said plurality of partitions comprises a nucleic acid molecule encoding a unique polypeptide; and
(d) subjecting said plurality of partitions to conditions sufficient to, in each of said subset of said plurality of partitions, (i) generate said common polypeptide from said nucleic acid molecule and (ii) couple said common polypeptide and a given nucleic acid molecule of said plurality of nucleic acid molecules to a given MHC molecule of said plurality of soluble MHC molecules to yield a plurality of labeled MHC molecules, including said labeled MHC molecule.

27. The method of claim 26, wherein at least a subset of said plurality of labeled MHC molecules are coupled to a carrier.

28. The method of claim 27, wherein said plurality of nucleic acid molecules comprises biotin, wherein said carrier comprises streptavidin, and wherein nucleic acid molecules of said plurality of nucleic acid molecules is coupled to said carrier through a biotin-streptavidin interaction.

29. The method of claim 28, wherein said carrier comprises dextran.

* * * * *

SEQUENCE LISTING

```
<160> NUMBER OF SEQ ID NOS: 85

<210> SEQ ID NO 1
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
agatgtgtat aagagaca                                                      18

<210> SEQ ID NO 2
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
tctacactct ttccctacac gacgctcttc cgatct                                  36

<210> SEQ ID NO 3
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
tcgtcggcag cgtcagatgt gtataagaga cag                                     33

<210> SEQ ID NO 4
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4
actacacgac gctcttccga tct                                                23

<210> SEQ ID NO 5
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide
```

```
<400> SEQUENCE: 5
gtgactggag ttcagacgtg tgctcttccg atct                              34

<210> SEQ ID NO 6
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6
gtctcgtggg ctcggagatg tgtataagag acag                              34

<210> SEQ ID NO 7
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 7
taatacgact cactatag                                                18

<210> SEQ ID NO 8
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 8

His His His His His His
1               5

<210> SEQ ID NO 9
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Glu Gly Ala Leu Ile Tyr Trp Pro Asn
1               5

<210> SEQ ID NO 10
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Ala His Met Arg Asp Ser Gln Gln
1               5

<210> SEQ ID NO 11
<211> LENGTH: 9
<212> TYPE: PRT
<213> ORGANISM: Epstein-Barr virus
```

```
<400> SEQUENCE: 11

Gly Leu Cys Thr Leu Val Ala Met Leu
1               5

<210> SEQ ID NO 12
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 12
aaaaaaaaaa a                                                             11

<210> SEQ ID NO 13
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 13
tttttttttt t                                                             11

<210> SEQ ID NO 14
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 14
aaaaaaaaaa aaaaaaaaaa                                                    20

<210> SEQ ID NO 15
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 15
atcctagcaa                                                               10

<210> SEQ ID NO 16
<211> LENGTH: 114
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (25)..(30)
<223> OTHER INFORMATION: a, c, t, g, unknown or other
<220> FEATURE:
<221> NAME/KEY: modified_base
<222> LOCATION: (33)..(38)
<223> OTHER INFORMATION: a, c, t, g, unknown or other
<220> FEATURE:
<221> NAME/KEY: modified_base
<222> LOCATION: (73)..(82)
<223> OTHER INFORMATION: a, c, t, g, unknown or other
<220> FEATURE:
<221> NAME/KEY: modified_base
```

<222> LOCATION: (114)..(114)
<223> OTHER INFORMATION: a, c, t, g, unknown or other

<400> SEQUENCE: 16
caagcagaag acggcatacg agatnnnnnn gtnnnnnngt gactggagtt cagacgtgtg    60
ctcttccgat ctnnnnnnnn nntttttttt tttttttttt tttttttttt ttvn         114

<210> SEQ ID NO 17
<211> LENGTH: 61
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (35)..(40)
<223> OTHER INFORMATION: a, c, t, g, unknown or other
<220> FEATURE:
<221> NAME/KEY: modified_base
<222> LOCATION: (43)..(48)
<223> OTHER INFORMATION: a, c, t, g, unknown or other

<400> SEQUENCE: 17
agatcggaag agcacacgtc tgaactccag tcacnnnnnn acnnnnnnat ctcgtatgcc    60
g                                                                    61

<210> SEQ ID NO 18
<211> LENGTH: 114
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (25)..(30)
<223> OTHER INFORMATION: a, c, t, g, unknown or other
<220> FEATURE:
<221> NAME/KEY: modified_base
<222> LOCATION: (33)..(38)
<223> OTHER INFORMATION: a, c, t, g, unknown or other
<220> FEATURE:
<221> NAME/KEY: modified_base
<222> LOCATION: (73)..(82)
<223> OTHER INFORMATION: a, c, t, g, unknown or other
<220> FEATURE:
<221> NAME/KEY: modified_base
<222> LOCATION: (114)..(114)
<223> OTHER INFORMATION: a, c, t, g, unknown or other

<400> SEQUENCE: 18
caagcagaag acggcatacg agatnnnnnn cannnnnngt gactggagtt cagacgtgtg    60
ctcttccgat ctnnnnnnnn nntttttttt tttttttttt tttttttttt ttvn         114

<210> SEQ ID NO 19
<211> LENGTH: 61
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (35)..(40)
<223> OTHER INFORMATION: a, c, t, g, unknown or other
<220> FEATURE:
<221> NAME/KEY: modified_base
<222> LOCATION: (43)..(48)
<223> OTHER INFORMATION: a, c, t, g, unknown or other

<400> SEQUENCE: 19
agatcggaag agcacacgtc tgaactccag tcacnnnnnn tgnnnnnnat ctcgtatgcc      60
g                                                                      61

<210> SEQ ID NO 20
<211> LENGTH: 114
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (25)..(30)
<223> OTHER INFORMATION: a, c, t, g, unknown or other
<220> FEATURE:
<221> NAME/KEY: modified_base
<222> LOCATION: (33)..(38)
<223> OTHER INFORMATION: a, c, t, g, unknown or other
<220> FEATURE:
<221> NAME/KEY: modified_base
<222> LOCATION: (73)..(82)
<223> OTHER INFORMATION: a, c, t, g, unknown or other
<220> FEATURE:
<221> NAME/KEY: modified_base
<222> LOCATION: (114)..(114)
<223> OTHER INFORMATION: a, c, t, g, unknown or other

<400> SEQUENCE: 20
caagcagaag acggcatacg agatnnnnnn agnnnnnngt gactggagtt cagacgtgtg      60
ctcttccgat ctnnnnnnnn nnttttttttt tttttttttt tttttttttt ttvn          114

<210> SEQ ID NO 21
<211> LENGTH: 61
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (35)..(40)
<223> OTHER INFORMATION: a, c, t, g, unknown or other
<220> FEATURE:
<221> NAME/KEY: modified_base
<222> LOCATION: (43)..(48)
<223> OTHER INFORMATION: a, c, t, g, unknown or other

<400> SEQUENCE: 21
agatcggaag agcacacgtc tgaactccag tcacnnnnnn ctnnnnnnat ctcgtatgcc      60
g                                                                      61

<210> SEQ ID NO 22
<211> LENGTH: 114
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (25)..(30)
<223> OTHER INFORMATION: a, c, t, g, unknown or other
<220> FEATURE:
<221> NAME/KEY: modified_base
<222> LOCATION: (33)..(38)
<223> OTHER INFORMATION: a, c, t, g, unknown or other
<220> FEATURE:
<221> NAME/KEY: modified_base

```
<222> LOCATION: (73)..(82)
<223> OTHER INFORMATION: a, c, t, g, unknown or other
<220> FEATURE:
<221> NAME/KEY: modified_base
<222> LOCATION: (114)..(114)
<223> OTHER INFORMATION: a, c, t, g, unknown or other

<400> SEQUENCE: 22
caagcagaag acggcatacg agatnnnnnn tcnnnnnngt gactggagtt cagacgtgtg      60
ctcttccgat ctnnnnnnnn nnttttttt  tttttttt  tttttttt  ttvn              114

<210> SEQ ID NO 23
<211> LENGTH: 61
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (35)..(40)
<223> OTHER INFORMATION: a, c, t, g, unknown or other
<220> FEATURE:
<221> NAME/KEY: modified_base
<222> LOCATION: (43)..(48)
<223> OTHER INFORMATION: a, c, t, g, unknown or other

<400> SEQUENCE: 23
agatcggaag agcacacgtc tgaactccag tcacnnnnnn gannnnnnat ctcgtatgcc      60
g                                                                      61

<210> SEQ ID NO 24
<211> LENGTH: 78
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (23)..(28)
<223> OTHER INFORMATION: a, c, t, g, unknown or other
<220> FEATURE:
<221> NAME/KEY: modified_base
<222> LOCATION: (31)..(46)
<223> OTHER INFORMATION: a, c, t, g, unknown or other
<220> FEATURE:
<221> NAME/KEY: modified_base
<222> LOCATION: (78)..(78)
<223> OTHER INFORMATION: a, c, t, g, unknown or other

<400> SEQUENCE: 24
ctacacgacg ctcttccgat ctnnnnnngt nnnnnnnnnn nnnnnntttt tttttttttt      60
tttttttttt tttttvn                                                     78

<210> SEQ ID NO 25
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(6)
<223> OTHER INFORMATION: a, c, t, g, unknown or other
<220> FEATURE:
<221> NAME/KEY: modified_base
<222> LOCATION: (9)..(14)
<223> OTHER INFORMATION: a, c, t, g, unknown or other
```

```
<400> SEQUENCE: 25
nnnnnnacnn nnnnagatcg gaagagcg                                          28

<210> SEQ ID NO 26
<211> LENGTH: 78
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (23)..(28)
<223> OTHER INFORMATION: a, c, t, g, unknown or other
<220> FEATURE:
<221> NAME/KEY: modified_base
<222> LOCATION: (31)..(46)
<223> OTHER INFORMATION: a, c, t, g, unknown or other
<220> FEATURE:
<221> NAME/KEY: modified_base
<222> LOCATION: (78)..(78)
<223> OTHER INFORMATION: a, c, t, g, unknown or other

<400> SEQUENCE: 26
ctacacgacg ctcttccgat ctnnnnnnca nnnnnnnnnn nnnnnntttt tttttttttt        60
tttttttttt tttttvn                                                      78

<210> SEQ ID NO 27
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(6)
<223> OTHER INFORMATION: a, c, t, g, unknown or other
<220> FEATURE:
<221> NAME/KEY: modified_base
<222> LOCATION: (9)..(14)
<223> OTHER INFORMATION: a, c, t, g, unknown or other

<400> SEQUENCE: 27
nnnnnntgnn nnnnagatcg gaagagcg                                          28

<210> SEQ ID NO 28
<211> LENGTH: 78
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (23)..(28)
<223> OTHER INFORMATION: a, c, t, g, unknown or other
<220> FEATURE:
<221> NAME/KEY: modified_base
<222> LOCATION: (31)..(46)
<223> OTHER INFORMATION: a, c, t, g, unknown or other
<220> FEATURE:
<221> NAME/KEY: modified_base
<222> LOCATION: (78)..(78)
<223> OTHER INFORMATION: a, c, t, g, unknown or other

<400> SEQUENCE: 28
ctacacgacg ctcttccgat ctnnnnnnag nnnnnnnnnn nnnnnntttt tttttttttt        60
tttttttttt tttttvn                                                      78
```

<210> SEQ ID NO 29
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(6)
<223> OTHER INFORMATION: a, c, t, g, unknown or other
<220> FEATURE:
<221> NAME/KEY: modified_base
<222> LOCATION: (9)..(14)
<223> OTHER INFORMATION: a, c, t, g, unknown or other

<400> SEQUENCE: 29
nnnnnnctnn nnnnagatcg gaagagcg                                      28

<210> SEQ ID NO 30
<211> LENGTH: 78
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (23)..(28)
<223> OTHER INFORMATION: a, c, t, g, unknown or other
<220> FEATURE:
<221> NAME/KEY: modified_base
<222> LOCATION: (31)..(46)
<223> OTHER INFORMATION: a, c, t, g, unknown or other
<220> FEATURE:
<221> NAME/KEY: modified_base
<222> LOCATION: (78)..(78)
<223> OTHER INFORMATION: a, c, t, g, unknown or other

<400> SEQUENCE: 30
ctacacgacg ctcttccgat ctnnnnnntc nnnnnnnnnn nnnnnntttt tttttttttt   60
tttttttttt tttttvn                                                  78

<210> SEQ ID NO 31
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(6)
<223> OTHER INFORMATION: a, c, t, g, unknown or other
<220> FEATURE:
<221> NAME/KEY: modified_base
<222> LOCATION: (9)..(14)
<223> OTHER INFORMATION: a, c, t, g, unknown or other

<400> SEQUENCE: 31
nnnnnngann nnnnagatcg gaagagcg                                      28

<210> SEQ ID NO 32
<211> LENGTH: 118
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:

```
<221> NAME/KEY: modified_base
<222> LOCATION: (30)..(35)
<223> OTHER INFORMATION: a, c, t, g, unknown or other
<220> FEATURE:
<221> NAME/KEY: modified_base
<222> LOCATION: (38)..(43)
<223> OTHER INFORMATION: a, c, t, g, unknown or other
<220> FEATURE:
<221> NAME/KEY: modified_base
<222> LOCATION: (77)..(86)
<223> OTHER INFORMATION: a, c, t, g, unknown or other
<220> FEATURE:
<221> NAME/KEY: modified_base
<222> LOCATION: (118)..(118)
<223> OTHER INFORMATION: a, c, t, g, unknown or other

<400> SEQUENCE: 32
aatgatacgg cgaccaccga gatctacacn nnnnngtnnn nnnacactct ttccctacac    60
gacgctcttc cgatctnnnn nnnnnntttt tttttttttt tttttttttt tttttvn     118

<210> SEQ ID NO 33
<211> LENGTH: 62
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (34)..(39)
<223> OTHER INFORMATION: a, c, t, g, unknown or other
<220> FEATURE:
<221> NAME/KEY: modified_base
<222> LOCATION: (42)..(47)
<223> OTHER INFORMATION: a, c, t, g, unknown or other

<400> SEQUENCE: 33
agatcggaag agcgtcgtgt agggaaagag tgtnnnnnna cnnnnngtg tagatctcgg    60 tg                                                                 62

<210> SEQ ID NO 34
<211> LENGTH: 78
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (23)..(28)
<223> OTHER INFORMATION: a, c, t, g, unknown or other
<220> FEATURE:
<221> NAME/KEY: modified_base
<222> LOCATION: (31)..(46)
<223> OTHER INFORMATION: a, c, t, g, unknown or other
<220> FEATURE:
<221> NAME/KEY: modified_base
<222> LOCATION: (78)..(78)
<223> OTHER INFORMATION: a, c, t, g, unknown or other

<400> SEQUENCE: 34
cagacgtgtg ctcttccgat ctnnnnnngt nnnnnnnnnn nnnnnntttt tttttttttt    60
tttttttttt tttttvn                                                  78

<210> SEQ ID NO 35
<211> LENGTH: 27
<212> TYPE: DNA
<213> ORGANISM: Artificial Sequence
<220> FEATURE:
<223> OTHER INFORMATION: Description of Artificial Sequence: Synthetic
```

```
        oligonucleotide
<220> FEATURE:
<221> NAME/KEY: modified_base
<222> LOCATION: (1)..(6)
<223> OTHER INFORMATION: a, c, t, g, unknown or other
<220> FEATURE:
<221> NAME/KEY: modified_base
<222> LOCATION: (9)..(14)
<223> OTHER INFORMATION: a, c, t, g, unknown or other

<400> SEQUENCE: 35
nnnnnnacnn nnnnagatcg gaagagc                                               27

<210> SEQ ID NO 36
<211> LENGTH: 52
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (23)..(38)
<223> OTHER INFORMATION: a, c, t, g, unknown or other
<220> FEATURE:
<221> NAME/KEY: modified_base
<222> LOCATION: (41)..(52)
<223> OTHER INFORMATION: a, c, t, g, unknown or other

<400> SEQUENCE: 36
ctacacgacg ctcttccgat ctnnnnnnnn nnnnnnnngt nnnnnnnnnn nn                   52

<210> SEQ ID NO 37
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 37
agatcggaag agcg                                                             14

<210> SEQ ID NO 38
<211> LENGTH: 52
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (23)..(38)
<223> OTHER INFORMATION: a, c, t, g, unknown or other
<220> FEATURE:
<221> NAME/KEY: modified_base
<222> LOCATION: (41)..(52)
<223> OTHER INFORMATION: a, c, t, g, unknown or other

<400> SEQUENCE: 38
ctacacgacg ctcttccgat ctnnnnnnnn nnnnnnnnca nnnnnnnnnn nn                   52

<210> SEQ ID NO 39
<211> LENGTH: 52
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
```

```
<222> LOCATION: (23)..(38)
<223> OTHER INFORMATION: a, c, t, g, unknown or other
<220> FEATURE:
<221> NAME/KEY: modified_base
<222> LOCATION: (41)..(52)
<223> OTHER INFORMATION: a, c, t, g, unknown or other

<400> SEQUENCE: 39
ctacacgacg ctcttccgat ctnnnnnnnn nnnnnnnnag nnnnnnnnnn nn          52

<210> SEQ ID NO 40
<211> LENGTH: 52
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (23)..(38)
<223> OTHER INFORMATION: a, c, t, g, unknown or other
<220> FEATURE:
<221> NAME/KEY: modified_base
<222> LOCATION: (41)..(52)
<223> OTHER INFORMATION: a, c, t, g, unknown or other

<400> SEQUENCE: 40
ctacacgacg ctcttccgat ctnnnnnnnn nnnnnnnntc nnnnnnnnnn nn          52

<210> SEQ ID NO 41
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 41
ctacacgacg ctctt                                                   15

<210> SEQ ID NO 42
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 42
gtcagatgtg tataa                                                   15

<210> SEQ ID NO 43
<211> LENGTH: 80
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (23)..(29)
<223> OTHER INFORMATION: a, c, t, g, unknown or other
<220> FEATURE:
<221> NAME/KEY: modified_base
<222> LOCATION: (32)..(48)
<223> OTHER INFORMATION: a, c, t, g, unknown or other
<220> FEATURE:
<221> NAME/KEY: modified_base
<222> LOCATION: (80)..(80)
<223> OTHER INFORMATION: a, c, t, g, unknown or other
```

<400> SEQUENCE: 43
ctacacgacg ctcttccgat ctnnnnnnng tnnnnnnnnn nnnnnnnntt tttttttttt    60
tttttttttt tttttttttvn                                              80

<210> SEQ ID NO 44
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(7)
<223> OTHER INFORMATION: a, c, t, g, unknown or other
<220> FEATURE:
<221> NAME/KEY: modified_base
<222> LOCATION: (10)..(16)
<223> OTHER INFORMATION: a, c, t, g, unknown or other

<400> SEQUENCE: 44
nnnnnnnacn nnnnnnagat cggaagagcg                                    30

<210> SEQ ID NO 45
<211> LENGTH: 80
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (23)..(29)
<223> OTHER INFORMATION: a, c, t, g, unknown or other
<220> FEATURE:
<221> NAME/KEY: modified_base
<222> LOCATION: (32)..(48)
<223> OTHER INFORMATION: a, c, t, g, unknown or other
<220> FEATURE:
<221> NAME/KEY: modified_base
<222> LOCATION: (80)..(80)
<223> OTHER INFORMATION: a, c, t, g, unknown or other

<400> SEQUENCE: 45
ctacacgacg ctcttccgat ctnnnnnnnc annnnnnnnn nnnnnnnntt tttttttttt    60
tttttttttt tttttttttvn                                              80

<210> SEQ ID NO 46
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(7)
<223> OTHER INFORMATION: a, c, t, g, unknown or other
<220> FEATURE:
<221> NAME/KEY: modified_base
<222> LOCATION: (10)..(16)
<223> OTHER INFORMATION: a, c, t, g, unknown or other

<400> SEQUENCE: 46
nnnnnnntgn nnnnnnagat cggaagagcg                                    30

<210> SEQ ID NO 47
<211> LENGTH: 80
<212> TYPE: DNA

```
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (23)..(29)
<223> OTHER INFORMATION: a, c, t, g, unknown or other
<220> FEATURE:
<221> NAME/KEY: modified_base
<222> LOCATION: (32)..(48)
<223> OTHER INFORMATION: a, c, t, g, unknown or other
<220> FEATURE:
<221> NAME/KEY: modified_base
<222> LOCATION: (80)..(80)
<223> OTHER INFORMATION: a, c, t, g, unknown or other

<400> SEQUENCE: 47
ctacacgacg ctcttccgat ctnnnnnna gnnnnnnnnn nnnnnnnntt tttttttttt      60
tttttttttt tttttttvn                                                  80

<210> SEQ ID NO 48
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(7)
<223> OTHER INFORMATION: a, c, t, g, unknown or other
<220> FEATURE:
<221> NAME/KEY: modified_base
<222> LOCATION: (10)..(16)
<223> OTHER INFORMATION: a, c, t, g, unknown or other

<400> SEQUENCE: 48
nnnnnnnctn nnnnnnagat cggaagagcg                                      30

<210> SEQ ID NO 49
<211> LENGTH: 80
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (23)..(29)
<223> OTHER INFORMATION: a, c, t, g, unknown or other
<220> FEATURE:
<221> NAME/KEY: modified_base
<222> LOCATION: (32)..(48)
<223> OTHER INFORMATION: a, c, t, g, unknown or other
<220> FEATURE:
<221> NAME/KEY: modified_base
<222> LOCATION: (80)..(80)
<223> OTHER INFORMATION: a, c, t, g, unknown or other

<400> SEQUENCE: 49
ctacacgacg ctcttccgat ctnnnnnnnt cnnnnnnnnn nnnnnnnntt tttttttttt      60
tttttttttt tttttttvn                                                  80

<210> SEQ ID NO 50
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide
```

```
<220> FEATURE:
<221> NAME/KEY: modified_base
<222> LOCATION: (1)..(7)
<223> OTHER INFORMATION: a, c, t, g, unknown or other
<220> FEATURE:
<221> NAME/KEY: modified_base
<222> LOCATION: (10)..(16)
<223> OTHER INFORMATION: a, c, t, g, unknown or other

<400> SEQUENCE: 50
nnnnnnngan nnnnnnagat cggaagagcg                                    30

<210> SEQ ID NO 51
<211> LENGTH: 70
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (23)..(29)
<223> OTHER INFORMATION: a, c, t, g, unknown or other
<220> FEATURE:
<221> NAME/KEY: modified_base
<222> LOCATION: (32)..(48)
<223> OTHER INFORMATION: a, c, t, g, unknown or other

<400> SEQUENCE: 51
gtcagatgtg tataagagac agnnnnnnng tnnnnnnnnn nnnnnnnngc ttcgtacgcg    60
aaactagcgt                                                          70

<210> SEQ ID NO 52
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(7)
<223> OTHER INFORMATION: a, c, t, g, unknown or other
<220> FEATURE:
<221> NAME/KEY: modified_base
<222> LOCATION: (10)..(16)
<223> OTHER INFORMATION: a, c, t, g, unknown or other

<400> SEQUENCE: 52
nnnnnnnacn nnnnnnctgt ctcttataca c                                  31

<210> SEQ ID NO 53
<211> LENGTH: 52
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(20)
<223> OTHER INFORMATION: a, c, t, g, unknown or other
<220> FEATURE:
<221> NAME/KEY: modified_base
<222> LOCATION: (52)..(52)
<223> OTHER INFORMATION: a, c, t, g, unknown or other

<400> SEQUENCE: 53
nnnnnnnnnn nnnnnnnnnn tttttttttt tttttttttt tttttttttt vn           52
```

```
<210> SEQ ID NO 54
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (32)..(32)
<223> OTHER INFORMATION: a, c, t, g, unknown or other

<400> SEQUENCE: 54
tttttttttt tttttttttt tttttttttt vn                              32

<210> SEQ ID NO 55
<211> LENGTH: 46
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (23)..(28)
<223> OTHER INFORMATION: a, c, t, g, unknown or other
<220> FEATURE:
<221> NAME/KEY: modified_base
<222> LOCATION: (31)..(46)
<223> OTHER INFORMATION: a, c, t, g, unknown or other

<400> SEQUENCE: 55
ctacacgacg ctcttccgat ctnnnnnntc nnnnnnnnnn nnnnnn              46

<210> SEQ ID NO 56
<211> LENGTH: 44
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (23)..(36)
<223> OTHER INFORMATION: a, c, t, g, unknown or other
<220> FEATURE:
<221> NAME/KEY: modified_base
<222> LOCATION: (39)..(44)
<223> OTHER INFORMATION: a, c, t, g, unknown or other

<400> SEQUENCE: 56
ctacacgacg ctcttccgat ctnnnnnnnn nnnnnntcnn nnnn                44

<210> SEQ ID NO 57
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 57
aaaaaaaaaa aaaaaa                                                16

<210> SEQ ID NO 58
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide
```

```
<220> FEATURE:
<221> NAME/KEY: modified_base
<222> LOCATION: (23)..(28)
<223> OTHER INFORMATION: a, c, t, g, unknown or other

<400> SEQUENCE: 58
ctacacgacg ctcttccgat ctnnnnnn                                          28

<210> SEQ ID NO 59
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (3)..(8)
<223> OTHER INFORMATION: a, c, t, g, unknown or other

<400> SEQUENCE: 59
acnnnnnnag atcggaagag cg                                                22

<210> SEQ ID NO 60
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (3)..(18)
<223> OTHER INFORMATION: a, c, t, g, unknown or other
<220> FEATURE:
<221> NAME/KEY: modified_base
<222> LOCATION: (50)..(50)
<223> OTHER INFORMATION: a, c, t, g, unknown or other

<400> SEQUENCE: 60
gtnnnnnnnn nnnnnnnntt tttttttttt tttttttttt ttttttttvn                  50

<210> SEQ ID NO 61
<211> LENGTH: 41
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (3)..(18)
<223> OTHER INFORMATION: a, c, t, g, unknown or other

<400> SEQUENCE: 61
gtnnnnnnnn nnnnnnnta cgctagtttc gcgtacgaag c                            41

<210> SEQ ID NO 62
<211> LENGTH: 69
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (23)..(28)
<223> OTHER INFORMATION: a, c, t, g, unknown or other
<220> FEATURE:
<221> NAME/KEY: modified_base
<222> LOCATION: (31)..(46)
```

<223> OTHER INFORMATION: a, c, t, g, unknown or other

<400> SEQUENCE: 62
ctacacgacg ctcttccgat ctnnnnnngt nnnnnnnnnn nnnnnntacg ctagtttcgc    60
gtacgaagc                                                            69

<210> SEQ ID NO 63
<211> LENGTH: 80
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (23)..(48)
<223> OTHER INFORMATION: a, c, t, g, unknown or other
<220> FEATURE:
<221> NAME/KEY: modified_base
<222> LOCATION: (80)..(80)
<223> OTHER INFORMATION: a, c, t, g, unknown or other

<400> SEQUENCE: 63
ctacacgacg ctcttccgat ctnnnnnnnn nnnnnnnnnn nnnnnnnntt tttttttttt    60
tttttttttt tttttttvn                                                 80

<210> SEQ ID NO 64
<211> LENGTH: 70
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (23)..(48)
<223> OTHER INFORMATION: a, c, t, g, unknown or other

<400> SEQUENCE: 64
ctacacgacg ctcttccgat ctnnnnnnnn nnnnnnnnnn nnnnnnnnac gctagtttcg    60
cgtacgaagc                                                           70

<210> SEQ ID NO 65
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (23)..(47)
<223> OTHER INFORMATION: a, c, t/u, g, unknown or other

<400> SEQUENCE: 65
ctacacgacg ctcttccgat ctnnnnnnnn nnnnnnnnnn nnnnnnnttt cttatatggg    60

<210> SEQ ID NO 66
<211> LENGTH: 43
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 66
caactttagc ggtccaaggt gcagtcagat cccatataag aaa                43

<210> SEQ ID NO 67
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 67
caactttagc ggtccaaggt gcat                                     24

<210> SEQ ID NO 68
<211> LENGTH: 88
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (56)..(65)
<223> OTHER INFORMATION: a, c, t, g, unknown or other

<400> SEQUENCE: 68
caccttggac cgctaaagtt ggtgactgga gttcagacgt gtgctcttcc gatctnnnnn    60
nnnnncagat ttgaccccat ataagaaa                                      88

<210> SEQ ID NO 69
<211> LENGTH: 67
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (37)..(48)
<223> OTHER INFORMATION: a, c, t, g, unknown or other

<400> SEQUENCE: 69
tctacactct ttccctacac gacgctcttc cgatctnnnn nnnnnnnnag atgtgtataa    60
gagacag                                                             67

<210> SEQ ID NO 70
<211> LENGTH: 65
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(31)
<223> OTHER INFORMATION: a, c, t, g, unknown or other

<400> SEQUENCE: 70
ctgtctctta tacacatctn nnnnnnnnnn nagatcggaa gagcacacgt ctgaactcca    60
gtcac                                                                65

<210> SEQ ID NO 71
<211> LENGTH: 71
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (37)..(52)
<223> OTHER INFORMATION: a, c, t, g, unknown or other

<400> SEQUENCE: 71
tctacactct ttccctacac gacgctcttc cgatctnnnn nnnnnnnnnn nnagatgtgt      60
ataagagaca g                                                          71

<210> SEQ ID NO 72
<211> LENGTH: 87
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (57)..(68)
<223> OTHER INFORMATION: a, c, t, g, unknown or other

<400> SEQUENCE: 72
aatgatacgg cgaccaccga tctacactct ttccctacac gacgctcttc cgatctnnnn      60
nnnnnnnnag atgtgtataa gagacag                                         87

<210> SEQ ID NO 73
<211> LENGTH: 97
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(31)
<223> OTHER INFORMATION: a, c, t, g, unknown or other
<220> FEATURE:
<221> NAME/KEY: modified_base
<222> LOCATION: (66)..(73)
<223> OTHER INFORMATION: a, c, t, g, unknown or other

<400> SEQUENCE: 73
ctgtctctta tacacatctn nnnnnnnnnn nagatcggaa gagcacacgt ctgaactcca      60
gtcacnnnnn nnnatctcgt atgccgtctt ctgcttg                              97

<210> SEQ ID NO 74
<211> LENGTH: 91
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (57)..(72)
<223> OTHER INFORMATION: a, c, t, g, unknown or other

<400> SEQUENCE: 74
aatgatacgg cgaccaccga tctacactct ttccctacac gacgctcttc cgatctnnnn      60
nnnnnnnnnn nnagatgtgt ataagagaca g                                    91

<210> SEQ ID NO 75
<211> LENGTH: 48
<212> TYPE: DNA

<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (37)..(48)
<223> OTHER INFORMATION: a, c, t, g, unknown or other

<400> SEQUENCE: 75
tctacactct ttccctacac gacgctcttc cgatctnnnn nnnnnnn                         48

<210> SEQ ID NO 76
<211> LENGTH: 46
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(12)
<223> OTHER INFORMATION: a, c, t, g, unknown or other

<400> SEQUENCE: 76
nnnnnnnnnn nnagatcgga agagcacacg tctgaactcc agtcac                          46

<210> SEQ ID NO 77
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 77
agatgtgtat aagagacag                                                        19

<210> SEQ ID NO 78
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 78
ctgtctctta tacacatct                                                        19

<210> SEQ ID NO 79
<211> LENGTH: 68
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (57)..(68)
<223> OTHER INFORMATION: a, c, t, g, unknown or other

<400> SEQUENCE: 79
aatgatacgg cgaccaccga tctacactct ttccctacac gacgctcttc cgatctnnnn           60 nnnnnnnn                                                                    68

<210> SEQ ID NO 80
<211> LENGTH: 78
<212> TYPE: DNA

<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(12)
<223> OTHER INFORMATION: a, c, t, g, unknown or other
<220> FEATURE:
<221> NAME/KEY: modified_base
<222> LOCATION: (47)..(54)
<223> OTHER INFORMATION: a, c, t, g, unknown or other

<400> SEQUENCE: 80
nnnnnnnnnn nnagatcgga agagcacacg tctgaactcc agtcacnnnn nnnnatctcg      60
tatgccgtct tctgcttg                                                   78

<210> SEQ ID NO 81
<211> LENGTH: 92
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (57)..(72)
<223> OTHER INFORMATION: a, c, t, g, unknown or other

<400> SEQUENCE: 81
aatgatacgg cgaccaccga tctacactct ttccctacac gacgctcttc cgatctnnnn      60
nnnnnnnnnn nnagatgtgt ataagagaca gt                                   92

<210> SEQ ID NO 82
<211> LENGTH: 87
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (53)..(68)
<223> OTHER INFORMATION: a, c, t, g, unknown or other

<400> SEQUENCE: 82
cgatgacgtt aatacgactc actataggga ctacacgacg ctcttccgat ctnnnnnnnn      60
nnnnnnnnag atgtgtataa gagacag                                         87

<210> SEQ ID NO 83
<211> LENGTH: 85
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (51)..(66)
<223> OTHER INFORMATION: a, c, t, g, unknown or other

<400> SEQUENCE: 83
cgatgactta atacgactca ctataggact acacgacgct cttccgatct nnnnnnnnnn      60
nnnnnnagat gtgtataaga gacag                                           85

<210> SEQ ID NO 84
<211> LENGTH: 53

```
-continued

<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (23)..(34)
<223> OTHER INFORMATION: a, c, t, g, unknown or other

<400> SEQUENCE: 84
ctacacgacg ctcttccgat ctnnnnnnnn nnnnagatgt gtataagaga cag            53

<210> SEQ ID NO 85
<211> LENGTH: 57
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (23)..(38)
<223> OTHER INFORMATION: a, c, t, g, unknown or other

<400> SEQUENCE: 85
ctacacgacg ctcttccgat ctnnnnnnnn nnnnnnnnag atgtgtataa gagacag        57
```